US008129366B2

(12) United States Patent
Machinaga et al.

(10) Patent No.: US 8,129,366 B2
(45) Date of Patent: Mar. 6, 2012

(54) VLA-4 INHIBITORY DRUG

(75) Inventors: Nobuo Machinaga, Edogawa-ku (JP); Shin Iimura, Edogawa-ku (JP); Yoshiyuki Yoneda, Edogawa-ku (JP); Jun Chiba, Edogawa-ku (JP); Fumihito Muro, Edogawa-ku (JP); Hideko Hoh, Edogawa-ku (JP); Atsushi Nakayama, Edogawa-ku (JP)

(73) Assignee: Daiichi Sankyo Company, Limited, Tokyo (JP)

( * ) Notice: Subject to any disclaimer, the term of this patent is extended or adjusted under 35 U.S.C. 154(b) by 729 days.

(21) Appl. No.: 12/097,269

(22) PCT Filed: Dec. 13, 2006

(86) PCT No.: PCT/JP2006/324825
§ 371 (c)(1),
(2), (4) Date: Jan. 8, 2009

(87) PCT Pub. No.: WO2007/069635
PCT Pub. Date: Jun. 21, 2007

(65) Prior Publication Data
US 2009/0233901 A1      Sep. 17, 2009

(30) Foreign Application Priority Data
Dec. 13, 2005   (JP) .................. 2005-358523

(51) Int. Cl.
A61K 31/553 (2006.01)
C07D 243/08 (2006.01)
(52) U.S. Cl. ................... 514/211.01; 540/575
(58) Field of Classification Search ............. 514/211.01; 540/575
See application file for complete search history.

(56) References Cited

U.S. PATENT DOCUMENTS

| | | | |
|---|---|---|---|
| 6,355,662 | B1 | 3/2002 | Duplantier et al. |
| 6,596,687 | B1 | 7/2003 | Lin et al. |
| 7,157,487 | B2 | 1/2007 | Nakayama et al. |
| 2007/0232601 | A1 | 10/2007 | Yoneda et al. |

FOREIGN PATENT DOCUMENTS

| | | |
|---|---|---|
| EP | 1 346 982 | 9/2003 |
| WO | 97/03094 | 1/1997 |
| WO | 99/23063 | 5/1999 |
| WO | 99/33789 | 7/1999 |
| WO | 01/00206 | 1/2001 |
| WO | 01/51487 | 7/2001 |
| WO | 02/053534 | 7/2002 |
| WO | 2004 099136 | 11/2004 |
| WO | 2005 009992 | 2/2005 |
| WO | 2005 063678 | 7/2005 |
| WO | 2005 066124 | 7/2005 |

OTHER PUBLICATIONS

Martin E. Hemler, "VLA Proteins in the Integrin Family: Structures, Functions, and Their Role on Leokocytes", Annual Review of Immunology, vol. 8, 1990, pp. 365-400.
Mariano J. Elices, et al., "VCAM-1 on Activated Endothelium Interacts with the Leukocyte Integrin VLA-4 at a Site Distinct from the VLA-4/Fibronectin Binding Site", Cell, Feb. 23, 1990, vol. 60, pp. 577-584.
Roy R. Lobb, et al., "The Pathophysiologic Role of α4 Intergrins In Vivo", J. Clin. Invest., Nov. 1994, vol. 94, pp. 1722-1728.
Marina Pretolani, et al., "Antibody to Very Late Activation Antigen 4 Prevents Antigen-induced Bronchial Hyperreactivity and Cellular Infiltration in the Guinea Pig Airways", J. Exp. Med., Sep. 1994, vol. 180, pp. 795-805.
Silvana Molossi, et al., "Blockade of Very Late Antigen-4 Integrin Binding to Fibronectin with Connecting Segment-1 Peptide Reduces Accelerated Coronary Arteriopathy in Rabbit Cardiac Allografts", J. Clin. Invest., Jun. 1995, vol. 95, pp. 2601-2610.
Jefferson W. Tiley, et al., "VLA-4 antagonists", Drugs of the Future, 2001, 26(1), pp. 985-998.
Jun Chiba, et al. "VLA-4 Sogaiyaku no Gosei Kenkyu", Nippon Yakugakukai Nenkai Koen Yoshishu, vol. 125th, No. 4, p. 204, (2005) (with partial English translation).

Primary Examiner — Taofiq A Solola
(74) Attorney, Agent, or Firm — Oblon, Spivak, McClelland, Maier & Neustadt, L.L.P.

(57) ABSTRACT

There is provided a VLA-4 inhibitory drug having good oral absorbability and exhibiting sufficient anti-inflammatory effects when administered orally.
A compound represented by the following formula (I):

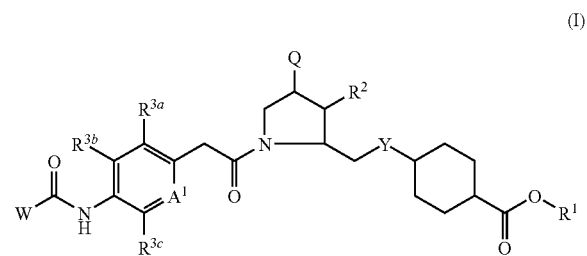

wherein $R^1$ represents a hydrogen atom or a C1-8 alkyl group; $R^2$ represents a hydrogen atom, a halogen atom, a C1-8 alkoxy group, or a benzyloxy group which may be substituted; Q represents a monocyclic or bicyclic nitrogen-containing heterocyclic group which may be substituted, and has a nitrogen atom as the bonding site; Y represents an oxygen atom or $CH_2$; W represents a bicyclic aromatic hydrocarbon ring group which may be substituted, or a bicyclic aromatic heterocyclic group which may be substituted; $R^{3a}$, $R^{3b}$ and $R^{3c}$ each independently represent a hydrogen atom, a halogen atom, a C1-8 alkoxy group or a C1-8 alkyl group; and $A^1$ represents a nitrogen atom or C—$R^{3d}$ (wherein $R^{3d}$ represents a hydrogen atom, a halogen atom, a C1-8 alkoxy group or a C1-8 alkyl group),
or a salt thereof, or a VLA-4 inhibitory drug comprising the compound or the salt as an active ingredient.

28 Claims, No Drawings

VLA-4 INHIBITORY DRUG

TECHNICAL FIELD

The present invention relates to a VLA-4 inhibitory drug that has a novel cyclohexanecarboxylic acid skeleton and is orally administrable.

BACKGROUND ART

Leukocyte is well known to play a critical role in inflammatory reactions that could be caused by microbial intrusion, the damaged tissue or the like. It is also known that leukocytes usually circulate in the blood vessel and, once the tissue is inflamed, leukocytes are infiltrated into the inflamed tissue by passing through the blood vessel wall adjacent to the such a tissue. This infiltration is found to be associated with the integrins expressed on the surface of a leukocyte cell.

An integrin is composed of a heterodimer of glycoprotein in which two noncovalently associated subunits (i.e., α-subunit and β-subunit) coalesce with each other. So far, at least 16 species are known to be included in the family of α-subunit, while at least 9 species are known to be included in the family of β-subunit, and thus these subunits form such a large family, respetively. An integrin "α4β1", which is known also as VLA-4 (very late antigen-4), is expressed on the cell surface of leukocytes such as monocytes, lymphocytes, eosinophiles, basophiles, mast cells and macrophages (Non-Patent Document 1). VCAM-1 (vascular cell adhesion molecule-1), as well as extracellular proteins such as fibronectin (FN), are known as the ligands of α4β1 (Non-Patent Document 2).

Among the effects obtainable by inhibiting the adhesion between VLA-4 and VCAM-1 are an anti-inflammatory action using an anti-α4 monoclonal antibody (Non-Patent Document 3), inhibitory action against bronchial hyperactivity at the time of antigen induction and inhibitory action against leukocyte infiltration into bronchoalveolar secretion in a guinea pig pulmonary inflammation model using an anti-α4 antibody (Non-Patent Document 4).

Also, there is a report focusing on a suppressive effect on inflammatory diseases by inhibiting the adhesion between VLA-4 and FN (Non-Patent Document 5). According to this report, an artificial CS-1 (connecting segment-1) tripeptide derivative [Phenylacetic acid-Leu(L)-Asp(D)-Phe(F)-d-Pro (d-P)-amide] in the amino acid sequence of CS-1, which is known as a region where binding of FN to VLA-4 occurs, suppressed a rejection reaction in rabbit heart transplantation.

The results of these researches suggest that if the cellular adhesion between VLA-4 and VCAM-1 and/or FN is effectively inhibited, it would be of great use as a means for the treatment of inflammatory diseases. However, any of the low molecular weight compounds, known as having a VLA-4 inhibitory action (Patent Document 1 to Patent Document 7, and Non-Patent Document 6), has yet to be used as a medicament.

Although an orally administrable agents is regarded as preferable in teaching inflammatory diseases, it is also known that most of such compounds have poor oral absorbability and tend to suffer a short retention time in blood. Hence, there are only a few, if any, reports showing that such a sufficient effect has been obtained by oral administration.

[Patent Document 1] WO 02/053534
[Patent Document 2] WO 97/03094
[Patent Document 3] WO 99/23063
[Patent Document 4] WO 99/33789
[Patent Document 5] U.S. Pat. No. 6,355,662
[Patent Document 6] WO 01/000206
[Patent Document 7] WO 01/051487
[Non-Patent Document 1] Helmer, M. Ann. Rev. Immunol., 8, 365 (1990)
[Non-Patent Document 2] Elices, et al., Cell, 60, 577 (1990)
[Non-Patent Document 3] Lobb R. R., et al., J. Clin., Invest., 94, 1722-28 (1994)
[Non-Patent Document 4] Pretolani, et al., J. Exp. Med., 180, 795 (1994)
[Non-Patent Document 5] Molossi et al., J. Clin. Invest., 95, 2601 (1995)
[Non-Patent Document 6] Jefferson W. Tilley and Achyutharao Sidduri, Drugs of the Future, 26(1), 985-998 (2001)

DISCLOSURE OF THE INVENTION

Problems to be Solved by the Invention

In order to develop an orally administrable VLA-4 inhibitory drug, it is necessary to improve its oral absorbability and its retention durability in blood alike.

Enhancement of oral absorbability of a compound requires an appropriate increase in the lipophilicity of the compound. However, if lipophilicity is too high, there is a risk so serious that non-specific binding of the compound to serum proteins (i.g., serum albumin) sharply increases, so that it becomes impossible for the compound to sufficiently bind to a target protein, thereby hampering the drug efficacy. Furthermore, when lipophilicity is increased, this leads to a decrease of the solubility in water, and provokes a decrease in oral absorbability adversely. Thus, many problems are likely to a rise, such as that the dose dependency of the drug cannot be secured on demand, and that the efficacy could vary widely depending on individual differences.

Therefore, in order to develop an orally administrable VLA-4 inhibitory drug, it is important to address the following four factors, i.e., 1) adequate lipophilicity, 2) adequate retention in blood, 3) adequate binding affinity to serum proteins, and 4) good water solubility.

An object of the present invention is to solve such problems, and to obtain a VLA-4 inhibitory drug having good oral absorbability and exhibiting sufficient anti-inflammatory effects through oral administration.

Means for Solving the Problems

The inventors of the present invention diligently conducted researches into the foregoing problems, and consequently arrived at the discovery that a compound represented by the following formula (I) exerts a sufficient anti-inflammatory effects when orally administered, thus leading to accomplishment of the present invention.

Specifically, the present invention is to provide a compound represented by the following formula (I):

[Formula 1]

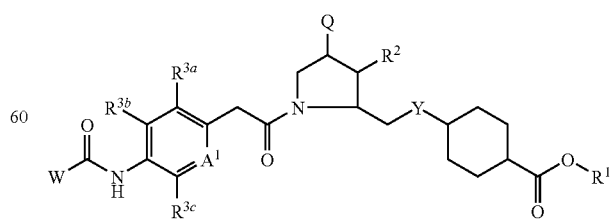

(I)

wherein $R^1$ represents a hydrogen atom or a lower alkyl group; $R^2$ represents a hydrogen atom, a halogen atom, a lower alkoxy group, or a benzyloxy group which may be substituted with one or a plurality of substituents; Q represents a monocyclic or bicyclic nitrogen-containing heterocyclic group which may be substituted with one or a plurality of substituents, and has a nitrogen atom as the bonding site; Y represents an oxygen atom or $CH_2$; W represents a bicyclic aromatic hydrocarbon ring group which may be substituted with one or a plurality of substituents, or a bicyclic aromatic heterocyclic group which may be substituted with one or a plurality of substituents; $R^{3a}$, $R^{3b}$ and $R^{3c}$ each independently represent a hydrogen atom, a halogen atom, a lower alkoxy group or a lower alkyl group; and $A^1$ represents a nitrogen atom or C—$R^{3d}$ (wherein $R^{3d}$ represents a hydrogen atom, a halogen atom, a lower alkoxy group or a lower alkyl group) or a salt thereof.

Furthermore, the present invention is to provide a medicine comprising the compound represented by the formula (I) or a salt thereof as an active ingredient, or a use of the compound represented by the formula (I) or a salt thereof, for the manufacture of medicine.

The present invention is also to provide a VLA-4 inhibitory drug comprising the compound represented by the formula (I) or a salt thereof as an active ingredient.

The present invention is to provide a prophylactic and/or therapeutic drug for diseases caused by cellular adhesion, or a prophylactic and/or therapeutic drug for diseases caused by cellular adhesion involving VLA-4, the drug comprising the compound represented by the formula (I) or a salt thereof as an active ingredient.

Furthermore, the present invention is to provide a preventive agent and/or therapeutic drug for diseases caused by cellular adhesion involving VLA-4, comprising the compound represented by the formula (I) or a salt thereof as an active ingredient.

Moreover, the present invention is to provide a method for preventing and/or a method for treating diseases caused by cellular adhesion, the method comprising administering the compound represented by the formula (I) or a salt thereof.

Effects of the Invention

The VLA-4 inhibitory drug of the present invention has high oral absorbability, and also exerts excellent effects on the predominant pharmacological and pathological in vivo model when administered orally. Thus the inhibitory drug of the invention makes it possible to prevent and/or treat various diseases caused by the migration and adhesion of leukocytes mediated by VLA-4, such as inflammatory response and autoimmune diseases.

BEST MODE FOR CARRYING OUT THE INVENTION

An explanation will be given in the following for the substituents for formula (I) of the compound of the present invention.

(1) The lower alkyl group means a C1 to C8, preferably C1 to C6, straight-chained or branched saturated hydrocarbon group, and examples thereof include a methyl group, an ethyl group, a n-propyl group, an isopropyl group, a n-butyl group, an isobutyl group, a tert-butyl group, a n-pentyl group, a n-hexyl group and the like.

(2) The halogen atom may be exemplified by a fluorine atom, a chlorine atom, a bromine atom or an iodine atom.

(3) The lower alkoxy group means a lower alkyloxy group including a C1 to C8, preferably C1 to C6, straight-chained or branched saturated hydrocarbon group, and examples thereof include a methoxy group, an ethoxy group, a n-propoxy group, an isopropoxy group, a n-butoxy group, an isobutyloxy group, a tert-butoxy group, a n-pentyloxy group, and n-hexyloxy group and the like.

(4) The benzyloxy group which may be substituted with one or a plurality of substituents means an unsubstituted benzyloxy group, or a benzyloxy group which may be substituted with one or a plurality of substituents on the benzene ring. The substituents for the benzyloxy group include a halogen atom, a methyl group, an ethyl group, a n-propyl group, an isopropyl group, a methoxy group, an ethoxy group, a n-propoxy group, an isopropoxy group, a methylthio group, an ethylthio group, a n-propylthio group, an isopropylthio group, a methanesulfonyl group, an ethanesulfonyl group, a n-propylsulfonyl group, an isopropylsulfonyl group, a nitro group, an acetyl group, a propionyl group, a cyano group, a carboxyl group, a methoxycarbonyl group, an ethoxycarbonyl group, a n-propoxycarbonyl group, an isopropoxycarbonyl group, a dimethylcarbamoyl group, a phenyl group and the like.

(5) The monocyclic nitrogen-containing heterocyclic group having a nitrogen atom as the bonding site, means a 4- to 7-membered saturated or unsaturated monocyclic heterocyclic group having at least one nitrogen atom as the ring constituting atom, which group is attached to the pyrrolidine ring in the formula (I) at the nitrogen atom. Specific examples include an azetidin-1-yl group, a pyrrolidin-1-yl group, an isoxazolidin-2-yl group, an isothiazolidin-2-yl group, an imidazolin-1-yl group, an imidazolin-3-yl group, an indazolin-1-yl group, an indazolin-2-yl group, a triazol-1-yl group, a triazol-2-yl group, a triazol-3-yl group, a piperidin-1-yl group, a piperazin-1-yl group, a morpholin-4-yl group, a thiomorpholin-4-yl group, a thiomorpholin-1,1-dioxide-4-yl group, a [1,2]thiazinan-2-yl group, a [1,2]thiazinan-1,1-dioxide-2-yl group, a homopiperidin-1-yl group, a [1,4]oxazepan-4-yl group, a [1,4]thiazepan-4-yl group, a [1,4]oxazepan-1,1-dioxide-4-yl group, a [1,4]diazepan-1-yl group and the like. Examples of groups which may be substituted on the above groups include a halogen atom, a phenyl group which may be substituted with one or a plurality of substituents, a lower alkyl group which may be substituted with one or a plurality of substituents, a lower cycloalkyl group, a lower alkoxy group which may be substituted with one or a plurality of substituents, an amino group which may be substituted with one or two substituents, a carboxyl group, a lower alkoxycarbonyl group, a carbamoyl group which may be substituted with one or two substituents, a lower alkylsulfonyl group which may be substituted with one or a plurality of substituents, a phenylsulfonyl group which may be substituted with one or a plurality of substituents, a sulfamoyl group which may be substituted with one or two substituents, a lower alkanoyl group which may be substituted with one or a plurality of substituents, an oxo group, a hydroxy group and the like.

Here, the phenyl group which may be substituted with one or a plurality of substituents means an unsubstituted phenyl group, as well as a phenyl group substituted with one or a plurality of groups selected from a halogen atom, a methyl group, an ethyl group, a n-propyl group, an isopropyl group, a methoxy group, an ethoxy group, a n-propoxy group, an isopropoxy group, a methylthio group, an ethylthio group, a n-propylthio group, an isopropylthio group, a methanesulfonyl group, an ethanesulfonyl group, a n-propylsulfonyl group, an isopropylsulfonyl group, a nitro group, an acetyl group, a propionyl group, a cyano group, a carboxyl group, a methoxycarbonyl group, an ethoxycarbonyl group, a n-propoxycarbonyl group, an isopropoxycarbonyl group, a dimethylcarbamoyl group and a phenyl group.

The lower alkyl group which may be substituted with one or a plurality of substituents means the above-mentioned unsubstituted lower alkyl group, as well as an alkyl group which may be substituted with one or a plurality of substituents selected from a halogen atom, a methoxy group, an ethoxy group, a methylthio group, an ethylthio group, a methanesulfonyl group, an ethanesulfonyl group, a carboxyl group, a methoxycarbonyl group, an ethoxycarbonyl group, a dimethylcarbamoyl group and a phenyl group.

The lower cycloalkyl group is a cycloalkyl group having 3 to 8 carbon atoms, and preferably a C3 to C6 cyclic alkyl group, and specific examples thereof include a cyclopropyl group, a cyclobutyl group, a cyclopentyl group, a cyclohexyl group and the like.

The lower alkoxy group which may be substituted with one or a plurality of substituents means the above-mentioned unsubstituted lower alkoxy group, as well as an alkoxy group substituted with one or a plurality of groups selected from a halogen atom, a methoxy group, an ethoxy group, a methylthio group, an ethylthio group, a methanesulfonyl group, an ethanesulfonyl group, a carboxyl group, a methoxycarbonyl group, an ethoxycarbonyl group, a dimethylcarbamoyl group and a phenyl group.

The amino group which may be substituted with one or two substituents means an unsubstituted amino group, as well as an amino group substituted with one or two groups selected from the above-mentioned lower alkyl group and lower cycloalkyl group. Specific examples thereof include a methylamino group, an ethylamino group, a dimethylamino group, a diethylamino group, an isopropylamino group, an N-methyl-N-ethylamino group, a cyclopropylamino group, a N,N-dicyclopropylamino group and the like.

The lower alkoxycarbonyl group means a lower alkyloxycarbonyl group having the above-mentioned lower alkyl group. Specific examples thereof include a methoxycarbonyl group, an ethoxycarbonyl group, a n-propoxycarbonyl group, an isopropoxycarbonyl group, a n-butoxycarbonyl group, an isobutyloxycarbonyl group, a tert-butoxycarbonyl group, a n-pentyloxycarbonyl group, a n-hexyloxycarbonyl group and the like.

The carbamoyl group which may be substituted with one or two substituents means an unsubstituted carbamoyl group, as well as a carbamoyl group substituted with one or two groups selected from the above-mentioned lower alkyl group. Specific examples thereof include a methylcarbamoyl group, a methylcarbamoyl group, a dimethylcarbamoyl group, a diethylcarbamoyl group, an N-methyl-N-ethylcarbamoyl group and the like.

The lower alkylsulfonyl group which may be substituted with one or a plurality of substituents means an alkylsulfonyl group having the above-mentioned lower alkyl group, and means an unsubstituted lower alkylsulfonyl group, as well as an alkylsulfonyl group substituted with one or a plurality of groups selected from a halogen atom and a methoxy group.

The sulfamoyl group which may be substituted with one or two substituents means an unsubstituted sulfamoyl group, as well as an aminosulfonyl group substituted on the nitrogen atom with one or a plurality of groups selected from the above-mentioned lower alkyl group and lower cycloalkyl group. Specific examples thereof include a methylsulfamoyl group, a methylsulfamoyl group, a dimethylsulfamoyl group, a diethylsulfamoyl group, an isopropyl sulfamoyl group, an N-methyl-N-ethylsulfamoyl group, a cyclopropyl sulfamoyl group, an N,N-dicyclopropyl sulfamoyl group and the like.

The lower alkanoyl group which may be substituted with one or two substituents means an acyl group formed from a C1 to C7, preferably C1 to C5, alkyl group and a carbonyl group, and means an unsubstituted lower alkanoyl group, as well as an alkanoyl group substituted with one or a plurality of groups selected from a halogen atom, a methoxy group, an ethoxy group and a phenyl group.

(6) The bicyclic nitrogen-containing heterocyclic group having a nitrogen atom as the bonding site, means a bicyclic heterocyclic group containing at least one nitrogen atom as a ring constituting atom, which group has two 3- to 7-membered saturated or unsaturated rings bound in a spiro form, a condensed form or a bridged form, and is attached to the pyrrolidine ring of formula (I) at the ring constituting nitrogen atom. Specific examples thereof include a [(3a,6a-cis)-hexahydrofuro[3,4-c]pyrrol]-5-yl group, a (3a,6a-cis)-tetrahydro[1,3]dioxolo[4,5-c]pyrrol-5-yl group, a 5-azaspiro[2.4]heptan-5-yl group, a 2-oxa-5-azabicyclo[2.2.1]heptan-5-yl group, a 2,5-diazabicyclo[2.2.1]heptan-5-yl group, a 1-homopiperidinyl group, a [1,4]oxazepan-4-yl group, a [1,4]thiazepan-4-yl group, a [1,4]oxazepan-1,1-dioxide-4-yl group, a [1,4]diazepam-1-yl group and the like. The bicyclic nitrogen-containing heterocyclic group may be substituted with one or a plurality of groups selected from a halogen atom, a phenyl group which may be substituted with one or a plurality of substituents, a lower alkyl group which may be substituted with one or a plurality of substituents, a lower cycloalkyl group, a lower alkoxy group which may be substituted with one or a plurality of substituents, an amino group which may be substituted with one or two substituents, a carboxyl group, a lower alkoxycarbonyl group, a carbamoyl group which may be substituted with one or two substituents, a lower alkylsulfonyl group which may be substituted with one or a plurality of substituents, a phenylsulfonyl group which may be substituted with one or a plurality of substituents, a sulfamoyl group which may be substituted with one or two substituents, a lower alkanoyl group which may be substituted with one or a plurality of substituents, an oxo group and a hydroxy group. The substituents substituted on the bicyclic nitrogen-containing heterocyclic group have the same meaning as defined for the previously mentioned monocyclic nitrogen-containing heterocyclic group, and examples are also the same.

(7) The bicyclic aromatic hydrocarbon ring group means an unsubstituted bicyclic aromatic hydrocarbon ring group, or a bicyclic aromatic hydrocarbon ring group substituted with one or a plurality of substituents on the bicyclic aromatic hydrocarbon ring group. The bicyclic aromatic hydrocarbon ring group may be exemplified by a naphthyl group, an indenyl group or the like. The substituents for the bicyclic aromatic hydrocarbon ring group include a halogen atom, a methyl group, an ethyl group, a n-propyl group, an isopropyl group, a methoxy group, an ethoxy group, a n-propoxy group, an isopropoxy group and the like.

(8) The bicyclic aromatic heterocyclic group means an aromatic heterocyclic group containing at least one oxygen atom, nitrogen atom or sulfur atom as a ring constituting atom, in which group two rings of a 6-membered ring and a 5- to 6-membered ring are bound in a condensed form. Specific examples thereof include an indolyl group, an indazolyl group, a benzothiophenyl group, a benzofuranyl group, a benzoxazolyl group, a benzothiazolyl group, a benzisoxazolyl group, a benzisothiazolyl group, a benzimidazolyl group, an oxazolo[4,5-b]pyridyl group, a 1H-pyrrolo[2,3-b]pyridyl group, a 1H-pyrrolo[2,3-c]pyridyl group, a 1H-pyrrolo[3,2-c]pyridyl group, a 1H-pyrrolo[3,2-b]pyridyl group, a thieno[2,3-b]pyridyl group, a thieno[2,3-c]pyridyl group, a thieno[3,2-c]pyridyl group, a thieno[3,2-b]pyridyl group, a furo[2,3-b]pyridyl group, a furo[2,3-c]pyridyl group, a furo[3,2-c]pyridyl group, a furo[3,2-b]pyridyl group, a pyrazolo[3,4-b]pyridyl group, a pyrazolo[3,4-c]pyridyl group, a pyrazolo[4,3-c]pyridyl group, a pyrazolo[4,3-b]pyridyl group, an isoquinolinyl group, a quinolinyl group, a phthalazinyl group, a naphthyridinyl group, a quinoxalinyl group, a quinazolinyl group, a cinnolinyl group and the like. The group which may be substituted on the bicyclic aromatic heterocyclic group, may be exemplified by a halogen atom, a methyl group, an ethyl group, a n-propyl group, an isopropyl group, a methoxy group, an ethoxy group, a n-propoxy group, an isopropoxy group or the like.

Hereinafter, the present invention will be described in more detail.

In the above formula (I), $R^1$ is preferably a hydrogen atom, a methyl group, an ethyl group, a n-propyl group, an isopropyl group, a n-butyl group, an isobutyl group, a tert-butyl group, a n-pentyl group, a n-heptyl group or the like; more preferably a hydrogen atom, a methyl group, an ethyl group or a tert-butyl group; and even more preferably a hydrogen atom.

Y is preferably an oxygen atom.

$R^2$ is preferably a hydrogen atom, a halogen atom, a C1 to C6 alkoxy group, a benzyloxy group which may be substituted with one or a plurality of substituents; more preferably a hydrogen atom, a fluorine atom, a methoxy group, an ethoxy group or an unsubstituted benzyloxy group; and even more preferably a hydrogen atom.

$R^{3a}$, $R^{3b}$ and $R^{3c}$ are each preferably a hydrogen atom, a halogen atom, a C1 to C6 alkoxy group, a C1 to C6 alkyl group or the like; and more preferably a hydrogen atom, a fluorine atom, a chlorine atom, a bromine atom, a methoxy group or a methyl group. Among these, $R^{3a}$ is more preferably a hydrogen atom, a fluorine atom or a chlorine atom; $R^{3b}$ is more preferably a hydrogen atom; and $R^{3c}$ is more preferably a fluorine atom, a chlorine atom, a methoxy group or a methyl group.

$A^1$ is preferably C—$R^{3d}$ (wherein $R^{3d}$ represents the same as described above).

When $A^1$ is C—$R^{3d}$, $R^{3d}$ is preferably a hydrogen atom, a halogen atom, a C1 to C6 alkoxy group, a C1 to C6 alkyl group or the like; more preferably a hydrogen atom, a fluorine atom, a chlorine atom, a bromine atom, a methoxy group, or a methyl group; and even more preferably a hydrogen atom.

As for W in the formula (I), the following formula (i) or (ii):

[Formula 2]

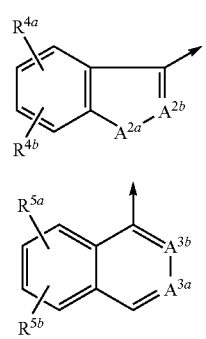

wherein symbol "→" represents the position of attachment; $R^{4a}$ and $R^{4b}$ each independently represent a hydrogen atom, a halogen atom, a lower alkoxy group or a lower alkyl group; $A^{2a}$ represents an oxygen atom, a sulfur atom or N—$R^{4c}$ (wherein $R^{4c}$ represents a hydrogen atom or a lower alkyl group); $A^{2b}$ represents a nitrogen atom or C—$R^{4d}$ (wherein $R^{4d}$ represents a hydrogen atom or a lower alkyl group); $R^{5a}$ and $R^{5b}$ each independently represent a hydrogen atom, a halogen atom, a lower alkoxy group or a lower alkyl group; $A^{3a}$ represents a nitrogen atom or C—$R^{5c}$ (wherein $R^{5c}$ represents a hydrogen atom or a lower alkyl group); and $A^{3b}$ represents a nitrogen atom or C—$R^{5d}$ (wherein $R^{5d}$ represents a hydrogen atom or a lower alkyl group), can be mentioned as a preferred group.

More specifically, groups represented by the following formulas (iii-a) to (iii-h):

[Formula 3]

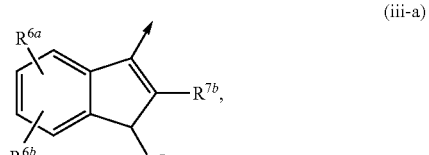

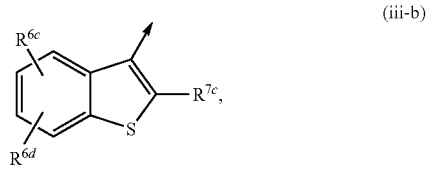

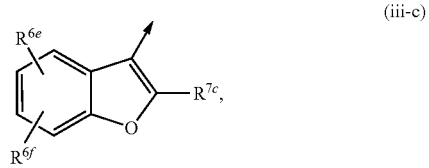

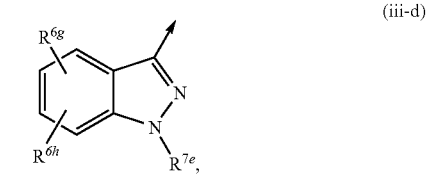

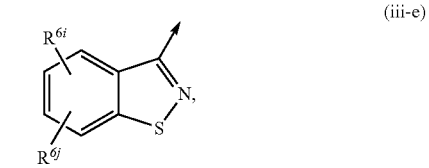

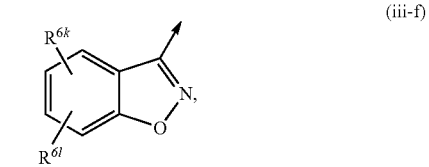

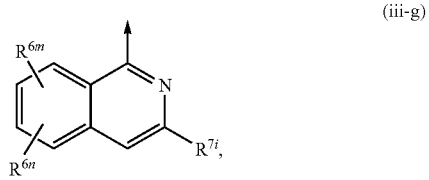

-continued

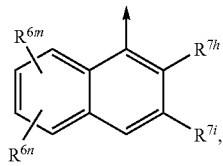
(iii-h)

wherein symbol "→" represents the position of attachment; $R^{6a}$, $R^{6b}$, $R^{6c}$, $R^{6d}$, $R^{6e}$, $R^{6f}$, $R^{6g}$, $R^{6h}$, $R^{6i}$, $R^{6j}$, $R^{6k}$, $R^{6l}$, $R^{6m}$, $R^{6n}$, $R^{6o}$ and $R^{6p}$ each independently represent a hydrogen atom, a halogen atom, a lower alkoxy group or a lower alkyl group; and $R^{7a}$, $R^{7b}$, $R^{7c}$, $R^{7d}$, $R^{7e}$, $R^{7f}$, $R^{7g}$ and $R^{7h}$ each independently represent a hydrogen atom or a lower alkyl group, may be mentioned as preferred examples.

Among these, formulas (iii-a), (iii-b), (iii-c), (iii-d) and (iii-g) are more preferred, and formulas (iii-a), (iii-b) and (iii-c) are even more preferred.

Among the formulas (iii-a) to (iii-h), $R^{6a}$, $R^{6b}$, $R^{6c}$, $R^{6d}$, $R^{6e}$, $R^{6f}$, $R^{6g}$, $R^{6h}$, $R^{6i}$, $R^{6j}$, $R^{6k}$, $R^{6l}$, $R^{6m}$, $R^{6n}$, $R^{6o}$ and $R^{6p}$ are each preferably a hydrogen atom, a halogen atom, a C1 to C6 alkoxy group or a C1 to C6 alkyl group, and more preferably a hydrogen atom, a halogen atom, a methoxy group or a methyl group.

Furthermore, $R^{7a}$, $R^{7b}$, $R^{7c}$, $R^{7d}$, $R^{7e}$, $R^{7f}$, $R^{7g}$ and $R^{7h}$ are each preferably a hydrogen atom or a C1 to C6 alkyl group, and more preferably a hydrogen atom or a methyl group.

Q in the formula (I) may be specifically exemplified by groups represented by the following formulas (iv-a) to (iv-x):

[Formula 4]

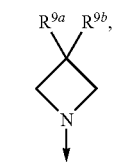
(iv-a)

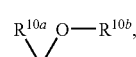
(iv-b)

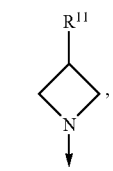
(iv-c)

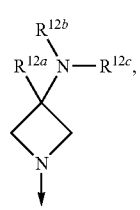
(iv-d)

(iv-e)

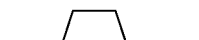
(iv-f)

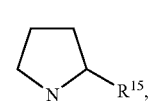
(iv-g)

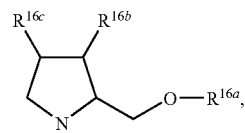
(iv-h)

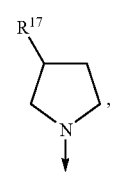
(iv-i)

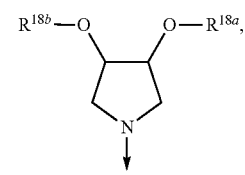
(iv-j)

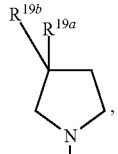
(iv-k)

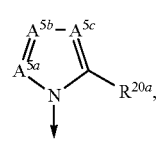
(iv-l)

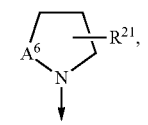
(iv-m)

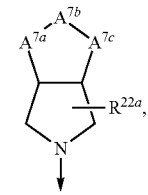
(iv-n)

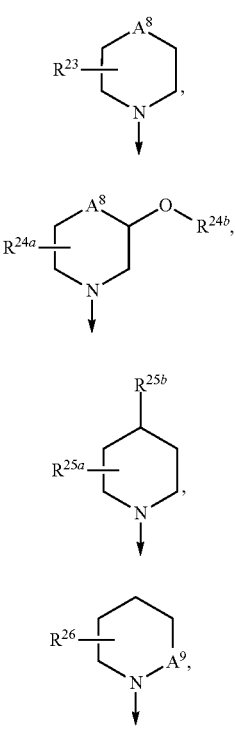

wherein symbol "→" represents the position of attachment;

$R^{9a}$ and $R^{9b}$ each independently represent a hydrogen atom, a halogen atom or a lower alkyl group;

$R^{10a}$ represents a hydrogen atom or a lower alkyl group; $R^{10b}$ represents a lower alkyl group;

$R^{11}$ represents a substituted lower alkyl group;

$R^{12a}$ represents a hydrogen atom or a lower alkyl group; $R^{12b}$ and $R^{12c}$ each independently represent a lower alkyl group or a lower cycloalkyl group which may be substituted with one or a plurality of substituents; or $R^{12b}$ and $R^{12c}$, together with the nitrogen atom to which they are bound, form an azetidin-1-yl group which may be substituted with one or a plurality of substituents, a pyrrolidin-1-yl group which may be substituted with one or a plurality of substituents, a piperidin-1-yl group which may be substituted with one or a plurality of substituents, or a morpholin-1-yl group which may be substituted with one or a plurality of substituents;

$R^{13a}$ and $R^{13b}$ each independently represent a hydrogen atom, a lower alkyl group or a lower alkoxymethyl group;

$R^{14a}$ and $R^{14b}$ each independently represent a lower alkyl group or a lower alkoxymethyl group;

$R^{15}$ represents a hydrogen atom, a lower alkyl group which may be substituted with one or a plurality of substituents, or a carbamoyl group which may be substituted with one or two substituents;

$R^{16a}$ represents a lower alkyl group; $R^{16b}$ and $R^{16c}$ each independently represent a hydrogen atom, a halogen atom or a lower alkoxy group;

$R^{17}$ represents a halogen atom, a lower alkoxy group or an amino group which may be substituted with one or two substituents;

$R^{18a}$ and $R^{18b}$ each independently represent a lower alkyl group;

$R^{19a}$ and $R^{19b}$ each independently represent a halogen atom, or $R^{19a}$ and $R^{19b}$, together with the carbon atoms on the pyrrolidine ring to which they are bound, form a C3 to C6 cycloalkyl ring; $R^{20a}$ represents a hydrogen atom, a halogen atom, a lower alkyl group or a lower alkoxy group; $A^{5a}$ represents a nitrogen atom or C—$R^{20b}$ (wherein $R^{20b}$ represents a hydrogen atom, a halogen atom, a lower alkyl group or a lower alkoxy group); $A^{5b}$ represents a nitrogen atom or C—$R^{20c}$ (wherein $R^{20c}$ represents a hydrogen atom, a halogen atom, a lower alkyl group or a lower alkoxy group); $A^{5c}$ represents a nitrogen atom or C—$R^{20d}$ (wherein $R^{20d}$ represents a hydrogen atom, a halogen atom, a lower alkyl group or a lower alkoxy group);

$R^{21}$ represents a hydrogen atom, or one or a plurality of lower alkyl groups; $A^6$ represents an oxygen atom, a sulfur atom or $S(O)_2$;

$R^{22a}$ represents a hydrogen atom, or one or a plurality of lower alkyl groups; $A^{7a}$ and $A^{7c}$ are directly bound to represent an oxygen atom or $CH_2$; $A^{7b}$ represents 1) an oxygen atom, a sulfur atom or $S(O)_2$ when $A^{7a}$ and $A^{7c}$ together form $CH_2$, 2) represents $CH_2$ when $A^{7a}$ and $A^{7c}$ together form a direct bond, or 3) represents $C(—R^{22b})—R^{22c}$ (wherein $R^{22b}$ and $R^{22c}$ each independently represent a hydrogen atom or a lower alkyl group);

$R^{23}$ represents a hydrogen atom, or one or a plurality of lower alkyl groups; $A^8$ represents an oxygen atom, a sulfur atom, $S(O)_2$ or $CF_2$;

$R^{24a}$ represents a hydrogen atom, or one or a plurality of lower alkyl groups; $R^{24b}$ represents a lower alkyl group;

$R^{25a}$ represents a hydrogen atom, or one or a plurality of lower alkyl groups; $R^{25b}$ represents a hydrogen atom, a halogen atom, a lower alkyl group, a lower alkoxymethyl group which may be substituted with one or a plurality of substituents, a lower alkoxyethyl group which may be substituted with one or a plurality of substituents, a lower alkoxy group which may be substituted with one or a plurality of substituents, a phenoxy group which may be substituted with one or a plurality of substituents, a carbamoyl group which may be substituted with one or two substituents, a lower alkylsulfonyl group which may be substituted with one or a plurality of substituents, an amino group which may be substituted with one or two substituents, or a morpholin-4-yl group which may be substituted with one or a plurality of substituents;

$R^{26}$ represents a hydrogen atom, or one or a plurality of lower alkyl groups; $A^9$ represents an oxygen atom or $S(O)_2$;

$R^{27a}$ represents a hydrogen atom, or one or a plurality of lower alkyl groups; $R^{27b}$ represents a hydrogen atom, a lower alkyl group, a fluoro-lower alkyl group, a lower cycloalkylmethyl group, a lower alkoxyethyl group which may be substituted with one or a plurality of substituents, or a benzyl group which may be substituted with one or a plurality of substituents;

$R^{28a}$ represents a hydrogen atom, or one or a plurality of lower alkyl groups; $R^{28b}$ represents a lower cycloalkyl group which may be substituted with one or a plurality of substituents, or a pyridyl group which may be substituted with one or a plurality of substituents;

$R^{29a}$ represents a hydrogen atom, or one or a plurality of lower alkyl groups; $A^{10}$ represents $C(O)$ or $S(O)_2$; $R^{29b}$ represents a lower alkyl group, a benzyl group which may be substituted with one or a plurality of substituents, or an amino group which may be substituted with one or two substituents;

$R^{30a}$ represents a hydrogen atom, or one or a plurality of lower alkyl groups; $R^{30b}$ represents a hydrogen atom, a lower alkyl group, or a benzyl group which may be substituted with one or a plurality of substituents; $R^{31a}$ represents a hydrogen atom, or one or a plurality of lower alkyl groups; $A^{11}$ represents an oxygen atom, $CH—R^{31b}$ (wherein $R^{31b}$ represents a hydrogen atom or a lower alkyl group), or $N—R^{31c}$ (wherein $R^{31c}$ represents a hydrogen atom, a lower alkyl group which may be substituted with one or a plurality of substituents, a lower cycloalkyl group which may be substituted with one or a plurality of substituents, or a lower alkylsulfonyl group which may be substituted with one or a plurality of substituents); and $A_{12}$ represents an oxygen atom or $N—R^{32}$ (wherein $R^{32}$ represents a hydrogen atom, a lower alkyl group or a lower cycloalkyl group).

Hereinafter, $R^{9a}$ to $R^{31a}$ and $A^{5a}$ to $A^{12}$ in the above formula will be described.

$R^{9a}$ and $R^{9b}$ are each preferably a hydrogen atom, a fluorine atom, a methyl group, an ethyl group, a n-propyl group or an isopropyl group.

$R^{10a}$ is preferably a hydrogen atom, a methyl group, an ethyl group or a n-propyl group.

$R^{10b}$ is preferably a methyl group, a methyl group, a n-propyl group or an isopropyl group.

$R^{11}$ represents a substituted lower alkyl group, and examples of substituents for the lower alkyl group include a C1 to C6 alkoxy group, a halogen atom, an amino group which may be substituted with one or two substituents, a morpholin-4-yl group which may be substituted with one or a plurality of substituents, a piperidin-1-yl group which may be substituted with one or a plurality of substituents, and the like. Specifically, a methoxymethyl group, an ethoxymethyl group, a n-propoxymethyl group, a fluoromethyl group, a 2-methoxyethyl group, a 2-ethoxyethyl group, a 2-(n-propoxy)ethyl group, a dimethylaminomethyl group, a morpholin-4-ylmethyl group, a 2,5-dimethylmorpholin-4-ylmethyl group, a piperidin-1-ylmethyl group and the like are preferred.

$R^{12a}$ is preferably a hydrogen atom, a methyl group or an ethyl group.

As for $R^{12b}$ and $R^{12c}$, it is preferable that $R^{12b}$ and $R^{12c}$ together represent a methyl group, an ethyl group or a cyclopropyl group, and that $R^{12b}$ and the nitrogen atom on which $R^{12b}$ is substituted, together form an azetidinyl group, a 3-methoxyazetidinyl group, a piperidinyl group, a morpholinyl group or a 2,6-dimethylmorpholinyl group.

For $R^{13a}$ and $R^{13b}$, the lower alkoxymethyl group means a methyl group substituted with the above-mentioned lower alkoxy group, and examples thereof include a methoxymethyl group, an ethoxymethyl group, a n-propoxymethyl group, an isopropoxymethyl group, a n-butoxymethyl group, an isobutyloxy methyl group, a tert-butoxymethyl group, a n-pentyloxy methyl group, a n-hexyloxy methyl group and the like. It is preferable that $R^{13a}$ and $R^{13b}$ are each independently a hydrogen atom, a methyl group, an ethyl group, a methoxymethyl group, an ethoxymethyl group, or a n-propoxymethyl group.

$R^{14a}$ and $R^{14b}$ are each preferably a methyl group, an ethyl group, a methoxymethyl group, or an ethoxymethyl group.

$R^{15}$ is preferably a hydrogen atom, a C1 to C6 alkyl group, or a carbamoyl group which may be substituted with one or two substituents; and more preferably a hydrogen atom, a methyl group, an ethyl group or a dimethylcarbamoyl group.

$R^{16a}$ is preferably a methyl group, an ethyl group, or a n-propyl group.

$R^{16b}$ is preferably a hydrogen atom or a C1 to C6 alkoxy group, and more preferably a hydrogen atom, a methoxy group, or an ethoxy group. $R^{16c}$ is preferably a hydrogen atom, a halogen atom, or a C1 to C6 alkoxy group, and more preferably a hydrogen atom, a fluorine atom, a methoxy group or an ethoxy group.

$R^{17}$ is preferably a halogen atom, a C1 to C6 alkoxy group, or an amino group which may be substituted with one or two substituents; and more preferably a fluorine atom, a methoxy group, an ethoxy group, an acetylamino group or the like.

$R^{18a}$ and $R^{18b}$ are each preferably a C1 to C6 alkyl group, and more preferably a methyl group, an ethyl group or a n-propyl group.

$R^{19a}$ and $R^{19b}$ are preferably both fluorine atoms, or preferably form a cyclopropane ring together with a carbon atom of the pyrrolidine ring on which $R^{19a}$ and $R^{19b}$ are substituted.

$R^{20a}$ is preferably a hydrogen atom, a halogen atom, a C1 to C6 alkyl group, or a C1 to C6 alkoxy group, and more preferably a hydrogen atom or a methyl group.

$A^{5a}$ represents a nitrogen atom or $C—R^{20b}$, and when $A^{5a}$ is $C—R^{20b}$, this $R^{20b}$ is preferably a hydrogen atom, a halogen atom, a C1- to 6 alkyl group or a C1 to C6 alkoxy group, and more preferably a hydrogen atom or a methyl group.

$A^{5b}$ represents a nitrogen atom or C—$R^{20c}$, and when $A^{5b}$ is C—$R^{20c}$, this $R^{20c}$ is preferably a hydrogen atom, a halogen atom, a C1 to C6 alkyl group, or a C1 to C6 alkoxy group, and more preferably a hydrogen atom or a methyl group.

$A^{5c}$ represents a nitrogen atom or C—$R^{20d}$, and when $A^{5c}$ is C—$R^{20d}$, this $R^{20d}$ is preferably a hydrogen atom, a halogen atom, a C1 to C6 alkyl group or a C1 to C6 alkoxy group, and more preferably a hydrogen atom or a methyl group.

$R^{21}$ is preferably a hydrogen atom or a C1 to C6 alkyl group, and more preferably a hydrogen atom.

$A^6$ is preferably an oxygen atom or $S(O)_2$.

$R^{22a}$ is preferably a hydrogen atom or a C1 to C6 alkyl group, and more preferably a hydrogen atom or a methyl group.

$A^{7a}$ and $A^{7c}$ are preferably together $CH_2$ or an oxygen atom. $A^{7b}$ is preferably 1) an oxygen atom when $A^{7a}$ and $A^{7c}$ together form $CH_2$, and 3) when $A^{7a}$ and $A^{7c}$ are together an oxygen atom, it is preferable that both $R^{22b}$ and $R^{22c}$ are hydrogen atoms or methyl groups.

$R^{23}$ is preferably a hydrogen atom, or one or two C1 to C6 alkyl groups; and more preferably a hydrogen atom, a methyl group or a dimethyl group.

$A^8$ is preferably an oxygen atom or $S(O)_2$.

$R^{24a}$ is preferably a hydrogen atom or a C1 to C6 alkyl group, and more preferably a hydrogen atom.

$R^{24b}$ is preferably a methyl group or an ethyl group.

$R^{25a}$ is preferably a hydrogen atom or a C1 to C6 alkyl group, and more preferably a hydrogen atom.

For $R^{25b}$, the lower alkoxymethyl group which may be substituted with one or a plurality of substituents means the above-mentioned unsubstituted lower alkoxymethyl group, or a lower alkyloxymethyl group substituted on the lower alkoxy group with one or a plurality of substituents, and substituents for the lower alkoxymethyl group include a halogen atom, a methoxy group, an ethoxy group and the like. The lower alkoxyethyl group which may be substituted with one or a plurality of substituents means an ethyl group substituted with the above-mentioned lower alkoxy group, and examples thereof include a 2-methoxyethyl group, a 2-ethoxyethyl group, a 2-(n-propoxy)ethyl group, a 2-isopoproxyethyl group, a 2-(n-butoxy)ethyl group, a 2-isobutyloxyethyl group, a 2-(tert-butoxy)ethyl group, a 2-(n-pentyloxy)ethyl group, a 2-(n-hexyloxy)ethyl group and the like. Substituents for the lower alkoxyethyl group include a halogen atom, a methoxy group, an ethoxy group and the like. The phenoxy group which may be substituted with one or a plurality of substituents means an unsubstituted phenoxy group, or a phenyloxy group which may be substituted with one or a plurality of substituents on the benzene ring. Substituents for the phenoxy group include a halogen atom, a methyl group, an ethyl group, a n-propyl group, an isopropyl group, a methoxy group, an ethoxy group, a n-propoxy group, an isopropoxy group, a methylthio group, an ethylthio group, a n-propylthio group, an isopropylthio group, a methanesulfonyl group, an ethanesulfonyl group, a n-propylsulfonyl group, an isopropylsulfonyl group, a nitro group, an acetyl group, a propionyl group, a cyano group, a carboxyl group, a methoxycarbonyl group, an ethoxycarbonyl group, a n-propoxycarbonyl group, an isopropoxycarbonyl group, a dimethylcarbamoyl group, a phenyl group and the like. $R^{25b}$ is preferably a hydrogen atom, a halogen atom, a C1 to C6 alkyl group, a C1 to C6 alkoxymethyl group, a C1 to C6 alkoxyethyl group, a C1 to C6 alkoxy group, an unsubstituted phenoxy group, a dimethylcarbamoyl group, a C1 to C6 alkylsulfonyl group, a di (lower alkyl)amino group, or a morpholin-4-yl group; and more preferably a hydrogen atom, a methyl group, an ethyl group, a methoxymethyl group, an ethoxymethyl group, a 2-methoxyethyl group, a 2-ethoxyethyl group, a methoxy group, an ethoxy group, a dimethylamino group, an unsubstituted phenoxy group, a dimethylcarbamoyl group, a morpholin-4-yl group, a 2,6-dimethylmorpholin-4-yl group or the like.

$R^{26}$ is preferably a hydrogen atom or alkyl group, and more preferably a hydrogen atom.

$A^9$ is preferably an oxygen atom.

$R^{27a}$ is preferably a hydrogen atom, or one or two C1 to C6 alkyl groups; and more preferably a hydrogen atom, a methyl group or a dimethyl group.

For $R^{27b}$, the fluoro-lower alkyl group means a lower alkyl group substituted with one or a plurality of fluorine atoms on the above-mentioned lower alkyl group, and specific examples thereof include a fluoromethyl group, a difluoromethyl group, a trifluoromethyl group, a 2-fluoroethyl group, a 2,2-difluoroethyl group, a 2,2,2-trifluoroethyl group, a 2-fluoropropyl group, a 2,2-difluoropropyl group, a 2,2,2-trifluoropropyl group, a 2-fluorobutyl group, a 2,2-difluorobutyl group, a 2,2,2-trifluorobutyl group, a 2-fluoroheptyl group, a 2,2-difluoroheptyl group, a 2,2,2-trifluoroheptyl group and the like. $R^{27b}$ is preferably a hydrogen atom, a lower alkyl group, a fluoro-lower alkyl group, a lower cycloalkylmethyl group, a lower alkoxyethyl group or the like; and more preferably a hydrogen atom, a methyl group, an ethyl group, a n-propyl group, an isopropyl group, a t-butyl group, a 2-fluoroethyl group, a 2,2-difluoroethyl group, a 2,2,2-trifluoroethyl group, a cyclopropylmethyl group, a methoxymethyl group, an ethoxymethyl group, a n-propoxymethyl group, a methoxyethyl group, an ethoxyethyl group, an unsubstituted benzyl group or the like.

$R^{28a}$ is preferably a hydrogen atom, or one or two C1 to C6 alkyl groups; and more preferably a hydrogen atom, a methyl group or a dimethyl group.

$R^{28b}$ is preferably a C3 to C6 cycloalkyl group, a 2-pyridyl group, or a 4-pyridyl group; and more preferably a cyclopropyl group, a (1-methyl)cyclopropan-1-yl group, a cyclobutyl group, a cyclopentyl group, a 2-pyridyl group or a 4-pyridyl group.

$R^{29a}$ is preferably a hydrogen atom, or one or two C1 to C6 alkyl groups; and more preferably a hydrogen atom, a methyl group or a dimethyl group.

$A^{10}$ is preferably $C(O)$ or $S(O)_2$.

$R^{29b}$ is preferably a methyl group, an ethyl group or an unsubstituted benzyl group when $A^{10}$ is $C(O)$, and is preferably a methyl group, an ethyl group or a dimethylamino group when $A^{10}$ is $S(O)_2$.

$R^{30a}$ is preferably a hydrogen atom, or one or two C1 to C6 alkyl groups; and more preferably a hydrogen atom, a methyl group or a dimethyl group.

$R^{30b}$ is preferably a hydrogen atom, a C1 to C6 alkyl group, or a benzyl group which may be substituted with one or a plurality of substituents; and more preferably a methyl group, an ethyl group or an unsubstituted benzyl group.

$R^{31a}$ is preferably a hydrogen atom or a C1 to C6 alkyl group, and more preferably a hydrogen atom.

$A^{11}$ is preferably an oxygen atom or N—$R^{31c}$. $R^{31c}$ is preferably a C1 to C6 alkyl group, a C1 to C6 cycloalkyl group or a C1 to C6 alkylsulfonyl group; and more preferably a methyl group, an ethyl group, a cyclopropyl group or a methanesulfonyl group.

When $A^{12}$ is an N—$R^{30}$ group, $R^{30}$ is preferably a C1 to C6 alkyl group or a C1-C6 cycloalkyl group; and more preferably a methyl group, an ethyl group or a cyclopropyl group.

Q in the formula (I) is preferably the group of formula (iv-a), (iv-b), (iv-c), (iv-d), (iv-h), (iv-i), (iv-j), (iv-n), (iv-o), (iv-p), (iv-q), (vi-s), (vi-t) or (vi-u); more preferably the group of formula (iv-b), (iv-h), (iv-j), (iv-o), (iv-q), (iv-s) or (iv-t); and even more preferably the group represented by formula (iv-j), (iv-o) or (iv-s).

Specific examples of the above formulas (iv-a) to (iv-x) include the following formulas (iv-1) to (iv-174) (here, symbol "→" in the following formulas means the position of attachment).

Preferred specific examples of formula (iv-a) include groups of the following formulas (iv-1) to (iv-8):

[Formula 6]

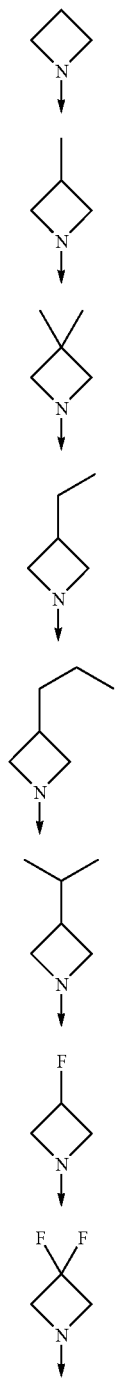

and the like, and preferred specific examples of formula (iv-b) include groups of the following formulas (iv-9) to (iv-15):

[Formula 7]

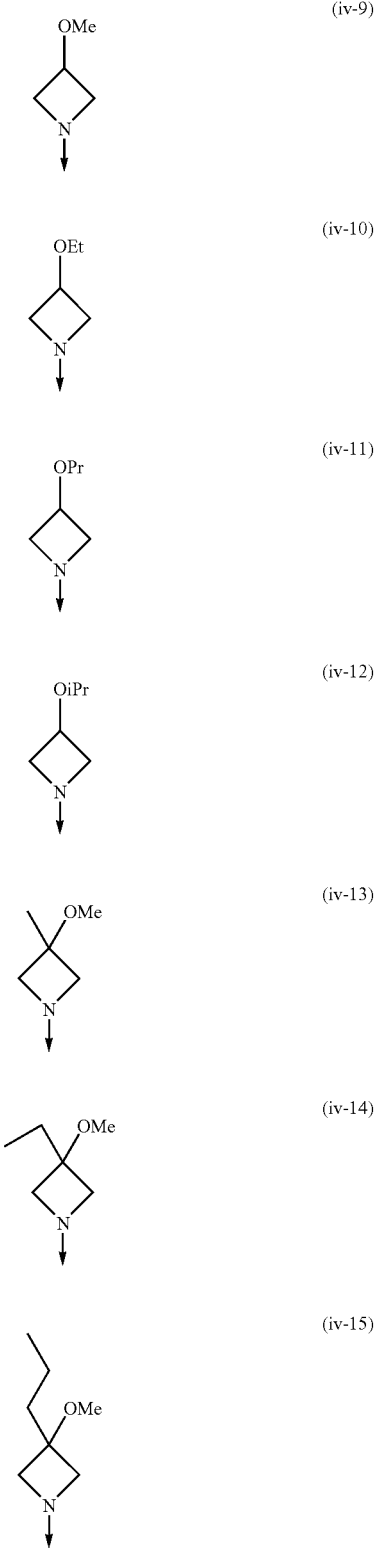

and the like.

Preferred specific examples of formula (iv-c) include groups of the following formulas (iv-16) to (iv-22):

[Formula 8]
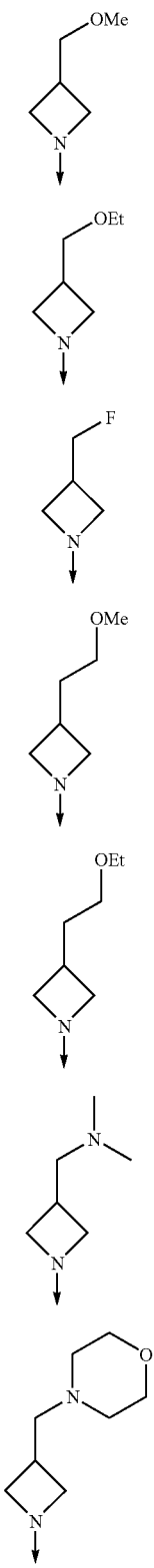
[Formula 9]
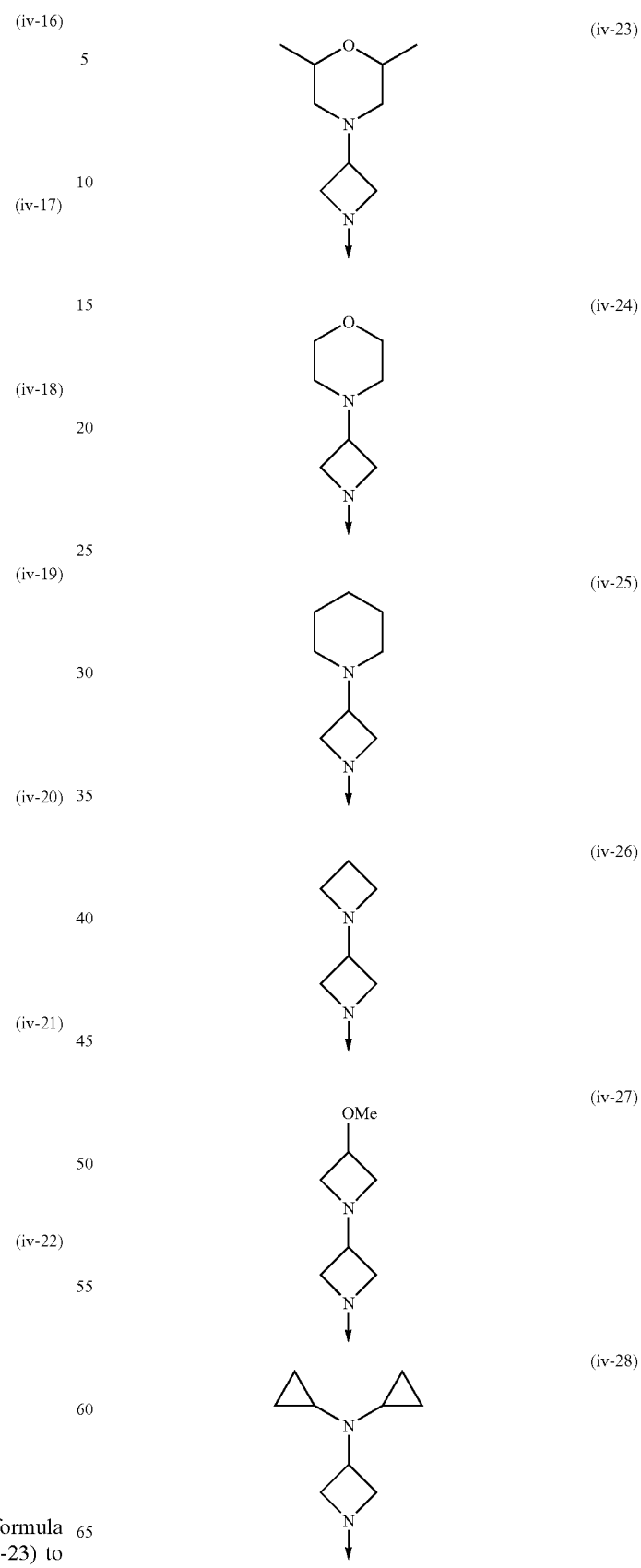
and the like, and preferred specific examples of formula (iv-d) include groups of the following formulas (iv-23) to (iv-30):

-continued (iv-29)

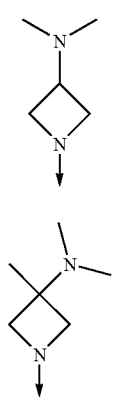

(iv-30)

and the like.

Preferred specific examples of formula (iv-e) include groups of the following formulas (iv-31) to (iv-40):

[Formula 10]

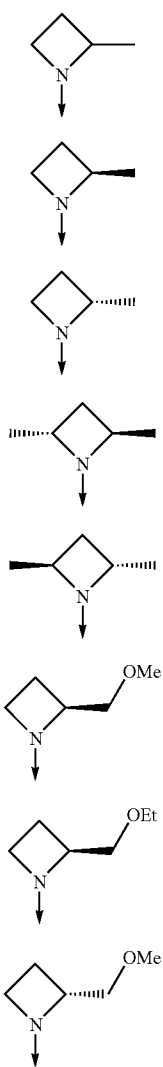

(iv-31)
(iv-32)
(iv-33)
(iv-34)
(iv-35)
(iv-36)
(iv-37)
(iv-38)

-continued (iv-39)

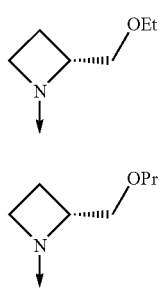

(iv-40)

and the like, and preferred specific examples of formula (iv-f) include groups of the following formulas (iv-41) to (iv-45):

[Formula 11]

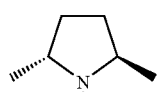

(iv-41)

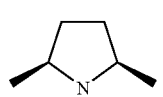

(iv-42)

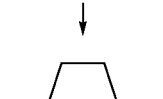

(iv-43)

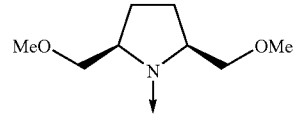

(iv-44)

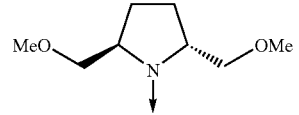

(iv-45)

and the like.

Preferred specific examples of formula (iv-g) include groups of the following formulas (iv-46) to (iv-51):

[Formula 12]

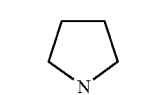

(iv-46)

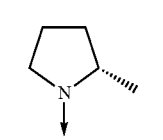

(iv-47)

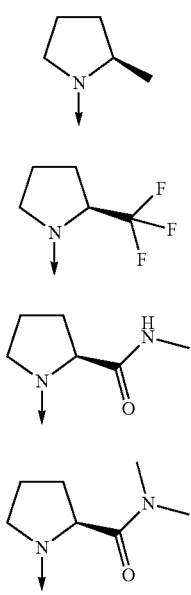
and the like, and preferred specific examples of formula (iv-h) include groups of the following formulas (iv-52) to (iv-64):
[Formula 13]
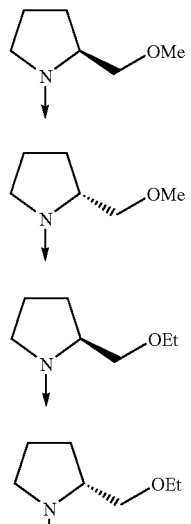
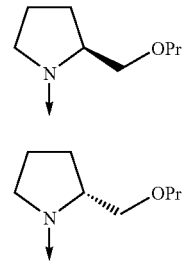
and the like.
Preferred specific examples of formula (iv-i) include groups of the following formulas (iv-65) to (iv-72):
[Formula 14]

-continued
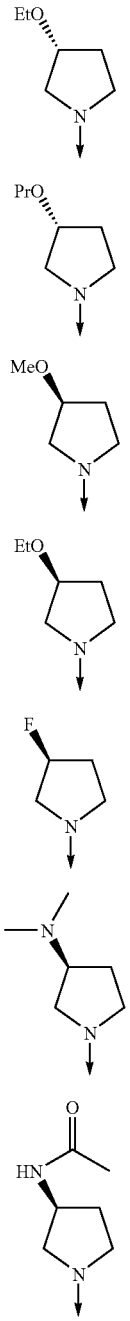
(iv-66)
(iv-67)
(iv-68)
(iv-69)
(iv-70)
(iv-71)
(iv-72)
and the like, and preferred specific examples of formula (iv-j) include groups of the following formulas (iv-73) to (iv-80):
[Formula 15]
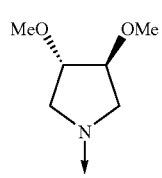
(iv-73)
-continued
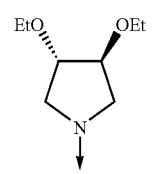 (iv-74)
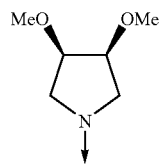 (iv-75)
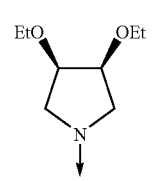 (iv-76)
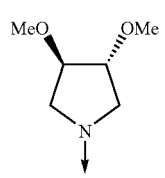 (iv-77)
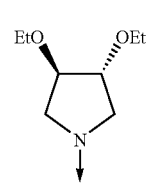 (iv-78)
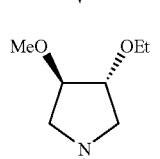 (iv-79)
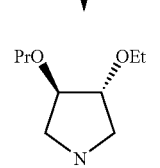 (iv-80)
and the like.
Preferred specific examples of formula (iv-k) include groups of the following formulas (iv-81) to (iv-82):
[Formula 16]
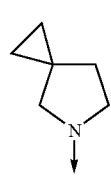 (iv-81)

(iv-82)

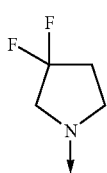

and the like, and specific examples of formula (iv-1) include groups of the following formulas (iv-83) to (iv-86):

[Formula 17]

(iv-83)

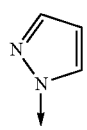

(iv-84)

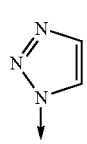

(iv-85)

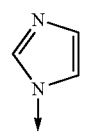

(iv-86)

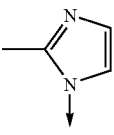

and the like.

Preferred specific examples of formula (iv-m) include groups of the following formulas (iv-87) to (iv-89):

[Formula 18]

(iv-87)

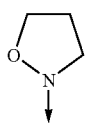

(iv-88)

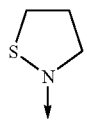

(iv-89)

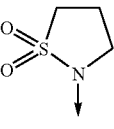

and the like, and specific examples of formula (iv-n) include groups of the following formulas (iv-90) to (iv-96):

[Formula 19]

(iv-90)

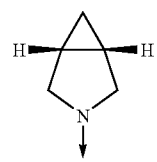

(iv-91)

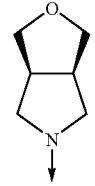

(iv-92)

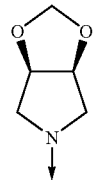

(iv-93)

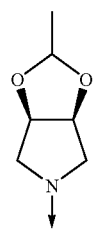

(iv-94)

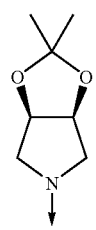

(iv-95)

(iv-96)

and the like.

Preferred specific examples of formula (iv-o) include groups of the following formulas (iv-97) to (iv-103):

[Formula 20]
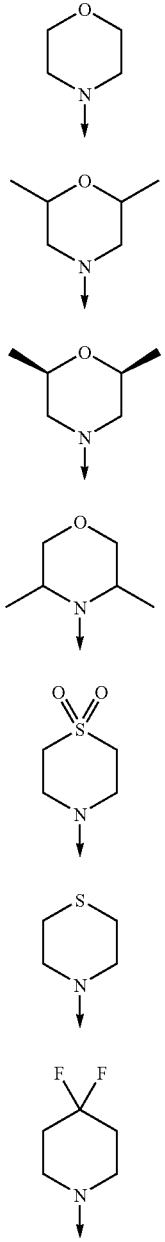
(iv-97)
(iv-98)
(iv-99)
(iv-100)
(iv-101)
(iv-102)
(iv-103)
and the like, and preferred specific examples of formula (iv-p) include groups of the following formulas (iv-104) to (iv-107):
[Formula 21]
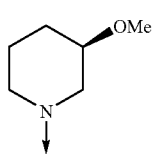
(iv-104)
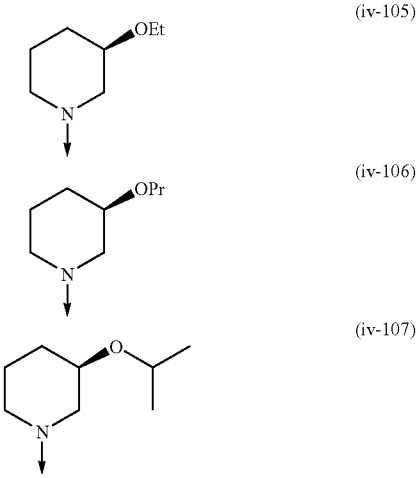
(iv-105)
(iv-106)
(iv-107)
and the like.
Preferred specific examples of formula (iv-q) include groups of the following formulas (iv-108) to (iv-126):
[Formula 22]
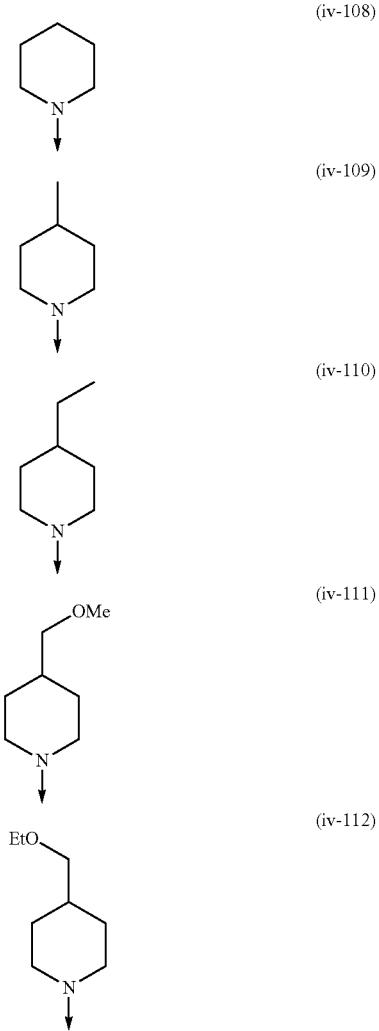
(iv-108)
(iv-109)
(iv-110)
(iv-111)
(iv-112)

(iv-113)
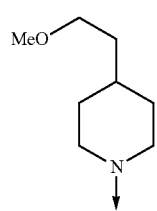
(iv-114)
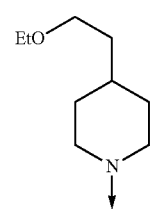
(iv-115)
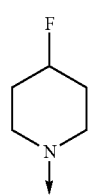
(iv-116)
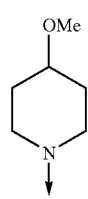
(iv-117)
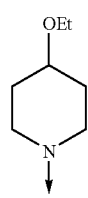
(iv-118)
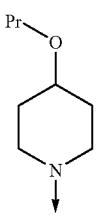
(iv-119)
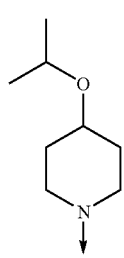
(iv-120)
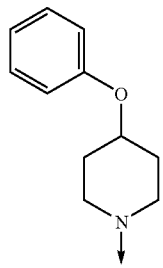
(iv-121)
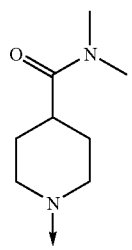
(iv-122)
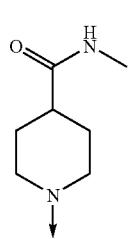
(iv-123)
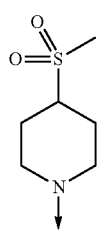
(iv-124)
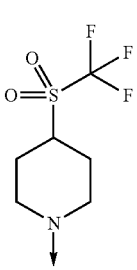
(iv-125)
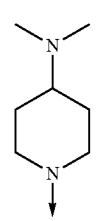

(iv-126)
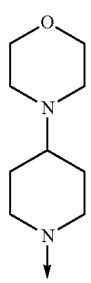
and the like, and preferred specific examples of formula (iv-r) include groups of the following formulas (iv-127) to (iv-128):
[Formula 23]
(iv-127)
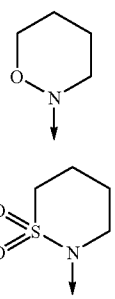
(iv-128)
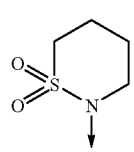
and the like.
Preferred specific examples of formula (iv-s) include groups of the following formulas (iv-129) to (iv-149):
[Formula 24]
(iv-129)
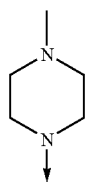
(iv-130)
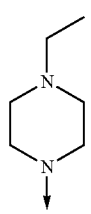
(iv-131)
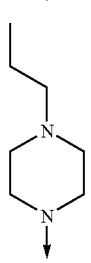
(iv-132)
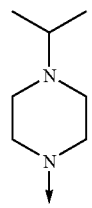
(iv-133)
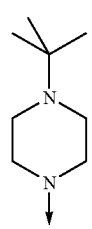
(iv-134)
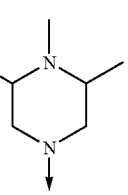
(iv-135)
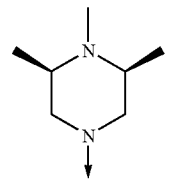
(iv-136)
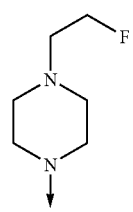
(iv-137)
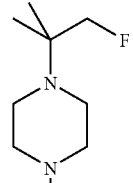
(iv-138)
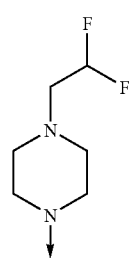

(iv-139)
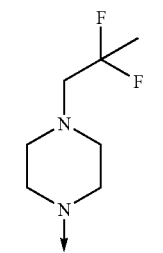
(iv-140)
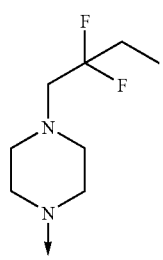
(iv-141)
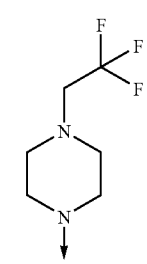
(iv-142)
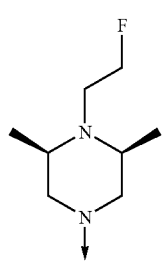
(iv-143)
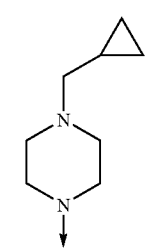
(iv-144)
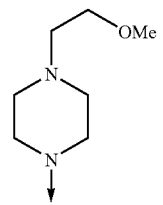
(iv-145)
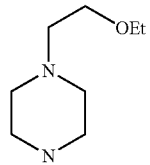
(iv-146)
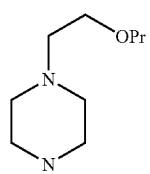
(iv-147)
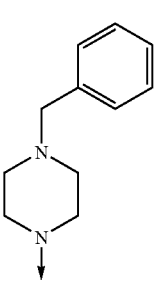
(iv-148)
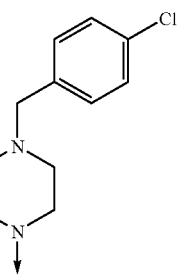
(iv-149)
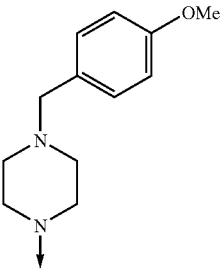
and the like, and preferred specific examples of formula (iv-t) include groups of the following formulas (iv-150) to (iv-156):
[Formula 25]
(iv-150)
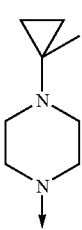

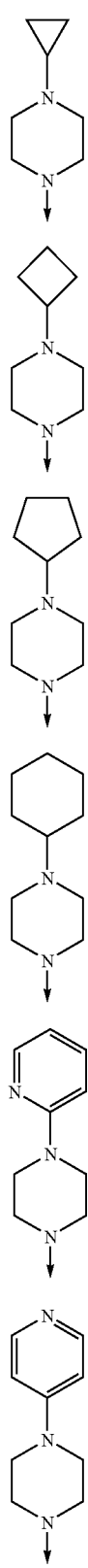
and the like.
Preferred specific examples of formula (iv-u) include groups of the following formulas (iv-157) to (iv-164):
[Formula 26]

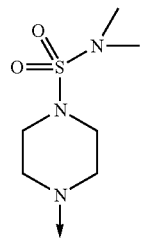
(iv-164)

and the like, and preferred specific examples of formula (iv-v) include groups of the following formulas (iv-165) to (iv-167):

[Formula 27]

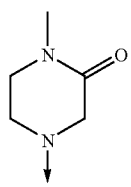
(iv-165)

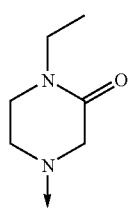
(iv-166)

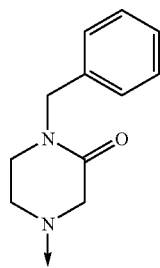
(iv-167)

and the like.

Preferred specific examples of formula (iv-w) include groups of the following formulas (iv-168) to (iv-171):

[Formula 28]

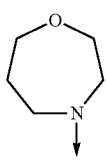
(iv-168)

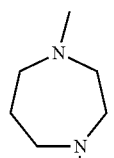
(iv-169)

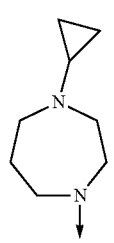
(iv-170)

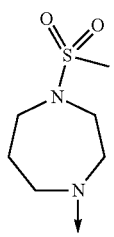
(iv-171)

and the like, and preferred specific examples of formula (iv-x) include groups of the following formulas (iv-172) to (iv-174):

[Formula 29]

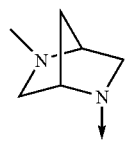
(iv-172)

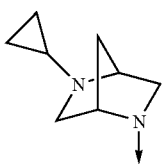
(iv-173)

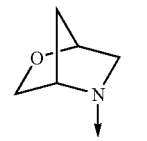
(iv-174)

and the like.

Furthermore, Q in the formula (I) is even more preferably one of the following (1), (2) and (3):

(1) Q is a group represented by the following formula:

[Formula 30]

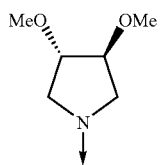
(iv-73)

-continued

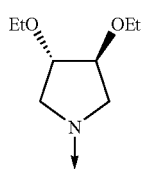 (iv-74)

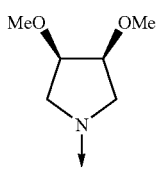 (iv-75)

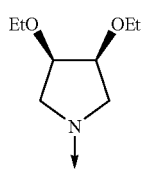 (iv-76)

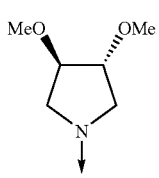 (iv-77)

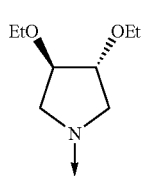 (iv-78)

wherein the formula is formula (iv-j), and both $R^{18a}$ and $R^{18b}$ in the formula (iv-j) are methyl groups or ethyl groups;

(2) Q is a group represented by the following formula:

[Formula 31]

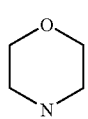 (iv-97)

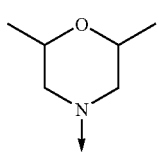 (iv-98)

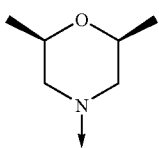 (iv-99)

-continued

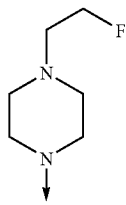 (iv-100)

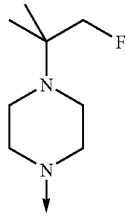 (iv-101)

wherein the formula is formula (iv-o), and $R^{23}$ in the formula (iv-o) is a hydrogen atom, a methyl group or a dimethyl group, and $A^8$ is an oxygen atom or $S(O)_2$; and (3) Q is a group represented by the following formula:

[Formula 32]

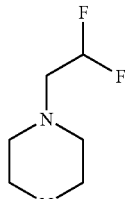 (iv-136)

(iv-137)

(iv-138)

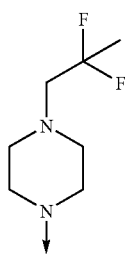 (iv-139)

-continued (iv-140)

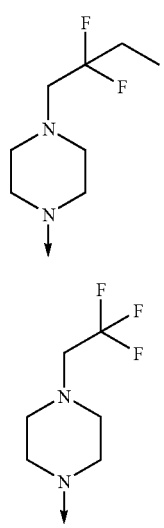

(iv-141)

wherein the formula is formula (iv-s), and $R^{27a}$ in the formula (iv-s) is a hydrogen atom, and $R^{27b}$ is a fluoro-lower alkyl group.

Among the compounds represented by the formula (I), compounds having a configuration represented by the following formula (I-a):

[Formula 33]

(I-a)

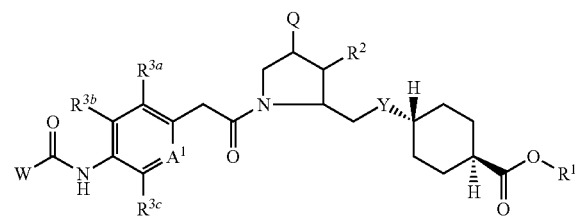

wherein $R^1$, $R^2$, Q, Y, $R^{3a}$, $R^{3b}$, $R^{3c}$, $A^1$ and W represent the same as described above, are preferred, and compounds having a configuration represented by the following formula (I-b):

[Formula 34]

(I-b)

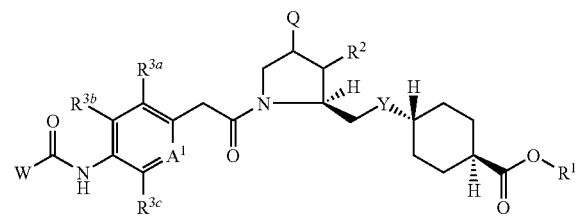

wherein $R^1$, $R^2$, Q, Y, $R^{3a}$, $R^{3b}$, $R^{3c}$, $A^1$ and W represent the same as described above, are more preferred.

Furthermore, compounds having a configuration represented by the following formula (I-c):

[Formula 35]

(I-c)

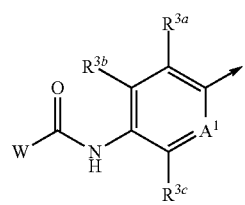

wherein $R^1$, $R^2$, Q, Y, $R^{3a}$, $R^{3b}$, $R^{3c}$, $A^1$ and W represent the same as described above, are even more preferred.

Moreover, in the formula (I), a group represented by the following formula (v):

[Formula 36]

(v)

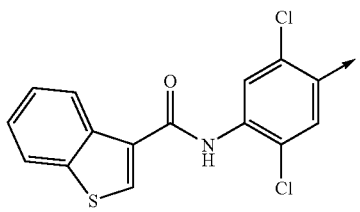

wherein symbol "→", $R^{3a}$, $R^{3b}$, $R^{3c}$, $A^1$ and W represent the same as described above, is preferably a group represented by one of the following formulas (v-1) to (v-110):

[Formula 37]

(v-1)

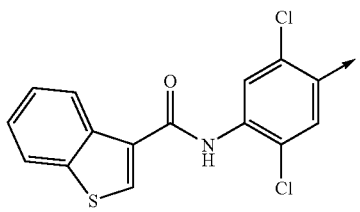

(v-2)

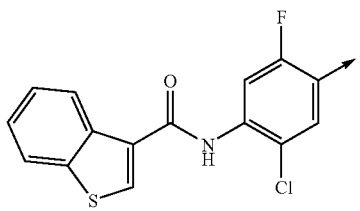

(v-3)

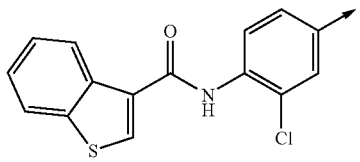

-continued
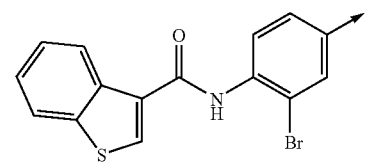 (v-4)
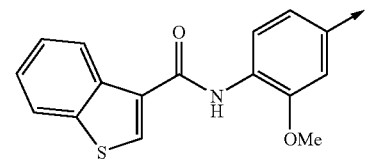 (v-5)
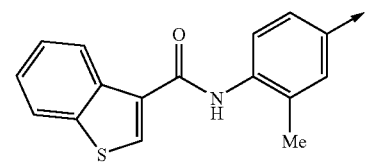 (v-6)
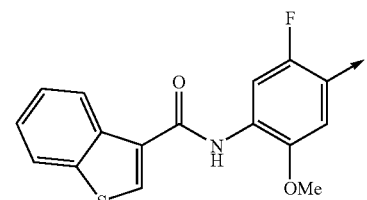 (v-7)
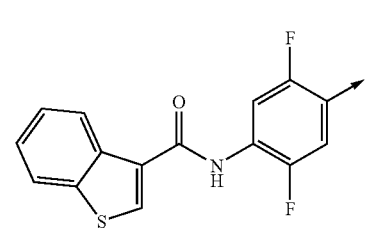 (v-8)
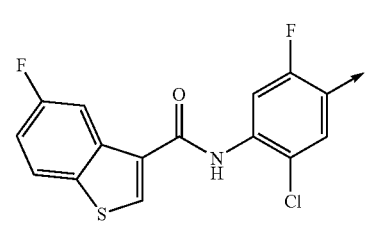 (v-9)
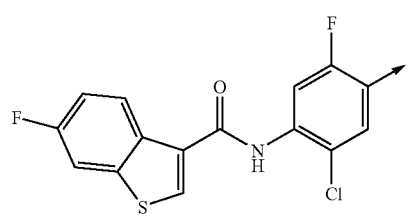 (v-10)
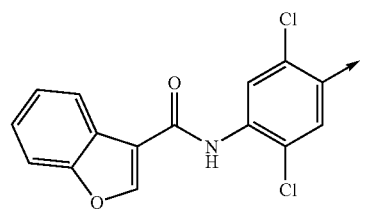 (v-11)
-continued
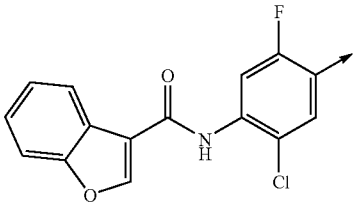 (v-12)
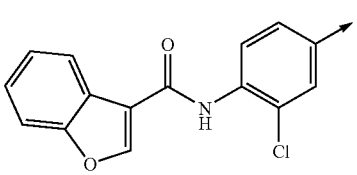 (v-13)
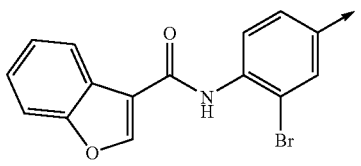 (v-14)
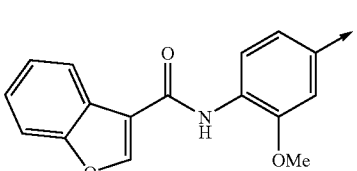 (v-15)
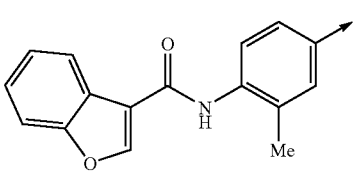 (v-16)
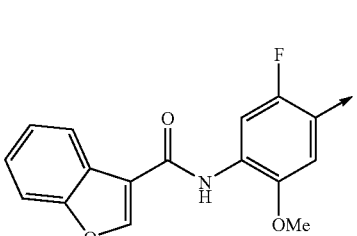 (v-17)
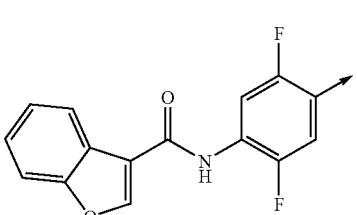 (v-18)
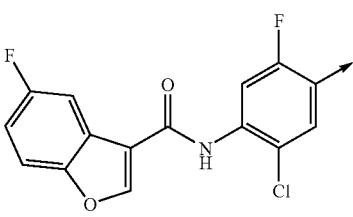 (v-19)

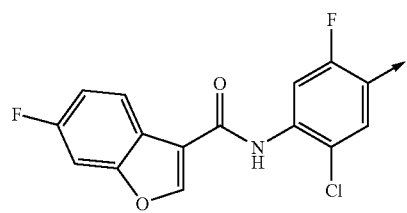
(v-20)
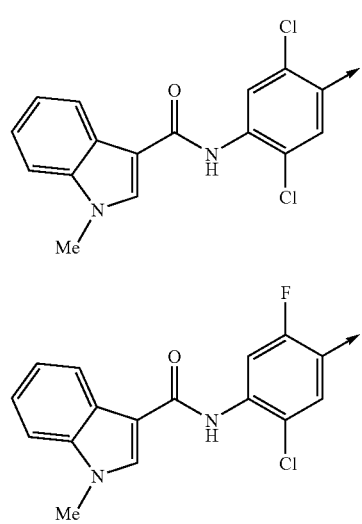
(v-21)
(v-22)
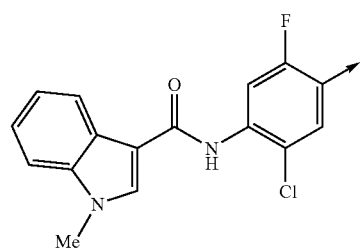
(v-23)
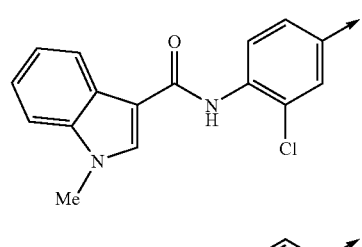
(v-24)
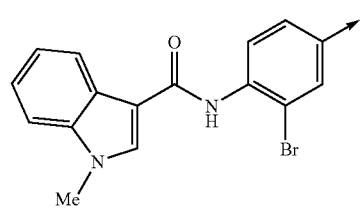
(v-25)
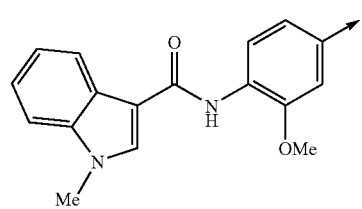
(v-26)
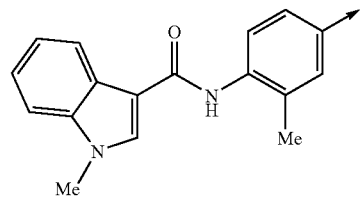
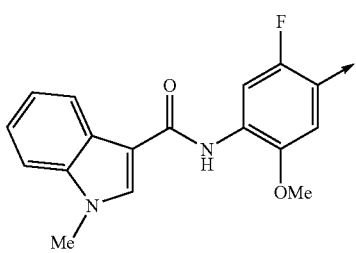
(v-27)
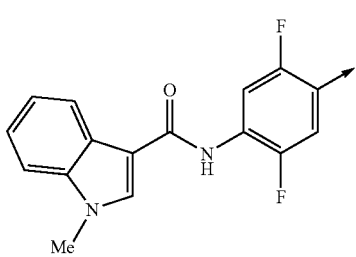
(v-28)
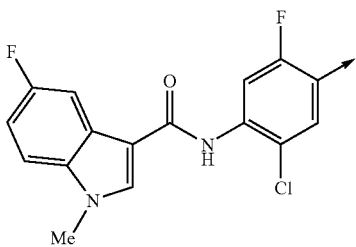
(v-29)
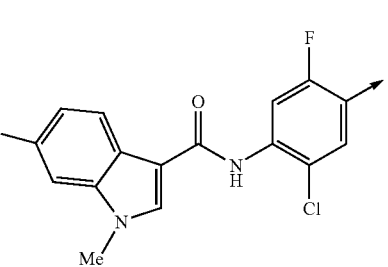
(v-30)
[Formula 38]
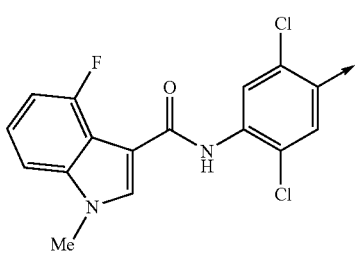
(v-31)
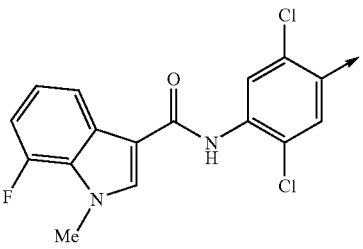
(v-32)

-continued (v-33), (v-34), (v-35), (v-36), (v-37), (v-38), (v-39), (v-40), (v-41), (v-42), (v-43), (v-44), (v-45)

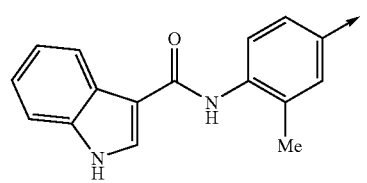 (v-46)
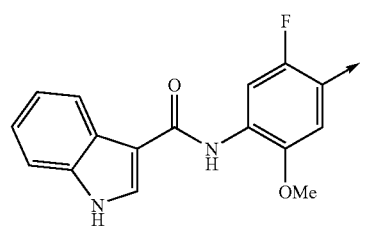 (v-47)
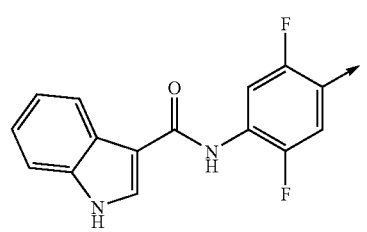 (v-48)
 (v-49)
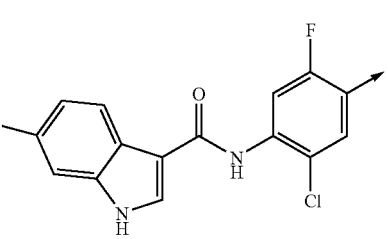 (v-50)
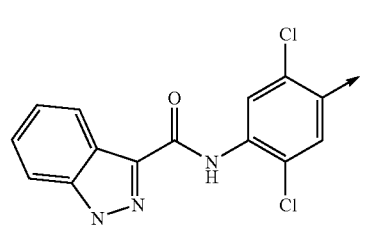 (v-51)
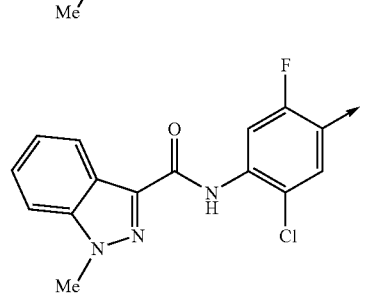 (v-52)
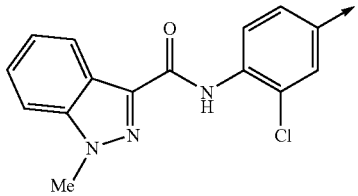 (v-53)
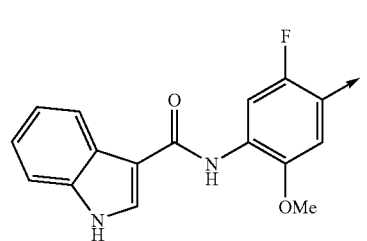 (v-54)
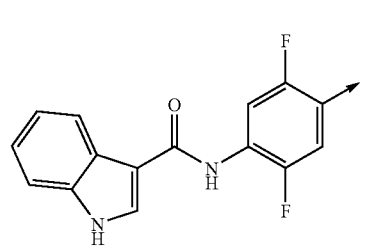 (v-55)
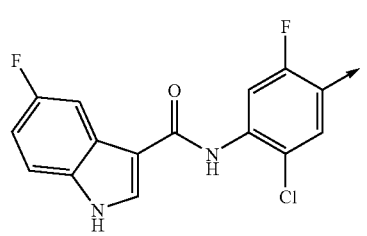 (v-56)
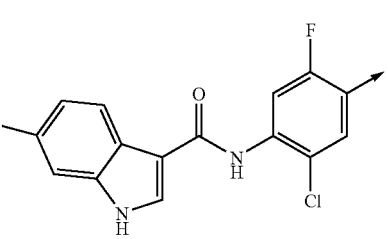 (v-57)
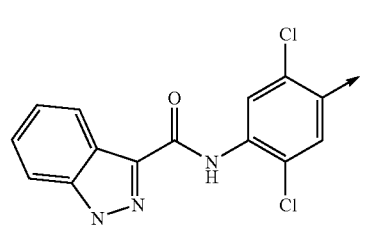 (v-58)
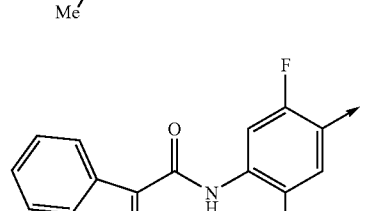 (v-59)

-continued (v-60) (v-68)
(v-61) (v-69)
(v-62) (v-70)

[Formula 39]

(v-63) (v-71)
(v-64) (v-72)
(v-65) (v-73)
(v-66) (v-74)
(v-67)

(v-75) 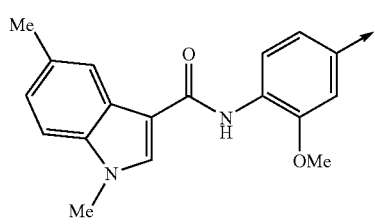
(v-76) 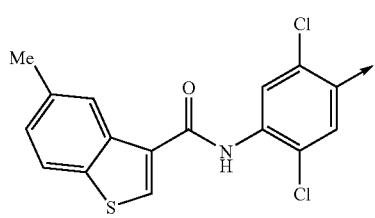
(v-77) 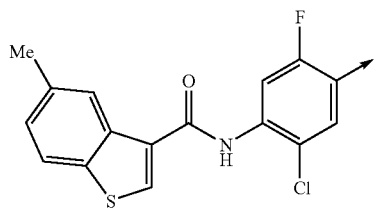
(v-78) 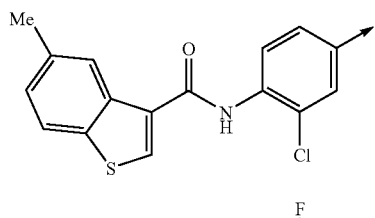
(v-79) 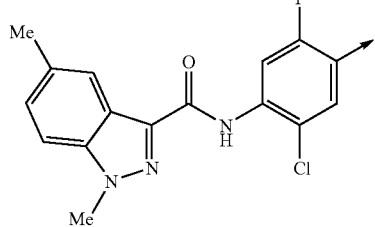
(v-80) 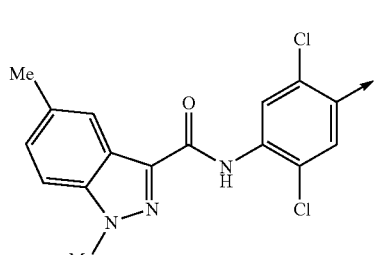
(v-81) 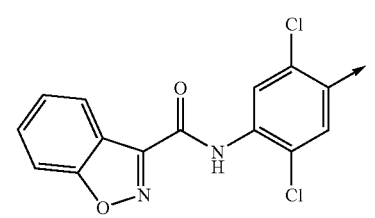
(v-82) 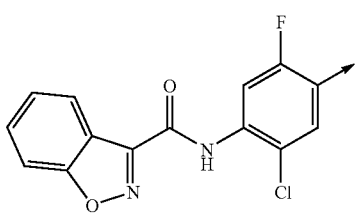
(v-83) 
(v-84) 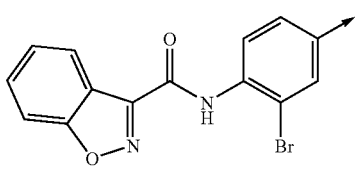
(v-85) 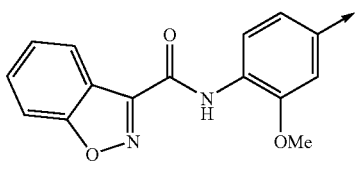
(v-86) 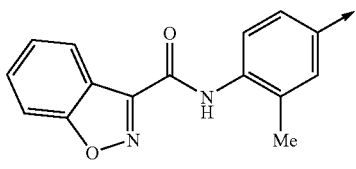
(v-87) 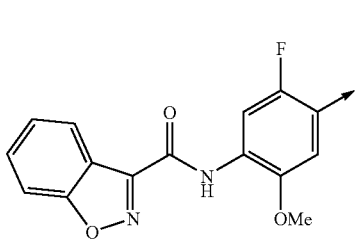
(v-88) 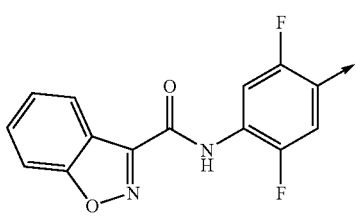
(v-89) 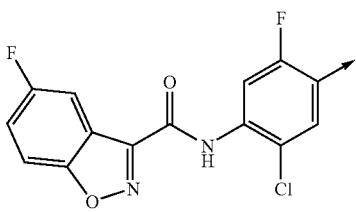

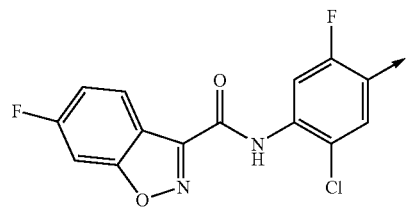 (v-90)
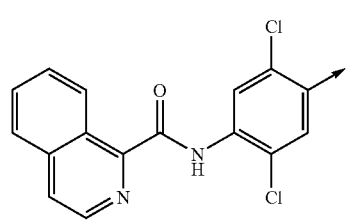 (v-91)
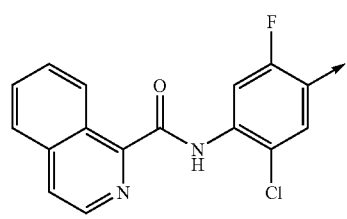 (v-92)
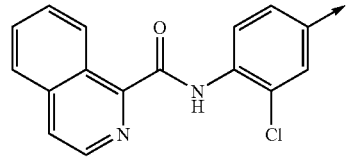 (v-93)
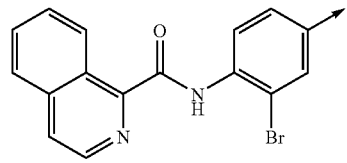 (v-94)
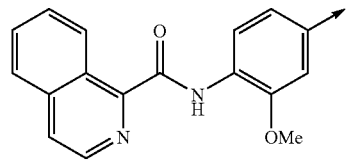 (v-95)
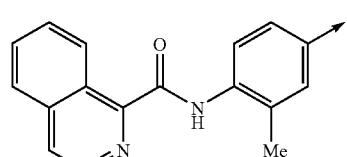 (v-96)
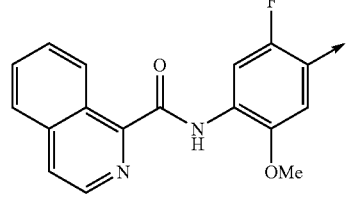 (v-97)
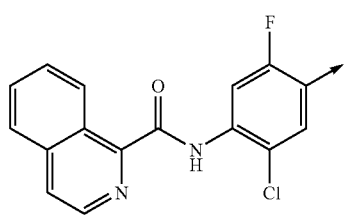 (v-98)
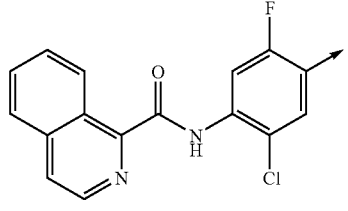 (v-99)
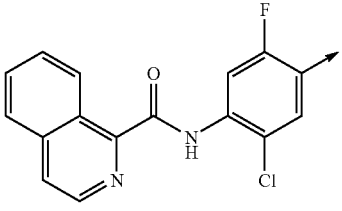 (v-100)
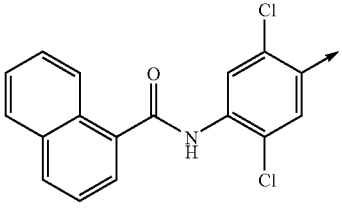 (v-101)
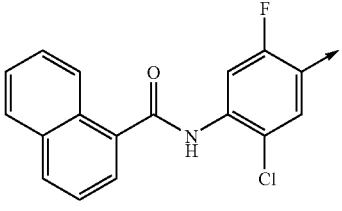 (v-102)
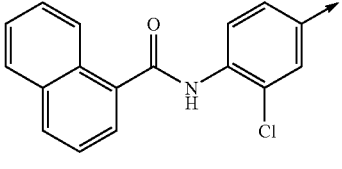 (v-103)
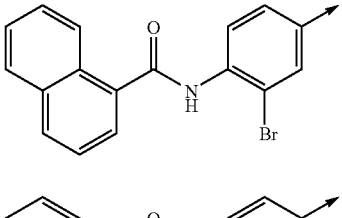 (v-104)
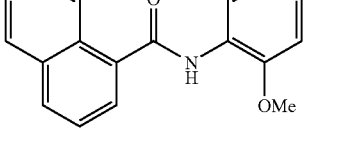 (v-105)

(v-106)
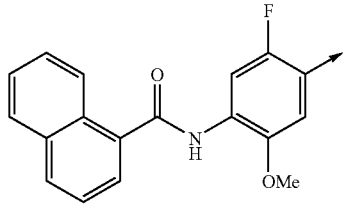
(v-107)
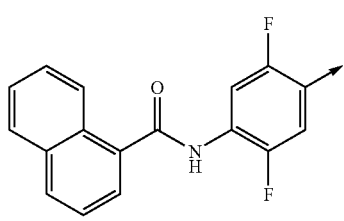
(v-108)
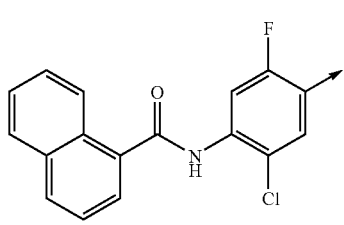
(v-109)
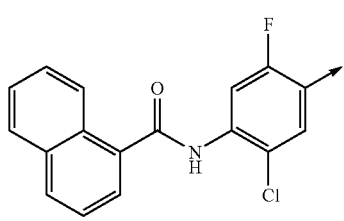
(v-110)
wherein symbol "→" represents the same as described above.
As the compound of the present invention represented by the formula (I), compounds represented by the following formula (vi-1) to (vi-127):
[Formula 40]
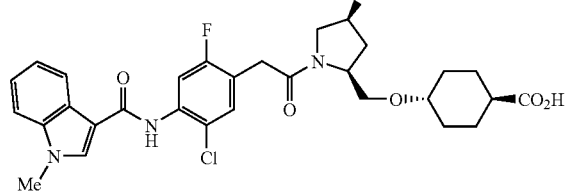
(vi-1)
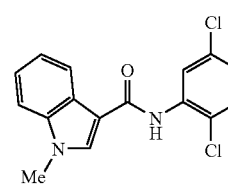
(vi-2)
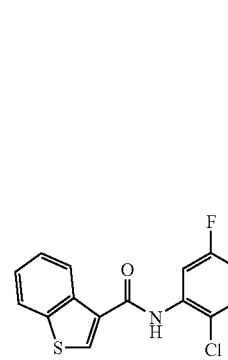
(vi-3)
(vi-4)
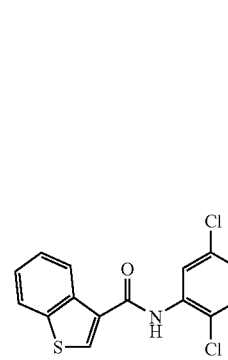
(vi-5)
(vi-6)
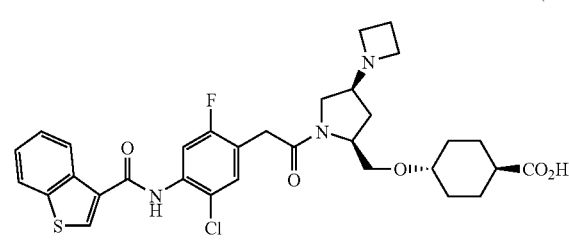

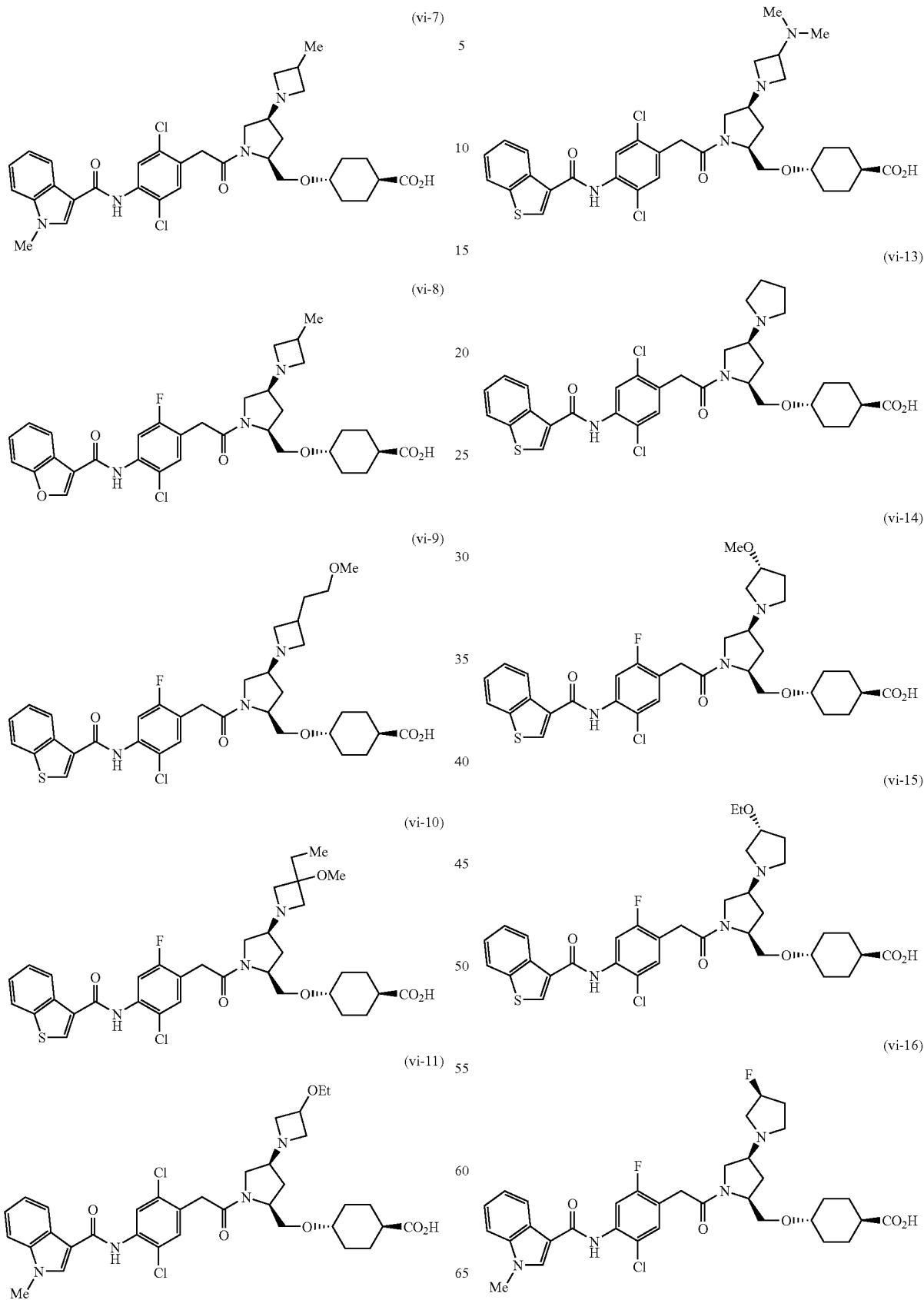

-continued
[Formula 42]
(vi-17)
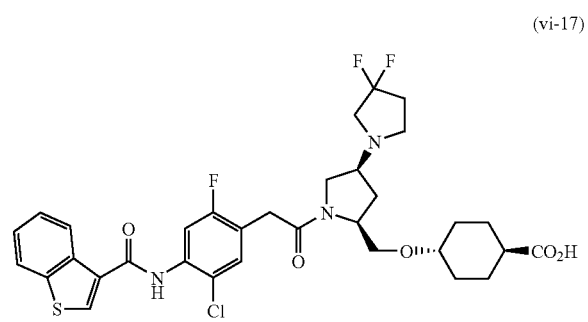
(vi-18)
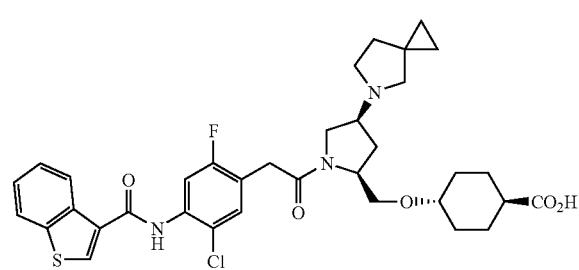
(vi-19)
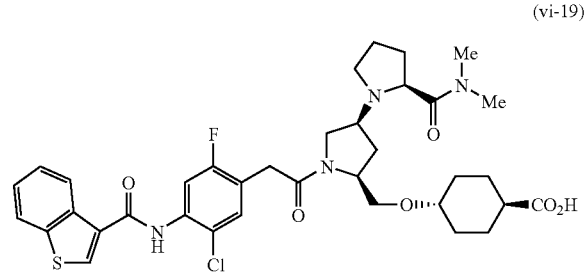
(vi-20)
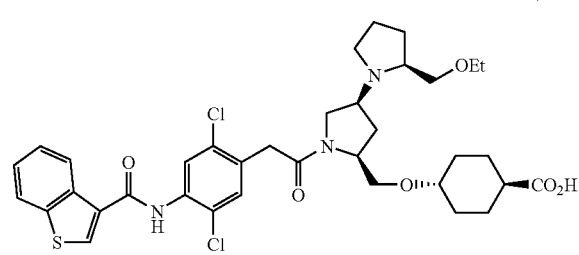
(vi-21)
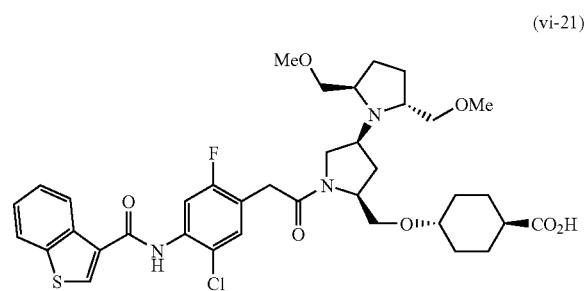
(vi-22)
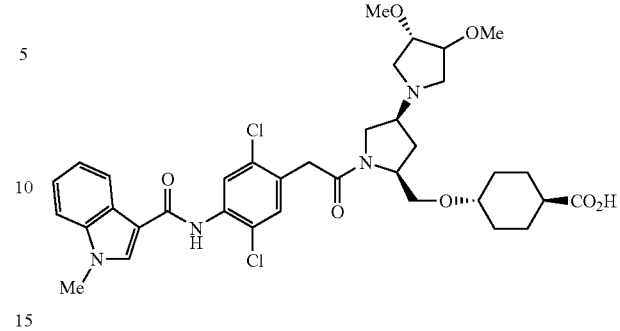
(vi-23)
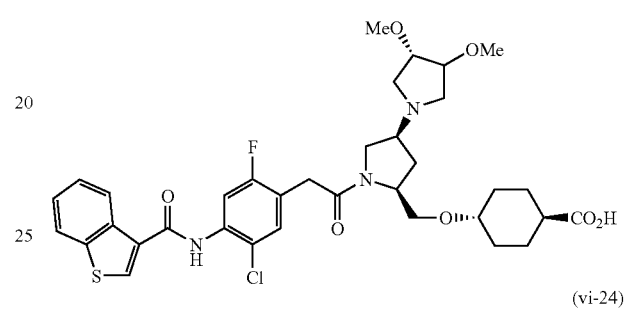
(vi-24)
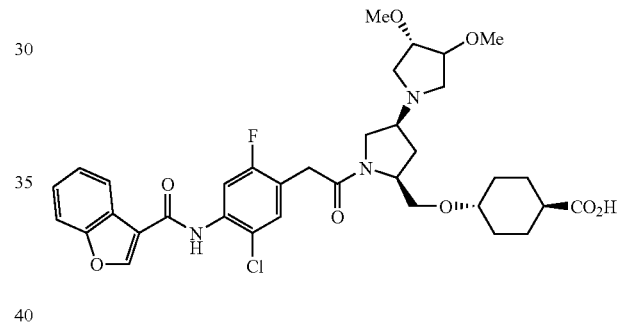
(vi-25)
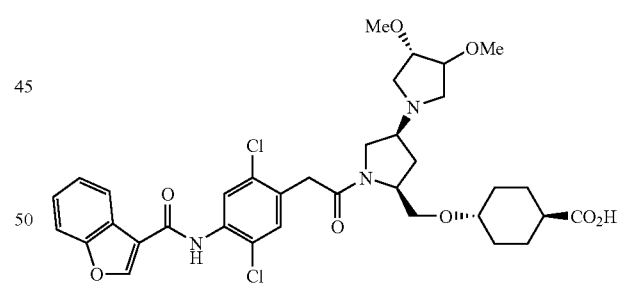
(vi-26)
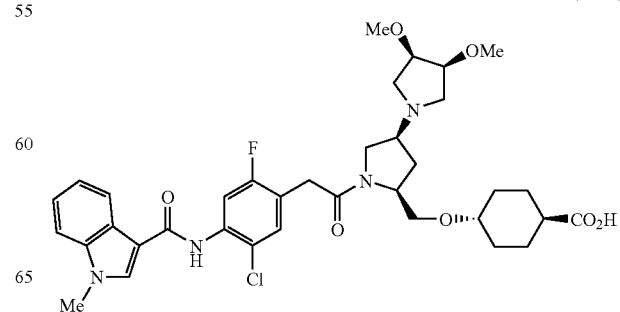

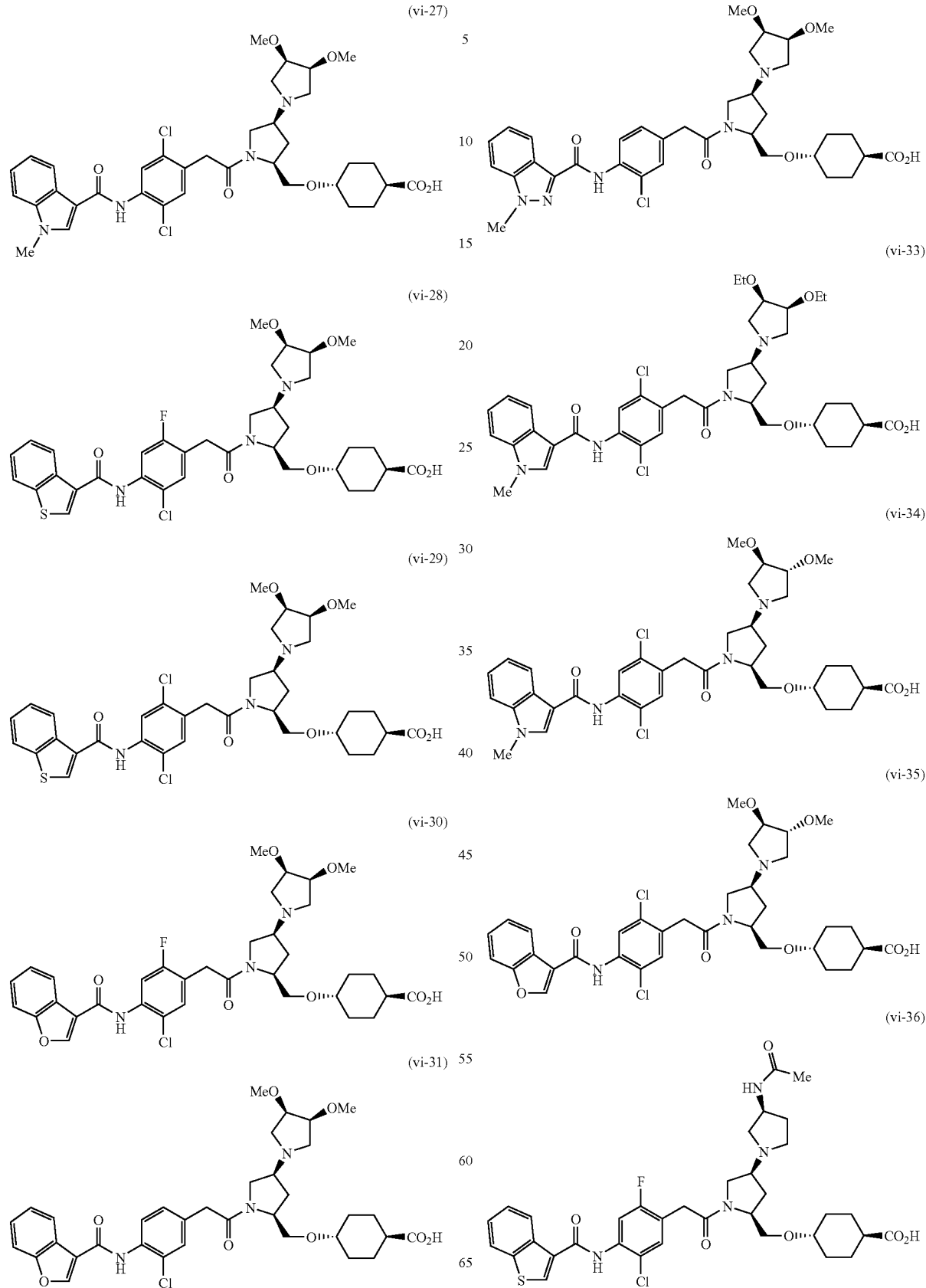

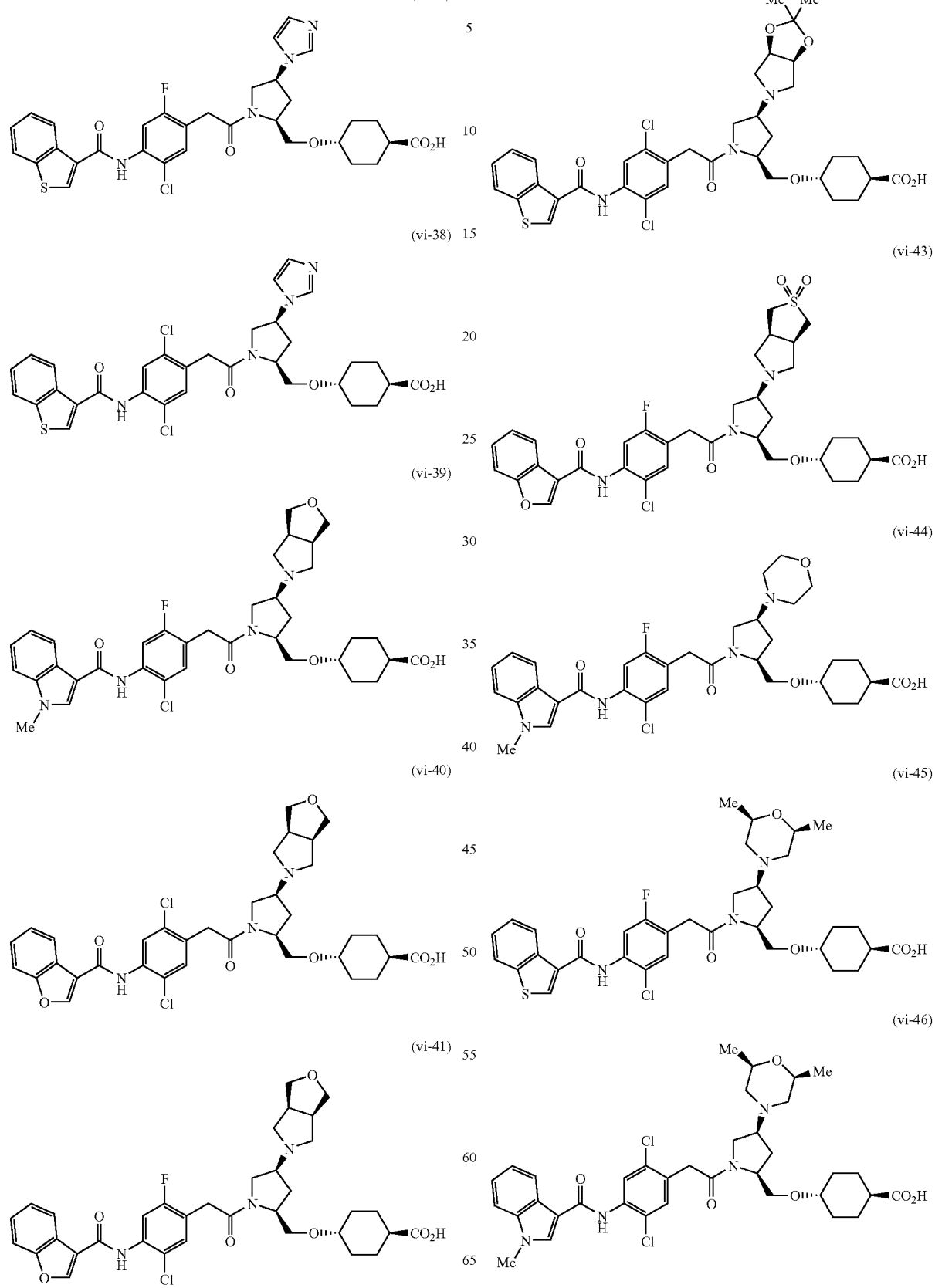

[Formula 45]
(vi-47)
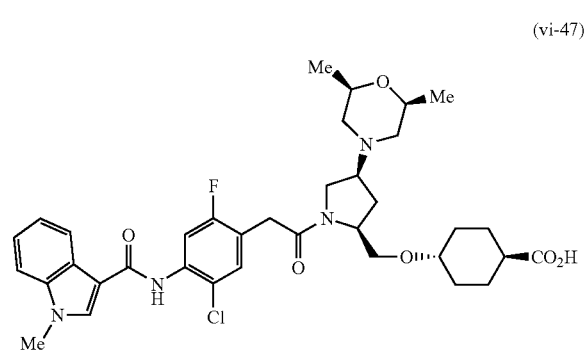
(vi-48)
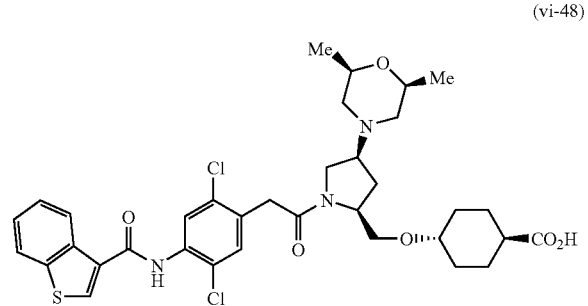
(vi-49)
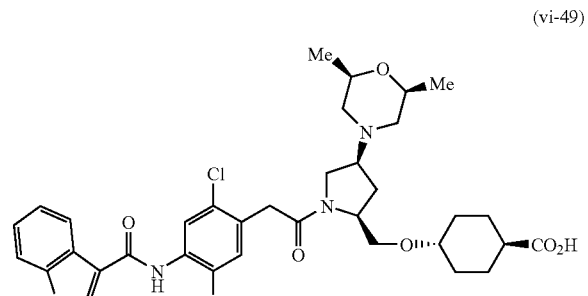
(vi-50)
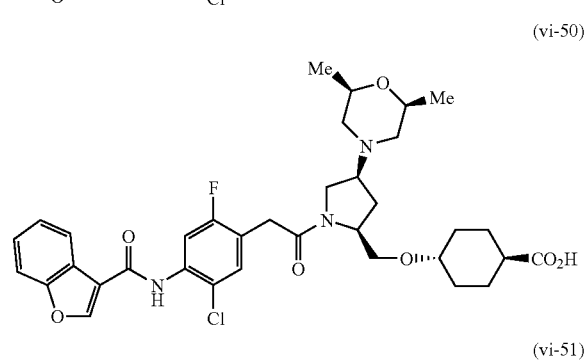
(vi-51)
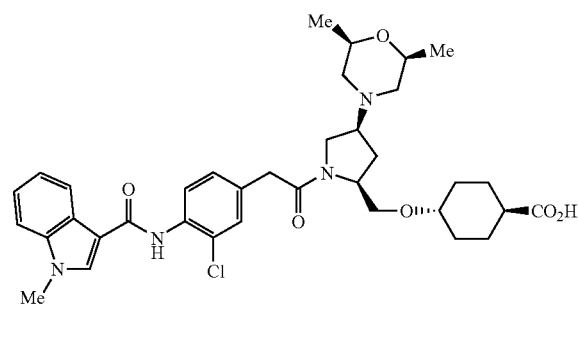
(vi-52)
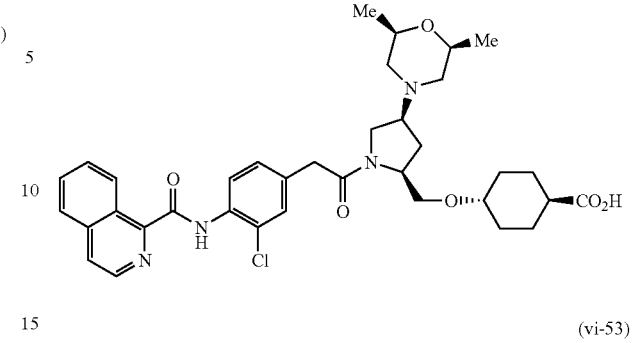
(vi-53)
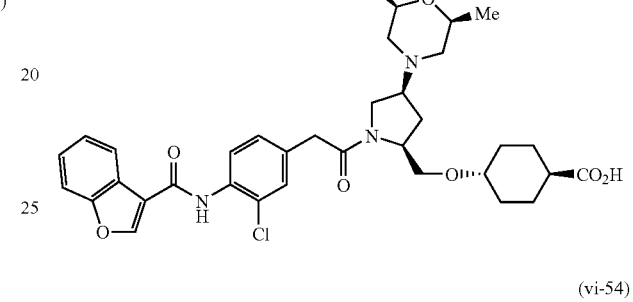
(vi-54)
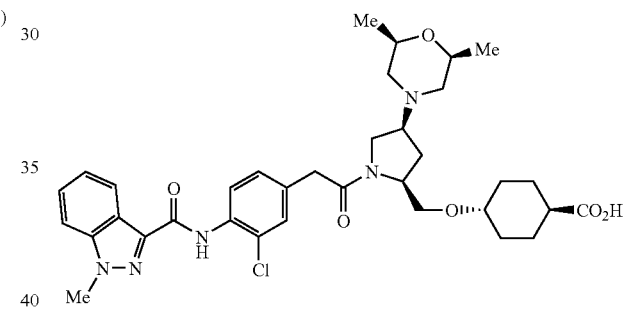
(vi-55)
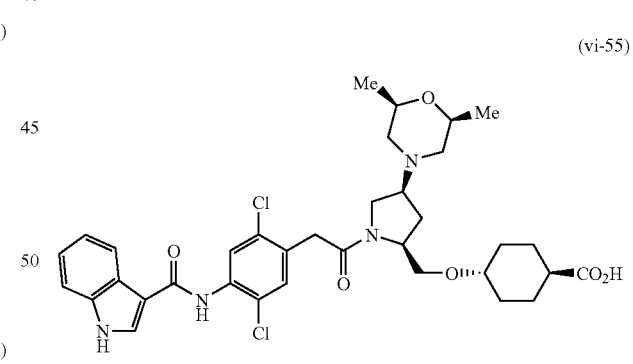
(vi-56)
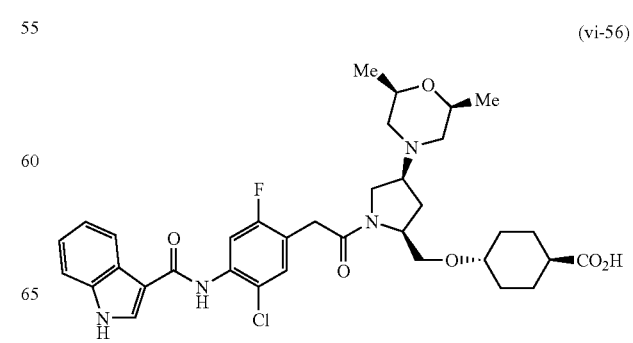

[Formula 46]
(vi-57)
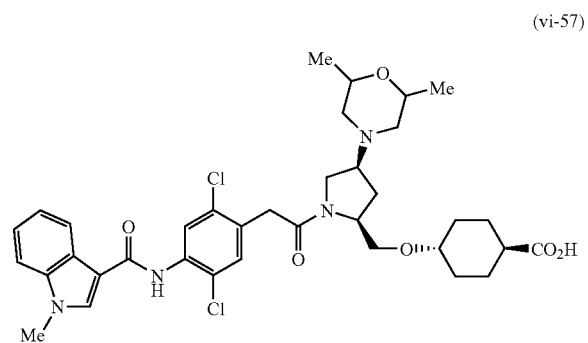
(vi-58)
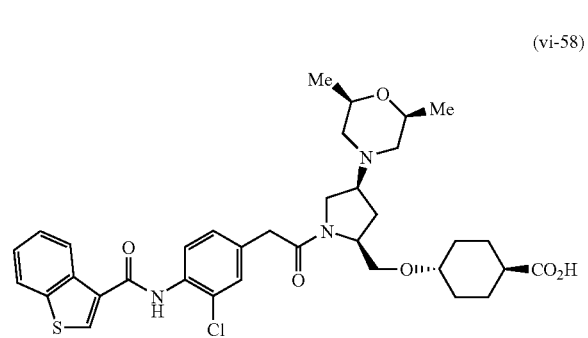
(vi-59)
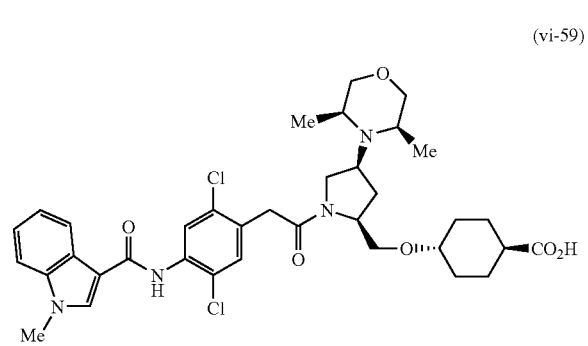
(vi-60)
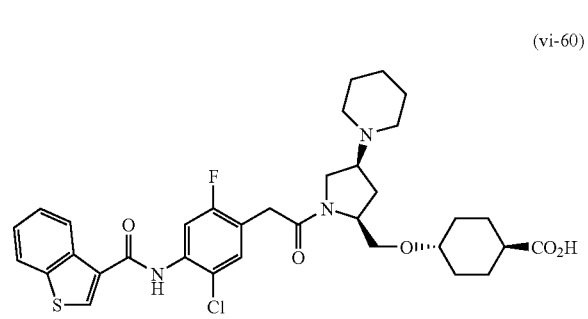
(vi-61)
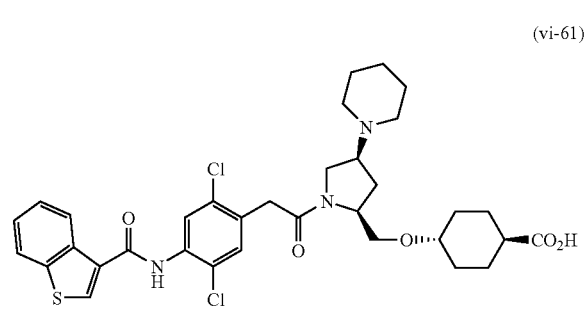
(vi-62)
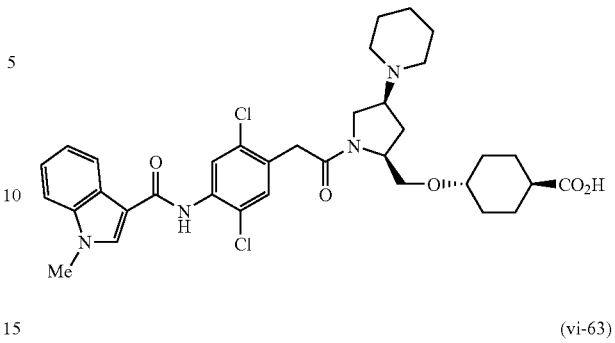
(vi-63)
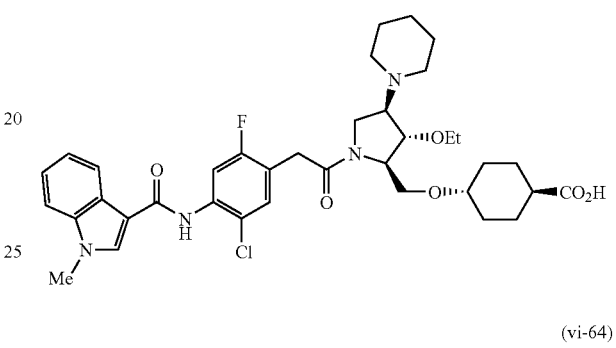
(vi-64)
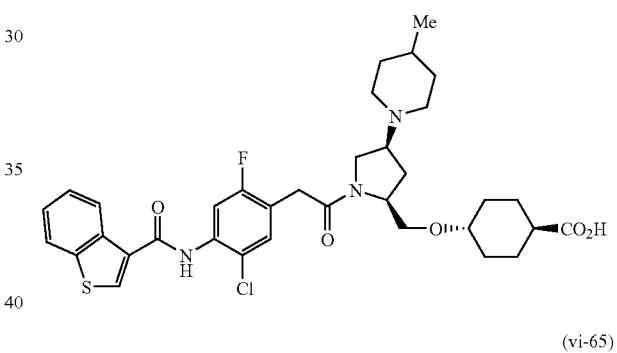
(vi-65)
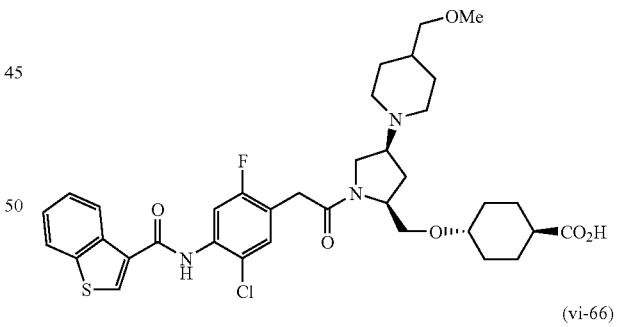
(vi-66)
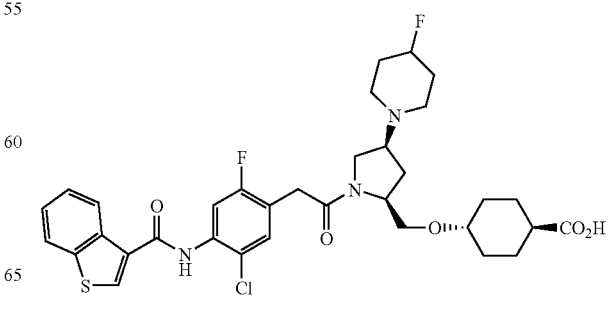

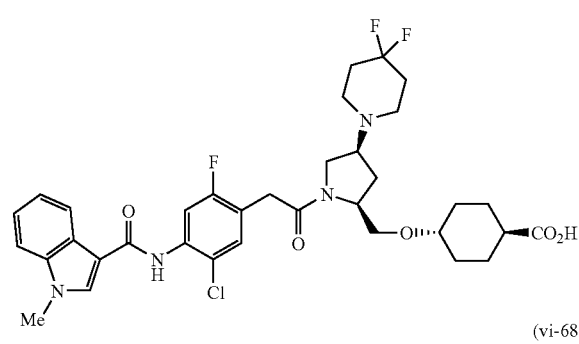
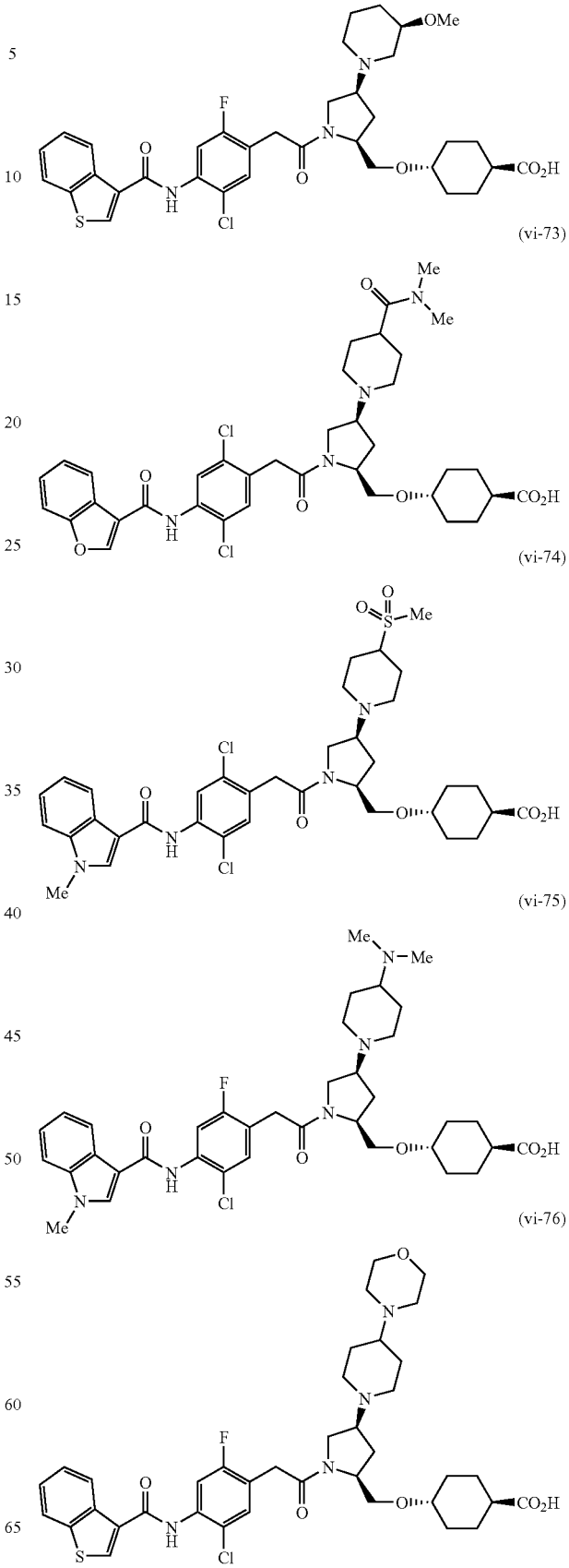

-continued
[Formula 48]
(vi-77)
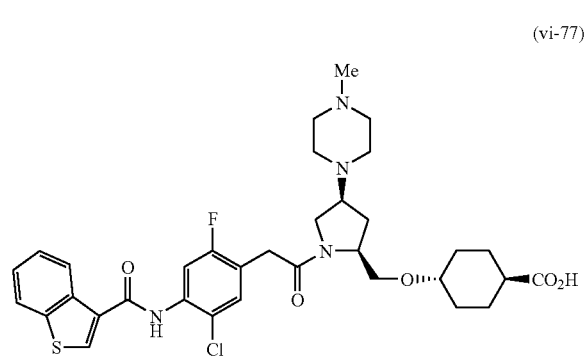
(vi-78)
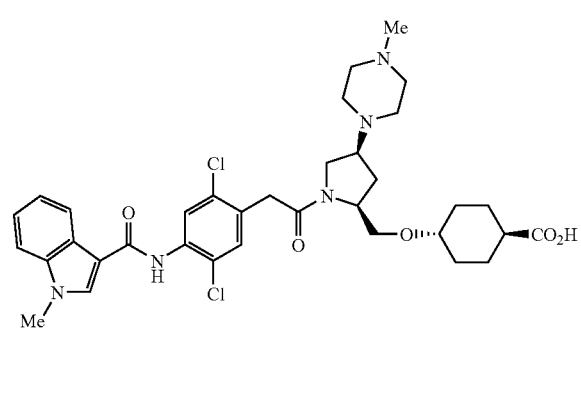
(vi-79)
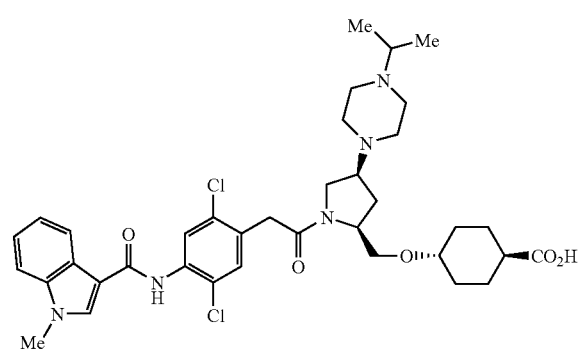
(vi-80)
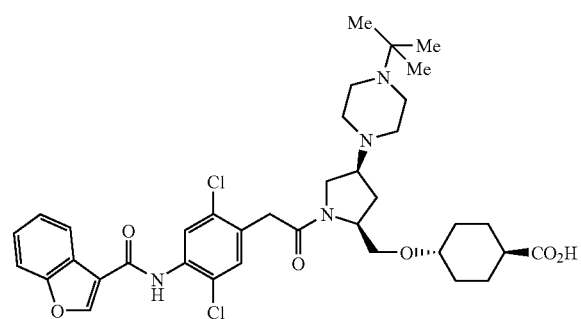
-continued
(vi-81)
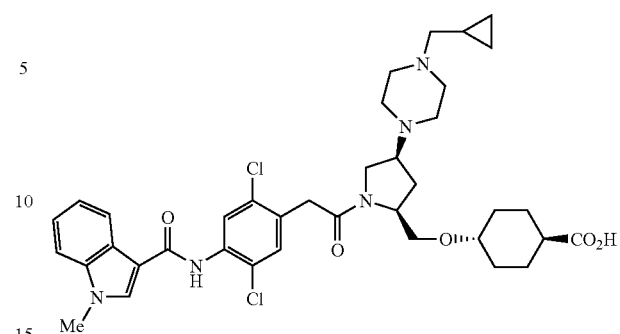
(vi-82)
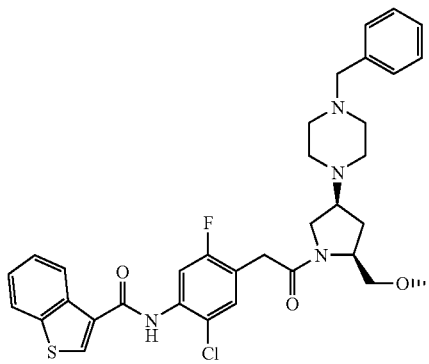
(vi-83)
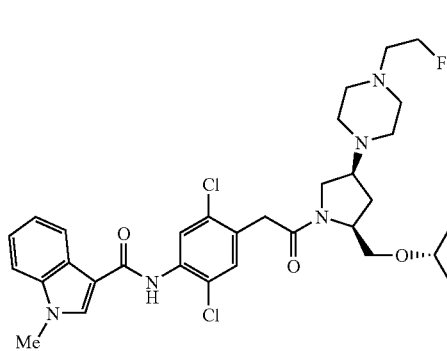
(vi-84)
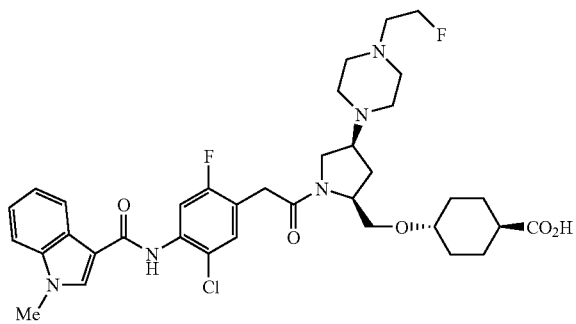

(vi-85)
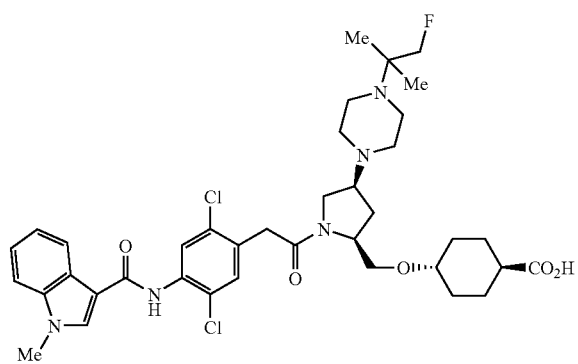
(vi-89)
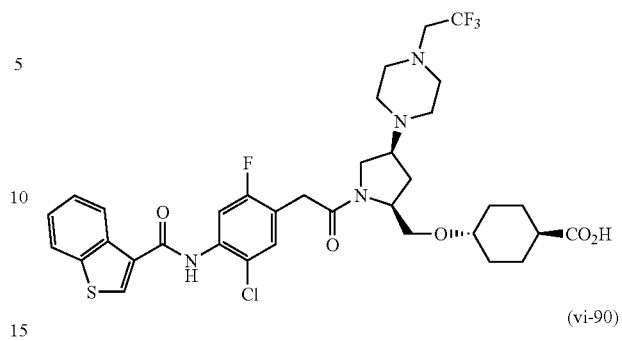
(vi-86)
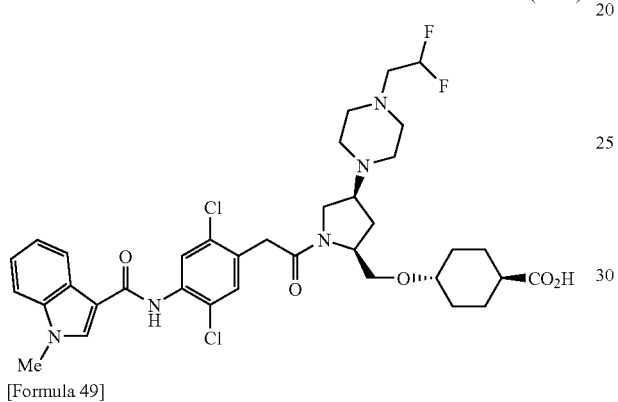
[Formula 49]
(vi-90)
(vi-87)
(vi-91)
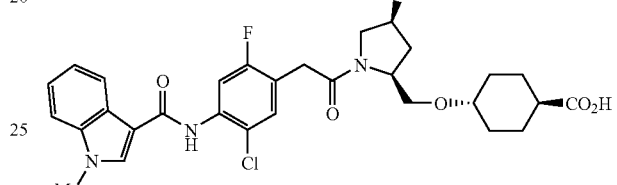
(vi-88)
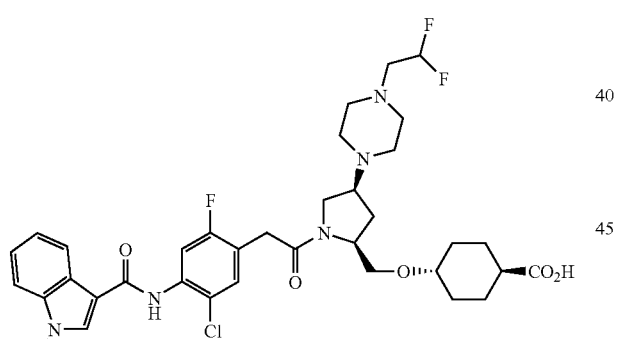
(vi-92)
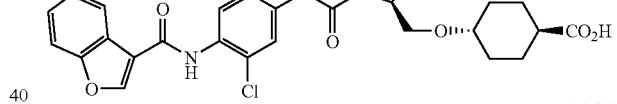
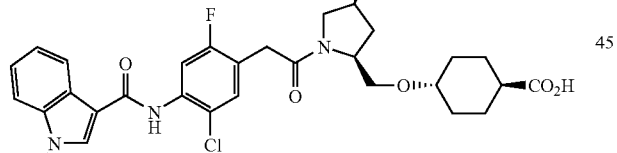
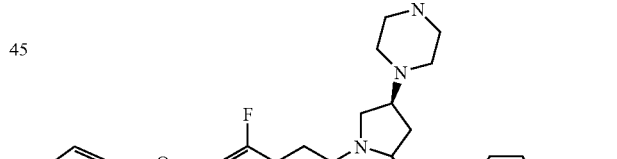
(vi-93)
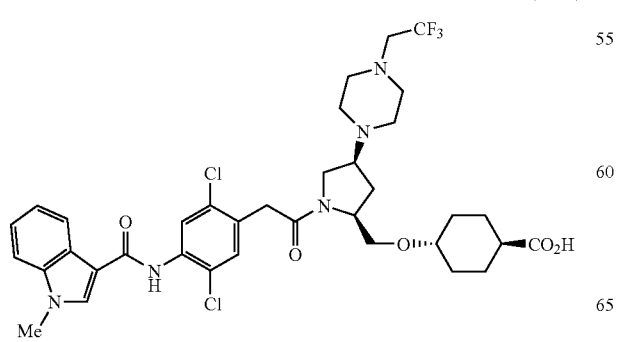
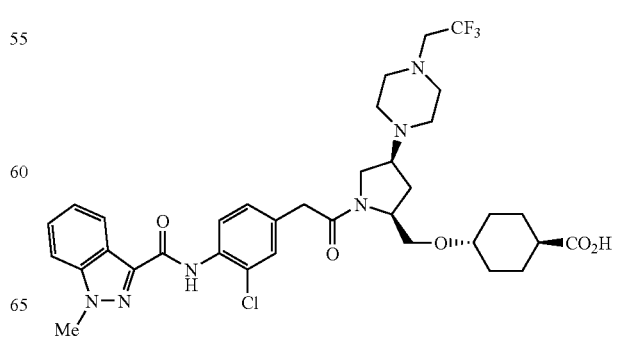

-continued
(vi-94)
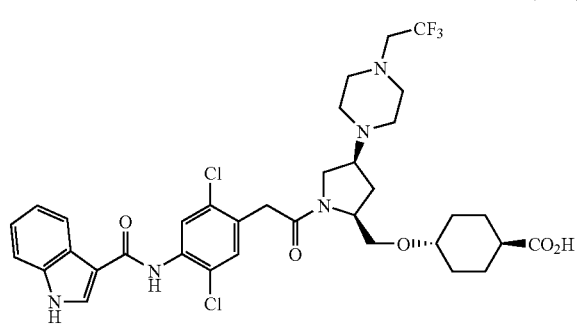
(vi-98)
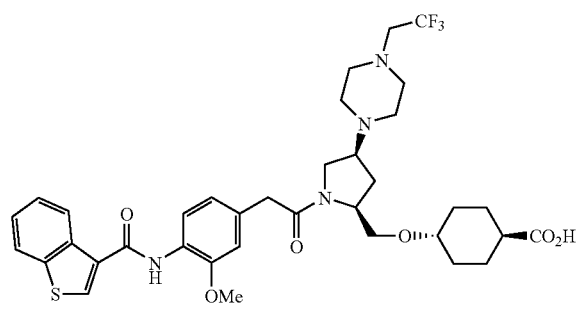
(vi-95)
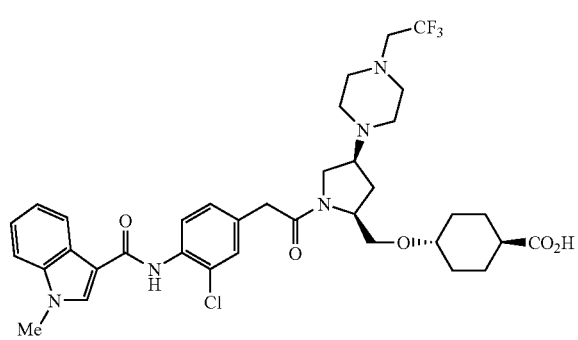
(vi-99)
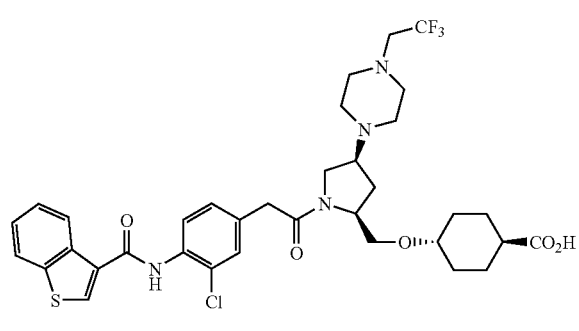
(vi-96)
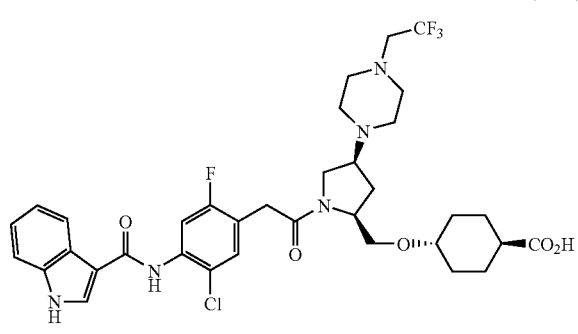
(vi-100)
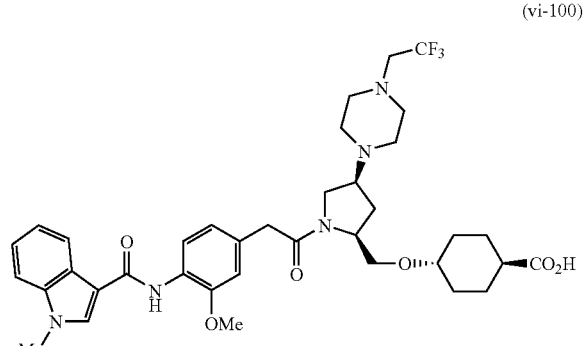
[Formula 50]
(vi-97)
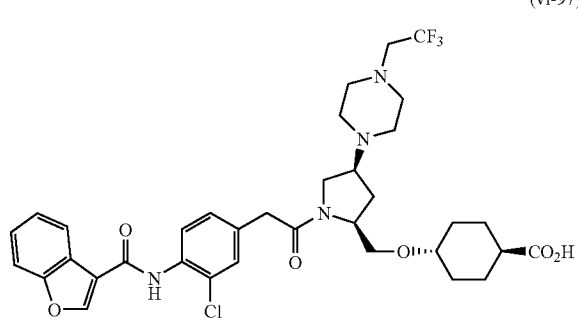
(vi-101)
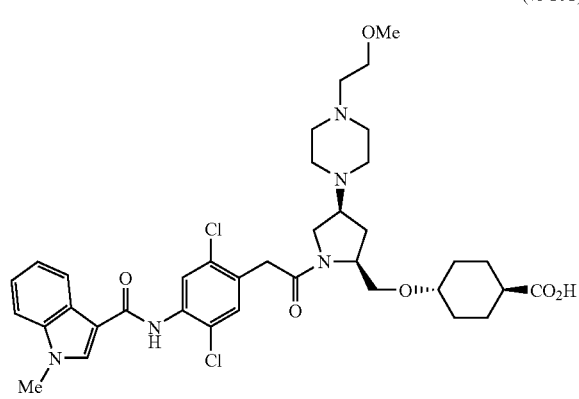

-continued
(vi-102)
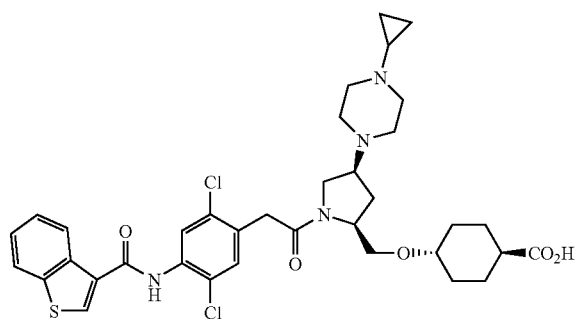
(vi-103)
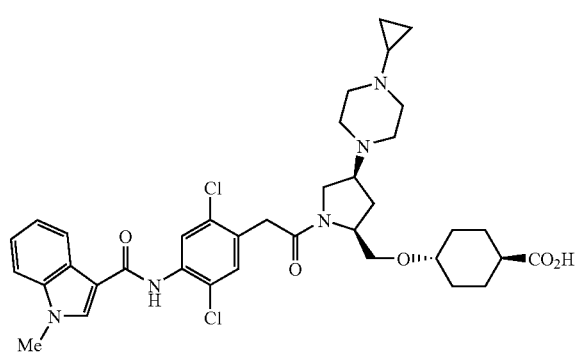
(vi-104)
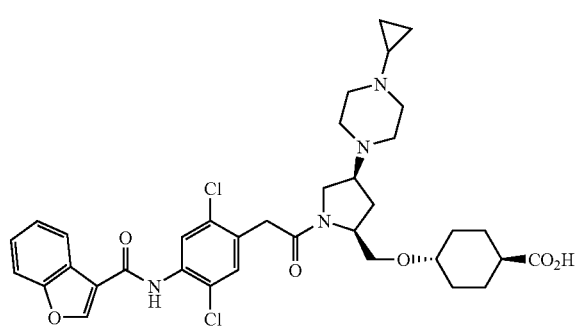
(vi-105)
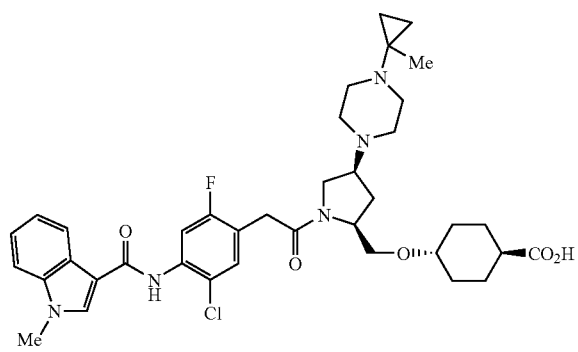
-continued
(vi-106)
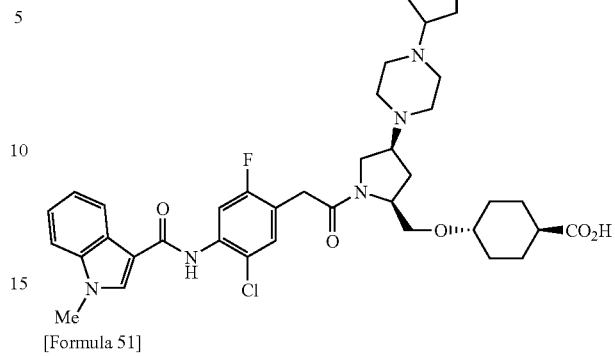
[Formula 51]
(vi-107)
(vi-108)
(vi-109)
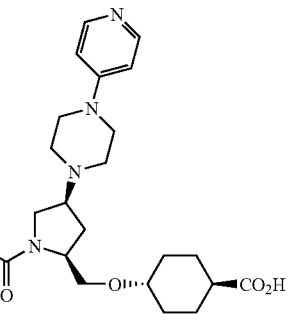

83
-continued
(vi-110)
(vi-111)
(vi-112)
(vi-113)
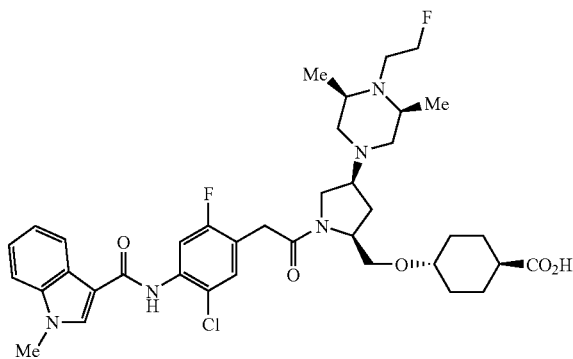
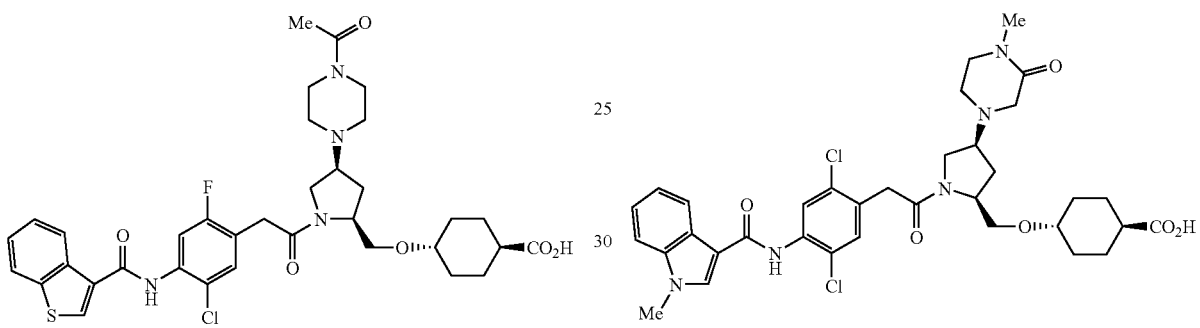
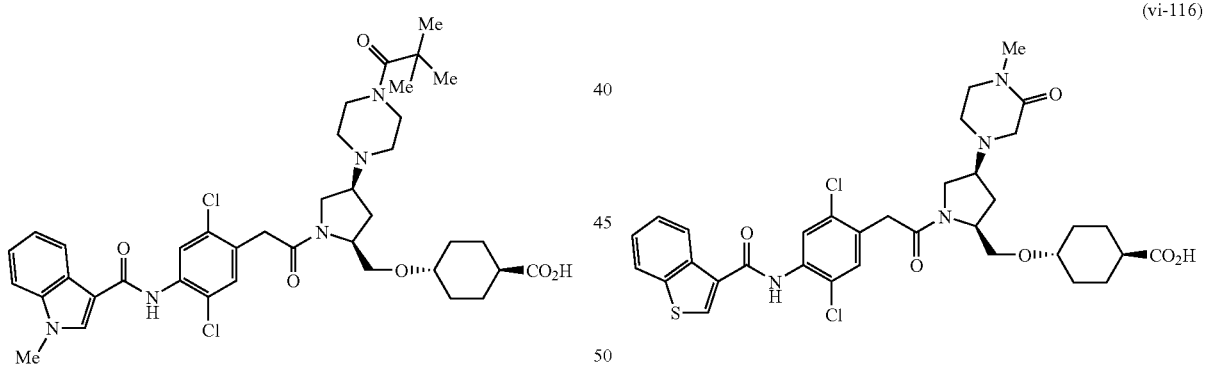
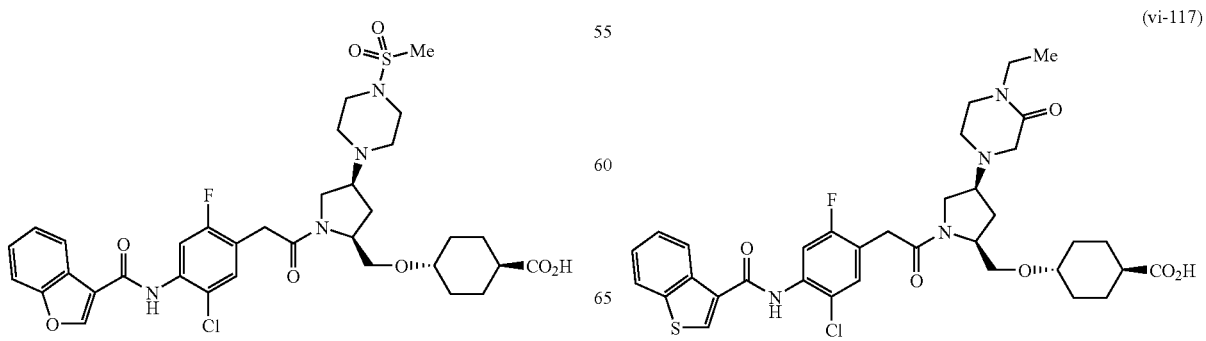
84
-continued
(vi-114)
(vi-115)
(vi-116)
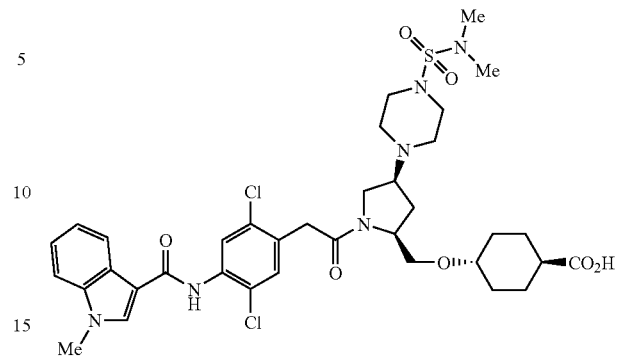
[Formula 52]
(vi-117)

(vi-118)
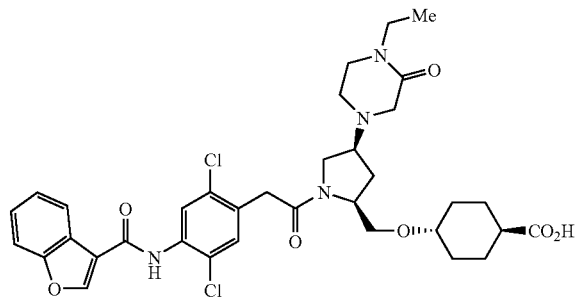
(vi-119)
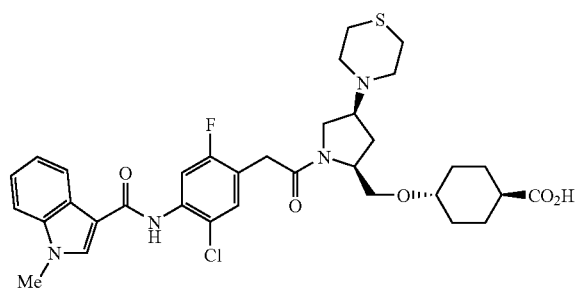
(vi-120)
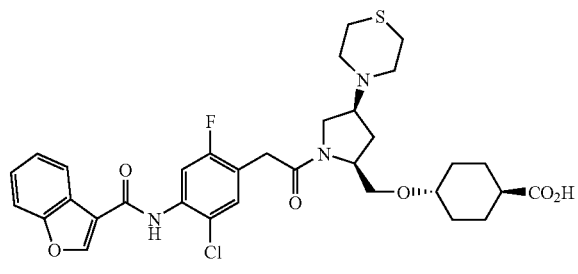
(vi-121)
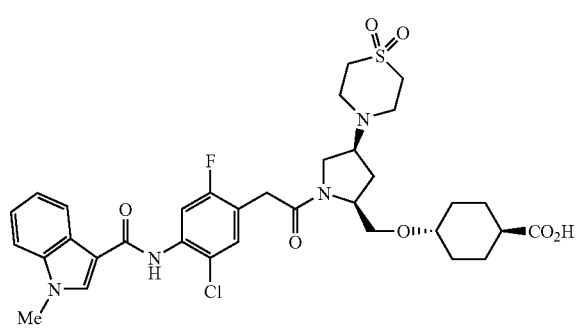
(vi-122)
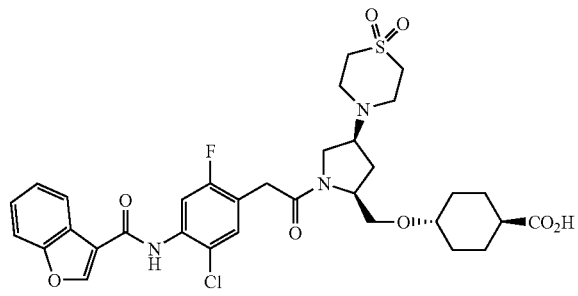
(vi-123)
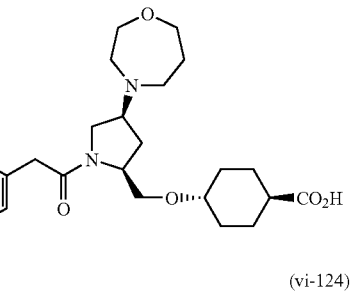
(vi-124)
(vi-125)
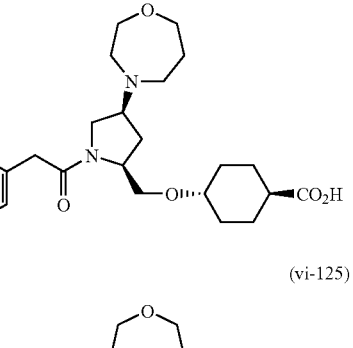
(vi-126)
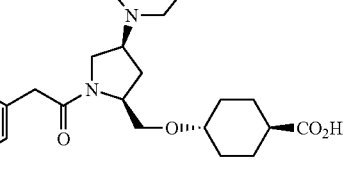
[Formula 53]
(vi-127)
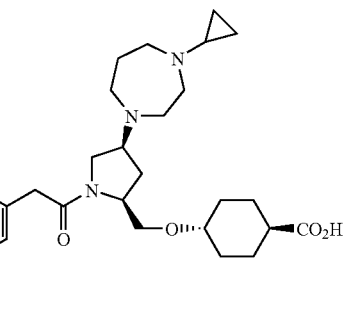
salts thereof, or lower alkyl esters thereof are preferred.
As more preferred compounds, compounds represented by the following (Group A), (Group B) or (Group C), salts thereof or lower alkyl esters thereof may be mentioned.

[Formula 54]
(Group A)
(A群)
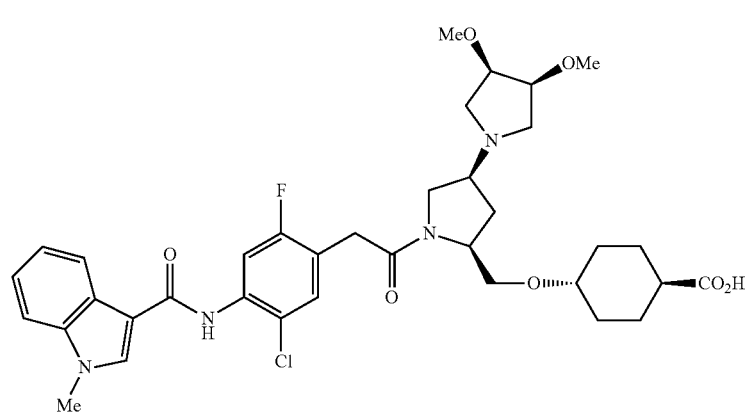
(vi-26)
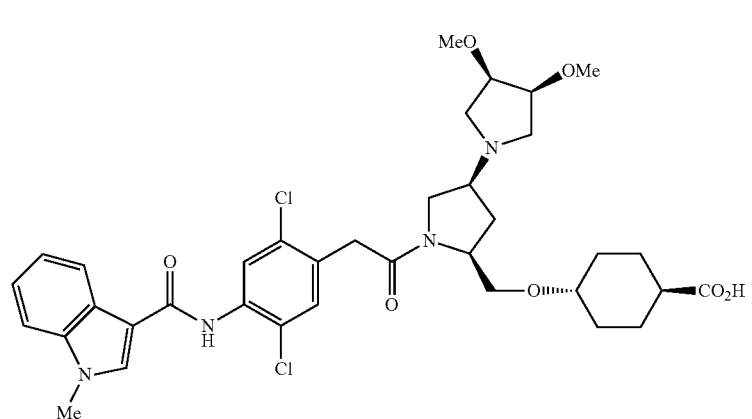
(vi-27)
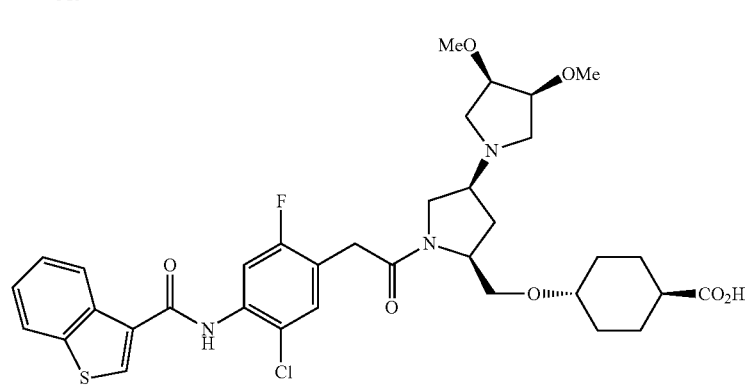
(vi-28)
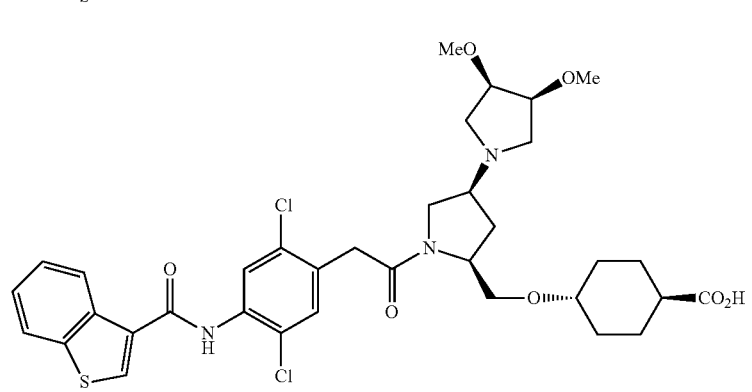
(vi-29)

(vi-30)
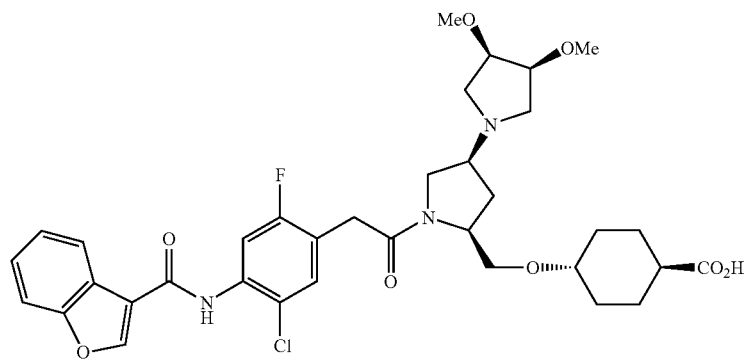
(vi-31)
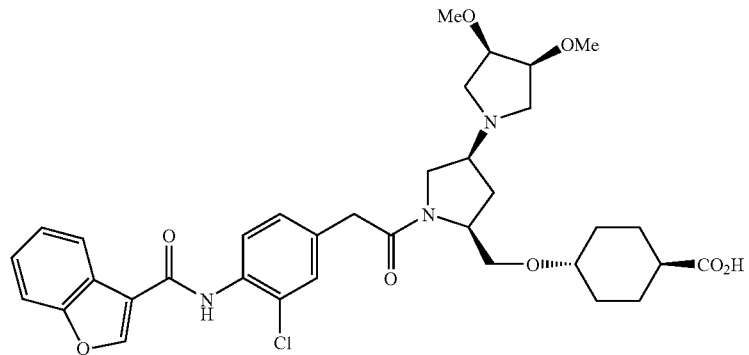
(vi-32)
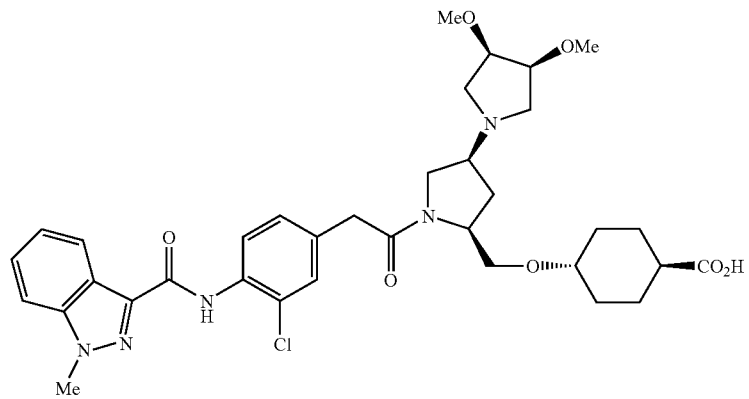
(vi-35)
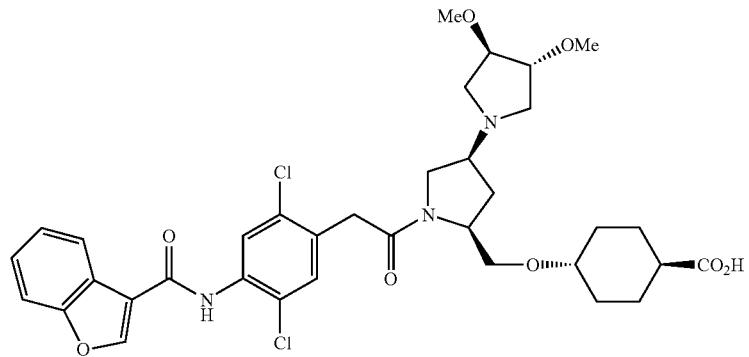

[Formula 55]
(Group B)
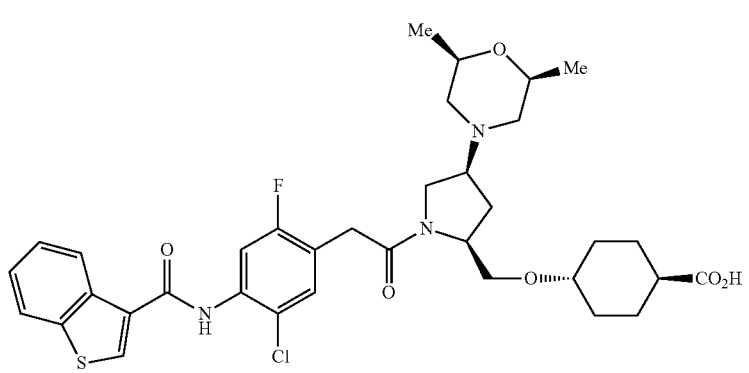
(vi-45)
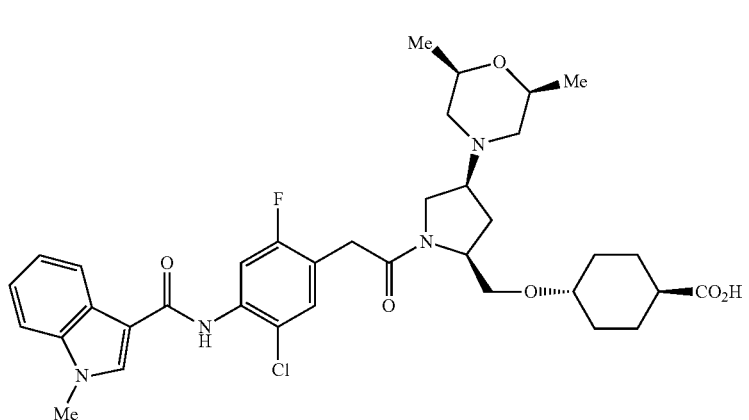
(vi-47)
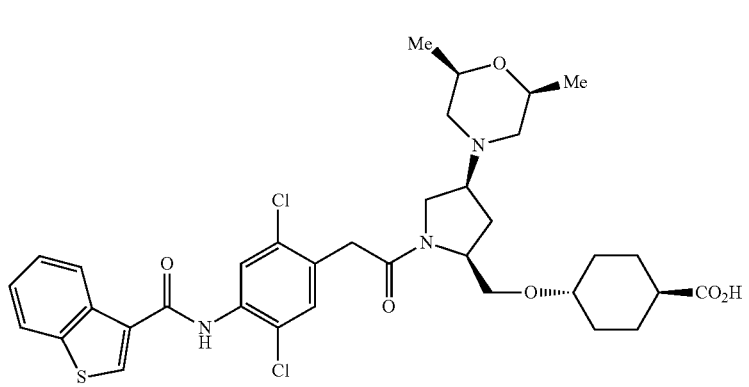
(vi-48)
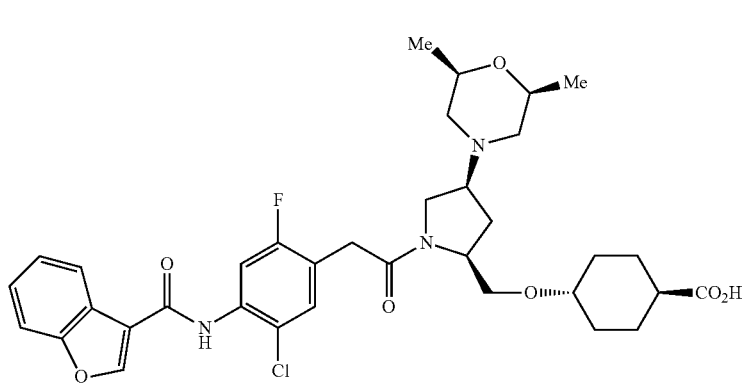
(vi-50)

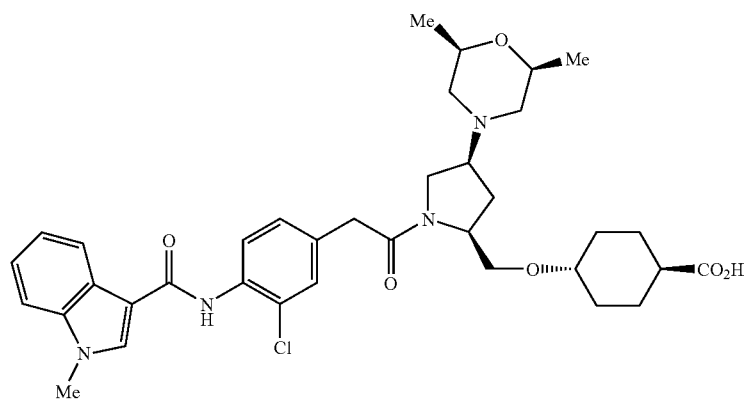
(vi-51)
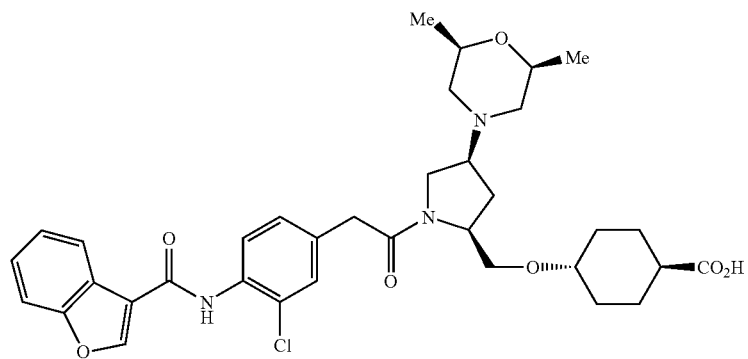
(vi-53)
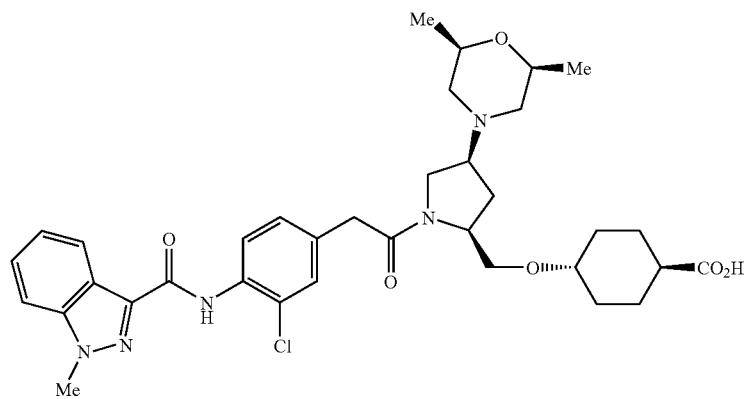
(vi-54)
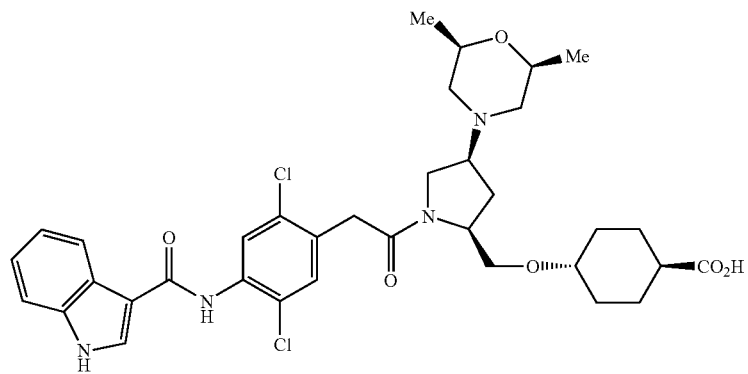
(vi-55)

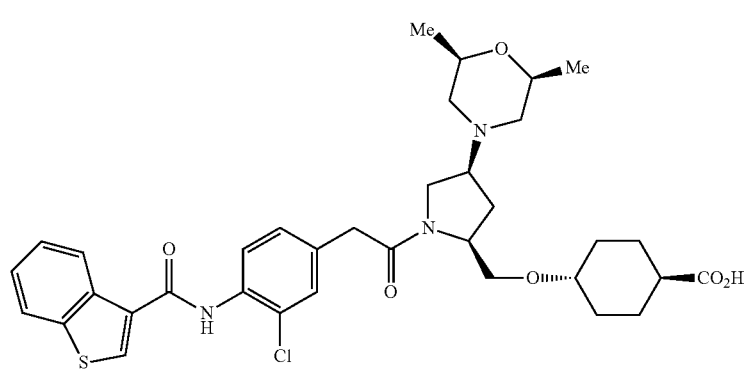
(vi-58)
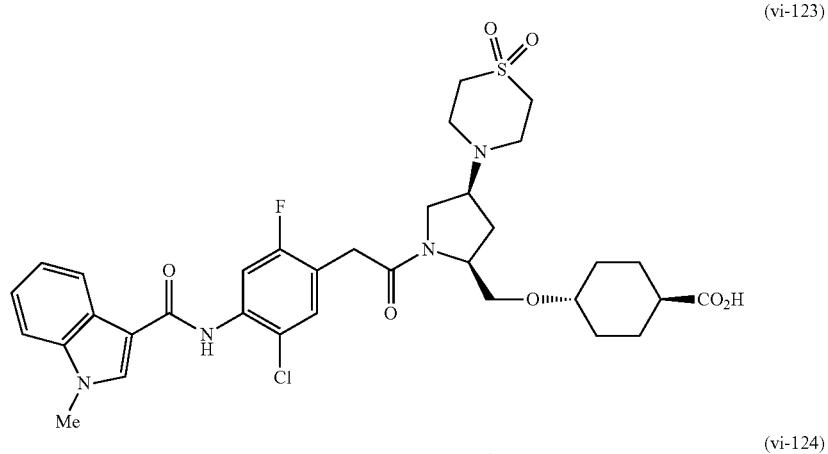
(vi-123)
(vi-124)
[Formula 56]
(Group C)
(C群)
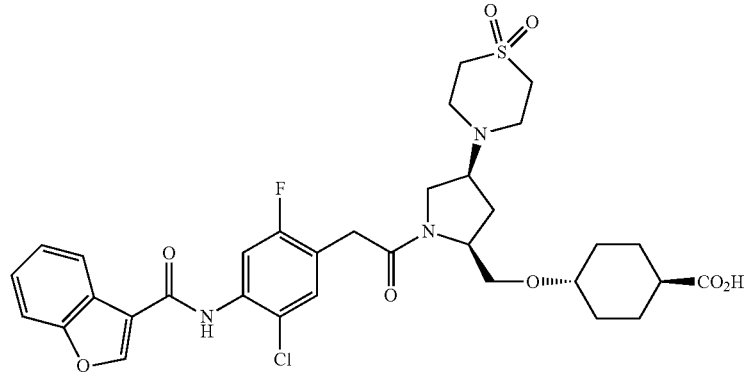
(vi-88)
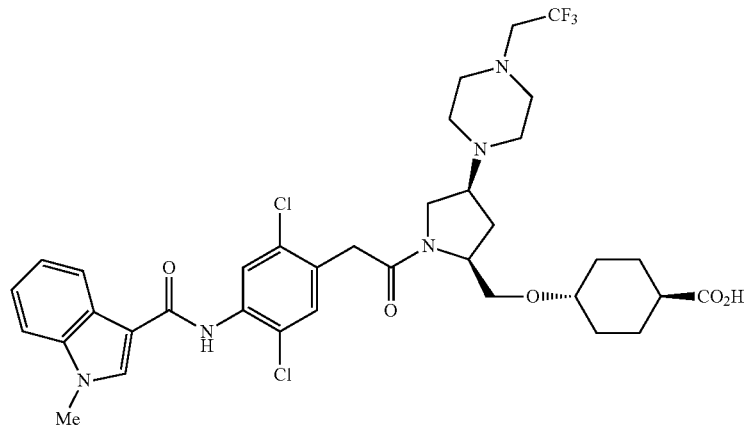

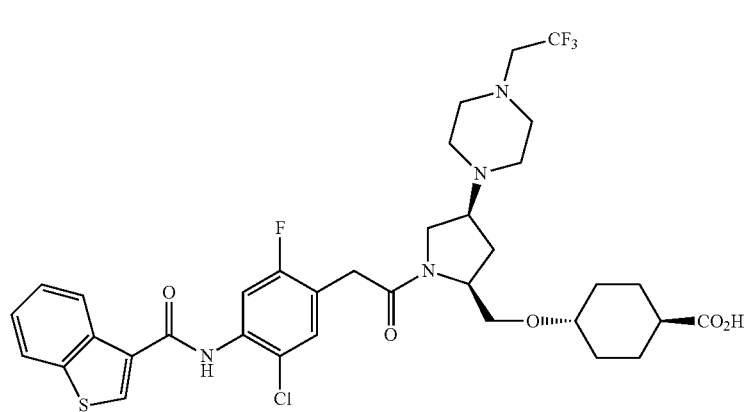
(vi-89)
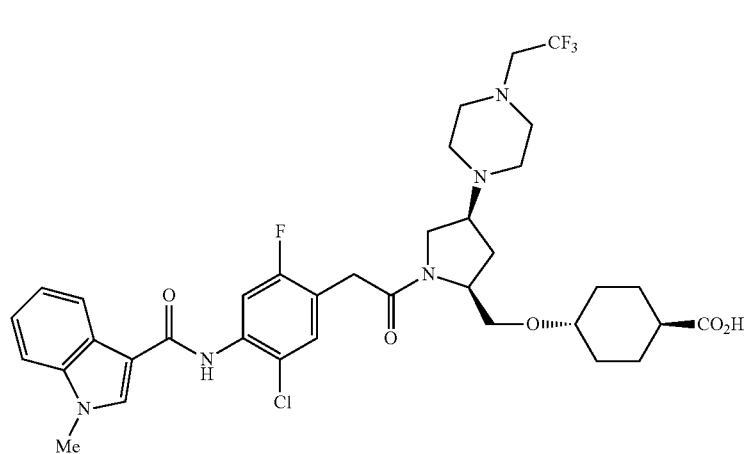
(vi-90)
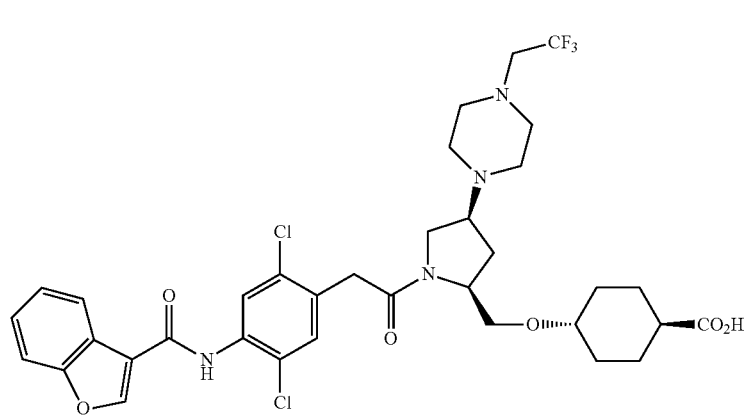
(vi-91)
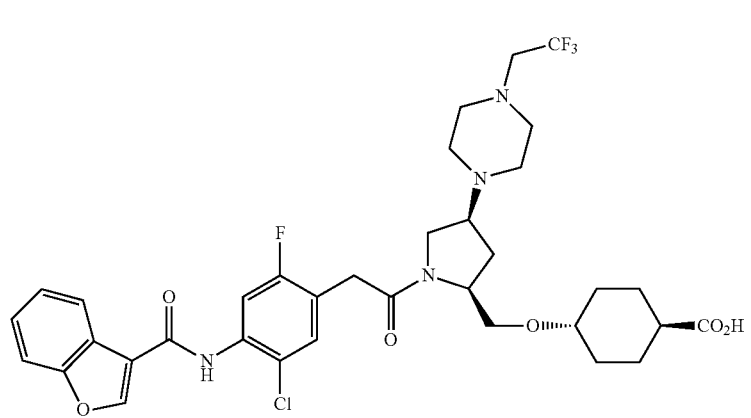
(vi-92)

(vi-93)
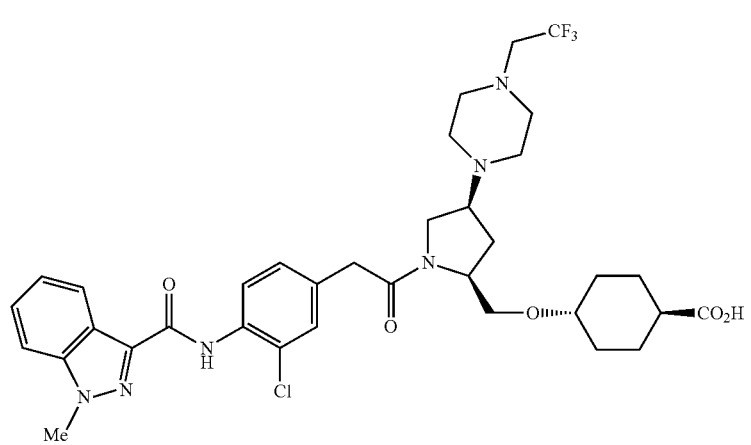
(vi-94)
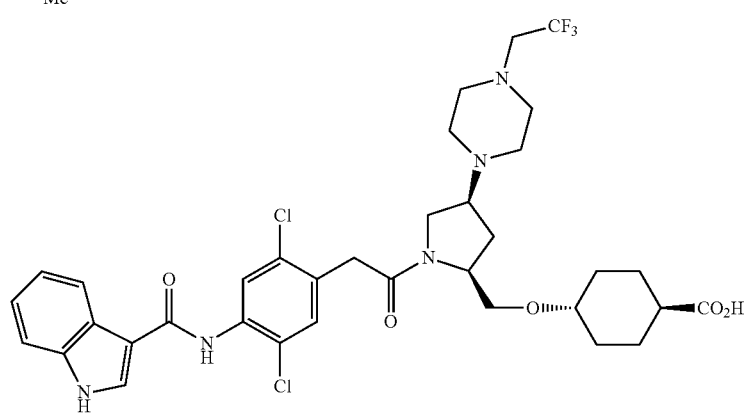
(vi-95)
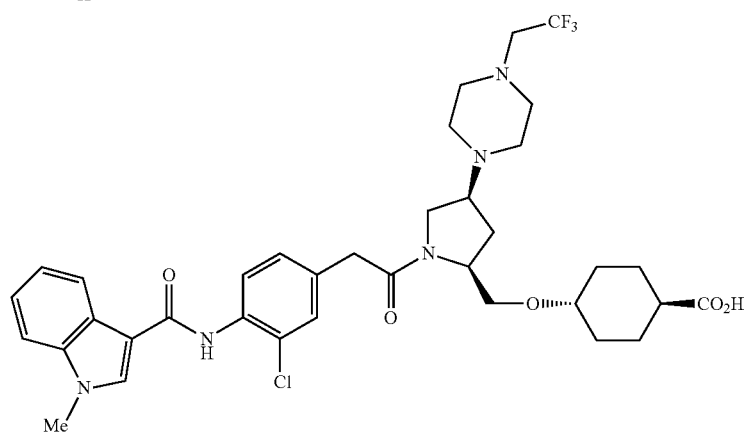
[Formula 57]
(vi-96)
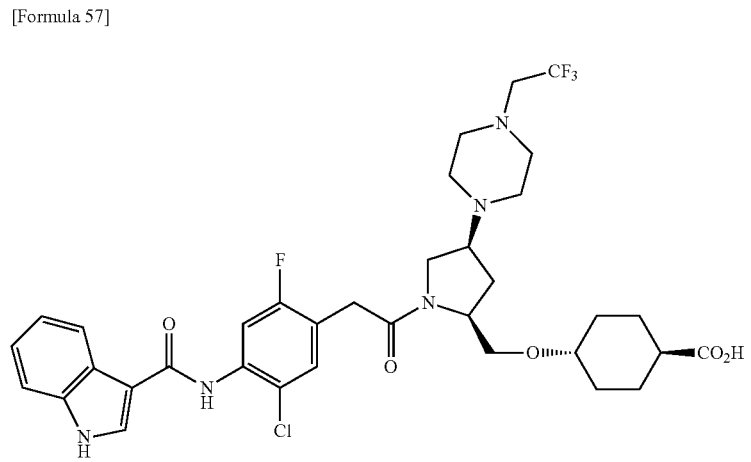

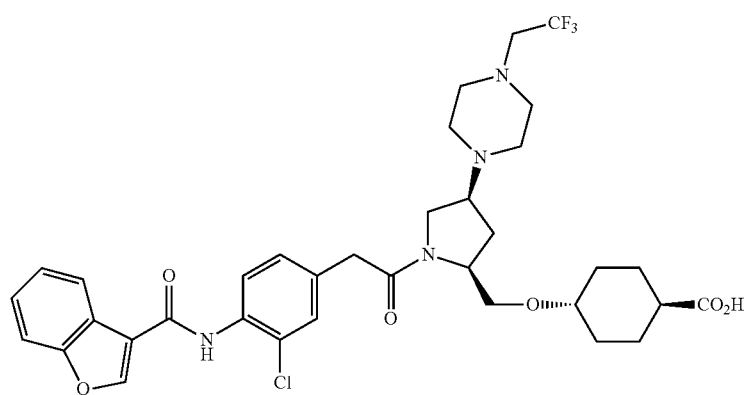
(vi-97)
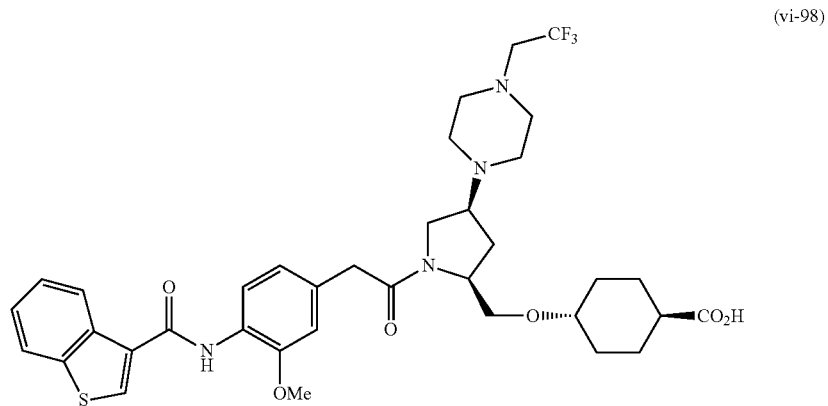
(vi-98)
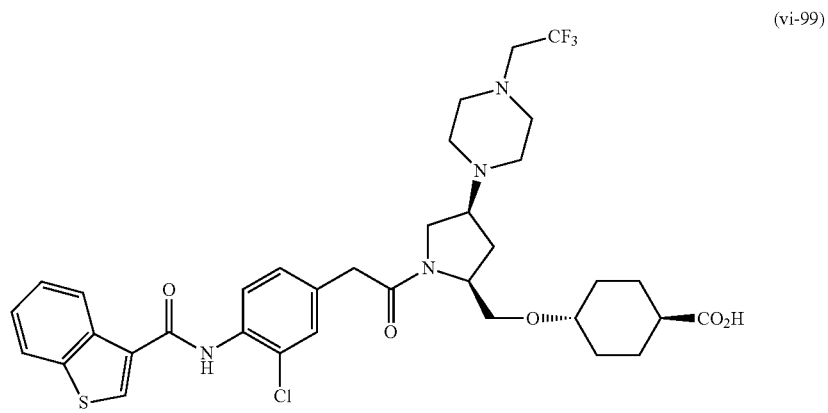
(vi-99)
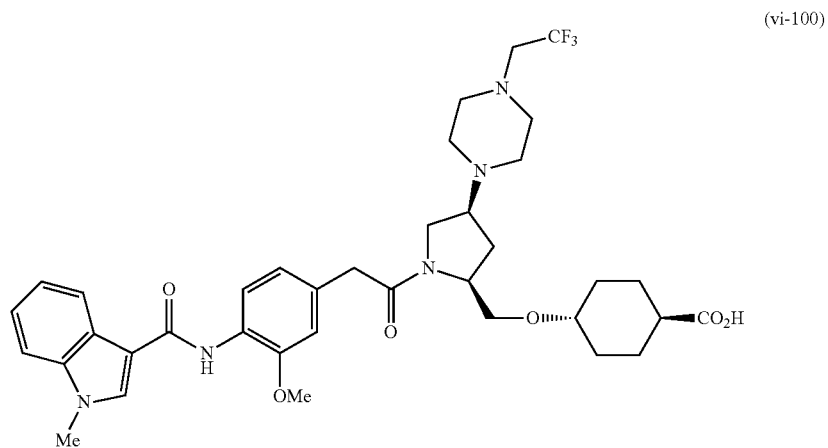
(vi-100)

When the compound represented by formula (I) of the present invention has a basic group such as an amino group, the compound can be made, if desired, into a physiologically acceptable salt using an inorganic acid such as hydrochloric acid, sulfuric acid or phosphoric acid, or an organic acid such as formic acid, acetic acid or methanesulfonic acid. Further, when the compound of the present invention represented by formula (I) has an acidic group such as a carboxyl group, it is generally possible to form a base addition salt. The physiologically acceptable salt may be any of organic salts or inorganic salts, and suitable examples include, for example, an alkali metal salt such as a lithium salt, a sodium salt or a potassium salt; an alkaline earth metal salt such as a magnesium salt or a calcium salt; an ammonium salt, a triethylamine salt, a cyclohexylamine salt, a piperazine salt, a piperidine salt, a morpholine salt, an N,N'-dimethylethylenediamine salt, an N-methylglucamine salt, a tris(hydroxymethyl)aminomethane salt and the like.

The compound represented by formula (I) of the present invention or a salt thereof may also exist as a free form or a solvate. The solvate is not particularly limited if pharmaceutically acceptable, but specific examples include hydrate, ethanolate and the like. If a nitrogen atom is present in the compound of the present invention represented by formula (I), the compound may be in an N-oxide form. These solvates and N-oxides are also included in the scope of the present invention.

The compound of the present invention represented by formula (I) or a salt thereof may also exist as various isomers, such as geometric isomers such as cis-isomer or trans-isomer, and optical isomers such as d-isomer or l-isomer, depending on the type or combination of the substituents. However, if not particularly limited, the compound of the present invention includes all those stereoisomers and mixtures of stereoisomers at any ratios.

The compound (I) of the present invention can be produced by a method represented by the following [Scheme 1].

[Scheme 1]

An ester product (3) and a compound (4), which correspond to compound (I) of the present invention, can be produced by subjecting a carboxylic acid derivative (1) and a pyrrolidine derivative (2) or a salt thereof to a dehydrating condensation reaction to produce the ester product (3), and subsequently subjecting the ester product (3) to alkaline or acid hydrolysis.

[Formula 58]

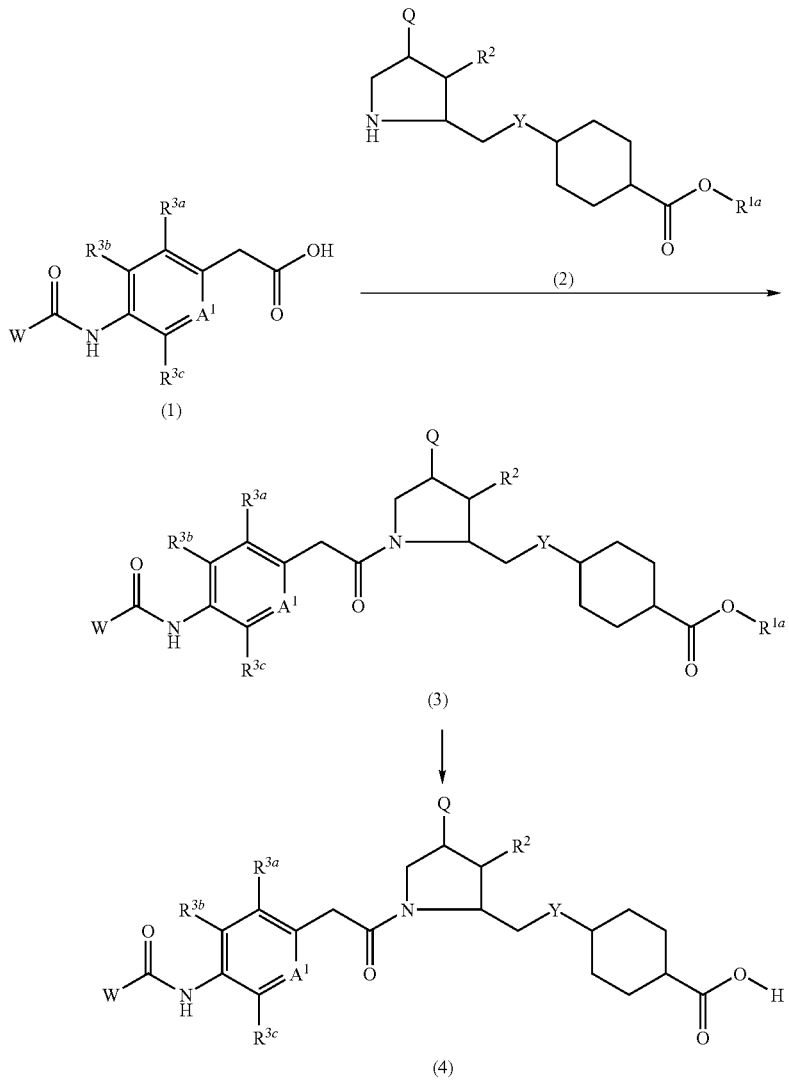

wherein $R^{1a}$ means a lower alkyl group; and $R^2$, $R^{3a}$, $R^{3b}$, $R^{3c}$, Y, Q, $A^1$ and W represent the same as described above.

The condensation reaction between the carboxylic acid derivative (1) and the pyrrolidine derivative (2) or a salt thereof (for example, hydrochloride or the like) may be performed using a known condensation method. The condensing agent may be exemplified by 1-ethyl-3-(3-dimethylaminopropyl)carbodiimide hydrochloride, N,N'-dicyclohexylcarbodiimide, N,N'-carbonyldiimidazole or substances of the same kind, and 1-ethyl-3-(3-dimethylaminopropyl)carbodiimide hydrochloride, N,N'-dicyclohexylcarbodiimide and the like are preferred. For the reaction solvent, an inert halogenated hydrocarbon-based solvent such as methylene chloride, an inert hydrocarbon-based solvent such as toluene, an inert ether-based solvent such as tetrahydrofuran, an inert polar solvent such as N,N'-dimethylformamide, or the like can be used, and methylene chloride, tetrahydrofuran, N,N-dimethylformamide and the like are preferred. The reaction temperature is in the range of −20° C. to the boiling point of the solvent, and is preferably in the range of 0° C. to room temperature. The reaction time is usually about 1 to 24 hours.

In the above condensation reaction, it is preferable to use an organic amine base such as triethylamine or 4-(N,N-dimethylamino)pyridine, in an amount range from 1 to 30 equivalents. Particularly in the case of using a salt of the pyrrolidine derivative (2), it is necessary to use the base in a stoichiometrically equivalent amount or more, in order to neutralize the salt. It is also preferable to use an active esterifying reagent such as 1-hydroxybenzotriazole, in an amount of 0.2 to 1.5 equivalents based on the carboxylic acid derivative (1).

The compound (4) among the compound (I) of the present invention can be produced through alkaline hydrolysis in the case where $R^1$ of the ester product (3) is a lower alkyl group, or through an acid treatment with trifluoroacetic acid or the like in the case where $R^1$ is a tert-butyl group.

Hereinafter, the method for producing the compound (1) and compound (2) used in the production method represented by [Scheme 1], and the method for producing an intermediated used in the production of the compound (2), will be described.

[Scheme 1A]

The carboxylic acid derivative (1) used in the above production method can be produced by the following method.

[Formula 59]

OR

W—CO$_2$H (1A-1)

または +

W—COCl (1A-2)

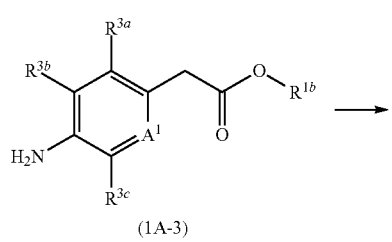

(1A-3)

-continued

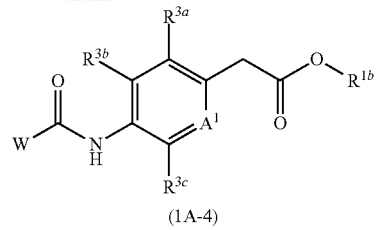

(1A-4)

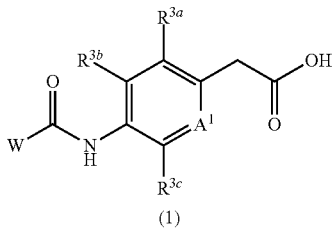

(1)

wherein $R^{1b}$ means a lower alkyl group; and $R^{3a}$, $R^{3b}$, $R^{3c}$, $A^1$ and W represent the same as described above.

The carboxylic acid derivative (1) can be produced by condensing a carboxylic acid (1A-1) or an acid chloride derivative (1A-2) with an aniline derivative (1A-3) to produce an ester product (1A-4), and subjecting this ester product (1A-4) to alkaline hydrolysis or an acid treatment.

In the condensation reaction between the carboxylic acid (1A-1) and the aniline derivative (1A-3), the same condensing agent, reaction solvent, base, and active esterifying reagent as those used in the production of the ester product (3) may be used.

Furthermore, the ester product (1A-4) can also produced by condensing an acid chloride derivative (1A-2) with the aniline derivative (1A-3). As the reaction solvent, an inert halogenated hydrocarbon-based solvent such as methylene chloride, an inert hydrocarbon-based solvent such as toluene, or an inert ether-based solvent such as tetrahydrofuran is preferred. The reaction temperature is in the range of −20° C. to the boiling point of the solvent, and is preferably in the range of room temperature to the boiling point of the solvent. In this reaction, an organic base such as triethylamine may be used. The reaction time is usually about 2 to 24 hours.

The carboxylic acid derivative (1) can be produced by subjecting the ester product (1A-4) to alkaline hydrolysis in the case where $R^{1b}$ is a lower alkyl group, or to an acid treatment in the case where $R^{1b}$ is a tert-butyl group.

The carboxylic acid derivative (1A-1), acid chloride derivative (1A-2) and aniline derivative (1A-3) may be commercially available products, or can be produced by known methods.

[Scheme 2A]

Among the pyrrolidine derivative (2) used in the above production method, a pyrrolidine derivative (2A-5) having an oxygen atom for Y and having a 1,4-trans-cyclohexanecarboxylic acid structure, can be produced by converting a compound (2A-1) to a 4-hydroxypyrrolidine derivative (2A-2) through hydrogenolysis, and subsequently subjecting the 4-hydroxypyrrolidine derivative (2A-2) to the following methods (A) to (C).

[Formula 60]

Method (A)
Method (B)
Method (C)

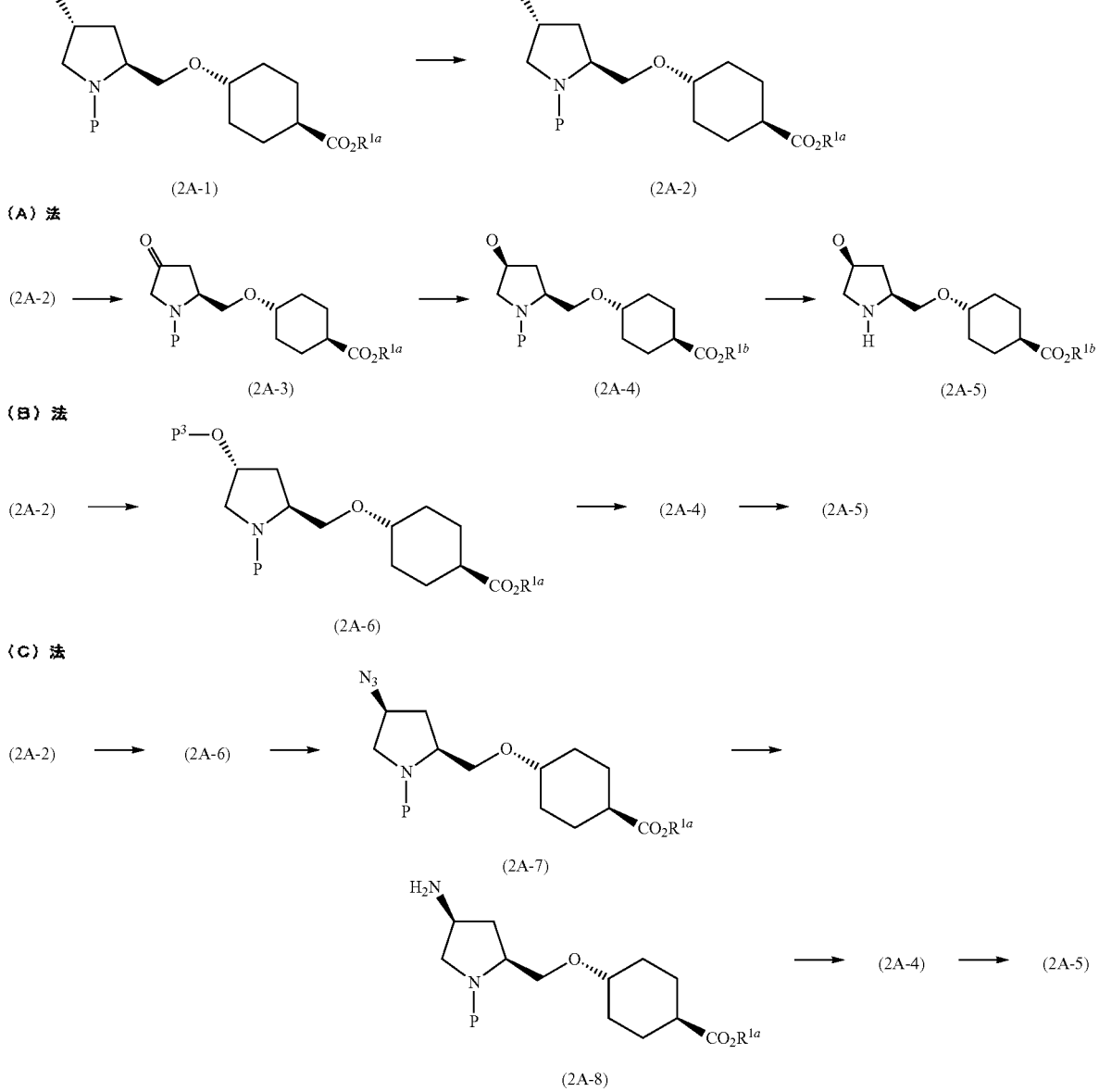

wherein P and P² mean protective groups; P³ means a trifluoromethanesulfonyl group or a methanesulfonyl group; and $R^{1a}$ and Q represent the same as described above.

Descriptions on the protection and deprotection (removal of protective group) used in the production methods of the present invention, are given in Protective Groups in Organic Synthesis (T. W. Greene and P. G. Wuts, John Wiley & Sons, Inc., New York, 1991).

The amine product (2A-5) can be produced by the following method (A) to method (C).

Method (A)

The amine product (2A-5) or a salt thereof can be produced by oxidizing the compound (2A-2) to obtain a 4-oxopyrrolidine product (2A-3), then reducing the imine generated from the reaction between the 4-oxopyrrolidine product (2A-3) and an amine product Q-H (wherein Q means the same as described above), to convert the imine to a compound (2A-4) in a 2,4-cis-specific manner, and subsequently removing the protective group of the compound (2A-4).

The oxidation reaction from the 4-hydroxypyrrolidine derivative (2A-2) to the 4-oxopyrrolidine derivative (2A-3) may be performed using the methods described in the following (a) to (e).

(a) Swern oxidation [method of Giordano, C. et al.; J. Org. Chem., 56(21), 6114-6118 (1991), method of Konradi, A. W., et al.; J. Org. Chem., 57(1), 28-32 (1992)], (b) Oxidation by a radical reaction using hypochloric acid-tempo (2,2,6,6-tetramethyl-1-piperidinyloxy, free radical) [method of Jurczak, J. et al.; Tetrahedron Letters, 34(44), 7107-7110 (1993)], (c) Oxidation using DMSO-cyanuric chloride [method of De Luca, L., et al.; J. Org. Chem., 66(23), 7907-7909 (2001), method of De Luca, L., et al.; Org. Letters, 3(19), 3041-3043 (2001)], (d) Oxidation using sulfur trioxide-pyridine complex [method of Konradi, A. W., et al.; J. Org. Chem., 55(15), 4506-4508 (1990)], and (e) Methods of [method of Takemoto, Y., et al.; Chem. Pharm. Bull., 39(9), 2425-2428 (1991)].

The reducing agent for the imine generated from the reaction between the 4-oxopyrrolidine product (2A-3) and the amine product Q-H (wherein Q means the same as described above), is preferably sodium triacetoxyborohydride, or sodium cyanoborohydride. As the reference material for the reduction reaction using sodium triacetoxyborohydride, the method of Gordon, D. W., et al. [Bioorg. Med. Chem. Lett., 5(1), 47-50 (1995)] may be mentioned, and as the reference material for the reduction reaction using sodium cyanoborohydride, the method of Kelley, J. L., et al. [J. Med. Chem., 33(7), 1910-1914 (1990)] may be mentioned.

The amine product (2A-5) or a salt thereof can be produced by subjecting the compound (2A-4) to hydrogenolysis in the case where the protective group P is a benzyloxycarbonyl (cbz) group, or to an acid treatment in the case where the protective group P is a tert-butoxycarbonyl (Boc) group.

Method (B)

The amine product (2A-5) or a salt thereof can be produced by treating the 4-hydroxypyrrolidine derivative (2A-2) with trifluoromethanesulfonic anhydride or methanesulfonyl chloride in the presence of a base to convert the derivative to a compound (2A-6), subsequently treating the compound (2A-6) with the amine product Q-H in the presence of an organic base such as diisopropylethylamine to derive a compound (2A-4), and then removing the protective group of the compound (2A-4).

As the reference material for the reaction to produce the compound (2A-4) from the 4-hydroxypyrrolidine derivative (2A-2), the method of Williams, M. A. et al. [J. Org. Chem., 59, 3616-3625 (1994)] may be mentioned.

The amine product (2A-5) or a salt thereof can be produced by subjecting the compound (2A-4) to hydrogenolysis in the case where the protective group P is a cbz group, or to an acid treatment in the case where the protective group P is a Boc group.

Method (C)

The amine product (2A-5) or a salt thereof can be produced by deriving an amino product (2A-8) from the compound (2A-6) which has been converted from the 4-hydroxypyrrolidine derivative (2A-2) as described above, via an intermediate of azide product (2A-7), forming a nitrogen-containing heterocyclic group (Q) such as a piperidine ring, from the amino product (2A-8), converting the heterocyclic group to the compound (2A-4), and then removing the protective group of the compound (2A-4).

As the reference material for the production of the azide product (2A-7) and the amino product (2A-8), there may be mentioned "JIKKENKAGAKUKOUZA" (4$^{th}$ edition, Vol. 20, edited by the Chemical Society of Japan, Maruzen Publishing Co.) "Organic Synthesis II: Alcohol/Amine, p 279-p 282 and p 415-p 424." With regard to the formation of the nitrogen-containing heterocyclic group (O), in the case where Q is a piperidinyl group, the method of Tseng, S.-L., et al. [Tetrahedron Asymmetry, 16, 773-782 (2005)] may be mentioned; in the case where Q is a 1,1-dioxo-1$\lambda^6$-1,2-isothiazolidinyl group, a 2-oxopyrrolidinyl group or a 2-oxazolidinyl group, the method of Alcaraz, L., et al. [Bioorg. Med. Chem. Lett., 13, 4043-4046 (2003)] may be mentioned; and in the case where Q is an imidazolyl group, the method of Perry, M. C., et al. [J. Am. Chem. Soc., 125, 113-123 (2003)] may be mentioned.

The amine product (2A-5) or a salt thereof can be produced by subjecting the compound (2A-4) to hydrogenolysis in the case where the protective group P is a cbz group, or to an acid treatment in the case where the protective group P is a Boc group.

[Scheme 2B]

The compound (2A-1) used in the above [Scheme 2A] can be produced by the following method.

[Formula 61]

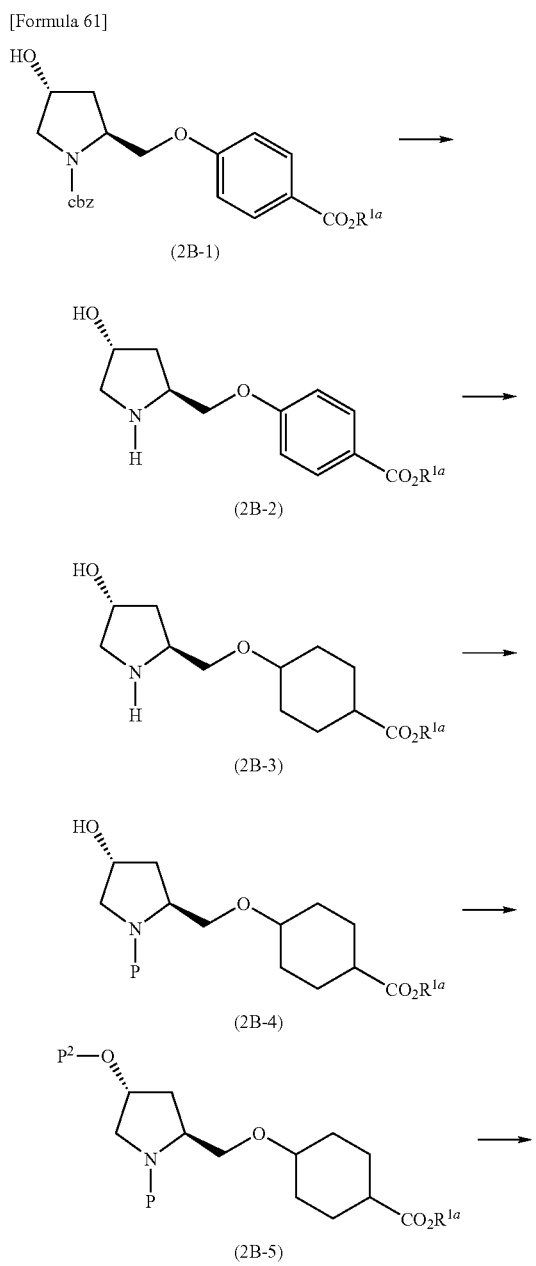

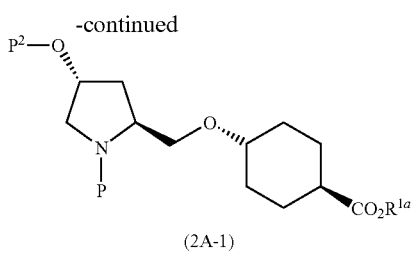

(2A-1)

wherein $R^{1a}$, P and $P^2$ represent the same as described above.

Specifically, the trans-cyclohexane derivative (2A-1) can be produced from a compound (2B-1) according to a method described in patent document (WO 2004/099136).

The compound (2B-1) (see WO 2004/099136) is converted to an amino product (2B-2) through hydrogenolysis, and subsequently the benzene ring of the amino product (2B-2) can be subjected to hydrogenolysis to derive a cyclohexane derivative (2B-3) (a mixture of cis:trans=about 4:1).

The catalyst in the above hydrogenolysis may be exemplified by palladium-carbon, platinum oxide, strontium carbonate, rhodium/alumina, rhodium/carbon or the like, and rhodium/alumina is preferred. The amount of use of the catalyst is in the range of 1 to 50% (W/W), and preferably in the range of 3 to 20% (W/W), based on the amino product (2B-2). The hydrogen pressure is in the range of normal pressure to 10 MPa, and preferably in the range of normal pressure to 1.5 MPa. The reaction temperature is in the range of 0 to 100° C., and preferably in the range of 20 to 60° C. The reaction time is usually about 3 to 24 hours. The solvent may be exemplified by an alcohol-based solvent such as ethanol or methanol, or an ether-based solvent such as tetrahydrofuran, and ethanol or methanol is preferred. In this hydrogenolysis, an acid such as acetic acid or trifluoroacetic acid may be added to the reaction solvent.

Next, a compound (2B-4) (a mixture of cis:trans=about 4:1) is produced from a cyclohexane derivative (2B-3) (a mixture of cis:trans=about 4:1), by introducing a protective group (P) to the nitrogen atom. The protective group P is preferably a carbonate-based protective group, and more preferably a Boc group or a cbz group. As the reagent for introducing Boc or introducing cbz, an acid anhydride such as di-tert-butyl dicarbonate, or an acyl halide such as benzyloxy carbonyl chloride can be used. The reaction solvent may be exemplified by an inert halogenated hydrocarbon-based solvent such as methylene chloride, an inert hydrocarbon-based solvent such as toluene, an inert ether-based solvent such as tetrahydrofuran, or a mixed-solvent of water and an inert polar solvent such as acetonitrile, with a mixed-solvent of water and acetonitrile being preferred. The base is preferably an organic amine base such as triethylamine, or an inorganic base such as potassium carbonate. The reaction temperature is in the range of –20 to 60° C., and preferably in the range of 0° C. to room temperature. The reaction time is usually about 0.5 to 6 hours.

Next, a compound (2B-5) (a mixture of cis:trans=about 4:1) can be produced by protecting the hydroxy group of the compound (2B-4).

As a protective group ($P^2$) of the hydroxy group is preferably a benzyloxymethyl (BOM) group. As a reagent for introducing BOM, benzyl chloromethyl ether can be used. The reaction solvent is preferably a halogenated hydrocarbon-based solvent such as dichloromethane or dichloroethane. The base is preferably an organic base such as triethylamine or diisopropylethylamine. The amount of use of the base is preferably in the range of 1- to 2-fold molar equivalents based on benzyl chloromethyl ether. The reaction temperature is in the range of –20° C. to the boiling point of the solvent, and preferably in the range of 0 to 50° C. The reaction time is usually about 1 to 5 hours.

Subsequently, the compound (2B-5) which is a mixture of cis:trans=about 4:1, is converted to a mixture of cis:trans=about 1:1 by isomerizing the compound using a base, and then the product is separated and purified by chromatography, to derive a trans-cyclohexane derivative (2A-1).

As the base used in the isomerization reaction for the compound (2B-5) (a mixture of cis:trans=about 4:1), an alkali metal hydride such as sodium hydride, potassium hydride or lithium hydride may be mentioned, and sodium hydride and lithium hydride are preferred. The reaction solvent is preferably a mixed-solvent in which an inert polar solvent such as N,N-dimethylformamide, N-methyl-2-pyrrolidone or DMSO, is co-present with 1- to 3-fold molar equivalent of an alcohol corresponding to $R^{1a}$ ($R^{1a}$—OH). The reaction temperature is in the range of –20 to 50° C., and preferably in the range of 0 to 25° C. The reaction time is usually completed within about 1 to 3 hours.

Production by separation of the trans-cyclohexane derivative (2A-1) from the compound (2A-5) which is a mixture of cis- and trans-isomers, may be performed, for example, using chromatography using a support such as silica gel. In this purification process, the cis-type isomer can also be isolated and purified. As the separation and purification apparatus, typical column chromatography, liquid chromatography (HPLC) or medium pressure preparative chromatography can be used, and medium pressure preparative chromatography is preferred.

[Scheme 2C]

Among the pyrrolidine derivative (2) which is one of the raw materials for formula (I), a pyrrolidine derivative (2C-10) having a trans-cyclohexane structure, wherein Y is an oxygen atom and $R^2$ is a lower alkoxy group, can be produced by a method represented in the following [Scheme 2C].

[Formula 62]

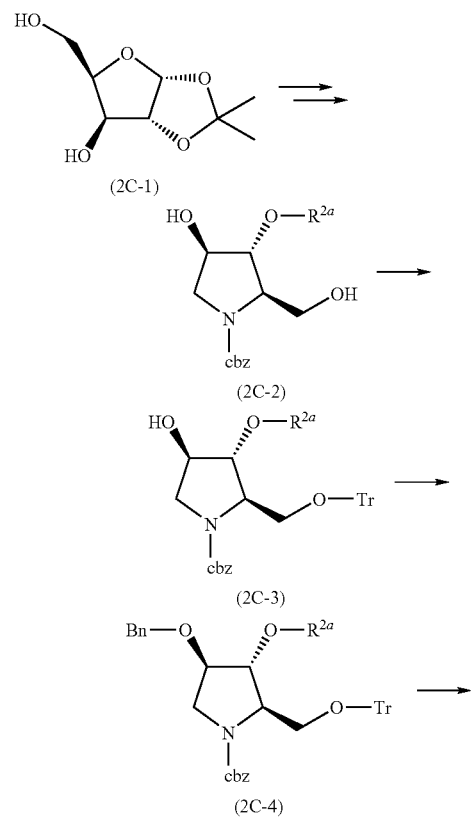

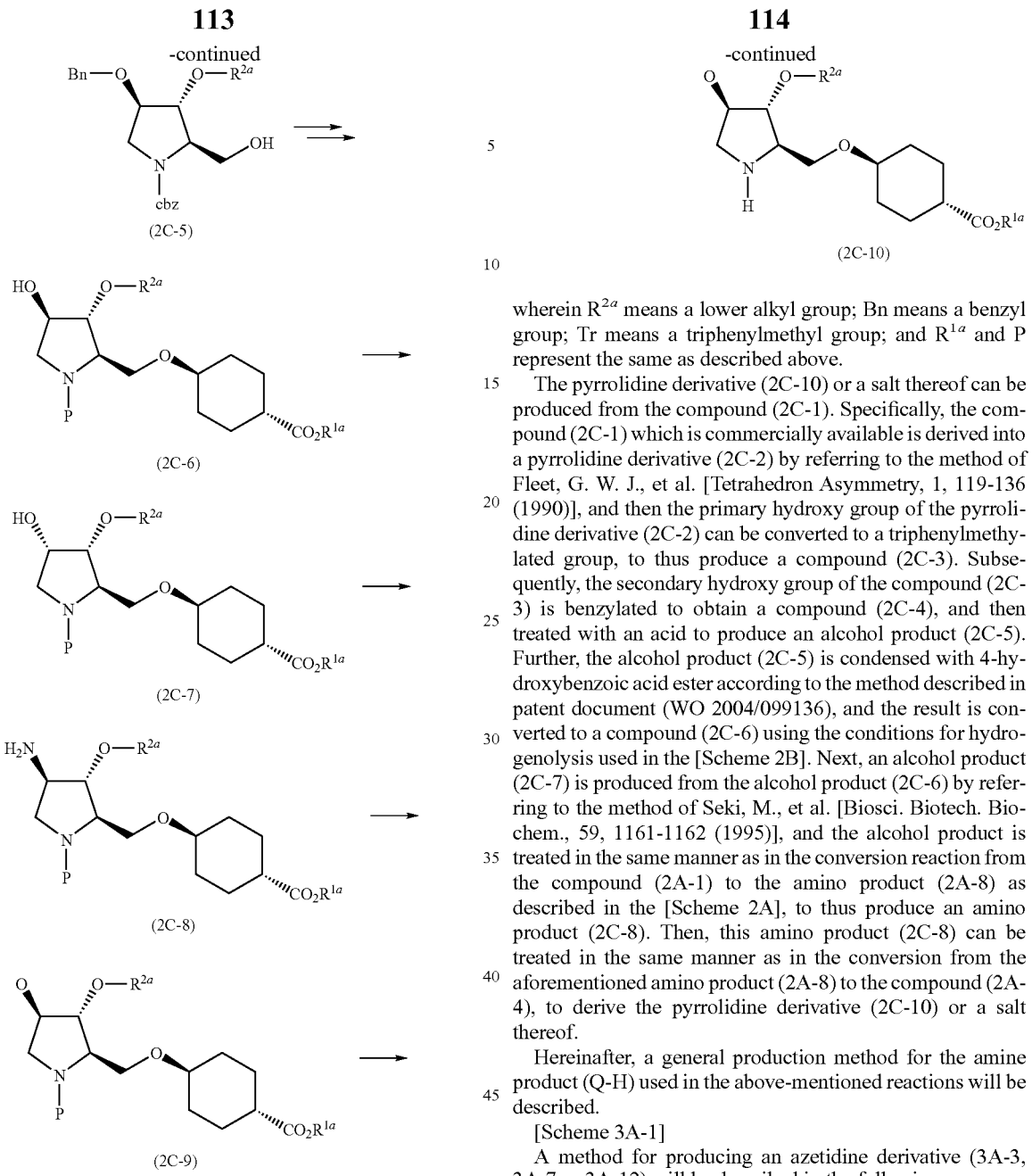

wherein $R^{2a}$ means a lower alkyl group; Bn means a benzyl group; Tr means a triphenylmethyl group; and $R^{1a}$ and P represent the same as described above.

The pyrrolidine derivative (2C-10) or a salt thereof can be produced from the compound (2C-1). Specifically, the compound (2C-1) which is commercially available is derived into a pyrrolidine derivative (2C-2) by referring to the method of Fleet, G. W. J., et al. [Tetrahedron Asymmetry, 1, 119-136 (1990)], and then the primary hydroxy group of the pyrrolidine derivative (2C-2) can be converted to a triphenylmethylated group, to thus produce a compound (2C-3). Subsequently, the secondary hydroxy group of the compound (2C-3) is benzylated to obtain a compound (2C-4), and then treated with an acid to produce an alcohol product (2C-5). Further, the alcohol product (2C-5) is condensed with 4-hydroxybenzoic acid ester according to the method described in patent document (WO 2004/099136), and the result is converted to a compound (2C-6) using the conditions for hydrogenolysis used in the [Scheme 2B]. Next, an alcohol product (2C-7) is produced from the alcohol product (2C-6) by referring to the method of Seki, M., et al. [Biosci. Biotech. Biochem., 59, 1161-1162 (1995)], and the alcohol product is treated in the same manner as in the conversion reaction from the compound (2A-1) to the amino product (2A-8) as described in the [Scheme 2A], to thus produce an amino product (2C-8). Then, this amino product (2C-8) can be treated in the same manner as in the conversion from the aforementioned amino product (2A-8) to the compound (2A-4), to derive the pyrrolidine derivative (2C-10) or a salt thereof.

Hereinafter, a general production method for the amine product (Q-H) used in the above-mentioned reactions will be described.

[Scheme 3A-1]

A method for producing an azetidine derivative (3A-3, 3A-7 or 3A-12) will be described in the following.

[Formula 63]

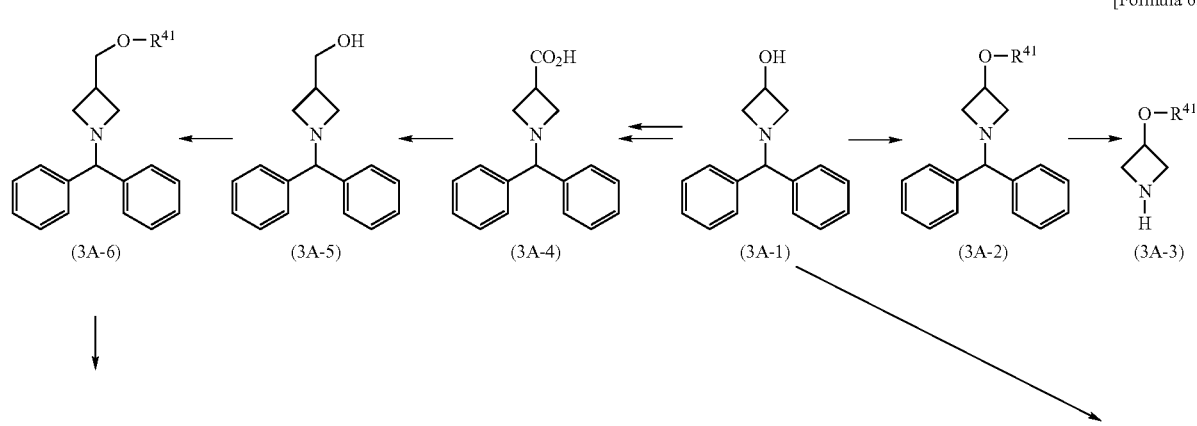

-continued

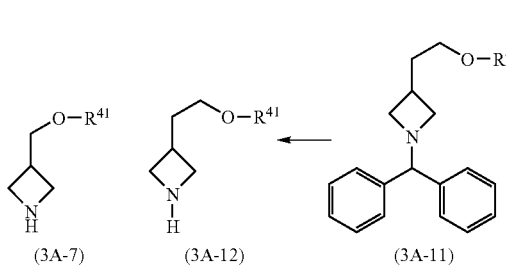
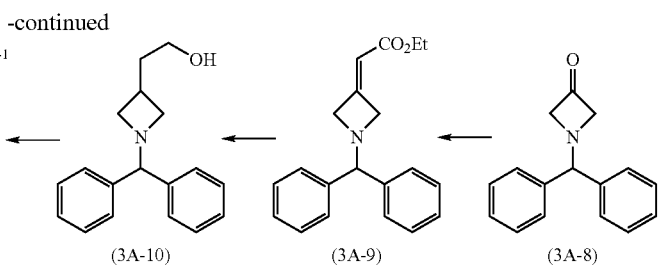

wherein R[41] means a lower alkyl group.

(1) The 3-alkoxyazetidine derivative (3A-3) or a salt thereof can be produced according to the method of Arthur, G. et al. [J. Org. Chem., 37, 3953-3955 (1972)], by alkylating 3-hydroxy-1-benzhydrylazetidine (3A-1) in the presence of a base to obtain a compound (3A-2), and subsequently removing the benzhydryl group through hydrogenolysis.

The base used in the above alkylation is preferably an alkali metal hydride such as sodium hydride or lithium hydride. The alkylating reagent used is preferably a halogenated alkyl compound such as iodomethane or iodoethane. The reaction temperature is in the range of −20 to 60° C., and preferably 0° C. to room temperature. The reaction time is usually about 1 to hours. The catalyst used in the hydrogenolysis may be exemplified by palladium-carbon, platinum oxide or palladium hydroxide, and is preferably palladium-carbon or palladium hydroxide. The reaction solvent may be exemplified by an alcohol-based solvent such as ethanol or methanol, or an ether-based solvent such as tetrahydrofuran, and ethanol or methanol is preferred. The hydrogen pressure is in the range of normal pressure to 10 MPa, and preferably in the range of normal pressure to 1.5 MPa. The reaction temperature is in the range of 0 to 100° C., and preferably in the range of 20 to 60° C. The reaction time is usually about 3 to 24 hours. When the hydrogenolysis is performed in a reaction solvent in the co-presence of an inorganic acid such as hydrochloric acid, or an organic acid such as acetic acid or trifluoroacetic acid, an inorganic acid salt or an organic acid salt of the 3-alkoxyazetidine derivative (3A-3) can be obtained. Furthermore, the 3-alkoxyazetidine derivative (3A-3) or a salt thereof can also be produced through alkylation using the reductive etherification reaction of Sassaman, M. B., et al. [J. Org. Chem., 52, 4314-4319 (1987)], and subsequent hydrogenolysis.

(2) The 3-alkoxymethylazetidine derivative (3A-7) or a salt thereof is produced as follows. According to the method of Arthur, G., et al. [J. Org. Chem., 37, 3953-3955 (1972)], the 3-position of 3-hydroxy-1-benzhydrylazetidine (3A-1) is cyanogenated and hydrolyzed to convert the compound to a carboxylic acid derivative (3A-4). Then, the carboxylic acid moiety is reduced with lithium aluminum hydride or diborane-dimethyl sulfide complex to derive a 3-hydroxymethyl derivative (3A-5). This derivative is treated in the same manner as in the alkylation of 3-hydroxy-1-benzhydrylazetidine (3A-1) to obtain an alkoxymethyl product (3A-6), and then the benzhydryl group is removed by hydrogenolysis, to produce the target compound.

(3) The 3-(2-alkoxy)ethylazetidine derivative (3A-12) or a salt thereof can be produced according to the method of Matassa, V. G., et al. (WO 93/18029), by converting 3-hydroxy-1-benzhydrylazetidine (3A-1) to a ketone product (3A-8) through Swern oxidation, then deriving thereform an α,β-unsaturated ester product (3A-9) through the Wittig-Horner-Emmons reaction, converting the compound (3A-9) to an alcohol product (3A-10) through reduction with lithium aluminum hydride, treating this alcohol product in the same manner as in the alkylation of 3-hydroxy-1-benzhydrylazetidien (3A-1) to convert the alcohol product to a 3-(2-alkoxyethyl) derivative (3A-11), and then subjecting the derivative (3A-11) to hydrogenolysis.

[Scheme 3A-2]

An azetidine derivative (3A-15a, 3A-15b or 3A-15c) can be produced by converting the hydroxy group of the alcohol product (3A-1, 3A-5 or 3A-10) shown in the above [Scheme 3A-1] to an amino group which may be substituted, a piperidinyl group or a morpholinyl group using the conditions of the methods (A) to (C) shown in the [Scheme 2A].

[Formula 64]
Method (A) OR
Method (B)
Method (C)

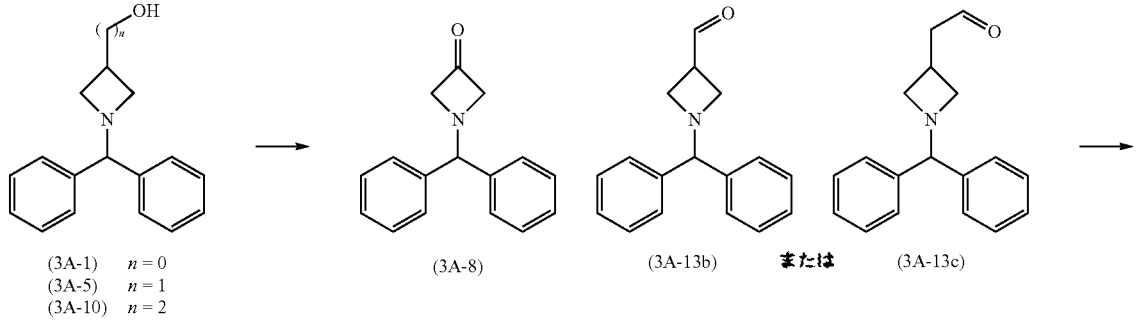

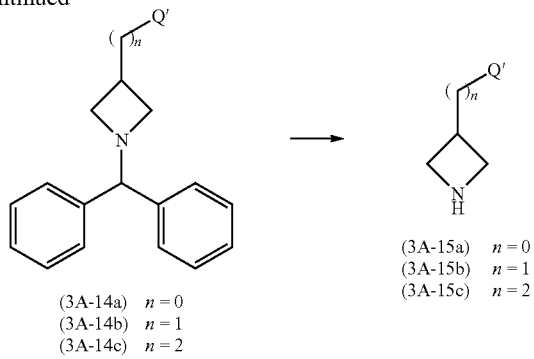

(3A-14a) n = 0
(3A-14b) n = 1
(3A-14c) n = 2

(3A-15a) n = 0
(3A-15b) n = 1
(3A-15c) n = 2

(B) 法

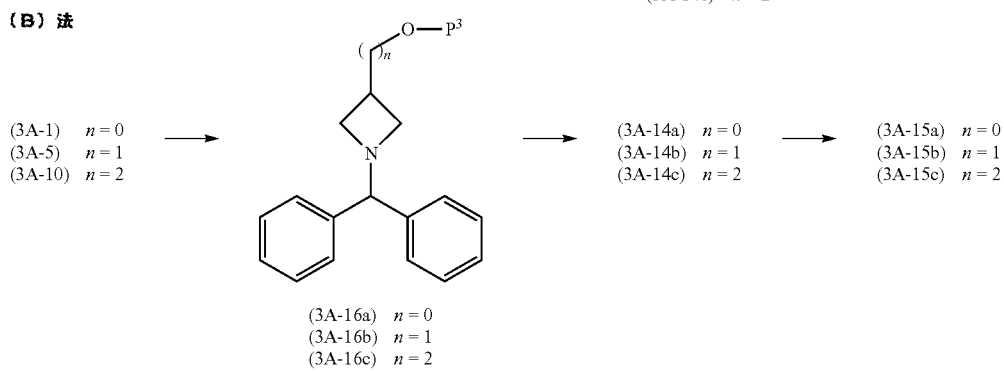

(3A-1) n = 0
(3A-5) n = 1
(3A-10) n = 2

(3A-16a) n = 0
(3A-16b) n = 1
(3A-16c) n = 2

(3A-14a) n = 0
(3A-14b) n = 1
(3A-14c) n = 2

(3A-15a) n = 0
(3A-15b) n = 1
(3A-15c) n = 2

(C) 法

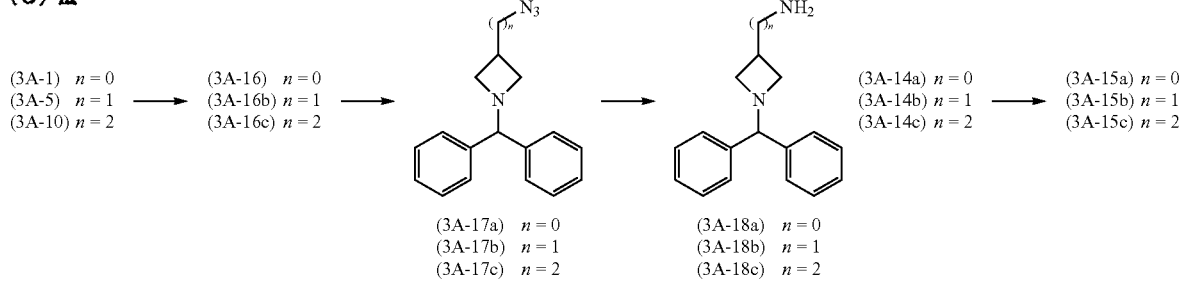

(3A-1) n = 0
(3A-5) n = 1
(3A-10) n = 2

(3A-16) n = 0
(3A-16b) n = 1
(3A-16c) n = 2

(3A-17a) n = 0
(3A-17b) n = 1
(3A-17c) n = 2

(3A-18a) n = 0
(3A-18b) n = 1
(3A-18c) n = 2

(3A-14a) n = 0
(3A-14b) n = 1
(3A-14c) n = 2

(3A-15a) n = 0
(3A-15b) n = 1
(3A-15c) n = 2 wherein $Q^1$ means an amino group which may be substituted, a piperidinyl group or a morpholinyl group; n means 0, 1 or 2; and $P^3$ represents the same as described above.

[Scheme 3B]

A 2-alkoxymethylazetidine derivative (3B-4) can be produced by the following method.

[Formula 65]

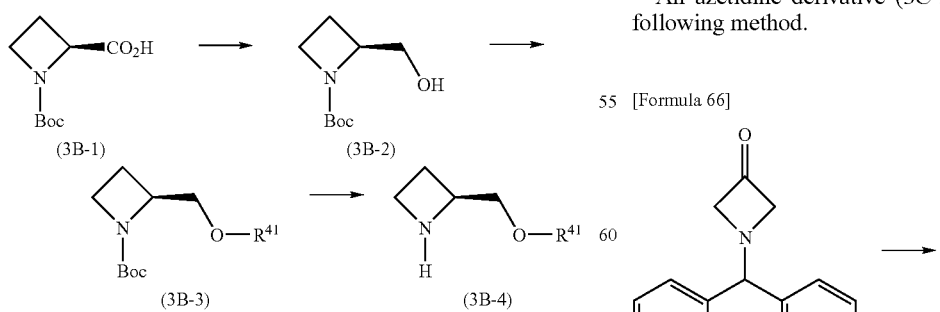

(3B-1)   (3B-2)

(3B-3)   (3B-4)

wherein $R^{41}$ represents the same as described above.

The 2-alkoxymethylazetidine derivative (3B-4) or a salt thereof can be produced by reducing a carboxylic acid (3B-1) with a diborane-dimethyl sulfide complex according to the method of Dolle, F., et al. [J. Med. Chem., 42, 2251-2259 (1999)] to an alcohol product (3B-2), treating the alcohol product (3B-2) in the same manner as in the alkylation of 3-hydroxy-1-benzhydrylazetidine (3A-1) shown in the [Scheme 3A-1] to derive a 2-lower alkoxymethyl derivative (3B-3), and then treating the derivative with an acid.

[Scheme 3C]

An azetidine derivative (3C-3) can be produced by the following method.

[Formula 66]

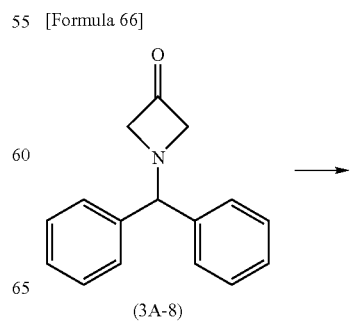

(3A-8)

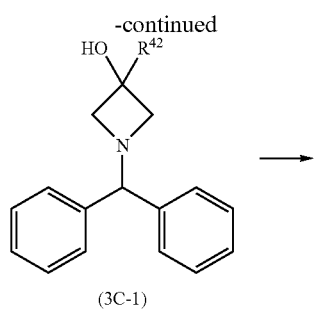

(3C-1)

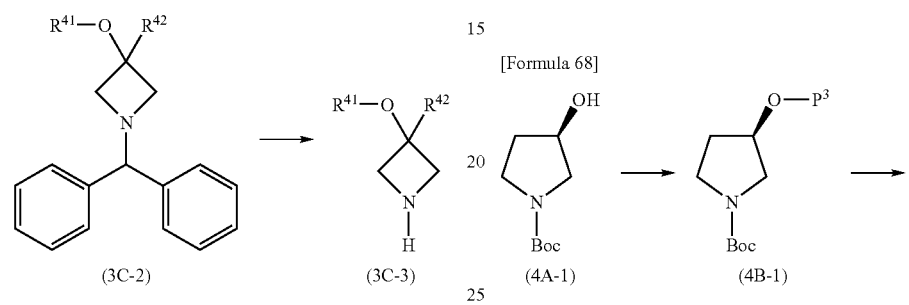

wherein $R^{42}$ means a lower alkyl group; and $R^{41}$ represents the same as described above.

The azetidine derivative (3C-3) or a salt thereof can be produced by converting a 3-oxo product (3A-8) to a compound (3C-1) through a treatment with a Grignard reagent such as methylmagnesium bromide according to the article of Chatterjee, S. S., et al. [Tetrahedron Lett., 50, 5063-5064 (1972)], subsequently treating the compound in the same manner as in the alkylation of 3-hydroxy-1-benzhydrylazetidine (3A-1) shown in the [Scheme 3A-1] to derive a compound (3C-2), and then subjecting the compound to hydrogenolysis.

[Scheme 4A]

A pyrrolidine derivative (4A-3) can be produced by the following method.

[Formula 67]

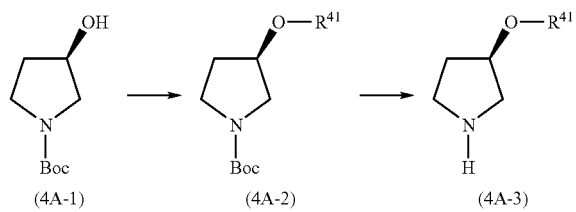

wherein $R^{41}$ represents the same as described above.

The pyrrolidine derivative (4A-3) or a salt thereof can be produced by treating an alcohol product (4A-1) which is commercially available, in the same manner as in the alkylation of 3-hydroxy-1-benzhydrylazetidine (3A-1) shown in the [Scheme 3A-1] to obtain a compound (4A-2), and then treating the compound with an acid.

The enantiomer of the pyrrolidine derivative (4A-3) can be produced in the same manner, from the enantiomer of the alcohol product (4A-1) which is commercially available.

[Scheme 4B]

A pyrrolidine derivative (4B-3) can be produced by the following method.

[Formula 68]

wherein $R^{44}$ means an amino group which may be substituted with one or two lower alkyl substituents, or a nitrogen-containing heterocyclic group which may be substituted with one or a plurality of substituents, and has a nitrogen atom as the bonding site; and $P^3$ represents the same as described above.

The pyrrolidine derivative (4B-3) or a salt thereof can be produced by converting the alcohol product (4A-1) to a compound (4B-2) applying mutatis mutandis the reaction conditions for the method (C) shown in the [Scheme 2A], and then treating the obtained compound with an acid.

The enantiomer of the pyrrolidine derivative (4BA-3) can be produced in the same manner as described above, from the enantiomer of the alcohol product (4A-1) which is commercially available.

[Scheme 4C]

A pyrrolidine derivative (4C-4 or 4C-6) can be produced by the following method.

[Formula 69]

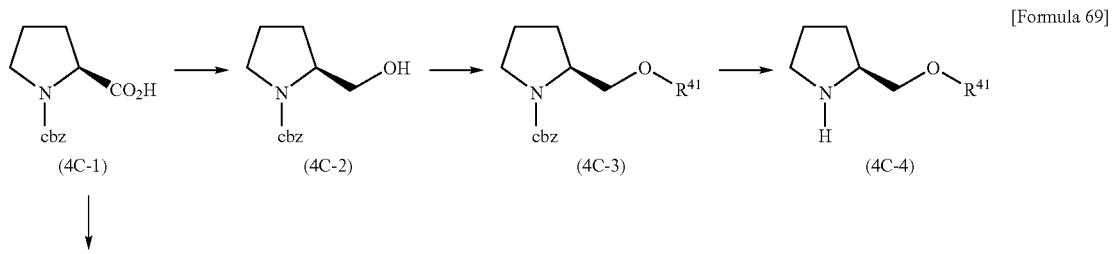

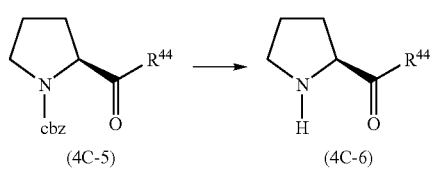

wherein $R^{41}$ and $R^{44}$ represent the same as described above.

The pyrrolidine derivative (4C-4) or a salt thereof can be produced by treating a proline derivative (4C-1) which is commercially available, in the same manner as in the alkylation of 3-hydroxy-1-benzhydrylazetidine (3A-1) shown in the [Scheme 3A-1] to obtain a compound (4C-3), and then subjecting the obtained compound to hydrogenolysis.

The pyrrolidine derivative (4C-6) or a salt thereof can be produced by converting a carboxylic acid (4C-1) and an amine ($R^{44}$—H) to an amide product (4C-5) using a reaction for forming an amide bond in general, and then subjecting the amide product to hydrogenolysis.

The enantiomers of the compounds (4C-4 and 4C-6) can be produced in the same manner, from the enantiomer of the proline derivative (4C-1) which is commercially available.

[Scheme 4D]

A pyrrolidine derivative (4D-5, 4D-10, 4D-14 or 4D-19) can be produced by the method shown in the following [Scheme 4D].

[Formula 70]

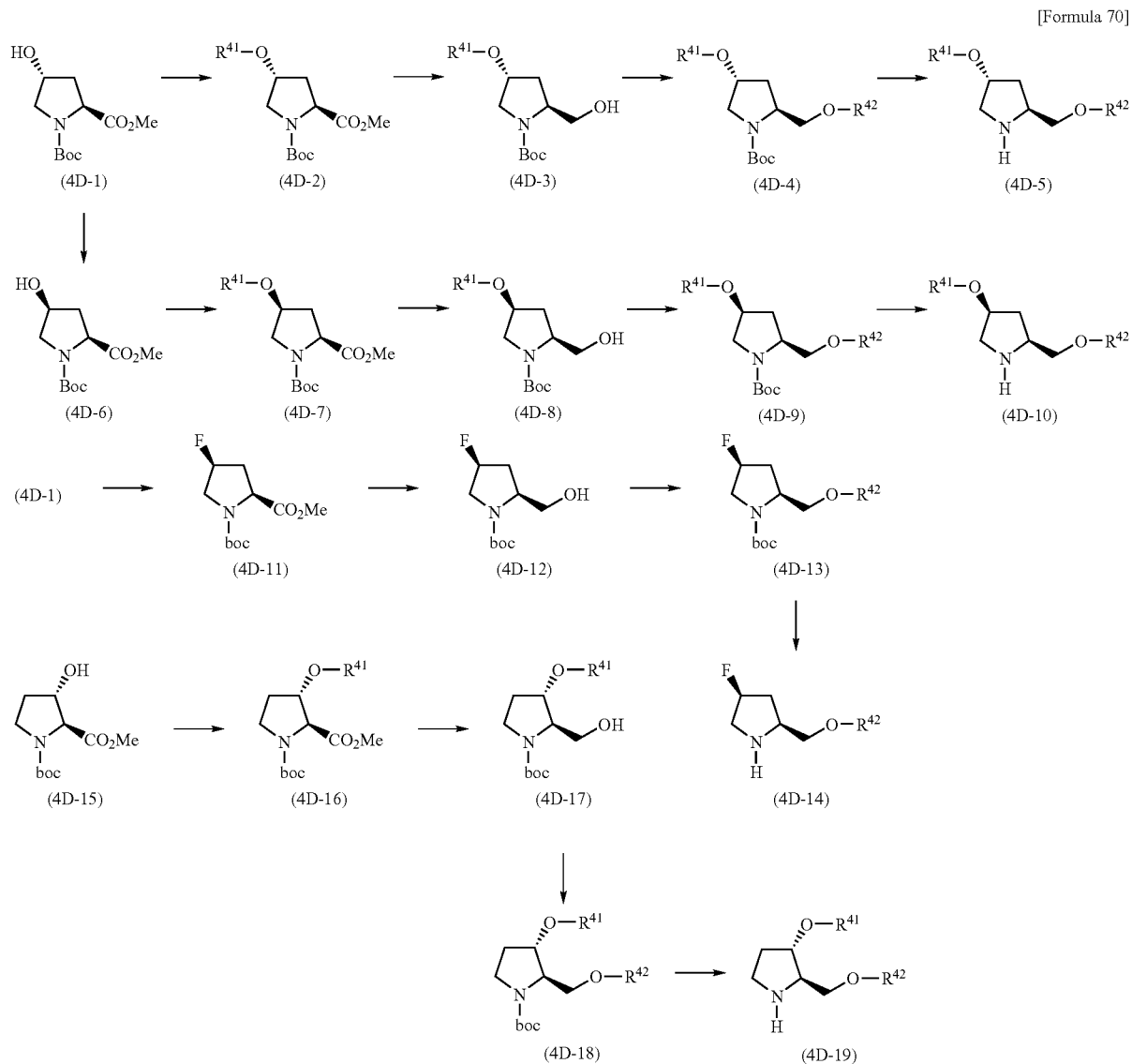

wherein $R^{41}$ and $R^{42}$ represent the same as described above.

(1) The pyrrolidine derivative (4D-5) or a salt thereof can be produced by treating a hydroxyproline derivative (4D-1) which is commercially available, in the same manner as in the alkylation of 3-hydroxy-1-benzhydrylazetidine (3A-1) shown in the [Scheme 3A-1] to produce a compound (4D-2), subjecting the compound (4D-2) to alkaline hydrolysis and then to reduction with a diborane-dimethyl sulfide complex, to produce an alcohol product (4D-3), alkylating the alcohol product (4D-3) under the same conditions as in the alkylation of the hydroxyproline derivative (4D-1), and then treating the resultant with an acid.

(2) The 4S-coordinated pyrrolidine derivative (4D-10) or a salt thereof can be produced by converting a 4R-configration compound (4D-1) to a 4S-configration alcohol product (4D-6) according to the method of Seki, M., et al. [Biotech. Biochem. 59, 1161-1162 (1995)], and performing the alkylation and acid treatment employed in the production of the pyrrolidine derivative (4D-5).

(3) The pyrrolidine derivative (4D-14) or a salt thereof can be produced by fluorinating the alcohol product (4D-1) using an electrophilic fluorinating reagent such as N,N-diethylaminosulfur trifluoride to derive a fluorinated product (4D-11), and then treating the compound in the same manner as in the production of the pyrrolidine derivative (4D-5).

(4) The pyrrolidine derivative (4D-19) or a salt thereof can be produced by treating a compound (4D-15) which is commercially available, in the same manner as in the production of the pyrrolidine derivative (4D-5).

The stereoisomers of the pyrrolidine derivatives (4D-5, 4D-10, 4D-14 and 4D-19) can be produced in the same manner, from the stereoisomers of the compounds (4D-1 and 4D-15) which are commercially available.

[Scheme 4E]

A pyrrolidine derivative (4E-4 or 4E-8) can be produced by the following method.

[Formula 71]

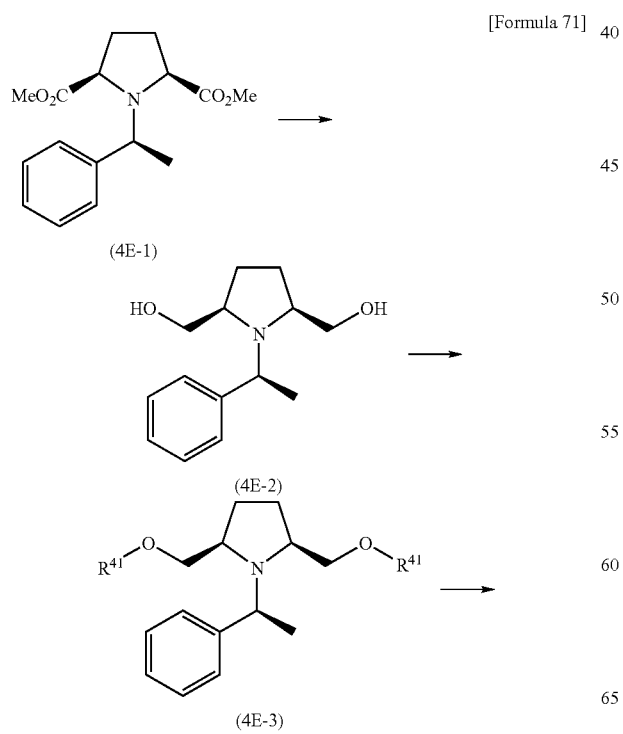

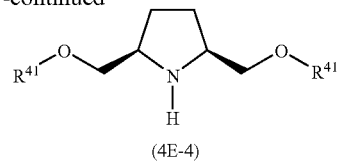

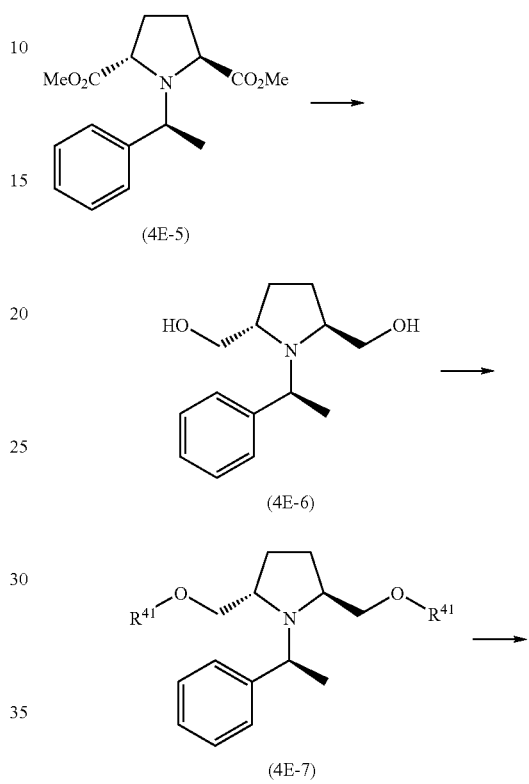

wherein $R^{41}$ represents the same as described above.

The pyrrolidine derivative (4E-4) or a salt thereof can produced by reducing an ester product (4E-1) which has been produced according to the method of Yamamoto, Y., et al. [Synthesis, 298-302 (1993)], with lithium aluminum hydride to obtain an alcohol product (4E-2), subsequently treating the alcohol product in the same manner as in the alkylation of 3-hydroxy-1-benzhydrylazetidine (3A-1) shown in the [Scheme 3A-1], and subjecting the resulting compound (4E-3) to hydrogenolysis.

The pyrrolidine derivative (4E-8) can also be produced from a compound (4E-5) in the same manner.

The enantiomer of the pyrrolidine derivative (4E-8) can be produced in the same manner, from the enantiomer of the compound (4E-5) described in the article of Yamamoto, Y., et al.

[Scheme 4F]

A pyrrolidine derivative (4F-3 or 4F-7) can be produced by the following method.

[Formula 72]

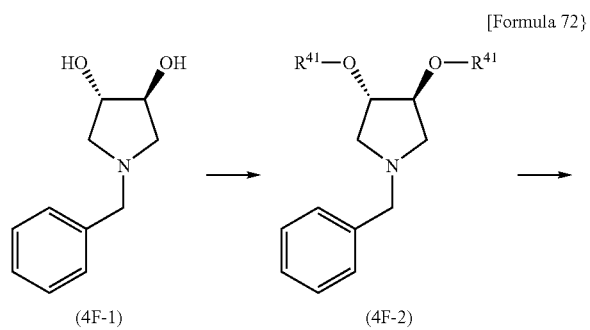

(4F-1)  (4F-2)

(4F-3)

(4F-4)  (4F-5)

(4F-6)  (4F-7)

wherein $R^{41}$ represents the same as described above.

The pyrrolidine derivative (4F-3) or a salt thereof can be produced by treating a diol product (4F-1) in the same manner as in the alkylation of 3-hydroxy-1-benzhydrylazetidine (3A-1) shown in the [Scheme 3A-1] to obtain a compound (4F-2), and then subjecting the obtained compound to hydrogenolysis.

The pyrrolidine derivative (4F-7) can also be produced from a compound (4F-4) in the same manner.

The diol product (4F-5) can be produced from a 3,4-dehydropyrrolidine derivative (4F-4) which is commercially available, according to the method of Goli, D. M., et al. [Carbohydr. Res., 259, 219-241 (1994)] through osmium tetroxide oxidation using N-methylmorpholine N-oxide as a co-oxidizing agent.

The enantiomer of the pyrrolidine derivative (4F-3) can be produced in the same manner, from the enantiomer of the diol product (4F-1) which is commercially available.

[Scheme 4G]

An amine product (4G-2) can be produced by the following method.

[Formula 73]

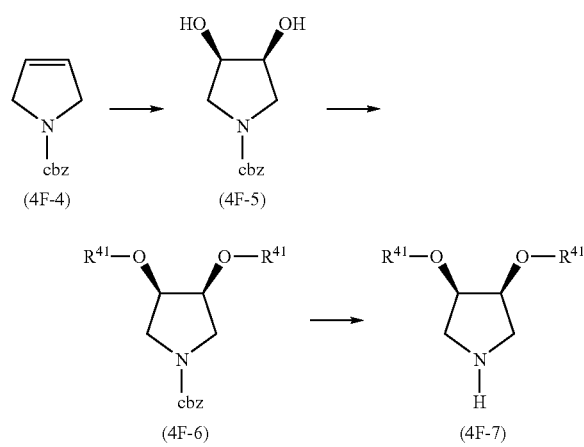

(4F-5)  (4G-1)  (4G-2)

wherein $R^{45}$ represents $CH_2$, CHMe or $CMe_2$; and $R^{41}$ represents the same as described above.

The amine product (4G-2) or a salt thereof can be produced by converting the diol product (4F-5) to a compound (4G-1) through cyclic cyclic-acetal formation reactionization, and then subjecting the obtained compound to hydrogenolysis.

The following documents (1) to (4) may be referred to for the conditions of the above-mentioned reaction.

(1) Method of Gras J.-L., et al. [Synth. Commun., 1992 22(3), 405-409.], method of Baum K., et al. [Tetrahedron Lett., 1992, 33(16), 2141-2144.], (2) method of Bradshaw J. S., et al. [J. Org. Chem., 1992, 57(23), 6112-6118.], (3) method of Boynton J. A., et al. [J. Chem. Res., 1992, (11), 378-379.], or (4) method of Nazhaoui M. et al. [Tetrahedron Lett., 1993, 34(8), 1287-1290.].

[Scheme 5A-1]

A piperidine derivative (5A-4) can be produced by the following method.

[Formula 74]

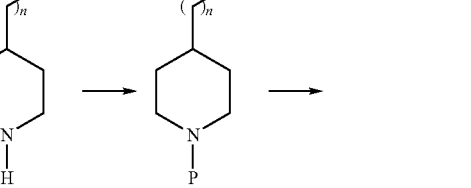

(5A-1)  (5A-2)

(5A-3)  (5A-4)

wherein $R^{51}$ means a lower alkyl group or a phenyl group which may be substituted; and P and n represent the same as described above.

The piperidine derivative (5A-4) or a salt thereof can be produced by converting a 4-(hydroxy-lower alkyl)piperidine derivative (5A-1) which is commercially available, to a compound (5A-2) through the introduction of cbz or Boc, subsequently treating the compound in the same manner as in the alkylation of 3-hydroxy-1-benzhydrylazetidine (3A-1) shown in the [Scheme 3A-1] to derive a compound (5A-3), and then subjecting the compound to hydrogenolysis or acid treatment.

[Scheme 5A-2]

A piperidine derivative (5A-7a, 5A-7b or 5A-7c) can be produced by the following method.

[Formula 75]

Method (A) OR
Method (B)
Method (C)

(A) 法

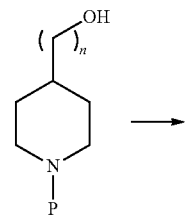

(5A-2a) n = 0
(5A-2b) n = 1
(5A-2c) n = 2

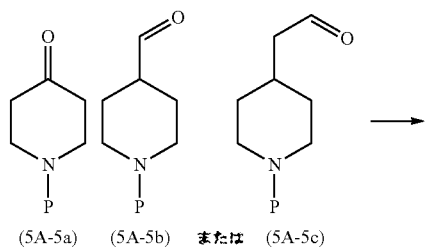

(5A-5a)   (5A-5b)   または (5A-5c)

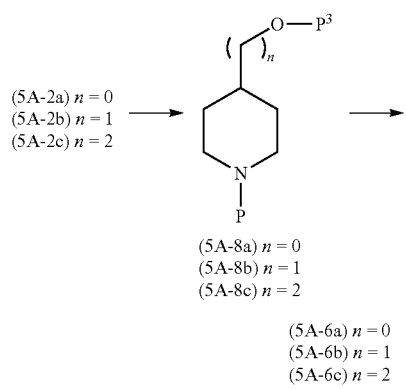

(5A-6a) n = 0    (5A-7a) n = 0
(5A-6b) n = 1    (5A-7b) n = 1
(5A-6c) n = 2    (5A-7c) n = 2

(B) 法

(5A-2a) n = 0
(5A-2b) n = 1
(5A-2c) n = 2

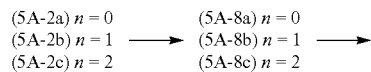

(5A-8a) n = 0
(5A-8b) n = 1
(5A-8c) n = 2

(5A-6a) n = 0    (5A-7a) n = 0
(5A-6b) n = 1 → (5A-7b) n = 1
(5A-6c) n = 2    (5A-7c) n = 2

(C) 法

(5A-2a) n = 0    (5A-8a) n = 0
(5A-2b) n = 1 → (5A-8b) n = 1 →
(5A-2c) n = 2    (5A-8c) n = 2

-continued

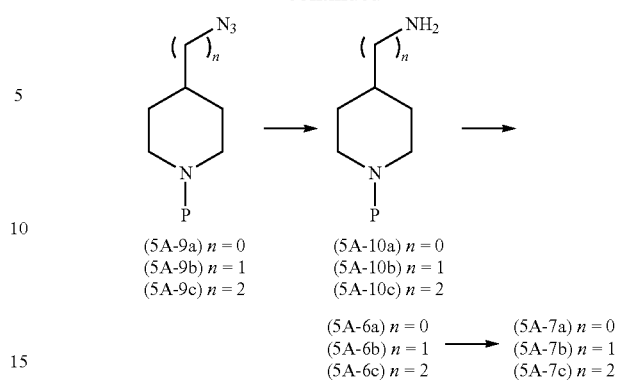

(5A-9a) n = 0    (5A-10a) n = 0
(5A-9b) n = 1    (5A-10b) n = 1
(5A-9c) n = 2    (5A-10c) n = 2

(5A-6a) n = 0    (5A-7a) n = 0
(5A-6b) n = 1 → (5A-7b) n = 1
(5A-6c) n = 2    (5A-7c) n = 2 wherein $Q^2$ means an amino group which may be substituted with one or a plurality of substituents, or a nitrogen-containing heterocyclic group which may be substituted with one or a plurality of substituents, and has a nitrogen atom as the bonding site; and P and n represent the same as described above.

The piperidine derivative (5A-7a, 5A-7b or 5A-7c) or a salt thereof can be produced from an alcohol product (5A-5), using any of the methods (A) to (C) shown in the above [Scheme 2A].

[Scheme 5B]

A piperidine derivative (5B-4) can be produced by the following method.

[Formula 76]

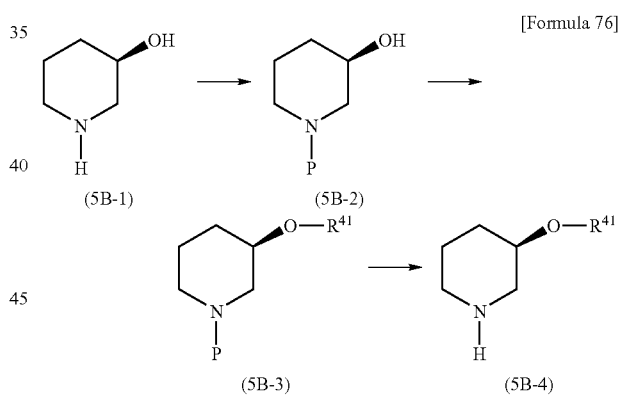

(5B-1)   (5B-2)

(5B-3)   (5B-4)

wherein $R^{41}$ and P represent the same as described above.

The piperidine derivative (5B-4) or a salt thereof can be produced by converting 3-hydroxypiperidine (5B-1) which is commercially available, to a compound (5B-2) through the introduction of cbz or Boc, subsequently treating the compound in the same manner as in the alkylation of 3-hydroxy-1-benzhydrylazetidine (3A-1) shown in the [Scheme 3A-1] to derive a compound (5B-3), and then subjecting the compound to hydrogenolysis or acid treatment.

The enantiomer of the compound (5B-4) or a salt thereof can be produced in the same manner, from the enantiomer of the compound (5B-1) which is commercially available.

[Scheme 5C]

A piperidine derivative (5C-5 or 5C-6) can be produced by the following method.

[Formula 77]

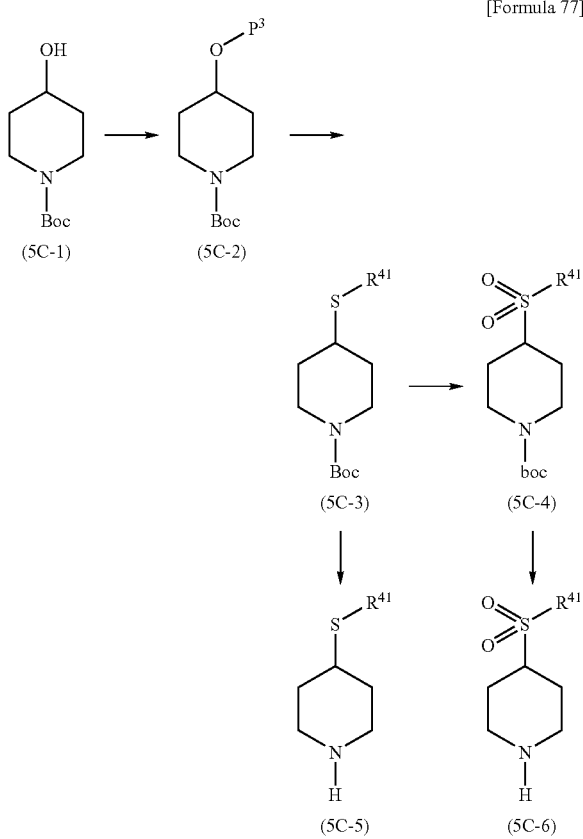

wherein $R^{41}$ and $P^3$ represent the same as described above.

The piperidine derivative (5C-5) or a salt thereof can be produced by converting an alcohol product (5C-1) which is commercially available, to a methanesulfonyloxy product or a trifluoromethanesulfonyloxy product (5C-2) according to the method of Iyobe, A. et al. [Chem. Pharm. Bull. 49, 822-829 (2001)], subsequently treating the resultant product with a lower alkylthiol in the presence of a base to obtain a compound (5C-3), and then treating the compound with an acid.

The base used in the production of the compound (5C-3) is preferably an alkali metal hydride such as sodium hydride or lithium hydride. The reaction solvent is preferably an inert polar solvent such as N,N-dimethylformamide. The reaction temperature is in the range of −20 to 100° C., and preferably in the range of 0 to 50° C. The reaction time is usually about 2 to 5 hours.

The piperidine derivative (5C-6) or a salt thereof can be produced by oxidizing the compound (5C-3) to derive a sulfone derivative (5C-4), and then treating the derivative with an acid.

The oxidizing agent for the compound (5C-3) is preferably a per acid such as m-chloroperbenzoic acid. The reaction solvent is preferably a halogen-based solvent such as methylenechloride. The reaction temperature is preferably in the range of 0° C. to room temperature. The reaction time is usually about 0.5 to 3 hours.

[Scheme 5D]

A piperidine derivative (5D-3) can be produced by the following method.

[Formula 78]

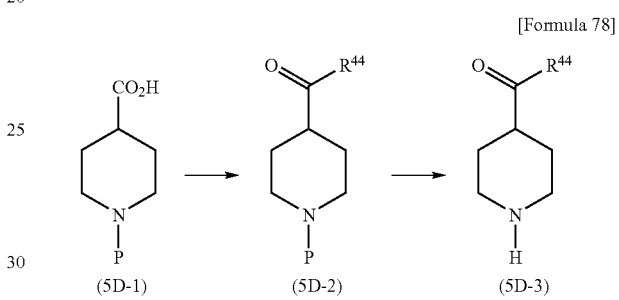

wherein $R^{44}$ and P represent the same as described above.

The piperidine derivative (5D-3) or a salt thereof can be produced by converting a carboxylic acid product (5D-1) which is commercially available, and an amine ($R^{44}$—H) to an amide product (5D-2) through a generally used amide bond forming reaction, and then removing the protective group.

[Scheme 6A]

A piperazine derivative (6A-3) can be produced by the following method.

[Formula 79]

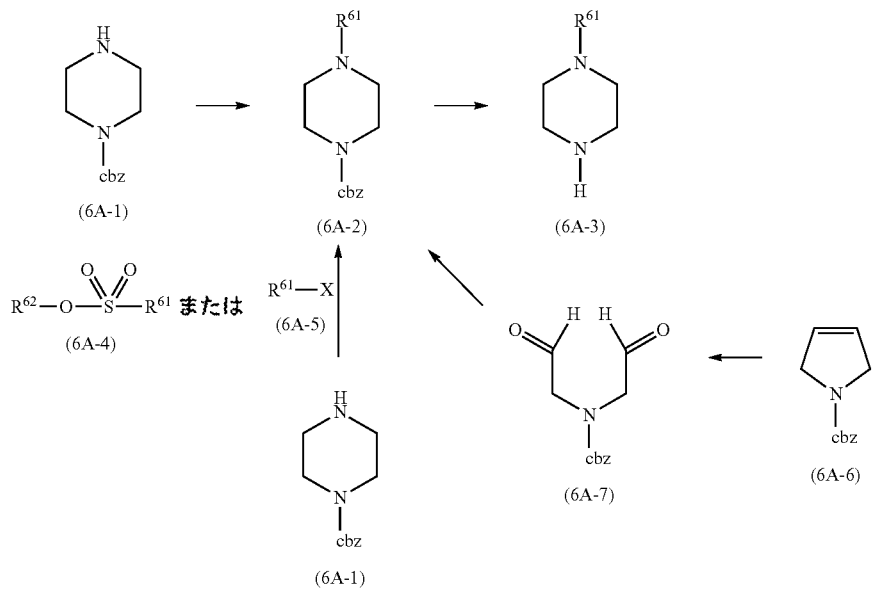

wherein $R^{61}$ means a lower alkyl group; $R^{62}$ means a methyl group, a trifluoromethyl group or a 4-methylphenyl group; and X means an iodine atom or a bromine atom.

The piperazine derivative (6A-3) or a salt thereof can be produced by converting a compound (6A-1) which is commercially available, and a ketone such as acetone or cyclohexanone, an aromatic aldehyde such as pyridyl aldehyde or a lower aliphatic aldehyde, or a ketone equivalent such as 1-ethoxy-1-trimethylsilyloxy cyclopropane, to a compound (6A-2) using a production method which is similar to the conversion from the 4-oxopyrrolidine product (2A-3) to the compound (2A-4) as shown in the method (A) of the [Scheme 2A], and then subjecting the obtained compound to hydrogenolysis. The hydrogenolysis is preferably performed by adding an inorganic acid such as hydrochloric acid or an organic acid such as trifluoroacetic acid. The compound (6A-2) can be produced through an alkylation reaction between the compound (6A-1) and a compound (6A-4 or 6A-5) according to the method of Reifenrath, W. G., et al. [J. Med. Chem. 23, 985-990 (1980)].

Furthermore, the compound (6A-2) can also be produced by oxidizing a 3,4-dehydropyrrolidine derivative (6A-6) which is commercially available, using osmium tetroxide or sodium metaperiodate according to the method of Florent, J.-C., et al. [J. Med. Chem. 36, 1364-1368 (1993)], to obtain a dialdehyde derivative (6A-7), subsequently forming a primary alkylamine ($R^{61}$—$NH_2$) and an imine, and then reducing the compounds. For the reaction conditions, the method (A) of the [Scheme 2A] may be applied mutatis mutandis.

[Scheme 6B]

A piperazine derivative (6B-5 or 6B-7) can be produced by the following method.

The piperazine derivative (6B-7) can be produced by reacting the piperazine derivative (6A-1) with a lower alkylsulfonyl chloride (6B-3) to obtain a compound (6B-6) by referring to the method of Kelley J. L., et al. [J. Heterocycl Chem., 1990, 27(6), 1821-1824], and then subjecting the obtained compound to hydrogenolysis.

The piperazine derivative (6B-5 or 6B-7) can also be produced by treating the piperazine derivative (6A-1) with alkyl isocyanate or dialkylsulfamoyl chloride by referring to the method of Shiau C.-Y., et al. [J. Heterocycl Chem., 1990, 27(5), 1467-1472.] or the method of Winter J., et al. [Synthesis, 1994, (3), 245-246.]

[Scheme 6C]

A piperazine derivative (6C-3) can be produced by the following method.

[Formula 81]

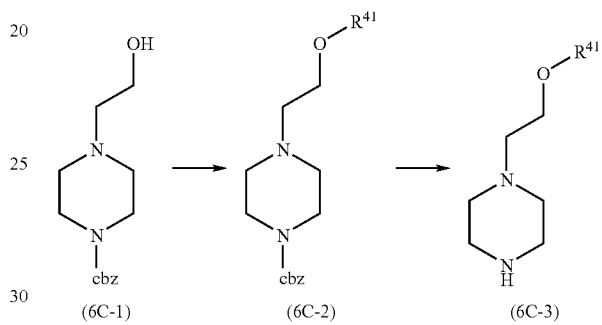

wherein $R^{41}$ represents the same as described above.

[Formula 80] OR

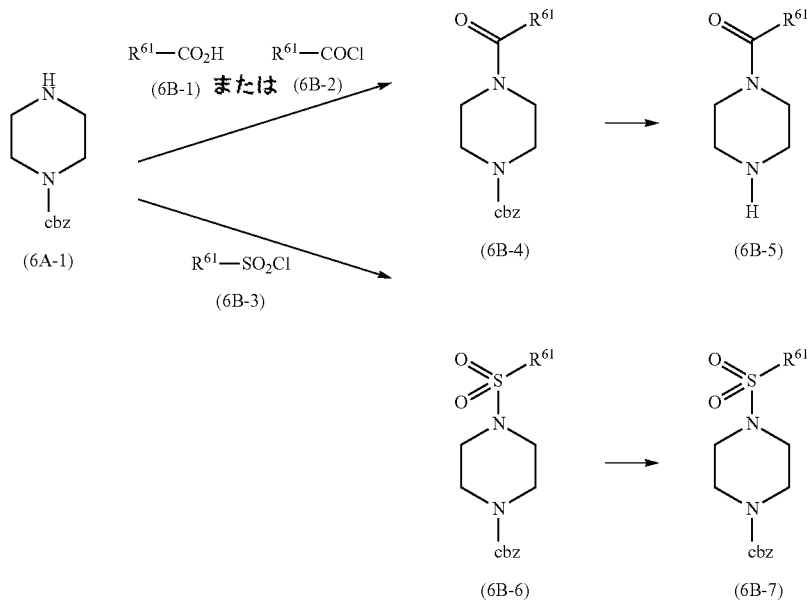

wherein $R^{61}$ represents the same as described above.

The piperazine derivative (6B-5) can be produced by converting the compound (6A-1) and a carboxylic acid derivative (6B-1) or a carboxylic acid chloride (6B-2) to a compound (6B-4) using a general amide bond forming reaction, and then subjecting the obtained compound to hydrogenolysis.

The piperazine derivative (6C-3) or a salt thereof can be produced by treating an alcohol product (6C-1) in the same manner as in the alkylation of 3-hydroxy-1-benzhydrylazetidine (3A-1) shown in the [Scheme 3A-1] to obtain a compound (6C-1), and then subjecting the compound to hydrogenolysis.

[Scheme 6D]

A piperazine derivative (6D-3) can be produced by the following method.

[Formula 82]

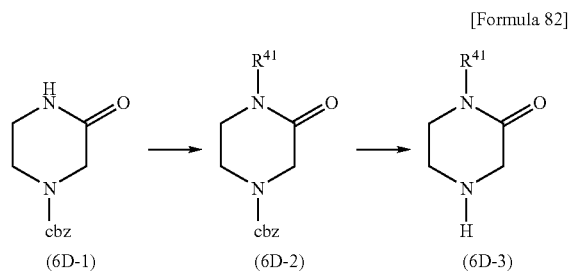

wherein R⁴¹ represents the same as described above.

The piperazine derivative (6D-3) or a salt thereof can be produced by converting a compound (6D-1) which is commercially available, in the same manner as in the alkylation of 3-hydroxy-1-benzhydrylazetidine (3A-1) shown in the [Scheme 3A-1] to obtain a compound (6D-2), and then subjecting the compound to hydrogenolysis.

[Scheme 7]

A homopiperazine derivative (7A-2, 7A-3 or 7A-4) can be produced by the following method.

[Formula 83]

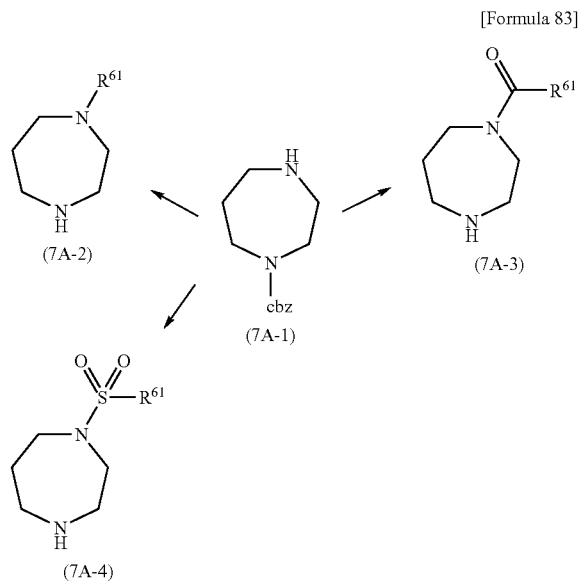

wherein R⁶¹ represents the same as described above.

The homopiperazine derivative (7A-2, 7A-3 or 7A-4) or a salt thereof can be produced by treating a homopiperazine derivative (7A-1) which is commercially available, in the same manner as in the production method for the piperazine derivative (6A-3, 6B-5 or 6B-7) shown in the [Scheme 6A].

The compound of the present invention or a salt thereof thus produced is useful as a main component of medicines, for example, preventive and/or therapeutic drugs, for various diseases. For example, as described later in the Test Examples, the compound of the present invention inhibits the binding between VLA-4 and VCAM-1, as well as exhibits high inhibitory activity even in the presence of proteins such as serum albumin. Furthermore, since the compound has excellent oral absorbability, the compound exhibits high effectiveness through oral administration in inflammatory models. Therefore, the compound of the present invention or a salt thereof is useful as a preventive and/or therapeutic drug for diseases caused by cellular adhesion, for example, diseases caused by the cellular adhesion involving VLA-4, that is, various diseases mediated by migration and adhesion of leukocytes, for example, inflammatory diseases, autoimmune diseases, cancer metastasis, bronchial asthma, nasal congestion, diabetes mellitus, arthritis, psoriasis, multiple sclerosis, inflammatory bowel diseases, graft-versus-host disease, rejection on transplantation, acute myelogenous leukemia, chronic myelogenous leukemia, allergic granulomatous angiitis, atherosclerosis, eosinophilic pustular folliculitis, uveitis, glomerulonephritis, prometastatic breast cancer, malignant melanoma and the like.

A medicine containing the compound of the present invention or a salt thereof can be administered according to various methods including oral administration.

Also, in the case of using as an injectable preparation, the medicine can be administered according to any method among intravenous injection, intramuscular injection, subcutaneous injection and the like.

With regard to the method for formulating such preparations, an appropriate preparation is selected in accordance to the administration method, and prepared by the formulation methods for various preparations that are conventionally used.

As for the oral preparation, for example, tablets, powders, granules, capsules, solutions, syrups, elixirs, oily or aqueous suspensions, and the like may be mentioned. As for the injectable preparation, a stabilizer, an anticeptic, or a dissolution aid may also be used, and a solution which may contain these auxiliary agents, may be placed in a container, and then processed to a solid preparation through lyophilization as desired, to obtain a preparation for production upon use. Further, as for the liquid preparation, solutions, suspensions, emulsions and the like may be mentioned, and upon formulating these preparations, a suspending agent, an emulsifier and the like may also be used as additives.

A medicine containing the compound of the present invention is administered once a day for an adult, as a compound, and the administration is preferably repeated at an appropriate interval. The dosage is in the range of 0.01 mg to 2000 mg, and preferably in the range of 0.1 mg to 1000 mg.

The medicine of the present invention can be used, within the scope of not impairing the effects of the invention, in combination with an anti-inflammatory agent, an anti-arthritic drug, an adrenocortical steroid (corticosteroid), an immunosuppressant, an anti-psoriatic drug, a bronchodilator, an anti-bronchial asthma drug or an anti-diabetic drug, according to necessity.

The present invention also encompasses a preventing method and/or treating method for the above-mentioned diseases, the method comprising administering the compound of the present invention or a salt thereof.

The present invention also encompasses a use of the compound of the present invention or a salt thereof for the manufacture of the above-mentioned medicine.

EXAMPLES

Hereinafter, the present invention will be specifically described by way of Examples.

Additionally, the symbols "IR", "NMR" and "MS" in the Examples mean "infrared absorption spectrum," "nuclear magnetic resonance spectrum," and "mass spectroscopy," respectively. A ratio of an eluting solvent described in the case of separation and purification by chromatography means a volumetric ratio, unless stated otherwise. The "IR" was determined by an ATR method or a KBr tablet method. "NMR" means ¹H-NMR, unless stated otherwise, and the description within the parentheses represents the solvent for measurement. TMS (tetramethylsilane) was used as an internal standard substance in all cases. Furthermore, "Anal. Calcd for rational formula" means a calculated value from elemental analysis, while a measured value is indicated after "Found." Following abbreviations are used in this description.

TABLE 1

| | |
|---|---|
| BH₃·DMS | Borane-dimethyl sulfide complex |
| Boc or boc | Tert-butoxycarbonyl |
| Boc₂O | Di-tert-butyl dicarbonate |
| Bn | Benzyl |
| CDCl₃ | Deuterated chloroform |
| DMSO-d₆ | Deuterated dimethylsulfoxide |
| DIAD | Diisopropyl azodicarboxylic acid |
| DMF | N,N-dimethylformamide |
| DMSO | Dimethylsulfoxide |
| EDC | 1-Ethyl-3-(3-dimethylaminopropyl)carbodiimide hydrochloride |
| HOBt | 1-Hydroxybenzotriazole |
| TBDMS | Tert-butyl dimethylsilyl |
| TBDMS-Cl | Tert-butyl dimethylsilyl chloride |
| THF | Tetrahydrofuran |
| TLC | Thin layer chromatography |
| cbz or Z | Benzyloxycarbonyl |
| TEMPO | 2,2,6,6-Tetramethyl-1-piperidinyloxy, free radical |

W—CH₂CO₂H in the formula (I) used in the following Examples was produced by referring to the method described in Patent Document 1, Examples 171 to 181 or Reference Patent Document (Pamphlet of WO 2005/063678).

Example 1

Trans-4-[1-[[5-chloro-2-fluoro-4-[(1-methyl-1H-indol-1-yl)-(2S)-pyrrolidinylmethoxy]cyclohexanecarboxylic acid 4-[(4R)-hydroxy-(2S)-pyrrolidinylmethoxy]benzoic acid ethyl ester

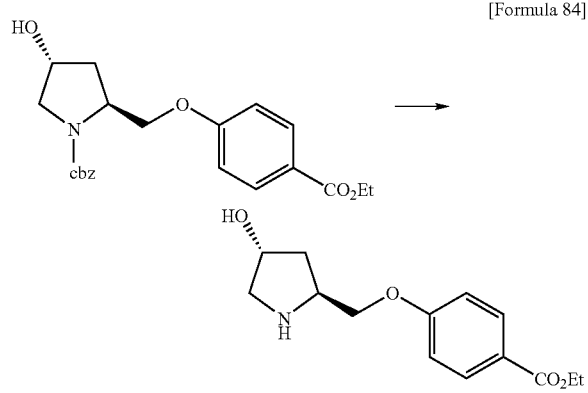

[Formula 84]

To a methanol solution (300 mL) of 4-[1-(benzyloxycarbonyl)-(4R)-hydroxy-(2S)-pyrrolidinylmethoxy]benzoic acid ethyl ester (25.5 g, 63.8 mmol), 106 palladium hydroxide/carbon (5.1 g) was added, and the mixture was stirred for 4 hours under a hydrogen stream at normal pressure. The reaction mixture was filtered to eliminate the catalyst, and then the filtrate was concentrated under reduced pressure and dried, to obtain the title compound (17.9 g, 100%) as a solid.

NMR (CDCl₃) δ: 1.38 (3H, t, J=7.1 Hz), 1.77-2.03 (total 3H, series of m, including 1H, broad s, at δ 1.91), 2.96-3.00 (1H, m), 3.11-3.15 (1H, m), 3.81-3.99 (3H, m), 4.34 (2H, q, J=7.1 Hz), 4.49-4.51 (1H, m), 6.91 (2H, d, J=8.8 Hz), 7.98 (2H, d, J=8.8 Hz).

4-[1-(Tert-butoxycarbonyl)-(4R)-hydroxy-(2S)-pyrrolidinylmethoxy]cyclohexanecarboxylic acid ethyl ester

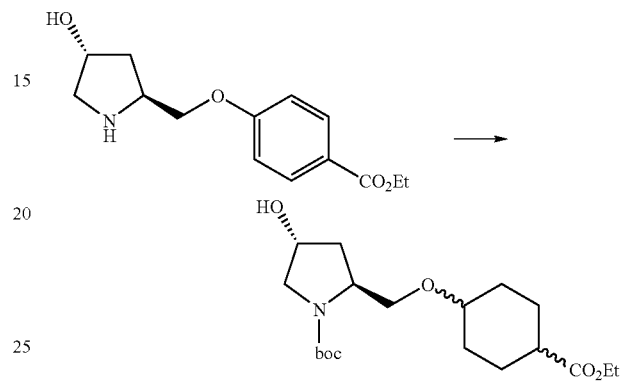

[Formula 85]

To a methanol/trifluoroacetic acid (210 mL, 20:1, v/v) solution of 4-[(4R)-hydroxy-(2S)-pyrrolidinylmethoxy]benzoic acid ethyl ester (17.9 g, 67.4 mmol), 56 rhodium/alumina (3.58 g) was added, and the mixture was stirred for 4 hours under a hydrogen stream at 7 atmospheres. The catalyst was separated by filtration, and then the filtrate was concentrated under reduced pressure. The residue was dissolved in 1,4-dioxane/saturated aqueous solution of sodium hydrogen carbonate (300 mL, 2:1, v/v), (Boc)₂O (16.2 g, 74.2 mmol) was added thereto, and the mixture was stirred for 2 days. The reaction liquor was acidified by adding 1N-hydrochloric acid, and was extracted with ethyl acetate. The extract was washed with saturated brine and dried over anhydrous sodium sulfate, and the solvent was concentrated under reduced pressure. The obtained residue was purified by column chromatography [n-hexane/ethyl acetate (1:1, v/v)] using silica gel, to obtain the title compound (22.9 g, 91%; yield from two processes) as an oily matter.

NMR (CDCl₃) δ: 1.22-2.04 (total 21H, series of m, including 3H, t, J=7.1 Hz, at δ 1.25, and including 9H, s, at δ 1.46), 2.10-2.31 (2H, m), 3.20 (1H, m), 3.44-3.74 (total 5H, series of m), 4.08-4.15 (total 3H, m, including 2H, q, J=7.1 Hz, at δ 4.12), 4.46-4.52 (1H, m).

Trans-4-[(4R)-(benzyloxy)methyloxy-1-(tert-butoxycarbonyl)-(2S)-pyrrolidinylmethoxy]cyclohexanecarboxylic acid ethyl ester

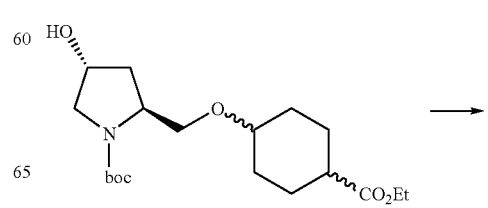

[Formula 86]

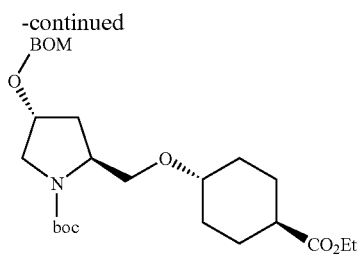

4-[1-(Tert-butoxycarbonyl)-(4R)-hydroxy-(2S)-pyrrolidinylmethoxy]cyclohexanecarboxylic acid ethyl ester (22.9 g, 61.6 mmol) and ethyldiisopropylamine (16.1 mL, 92.4 mmol) were dissolved in methylene chloride (230 mL), (benzyloxy)methyl chloride (17.1 mL, 123.4 mmol) was added thereto, and the mixture was stirred for one day at room temperature. 1N-hydrochloric acid (100 mL) was added to the reaction liquor, and the mixture was extracted with ethyl acetate. The extract was washed with saturated brine, and dried over anhydrous sodium sulfate, and then the solvent was concentrated under reduced pressure. The obtained residue was purified by column chromatography [n-hexane/ethyl acetate (2:1, v/v)] using silica gel, to obtain 4-[(4R)-(benzyloxy)methyloxy-1-(tert-butoxycarbonyl)-(2S)-pyrrolidinylmethoxy]cyclohexanecarboxylic acid ethyl ester (20.0 g, 66%) as an oily matter.

4-[(4R)-(benzyloxy)methyloxy-1-(tert-butoxycarbonyl)-(2S)-pyrrolidinylmethoxy]cyclohexanecarboxylic acid ethyl ester was dissolved in DMF/ethanol (210 mL, 20:1, v/v), sodium hydride (60% oily, 2.43 g, 60.8 mmol) was slowly added thereto while stirring at 0° C., and then the reaction mixture was stirred for 1 hour at room temperature. The reaction liquor was poured onto 1N-hydrochloric acid (200 mL), and then the mixture was extracted with ethyl acetate. The extract was washed with saturated brine, and dried over anhydrous sodium sulfate, and then the solvent was concentrated under reduced pressure. The obtained residue was purified by column chromatography [n-hexane/ethyl acetate (3:1, v/v)] using silica gel, and further purified by column chromatography (Flash Chromatography System of Biotage AB, column size: 150 L) [n-hexane/ethyl acetate (6:1 to 1:1)], to obtain the title compound (7.47 g, 376; yield from two processes) as an oily matter.

NMR (CDCl$_3$) δ: 1.20-1.28 (total 5H, m), 1.40-1.50 (total 11H, including 9H, s, at δ 1.46), 1.97-2.23 (total 7H, series of m), 3.17-3.19 (1H, m), 3.48-3.58 (total 4H, series of m), 3.96-4.15 (total 3H, series of m), 4.34-4.40 (1H, m), 4.56-4.61 (2H, m), 4.77 (2H, s), 7.28-7.37 (5H, m).

Trans-4-[1-(tert-butoxycarbonyl)-(4R)-hydroxy-(2S)-pyrrolidinylmethoxy]cyclohexanecarboxylic acid ethyl ester

[Formula 87]

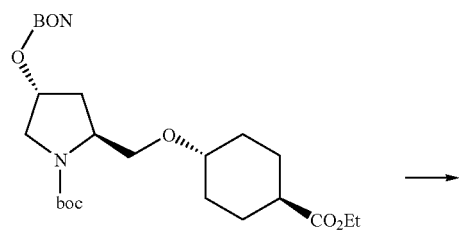

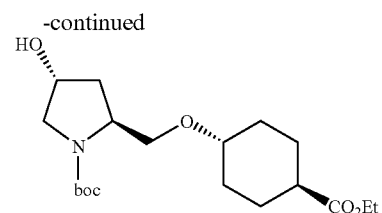

To a methanol solution (75 mL) of trans-4-[(4R)-(benzyloxy)methyloxy-1-(tert-butoxycarbonyl)-(2S)-pyrrolidinylmethoxy]cyclohexanecarboxylic acid ethyl ester (7.47 g, 15.2 mmol), 10% palladium hydroxide/carbon was added, and the mixture was stirred for 16 hours under a hydrogen stream at 4 atmospheres. The catalyst was separated by filtration, and then the filtrate was concentrated under reduced pressure. The obtained residue was purified by column chromatography [n-hexane/ethyl acetate (1:1, v/v)] using silica gel, to obtain the title compound (5.66 g, 100%) as an oily matter.

NMR (CDCl$_3$) δ: 1.21-1.31 (total 5H, m, including 3H, t, J=7.1 Hz, at 61.24), 1.40-1.50 (total 11H, including 9H, s, at 1.47), 1.97-2.05 (5H, m), 2.12-2.26 (2H, m), 3.17-3.22 (1H, m), 3.43-3.66 (total 5H, series of m), 4.00-4.15 (total 3H, m, including 2H, q, J=7.1 Hz, at δ 4.11), 4.46-4.48 (1H, m).

<Method for Introducing Cyclic Amino Group-1>

Trans-4-[1-(tert-butoxycarbonyl)-(4S)-(3-methoxyazetidin-1-yl)-(2S)-pyrrolidinylmethoxy]cyclohexanecarboxylic acid ethyl ester

[Formula 88]

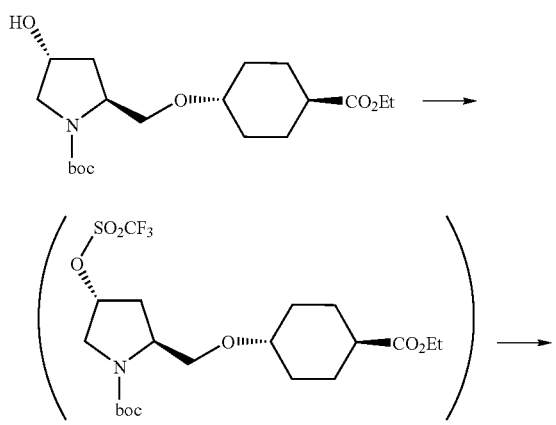

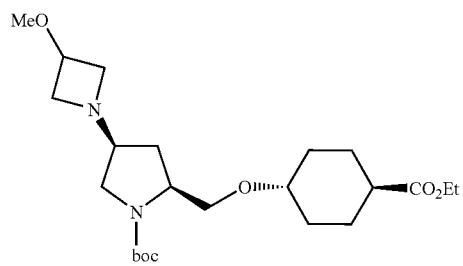

Trans-4-[1-(tert-butoxycarbonyl)-(4R)-hydroxy-(2S)-pyrrolidinylmethoxy]cyclohexanecarboxylic acid ethyl ester (1.57 g, 4.23 mmol) was dissolved in dichloromethane (50 mL), ethyldiisopropylamine (5.16 mL, 29.6 mmol) was added at −78° C. while stirring the content under a nitrogen stream, and the mixture was stirred for 20 minutes at the same temperature. Furthermore, trifluoromethane sulfonic anhydride (1.42 mL, 8.45 mmol) was added at the same temperature, and the mixture was stirred for 30 minutes. 3-Methoxyazetidine hydrochloride (680 mg, 5.50 mmol) was added to the reaction liquor, which was then stirred for 40 minutes at −78° C. The reaction mixture was allowed to warm to 0° C., and further stirred for 14 hours. The reaction liquor was poured onto 2M-potassium phosphate buffer solution (100 mL) and extracted with dichloromethane. The extract was washed with saturated brine, dried over anhydrous sodium sulfate, and then concentrated under reduced pressure to obtain the title compound (1.17 g, 63%) as an oily matter.

NMR (CDCl$_3$) δ: 1.16-1.30 (6H, m, including 1.24, 3H, t, J=7.1 Hz), 1.33-1.51 (11H, m, including 1.45, 9H, s), 1.78-2.28 (7H, m), 2.81-2.93 (3H, m), 3.00-3.09 (1H, m), 3.16-3.27 (4H, m, including 3.25, 3H, s), 3.36-4.30 (8H, m).

MS (ESI) m/z: 441 (M$^+$+1).

<Method for Introducing Cyclic Amino Group-2>

Trans-4-[1-(tert-butoxycarbonyl)-4-oxo-(2S)-pyrrolidinylmethoxy]cyclohexanecarboxylic acid ethyl ester

[Formula 89]

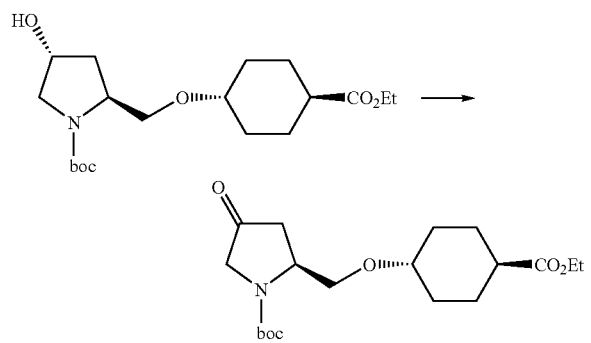

A dichloromethane solution (100 mL) of oxalyl chloride mL, 269 mmol) was stirred under a nitrogen stream, dimethylsulfoxide (38 mL, 538 mmol) was added dropwise over 25 minutes at −78° C., and the mixture was stirred for 30 minutes at the same temperature. To the reaction liquor, a dichloromethane (130 mL) solution of trans-4-[1-(tert-butoxycarbonyl)-(4R)-hydroxy-(2S)-pyrrolidinylmethoxy]cyclohexanecarboxylic acid ethyl ester (50 g, 135 mmol) was added dropwise over 45 minutes at −78° C., and the reaction mixture was stirred for another 1 hour. To the reaction mixture, triethylamine (113 mL, 808 mmol) was added dropwise over 20 minutes at the same temperature. The reaction mixture was allowed to warm to 0° C. and stirred for 10 minutes, and then was further stirred for 20 minutes while slowly returning to room temperature. Water (100 mL) was added to the reaction liquor under stirring, and the mixture was extracted with dichloromethane. The extract was washed with saturated brine, and dried over anhydrous sodium sulfate, and then the solvent was concentrated under reduced pressure. The obtained residue was purified by column chromatography using silica gel (Flash Chromatography System of Biotage AB, column size: 65 L, ethyl acetate:n-hexane=1:9 to 7:3), to obtain the title compound g, 87%) as a solid.

NMR (CDCl$_3$) δ: 1.11-1.33 (5H, m), 1.37-1.52 (2H, m), 1.49 (9H, s), 1.91-2.76 (8H, m), 3.14-3.23 (1H, m), 3.45 (1H, dd, J=9.4, 2.1 Hz), 3.59-3.95 (3H, m), 4.11 (2H, q, J=6.9 Hz).

MS (ESI) m/z: 370 (M$^+$+1).

Trans-4-[1-(tert-butoxycarbonyl)-(4S)-(3-methoxyazetidin-1-yl)-(2S)-pyrrolidinylmethoxy]cyclohexanecarboxylic acid ethyl ester

[Formula 90]

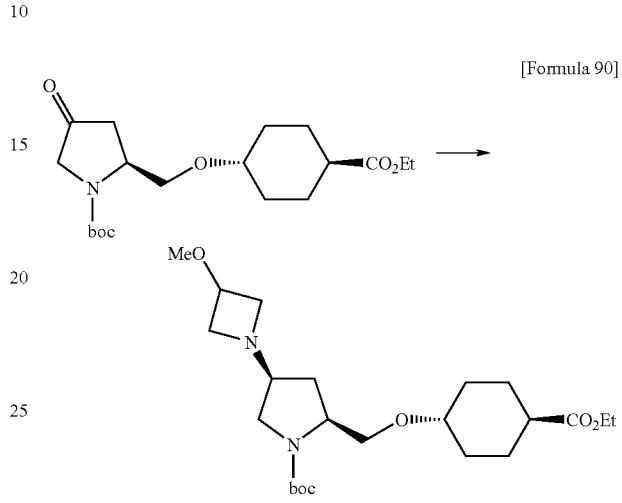

To a tetrahydrofuran (5 mL) solution of trans-4-[1-(tert-butoxycarbonyl)-4-oxo-(2S)-pyrrolidinylmethoxy]cyclohexanecarboxylic acid ethyl ester (0.91 g, 2.46 mmol) and 3-methoxyazetidine hydrochloride (0.30 g, 2.46 mmol), sodium triacetoxyborohydride (1.56 g, 7.38 mmol) was added, and the mixture was stirred for 4 days. A saturated aqueous solution of sodium hydrogen carbonate (30 mL) was added to the reaction liquor, and the mixture was stirred for 15 minutes, and then extracted with ethyl acetate. The extract was washed with saturated brine, and dried over anhydrous sodium sulfate, and then the solvent was concentrated under reduced pressure. The obtained residue was purified by column chromatography using silica gel (Flash Chromatography System of Biotage AB, column size: 40S, eluent: ethyl acetate), to obtain the title compound (580 mg, 54%) as an oily matter.

The data from various instruments for the obtained compound completely coincided with the data obtained by the <method for introducing cyclic amino group-1>.

Trans-4-[(4S)-(3-methoxyazetidin-1-yl)-(2S)-pyrrolidinylmethoxy]cyclohexanecarboxylic acid ethyl ester Trans-4-[1-(tert-butoxycarbonyl)-(4S)-(3-methoxyazetidin-1-yl)-(2S)-pyrrolidinylmethoxy]cyclohexanecarboxylic acid ethyl ester (1.17 g, 2.66 mmol) was dissolved in 4NHydrogen Clhloride/dioxane (50 mL), and the solution was stirred for two days at room temperature. The reaction liquor was concentrated under reduced pressure. The obtained residue was dissolved in dichloromethane, and the solution was adjusted to pH 10 with a 1N-aqueous solution of sodium hydroxide, and extracted with dichloromethane. The combined extracts were washed with saturated brine, dried over anhydrous sodium sulfate, and then concentrated under reduced pressure, to obtain the title compound (750 mg, 83%) as an oily matter.

NMR (CDCl$_3$) δ: 1.14-1.30 (7H, m), 1.44-1.44 (2H, m), 2.11-2.12 (2H, q, J=7.2 Hz).

MS (ESI) m/z: 341 (M$^+$+1).

Trans-4-[1-[[5-chloro-2-fluoro-4-[(1-methyl-1H-indol-3-ylcarbonyl)amino]phenyl]acetyl]-(4S)-(3-methoxyazetidin-1-yl)-(2S)-pyrrolidinylmethoxy]cyclohexanecarboxylic acid ethyl ester

[Formula 91]

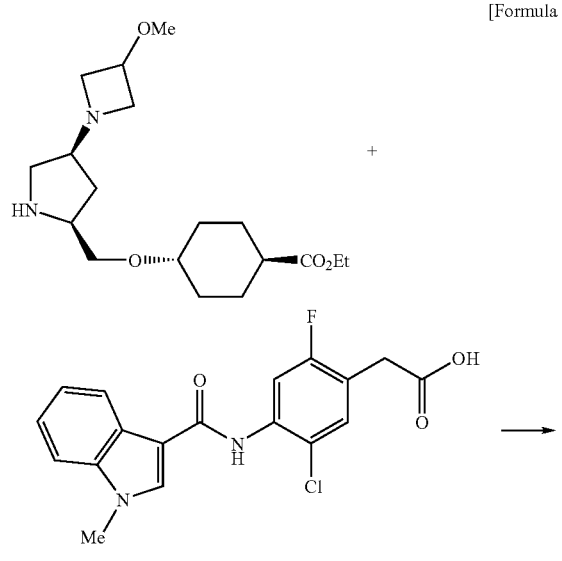

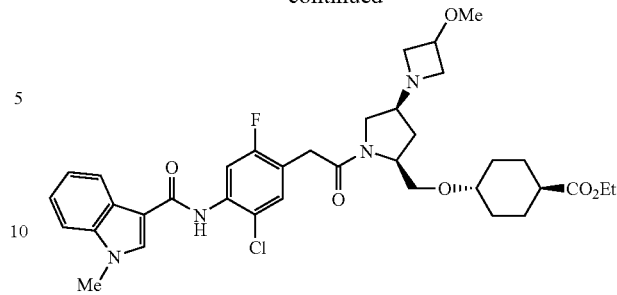

To a dichloromethane solution (5 mL) of [5-chloro-2-fluoro-4-[(1-methyl-1H-indol-3-ylcarbonyl)amino]phenyl]acetic acid (159 mg, 0.441 mmol), trans-4-[(4S)-(3-methoxyazetidin-1-yl)-(2S)-pyrrolidinylmethoxy]cyclohexanecarboxylic acid ethyl ester (150 mg, 0.441 mmol), EDC.HCl (127 mg, 0.662 mmol) and HOBt (89 mg, 0.662 mmol), triethylamine (0.307 mL, 2.21 mmol) was added at room temperature, and the mixture was stirred for three days. The reaction liquor was concentrated under reduced pressure, and the obtained residue was purified by thin layer chromatography (ethyl acetate:methanol=20:1, v/v), to obtain the title compound (238 mg, 79%) as an oily matter.

NMR (CDCl$_3$) δ: 1.17-1.29 (7H, m), 1.37-1.54 (2H, m), 1.86-2.33 (6H, m), 2.79-3.02 (3H, m), 3.16-3.25 (1H, m), 3.27 (3H, s), 3.88-3.88 (7H, m), 3.88 (3H, s), 3.96-4.22 (4H, m), 7.32-7.45 (4H, m), 7.80 (1H, d, J=2.9 Hz), 8.11-8.18 (1H, m), 8.29 (1H, s), 8.49 (1H, dd, J=12.0, 8.8H z).

MS (ESI) m/z: 683 (M$^+$+1), 685 (M$^+$+3)

Trans-4-[1-[[5-chloro-2-fluoro-4-[(1-methyl-1H-indol-1-yl)-(2S)-pyrrolidinylmethoxy]cyclohexane carboxylic acid

[Formula 92]

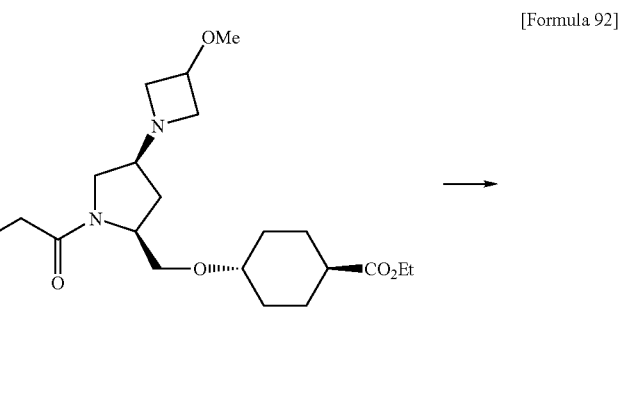

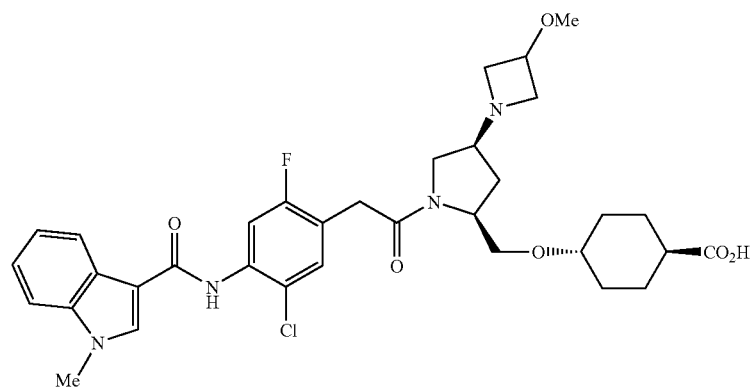

To a mixed solution (6 mL, 2:1) of trans-4-[1-[[5-chloro-2-fluoro-4-[(1-methyl-1H-indol-3-ylcarbonyl)amino]phenyl]acetyl]-(4S)-(3-methoxyazetidin-1-yl)-(2S)-pyrrolidinylmethoxy]cyclohexanecarboxylic acid ethyl ester (238 mg, 0.348 mmol) in tetrahydrofuran/methanol, a 1N-aqueous solution of sodium hydroxide (2 mL, 2 mmol) was added at room temperature, and the mixture was stirred for 14 hours. The reaction liquor was concentrated under reduced pressure, and the obtained residue was adjusted to pH 8 with 1N-hydrochloric acid, and extracted with a mixed solution of chloroform/methanol [10/1 (v/v)]. The combined extract was washed with saturated brine, and dried over anhydrous sodium sulfate. The solvent was concentrated under reduced pressure to obtain the title compound (235 mg, quant.) as a brown glassy solid, and this solid was freeze-dried from 1,4-dioxane/water to obtain 243 mg of the compound as a glassy solid.

NMR (CDCl$_3$) δ: 1.14-1.55 (4H, m), 1.91-2.37 (7H, m), 3.04-3.37 (7H, m, including 3.22 and 3.28, total 3H, each s, amide isomers), 3.41-3.93 (10H, m), 4.05-4.35 (2H, m), 7.31-7.43 (4H, m), 7.81 (1H, s), 8.09-8.16 (1H, m), 8.29 (1H, d, J=3.2 Hz), 8.49 (1H, t, J=11.4 Hz).

MS (ESI) m/z: 655 (M$^+$+1), 657 (M$^+$+3)

IR (ATR) cm$^{-1}$: 2933, 2856, 1720, 1643, 1518.

Anal. Calcd for C$_{34}$H$_{40}$ClFN$_4$O$_6$.0.25HCl.0.5 EtOH.1.5H$_2$O: C, 58.85; H, 6.53; Cl, 6.22; F, 2.66; N, 7.84.

Found: C, 58.89; H, 6.38; Cl, 6.03; F, 2.53; N, 7.45.

The nitrogen-containing heterocycles used in the following Examples, in which the nitrogen atom represented by Q in the formula (I) is the bonding site, were commercially available, or were synthesized by referring to the methods described in the literature. The data obtained from various instruments were as described in the respective experimental sections. The method for introducing a nitrogen-containing heterocyclic group having a nitrogen atom as the bonding site to the pyrrolidine ring, was carried out using the synthesis method described in Example 1, unless stated otherwise. Furthermore, W—CH$_2$CO$_2$H in the formula (I) used in the following was produced by referring to the Patent Document 1, Examples 171 to 181, or the compound or synthesis method described in reference patent document (pamphlet of WO 2005/063678).

Furthermore, in the following Examples, the compounds were produced by methods equivalent to that of Example 1, unless stated otherwise.

Example 2

Trans-4-[1-[[2,5-dichloro-4-[(1-methyl-1H-indol-3-ylcarbonyl)amino]phenyl]acetyl]-(4S)-(3-methoxyazetidin-1-yl)-(2S)-pyrrolidinylmethoxy]cyclohexanecarboxylic acid Trans-4-[1-[[2,5-dichloro-4-[(1-methyl-1H-indol-3-ylcarbonyl)amino]phenyl]acetyl]-(4S)-(3-methoxyazetidin-1-yl)-(2S)-pyrrolidinylmethoxy]cyclohexanecarboxylic acid ethyl ester NMR (CDCl$_3$) δ: 1.19-1.51 (9H, m), 1.87-2.33 (6H, m), 2.80-3.01 (3H, m), 3.16-3.25 (1H, m), 3.26 (0H, s), 3.26 (3H, s), 3.43-3.83 (7H, m), 3.87 (3H, s), 3.92-4.25 (4H, m), 7.32-7.44 (4H, m), 7.78-7.81 (1H, m), 8.10-8.17 (1H, m), 8.23 (1H, s), 8.77 (1H, dd, J=6.7, 1.1 Hz).

MS (ESI) m/z: 699 (M$^+$+1), 701 (M$^+$+3)

Trans-4-[1-[[2,5-dichloro-4-[(1-methyl-1H-indol-3-ylcarbonyl)amino]phenyl]acetyl]-(4S)-(3-methoxyazetidin-1-yl)-(2S)-pyrrolidinylmethoxy]cyclohexanecarboxylic acid

[Formula 93]

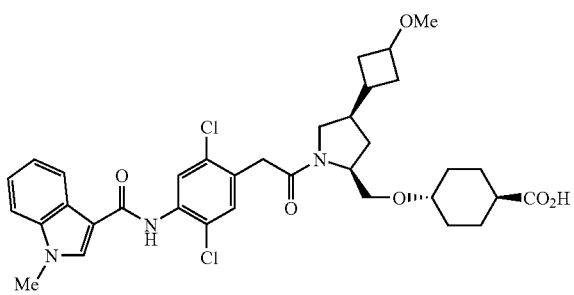

NMR (CDCl$_3$) δ: 1.15-1.57 (4H, m), 1.92-2.42 (6H, m), 3.28-3.96 (18H, m), 4.09-4.43 (2H, m), 7.29-7.45 (4H, m), 7.81 (1H, s), 8.12 (1H, t, J=4.5 Hz), 8.24 (1H, d, J=4.9 Hz), 8.77 (1H, d, J=9.1 Hz).

MS (ESI) m/z: 671 (M$^+$+1), 672 (M$^+$+3).

IR (ATR) cm$^{-1}$: 2933, 2854, 1718, 1647, 1533, 1500.

Anal. Calcd for C$_{34}$H$_{40}$Cl$_2$N$_4$O$_6$.0.25HCl.1H$_2$O: C, 58.44; H, 6.09; Cl, 11.42; N, 8.02.

Found: C, 58.06; H, 6.20; Cl, 11.42; N, 7.64.

Example 3

Trans-4-[1-[[4-[(benzo[b]thiophen-3-ylcarbonyl)amino]-5-chloro-2-fluorophenyl]acetyl]-(4S)-(3-methoxyazetidin-1-yl)-(2S)-pyrrolidinylmethoxy] cyclohexanecarboxylic acid Trans-4-[1-[[4-[(benzo[b]thiophen-3-ylcarbonyl)amino]-5-chloro-2-fluorophenyl]acetyl]-(4S)-(3-methoxyazetidin-1-yl)-(2S)-pyrrolidinylmethoxy] cyclohexanecarboxylic acid ethyl ester NMR (CDCl$_3$) δ: 1.13-1.55 (9H, m), 1.88-2.34 (6H, m), 2.80-3.01 and 3.27 (total 3H, each s, amide isomers), 3.44-3.85 (7H, m), 3.97-4.21 (4H, m), 7.39-7.55 (3H, m), 7.92 (1H, d, J=8.1 Hz), 8.10 (1H, d, J=5.9 Hz), 8.34 (1H, d, J=7.4 Hz), 8.39-8.51 (2H, m).

MS (ESI) m/z: 685 (M$^+$+1), 687 (M$^+$+3)

Trans-4-[1-[[4-[(benzo[b]thiophen-3-ylcarbonyl)amino]-5-chloro-2-fluorophenyl]acetyl]-(4S)-(3-methoxyazetidin-1-yl)-(2S)-pyrrolidinylmethoxy] cyclohexanecarboxylic acid

[Formula 94]

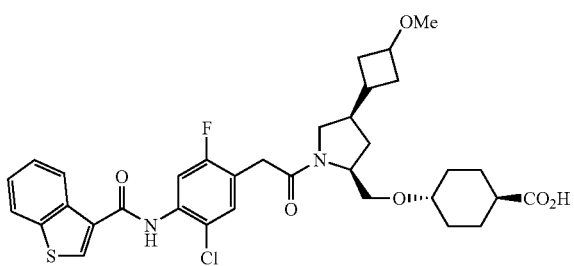

NMR (CDCl$_3$) δ: 1.37-1.37 (4H, m), 1.87-2.35 (7H, m), 2.99-3.30 and 7.91 (total 1H, each d, J=8.3 and 8.1 Hz, respectively, amide isomers), 8.09 (1H, d, J=4.4 Hz), 8.34 (1H, d, J=8.3 Hz), 8.40-8.45 (1H, m), 8.47 (1H, d, J=8.1 Hz).

MS (ESI) m/z: 658 (M$^+$+1), 660 (M$^+$+3)

IR (ATR) cm$^{-1}$: 2935, 2858, 1718, 1672, 1637.

Anal. Calcd for C$_{33}$H$_{37}$ClFN$_3$O$_6$S.1.75H$_2$O: C, 57.47; H, 5.92; Cl, 5.14; F, 2.75; N, 6.09; S, 4.65.

Found: C, 57.68; H, 5.73; Cl, 5.25; F, 2.58; N, 5.70; S, 4.89.

Example 4

Trans-4-[1-[[4-[(benzo[b]thiophen-3-ylcarbonyl)amino]-2,5-dichlorophenyl]acetyl]-(4S)-(3-methoxyazetidin-1-yl)-(2S)-pyrrolidinylmethoxy]cyclohexanecarboxylic acid Trans-4-[1-[[4-[(benzo[b]thiophen-3-ylcarbonyl)amino]-2,5-dichlorophenyl]acetyl]-(4S)-(3-methoxyazetidin-1-yl)-(2S)-pyrrolidinylmethoxy]cyclohexanecarboxylic acid ethyl ester NMR (CDCl$_3$) δ: 1.20-1.52 (8H, m), 1.91-2.29 (6H, m), 2.79-3.01 (3H, m), 3.17-3.26 (1H, m), 3.26 (0H, s), 3.27 (3H, s), 3.44-3.82 (8H, m), 3.91-4.26 (4H, m), 7.55-7.40 (3H, m), 7.92 (1H, d, J=8.1 Hz), 8.09 (1H, d, J=4.2 Hz), 8.29 (1H, d, J=5.1 Hz), 8.48 (1H, d, J=8.1 Hz), 8.70 (1H, d, J=6.9 Hz).

MS (ESI) m/z: 701 (M$^+$+1), 703 (M$^+$+3)

Trans-4-[1-[[4-[(benzo[b]thiophen-3-ylcarbonyl)amino]-2,5-dichlorophenyl]acetyl]-(4S)-(3-methoxyazetidin-1-yl)-(2S)-pyrrolidinylmethoxy]cyclohexanecarboxylic acid

[Formula 95]

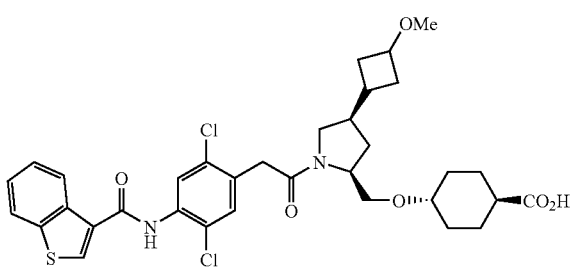

NMR (CDCl$_3$) δ: 1.13-1.56 (4H, m), 1.84-2.33 (7H, m), 2.95-3.12 (4H, m), 3.19-3.25 (2H, m), 3.25 (0H, s), 3.27 (3H, s), 3.42-3.97 (7H, m), 4.05-4.30 (3H, m), 7.40 (1H, s), 7.42-7.54 (2H, m), 7.84-7.93 (1H, m), 8.09 (1H, d, J=2.5 Hz), 8.29 (1H, d, J=6.9 Hz), 8.46 (1H, t, J=9.4 Hz), 8.70 (1H, d, J=7.1 Hz).

MS (ESI) m/z: 673 (M$^+$+1), 675 (M$^+$+3).

IR (ATR) cm$^{-1}$: 2933, 2858, 1718, 1637, 1572.

Anal. Calcd for C$_{33}$H$_{37}$Cl$_2$N$_3$O$_6$S.1.25H$_2$O: C, 56.85; H, 5.71; Cl, 10.17; N, 6.03; S, 4.60.

Found: C, 56.80; H, 5.63; Cl, 9.75; N, 5.72; S, 4.52.

Example 5

Trans-4-[1-[[4-[(benzo[b]furan-3-ylcarbonyl)amino]-5-chloro-2-fluorophenyl]acetyl]-(4S)-(3-methoxyazetidin-1-yl)-(2S)-pyrrolidinylmethoxy]cyclohexanecarboxylic acid Trans-4-[1-[[4-[(benzo[b]furan-3-ylcarbonyl)amino]-5-chloro-2-fluorophenyl]acetyl]-(4S)-(3-methoxyazetidin-1-yl)-(2S)-pyrrolidinylmethoxy]cyclohexanecarboxylic acid ethyl ester NMR (CDCl$_3$) δ: 1.36-1.36 (9H, m), 1.89-2.37 (6H, m), 2.80-3.03 (3H, m), 3.15-3.29 (4H, m), 3.43-3.87 (7H, m), 3.94-4.30 (4H, m), 7.39-7.48 (3H, m), 7.57-7.65 (1H, m), 8.03-8.10 (1H, m), 8.26-8.34 (2H, m), 8.38-8.47 (1H, m).

MS (ESI) m/z: 670 (M$^+$+1), 672 (M$^+$+3).

Trans-4-[1-[[4-[(benzo[b]furan-3-ylcarbonyl)amino]-5-chloro-2-fluorophenyl]acetyl]-(4S)-(3-methoxyazetidin-1-yl)-(2S)-pyrrolidinylmethoxy]cyclohexanecarboxylic acid

[Formula 96]

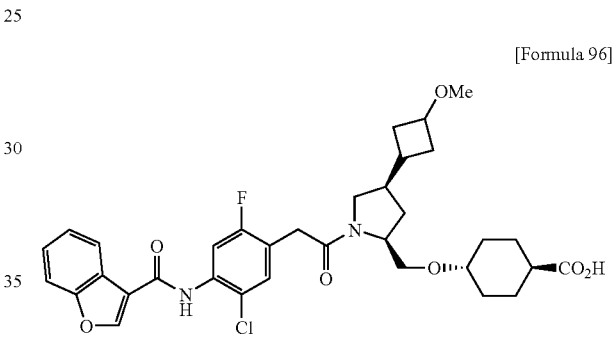

NMR (CDCl$_3$) δ: 1.14-1.53 (4H, m), 1.84-2.31 (7H, m), 2.91-3.24 (6H, m), 3.25 (0H, s), 3.26 (3H, s), 3.45-3.87 (7H, m), 3.95-4.27 (2H, m), 7.37-7.45 (3H, m), 7.56-7.63 (1H, m), 8.02-8.08 (1H, m), 8.31 (2H, d, J=4.9 Hz), 8.40 (1H, dd, J=11.6, 6.5 Hz).

MS (ESI) m/z: 642 (M$^+$+1), 644 (M$^+$+3).

IR (ATR) cm$^{-1}$: 2935, 2858, 1678, 1626, 1587, 1558.

Anal. Calcd for C$_{33}$H$_{37}$ClFN$_3$O$_7$.0.25HCl.2.5H$_2$O: C, 56.93; H, 6.12; Cl, 6.36; F, 2.73; N, 6.03.

Found: C, 57.31; H, 5.83; Cl, 6.11; F, 2.52; N, 5.63.

Example 6

Trans-4-[1-[[4-[(benzo[b]furan-3-ylcarbonyl)amino]-2,5-dichlorophenyl]acetyl]-(4S)-(3-methoxyazetidin-1-yl)-(2S)-pyrrolidinylmethoxy]cyclohexanecarboxylic acid Trans-4-[1-[[4-[(benzo[b]furan-3-ylcarbonyl)amino]-2,5-dichlorophenyl]acetyl]-(4S)-(3-methoxyazetidin-1-yl)-(2S)-pyrrolidinylmethoxy]cyclohexanecarboxylic acid ethyl ester NMR (CDCl$_3$) δ: 1.16-1.56 (7H, m), 1.68-2.36 (6H, m), 2.80-3.02 (3H, m), 3.16-3.31 (5H, m), 3.43-3.83 (7H, m), 3.89-4.36 (5H, m), 7.39-7.45 (3H, m), 7.56-7.63 (1H, m), 8.02-8.08 (1H, m), 8.24 (1H, d, J=3.2 Hz), 8.30 (1H, d, J=2.4 Hz), 8.67 (1H, d, J=7.3 Hz).

MS (ESI) m/z: 686 (M$^+$+1), 688 (M$^+$+3).

Trans-4-[1-[[4-[(benzo[b]furan-3-ylcarbonyl)amino]-2,5-dichlorophenyl]acetyl]-(4S)-(3-methoxyazetidin-1-yl)-(2S)-pyrrolidinylmethoxy]cyclohexanecarboxylic acid

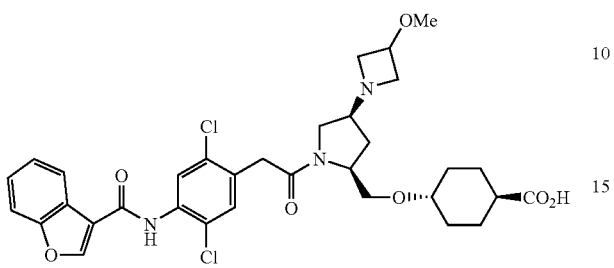

[Formula 97]

NMR (DMSO-d$_6$) δ: 1.07-1.44 (4H, m), 1.64-2.21 (6H, m), 2.64-3.04 (4H, m), 3.15 and 3.17 (total 3H, each s, amide isomers), 3.21-3.32 (1H, m), 3.44 (1H, t, J=6.1 Hz), 3.49-3.56 (1H, m), 3.57 (3H, s), 3.59-3.66 (1H, m), 3.75 (2H, s), 3.90-4.00 (3H, m), 7.37-7.46 (2H, m), 7.54 (1H, d, J=10.0 Hz), 7.72 (1H, dd, J=7.6, 1.2 Hz), 7.76 (1H, d, J=3.7 Hz), 8.07-8.11 (1H, m), 8.82 (1H, d, J=1.7 Hz), 10.05 (1H, d, J=3.9 Hz), 12.06 (1H, s).
MS (ESI) m/z: 658 (M$^+$+1), 660 (M$^+$+3).
IR (ATR) cm$^{-1}$: 2933, 2858, 1678, 1637, 1572, 1508.
Anal. Calcd for C$_{33}$H$_{37}$Cl$_2$N$_3$O$_7$·H$_2$O: C, 58.58; H, 5.81; Cl, 10.48; N, 6.21.
Found: C, 58.72; H, 5.83; Cl, 10.22; N, 5.91.

Example 7

Trans-4-[1-[[5-chloro-2-fluoro-4-(isoquinolin-1-ylcarbonylamino)phenyl]acetyl]-(4S)-(3-methoxyazetidin-1-yl)-(2S)-pyrrolidinylmethoxy]cyclohexanecarboxylic acid Trans-4-[1-[[5-chloro-2-fluoro-4-(isoquinolin-1-ylcarbonylamino)phenyl]acetyl]-(4S)-(3-methoxyazetidin-1-yl)-(2S-pyrrolidinylmethoxy]cyclohexanecarboxylic acid ethyl ester NMR (CDCl$_3$) δ: 1.10-1.32 (5H, m), 1.33-1.56 (2H, m), 1.85-2.34 (7H, m), 2.57-3.02 (3H, m), 3.13-3.26 (2H, m), 3.26 and 3.27 (total 3H, each0 s, amide isomers), 3.65-3.87 (7H, m), 3.89-4.34 (4H, m), 7.41 (1H, d, J=7.4 Hz), 7.71-7.79 (2H, m), 7.87-7.92 (2H, m), 8.52-8.61 (2H, m), 9.73-9.67 (1H, m), 11.09 (1H, d, J=8.1 Hz).
MS (ESI) m/z: 681 (M$^+$+1), 683 (M$^+$+3)

Trans-4-[1-[[5-chloro-2-fluoro-4-(isoquinolin-1-ylcarbonylamino)phenyl]acetyl]-(4S)-(3-methoxyazetidin-1-yl)-(2S)-pyrrolidinylmethoxy]cyclohexanecarboxylic acid

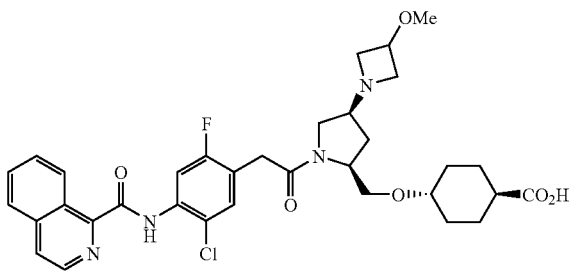

[Formula 98]

NMR (CDCl$_3$) δ: 1.19-1.67 (4H, m), 1.86-2.34 (7H, m), 2.94-3.11 (4H, m), 3.18-3.25 (1H, m), 3.25 and 3.26 (total 3H, d and s, J=1.0 Hz, amide isomers), 3.48-3.88 (7H, m), 4.04-4.27 (2H, m), 7.40 (1H, d, J=6.8 Hz), 7.72-7.79 (2H, m), 7.89 (2H, t, J=6.3 Hz), 8.53 and 8.58 (total 1H, each s, amide isomers), 8.56 and 8.59 (total 1H, each s, amide isomers), 9.67-9.73 (1H, m), 11.09 (1H, d, J=5.1 Hz).
MS (ESI) m/z: 653 (M$^+$+1), 655 (M$^+$+3).
IR (ATR) cm$^{-1}$: 3288, 2935, 2860, 1718, 1691, 1647, 1622.

Example 8

Trans-4-[1-[[2,5-dichloro-4-(isoquinolin-1-ylcarbonyl amino)phenyl]acetyl]-(4S)-(3-methoxyazetidin-1-yl)-(2S)-pyrrolidinylmethoxy]cyclohexanecarboxylic acid Trans-4-[1-[[2,5-dichloro-4-(isoquinolin-1-ylcarbonyl amino)phenyl]acetyl]-(4S)-(3-methoxyazetidin-1-yl)-(2S)-pyrrolidinylmethoxy]cyclohexanecarboxylic acid ethyl ester NMR (CDCl$_3$) δ: 1.15-1.54 (7H, m), 1.85-2.32 (7H, m), 2.78-3.03 (3H, m), 3.13-3.31 (5H, m), 3.47-3.89 (7H, m), 4.09-4.09 (4H, m), 7.42 (1H, d, J=1.7 Hz), 7.71-7.80 (2H, m), 7.87-7.94 (2H, m), 8.58 (1H, d, J=5.4 Hz), 8.84 (1H, d, J=8.1 Hz), 9.74-9.67 (1H, m), 11.07 (1H, d, J=7.1H z).
MS (ESI) m/z: 697 (M$^+$+1), 699 (M$^+$+3)

Trans-4-[1-[[2,5-dichloro-4-(isoquinolin-1-ylcarbonyl amino)phenyl]acetyl]-(4S)-(3-methoxyazetidin-1-yl)-(2S)-pyrrolidinylmethoxy]cyclohexanecarboxylic acid

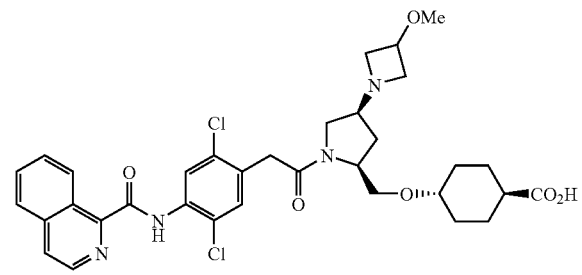

[Formula 99]

NMR (CDCl$_3$) δ: 1.13-1.57 (4H, m), 1.82-2.33 (7H, m), 2.92-3.24 (2H, m), 7.42 (1H, s), 7.68-7.83 (2H, m), 7.89 (2H, t, J=5.4 Hz), 8.58 (1H, d, J=5.1 Hz), 8.84 (1H, d, J=9.0 Hz), 9.66-9.74 (1H, m), 11.06 (1H, d, J=4.9 Hz).
MS (ESI) m/z: 669 (M$^+$+1), 671 (M$^+$+3)
IR (ATR) cm$^{-1}$: 3286, 2933, 2860, 1718, 1691, 1643, 1601.
Anal. Calcd for C$_{34}$H$_{38}$Cl$_2$N$_4$O$_6$·0.5HCl·0.5H$_2$O: C, 58.60; H, 5.71; Cl, 12.72; N, 8.04.
Found: C, 58.40; H, 5.70; Cl, 12.94; N, 7.63.

Example 9

Trans-4-[(4S)-(azetidin-1-yl)-1-[[4-[(benzo[b]thiophen-3-ylcarbonyl)amino]-5-chloro-2-fluorophenyl]acetyl]-(2S)-pyrrolidinylmethoxy]cyclohexanecarboxylic acid

Trans-4-[(4S)-(azetidin-1-yl)-1-(tert-butoxycarbonyl)-(2S)-pyrrolidinylmethoxy]cyclohexanecarboxylic acid ethyl ester NMR (CDCl$_3$) δ: 1.20-1.31 (5H, m), 1.41-1.50 (10H, m), 1.73-2.35 (8H, m), 2.76-2.86 (1H, m), 2.95-3.30 (7H, m), 3.31-3.97 (4H, m), 4.11 (2H, q, J=7.1 Hz).
MS (ESI) m/z: 411 (M$^+$+1).

Trans-4-[(4S)-(azetidin-1-yl)-(2S)-pyrrolidinylmethoxy]cyclohexanecarboxylic acid ethyl ester NMR (CDCl$_3$) δ: 1.13-1.58 (8H, m), 1.87-2.36 (8H, m), 2.52-3.01 (5H, m), 3.14-3.35 (4H, m), 3.43-3.59 (2H, m), 4.05-4.27 (2H, m).
MS (ESI) m/z: 311 (M$^+$+1).

Trans-4-[(4S)-(azetidin-1-yl)-1-[[4-[(benzo[b]thiophen-3-ylcarbonyl)amino]-5-chloro-2-fluorophenyl]acetyl]-(2S)-pyrrolidinylmethoxy]cyclohexanecarboxylic acid ethyl ester NMR (CDCl$_3$) δ: 1.10-1.57 (7H, m), 1.64-2.36 (9H, m), 2.84-2.97 (1H, m), 3.05-3.32 (6H, m), 3.49-3.88 (5H, m), 4.04-4.33 (3H, m), 7.40-7.44 (1H, m), 7.46 (1H, d, J=7.8 Hz), 7.52 (1H, t, J=7.6 Hz), 7.92 (1H, d and 8.44 (total 1H, each dd, J=12.0, 1.2 and 11.5, 1.0 Hz respectively, amide isomers), 8.48 (1H, d, J=7.8 Hz).
MS (ESI) m/z: 656 (M$^+$+1), 658 (M$^+$+3).

Trans-4-[(4S)-(azetidin-1-yl)-1-[[4-[(benzo[b]thiophen-3-ylcarbonyl)amino]-5-chloro-2-fluorophenyl]acetyl]-(2S)-pyrrolidinylmethoxy]cyclohexanecarboxylic acid

[Formula 100]

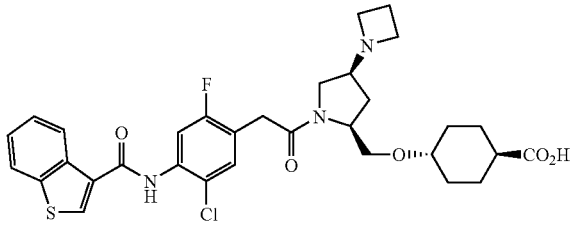

NMR (CDCl$_3$) δ: 1.14-1.53 (4H, m), 1.68-2.39 (7H, m), 2.55-2.62 (3H, m), 3.05-3.90 (10H, m), 4.17-4.29 (1H, m), 7.39-7.49 (2H, m), 7.52 (2H, t, J=8.1 Hz), 7.89 (1H, d, J=8.1 Hz), 8.10 (1H, t, J=3.2 Hz), 8.40-8.50 (3H, m).
MS (ESI) m/z: 628 (M$^+$+1), 630 (M$^+$+3).
IR (ATR) cm$^{-1}$: 3415, 3070, 2937, 2860, 1720, 1676, 1620.
Anal. Calcd for C$_{32}$H$_{35}$ClFN$_3$O$_5$S.1HCl.1H$_2$O: C, 54.86; H, 5.75; Cl, 10.12; F, 2.71; N, 6.00; S, 4.58.
Found: C, 54.54; H, 5.77; Cl, 10.14; F, 2.65; N, 5.98; S, 4.78.

Example 10

Trans-4-[1-[[2,5-dichloro-4-[(1-methyl-1H-indol-3-ylcarbonyl)amino]phenyl]acetyl]-(4S)-(3-methylazetidin-1-yl)-(2S)-pyrrolidinylmethoxy]cyclohexanecarboxylic acid

Trans-4-[1-(tert-butoxycarbonyl)-(4S)-(3-methylazetidin-1-yl)-(2S)-pyrrolidinylmethoxy]cyclohexanecarboxylic acid ethyl ester NMR (CDCl$_6$) δ: 1.13 (3H, d, J=6.6 Hz), 1.21-1.30 (6H, m), 1.42-1.49 (11H, m), 1.54-1.85 (1H, m), 1.86-2.15 (6H, m), 2.16-2.30 (1H, m), 2.41-2.83 (3H, m), 2.94-3.08 (1H, m), 3.16-3.92 (6H, m), 4.07-4.15 (3H, m).
MS (ESI) m/z: 425 (M$^+$+1).

Trans-4-[(4S)-(3-methylazetidin-1-yl)-(2S)-pyrrolidinylmethoxy]cyclohexanecarboxylic acid ethyl ester NMR (CDCl$_3$) δ: 1.09-1.28 (8H, m), 1.37-1.52 (4H, m), 1.54-1.86 (1H, m), 1.86-2.31 (6H, m), 2.48-2.97 (6H, m), 3.17-3.27 (1H, m), 3.36-3.56 (4H, m), 4.11 (2H, q, J=7.1 Hz).
MS (ESI) m/z: 324 (M$^+$+1).

Trans-4-[1-[[2,5-dichloro-4-[(1-methyl-1H-indol-3-ylcarbonyl)amino]phenyl]acetyl]-(4S)-(3-methylazetidin-1-yl)-(2S)-pyrrolidinylmethoxy]cyclohexanecarboxylic acid ethyl ester NMR (CDCl$_3$) δ: 1.12-1.33 (10H, m), 1.36-1.55 (2H, m), 1.59-2.15 (5H, m), 2.16-2.32 (1H, m), 2.42-2.58 (1H, m), 2.60-2.77 (2H, m), 2.83-2.94 (1H, m), 3.14-3.84 (9H, m), 3.88 (3H, s), 4.10 (2H, q, J=7.3 Hz), 4.15-4.23 (1H, m), 7.32-7.44 (4H, m), 7.79 (1H, d, J=2.2 Hz), 8.17-8.11 (1H, m), 8.23 (1H, d, J=3.2 Hz), 8.77 (1H, d, J=6.6 Hz).
MS (ESI) m/z: 683 (M$^+$+1), 685 (M$^+$+3).

Trans-4-[1-[[2,5-dichloro-4-[(1-methyl-1H-indol-3-ylcarbonyl)amino]phenyl]acetyl]-(4S)-(3-methylazetidin-1-yl)-(2S)-pyrrolidinylmethoxy]cyclohexanecarboxylic acid

[Formula 101]

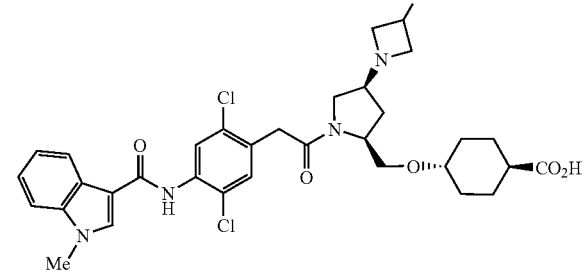

NMR (CDCl$_3$) δ: 0.93-1.69 (7H, m), 1.78-2.40 (7H, m), 2.57-3.36 (6H, m), 3.39-4.03 (9H, m), 4.15-4.32 (2H, m), 6.01 (1H, br s), 7.29-7.53 (4H, m), 7.78 (1H, d, J=2.9 Hz), 8.08-8.10 (1H, m), 8.22 (1H, d, J=2.9 Hz), 8.75 (1H, d, J=9.0 Hz).
MS (ESI) m/z: 655 (M$^+$+1), 655 (M$^+$+3).
IR (ATR) cm$^{-1}$: 2935, 2860, 1716, 1643, 1568, 1533, 1500.

Example 11

Trans-4-[1-[[4-[(benzo[b]furan-3-ylcarbonyl)amino]-5-chloro-2-fluorophenyl]acetyl]-(4S)-(3-methylazetidin-1-yl)-(2S)-pyrrolidinylmethoxy]cyclohexanecarboxylic acid Trans-4-[1-[[4-[(benzo[b]furan-3-ylcarbonyl)amino]-5-chloro-2-fluorophenyl]acetyl]-(4S)-(3-methylazetidin-1-yl)-(2S)-pyrrolidinylmethoxy]cyclohexanecarboxylic acid ethyl ester NMR (CDCl$_3$) δ: 1.01-1.73 (11H, m), 1.77-2.34 (7H, m), 2.40-2.96 (4H, m), 3.01-3.91 (10H, m), 4.06-4.22 (3H, m), 7.38-7.48 (2H, m), 7.56-7.65 (1H, m), 8.02-8.09 (1H, m), 8.27-8.34 (2H, m), 8.40 (1H, dd, J=11.5, 7.8 Hz).
MS (ESI) m/z: 653 (M$^+$+1), 655 (M$^+$+3).

Trans-4-[1-[[4-[(benzo[b]furan-3-ylcarbonyl)amino]-5-chloro-2-fluorophenyl]acetyl]-(4S)-(3-methylazetidin-1-yl)-(2S)-pyrrolidinylmethoxy]cyclohexanecarboxylic acid

[Formula 102]

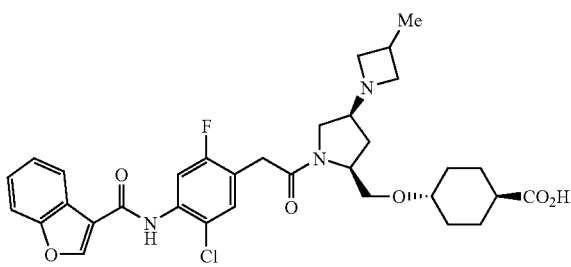

NMR (CDCl$_3$) δ: 1.09-1.63 (7H, m), 1.84-2.40 (7H, m), 2.67-3.31 (6H, m), 3.46-3.90 (6H, m), 4.13-4.29 (2H, m), 7.37-7.45 (3H, m), 7.56-7.62 (1H, m), 8.02-8.08 (1H, m), 8.27 (1H, s), 8.30 (1H, d, J=3.9 Hz), 8.40 (1H, dd, J=11.6, 4.8 Hz).
MS (ESI) m/z: 626 (M$^+$+1), 628 (M$^+$+3)
IR (ATR) cm$^{-1}$: 3413, 3132, 3070, 2935, 2860, 1678, 1637, 1587.
Anal. Calcd for C$_{33}$H$_{37}$ClFN$_3$O$_6$·H$_2$O: C, 61.53; H, 6.10; Cl, 5.50; F, 2.95; N, 6.10.
Found: C, 61.62; H, 6.12; Cl, 5.32; F, 2.78; N, 6.18.

Example 12

Trans-4-[1-[[4-[(benzo[b]thiophen-3-ylcarbonyl)amino]-5-chloro-2-fluorophenyl]acetyl]-(4S)-[3-(2-methoxyethyl)azetidin-1-yl]-(2S)-pyrrolidinylmethoxy]cyclohexanecarboxylic acid 1-Benzhydryl-3-(2-hydroxyethyl)azetidine Lithium aluminumhydride (889 mg, 23.4 mmol) was suspended in tetrahydrofuran (50 mL), and under a nitrogen stream, a tetrahydrofuran (30 mL) solution of (1-benzhydrylazetidin-3-ylidene)acetic acid ethyl ester (2.40 g, 7.81 mmol) was added dropwise over 20 minutes at 0° C. with stirring. The reaction liquor was stirred for two hours at the same temperature, and then while cooling the reaction liquor in ice, water (889 μl), 1 N sodium hydroxide (889 μl) and water (8.57 mL) were added in this order. The resulting mixture was dried over anhydrous sodium sulfate. The insoluble was separated by filtration, and the mother liquor was concentrated under reduced pressure. The obtained residue was purified by flash chromatography (Flash Chromatography System from Biotage AB, column size: 40M, ethyl acetate:n-hexane=1:1 to ethyl acetate), to obtain the title compound (1.58 g, 76%) as an oily matter.
NMR (CDCl$_3$) δ: 1.83 (2H, dq, J=1.5, 6.6 Hz), 2.50-2.60 (1H, m), 2.87-2.92 (2H, m), 3.28-3.33 (2H, m), 3.70 (2H, dt, J=1.7, 6.3 Hz), 4.33 (1H, s), 7.16-7.21 (3H, m), 7.45-7.35 (5H, m), 7.36-7.45 (7H, m).
MS (ESI) m/z: 268 (M$^+$+1).

1-Benzhydryl-3-(2-methoxyethyl)azetidine

1-Benzhydryl-3-(2-hydroxyethyl)azetidine (1.58 g, 5.91 mmol) was suspended in DMF (30 mL), and under a nitrogen stream, methyl iodide (0.37 mL, 5.91 mmol) and 60% sodium hydride (355 mg, 8.87 mmol) were added at 0° C. with stirring. The reaction mixture was stirred for two hours at the same temperature and then poured onto ice water, and the mixture was extracted with ethyl acetate. The combined extract was washed with ice water and saturated brine, and dried over anhydrous sodium sulfate, and then the solvent was concentrated under reduced pressure. The obtained residue was purified by flash chromatography (Flash Chromatography System from Biotage AB, column size: 40M, ethyl acetate:n-hexane=5:95), to obtain the title compound (700 mg, 42%) as an oily matter.
NMR (CDCl$_3$) δ: 1.80 (2H, dd, J=13.9, 6.6 Hz), 2.48-2.58 (1H, m), 2.73 (2H, t, J=7.6 Hz), 3.27 (3H, s), 3.29 (2H, t, J=6.3 Hz), 3.36 (2H, t, J=7.6 Hz), 4.30 (1H, s), 7.47-7.12 (10H, m).
MS (ESI) m/z: 282 (M$^+$+1).

1-(Tert-butoxycarbonyl)-3-(2-methoxyethyl)azetidine

1-Benzhydryl-3-(2-methoxyethyl)azetidine (700 mg, 2.49 mmol) was dissolved in ethyl acetate (50 mL), and Boc$_2$O (543 mg, 2.49 mmol) and 10% palladium hydride-carbon (700 mg) were added at room temperature. The mixture was stirred for 17 hours under a hydrogen stream. The catalyst was separated by filtration, and the reaction liquor was concentrated under reduced pressure. The obtained residue was purified by flash chromatography (Flash Chromatography System from Biotage AB, column size: 40M, ethyl acetate:n-hexane=5:95), to obtain the title compound (430 mg, 61%) as an oily matter.
NMR (CDCl$_3$) δ: 1.21 (3H, t, J=7.1 Hz), 1.43 (9H, s), 3.43 (2H, q, J=6.8 Hz), 3.82 (2H, ddd, J=9.3, 4.2, 1.0 Hz), 4.04-4.10 (2H, m), 4.18-4.24 (1H, m).

3-(2-Methoxyethyl)azetidine hydrochloride 1-(Tert-butoxycarbonyl)-3-(2-methoxyethyl)azetidine (0.82 g, 4.07 mmol) was dissolved in 4N Hydrogen Chloride/dioxane (10 mL), and the mixture was stirred for two days at room temperature. The reaction liquor was concentrated under reduced pressure. The obtained colorless oily matter was supplied to the subsequent reaction.

Anal. Calcd for C$_{34}$H$_{40}$Cl$_2$N$_4$O$_5$·1.5H$_2$O: C, 59.82; H, 6.35; Cl, 10.39; N, 8.21.
Found: C, 60.25; H, 6.40; Cl, 10.16; N, 7.73.

Trans-4-[1-(tert-butoxycarbonyl)-(4S)-[3-(2-methoxyethyl)azetidin-1-yl]-(2S)-pyrrolidinylmethoxy]cyclohexanecarboxylic acid ethyl ester MS (ESI) m/z: 469 (M$^+$+1).

Trans-4-[(4S)-[3-(2-methoxyethyl)azetidin-1-yl]-(2S)-pyrrolidinylmethoxy]cyclohexanecarboxylic acid ethyl ester NMR (CDCl$_3$) δ: 1.11-1.31 (6H, m), 1.37-1.55 (2H, m), 1.77 (1H, q, J=7.1 Hz), 1.84-1.93 (1H, m), 1.95-2.16 (6H, m), 2.23 (1H, tt, J=11.7, 3.7 Hz), 2.43-2.56 (1H, m), 2.62-2.93 (4H, m), 3.15-3.53 (11H, m), 3.66 (1H, d, J=1.5 Hz), 4.11 (2H, q, J=7.2 Hz).
MS (ESI) m/z: 368 (M$^+$+1).

Trans-4-[1-[[4-[(benzo[b]thiophen-3-ylcarbonyl)amino]-5-chloro-2-fluorophenyl]acetyl]-(4S)-[3-(2-methoxyethyl)azetidin-etidin-1-yl]-(2S)-pyrrolidinylmethoxy]cyclohexanecarboxylic acid ethyl ester NMR (CDCl$_3$) δ: 1.16-1.29 (5H, m), 1.36-1.58 (1H, m), 1.57-1.86 (3H, m), 1.88-2.13 (4H, m), 2.16-2.31 (1H, m), 2.34-3.02 (3H, m), 3.13-3.88 (16H, m), 4.06-4.20 (3H, m), 7.40-7.45 (1H, m), 7.46 (1H, d, J=7.8 Hz), 7.52 (1H, t, J=8.1 Hz), 7.92 (1H, d, J=8.1 Hz), 8.09 (1H, d, J=5.9 Hz), 8.33 (1H, d, J=7.1 Hz), 8.40-8.50 (2H, m).
MS (ESI) m/z: 714 (M$^+$+1), 716 (M$^+$+3).

Trans-4-[1-[[4-[(benzo[b]thiophen-3-ylcarbonyl)amino]-5-chloro-2-fluorophenyl]acetyl]-(4S)-[3-(2-methoxyethyl)azetidin-1-yl]-(2S)-pyrrolidinylmethoxy]cyclohexanecarboxylic acid

[Formula 103]

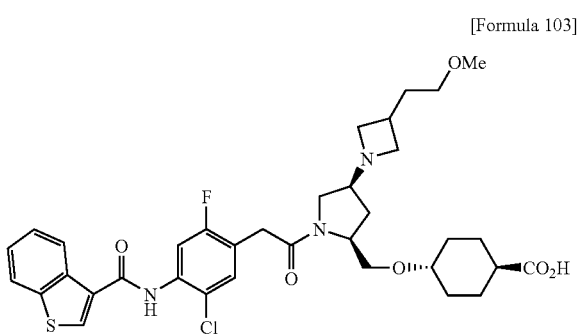

NMR (CDCl$_3$) δ: 1.17-1.34 (4H, m), 1.36-1.63 (3H, m), 1.72-1.96 (2H, m), 1.96-2.17 (3H, m), 2.17-2.41 (2H, m), 2.67-2.79 (1H, m), 2.97-3.27 (7H, m), 3.28 (3H, s), 3.29 (0H, s), 3.32 (1H, q, J=5.9 Hz), 3.46-3.87 (7H, m), 4.13-4.29 (1H, m), 7.39 (1H, d, J=7.3 Hz), 7.91 (1H, dd, J=8.1, 3.7 Hz), 8.10 (1H, d, J=6.3 Hz), 8.34 (1H, d, J=10.7 Hz), 8.42 (1H, dd, J=11.7, 6.8 Hz), 8.47 (1H, d, J=8.3 Hz).
MS (ESI) m/z: 686 (M$^+$+1), 688 (M$^+$+3).

Example 13

Trans-4-[1-[[4-[(benzo[b]furan-3-ylcarbonyl)amino]-5-chloro-2-fluorophenyl]acetyl]-(4S)-[3-(fluoromethyl)azetidin-1-yl]-(2S)-pyrrolidinylmethoxy]cyclohexanecarboxylic acid (1-Benzhydrylazetidin-3-yl)methanol To an anhydrous tetrahydrofuran solution (100 mL) of lithium aluminum hydride (1.14 g, 29.93 mmol), a tetrahydrofuran solution (50 mL) of 1-benzhydrylazetidin-3-carboxylic acid methyl ester (Oakwood Products, Inc.: Code No. W07L) (2.00 g, 7.16 mmol) was added dropwise over 10 minutes under ice cooling and stirring, and the reaction mixture was stirred for 3.5 hours. While the reaction mixture was stirred again under ice cooling, water (1.14 mL), a 4N-aqueous solution of sodium hydroxide (1.14 mL) and water (4.50 mL) were added to the reaction liquor, and the mixture was stirred for 20 minutes. Precipitated insoluble matter was removed through separation by filtration, and the obtained mother liquor was concentrated under reduced pressure to obtain the title compound (1.97 g, over yield) as an oily matter.

NMR (CDCl$_3$) δ: 2.52-2.62 (1H, m), 3.00-3.07 (2H, m), 3.24 (2H, t, J=7.5 Hz), 3.68-3.77 (1H, m), 3.80 (2H, d, J=5.1 Hz), 4.34 (1H, s), 7.13-7.42 (11H, m).
MS (ESI) m/z: 254 (M$^+$+1).

3-Azetidinemethanol acetate (1-Benzhydrylazetidin-3-yl)methanol (1.81 g, 7.16 mmol) was dissolved in ethanol (50 mL), and acetic acid (0.82 mL, 14.32 mmol) and 10% palladium hydroxide/carbon (1.2 g) were added at room temperature. The mixture was stirred for three days under a hydrogen stream at normal pressure. The catalyst was separated by filtration, and the reaction liquor was concentrated under reduced pressure, to obtain the title compound as an oily matter. This compound was used in the subsequent reaction without being subjected to further purification.

Trans-4-[1-(tert-butoxycarbonyl)-(4S)-[(3-hydroxymethyl)azetidin-1-yl]-(2S)-pyrrolidinylmethoxy]cyclohexanecarboxylic acid ethyl ester NMR (CDCl$_3$) δ: 1.17-1.30 (7H, m), 1.39-1.51 (11H, m), 1.77-2.34-3.60 (1H, m), 3.93-3.62 (4H, m), 3.99 (1H, s), 4.11 (2H, q, J=7.2 Hz).
MS (ESI) m/z: 441 (M$^+$+1).

Trans-4-[1-(tert-butoxycarbonyl)-(4S)-[3-(fluoromethyl)azetidin-1-yl]-(2S)-pyrrolidinylmethoxy]cyclohexanecarboxylic acid ethyl ester To a dichloroethane solution (50 mL) of trans-4-[1-(tert-butoxycarbonyl)-(4S)-1-[(3-fluoromethyl)azetidinyl]-(2S)-pyrrolidinylmethoxy]cyclohexanecarboxylic acid ethyl ester (0.92 g, 2.09 mmol), diethylaminosulfur trifluoride (DAST) (0.33 mL, 2.51 mmol) was added at −78° C. under a nitrogen stream while stirring. The reaction liquor was stirred for 23 hours while slowly elevating the temperature to room temperature. The reaction liquor was poured onto ice water, and extracted with dichloromethane. The extract was washed with a saturated aqueous solution of sodium hydrogen carbonate and saturated brine in this order, and dried over anhydrous sodium sulfate, and the solvent was concentrated under reduced pressure. The obtained residue was purified by flash chromatography (Flash Chromatography System from Biotage AB, column size: 25S, ethyl acetate to methanol/ethyl acetate=1/3), to obtain the title compound (0.74 g, 80%) as an oily matter.

NMR (CDCl$_3$) δ: 1.16-1.30 (7H, m), 1.39-1.51 (11H, m), 1.71-2.30 (7H, m), 2.63-3.94 (8H, m), 3.99 (2H, s), 4.11 (2H, q, J=7.1 Hz), 4.49 (2H, dd, J=47.7, 5.8 Hz).
MS (ESI) m/z: 443 (M$^+$+1).

Trans-4-[(4S)-[3-(fluoromethyl)azetidin-1-yl]-(2S)-pyrrolidinylmethoxy]cyclohexanecarboxylic acid ethyl ester NMR (CDCl$_3$) δ: 1.11-1.57 (7H, m), 1.87-2.33 (7H, m), 2.16-2.31 (1H, m), 2.70-3.77 (7H, m), 3.99 (4H, s), 4.12 (2H, q, J=7.1 Hz), 4.49 (2H, dd, J=47.4, 5.5 Hz).
MS (ESI) m/z: 343 (M$^+$+1).

Trans-4-[1-[[4-[(benzo[b]furan-3-ylcarbonyl)amino]-5-chloro-2-fluorophenyl]acetyl]-(4S)-[3-(fluoromethyl)azetidin-1-yl]-(2S)-pyrrolidinylmethoxy]cyclohexanecarboxylic acid ethyl ester NMR (CDCl$_3$) δ: 1.13-1.55 (7H, m), 1.89-2.32 (8H, m), 2.66-3.41 (7H, m), 3.47-3.87 (5H, m), 4.06-4.23 (3H, m), 4.50 (2H, dt, J=47.5, 5.2 Hz), 7.41-7.46 (3H, m), 7.58-7.64 (1H, m), 8.03-8.08 (1H, m), 8.27 (1H, d, J=5.9 Hz), 8.30 and 8.31 (total 1H, each s, amide isomers), 8.43 and 8.45 (total 1H, each d, each J=11.8 Hz, amide isomers).
MS (ESI) m/z: 672 (M$^+$+1), 674 (M$^+$+3).

Trans-4-[1-[[4-[(benzo[b]furan-3-ylcarbonyl)amino]-5-chloro-2-fluorophenyl]acetyl]-(4S)-[3-(fluoromethyl)azetidin-1-yl]-(2S)-pyrrolidinylmethoxy]cyclohexanecarboxylic acid

[Formula 104]

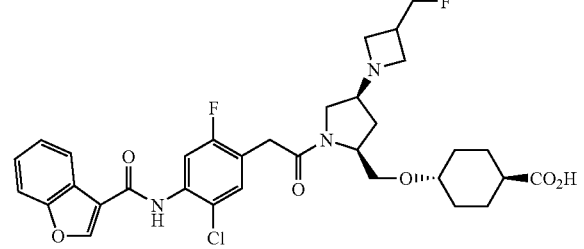

NMR (CDCl$_3$) δ: 1.09-180 (4H, m), 1.84-2.39 (8H, m), 2.80-3.30 (6H, m), 3.38-4.04 (8H, m) 4.47 (2H, ddd, J=47.4, 8.0, 5.2 Hz), 7.41-7.46 (2H, m), 7.57-7.64 (1H, m), 8.02-8.10 (1H, m), 8.27 (1H, d, J=5.1 Hz), 8.30 (1H, d, J=2.0 Hz), 8.44 (1H, dd, J=11.6, 8.9 Hz).
MS (ESI) m/z: 644 (M$^+$+1), 646 (M$^+$+3).
IR (ATR) cm$^{-1}$: 3415, 2941, 2858, 1707, 1676, 1635, 1587, 1558.
Anal. Calcd for C$_{34}$H$_{39}$ClFN$_3$O$_6$.1.75H$_2$O: C, 58.66; H, 5.89; Cl, 5.25; F, 5.62; N, 6.22.
Found: C, 59.07; H, 5.65; Cl, 5.57; F, 5.19; N, 5.88.

Example 14

Trans-4-[1-[[5-chloro-2-fluoro-4-[(1-methyl-1H-indol-3-ylcarbonyl)amino]phenyl]acetyl]-(4S)-(3,3-dimethylazetidin-1-yl)-(2S)-pyrrolidinylmethoxy]cyclohexanecarboxylic acid Trans-4-[1-(tert-butoxycarbonyl)-(4S)-(3,3-dimethylazetidin-1-yl)-(2S)-pyrrolidinylmethoxy]cyclohexanecarboxylic acid ethyl ester NMR (CDCl$_3$) δ: 1.13-1.31 (11H, m), 1.37-1.53 (11H, m), 1.72-2.29 (7H, m), 2.80-3.10 (4H, m), 3.14-3.47 (3H, m), 3.55-3.94 (4H, m), 4.06-4.16 (2H, m).
MS (ESI) m/z: 439 (M$^+$+1).

Trans-4-[(4S)-(3,3-dimethylazetidin-1-yl)-(2S)-pyrrolidinylmethoxy]cyclohexanecarboxylic acid ethyl ester NMR (CDCl$_3$) δ: 1.19-1.31 (11H, m), 1.36-1.55 (2H, m), 1.82-2.46-3.69 (4H, m), 4.08 (2H, q, J=7.2 Hz).
MS (ESI) m/z: 339 (M$^+$+1).

Trans-4-[1-[[5-chloro-2-fluoro-4-[(1-methyl-1H-indol-3-ylcarbonyl)amino]phenyl]acetyl]-(4S)-(3,3-dimethylazetidin-1-yl)-(2S)-pyrrolidinylmethoxy]cyclohexanecarboxylic acid ethyl ester NMR (CDCl$_3$) δ: 1.09-1.34 (12H, m), 1.35-1.77 (2H, m), 1.81-2.33-7.27 (1H, m), 7.33-7.33 (2H, m), 7.53-7.71 (1H, m), 7.81 (1H, d, J=1.7 Hz), 8.01-8.19 (1H, m), 8.30 (1H, s), 8.50 (1H, dd, J=12.0, 9.3 Hz).
MS (ESI) m/z: 681 (M$^+$+1), 683 (M$^+$+3).

Trans-4-[1-[[5-chloro-2-fluoro-4-[(1-methyl-1H-indol-3-ylcarbonyl)amino]phenyl]acetyl]-(4S)-(3,3-dimethylazetidin-1-yl)-(2S)-pyrrolidinylmethoxy]cyclohexanecarboxylic acid

[Formula 105]

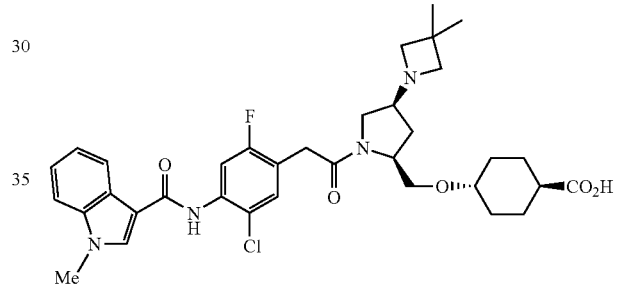

NMR (CDCl$_3$) δ: 1.15-1.33 (8H, m), 1.37-1.67 (2H, m), 1.79-2.69 (1H, m), 8.29 (1H, d, J=2.9 Hz), 8.49 (1H, t, J=12.1 Hz).
MS (ESI) m/z: 653 (M$^+$+1), 655 (M$^+$+3).
IR (ATR) cm$^{-1}$: 3419, 2935, 2860, 1716, 1644, 1583, 1518.
Anal. Calcd for C$_{35}$H$_{42}$ClFN$_4$O$_5$.1.5H$_2$O: C, 61.80; H, 6.67; Cl, 5.21; F, 2.79; N, 8.24.
Found: C, 61.91; H, 6.48; Cl, 5.11; F, 2.76; N, 7.96.

Example 15

Trans-4-[1-[[2,5-dichloro-4-[(1-methyl-1H-indol-3-ylcarbonyl)amino]phenyl]acetyl]-(4S)-(3,3-dimethylazetidin-1-yl)-(2S)-pyrrolidinylmethoxy]cyclohexanecarboxylic acid Trans-4-[1-[[2,5-dichloro-4-[(1-methyl-1H-indol-3-ylcarbonyl)amino]phenyl]acetyl]-(4S)-(3,3-dimethylazetidin-1-yl)-(2S)-pyrrolidinylmethoxy]cyclohexanecarboxylic acid ethyl ester NMR (CDCl$_3$) δ: 1.16-1.50 (13H, m), 1.84-2.31 (7H, m), 2.79-2.98 (4H, m), 3.16-3.56 (3H, m), 3.62-4.00 (7H, m), 4.05-4.26 (3H, m), 7.31-7.49 (4H, m), 7.53-7.70 (1H, m), 7.81 (1H, t, J=2.1 Hz), 8.10-8.17 (1H, m), 8.24 (1H, d, J=2.9 Hz), 8.78 (1H, d, J=7.1 Hz).
MS (ESI) m/z: 697 (M$^+$+1), 699 (M$^+$+3).

Trans-4-[1-[[2,5-dichloro-4-[(1-methyl-1H-indol-3-ylcarbonyl)amino]phenyl]acetyl]-(4S)-(3,3-dimethylazetidin-1-yl)-(2S)-pyrrolidinylmethoxy]cyclohexanecarboxylic acid

[Formula 106]

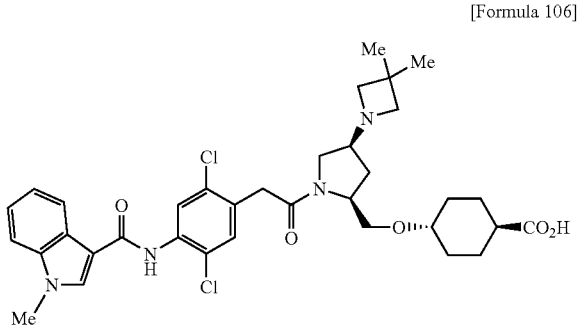

NMR (CDCl$_3$) δ: 1.07-1.32 (8H, m), 1.38-1.65 (2H, m), 1.87-2.30 (6H, m), 2.62 (4H, s), 3.05-3.29 (6H, m), 3.42-3.83 (4H, m), 3.90 (3H, d t, J=31.7, 13.2 Hz), 4.07-4.24 (1H, m), 7.32-7.52 (4H, m), 7.79 (1H, d, J=2.7 Hz), 8.12 (1H, dt, J=6.3, 2.2 Hz), 8.23 (1H, d, J=2.2 Hz), 8.77 (1H, d, J=10.8 Hz).

MS (ESI) m/z: 669 (M$^+$+1), 671 (M$^+$+3).

IR (ATR) cm$^{-1}$: 3419, 2937, 2861, 1720, 1645, 1568, 1533.

Anal. Calcd for C$_{35}$H$_{42}$Cl$_2$N$_4$O$_5$·1.5H$_2$O: C, 60.34; H, 6.51; Cl, 10.18; N, 8.04.

Found: C, 60.47; H, 6.34; Cl, 10.33; N, 7.62.

Example 16

Trans-4-[1-[[5-chloro-2-fluoro-4-[(1-methyl-1H-indol-3-ylcarbonyl)amino]phenyl]acetyl]-(4S)-(3-methoxy-3-methylazetidin-1-yl)-(2S)-pyrrolidinylmethoxy]cyclohexanecarboxylic acid

1-Benzhydryl-3-methylazetidin-3-ol

To a tetrahydrofuran solution (10 mL) of 1-benzhydrylazetidin-3-one (530 mg, 1.94 mmol), methylmagnesium iodide (0.84 M ether solution) (4.62 mL, 3.88 mmol) was added at 0° C. under a nitrogen stream, and the mixture was stirred for one hour at the same temperature. A saturated aqueous solution of sodium hydrogen carbonate (20 mL) was added to the reaction liquor, and the mixture was stirred for 15 minutes. Then, the reaction liquor was filtered through celite, and the filtrate was extracted with ethyl acetate. The extract was washed with saturated brine, and then dried over anhydrous sodium sulfate. Sodium sulfate was separated by filtration, and the solvent was concentrated under reduced pressure. The obtained residue was purified by flash chromatography (Flash Chromatography System from Biotage AB, column size: 40S, ethyl acetate/n-hexane=1/4 to ethyl acetate), to obtain the title compound (511 mg, quant.) as an oily matter.

NMR (CDCl$_3$) δ: 1.52 (3H, s), 2.98 (2H, d, J=8.1 Hz), 3.19 (2H, dd, J=7.1, 1.7 Hz), 4.35 (1H, s), 7.31-7.14 (6H, m), 7.43-7.38 (4H, m).

MS (ESI) m/z: 254 (M$^+$+1)

1-Benzhydryl-3-methoxy-3-methylazetidine

To a DMF (2 mL) solution of 1-benzhydryl-3-methylazetidin-3-ol (123 mg, 0.486 mmol), methyl iodide (33.2 μl, 0.534 mmol) and 60% sodium hydride (29 mg, 0.729 mmol) were added at 0° C. under a nitrogen stream, and the mixture was stirred for one hour at the same temperature. The reaction liquor was poured onto ice water, and the mixture was extracted with ethyl acetate. The extract was washed with ice water and saturated brine in this order, and then dried over anhydrous sodium sulfate. Sodium sulfate was removed, and then the solvent was concentrated under reduced pressure. The obtained residue was purified by thin layer chromatography (ethyl acetate/n-hexane=10/1, v/v), to obtain the title compound (38 mg, 29%) as an oily matter.

NMR (CDCl$_3$) δ: 1.49 (3H, s), 3.01 (2H, d, J=7.3 Hz), 3.10 (2H, dd, J=8.3, 1.7 Hz), 3.18 and 3.19 (total 3H, each s), 3.19 (3H, s), 4.38 (1H, s), 7.14-7.22 (2H, m), 7.23-7.29 (4H, m), 7.45-7.40 (4H, m).

MS (ESI) m/z: 268 (M$^+$+1).

1-(Tert-butoxycarbonyl)-3-methoxy-3-methylazetidine

1-Benzhydryl-3-methoxy-3-methylazetidine (1.72 g, 6.43 mmol) was dissolved in ethyl acetate (50 mL), and Boc$_2$O (2.11 g, 9.65 mmol) and 10% palladium hydride/carbon (1.72 g) were added at room temperature. The mixture was stirred for two days under a hydrogen stream at normal pressure. The catalyst was separated by filtration, and the obtained reaction liquor was concentrated under reduced pressure. The obtained residue was purified by flash chromatography (Flash Chromatography System from Biotage AB, column size: 40S, ethyl acetate/n-hexane=1/9 to 3/7), to obtain the title compound (1.20 g, 93%) as an oily matter.

NMR (CDCl$_3$) δ: 1.44 (3H, s), 1.45 (9H, s), 3.24 (3H, s), 3.66 (2H, d, J=8.8 Hz), 3.91 (2H, d, J=9.0 Hz).

MS (ESI) m/z: 202 (M$^+$+1).

3-Methoxy-3-methylazetidine hydrochloride 1-(Tert-butoxycarbonyl) 3-methoxy-3-methylazetidine (1.20 g, 5.96 mmol) was dissolved in 4NHydrogen Clhloride/dioxane (10 mL), and the mixture was stirred for 6 hours at room temperature. The reaction liquor was concentrated under reduced pressure to obtain the title compound (831 mg, quantitative) as a solid.

NMR (DMSO-d$_6$) δ: 1.45 (3H, s), 3.17 (3H, s), 3.57 (1H, s), 3.70-3.80 (2H, m), 3.84-3.97 (2H, m), 9.64-9.03 (1H, m).

MS (ESI) m/z: 102 (M$^+$+1).

Trans-4-[1-(tert-butoxycarbonyl)-(4S)-(3-methoxy-3-methylazetidin-1-yl)-(2S)-pyrrolidinylmethoxy]cyclohexanecarboxylic acid ethyl ester NMR (CDCl$_3$) δ: 1.24-1.27 (6H, m), 1.42-1.49 (5H, m), 1.58 (9H, s), 2.85-3.28 (8H, m), 3.34-4.00 (5H, m), 3.74-3.74 (7H, m), 4.08-4.16 (2H, m).

MS (ESI) m/z: 455 (M$^+$+1).

Trans-4-[(4S)-(3-methoxy-3-methylazetidin-1-yl)-(2S)-pyrrolidinylmethoxy]cyclohexanecarboxylic acid ethyl ester NMR (CDCl$_3$) δ: 1.17-1.32 (5H, m), 1.36-1.52 (4H, m), 1.78-2.14 (10H, m), 2.15-2.29 (1H, m), 2.45-2.75 (1H, m), 2.83-3.06 (4H, m), 3.18 (3H, s), 3.19-3.29 (2H, m), 3.41 (0H, s), 3.68-3.44 (1H, m), 4.11 (2H, q, J=7.2 Hz).

MS (ESI) m/z: 355 (M$^+$+1).

Trans-4-[1-[[5-chloro-2-fluoro-4-[(1-methyl-1H-indol-3-ylcarbonyl)amino]phenyl]acetyl]-(4S)-(3-methoxy-3-methylazetidin-1-yl)-(2S)-pyrrolidinylmethoxy]cyclohexanecarboxylic acid ethyl ester NMR (CDCl$_3$) δ: 1.17-1.29 (5H, m), 1.38-1.54 (5H, m), 1.85-2.37 Hz), 3.59-3.83 (2H, m), 3.86 and 3.86 (total 3H, each s, amide isomers), 4.03-4.38 (4H, m), 7.30-7.44 (4H, m), 7.79 (1H, d, J=3.2 Hz), 8.10-8.16 (1H, m), 8.27 (1H, d, J=3.7 Hz), 8.49 (1H, dd, J=12.0, 8.1 Hz).
MS (ESI) m/z: 697 (M$^+$+1), 699 (M$^+$+3).

Trans-4-[1-[[5-chloro-2-fluoro-4-[(1-methyl-1H-indol-3-ylcarbonyl)amino]phenyl]acetyl]-(4S)-(3-methoxy-3-methylazetidin-1-yl)-(2S)-pyrrolidinylmethoxy]cyclohexanecarboxylic acid

[Formula 107]

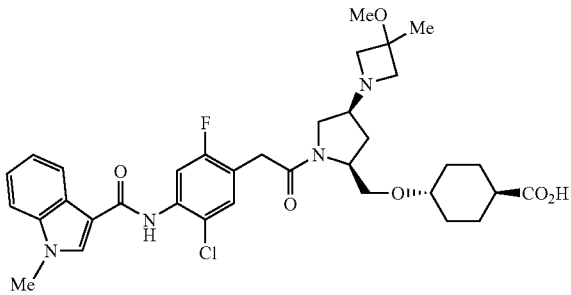

NMR (CDCl$_3$) δ: 1.16-1.33 (3H, m), 1.38-1.54 (5H, m), 1.97-2.36 (6H, m), 3.00-3.36 (8H, m), 3.48 (3H, s), 3.78-3.53 (5H, m), 3.96-3.81 (4H, m), 4.26-4.15 (1H, m), 7.43-7.32 (3H, m), 7.81 (1H, s), 8.16-8.10 (1H, m), 8.29 (1H, d, J=2.9 Hz), 8.48 (1H, t, J=11.5 Hz).
MS (ESI) m/z: 669 (M$^+$+1), 671 (M$^+$+3).
IR (ATR) cm$^{-1}$: 3421, 3109, 3051, 2935, 2858, 1720, 1645.
Anal. Calcd for C$_{35}$H$_{42}$Cl$_2$FN$_4$O$_6$·1.25H$_2$O: C, 60.77; H, 6.48; N, 8.10.
Found: C, 61.03; H, 6.54; N, 7.65

Example 17

Trans-4-[1-[[4-[(benzo[b]thiophen-3-ylcarbonyl)amino]-5-chloro-2-fluorophenyl]acetyl]-(4S)-(3-ethyl-3-methoxyazetidin-1-yl)-(2S)-pyrrolidinylmethoxy]cyclohexanecarboxylic acid 1-Benzhydryl-3-ethylazetidin-3-ol To a tetrahydrofuran solution (10 mL) of 1-benzhydrylazetidin-3-one (3.23 g, 13.61 mmol), a 1M-tetrahydrofuran solution of ethylmagnesium bromide (13.61 mL, 27.22 mmol) was added at –78° C. under a nitrogen stream, and the mixture was allowed to warm to –10° C. over 5 hours. A saturated aqueous solution of sodium hydrogen carbonate (20 mL) was added to the reaction liquor, and the mixture was stirred for 15 minutes. Then, the reaction liquor was filtered through celite, and the filtrate was extracted with ethyl acetate. The extract was washed with saturated brine, and then dried over anhydrous sodium sulfate. Sodium sulfate was separated by filtration, and the solvent was concentrated under reduced pressure. The obtained residue was purified by flash chromatography (Flash Chromatography System from Biotage AB, column size: 40M, ethyl acetate/n-hexane=1/9 to 6/4), to obtain the title compound (2.18 g, 60%) as an oily matter.
NMR (CDCl$_3$) δ: 0.96 (3H, t, J=7.5 Hz), 1.80 (2H, q, J=7.4 Hz), 2.89-3.00 (2H, m), 3.17-3.25 (2H, m), 4.36 (1H, s), 7.31-7.09 (7H, m), 7.32-7.52 (4H, m).
MS (ESI) m/z: 268 (M$^+$+1).

1-Benzhydryl-3-ethyl-3-methoxyazetidine

To a DMF (50 mL) solution of 1-benzhydryl-3-ethylazetidin-3-ol (2.18 g, 8.15 mmol), methyl iodide (0.51 mL, 8.15 mmol) and 60% sodium hydride (0.65 g, 16.31 mmol) were added at 0° C. under a nitrogen stream, and the mixture was stirred for 1.5 hours at the same temperature. This reaction liquor was poured onto ice water, and the mixture was extracted with ethyl acetate. The extract was washed with ice water and saturated brine in this order, and then dried over anhydrous sodium sulfate. Sodium sulfate was separated by filtration, and then the solvent was concentrated under reduced pressure. The obtained residue was purified by flash chromatography (Flash Chromatography System from Biotage AB, column size: 25S, ethyl acetate/n-hexane=1/9-4/6), to obtain the title compound (1.18 g, 52%) as an oily matter.
NMR (CDCl$_3$) δ: 0.89 (3H, t, J=7.4 Hz), 1.86 (2H, q, J=7.4 Hz), 2.97 (2H, d, J=8.6 Hz), 3.11 (2H, dd, J=6.9, 1.7 Hz), 3.14 (3H, s), 4.39 (1H, s), 7.00-7.30 (7H, m), 7.39-7.44 (4H, m).
MS (ESI) m/z: 282 (M$^+$+1).

1-(Tert-butoxycarbonyl)-3-ethyl-3-methoxyazetidine

1-Benzhydryl-3-ethyl-3-methoxyazetidine (1.18 g, 4.19 mmol) was dissolved in ethyl acetate (50 mL), and Boc$_2$O (0.92 g, 4.19 mmol) and 10% palladium hydride/carbon (0.50 g) were added at room temperature. The mixture was stirred for two days under a hydrogen stream. The catalyst was separated by filtration, and the obtained reaction liquor was concentrated under reduced pressure. The obtained residue was purified by flash chromatography (Flash Chromatography System from Biotage AB, column size: 40S, ethyl acetate/n-hexane=1/9 to 4/6), to obtain the title compound (0.44 g, 49%) as an oily matter.
NMR (CDCl$_3$) δ: 0.89 (3H, t, J=7.4 Hz), 1.44 (9H, s), 1.78 (2H, q, J=7.4 Hz), 3.18 (3H, s), 3.66 (2H, d, J=9.3 Hz), 3.85 (2H, d, J=9.1 Hz).
MS (ESI) m/z: 216 (M$^+$+1).

3-Ethyl-3-methoxyazetidine hydrochloride 1-(Tert-butoxycarbonyl)-3-ethyl-3-methoxyazetidine (0.44 g, 2.04 mmol) was dissolved in 4 N Hydrogen Clhloride/dioxane (30 mL), and the solution was stirred for three days at room temperature. The reaction liquor was concentrated under reduced pressure to obtain the title compound as an oily matter. This compound was used in the subsequent reaction without performing further purification.

Trans-4-[1-(tert-butoxycarbonyl)-(4S)-(3-ethyl-3-methoxyazetidin-1-yl)-(2S)-pyrrolidinylmethoxy]cyclohexanecarboxylic acid ethyl ester To a dichloroethane solution (40 mL) of trans-4-[1-(tert-butoxycarbonyl)-4-oxo-(2S)-pyrrolidinylmethoxy]cyclohexanecarboxylic acid ethyl ester (0.75 g, 2.04 mmol) and 3-ethyl-3-methoxyazetidine hydrochloride (2.04 mmol), sodium triacetoxyborohydride (1.30 g, 6.12 mmol) was added, and the mixture was stirred for two days. A saturated MS (ESI) m/z: 662 (M$^+$+1). aqueous solution of sodium hydrogen carbonate (20 mL) was added to the reaction liquor, and the mixture was stirred for 15 minutes, and then extracted with dichloromethane. The extract was washed with saturated brine, and dried over anhydrous sodium sulfate, and the solvent was concentrated under reduced pressure. The obtained residue was purified by flash chromatography (Flash Chromatography System from Biotage AB, column size: 40M, ethyl acetate to methanol/ethyl acetate=1/9), to obtain the title compound [0.95 g, 99% (from two processes)] as an oily matter.

NMR (CDCl$_3$) δ: 0.83-0.92 (3H, m), 1.12-1.32 (6H, m), 1.45 (9H, s), 1.57-2.30 (10H, m), 2.85-3.25 (10H, m), 3.27-4.02 (3H, m), 4.11 (2H, q, J=7.1 Hz).

MS (ESI) m/z: 469 (M$^+$+1).

Trans-4-[(4S)-(3-ethyl-3-methoxyazetidin-1-yl)-(2S)-pyrrolidinylmethoxy]cyclohexanecarboxylic acid ethyl ester hydrochloride Trans-4-[1-(tert-butoxycarbonyl)-(4S)-(3-ethyl-3-methoxyazetidin-1-yl)-(2S)-pyrrolidinylmethoxy]cyclohexanecarboxylic acid ethyl ester (0.95 g, 2.03 mmol) was dissolved in a 4NHydrogen Clhloride/dioxane solution (40 mL), and the solution was stirred for two days. A small amount of ethanol was added to the reaction liquor, and the mixture was concentrated under reduced pressure, to obtain the title compound as an oily matter. This compound was used in the subsequent reaction without performing further purification.

MS (ESI) m/z: 369 (M$^+$+1).

Trans-4-[1-[4-[(benzo[b]thiophen-3-ylcarbonyl)amino]-5-chloro-2-fluorophenylacetyl]-(4S)-(3-ethyl-3-methoxyazetidin-1-yl)-(2S)-pyrrolidinylmethoxy]cyclohexanecarboxylic acid ethyl ester NMR (CDCl$_3$) δ: 0.85-0.93 (3H, m), 1.05-1.58 (7H, m), 1.66-2.35-7.72 (5H, m), 7.91 (1H, d, J=8.1 Hz), 7.99-8.05 (1H, m), 8.26-8.50 (3H, m).

MS (ESI) m/z: 714 (M$^+$+1), 716 (M$^+$+3).

Trans-4-[1-[4-[(benzo[b]thiophen-3-ylcarbonyl)amino]-5-chloro-2-fluorophenylacetyl]-(4S)-(3-ethyl-3-methoxyazetidin-1-yl)-(2S)-pyrrolidinylmethoxy]cyclohexanecarboxylic acid

[Formula 108]

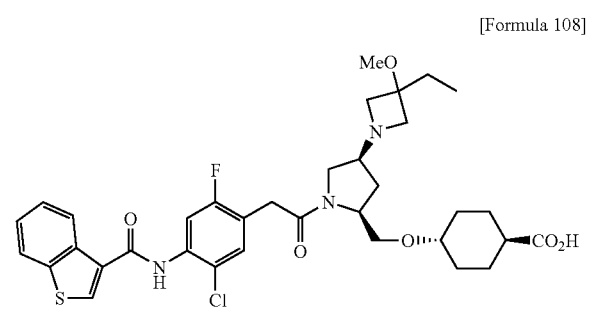

NMR (CDCl$_3$) δ: 0.82-0.93 (3H, m), 1.05-2.41 (14H, m), 2.98-3.41 (10H, m), 3.49-4.43 (7H, m), 7.37-7.58 (3H, m), 7.91 (1H, d, J=7.8 Hz), 8.09 and 8.10 (total 1H, each s, amide isomers), 8.56-8.27 (2H, m).

MS (ESI) m/z: 686 (M$^+$+1), 688 (M$^+$+3).

IR (ATR) cm$^{-1}$: 2933, 2858, 1718, 1672, 1637, 1624.

Example 18

Trans-4-[[1-[2-[4-[(1-benzo[b]thiophen-3-ylcarbonyl)amino]-2,5-dichlorophenyl]acetyl]-(4S)-(3-fluoroazetidin-1-yl)-(2S)-pyrrolidinyl]methoxy]cyclohexanecarboxylic acid

3-Hydroxyazetidine trifluoroacetate

1-Benzhydryl-3-hydroxyazetidine (3.0 g, 12.6 mmol) was dissolved in methanol (60 mL), and 10 mL of TFA and 10% palladium hydroxide (1.0 g) were added thereto. The mixture was stirred for 24 hours under a hydrogen stream at normal pressure. The catalyst was removed by filtration, water (100 mL) was added to the filtrate, and the mixture was washed three times with ether. The aqueous layer was concentrated under reduced pressure, and the title compound (2.33 g, 99%) was obtained as an amorphous matter.

NMR (CD$_3$OD) δ: 3.30-3.32 (2H, m), 3.87-3.93 (2H, m), 4.18-4.24 (2H, m), 4.65-4.72 (1H, m).

Trans-4-[1-(tert-butoxycarbonyl)-(4S)-(3-hydroxy-1-azetidinyl)-(2S)-pyrrolidinylmethoxy]cyclohexanecarboxylic acid ethyl ester NMR (CDCl$_3$) δ: 1.25 (3H, t, J=7.1 Hz), 1.43 (9H, s), 1.55-2.27 (15H, m), 3.08-3.92 (8H, m), 4.11 (2H, q, J=7.1 Hz), 4.46 (1H, s).

MS (ESI) m/z: 427 (M$^+$+1).

Trans-4-[1-(tert-butoxycarbonyl)-(4S)-(3-fluoro-1-azetidinyl)-(2S)-pyrrolidinylmethoxy]cyclohexanecarboxylic acid ethyl ester NMR (CDCl$_3$) δ: 1.17-2.29 (12H, m), 1.24 (3H, t, J=7.1 Hz), 1.45 (9H, s), 2.88-3.91 (10H, m), 4.08-4.15 (2H, m), 4.98-5.18 (1H, m).

MS (ESI) m/z: 429 (M$^+$+1).

Trans-4-[[1-[2-[4-[(1-benzo[b]thiophen-3-ylcarbonyl)amino]-2,5-dichlorophenyl]acetyl]-(4S)-(3-fluoroazetidin-1-yl)-(2S)-pyrrolidinyl]methoxy]cyclohexanecarboxylic acid

[Formula 109]

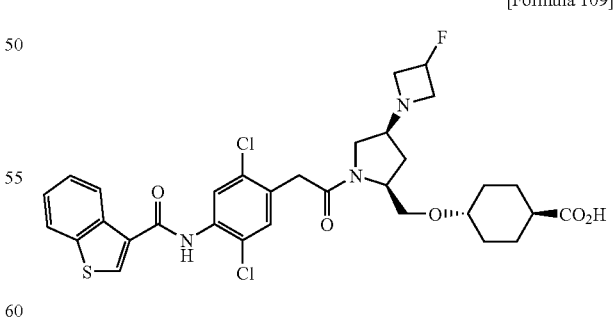

NMR (DMSO-d$_6$) δ: 1.10-1.42 (7H, m), 1.67-2.22 (8H, m), 2.95-4.24 (13H, m), 5.06-5.28 (1H, m), 7.44-7.51 (2H, m), 7.54 (1H, d, J=10.5Hz), 7.76 (1H, d, J=3.7 Hz), 8.10 (1H, d, J=7.4 Hz), 8.45 (1H, d, J=7.4 Hz), 8.65 (1H, d, J=1.7 Hz), 10.16 (1H, d, J=3.9 Hz).

IR (ATR) cm$^{-1}$: 2937, 2859, 1637, 1504, 1079.

MS (ESI) m/z: 662 (M$^+$+1).

Anal. Calcd for $C_{32}H_{34}Cl_2FN_3O_5S \cdot 0.5H_2O$: C, 57.23; H, 5.25; Cl, 10.56; F, 2.83; N, 6.26; S, 4.77.

Found: C, 57.17; H, 5.27; Cl, 10.93; F, 2.65; N, 5.95; S, 4.72.

Example 19

Trans-4-[[1-[2-[4-[(1-benzo[b]thiophen-3-ylcarbonyl)amino]-2,5-dichlorophenyl]acetyl]-(4S)-(3,3-difluoroazetidin-1-yl)-(2S)-pyrrolidinyl]methoxy]cyclohexanecarboxylic acid Trans-3-[1-(tert-butoxycarbonyl)-(4S)-(3,3-difluoro-1-azetidinyl)-(2S)-pyrrolidinylmethoxy]cyclohexanecarboxylic acid ethyl ester NMR (CDCl$_3$) δ: 1.21-1.27 (5H, m), 1.46 (9H, s), 1.63-4.47 (22H, m).

Trans-4-[[1-[2-[4-[(1-benzo[b]thiophen-3-ylcarbonyl)amino]-2,5-dichlorophenyl]acetyl]-(4S)-(3,3-difluoroazetidin-1-yl)-(2S)-pyrrolidinyl]methoxy]cyclohexanecarboxylic acid

[Formula 110]

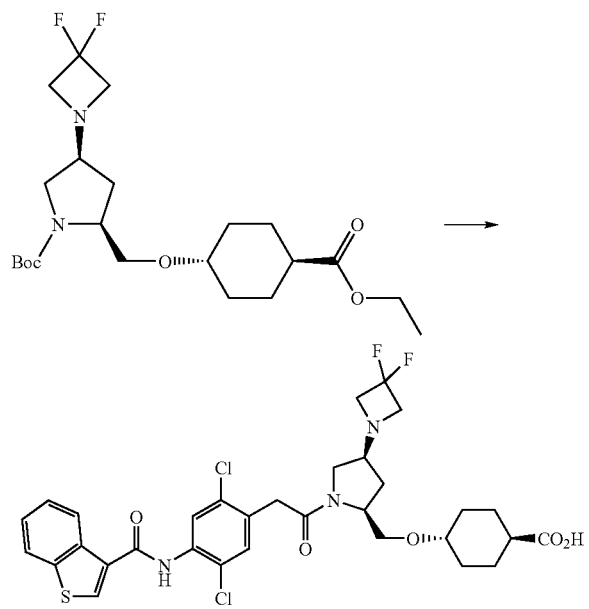

To trans-4-[1-(tert-butoxycarbonyl)-(4S)-(3,3-difluoro-1-azetidinyl)-(2S)-pyrrolidinylmethoxy]cyclohexanecarboxylic acid ethyl ester (167.4 mg, 0.38 mmol), 4N—HCl/1,4-dioxane (2 mL) was added, and the mixture was stirred for 2 hours at room temperature. The solvent of the reaction liquor was concentrated under reduced pressure to obtain solids, and toluene (5 mL) was added to the residue. Subsequently, the mixture was concentrated under reduced pressure and dried, to obtain trans-4-[(4S)-(3,3-difluoro-1-azetidinyl)-(2S)-pyrrolidinyl methoxy]cyclohexanecarboxylic acid ethyl ester dihydrochloride as an amorphous matter. This compound was used in the subsequent reaction without performing further purification.

Next, the obtained trans-4-[(4S)-(3,3-difluoro-1-azetidinyl)-(2S)-pyrrolidinyl methoxy]cyclohexanecarboxylic acid ethyl ester dihydrochloride, [2-[4-[(1-benzo[b]thiophen-3-ylcarbonyl)amino]-2,5-dichloro phenyl]]acetic acid (142.6 mg, 0.38 mmol), HOBt (50.7 mg, 0.38 mmol) and triethylamine (313.6 mL, 2.25 mmol) were dissolved in DMF (5 mL), and EDC-HCl (86.3 mg, 0.45 mmol) was added at room temperature with stirring. The mixture was stirred for 24 hours at room temperature. The reaction solution was poured onto a mixed solution of ethyl acetate (10 mL) and water (20 mL), and the mixture was extracted with ethyl acetate. The extract was washed with saturated brine, and dried over anhydrous sodium sulfate, and the solvent was concentrated under reduced pressure. The obtained residue was purified by medium pressure column chromatography using silica gel (PURIF-pack manufactured by Moritex USA, Inc.: diameter 26 mm, total length 100 mm, hexane/ethyl acetate, 4:1 to 1:1), to obtain an ester product. The obtained ester product was dissolved in a mixed solvent of tetrahydrofuran and methanol (5 mL, 2:1), and a 1N-aqueous solution of sodium hydroxide (4.5 mL) was added thereto. The mixture was stirred for 24 hours at room temperature. The reaction solution was diluted with ethyl acetate (10 mL), and a 1N-hydrochloric acid (4.5 mL) was added. After stirring, the mixture was extracted with ethyl acetate. The extract was washed with saturated brine, and dried over anhydrous sodium sulfate, and then the solvent was concentrated under reduced pressure. The obtained residue was purified by column chromatography using medium pressure silica gel (High-Flash-L manufactured by Yamazen Corp.: diameter 26 mm, total length 100 mm, chloroform/methanol, 99:1 to 9:1), and the obtained fraction of the title compound was concentrated. The obtained oily title compound was dissolved in 1,4-dioxane and lyophilized, to obtain the title compound (39 mg, 15.3%) as a amorphous solid.

NMR (CDCl$_3$) δ: 1.17-2.35 (13H, m), 3.05-3.32 (3H, m), 3.51-4.28 (9H, m), 7.42 (1H, d, J=3.7 Hz), 7.46 (1H, t, J=7.4 Hz), 7.52 (1H, t, J=7.4 Hz), 7.92 (2H, d, J=7.8 Hz), 8.09 (1H, d, J=2.9 Hz), 8.29 (1H, d, J=4.4 Hz), 8.48 (1H, d, J=7.6 Hz), 8.72 (1H, d, J=8.6 Hz).

IR (ATR) cm$^{-1}$: 2935, 2857, 1637, 1504, 1209.

MS (FAB) m/z: 680.1569 (Calcd. for $C_{32}H_{34}Cl_2F_2N_3O_5S$: 680.1564).

Anal. Calcd for $C_{32}H_{33}Cl_2F_2N_3O_5S$: C, 56.47; H, 4.89; N, 6.17; S, 4.71.

Found: C, 56.66; H, 5.28; N, 5.69; S, 4.56.

The title compounds of Examples 123, 124, 125, 126, 139, 140, 166, 167 and 168 shown below were produced by the same methods as in Example 19.

Example 20

Trans-4-[1-[[2,5-dichloro-4-[(1-methyl-1H-indol-3-ylcarbonyl)amino]phenyl]acetyl]-(4S)-(3-ethoxyazetidin-1-yl)-(2S)-pyrrolidinylmethoxy]cyclohexanecarboxylic acid Trans-4-[1-(tert-butoxycarbonyl)-(4S)-(3-ethoxyazetidin-1-yl)-(2S)-pyrrolidinylmethoxy]cyclohexanecarboxylic acid ethyl ester NMR (CDCl$_3$) δ: 1.16-1.30 (8H, m), 1.42-1.49 (10H, m), 1.58-1.70 (2H, m), 1.78-2.37 (7H, m), 2.79-2.93 (2H, m), 2.99-3.11 (1H, m), 3.16-3.27 (1H, m), 3.31-3.98 (9H, m), 4.02-4.16 (3H, m).

MS (ESI) m/z: 455 (M$^+$+1).

Trans-4-[(4S)-(3-ethoxyazetidin-1-yl)-(2S)-pyrrolidinylmethoxy]cyclohexanecarboxylic acid ethyl ester NMR (CDCl$_3$) δ: 1.13-1.31 (8H, m), 1.39-1.53 (4H, m), 1.87-2.14 (5H, m), 2.15-2.30 (1H, m), 2.68-3.02 (5H, m), 3.19-3.29 (1H, m), 3.37-3.52 (5H, m), 3.54-3.64 (1H, m), 4.02-4.17 (4H, m).
MS (ESI) m/z: 355 (M$^+$+1).

Trans-4-[1-[[2,5-dichloro-4-[(1-methyl-1H-indol-3-ylcarbonyl)amino]phenyl]acetyl]-(4S)-(3-ethoxyazetidin-1-yl)-(2S)-pyrrolidinylmethoxy]cyclohexanecarboxylic acid ethyl ester NMR (CDCl$_3$) δ: 1.09-1.56 (10H, m), 1.69-2.36 (8H, m), 2.76-3.07 (4H, m), 7.30-7.44 (3H, m), 7.78 (1H, d, J=2.9 Hz), 8.11-8.15 (1H, m), 8.22 (1H, d, J=3.9 Hz), 8.76 (1H, d, J=6.6 Hz).
MS (ESI) m/z: 713 (M$^+$+1), 715 (M$^+$+3).

Trans-4-[1-[[2,5-dichloro-4-[(1-methyl-1H-indol-3-ylcarbonyl)amino]phenyl]acetyl]-(4S)-(3-ethoxyazetidin-1-yl)-(2S)-pyrrolidinylmethoxy]cyclohexanecarboxylic acid

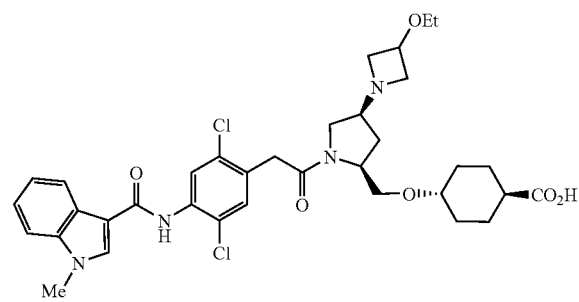

[Formula 111]

NMR (CDCl$_3$) δ: 1.15-1.57 (4H, m), 1.92-2.42 (6H, m), 3.28-3.96 (18H, m), 4.09-4.43 (2H, m), 7.29-7.45 (4H, m), 7.81 (1H, s), 8.12 (1H, t, J=4.5 Hz), 8.24 (1H, d, J=4.9 Hz), 8.77 (1H, d, J=9.1 Hz).
MS (ESI) m/z: 685 (M$^+$+1), 687 (M$^+$+3).
IR (ATR) cm$^{-1}$: 3419, 2935, 2858, 1722, 1641, 1568.
Anal. Calcd for $C_{35}H_{42}Cl_2N_4O_6 \cdot 1.5H_2O$: C, 58.99; H, 6.36; Cl, 9.95; N, 7.86.
Found: C, 58.28; H, 6.45; Cl, 9.64; N, 7.44.

Example 21

Trans-4-[1-[[2,5-dichloro-4-[(1-methyl-1H-indol-3-ylcarbonyl)amino]phenyl]acetyl]-(4S)-[(2S,4S)-dimethylazetidin-1-yl]-(2S)-pyrrolidinylmethoxy]cyclohexanecarboxylic acid Trans-4-[1-(tert-butoxycarbonyl)-(4S)-[(2S,4S)-dimethylazetidin-1-yl]-(2S)-pyrrolidinylmethoxy]cyclohexanecarboxylic acid ethyl ester NMR (CDCl$_3$) δ: 0.93-1.31 (13H, m), 1.38-1.45 (2H, m), 1.46 (9H, 2 (2H, m), 4.07-4.16 (2H, m).
MS (ESI) m/z: 439 (M$^+$+1).

Trans-4-[(4S)-[(2S,4S)-dimethylazetidin-1-yl]-(2S)-pyrrolidinylmethoxy]cyclohexanecarboxylic acid ethyl ester NMR (CDCl$_3$) δ: 1.16-1.51 (13H, m), 1.64-2.30 (12H, m), 2.93-3.00 (1H, m), 3.16-3.68 (5H, m), 3.82 (1H, br s), 4.11 (2H, q, J=7.1 Hz).
MS (ESI) m/z: 338 (M$^+$+1).

Trans-4-[1-[[2,5-dichloro-4-[(1-methyl-1H-indol-3-ylcarbonyl)amino]phenyl]acetyl]-(4S)-[(2S,4S)-dimethylazetidin-1-yl]-(2S)-pyrrolidinylmethoxy]cyclohexanecarboxylic acid ethyl ester NMR (CDCl$_3$) δ: 1.12-1.58 (13H, m), 1.68-2.38 (7H, m), 3.02-3.32 (4H, m), 7.31-7.44 (4H, m), 7.789 and 7.794 (total 1H, each s, amide isomers), 8.11-8.16 (1H, m), 8.22 and 8.23 (total 1H, each s, amide isomers), 8.75-8.82 (1H, m).
MS (ESI) m/z: 697 (M$^+$+1), 699 (M$^+$+3).

Trans-4-[1-[[2,5-dichloro-4-[(1-methyl-1H-indol-3-ylcarbonyl)amino]phenyl]acetyl]-(4S)-[(2S,4S)-dimethylazetidin-1-yl]-(2S)-pyrrolidinylmethoxy]cyclohexanecarboxylic acid

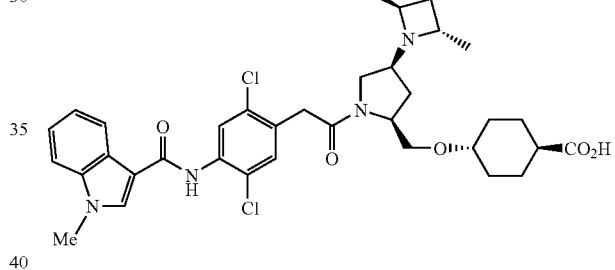

[Formula 112]

NMR (CDCl$_3$) δ: 1.13-1.71 (10H, m), 1.81-2.48 (9H, m), 3.09-3.79 (6H, m), 3.82-4.06 (6H, m), 4.13-4.44 (2H, m), 7.30-7.44 (4H, m), 7.77-7.80 (1H, m), 8.10-8.16 (1H, m), 8.23 (1H, s), 8.24 (0H, s), 8.80-8.74 (1H, m).
MS (ESI) m/z: 669 (M$^+$+1), 671 (M$^+$+3).
IR (ATR) cm$^{-1}$: 2937, 2856, 1720, 1643, 1568, 1533, 1500, 1468, 1425.
Anal. Calcd for $C_{35}H_{42}Cl_2N_4O_5 \cdot 1.5H_2O$: C, 60.34; H, 6.51; Cl, 10.18; N, 8.04.
Found: C, 60.78; H, 6.42; Cl, 10.20; N, 7.51.

Example 22

Trans-4-[1-[[5-chloro-2-fluoro-4-[(1-methyl-1H-indol-3-ylcarbonyl)amino]phenyl]acetyl]-(4S)-[(2S)-methoxymethylazetidin-1-yl]-(2S)-pyrrolidinylmethoxy]cyclohexanecarboxylic acid (S)-1-(tert-butoxycarbonyl)azetidine-2-methanol (S)-1-(tert-butoxycarbonyl)-2-azetidinecarboxylic acid (10.42 g, 49.4 mmol) was introduced into a 500-mL pear-shaped flask, and tetrahydrofuran (200 mL) was added to dissolve the compound. Then, a tetrahydrofuran solution of 10 M borane-dimethyl sulfide complex salt (9.87 mL, 98.7 mmol) was slowly added at 0° C., and the mixture was heated to reflux for 2 hours while stirring. The reaction solution was left to cool, and then was concentrated under reduced pressure. Ice water (100 mL) was poured thereto, and the mixture was extracted with ethyl acetate (200 mL×2). The extract was washed with saturated brine (200 mL), and then dried over anhydrous sodium sulfate. After filtering the extract, the filtrate was concentrated under reduced pressure to obtain the title compound (8.03 g, 42.9 mmol, 87%) as an oily matter.

NMR (CDCl$_3$) δ: 1.45 (9H, s), 1.93 (1H, br s), 2.13-2.22 (1H, m), 3.67-3.81 (3H, m), 3.87 (1H, q, J=8.8 Hz), 4.21 (1H, br s), 4.44 (1H, br s).

MS (ESI) m/z: 188 (M$^+$+1).

1-(Tert-butoxycarbonyl)-(2S)-methoxymethylazetidine (S)-1-(tert-butoxycarbonyl)azetidine-2-methanol (5) (8.03 g, 42.9 mmol) was introduced into a 200-mL pear-shaped flask, and N,N-dimethylformamide (60 mL) was added to dissolve the compound. Methyl iodide (5.34 mL, 85.8 mmol) was added thereto. While stirring the content under ice cooling, sodium hydride (commercial product, purity 55%) (2.81 g, 64.3 mmol) was slowly added, and the mixture was stirred for one hour at room temperature. The reaction liquor was transferred to ice water, and the mixture was extracted with ethyl acetate (250 mL×2). The extract was dried over anhydrous sodium sulfate. After filtering the extract, the filtrate was concentrated under reduced pressure, and azeotropically boiled with toluene. The obtained concentrated residue was subjected to flash column chromatography (column size: 40M) manufactured by Biotage AB, and the fraction obtained from an elution with n-hexane:ethyl:acetate (4:1, v/v) was concentrated under reduced pressure and dried, to obtain the title compound (8.05 g, 40.0 mmol, 93%) as a solid.

NMR (CDCl$_3$) δ: 1.44 (9H, s), 2.11-2.27 (2H, m), 3.41-3.41 (3H, m), 3.55 (1H, d, J=3.1 Hz), 3.62-3.69 (1H, m), 3.82 (2H, t, J=8.1 Hz), 4.27-4.34 (1H, m).

MS (ESI) m/z: 102 (M$^+$+1-Boc).

(2S)-methoxymethylazetidine TFA salt 1-(Tert-butoxycarbonyl)-(2S)-methoxymethylazetidine (8.05 g, 40.0 mmol) was dissolved in dichloromethane (40 mL), and TFA (40 mL) was added thereto. The mixture was stirred for 25 hours at room temperature. The reaction liquor was concentrated under reduced pressure, toluene was added, and the mixture was azeotropically boiled and dried, to obtain the title compound (12.0 g, quant.) as an oily matter.

NMR (CDCl$_3$) δ: 2.52-2.67 (2H, m), 3.45 (3H, s), 3.62 (2H, ddd, J=21.4, 11.2, 3.4 Hz), 3.94-4.16 (2H, m), 4.67-4.76 (1H, m), 7.62 (1H, br s), 9.12 (1H, br s).

Trans-4-[1-(tert-butoxycarbonyl)-(4S)-[(2S)-methoxymethylazetidin-1-yl]-(2S)-pyrrolidinylmethoxy]cyclohexanecarboxylic acid ethyl ester NMR (CDCl$_3$) δ: 1.18-1.29 (total 5H, m, including 3H t, J=7.0 Hz, δ 1.24), 1.38-1.49 (total 11H, m), 1.83-1.91 (1H, m), 1.95-2.10 (total 7H, series of m), 2.23 (1H, t, J=10.8 Hz), 2.78-3.04 (3H, m), 3.18-3.60 (total 10H, series of m, including 3H s, δ 3.36), 3.67-3.90 (2H, m), 4.11 (2H, q, J=6.9 Hz).

MS (ESI) m/z: 455 (M$^+$+1).

Trans-4-[(4S)-[(2S)-methoxymethylazetidin-1-yl]-(2S)-pyrrolidinylmethoxy]cyclohexanecarboxylic acid ethyl ester bis(trifluoroacetate)

NMR (CDCl$_3$) δ: 1.16-1.28 (total 5H, m, including 3H t, J=7.1 Hz, δ 1.25), 1.38-1.50 (2H, m), 1.97-2.05 (total 4H, series of m), 2.24 (1H, tt, J=11.7, 3.2 Hz), 2.32-2.43 (1H, m), 2.53-2.67 (2H, m), 3.29 (1H, tt, J=10.5, 3.7 Hz), 3.41 (3H, s), 3.58-3.65 (total 3H, m), 3.78-4.04 (5H, m), 4.12 (2H, q, J=7.1 Hz), 4.24-4.56 (total 3H, m), 9.01 (1H, br s).

MS (ESI) m/z: 355 (M$^+$+1-2TFA).

Trans-4-[1-[[5-chloro-2-fluoro-4-[(1-methyl-1H-indol-3-ylcarbonyl)amino]phenyl]acetyl]-(4S)-[(2S)-methoxymethylazetidin-1-yl]-(2S)-pyrrolidinylmethoxy]cyclohexanecarboxylic acid ethyl ester NMR (CDCl$_3$) δ: 1.15-1.32 (total 5H, series of m), 1.36-1.54 (2H, m), 1.79-2.35 (total 10H, series of m), 2.71-3.91 (total 18H, series of m), 4.03-4.18 (total 3H, m), 7.31-7.42 (total 4H, series of m), 7.78 and 7.79 (total 1H, each s, amide isomers), 8.11-8.16 (1H, m), 8.25-8.29 (1H, m), 8.47 and 8.49 (total 1H, each d, each J=12.1 Hz, amide isomers).

IR (ATR) ν: 2935, 2862, 1726, 1643 cm$^{-1}$.

MS (ESI) m/z: 697 [(M$^+$+1), $^{35}$Cl].

Anal. Calcd for C$_{37}$H$_{46}$ClFN$_4$O$_6$.2H$_2$O: C, 60.61; H, 6.87; N, 7.64.

Found: C, 60.96; H, 6.53; N, 7.70.

Trans-4-[1-[[5-chloro-2-fluoro-4-[(1-methyl-1H-indol-3-ylcarbonyl)amino]phenyl]acetyl]-(4S)-[(2S)-methoxymethylazetidin-1-yl]-(2S)-pyrrolidinylmethoxy]cyclohexanecarboxylic acid

[Formula 113]

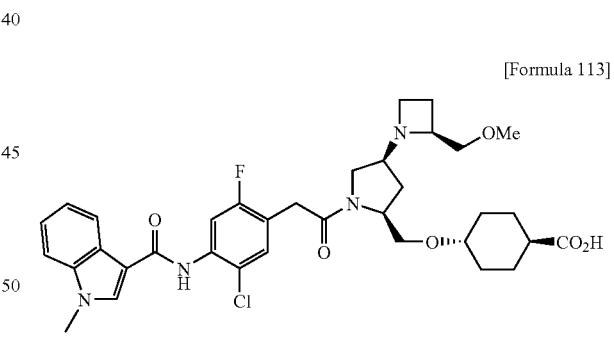

NMR (CDCl$_3$) δ: 1.09-1.44 (total 5H, series of m), 1.78-2.17 (total 9H, series of m), 2.75-3.21 (total 4H, series of m), 3.30-3.93 (total 13H, series of m), 4.06-4.16 (1H, m), 4.76 (2H, s), 7.27-7.36 (total 4H, series of m), 7.80 (1H, s), 8.06-8.11 (1H, m), 8.22 and 8.25 (total 1H, each s, amide isomers), 8.40 and 8.41 (total 1H, each d, each J=12.0 Hz, amide isomers).

IR (ATR) ν: 2933, 2860, 1639, 1583 cm$^{-1}$.

MS (ESI) m/z: 669 [(M$^+$+1), $^{35}$Cl], 671 [(M$^+$+3), $^{37}$Cl].

Anal. Calcd for C$_{35}$H$_{42}$ClFN$_4$O$_6$.3H$_2$O: C, 58.13; H, 6.69; N, 7.75.

Found: C, 58.11; H, 6.58; N, 7.58.

Example 23

Trans-4-[1-[[4-[(benzo[b]thiophen-3-ylcarbonyl) amino]-2,5-dichlorophenyl]acetyl]-(4S)-[3-(N,N-dimethylamino)azetidin-1-yl]-(2S)-pyrrolidinyl-methoxy]cyclohexanecarboxylic acid

Trans-4-[1-(tert-butoxycarbonyl)-(4S)-[3-(N,N-dimethylamino)azetidin-1-yl]-(2S)-pyrrolidinylmethoxy] cyclohexanecarboxylic acid ethyl ester Trans-4-[1-(tert-butoxycarbonyl)-4-oxo-(2S)-pyrrolidinylmethoxy]cyclohexanecarboxylic acid ethyl ester (1.07 g, 2.89 mmol) was dissolved in methanol (20 mL), and 3-(N,N-dimethylamino)-1-azetidinehydrochloride (0.999 g, 5.78 mmol) was added thereto. The mixture was stirred for 30 minutes at room temperature, and then sodium cyanoborohydride (272 mg, 4.34 mmol) was added. The mixture was stirred for 6 hours at room temperature. The solvent of the reaction mixture was concentrated under reduced pressure, and the residue was diluted with methylene chloride (20 mL). A saturated aqueous solution of sodium hydrogen carbonate was added thereto, and then saturated brine was added. The mixture was extracted with methylenechloride. The extract was dried over an hydrous sodium sulfate, and then the solvent was concentrated under reduced pressure. The obtained residue was purified by column chromatography using silica gel (Flash Chromatography System from Biotage AB, column size: 25M, hexane:ethyl acetate=3:1 to ethyl acetate to dichloromethane/methanol 5/95 to 1/9), to obtain the title compound (920 mg, 71%) as an oily matter.

NMR (CDCl$_3$) δ: 1.20-1.29 (6H, m), 1.45 (9H, s), 1.78-2.29 (13H, m), 2.77-3.89 (13H, m), 4.11 (2H, q, J=7.1 Hz).

MS (ESI) m/z: 454 (M$^+$+1).

Trans-4-[1-[[4-[(benzo[b]thiophen-3-ylcarbonyl) amino]-2,5-dichlorophenyl]acetyl]-(4S)-[3-(N,N-dimethylamino)azetidin-1-yl]-(2S)-pyrrolidinyl-methoxy]cyclohexanecarboxylic acid

[Formula 114]

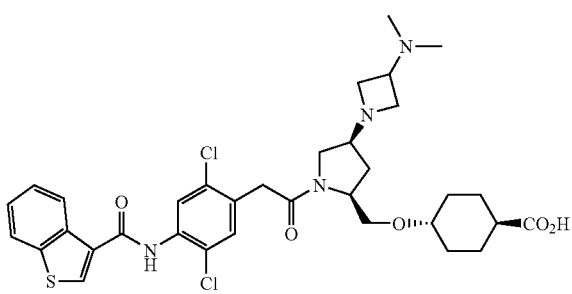

NMR (CD$_3$OD) δ: 1.15-4.37 (31H, m), 7.42-7.52 (4H, m), 7.97 (1H, d, J=7.1 Hz), 8.04 (1H, d, J=5.1 Hz), 8.44-8.47 (3H, m).

MS (FAB) m/z: 687.2201 (Calcd for C$_{34}$H$_{41}$Cl$_2$N$_4$O$_5$S: 687.2175)

Example 24

Trans-4-[1-[[5-chloro-2-fluoro-4-[(1-methyl-1H-indol-3-ylcarbonyl)amino]phenyl]acetyl]-(4S)-(3-methoxymethylazetidin-1-yl)-(2S)-pyrrolidinyl-methoxy]cyclohexanecarboxylic acid

1-(Tert-butoxycarbonyl)-3-hydroxymethylazetidine

To a tetrahydrofuran (100 mL) solution of 1-(tert-butoxycarbonyl)-3-azetidinecarboxylic acid (2.0 g, 9.94 mmol), 10M-borane-dimethyl sulfide complex (2.98 mL, 29.8 mmol) was added at room temperature, and the mixture was stirred for 14 hours. The reaction liquor was poured onto ice water (100 mL), and the mixture was extracted with ethyl acetate. The extract was washed with saturated brine, and dried over anhydrous sodium sulfate, and then the solvent was concentrated under reduced pressure. The obtained residue was purified by flash chromatography (Flash Chromatography System from Biotage AB, column size: 40S, 2% methanol/ethyl acetate), to obtain the title compound (1.83 g, 98%) as an oily matter.

NMR (CDCl$_3$) δ: 1.44 (9H, s), 2.63-2.76 (1H, m), 3.69 (2H, dd, J=8.4, 5.2 Hz), 3.79 (2H, d, J=4.6 Hz), 4.00 (2H, t, J=8.5 Hz).

1-(Tert-butoxycarbonyl)-3-methoxymethylazetidine 1-(Tert-butoxycarbonyl)-3-hydroxymethylethoxyazetidine (1.83 g, 9.77 mmol) was dissolved in DMF (50 mL), and under a nitrogen stream, methyl iodide (0.182 mL, 29.3 mmol) and then 40% sodium hydride (508 mg, 12.7 mmol) were added at 0° C. while stirring. The reaction mixture was stirred for 1 hour at the same temperature, and then poured onto ice water (100 mL). The mixture was extracted with ethyl acetate. The extract was washed with ice water and saturated brine, and dried over anhydrous sodium sulfate, and then the solvent was concentrated under reduced pressure. The obtained residue was purified by flash chromatography (Flash Chromatography System from Biotage AB, column size: 40S, ethyl acetate:n-hexane=1/3) to obtain the title compound (1.16 g, 59%) as an oily matter.

NMR (CDCl$_3$) δ: 1.43 (9H, s), 2.69-2.79 (1H, m) 3.36 (3H, s), 3.51 (2H, d, J=6.9 Hz), 3.65 (2H, dd, J=8.8, 5.4 Hz), 3.99 (2H, t, J=8.6 Hz).

MS (ESI) m/z: 224 (M$^+$+Na).

3-Methoxymethylazetidine hydrochloride 1-(Tert-butoxycarbonyl)-3-methoxymethylazetidine (1.16 g, 5.76 mmol) was dissolved in 4NHydrogen Clhloride/dioxane (10 mL), and the solution was stirred for three days at room temperature. The reaction liquor was concentrated under reduced pressure. The obtained colorless oily matter was supplied to the subsequent reaction.

Trans-4-[1-(tert-butoxycarbonyl)-(4S)-(3-methoxymethylazetidin-1-yl)-(2S)-pyrrolidinylmethoxy]cyclohexanecarboxylic acid ethyl ester NMR (CDCl$_3$) δ: 1.12-1.32 (7H, m), 1.49-1.43 (4H, m), 1.49 (9H, s), 1.71-1.82 (1H, m), 1.95-2.11 (4H, m), 2.14-2.30 (1H, m), 2.65 (1H, d d, J=14.3, 6.0 Hz), 2.99-3.09 (1H, m), 3.15-3.27 (2H, m), 3.34 (3H, s), 3.43 (1H, d, J=6.1 Hz), 3.60-3.70 (5H, m), 4.06-4.16 (2H, m).

MS (ESI) m/z: 455 (M$^+$+1).

Trans-4-[(4S)-(3-methoxymethylazetidin-1-yl)-(2S)-pyrrolidinylmethoxy]cyclohexanecarboxylic acid ethyl ester NMR (CDCl$_3$) δ: 1.15-1.54 (8H, m), 1.94-2.32 (8H, m), 2.59-2.73 (2H, m), 2.85-3.06 (2H, m), 3.21-3.31 (1H, m), 3.34 (3H, s), 3.41-3.62 (5H, m), 3.68 (2H, d, J=4.9 Hz), 4.11 (2H, q, J=7.2 Hz).
MS (ESI) m/z: 355 (M$^+$+1).

Trans-4-[1-[[5-chloro-2-fluoro-4-[(1-methyl-1H-indol-3-ylcarbonyl)amino]phenyl]acetyl]-(4S)-(3-methoxymethylazetidin-1-yl)-(2S)-pyrrolidinylmethoxy]cyclohexanecarboxylic acid ethyl ester NMR (CDCl$_3$) δ: 1.14-1.29 (7H, m), 1.35-1.54 (2H, m), 1.58-1.77 (1H, m), 1.83 (2H, dt, J=13.2, 4.9 Hz), 1.93-2.11 (4H, m), 2.15-2.42 (2H, m), 2.57-2.77 (2H, m), 3.05-3.33 (2H, m), 3.34 and 3.34 (total 3H, each s, amide isomers), 3.42-3.46 (2H, m), 3.51-3.75 (3H, m), 3.75-3.87 (2H, m), 3.88 (3H, s), 3.98-4.28 (3H, m), 7.30-7.46 (4H, m), 7.80 (1H, d, J=4.9 Hz), 8.11-8.17 (1H, m), 8.29 (1H, s), 8.50 (1H, dd, J=12.0, 10.0 Hz).
MS (ESI) m/z: 697 (M$^+$+1), 699 (M$^+$+3).

Trans-4-[1-[[5-chloro-2-fluoro-4-[(1-methyl-1H-indol-3-ylcarbonyl)amino]phenyl]acetyl]-(4S)-(3-methoxymethylazetidin-1-yl)-(2S)-pyrrolidinylmethoxy]cyclohexanecarboxylic acid

[Formula 115]

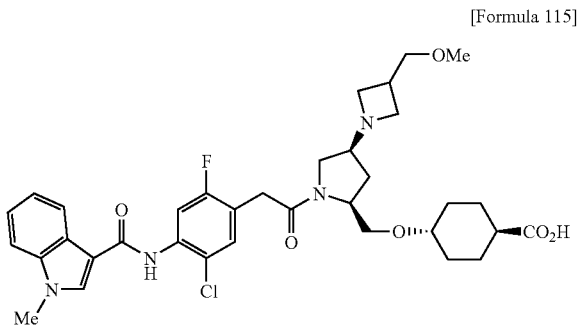

NMR (CDCl$_3$) δ: 1.08-1.56 (4H, m), 1.81-2.40 (8H, m), 2.62-2.79 (2H, m), 3.01-3.27 (1H, m), 3.29-3.47 (6H, m), 3.51-3.73 (5H, m), 3.75-3.93 (5H, m), 4.04-4.61 (3H, m), 7.30-7.43 (4H, m), 7.80 (1H, s), 8.09-8.16 (1H, m), 8.28 (1H, s), 8.47 and 8.49 (total 1H, each d, J=10.0 and 11.8 Hz respectively, amide isomers).
MS (ESI) m/z: 669 (M$^+$+1), 671 (M$^+$+3).
IR (ATR) cm$^{-1}$: 2933, 2860, 1712, 1643, 1626, 1583, 1518.
Anal. Calcd for C$_{35}$H$_{42}$ClFN$_4$O$_6$.1HCl.1H$_2$O: C, 58.09; H, 6.27; Cl, 9.80; F, 2.63; N, 7.74.
Found: C, 58.24; H, 6.24; Cl, 9.50; F, 2.62; N, 7.47.

Example 25

Trans-4-[1-[[2,5-dichloro-4-[(1-methyl-1H-indol-3-ylcarbonyl)amino]phenyl]acetyl]-(4S)-[3-(cis-2,6-dimethylmorpholin-4-yl)azetidin-1-yl]-(2S)-pyrrolidinylmethoxy]cyclohexa necarboxylic acid Cis-4-(1-benzhydryl-3-azetidinyl)-2,6-dimethylmorpholine 3-Methanesulfonyloxy-1-benzhydrylazetidine (3.84 g, 12.1 mmol) and cis-2,6-dimethylmorpholine (6.97 mL, 60.5 mmol) were introduced into a screw vial, and IPA (10 mL) and dioxane (3 mL) were added thereto. The mixture was left to stand for 4 hours at 100° C. The reaction liquor was diluted with ethyl acetate, and saturated brine was added thereto. The mixture was partitioned. The obtained organic layer was washed with saturated brine, subsequently dried over anhydrous sodium sulfate, and then concentrated. The residue was purified by column chromatography using silica gel (Flash Chromatography System from Biotage AB, column size: 40M, hexane/ethyl acetate=9:1 to 1:1), to obtain the title compound (2.63 g, 65%) as an oily matter.
NMR (CDCl$_3$) δ: 1.12 (6H, d, J=6.4 Hz), 1.55 (2H, t, J=10.8 Hz), 2.56 (2H, d, J=10.8 Hz), 2.85-2.97 (2H, m), 3.60-3.70 (2H, m), 3.61-3.70 (2H, m), 4.41 (1H, s), 7.16-7.20 (2H, m), 7.23-7.29 (4H, m), 7.37-7.42 (4H, m).
MS (ESI) m/z: 337 (M$^+$+1).

Cis-4-(3-azetidinyl)-2,6-dimethylmorpholine hydrochloride

Cis-4-(1-benzhydryl-3-azetidinyl)-2,6-dimethylmorpholine (2.63 g, 7.82 mmol) was dissolved in methanol (40 mL), and 10% palladium hydroxide (wet) (500 mg) and a 1N-hydrochloric acid (5 mL) were added thereto. The mixture was stirred for 24 hours at room temperature under a hydrogen stream at normal pressure. The catalyst was removed by filtration, and the solvent was concentrated under reduced pressure. A 1N-hydrochloric acid (10 mL) was added to the obtained residue, and the mixture was washed with diethyl-ether. The aqueous layer was concentrated to obtain the title compound (1.9 g, 100%) as an amorphous matter.
NMR (D$_2$O) δ: 1.26 (6H, d, J=6.4 Hz), 2.76 (2H, dd, J=12.4, 11.2 Hz), 3.51 (2H, dd, J=10.2, 1.8 Hz), 3.98-4.07 (2H, m), 4.47-4.56 (5H, m).

Trans-4-[(4S)-[3-(cis-2,6-dimethyl-4-morpholinyl)-1-azetidinyl]-(2S)-pyrrolidinylmethoxy]cyclohexanecarboxylic acid ethyl ester NMR (CDCl$_3$) δ: 1.16 (3H, d, J=6.1 Hz), 1.24 (3H, t, J=7.4 Hz), 1.45 (9H, s), 1.55-1.65 (5H, m), 1.62 (6H, s), 1.78-4.00 (21H, m), 4.11 (2H, q, J=7.1 Hz).

Trans-4-[1-[[2,5-dichloro-4-[(1-methyl-1H-indol-3-ylcarbonyl)amino]phenyl]acetyl]-(4S)-[3-(cis-2,6-dimethylmorpholin-4-yl)azetidin-1-yl]-(2S)-pyrrolidinylmethoxy]cyclohexa necarboxylic acid

[Formula 116]

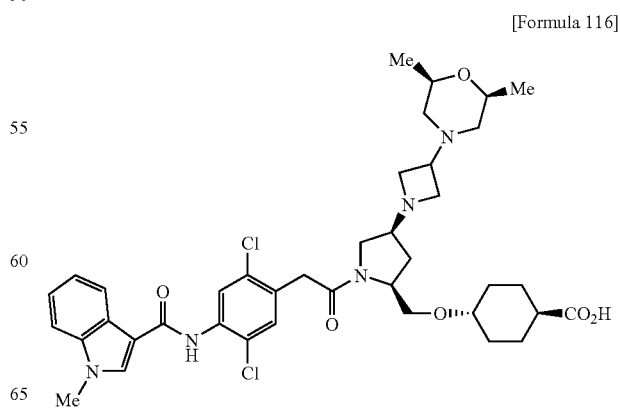

NMR (DMSO-d$_6$) δ: 1.06-4.24 (40H, m), 7.20 (1H, t, J=7.4 Hz), 7.27 (1H, t, J=7.4 Hz), 7.49 (1H, d, J=9.6 Hz), 7.55 (1H, d, J=8.3 Hz), 7.87 (1H, d, J=4.4 Hz), 8.14 (1H, d, J=7.8 Hz), 8.29 (1H, s), 9.37 (1H, d, J=3.4 Hz), 12.03 (1H, br s).
IR (ATR) cm$^{-1}$: 2935, 2863, 1644, 1500, 1373.
MS (FAB) m/z: 754.3123 (calcd for $C_{39}H_{50}Cl_2N_5O_6$: 754.3138).
Anal. Calcd for $C_{39}H_{49}Cl_2N_5O_6 \cdot 0.75H_2O$: C, 60.97; H, 6.63; Cl, 9.23; F, 0.00; N, 9.12.
Found: C, 61.29; H, 6.84; Cl, 8.98; F, 0.00; N, 8.63.

Example 26

Trans-4-[1-[[4-[(benzo[b]thiophen-3-ylcarbonyl)amino]-2,5-dichlorophenyl]acetyl]-(4S)-[3-(N,N-dicyclopropylamino)azetidin-1-yl]-(2S)-pyrrolidinylmethoxy]cyclohexanecarboxylic acid 1-Benzhydryl-3-(N,N-dicyclopropylamino)-3-azetidine 3-Amino-1-benzhydrylazetidine (1.86 g, 7.80 mmol) was dissolved in methanol (40 mL), and (1-ethoxycyclopropoxy)trimethylsilane (3.94 mL, 19.5 mmol), acetic acid (0.94 mL, 15.6 mmol) and sodium cyanoborohydride (1.09 g, 15.6 mmol) were added. The mixture was refluxed for 24 hours. The residue obtained after concentrating the mixture was dissolved in dichloromethane, then saturated brine and sodium hydrogen carbonate were added thereto, and the mixture was partitioned. The organic layer was washed with saturated brine, subsequently dried over anhydrous sodium sulfate, and concentrated. The obtained residue was purified by column chromatography using silica gel (Flash Chromatography System from Biotage AB, column size: 40M, from hexane to hexane/ethyl acetate=9:1), to obtain the title compound (1.46 g, 59%) as an oily matter.
NMR (CDCl$_3$) δ: 0.94-1.16 (1H, m), 1.58-1.76 (6H, m), 2.92-2.98 (2H, m), 3.42-3.59 (6H, m), 4.30 (1H, s), 7.16-7.43 (10H, m).
MS (ESI) m/z: 319 (M$^+$+1).

3-(N,N-dicyclopropylamino)-3-azetidine dihydrochloride

1-Benzhydryl-3-(N,N-dicyclopropylamino)-3-azetidine (1.46 g, 4.58 mmol) was dissolved in methanol (40 mL), and 10% palladium hydroxide (500 mg) and a 1N-hydrochloric acid (5 mL) were added. The mixture was stirred for 24 hours at room temperature under a hydrogen stream at normal pressure. The catalyst was removed by filtration, and the solvent was concentrated under reduced pressure. A 1N-hydrochloric acid was added to the obtained residue, and the mixture was washed with diethyl ether. The aqueous solution was concentrated to obtain the title compound (1.05 g, 102%) as an amorphous matter.
NMR (CD$_3$OD) δ: 0.93 (4H, q, J=6.9 Hz), 1.20-1.26 (4H, m), 2.85-2.92 (2H, m), 3.30-3.31 (2H, m), 3.35 (1H, s), 4.31-4.39 (2H, m), 4.76-4.84 (1H, m).
MS (ESI) m/z: 153 (M$^+$+1).

Trans-4-[(4S)-[3-(N,N-dicyclopropylamino)azetidin-1-yl]-(2S)-pyrrolidinylmethoxy]cyclohexanecarboxylic acid ethyl ester NMR (CDCl$_3$) δ: 0.36-0.44 (8H, m), 1.24 (3H, t, J=6.9 Hz), 1.45 (9H, s), 1.70-2.23 (11H, m), 2.76-3.89 (13H, m), 4.08-4.15 (1H, m), 4.11 (2H, q, J=5.9 Hz).
MS (ESI) m/z: 506 (M$^+$+1).

Trans-4-[1-[[4-[(benzo[b]thiophen-3-ylcarbonyl)amino]-2,5-dichlorophenyl]acetyl]-(4S)-[3-(N,N-dicyclopropylamino)azetidin-1-yl]-(2S)-pyrrolidinylmethoxy]cyclohexanecarboxylic acid

[Formula 117]

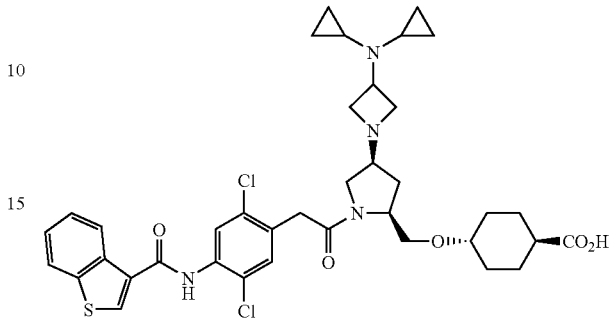

NMR (DMSO-d$_6$) δ: 0.29-0.43 (8H, m), 1.12-1.41 (5H, m), 1.69-2.20 (10H, m), 2.76-4.23 (12H, m), 7.43-7.52 (2H, m), 7.54 (1H, d, J=11.5 Hz), 7.76 (1H, d, J=3.9 Hz), 8.10 (1H, d, J=7.4 Hz), 8.45 (1H, d, J=7.4 Hz), 8.65 (1H, s), 10.17 (1H, s).
IR (ATR) cm$^{-1}$: 2933, 2857, 1637, 1504, 1079.
MS (FAB) m/z: 739.2488 (Calcd for $C_{38}H_{45}Cl_2N_4O_5S$: 739.2488).
Anal. Calcd for $C_{38}H_{44}Cl_2N_4O_5S \cdot 0.5HCl \cdot H_2O$: C, 58.82; H, 6.04; N, 7.22; S, 4.13.
Found: C, 58.72; H, 5.67; N, 6.87; S, 4.32.

Example 27

Trans-4-[1-[[4-[(benzo[b]thiophen-3-ylcarbonyl)amino]-5-chloro-2-fluorophenyl]acetyl]-(4S)-[3-(4-morpholinyl)azetidin-1-yl]-(2S)-pyrrolidinylmethoxy]cyclohexanecarboxylic acid Trans-4-[1-(tert-butoxycarbonyl)-(4S)-[3-(4-morpholinyl)azetidin-1-yl]-(2S)-pyrrolidinylmethoxy]cyclohexanecarboxylic acid ethyl ester NMR (CDCl$_3$) δ: 1.20-1.29 (2H, m), 1.24 (2H, t, J=7.4 Hz), 1.39-1.51 (2H, m), 1.45 (9H, s), 1.73-2.32 (13H, m), 2.84-3.78 (15H, m), 4.11 (2H, q, J=7.4 Hz).
MS (ESI) m/z: 496 (M$^+$+1).

Trans-4-[1-[[4-[(benzo[b]thiophen-3-ylcarbonyl)amino]-5-chloro-2-fluorophenyl]acetyl]-(4S)-[3-(4-morpholinyl)azetidin-1-yl]-(2S)-pyrrolidinylmethoxy]cyclohexanecarboxylic acid

[Formula 118]

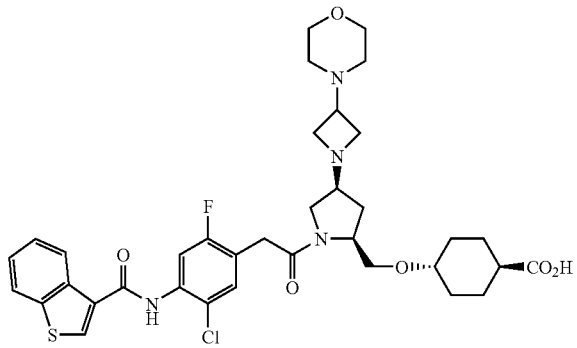

NMR (DMSO-d$_6$) δ: 1.09-1.41 (4H, m), 1.67-4.19 (29H, m) 7.44-7.52 (3H, m), 7.55 (1H, dd, J=10.5, 5.1 Hz), 8.10 (1H, d, J=7.8 Hz), 8.45 (1H, d, J=7.8 Hz), 8.66 (1H, d, J=3.2 Hz), 10.13 (1H, d, J=3.2 Hz).

IR (ATR) cm$^{-1}$: 2940, 2856, 1637, 1519, 1114.

MS (FAB) m/z: 713.2573 (Calcd for C$_{36}$H$_{43}$ClFN$_4$O$_6$S: 713.2576).

Anal. Calcd for C$_{36}$H$_{42}$ClFN$_4$O$_6$S.0.4HCl.2.7H$_2$O: C, 55.69; H, 6.20; Cl, 6.39; F, 2.45; N, 7.22; S, 4.13.

Found: C, 56.13; H, 5.72; Cl, 6.07; F, 2.62; N, 6.69; S, 4.38.

Example 28

Trans-4-[1-[[4-[(benzo[b]thiophen-3-ylcarbonyl)amino]-5-chloro-2-fluorophenyl]acetyl]-(4S)-[3-(piperidin-1-yl)azetidin-1-yl]-(2S)-pyrrolidinylmethoxy]cyclohexanecarboxylic acid Trans-4-[1-(tert-butoxycarbonyl)-(4S)-[3-(piperidin-1-yl)azetidin-1-yl]-(2S)-pyrrolidinylmethoxy]cyclohexanecarboxylic acid NMR (CDCl$_3$) δ: 1.24-1.26 (7H, m), 1.45 (9H, s), 1.58-2.49 (20H, m), 2.93-3.95 (9H, m), 4.12 (2H, dq, J=3.2, 7.4 Hz).

Trans-4-[1-[[4-[(benzo[b]thiophen-3-ylcarbonyl)amino]-5-chloro-2-fluorophenyl]acetyl]-(4S)-[3-(piperidin-1-yl)azetidin-1-yl]-(2S)-pyrrolidinylmethoxy]cyclohexanecarboxylic acid

[Formula 119]

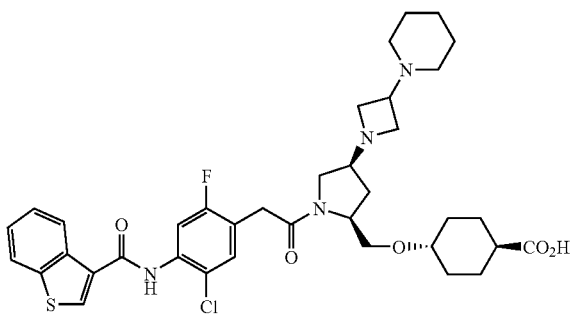

NMR (DMSO-d$_6$) δ: 1.14-4.21 (35H, m), 7.44-7.51 (3H, m), 7.55 (1H, dd, J=10.8, 5.1 Hz), 8.10 (1H, d, J=7.1 Hz), 8.45 (1H, d, J=7.8 Hz), 8.65 (1H, d, J=2.0 Hz), 10.12 (1H, d, J=3.4 Hz).

IR (ATR) cm$^{-1}$: 2935, 2857, 1639, 1517, 1402.

MS (FAB) m/z: 711.2797 (Calcd for C$_{37}$H$_{45}$ClFN$_4$O$_5$S: 711.2783).

Anal. Calcd for C$_{37}$H$_{44}$ClFN$_4$O$_5$S.0.4HCl.H$_2$O: C, 59.74; H, 6.29; Cl, 6.67; F, 2.55; N, 7.53; S, 4.31.

Found: C, 59.44; H, 6.13; Cl, 6.53; F, 2.61; N, 7.46; S, 4.37.

Example 29

Trans-4-[1-[[5-chloro-2-fluoro-4-[(1-methyl-1H-indol-3-ylcarbonyl)amino]phenyl]acetyl]-(4S)-[3-(N,N-dimethylaminomethyl)azetidin-1-yl]-(2S)-pyrrolidinylmethoxy]cyclohexane carboxylic acid Trans-4-[1-(tert-butoxycarbonyl)-(4S)-[3-(N,N-dimethylaminomethyl)azetidin-1-yl]-(2S)-pyrrolidinylmethoxy]cyclohexanecarboxylic acid ethyl ester NMR (CDCl$_3$) δ: 1.17-1.30 (6H, m), 1.45 (9H, s), 1.74-2.12 (6H, m), 2.18-2.20 (2H, m), 2.21 (6H, s), 2.33-3.28 (8H, m), 3.30-3.59 (4H, m), 3.62-3.97 (2H, m), 4.11 (2H, q, J=7.1 Hz).

MS (ESI) m/z: 468 (M$^+$+1).

Trans-4-[(4S)-[3-(N,N-dimethylaminomethyl)azetidin-1-yl]-(2S)-pyrrolidinylmethoxy]cyclohexanecarboxylic acid ethyl ester NMR (CDCl$_3$) δ: 1.18-1.52 (7H, m), 1.90-2.33 (15H, m), 2.46 (2H, d, J=7.4 Hz), 2.56-2.97 (6H, m), 3.19-3.32 (2H, m), 3.41-3.55 (4H, m), 4.11 (2H, q, J=7.1 Hz).

MS (ESI) m/z: 368 (M$^+$+1).

Trans-4-[1-[[5-chloro-2-fluoro-4-[(1-methyl-1H-indol-3-ylcarbonyl)amino]phenyl]acetyl]-(4S)-[3-(N,N-dimethylaminomethyl)azetidin-1-yl]-(2S)-pyrrolidinylmethoxy]cyclohexane carboxylic acid ethyl ester NMR (CDCl$_3$) δ: 1.07-1.54 (7H, m), 1.84-2.32 (7H, m), 2.38 (3H, d, J=2.5 Hz), 2.64-2.97 (5H, m), 3.10-3.30 (3H, m), 3.35-3.81 (7H, m), 3.85 (2H, s), 3.87 (3H, s), 4.03-4.23 (3H, m), 7.30-7.43 (4H, m), 7.76-7.82 (1H, m), 8.10-8.16 (1H, m), 8.27 (1H, s), 8.47 (1H, dd, J=12.0, 3.7 Hz).

MS (ESI) m/z: 710 (M$^+$+1), 712 (M$^+$+3).

Trans-4-[1-[[5-chloro-2-fluoro-4-[(1-methyl-1H-indol-3-ylcarbonyl)amino]phenyl]acetyl]-(4S)-[3-(N,N-dimethylaminomethyl)azetidin-1-yl]-(2S)-pyrrolidinylmethoxy]cyclohexane carboxylic acid

[Formula 120]

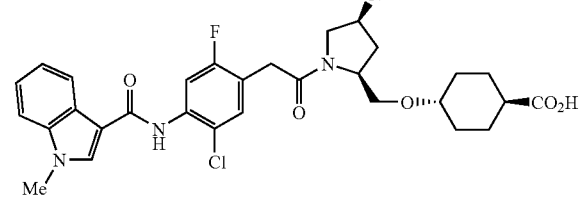

NMR (CDCl$_3$) δ: 1.07-1.57 (4H, m), 1.88-2.28 (7H, m), 2.46 (3H, s), 2.47 (3H, s), 2.77-3.35 (7H, m), 3.45-3.85 (11H, m), 3.88 (3H, d, J=1.0 Hz), 4.11-4.25 (1H, m), 7.62 (1H, d, J=7.8 Hz), 7.81 (1H, d, J=3.4 Hz) and 8.30 (total 1H, each s, amide isomers), 8.46 and 8.49 (total 1H, each d, each J=5.6 Hz, amide isomers).

MS (ESI) m/z: 681 (M$^+$+1), 683 (M$^+$+3).

Example 30

Trans-4-[1-[[4-[(benzo[b]furan-3-ylcarbonyl)amino]-5-chloro-2-fluorophenyl]acetyl]-(4S)-[3-(4-morpholinylmethyl) azetidin-1-yl]-(2S)-pyrrolidinylmethoxy]cyclohexanecarboxylic acid To a dichloromethane solution (20 mL) of trans-4-[1-(tert-butoxycarbonyl)-(4S)-(3-formylazetidin-1-yl)-(2S)-pyrrolidinylmethoxy]cyclohexanecarboxylic acid ethyl ester oxalyl chloride (1.92 mL, 15.12 mmol), a dichloromethane (20 mL) solution of dimethylsulfoxide (2.15 mL, 30.23 mmol) was added over 10 minutes under a nitrogen stream at −78° C. while stirring. To the reaction liquor, a dichloromethane (50 mL) solution of trans-4-[1-(tert-butoxycarbonyl)-(4S)-(3-hydroxymethylazetidin-1-yl)-(2S)-pyrrolidinylmethoxy]cyclohexanecarboxylic acid ethyl ester (2.22 g, 5.04 mmol) was added dropwise over 20 minutes at the same temperature, and the mixture was stirred for one hour. Subsequently, triethylamine (6.32 mL, 45.35 mmol) was added dropwise over 10 minutes at the same temperature, and the mixture was stirred for two hours. The reaction liquor was poured onto a saturated aqueous solution of sodium hydrogen carbonate (50 mL), and the mixture was extracted with dichloromethane. The extract was washed with saturated brine, and dried over anhydrous sodium sulfate, and then the solvent was concentrated under reduced pressure to obtain the title compound (2.70 g, quantitative) as a brown oily matter. This compound was used in the subsequent reaction without performing further purification.
MS (ESI) m/z: 471 (M$^+$+33).

Trans-4-[1-(tert-butoxycarbonyl)-(4S)-[3-(4-morpholinylmethyl)azetidin-1-yl]-(2S)-pyrrolidinylmethoxy]cyclohexanecarboxylic acid ethyl ester To a dichloroethane (50 mL) solution of trans-4-[1-(tert-butoxycarbonyl)-(4S)-(3-formylazetidin-1-yl)-(2S)-pyrrolidinylmethoxy]cyclohexanecarboxylic acid ethyl ester (1.11 g, 2.52 mmol) and morpholine (0.88 mL, 10.08 mmol), sodium triacetoxyborohydride (1.07 g, 5.04 mmol) was added, and the mixture was stirred for four days. A saturated aqueous solution of sodium hydrogen carbonate (100 mL) was added to the reaction liquor, and the mixture was stirred for 15 minutes, and then extracted with dichloromethane. The extract was washed with saturated brine, and dried over anhydrous sodium sulfate, and then the solvent was concentrated under reduced pressure. The obtained residue was purified by flash chromatography (Flash Chromatography System from Biotage AB, column size: 40S, methanol/chloroform=5/95 to 1/9), to obtain the title compound (1.14 g, 89%) as an oily matter.
NMR (CDCl$_3$) δ: 1.17-1.30 (5H, m), 1.39-1.51 (11H, m), 1.75-2.29 (8H, m), 2.30-2.89 (9H, m), 2.96-3.08 (1H, m), 3.16-3.27 (1H, m), 3.33-3.92 (10H, m), 4.11 (2H, q, J=7.1 Hz).
MS (ESI) m/z: 510 (M$^+$+1).

Trans-4-[(4S)-[3-(4-morpholinylmethyl)azetidin-1-yl]-(2S)-pyrrolidinylmethoxy]cyclohexanecarboxylic acid ethyl ester NMR (CDCl$_3$) δ: 1.18-1.32 (5H, m), 1.38-1.53 (2H, m), 1.93-2.31-3.77 (13H, m), 4.11 (2H, q, J=7.1 Hz).
MS (ESI) m/z: 410 (M$^+$+1).

Trans-4-[1-[[4-[(benzo[b]furan-3-ylcarbonyl)amino]-5-chloro-2-fluorophenyl]acetyl]-(4S)-[3-(4-morpholinylmethyl) azetidin-1-yl]-(2S)-pyrrolidinylmethoxy]cyclohexanecarboxylic acid ethyl ester NMR (CDCl$_3$) δ: 1.13-1.55 (7H, m), 1.62-1.81 (1H, m), 1.86-2.32 (6H, m), 2.35-2.58 (6H, m), 2.58-2.98 (3H, m), 3.08-3.88 (13H, m), 4.05-4.21 (3H, m), 7.40-7.47 (3H, m), 7.58-7.64 (1H, m), 8.02-8.09 (1H, m), 8.28 (1H, d, J=6.6 Hz), 8.31 (1H, d, J=4.4 Hz), 8.43 (1H, d, J=11.6 Hz), 8.44 (1H, d, J=11.8 Hz).
MS (ESI) m/z: 739 (M$^+$+1), 741 (M$^+$+3).

Trans-4-[1-[[4-[(benzo[b]furan-3-ylcarbonyl)amino]-5-chloro-2-fluorophenyl]acetyl]-(4S)-[3-(4-morpholinylmethyl) azetidin-1-yl]-(2S)-pyrrolidinylmethoxy]cyclohexanecarboxylic acid

[Formula 121]

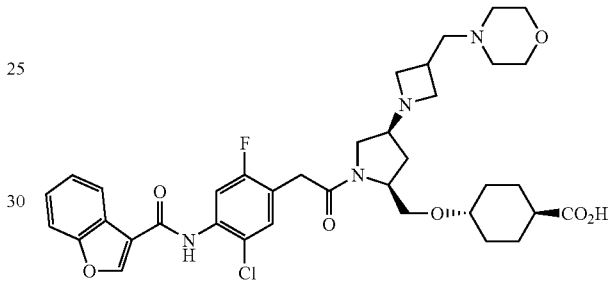

NMR (CDCl$_3$) δ: 1.14-1.68 (6H, m), 1.81-2.40 (8H, m), 2.79-3.29 (6H, m), 3.37-3.90 (11H, m), 3.92-4.31 (1H, m), 4.41 (1H, dd, J=7.8, 5.1 Hz), 4.53 (1H, dd, J=8.3, 5.1 Hz), 7.41-7.46 (4H, m), 7.57-7.63 (1H, m), 8.02-8.08 (1H, m), 8.27 (1H, d, J=4.9 Hz), 8.30 (1H, d, J=2.0 Hz), 8.44 (1H, dd, J=11.6, 8.9 Hz).
MS (ESI) m/z: 711 (M$^+$+1) 713 (M$^+$+3).
IR (ATR) cm$^{-1}$: 2937, 2856, 1678, 1587, 1558, 1522.

Example 31

Trans-4-[1-[[4-[(benzo[b]thiophen-3-ylcarbonyl) amino]-2,5-dichlorophenyl]acetyl]-(4S)-(pyrrolidin-1-yl)-(2S)-pyrrolidinylmethoxy]cyclohexanecarboxylic acid Trans-4-[1-(tert-butoxycarbonyl)-(4S)-(pyrrolidin-1-yl)-(2S)-pyrrolidinylmethoxy]cyclohexanecarboxylic acid ethyl ester NMR (CDCl$_3$) δ: 1.22-1.28 (total 6H, series of m, including 3H of t, J=7.2 Hz, at δ 1.24), 1.39-1.46 (total 11H, series of m), 1.78-2.06 (total 8H, series of m), 2.23 (2H, m), 2.51-2.54 (total 5H, series of m), 3.05 (1H, t, J=9.6 Hz), 3.20 (1H, m), 3.41-3.85 (total 4H, series of m), 4.11 (2H, q, J=7.2 Hz).
MS (ESI) m/z: 425 (M$^+$+1).

Trans-4-[1-(tert-butoxycarbonyl)-(4S)-(pyrrolidin-1-yl)-(2S)-pyrrolidinylmethoxy]cyclohexanecarboxylic acid ethyl ester dihydrochloride NMR (CDCl$_3$) δ: 1.21-1.32 (total 5H, series of m), 1.46 (2H, q, J=12.0 Hz), 1.99-2.28 (total 8H, series of m), 2.68

(1H, m), 3.16-3.40 (total 4H, series of m), 3.63-3.86 (total 6H, series of m), 4.08-4.13 (total 4H, series of m), 4.22 (1H, m), 9.30 (1H, m), 10.64 (1H, m), 12.02 (1H, m).

MS (ESI) m/z: 325 (M$^+$−72).

Trans-4-[1-[[4-[(benzo[b]thiophen-3-ylcarbonyl)amino]-2,5-dichlorophenyl]acetyl]-(4S)-(pyrrolidin-1-yl)-(2S)-pyrrolidinylmethoxy]cyclohexanecarboxylic acid ethyl ester NMR (CDCl$_3$) δ: 0.82-1.52 (total 7H, series of m), 1.71-2.47 (total 11H, series of m), 2.59-2.84 (total 5H, series of m), 3.11-4.37 (total 10H, series of m), 7.23-7.64 (total 3H, series of m), 7.84 and 7.89 (total 1H, each d, each J=8.1 Hz, amide and 8.63 (total 1H, each s, amide isomers).

MS (ESI) m/z: 687 (M$^+$+1).

Anal. Calcd for C$_{35}$H$_{41}$N$_3$Cl$_2$O$_5$S: C, 61.22; H, 6.02; N, 6.12.

Found: C, 61.12; H, 6.22; N, 6.47.

Trans-4-[1-[[4-[(benzo[b]thiophen-3-ylcarbonyl)amino]-2,5-dichlorophenyl]acetyl]-(4S)-(pyrrolidin-1-yl)-(2S)-pyrrolidinylmethoxy]cyclohexanecarboxylic acid

[Formula 122]

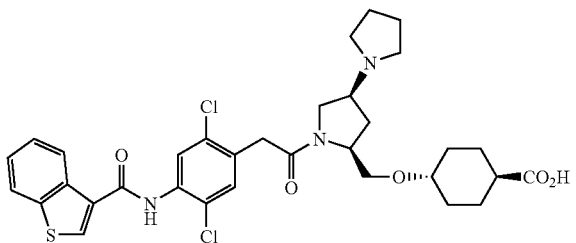

NMR (CDCl$_3$) δ: 1.16-1.52 (total 5H, series of m), 1.78-2.52 (total 10H, series of m), 2.71-2.94 (total 5H, series of m), 3.14-3.25 (1H, m), 3.40-3.98 (total 5H, series of m), 4.09-4.46 (2H, m), 7.40-7.54 (total 3H, series of m), 7.91 (1H, dd, J=8.4, 4.2 Hz), 8.09 (1H, d, J=4.2 Hz), 8.30 (1H, d, J=11.0 Hz), 8.47 (1H, d, J=8.1 Hz), 8.70 (1H, d, J=4.6 Hz).

IR (ATR) ν: 2933, 2859, 1639, 1569 cm$^{-1}$.

MS (ESI) m/z 658 (M$^+$+1).

Anal. Calcd for C$_{33}$H$_{37}$N$_3$Cl$_2$O$_5$S 0.75H$_2$O: C, 58.97; H, 5.77; N, 6.25.

Found: C, 58.99; H, 5.72; N, 6.33.

Example 32

Trans-4-[1-[[4-[(benzo[b]thiophen-3-ylcarbonyl)amino]-5-chloro-2-fluorophenyl]acetyl]-(4S)-[(3R)-methoxypyrrolidin-1-yl]-(2S)-pyrrolidinylmethoxy]cyclohexanecarboxylic acid

Trans-4-[1-(tert-butoxycarbonyl)-(4S)-[(3R)-methoxypyrrolidin-1-yl]-(2S)-pyrrolidinylmethoxy]cyclohexanecarboxylic acid ethyl ester NMR (CDCl$_3$) δ: 1.22-1.28 (total 5H, series of m, including 3H, t, J=7.1 Hz at δ 1.24), 1.41-1.51 (total 11H, series of m), 1.84-2.11 (total 6H, series of m), 2.18-2.27 (total 2H, series of m), 2.39-2.76 (total 6H, series of m), 3.09 (1H, dd, J=10.3, 8.8 Hz), 3.16-3.30 (total 4H, series of m, including 3H, s at δ 3.20), 3.38-3.58 (total 1H, series of m), 3.64-3.95 (total 4H, series of m), 4.11 (2H, q, J=7.1 Hz).

MS (ESI) m/z: 455 (M$^+$+1).

Trans-4-[(4S)-[(3R)-methoxypyrrolidin-1-yl]-(2S)-pyrrolidinylmethoxy]cyclohexanecarboxylic acid ethyl ester dihydrochloride NMR (CDCl$_3$) δ: 1.12-1.53 (total 7H, series of m, including 3H, t, J=7.2 Hz at δ 1.24), 1.60-2.89 (total 9H, series of m), 3.08-4.73 (total 17H, series of m, including 2H, q, J=7.2 Hz at δ 4.10), 9.32-9.58 (total 1H, m), 10.36-10.59 (total 1H, m), 11.49 and 12.23 (total 1H, each br s).

Trans-4-[1-[[4-[(benzo[b]thiophen-3-ylcarbonyl)amino]-5-chloro-2-fluoro]phenyl]acetyl]-(4S)-[(3R)-methoxypyrrolidin-1-yl]-(2S)-pyrrolidinylmethoxy]cyclohexanecarboxylic acid ethyl ester NMR (CDCl$_3$) δ: 1.11-1.52 (total 7H, series of m), 1.58-2.81 (total 16H, series of m), 3.11-3.34 (total 4H, series of m), 3.40-4.26 (total 8H, series of m), 7.39-7.55 (total 3H, series of m), 7.92 (1H, d, J=7.8 Hz), 8.09 and 8.12 (total 1H, each s, amide isomers), 8.33-8.50 (3H, m).

IR (ATR) ν: 2933, 1724, 1674, 1639 cm$^{-1}$.

MS (ESI) m/z: 700 [(M$^+$+1), 5Cl].

Anal. Calcd for C$_{36}$H$_{43}$ClFN$_3$O$_5$S·0.25H$_2$O: C, 61.35; H, 6.22; N, 5.96; S, 4.55.

Found: C, 61.15; H, 6.02; N, 5.78; S, 4.43.

Trans-4-[1-[[4-[(benzo[b]thiophen-3-ylcarbonyl)amino]-5-chloro-2-fluorophenyl]acetyl]-(4S)-[(3R)-methoxypyrrolidin-1-yl]-(2S)-pyrrolidinylmethoxy]cyclohexanecarboxylic acid

[Formula 123]

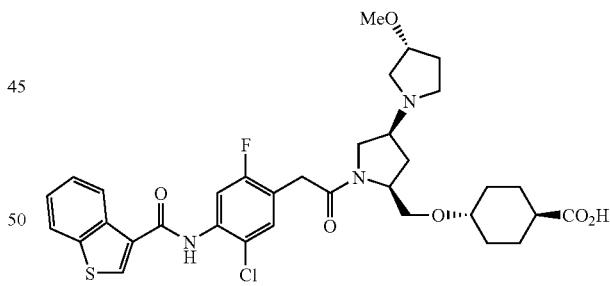

NMR (CDCl$_3$) δ: 1.14-1.51 (total 5H, series of m), 1.72-2.47 (total 10H, series of m), 2.62-4.36 (total 16H, series of m), 7.40 (1H, d, J=7.1 Hz), 7.44 (1H, t, J=7.1 Hz), 7.51 (1H, t, J=7.8 Hz), 7.91 (1H, d, J=7.8 Hz), 8.09 and 8.11 (total 1H, each s, amide isomers), 8.33 and 8.36 (total 1H, each s), 8.41 and 8.43 (total 1H, each d, each J=10.0 Hz, amide isomers), 8.47 (1H, d, J=8.3 Hz).

IR (ATR) ν: 2933, 1718, 1672, 1639 1585 cm$^{-1}$.

MS (ESI) m/z: 672 [(M$^+$+1), $^{35}$Cl], 674 [(M$^+$+3), $^{37}$Cl].

Anal. Calcd for C$_{34}$H$_{39}$ClFN$_3$O$_6$S·0.75H$_2$O: C, 59.55; H, 5.95; N, 6.13; S, 4.68.

Found: C, 59.29; H, 5.67; N, 6.06; S, 4.74.

Example 33

Trans-4-[1-[[2,5-dichloro-4-[(1-methyl-1H-indol-3-ylcarbonyl)amino]phenyl]acetyl]-(4S)-[(3R)-methoxypyrrolidin-1-yl]-(2S)-pyrrolidinylmethoxy]cyclohexanecarboxylic acid Trans-4-[1-[[2,5-dichloro-4-[(1-methyl-1H-indol-3-ylcarbonyl)amino]phenyl]acetyl]-(4S)-[(3R)-methoxypyrrolidin-1-yl]-(2S)-pyrrolidinylmethoxy]cyclohexanecarboxylic acid ethyl ester NMR (CDCl$_3$) δ: 1.15-1.30 (total 5H, series of m), 1.35-1.52 (2H, m), 1.63-2.48 (total 10H, series of m), 2.56-2.79 (total 4H, series of m), 3.12-3.33 (total 5H, series of m), 3.48-3.97 (total 9H, series of m), 4.06-4.23 (total 3H, series of m), 7.28-7.36 (total 4H, series of m), 7.73 and 7.74 (total 1H, each s, amide isomers), 8.09-8.19 (2H, m), 8.70 and 8.73 (total 1H, each s, amide isomers).
IR (ATR) ν: 2935, 1724, 1641 cm$^{-1}$.
MS (ESI) m/z: 713 [(M$^+$+1), $^{35}$Cl], 715 [(M$^+$+3), $^{37}$Cl].

Trans-4-[1-[[2,5-dichloro-4-[(1-methyl-1H-indol-3-ylcarbonyl)amino]phenyl]acetyl]-(4S)-[(3R)-methoxypyrrolidin-1-yl]-(2S)-pyrrolidinylmethoxy]cyclohexanecarboxylic acid

[Formula 124]

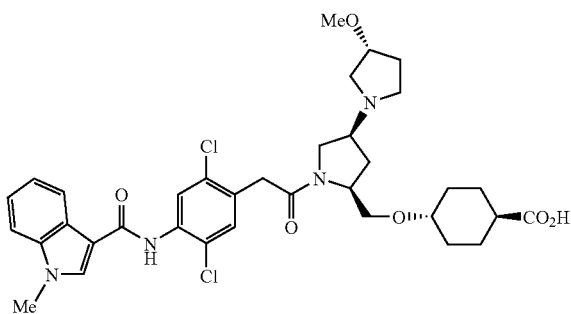

NMR (CDCl$_3$) δ: 1.15-1.52 (total 5H, series of m), 158-2.47 (total 9H, series of m), 2.62-4.39 (total 19H, series of m), 5.89 (1H, br s), 7.30-7.43 (total 4H, series of m), 7.78-7.78 (1H, m), 8.10-8.24 (2H, m), 8.71-8.78 (1H, m).
IR (ATR) ν: 2931, 1718, 1641 cm$^{-1}$.
MS (ESI) m/z: 685 [(M$^+$+1), $^{35}$Cl], 687 [(M$^+$+1), $^{37}$Cl].
Anal. Calcd for C$_{35}$H$_{42}$Cl$_2$N$_4$O$_6$·0.75H$_2$O: C, 60.13; H, 6.27; N, 8.01.
Found: C, 60.25; H, 6.30; N, 7.71.

Example 34

Trans-4-[1-[[4-[(benzo[b]thiophen-3-ylcarbonyl)amino]-5-chloro-2-fluorophenyl]acetyl]-(4S)-[(3R)-ethoxypyrrolidin-1-yl]-(2S)-pyrrolidinylmethoxy]cyclohexanecarboxylic acid Trans-4-[1-(tert-butoxycarbonyl)-(4S)-[(3R)-ethoxypyrrolidin-1-yl]-(2S)-pyrrolidinylmethoxy]cyclohexanecarboxylic acid ethyl ester NMR (CDCl$_3$) δ: 1.17-1.28 (total 8H, series of m, including 3H, t, J=6.8 Hz 51.19, and 3H, t, J=7.1 Hz δ 1.24), 1.46 (11H, s), 1.72-2.27 (total 9H, series of m), 2.43-2.75 (total 5H, series of m), 3.08 (1H, t, J=9.5 Hz), 3.15-3.25 (1H, m), 3.36-3.86 (total 6H, series of m), 4.01-4.01 (1H, m), 4.11 (2H, q, J=7.1 Hz).
MS (ESI) m/z: 469 (M$^+$+1).

Trans-4-[(4S)-[(3R)-ethoxypyrrolidin-1-yl]-(2S)-pyrrolidinylmethoxy]cyclohexanecarboxylic acid ethyl ester dihydrochloride NMR (CDCl$_3$) δ: 1.16-1.54 (total 10H, series of m), 1.85-2.86 (total 7H, series of m), 3.23-4.44 (total 16H, series of m, including 2H, q, J=7.2 Hz, δ 4.11), 9.35 (1H, s), 10.27 and 10.58 (total 1H, each s), 11.41 and 12.24 (total 1H, each s).
MS (ESI) m/z: 369 (M$^+$−73).

Trans-4-[1-[[4-[(benzo[b]thiophen-3-ylcarbonyl)amino]-5-chloro-2-fluorophenyl]acetyl]-(4S)-[(3R)-ethoxypyrrolidin-1-yl]-(2S)-pyrrolidinylmethoxy]cyclohexanecarboxylic acid ethyl ester NMR (CDCl$_3$) δ: 1.13-1.29 (total 8H, series of m), 1.34-1.48 (2H, m), 1.73-2.75 (total 15H, series of m), 3.11-3.33 (2H, m), 3.38-3.87 (6H, m), 3.98-4.23 (4H, m), 7.41 and 7.42 (total 1H, each d, each J=7.3 Hz, amide isomers), 7.45 (1H, td, J=7.3, 1.0 Hz), 7.52 (1H, tdd, J=7.1, 2.2, 1.2H z), 7.91 (1H, d, J=8.1 Hz), 8.09 and 8.12 (total 1H, each s, amide isomers), 8.34 and 8.37 (total 1H, each br s, amide isomers), 8.42 and 8.44 (total 1H, each d, each J=11.7 Hz, amide isomers), 8.46-8.50 (1H, m).
IR (ATR) ν: 2937, 2863, 1724, 1676, 1637 cm$^{-1}$.
MS (ESI) m/z: 714 [(M$^+$+1), $^{35}$Cl], 716 [(M$^+$+3), $^{37}$Cl].
Anal. Calcd for C$_{37}$H$_{45}$ClFN$_3$O$_5$S·0.5H$_2$O: C, 61.44; H, 6.41; N, 5.81; S, 4.43.
Found: C, 61.35; H, 6.20; N, 5.86; S, 4.58.

Trans-4-[1-[[4-[(benzo[b]thiophen-3-ylcarbonyl)amino]-5-chloro-2-fluorophenyl]acetyl]-(4S)-[(3R)-ethoxypyrrolidin-1-yl]-(2S)-pyrrolidinylmethoxy]cyclohexanecarboxylic acid

[Formula 125]

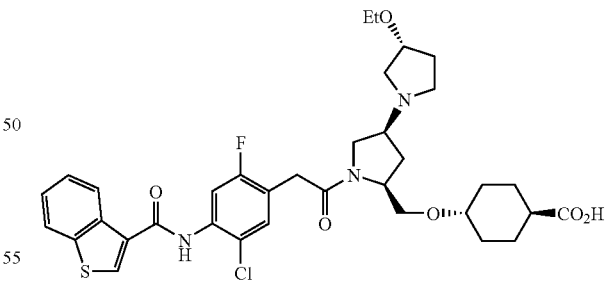

NMR (CDCl$_3$) δ: 1.12-1.51 (total 7H, series of m), 1.61-2.46 (total 9H, series of m), 2.61-4.38 (total 16H, series of m), 7.35 (1H, d, J=7.1 Hz), 7.40 (1H, t, J=7.6 Hz), 7.47 (1H, t, J=7.6 Hz), 7.87 (1H, d, J=8.1 Hz), 8.07-8.13 (1H, m), 8.49-8.30 (total 3H, series of m), 10.28 (1H, br s).
IR (ATR) ν: 2935, 2861, 1718, 1672, 1641 cm$^{-1}$.
MS (ESI) m/z: 686 [(M$^+$+1), $^{35}$Cl], 687 (M$^+$+2).
Anal. Calcd for C$_{35}$H$_{41}$ClFN$_3$O$_6$S·0.5 H$_2$O: C, 60.47; H, 6.09; N, 6.04; S, 4.61.
Found: C, 60.25; H, 5.84; N, 5.89; S, 4.71.

Example 35

Trans-4-[1-[[2,5-dichloro-4-[(1-methyl-1H-indol-3-ylcarbonyl)amino]phenyl]acetyl]-(4S)-[(3S)-methoxypyrrolidin-1-yl]-(2S)-pyrrolidinylmethoxy]cyclohexanecarboxylic acid Trans-4-[1-(tert-butoxycarbonyl)-(4S)-[(3S)-methoxypyrrolidin-1-yl]-(2S)-pyrrolidinylmethoxy]cyclohexanecarboxylic acid ethyl ester NMR (CDCl$_3$) δ: 1.18-1.31 (total 5H, series of m, including δ 1.24 t, J=7.0 Hz), 1.42-1.46 (total 11H, series of m), 1.63-2.31 (total 11H, series of m), 2.40-2.76 (total 4H, series of m), 3.08 (1H, t, J=9.8 Hz), 3.20 (1H, t, J=9.8 Hz), 3.28 (3H, s), 3.33-3.97 (total 4H, series of m), 4.11 (2H, q, J=7.1 Hz).
MS (ESI) m/z: 455 (M$^+$+1).

Trans-4-[(4S)-[(3S)-methoxypyrrolidin-1-yl]-(2S)-pyrrolidinylmethoxy]cyclohexanecarboxylic acid ethyl ester dihydrochloride MS (ESI) m/z: 427 (M$^+$+1), 355 (M$^+$−2HCl).

Trans-4-[1-[[2,5-dichloro-4-[(1-methyl-1H-indol-3-ylcarbonyl)amino]phenyl]acetyl]-(4S)-[(3S)-methoxypyrrolidin-1-yl]-(2S)-pyrrolidinylmethoxy]cyclohexanecarboxylic acid ethyl ester NMR (CDCl$_3$) δ: 1.14-1.52 (total 7H, series of m), 1.74-2.12 (total 7H, series of m), 2.16-2.79 (total 7H, series of m, including 3H, s, δ 3.28), 3.11-3.34 (total 5H, series of m), 3.48-3.96 (total 9H, series of m, including 3H, s, δ 3.82), 4.06-4.25 (3H, m, including 2H, q, J=7.0 Hz, δ 4.09), 7.28-7.38 (total 4H, series of m), 7.74 and 7.75 (total 1H, each s, amide isomers), 8.10-8.14 (1H, m), 8.18 and 8.19 (total 1H, each s, amide isomers), 8.72 and 8.74 (total 1H, each s, amide isomers).
IR (ATR) ν: 2935, 2862, 1726, 1641 cm$^{-1}$.
MS (ESI) m/z: 713 [(M$^+$+1), $^{35}$Cl], 715 [(M$^+$+3), $^{37}$Cl].
Anal. Calcd for C$_{37}$H$_{46}$Cl$_2$N$_4$O$_6$ 0.75H$_2$O: C, 61.11; H, 6.58; N, 7.70.
Found: C, 61.31; H, 6.30; N, 7.41.

Trans-4-[1-[[2,5-dichloro-4-[(1-methyl-1H-indol-3-ylcarbonyl)amino]phenyl]acetyl]-(4S)-[(3S)-methoxypyrrolidin-1-yl]-(2S)-pyrrolidinylmethoxy]cyclohexanecarboxylic acid

[Formula 126]

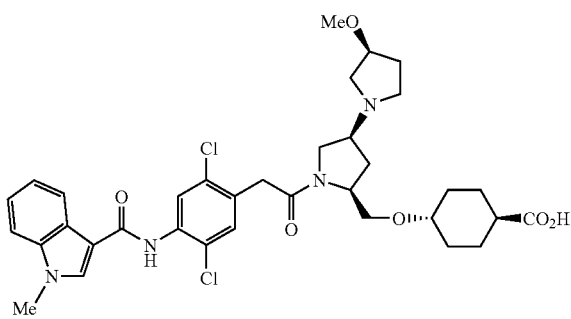

NMR (CDCl$_3$) δ: 1.57-0.79 (total 5H, series of m) 1.64-2.52 (total 9H, series of m), 2.62-4.39 (total 19H, series of m), 7.26-7.36 (total 4H, series of m), 7.68-7.77 (1H, m), 8.08-8.21 (2H, m), 8.67-8.74 (1H, m), 9.62 (1H, br s).
IR (ATR) ν: 2933, 2862, 1720, 1641 cm$^{-1}$.
MS (ESI) m/z: 685 [(M$^+$+1), $^{35}$Cl], 687 [(M$^+$+1), $^{37}$Cl].
Anal. Calcd for C$_{35}$H$_{42}$Cl$_2$N$_4$O$_6$·H$_2$O: C, 59.74; H, 6.30; N, 7.96.
Found: C, 59.61; H, 6.05; N, 7.79.

Example 36

Ttrans-4-[1-[[2,5-dichloro-4-[(1-methyl-1H-indol-3-ylcarbonyl)amino]phenyl]acetyl]-(4S)-[(3S)-ethoxypyrrolidin-1-yl]-(2S)-pyrrolidinylmethoxy]cyclohexanecarboxylic acid Trans-4-[1-(tert-butoxycarbonyl)-(4S)-[(3S)-ethoxypyrrolidin-1-yl]-(2S)-pyrrolidinylmethoxy]cyclohexanecarboxylic acid ethyl ester NMR (CDCl$_3$) δ: 1.17-1.28 (total 8H, series of m, including 3H, t, J=6.8 Hz δ 1.19, and 3H, t, J=7.1 Hz δ 1.24), 1.46 (11H, s), 1.72-2.27 (total 9H, series of m), 2.43-2.75 (total 5H, series of m), 3.08 (1H, t, J=9.5 Hz), 3.15-3.25 (1H, m), 3.36-3.86 (total 6H, series of m), 4.01-4.01 (1H, m), 4.11 (2H, q, J=7.1 Hz).
MS (ESI) m/z: 469 (M$^+$+1).

Trans-4-[(4S)-[(3S)-ethoxypyrrolidin-1-yl]-(2S)-pyrrolidinylmethoxy]cyclohexanecarboxylic acid ethyl ester dihydrochloride NMR (CDCl$_3$) δ: 0.88-1.52 (total 9H, series of m), 1.62-2.99 (total 9H, series of m), 3.17-4.70 (total 16H, series of m), 9.46 (1H, br s), 10.39-10.82 (1H, m), 11.49-12.49 (1H, m).
MS (ESI) m/z: 369 (M$^+$−2HCl).

Trans-4-[1-[[2,5-dichloro-4-[(1-methyl-1H-indol-3-ylcarbonyl)amino]phenyl]acetyl]-(4S)-[(3S)-ethoxypyrrolidin-1-yl]-(2S)-pyrrolidinylmethoxy]cyclohexanecarboxylic acid ethyl ester NMR (CDCl$_3$) δ: 1.14-1.31 (total 8H, series of m), 1.34-1.53 (2H, m), 1.73-2.77 (15H, series of m), 3.12-3.78 (8H, series of m), 3.87 (3H, s), 3.93-4.24 (4H, series of m), 7.31-7.43 (total 4H, series of m, including 2H, q, J=7.1 Hz, 54.09), 7.785 and 7.793 (total 1H, each s), 8.10-8.16 (1H, m), 8.21-8.24 (1H, m), 8.76 and 7.78 (total 1H, each s).
IR (ATR) ν: 2937, 2864, 1726, 1641 cm$^{-1}$.
MS (ESI) m/z: 727 [(M$^+$+1), $^{35}$Cl], 729 [(M$^+$+3), $^{37}$Cl].
Anal. Calcd for C$_{38}$H$_{48}$Cl$_2$N$_4$O$_y$·0.5H$_2$O: C, 61.95; H, 6.70; N, 7.60.
Found: C, 62.04; H, 6.64; N, 7.43.

Trans-4-[1-[[2,5-dichloro-4-[(1-methyl-1H-indol-3-ylcarbonyl)amino]phenyl]acetyl]-(4S)-[(3S)-ethoxypyrrolidin-1-yl]-(2S)-pyrrolidinylmethoxy]cyclohexanecarboxylic acid

[Formula 127]

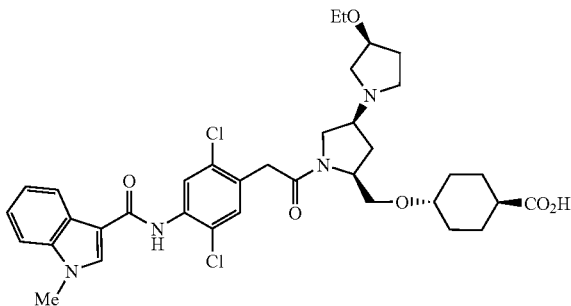

NMR (CDCl₃) δ: 0.86-1.52 (total 7H, series of m), 1.75-2.47 (total 9H, series of m), 2.58-4.42 (total 20H, series of m), 7.30-7.42 (total 4H, series of m), 7.79 (1H, s), 8.10-8.15 (1H, m), 8.22 and 8.23 (total 1H, each s, amide isomers), 8.74 and 8.77 (total 1H, each s, amide isomers)
IR (ATR) ν: 2937, 2860, 1714, 1643 cm⁻¹.
MS (ESI) m/z: 699 [(M⁺+1), ³⁵Cl], 701 [(M⁺+1), ³⁷Cl].
Anal. Calcd for C₃₆H₄₄Cl₂N₄O₆·1.25H₂O: C, 59.87; H, 6.49; N, 7.76.
Found: C, 59.96; H, 6.47; N, 7.82.

Example 37

Trans-4-[1-[[5-chloro-2-fluoro-4-[(1-methyl-1H-indol-3-ylcarbonyl)amino]phenyl]acetyl]-(4S)-[(3S)-fluoropyrrolidin 1-yl]-(2S)-pyrrolidinylmethoxy] cyclohexanecarboxylic acid Trans-4-[1-(tert-butoxycarbonyl)-(4S)-[(3S)-fluoropyrrolidinyl]-(2S)-pyrrolidinylmethoxy]cyclohexanecarboxylic acid ethyl ester NMR (CDCl₃) δ: 1.20-1.31 (total 7H, series of m), 1.45-1.47 (total 11H, series of m), 1.87-2.28 (total 9H, series of m), 2.40-2.93 (total 4H, series of m), 3.07 (1H, dd, J=8.8, 10.5 Hz), 3.16-3.96 (total 4H, series of m), 4.08-4.17 (2H, m), 5.07-5.26 (1H, m).
MS (ESI) m/z: 443 (M⁺+1).

Trans-4-[(4S)-[(3S)-fluoropyrrolidin-1-yl]-(2S)-pyrrolidinylmethoxy]cyclohexanecarboxylic acid ethyl ester dihydrochloride NMR (DMSO-d₆) δ: 1.13-1.39 (total 7H, series of m), 1.84-2.04 (total 5H, series of m), 2.11-2.57 (total 5H, series of m), 3.24-3.76 (total 10H, series of m), 4.00-4.36 (total 3H, series of m), 5.38-5.51 (1H, m), 9.40 (1H, s), 10.25 (1H, s).
MS (ESI) m/z: 343 (M⁺−72).

Trans-4-[1-[[5-chloro-2-fluoro-4-[(1-methyl-1H-indol-3-ylcarbonyl)amino]phenyl]acetyl]-(4S)-[(3S)-fluoropyrrolidin-1-yl]-(2S)-pyrrolidinylmethoxy] cyclohexanecarboxylic acid ethyl ester NMR (CDCl₃) δ: 1.11-1.52 (total 7H, series of m), 1.71-1.84 (total 3H, series of m), 1.93-2.37 (total 8H, series of m), 2.39-2.52 (1H, m), 2.63-2.98 (total 3H, series of m), 3.12-3.33 (2H, m), 3.50-3.90 (total 7H, series of m), 4.05-4.25 (total 3H, series of m), 5.07-5.28 (1H, m), 7.32-7.44 (total 4H, series of m), 7.80-7.83 (1H, m), 8.12-8.17 (1H, m), 8.30 (1H, br s), 8.47-8.55 (1H, m).
IR (ATR) ν: 2937, 1724, 1643 cm⁻¹.
Anal. Calcd for C₃₆H₄₃ClF₂N₄O₅·0.75H₂O: C, 61.88; H, 6.42; N, 8.02.
Found: C, 61.92; H, 6.15; N, 7.98.

Trans-4-[1-[[5-chloro-2-fluoro-4-[(1-methyl-1H-indol-3-ylcarbonyl)amino]phenyl]acetyl]-(4S)-[(3S)-fluoropyrrolidin-1-yl]-(2S)-pyrrolidinylmethoxy] cyclohexanecarboxylic acid

[Formula 128]

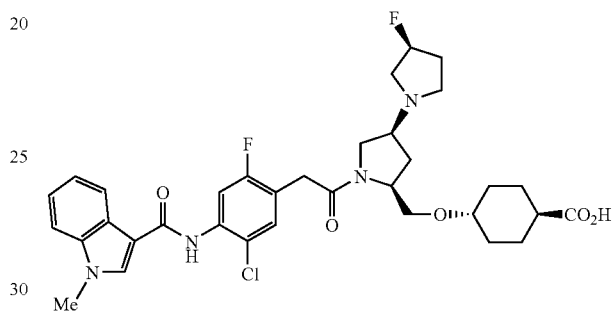

NMR (CDCl₃) δ: 1.13-1.51 (total 4H, series of m), 1.70-2.45 (total 9H, series of m), 2.63-3.90 (total 15H, series of m), 4.01-4.34 (1H, m), 5.11-5.29 (total 2H, series of m), 7.30-7.43 (total 4H, series of m), 7.80 (1H, s), 8.14-8.10 (1H, m), 8.29 (1H, s), 8.49 (1H, t, J=12.2 Hz)
IR (ATR) ν: 2937, 1729, 1643, 1585 cm⁻¹.
MS (ESI) m/z: 657 [(M⁺+1), ³⁵Cl], 659 [(M⁺+3), ³⁷Cl].
Anal. Calcd for C₃₄H₃₉ClF₂N₄O₅—H₂O: C, 60.48; H, 6.12; N, 8.30.
Found: C, 60.46; H, 6.20; N, 8.05.

Example 38

Trans-4-[1-[[4-[(benzo[b]thiophen-3-ylcarbonyl)amino]-5-chloro-2-fluorophenyl]acetyl]-(4S)-(3,3-difluoropyrrolidin-1-yl)-(2S)-pyrrolidinylmethoxy] cyclohexanecarboxylic acid Trans-4-[1-(tert-butoxycarbonyl)-(4S)-(3,3-difluoropyrrolidin-1-yl)-(2S)-pyrrolidinylmethoxy]cyclohexanecarboxylic acid ethyl ester NMR (CDCl₃) δ: 1.04-1.31 (total 5H, series of m, including 3H, t, J=7.2 Hz, δ 1.24), 1.41-1.49 (total 10H, series of m), 1.60-2.35 (total 6H, series of m), 2.65-4.36 (total 7H, series of m).
MS (ESI) m/z: 461 (M+1).

Trans-4-[(4S)-(3,3-difluoropyrrolidin-1-yl)-(2S)-pyrrolidinylmethoxy]cyclohexanecarboxylic acid ethyl ester dihydrochloride NMR (CDCl₃) δ: 1.06-1.56 (total 7H, series of m, including 3H, t, J=7.1 Hz, δ 1.24), 1.60-2.39 (total 6H, series of m), 3.11-2.46 (2H, m), 3.19-4.42 (total 13H, series of m, including 2H, q, J=7.1 Hz, δ 4.10), 4.51-4.88 (1H, m), 9.21-10.54 (total 2H, series of m).
MS (ESI) m/z: 361 (M$^+$+H-2HCl).

Trans-4-[1-[[4-[(benzo[b]thiophen-3-ylcarbonyl)amino]-5-chloro-2-fluorophenyl]acetyl]-(4S)-(3,3-difluoropyrrolidin-1-yl)-(2S)-pyrrolidinylmethoxy]cyclohexanecarboxylic acid ethyl ester NMR (CDCl$_3$) δ: 0.77-1.46 (total 7H, series of m), 1.48-4.47 (total 24H, series of m), 7.23-7.32 (1H, m), 7.34 (1H, t, J=8.1 Hz), 7.41 (1H, t, J=8.1 Hz), 7.81 (1H, d, J=8.1 Hz), 8.00-8.04 (1H, m), 8.27-8.33 (total 2H, m), 8.39 (1H, d, J=8.1 Hz).
MS (ESI) m/z: 706 [(M$^+$+1), $^{35}$Cl], 708 [(M$^+$+3), $^{37}$Cl].
IR (ATR) ν: 2937, 2862, 1724, 1676, 1641 cm$^{-1}$.
Anal. Calcd for C$_{35}$H$_{39}$ClF$_3$N$_3$O$_5$S·0.25H$_2$O: C, 59.15; H, 5.60; N, 5.91; S, 4.51.
Found: C, 59.20; H, 5.66; N, 5.75; S, 4.23.

Trans-4-[1-[[4-[(benzo[b]thiophen-3-ylcarbonyl)amino]-5-chloro-2-fluorophenyl]acetyl]-(4S)-(3,3-difluoropyrrolidin-1-yl)-(2S)-pyrrolidinylmethoxy]cyclohexanecarboxylic acid

[Formula 129]

NMR (DMSO-d$_6$) δ: 1.09-1.42 (total 5H, series of m), 1.72-2.04 (total 5H, series of m), 2.07-2.33 (total 4H, series of m), 2.66-3.74 (total 11H, series of m), 3.76-4.30 (2H, m), 7.44-7.59 (total 4H, series of m), 8.10 (1H, d, J=7.3 Hz), 8.43-8.47 (1H, m), 8.65 (1H, s), 10.11 (1H,s).
MS (ESI) m/z: 678 [(M$^+$+1), $^{35}$Cl], 680 [(M$^+$+3), $^{37}$Cl].
IR (ATR) ν: 2937, 2860, 1722, 1677, 1621 cm$^{-1}$.
Anal. Calcd for C$_{33}$H$_{35}$ClF$_3$N$_3$O$_5$S·1.25H$_2$O: C, 56.57; H, 5.39; N, 6.00; S, 4.47.
Found: C, 56.63; H, 5.33; N, 5.78.

Example 39

Trans-4-[(4S)-(5-azaspiro[2.4]heptan-5-yl)-1-[[4-[(benzo[b]thiophen-3-ylcarbonyl)amino]-5-chloro-2-fluorophenyl]acetyl]-(2S)-pyrrolidinylmethoxy]cyclohexanecarboxylic acid Trans-4-[(4S)-(5-azaspiro[2.4]heptan-5-yl)-1-(tert-butoxycarbonyl)-(2S)-pyrrolidinylmethoxy]cyclohexanecarboxylic acid ethyl ester NMR (CDCl$_3$) δ: 0.57 (4H, d, J=8.3 Hz), 1.26 (5H, t, J=7.0 Hz), 1.47 (11H, s), 1.76-2.11 (7H, m), 2.17-2.31 (2H, m), 2.46-2.66 (3H, m), 2.69-2.81 (2H, m), 3.08 (1H, t, J=9.8 Hz), 3.15-3.30 (1H, m), 4.01-3.32 (4H, m), 4.13 (2H, q, J=7.0 Hz).
MS (ESI) m/z: 451 (M$^+$+1)

Trans-4-[(4S)-(5-azaspiro[2.4]heptan-5-yl)-(2S)-pyrrolidinylmethoxy]cyclohexanecarboxylic acid ethyl ester NMR (CDCl$_3$) δ: 0.52-0.56 (4H, m), 1.08-1.54 (8H, m), 1.82 (1H, t, J=6.8 Hz), 1.94-2.35 (7H, m), 2.50 (2H, s), 2.65-2.93 (4H, m), 3.03 (1H, dd, J=10.4, 7.0 Hz), 3.12-3.79 (4H, m), 4.11 (2H, q, J=7.3 Hz).
MS (ESI) m/z: 351 (M$^+$+1).

Trans-4-[(4S)-(5-azaspiro[2.4]heptan-5-yl)-1-[[4-[(benzo[b]thiophen-3-ylcarbonyl)amino]-5-chloro-2-fluorophenyl]acetyl]-(2S)-pyrrolidinylmethoxy]cyclohexanecarboxylic acid ethyl ester NMR (CDCl$_3$) δ: 0.54-0.62 (4H, m), 1.11-1.31 (5H, m), 1.33-1.55 (2H, m), 1.68-2.12 (7H, m), 2.15-2.40 (2H, m), 2.46-2.85 (4H, m), 3.06-3.37 (2H, m), 3.44-3.91 (6H, m), 4.04-4.26 (3H, m), 7.41 (1H, d, J=7.1 Hz), 7.45 (1H, t, J=7.8 Hz), 7.51 (1H, tt, J=7.8, 1.0 Hz), 7.91 (1H, d, J=8.1 Hz), 8.10 (1H, dd, J=8.1, 0.7 Hz), 8.35 (0H, s), 8.37 (1H, s), 8.41 and 8.43 (total 1H, each d, J=11.7 and 11.5 Hz respectively, amide isomers), 8.48 (1H, d, J=8.3 Hz).
MS (ESI) m/z: 696 (M$^+$+1), 698 (M$^+$+3).

Trans-4-[(4S)-(5-azaspiro[2.4]heptan-5-yl)-1-[[4-[(benzo[b]thiophen-3-ylcarbonyl)amino]-5-chloro-2-fluorophenyl]acetyl]-(2S)-pyrrolidinylmethoxy]cyclohexanecarboxylic acid

[Formula 130]

NMR (DMSO-d$_6$) δ: 0.45-0.68 (4H, m), 1.09-1.44 (6H, m), 1.66-2.24 (8H, m), 2.54-2.97 (1H, m), 3.12-3.49 (5H, m), 3.53-4.14 (5H, m), 4.24-4.42 (1H, m), 7.42-7.62 (5H, m), 8.10 (1H, dd, J=6.8, 1.2 Hz), 8.42-8.47 (1H, m), 8.63 and 8.65 (total 1H, each s, amide isomers), 10.12 (1H, s).
MS (ESI) m/z: 668 (M$^+$+1), 670 (M$^+$+3)
IR (ATR) cm$^{-1}$: 2933, 2860, 1716, 1641, 1585, 1516.

Example 40

Trans-4-[1-[[4-[(benzo[b]thiophen-3-ylcarbonyl)amino]-5-chloro-2-fluorophenyl]acetyl]-(4S)-(2-methylpyrrolidin-1-yl)-(2S)-pyrrolidinylmethoxy]cyclohexanecarboxylic acid Trans-4-[1-(tert-butoxycarbonyl)-(4S)-(2-methylpyrrolidin-1-yl)-(2S)-pyrrolidinylmethoxy]cyclohexanecarboxylic acid ethyl ester NMR (CDCl$_3$) δ: 1.03-1.11 (4H, m), 1.24 (5H, t, J=7.1 Hz), 1.46 (9H, s), 1.72-2.54 (14H, m), 2.74-3.93 (8H, m), 4.11 (2H, q, J=7.1 Hz).
MS (ESI) m/z: 439 (M$^+$+H).

Trans-4-[1-[[4-[(benzo[b]thiophen-3-ylcarbonyl) amino]-5-chloro-2-fluorophenyl]acetyl]-(4S)-(2-methylpyrrolidin-1-yl)-(2S)-pyrrolidinylmethoxy]cyclohexanecarboxylic acid

[Formula 131]

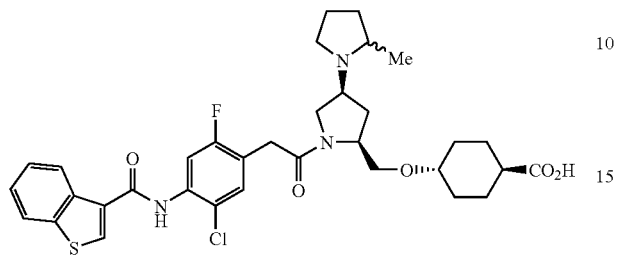

NMR (DMSO-d$_6$) δ: 0.84-1.40 (12H, m), 1.65-2.33 (9H, m), 2.74-4.32 (9H, m), 7.44-7.58 (4H, m), 8.10 (1H, d, J=8.0 Hz), 8.45 (1H, d, J=8.0 Hz), 8.66 (1H, s), 10.12 (1H, s).
IR (ATR) cm$^{-1}$: 3409, 3060, 2933, 2859, 1639, 1517, 1402.
MS (ESI) m/z: 656 (M$^+$+H), MS (FAB) m/z: 656 (M$^+$+H).
MS (FAB) m/z: 656.2360 (Calcd. for C$_{34}$H$_{40}$ClFN$_3$O$_5$S: 656.2361)
Anal. Calcd for C$_{34}$H$_{39}$ClFN$_3$O$_5$S.0.4HCl.0.2H$_2$O: C, 60.55; H, 5.95; Cl, 7.36; F, 2.82; N, 6.23; S, 4.35.
Found: C, 60.20; H, 5.85; Cl, 7.16; F, 2.81; N, 5.96; S, 4.61.

Example 41

Trans-4-[1-[[2,5-dichloro-4-[(1-methyl-1H-indol-3-ylcarbonyl)amino]phenyl]acetyl]-(4S)-[(2S)-trifluoromethylpyrrolidin-1-yl]-(2S)-pyrrolidinylmethoxy]cyclohexanecarboxylic acid Trans-4-[1-(tert-butoxycarbonyl)-(4S)-[(2S)-trifluoromethylpyrrolidin-1-yl]-(2S)-pyrrolidinylmethoxy]cyclohexane carboxylic acid ethyl ester NMR (CDCl$_3$) δ: 1.18-1.28 (3H, m), 1.25 (3H, t, J=7.1 Hz), 1.44 (9H, s), 1.77-2.07 (10H, m), 2.36-2.45 (3H, m), 2.80-3.37 (6H, m), 3.46-3.95 (2H, m), 4.11 (2H, q, J=7.1 Hz), 4.11-4.17 (1H, m).
MS (ESI) m/z: 493 (M$^+$+H).

Trans-4-[1-[[2,5-dichloro-4-[(1-methyl-1H-indol-3-ylcarbonyl)amino]phenyl]acetyl]-(4S)-[(2S)-trifluoromethylpyrrolidin-1-yl]-(2S)-pyrrolidinylmethoxy] cyclohexanecarboxylic acid

[Formula 132]

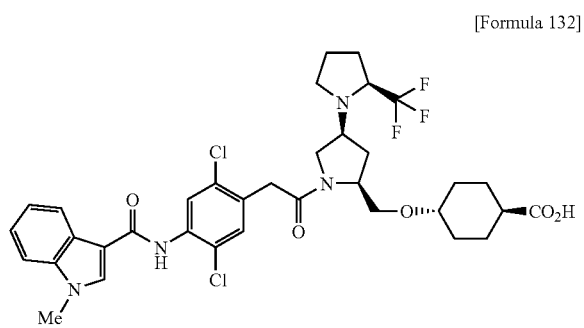

NMR (DMSO-d$_6$) δ: 1.07-1.40 (7H, m), 1.68-2.18 (12H, m), 2.83-4.34 (11H, m), 7.22 (1H, t, J=7.5 Hz), 7.28 (1H, dt, J=1.2, 7.5 Hz), 7.53 (1H, s), 7.56 (1H, d, J=8.1 Hz), 7.88-7.90 (1H, m), 8.15 (1H, d, J=7.8 Hz), 8.31 (1H, s), 9.39 (1H, s).
IR (ATR) cm$^{-1}$: 2935, 2863, 1500, 1375, 1099.
MS (ESI) m/z: 723 (M$^+$+1).
Anal. Calcd for C$_{35}$H$_{39}$Cl$_2$F$_3$N$_4$O$_5$.0.5H$_2$O: C, 57.38; H, 5.50; Cl, 9.68; F, 7.78; N, 7.65.
Found: C, 57.19; H, 5.61; Cl, 9.66; F, 7.46; N, 7.35.

Example 42

Trans-4-[1-[[4-[(benzo[b]thiophen-3-ylcarbonyl) amino]-5-chloro-2-fluorophenyl]acetyl]-]-(4S)-[(2S)-dimethylcarbamoylpyrrolidin-1-yl]-(2S)-pyrrolidinylmethoxy]cyclohexanecarboxylic acid Trans-4-[1-(tert-butoxycarbonyl)-(4S)-[(2S)-dimethylcarbamoylpyrrolidin-1-yl]-(2S)-pyrrolidinylmethoxy]cyclohexa necarboxylic acid ethyl ester NMR (CDCl$_3$) δ: 1.20-1.29 (3H, m), 1.24 (3H, t, J=7.0 Hz), 1.45 (9H, s), 1.61-2.33 (12H, m), 2.92-3.87 (10H, m), 2.98 (3H, s), 3.07 (3H, s), 4.11 (2H, q, J=7.1 Hz).
MS (ESI) m/z: 496 (M$^+$+1).

Trans-4-[1-[[4-[(benzo[b]thiophen-3-ylcarbonyl) amino]-5-chloro-2-fluorophenyl]acetyl]-]-(4S)-[(2S)-dimethylcarbamoylpyrrolidin-1-yl]-(2S)-pyrrolidinylmethoxy]cyclohexanecarboxylic acid

[Formula 133]

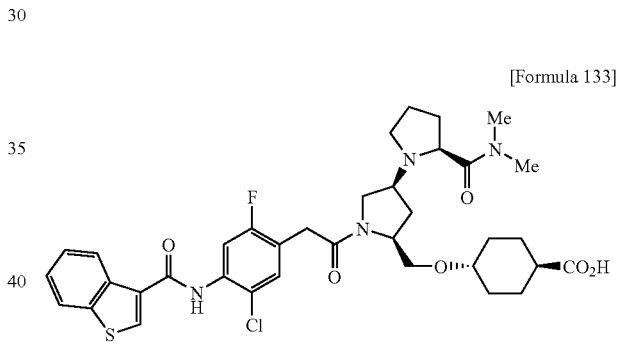

NMR (DMSO-d$_6$) δ: 1.09-1.40 (4H, m), 1.61-2.20 (11H, m), 2.48-4.29 (33H, m), 7.44-7.58 (4H, m), 8.10 (1H, d, J=8.0 Hz), 8.45 (1H, d, J=8.0 Hz), 8.66-8.68 (1H, m), 10.14 (1H, br s).
IR (ATR) cm$^{-1}$: 2933, 2859, 1631, 1517, 1402.
MS (ESI) m/z: 713 (M$^+$+H).
Anal. Calcd for C$_{36}$H$_{42}$ClFN$_4$O$_6$S.0.5HCl.2.5H$_2$O: C, 55.68; H, 6.17; Cl, 6.85; F, 2.45; N, 7.21; S, 4.13.
Found: C, 55.81; H, 5.67; Cl, 6.71; F, 2.39; N, 7.06; S, 4.31.

Example 43

Trans-4-[1-[[4-[(benzo[b]thiophen-3-ylcarbonyl) amino]-2,5-dichlorophenyl]acetyl]-(4S)-[(2S)-ethoxymethylpyrrolidin-1-yl]-(2S)-pyrrolidinylmethoxy]cyclohexanecarboxylic acid Trans-4-[1-(tert-butoxycarbonyl)-(4S)-[(2S)-ethoxymethylpyrrolidin-1-yl]-(2S)-pyrrolidinylmethoxy]cyclohexanecarboxylic acid ethyl ester NMR (CDCl$_3$) δ: 1.16-1.31 (4H, m), 1.19 (3H, t, J=7.1 Hz), 1.24 (3H, t, J=7.4 Hz), 1.36 (9H, s), 1.59-2.47 (15H, m), 2.89-3.86 (11H, m), 4.11 (2H, q, J=7.2 Hz).

Trans-4-[1-[[4-[(benzo[b]thiophen-3-ylcarbonyl)amino]-2,5-dichlorophenyl]acetyl]-(4S)-[(2S)-ethoxymethylpyrrolidin-1-yl]-(2S)-pyrrolidinylmethoxy]cyclohexanecarboxylic acid

[Formula 134]

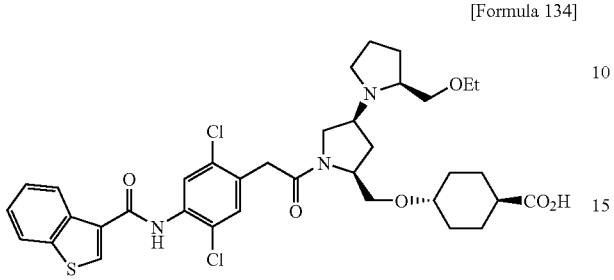

NMR (DMSO-$d_6$) δ: 0.84-4.26 (34H, m), 7.43-7.52 (2H, m), 7.53 (1H, s), 7.76 (1H, d, J=6.1 Hz), 8.10 (1H, dd, J=7.0, 1.6 Hz), 8.45 (1H, dd, J=6.7, 1.3 Hz), 8.65 (1H, s), 10.16 (1H, s), 12.06 (1H, br s).
IR (ATR) cm$^{-1}$: 2933, 2861, 1637, 1504, 1079.
MS (ESI) m/z: 716 (M$^+$+1).
Anal. Calcd for $C_{36}H_{43}Cl_2N_3OyS \cdot 0.2H_2O$: C, 60.03; H, 6.07; Cl, 9.84; N, 5.83; S, 4.45.
Found: C, 59.91; H, 6.17; Cl, 9.36; N, 5.61; S, 4.40.

Example 44

Trans-4-[1-[[4-[(benzo[b]thiophen-3-ylcarbonyl)amino]-5-chloro-2-fluorophenyl]acetyl]-(4S)-[(2R)-methoxymethylpyrrolidin-1-yl]-(2S)-pyrrolidinylmethoxy]cyclohexanecarboxylic acid Trans-4-[1-(tert-butoxycarbonyl)-(4S)-[(2R)-methoxymethylpyrrolidin-1-yl]-(2S)-pyrrolidinylmethoxy]cyclohexanecarboxylic acid ethyl ester NMR (CDCl$_3$) δ: 1.14-1.53 (5H, m), 1.24 (3H, t, J=7.2 Hz), 1.46 (9H, s), 1.67-2.55 (10H, m), 2.84-3.88 (15H, m), 4.11 (2H, q, J=7.1 Hz).
MS (ESI) m/z: 469 (M$^+$+H).

Trans-4-[1-[[4-[(benzo[b]thiophen-3-ylcarbonyl)amino]-5-chloro-2-fluorophenyl]acetyl]-(4S)-[(2R)-methoxymethylpyrrolidin-1-yl]-(2S)-pyrrolidinylmethoxy]cyclohexanecarboxylic acid

[Formula 135]

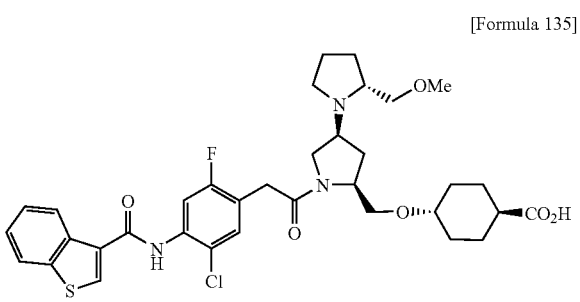

NMR (DMSO-$d_6$) δ: 1.07-1.43 (4H, m), 1.54-2.50 (13H, m), 2.83-4.28 (9H, m), 7.44-7.59 (4H, m), 8.10 (1H, d, J=7.8 Hz), 8.45 (1H, d, J=7.6 Hz), 8.66-8.70 (1H, m), 10.13 (1H, br).
IR (ATR) cm$^{-1}$: 3415, 3064, 2931, 2859, 1637, 1517, 1402.
MS (ESI) m/z: 686 (M$^+$+H).
Anal. Calcd for $C_{34}H_{40}ClFN_4O_5S \cdot 0.3HCl \cdot 1.5H_2O$: C, 58.05; H, 6.17; Cl, 6.36; F, 2.62; N, 5.80; S, 4.43.
Found: C, 58.07; H, 6.02; Cl, 6.27; F, 2.51; N, 5.50; S, 4.18.

Example 45

Trans-4-[1-[[2,5-dichloro-4-[(1-methyl-1H-indol-3-ylcarbonyl)amino]phenyl]acetyl]-(4S)-[(4S)-fluoro-(2S)-methoxymethylpyrrolidin-1-yl]-(2S)-pyrrolidinylmethoxy]cyclohexane carboxylic acid 1-(Tert-butoxycarbonyl)-(4S)-fluoro-(2S)-methoxymethylpyrrolidine 1-(Tert-butoxycarbonyl)-(4S)-fluoro-(2S)-hydroxymethylpyrrolidine (2.01 g, 9.18 mmol) was introduced to a 100-mL pear-shaped flask, and N,N-dimethyl formamide (10 mL) was added to dissolve the compound. Then, methyl iodide (857 μl, 13.8 mmol) was added, and while stirring the mixture under ice cooling, sodium hydride (55%) (801 mg, 18.3 mmol) was added thereto. The mixture was stirred for 1.5 hours at room temperature. Water (80 mL) was added to the reaction liquor, and the mixture was extracted with toluene (80 mL×2). The combined organic layer was washed with saturated brine (60 mL), and then dried over anhydrous sodium sulfate. After filtering, the filtrate was concentrated under reduced pressure, and the obtained concentrated residue was subjected to column chromatography using silica gel. The fraction obtained from an elution with n-hexane-ethyl acetate (4:1, v/v) was concentrated under reduced pressure, and dried to obtain the title compound (2.00 g, 8.59 mmol, 94%) as an oily matter.
NMR (CDCl$_3$) δ: 1.47 (9H, s), 1.98-2.17 (1H, m), 2.39 (1H, dd, J=20.3, 15.0 Hz), 3.31 (1H, ddd, J=9.8, 8.6, 1.5 Hz), 3.37 (3H, s), 3.53-3.73 (total 3H, series of m), 4.02-4.15 (1H, m), 5.13-5.29 (1H, m).

(4S)-fluoro-(2S)-methoxymethylpyrrolidine hydrochloride 1-(Tert-butoxycarbonyl)-(4S)-fluoro-(2S)-methoxymethylpyrrolidine (2.00 g, 8.59 mmol) was introduced to a 100-mL pear-shaped flask, and 4N-hydrochloric acid/1,4-dioxane (10.0 mL, 40.0 mmol) was added thereto. The mixture was stirred for 3.5 hours at room temperature. The reaction liquor was concentrated under reduced pressure, and then dried under reduced pressure, to obtain the title compound (1.46 g, quant.) as a solid.
NMR (DMSO-$d_6$) δ: 2.20 (1H, dd, J=21.7, 15.4 Hz), 2.57-2.40 (1H, m), 3.45 (3H, s), 3.54-3.90 (total 4H, series of m), 4.07-4.16 (1H, m), 5.30-5.47 (1H, m), 9.51 (1H, br s), 10.51 (1H, br s).

Trans-4-[1-(tert-butoxycarbonyl)-(4S)-[(4S)-fluoro-(2S)-methoxymethylpyrrolidin-1-yl]-(2S)-pyrrolidinylmethoxy]cyclohexanecarboxylic acid ethyl ester NMR (CDCl$_3$) δ: 1.21-1.28 (total 5H, seDMSO-$d_6$ries of m, including 2H, q, J=7.2 Hz, 51.25), 1.38-1.50 (total 11H, series of m), 1.87-2.33 (total 9H, series of m), 2.66-2.75 (1H, m), 2.93-3.37 (total 9H, series of m, including 3H, s, δ 3.36), 3.45-3.92 (total 5H, series of m), 4.11 (2H, q, J=7.2 Hz), 5.05-5.21 (1H, m).
MS (ESI) m/z: 486 (M$^+$+1).

Trans-4-[(4S)-[(4S)-fluoro-(2S)-methoxymethylpyr-rolidin-1-yl]-(2S)-pyrrolidinylmethoxy]cyclohexan-ecarboxylic acid ethyl ester dihydrochloride NMR (CDCl₃) δ: 0.88-1.55 (total 7H, series of m, including 3H, t, J=7.1 Hz, δ 1.24), 1.96-2.29 (total 5H, series of m), 2.58-3.08 (2H, m), 3.33-3.58 (total 5H, series of m), 3.70 (3H, s), 3.71-4.43 (total 8H, series of m, including 2H, q, J=7.1 Hz, δ 4.12), 4.71-4.89 (2H, m), 5.41-5.61 (1H, m), 9.45 (1H, br s), 10.23 (1H, br s), 11.41 (1H, br s).
MS (ESI) m/z: 387 (M⁺−2HCl).

Trans-4-[1-[[2,5-dichloro-4-[(1-methyl-1H-indol-3-ylcarbonyl)amino]phenyl]acetyl]-(4S)-[(4S)-fluoro-(2S)-methoxymethylpyrrolidin-1-yl]-(2S)-pyrrolidi-nylmethoxy]cyclohexane carboxylic acid ethyl ester NMR (CDCl₃) δ: 1.17-1.52 (total 7H, m, including 3H, t, J=7.1 Hz, δ 1.22), 1.76-2.46 (total 10H, series of m), 2.63-2.82 (1H, m), 3.00-3.36 (total 8H, series of m), 3.44-3.97 (total 9H, series of m), 4.06-4.28 (total 3H, series of m, including 2H, q, J=7.1 Hz, δ 4.09), 5.04-5.24 (1H, m), 7.30-7.41 (total 4H, series of m), 7.77 and 7.78 (total 1H, each s, amide isomers), 8.10-8.15 (1H, m), 8.20 and 8.22 (total 1H, each s, amide isomers), 8.74 and 8.76 (total 1H, each s, amide isomers).
MS (ESI) m/z: 745 [(M⁺+1), ³⁵Cl], 747 [(M⁺+3), ³⁷Cl].
IR (ATR) ν: 2937, 2864, 1726, 1641 cm⁻¹.
Anal. Calcd for C₃₈H₄₇Cl₂FN₄O₆·H₂O: C, 59.76; H, 6.47; N, 7.34.
Found: C, 59.53; H, 6.39; N, 7.32.

Trans-4-[1-[[2,5-dichloro-4-[(1-methyl-1H-indol-3-ylcarbonyl)amino]phenyl]acetyl]-(4S)-[(4S)-fluoro-(2S)-methoxymethylpyrrolidin-1-yl]-(2S)-pyrrolidi-nylmethoxy]cyclohexane carboxylic acid

[Formula 136]

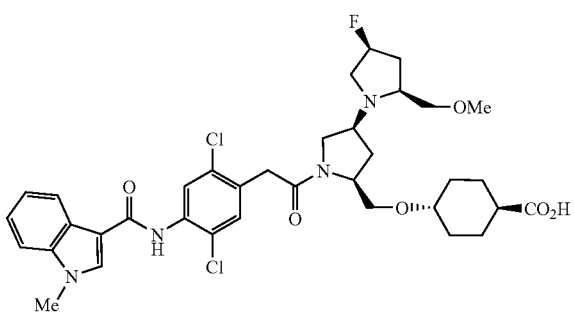

NMR (CDCl₃) δ: 1.14-1.53 (total 4H, series of m), 1.76-2.45 (total 9H, series of m), 2.72 and 2.78 (total 1H, ddd, J=34.1, 11.3, 3.7 Hz), 3.04-3.95 (total 18H, series of m), 4.13-4.32 (1H, m), 5.04-5.22 (1H, m), 7.03 (1H, br s), 7.28-7.37 (total 4H, series of m), 7.75 (1H, s), 8.07-8.12 (1H, m), 8.18 and 8.20 (total 1H, each s, amide isomers), 8.69 and 8.72 (total 1H, each s, amide isomers).
MS (ESI) m/z: 717 [(M⁺+1), ³⁵Cl], 719 [(M⁺+1), ³⁷Cl].
IR (ATR) ν: 2933, 2864, 1724, 1641 cm⁻¹.
Anal. Calcd for C₃₆H₄₃Cl₂FN₄O₆·0.25H₂O: C, 59.87; H, 6.07; N, 7.76.
Found: C, 60.05; H, 6.40; N, 7.40.

Example 46

Trans-4-[1-[[2,5-dichloro-4-[(1-methyl-1H-indol-3-ylcarbonyl)amino]phenyl]acetyl]-(4S)-[(2S)-meth-oxymethyl-(4S)-methoxypyrrolidin-1-yl]-(2S)-pyrro-lidinylmethoxy]cyclohexanecarboxylic acid 1-Benzyloxycarbonyl-(2S)-hydroxymethyl-(4S)-hydroxypyrrolidine 1-Benzyloxycarbonyl-cis-4-hydroxy-L-proline (10.03 g, mmol) was introduced to a 200-mL pear-shaped flask, and while stirring the content under ice cooling, tetrahydrofuran (60 mL) was added to dissolve the compound. Then, a borane-dimethyl sulfide complex (2.0 M tetrahydrofuran solution) (37.8 mL, 75.6 mmol) was slowly added, and then the mixture was stirred for 2.5 hours at room temperature. The reaction solution was concentrated under reduced pressure, and poured onto ice water, and the mixture was extracted with ethyl acetate (200 mL×2). The combined organic layer was washed with saturated brine (200 mL), and then dried over anhydrous sodium sulfate. After filtering, the filtrate was concentrated under reduced pressure, to obtain the title compound (9.93 g, q.y.) as an oily matter.

1-Benzyloxycarbonyl-(2S)-methoxymethyl-(4S)-methoxypyrrolidine

1-Benzyloxycarbonyl-(2S)-hydroxymethyl-(4S)-hy-droxypyrrolidine (9.43 g, 37.8 mmol) was introduced into a 200-mL pear-shaped flask, and N,N-dimethylformamide (80 mL) was added to dissolve the compound. Then, methyl iodide (1.18 mL, 189 mmol) was added thereto, and while stirring the mixture under ice cooling, sodium hydride (purity 55%) (2.59 g, 75.6 mmol) was slowly added. The mixture was stirred for 18 hours at room temperature. The reaction liquor was poured onto ice water, the mixture was extracted with ethyl acetate (250 mL×2), and the combined organic layer was dried over anhydrous sodium sulfate. The insoluble was separated by filtration, and then the filtrate was concentrated under reduced pressure. The obtained concentrated residue was subjected to column chromatography using silica gel, and the fraction obtained from an elution with n-hexane:ethyl acetate (2:1→1:1, v/v) was concentrated under reduced pressure and dried, to obtain the title compound (8.95 g, 19.5 mmol, 85%) as a solid.
NMR (CDCl₃) δ: 1.95-2.03 (1H, m), 2.14-2.19 (1H, m), 3.27-3.46 (total 7H, series of m, including 3H, s, δ 3.28), 3.53-3.70 (total 2H, m), 3.88-3.93 (1H, m), 3.99-4.09 (1H, m), 5.05-5.16 (2H, m), 7.27-7.36 (total 5H, series of m).
MS (ESI) m/z: 280 (M⁺+1).

Trans-4-[1-(tert-butoxycarbonyl)-(4S)-[(2S)-meth-oxymethyl-(4S)-methoxypyrrolidin-1-yl]-(2S)-pyrro-lidinylmethoxy]cyclohexanecarboxylic acid ethyl ester NMR (CDCl₃) δ: 1.19-1.24 (total 5H, series of m, including 3H, t, J=7.2 Hz, δ 1.21), 1.37-1.52 (1H, series of m, including 9H, s, δ 1.42), 1.74-2.26 (total 10H, series of m), 2.60 (1H, s), 2.88 (1H, s), 2.98-3.33 (total 10H, series of m, including each 3H, each s, δ 3.26 and 3.32), 3.40-3.83 (total 6H, series of m), 4.08 (2H, q, J=7.1 Hz).
MS (ESI) m/z: 499 (M⁺+1).

Trans-4-[(4S)-[(2S)-methoxymethyl-(4S)-methoxypyrrolidin-1-yl]-(2S)-pyrrolidinylmethoxy]cyclohexanecarboxylic acid ethyl ester dihydrochloride NMR (CDCl$_3$) δ: 1.21-1.55 (total 7H, series of m), 1.95-2.29 (total 7H, series of m), 2.61-2.80 (total 3H, series of m), 3.30-4.21 (total 19H, series of m), 4.68 (1H, br s), 9.62 (1H, br s), 10.46 (1H, br s), 11.23 (1H, br s).
MS (ESI) m/z: 399 (M$^+$+1-2HCl).

Trans-4-[1-[[2,5-dichloro-4-[(1-methyl-1H-indol-3-ylcarbonyl)amino]phenyl]acetyl]-(4S)-[(2S)-methoxymethyl-(4S)-methoxypyrrolidin-1-yl]-(2S)-pyrrolidinylmethoxy]cyclohexanecarboxylic acid ethyl ester NMR (CDCl$_3$) δ: 1.17-1.27 (total 5H, series of m, including 3H, t, J=7.1 Hz, δ 1.22), 1.36-1.54 (2H, m), 1.71-2.43 (total 10H, series of m), 2.62 and 2.68 (total 1H, each dd, each J=10.0, 5.1 Hz, amide isomers), 2.91-3.95 (total 20H, series of m), 4.03-4.31 (3H, series of m, including 2H, q, J=7.1 Hz, δ 4.09), 7.09-7.40 (total 5H, series of m), 7.70-7.78 (1H, m), 8.09-8.22 (2H, m), 8.71-8.77 (1H, m).
MS (ESI) m/z: 757 [(M$^+$+1), $^{35}$Cl], 759 [(M$^+$+3), $^{37}$Cl].
IR (ATR) ν: 2933, 2864, 2821, 1724, 1641 cm$^{-1}$.
Anal. Calcd for C$_{39}$H$_{50}$Cl$_2$N$_4$O$_7$·0.25H$_2$O: C, 61.45; H, 6.68; N, 7.35; Cl, 9.30.
Found: C, 61.34; H, 6.62; N, 7.13; Cl, 9.17.
Anal. Calcd for C$_{38}$H$_{47}$Cl$_2$N$_3$O$_8$·0.75H$_2$O: C, 60.20; H, 6.45; N, 5.54; Cl, 9.35.
Found: C, 60.33; H, 6.33; N, 5.40; Cl, 9.72.

Trans-4-[1-[[2,5-dichloro-4-[(1-methyl-1H-indol-3-ylcarbonyl)amino]phenyl]acetyl]-(4S)-[(2S)-methoxymethyl-(4S)-methoxypyrrolidin-1-yl]-(2S)-pyrrolidinylmethoxy]cyclohexanecarboxylic acid

[Formula 137]

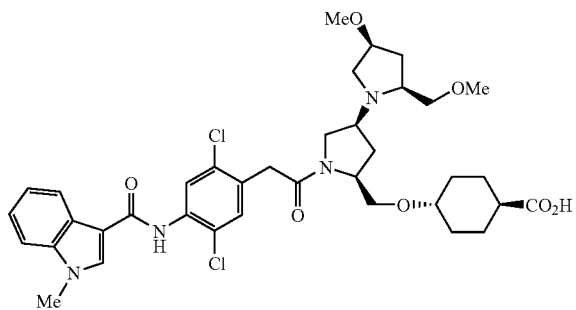

NMR (CDCl$_3$) δ: 1.14-1.30 (2H, m), 1.44 (2H, q, J=11.5 Hz), 1.75-2.45 (total 9H, series of m), 2.67 and 2.73 (total 1H, each dd, each J=10.3, 5.5 Hz, amide isomers), 2.96-3.36 (total 12H, series of m), 3.45-3.96 (total 10H, series of m), 4.14-4.34 (1H, m), 6.73 (1H, brs), 7.30-7.41 (total 4H, series of m), 7.78 (1H, s), 8.09-8.14 (1H, m), 8.22 and 8.23 (total 1H, each s, amide isomers), 8.74 and 8.76 (total 1H, each s, amide isomers)
MS (ESI) m/z: 729 [(M$^+$+1), $^{35}$Cl], 731 [(M$^+$+3), $^{37}$Cl].
IR (ATR) ν: 2931, 2862, 2825, 1720, 1643 cm$^{-1}$.
Anal. Calcd for C$_{37}$H$_{46}$Cl$_2$N$_4$O$_7$·0.75H$_2$O: C, 59.80; H, 6.44; N, 7.54; Cl, 9.54.
Found: C, 59.89; H, 6.38; N, 7.50; Cl, 9.57.

Example 47

Trans-4-[1-[[4-[(benzo[b]furan-3-ylcarbonyl)amino]-5-chloro-2-fluorophenyl]acetyl]-(4S)-[(2R,5R)-dimethylpyrrolidin-1-yl]-(2S)-pyrrolidinylmethoxy]cyclohexanecarboxylic acid Trans-4-[1-(tert-butoxycarbonyl)-(4S)-[(2R,5R)-dimethylpyrrolidin-1-yl]-(2S)-pyrrolidinylmethoxy]cyclohexanecarboxylic acid ethyl ester MS (ESI) m/z: 453 (M$^+$+1).

Trans-4-[(4S)-[(2R,5R)-dimethylpyrrolidin-1-yl]-(2S)-pyrrolidinylmethoxy]cyclohexanecarboxylic acid ethyl ester MS (ESI) m/z: 353 (M$^+$+1).

Trans-4-[1-[[4-[(benzo[b]furan-3-ylcarbonyl)amino]-5-chloro-2-fluorophenyl]acetyl]-(4S)-[(2R,5R)-dimethylpyrrolidin-1-yl]-(2S)-pyrrolidinylmethoxy]cyclohexanecarboxylic acid ethyl ester NMR (CDCl$_3$) δ: 0.96-1.54 (17H, m), 1.69-2.65 (8H, m), 2.85-3.94 (9H, m), 3.98-4.48 (3H, m), 7.40-7.47 (3H, m), 7.56-7.64 (1H, m), 8.03-8.10 (1H, m), 8.26-8.34 (2H, m), 8.39-8.48 (1H, m).
MS (ESI) m/z: 682 (M$^+$+1), 684 (M$^+$+3).

Trans-4-[1-[[4-[(benzo[b]furan-3-ylcarbonyl)amino]-5-chloro-2-fluorophenyl]acetyl]-(4S)-[(2R,5R)-dimethylpyrrolidin-1-yl]-(2S)-pyrrolidinylmethoxy]cyclohexanecarboxylic acid

[Formula 138]

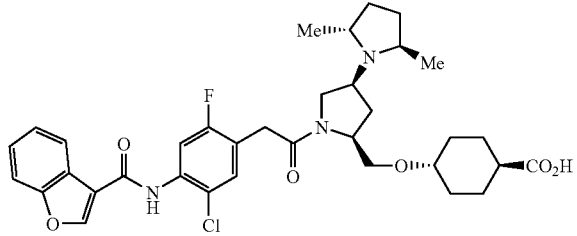

NMR (CDCl$_3$) δ: 1.06-1.60 (14H, m), 1.75-2.56 (8H, m), 3.68-3.69 (11H, m), 7.39-7.45 (3H, m), 7.56-7.62 (1H, m), 8.01-8.07 (1H, m), 8.26-8.33 (2H, m), 8.40 (1H, d, J=11.8 Hz), 8.42 (0H, dd, J=11.8, 1.5 Hz).
MS (ESI) m/z: 654 (M$^+$+1), 656 (M$^+$+3).
IR (ATR) cm$^{-1}$: 2935, 2860, 1676, 1587, 1558, 1522, 1448.
Anal. Calcd for C$_{34}$H$_{41}$ClFN$_3$O$_6$·2H$_2$O: C, 60.91; H, 6.57; Cl, 5.14; F, 2.75; N, 6.09.
Found: C, 61.12; H, 6.29; Cl, 5.36; F, 2.60; N, 5.66.

Example 48

Trans-4-[1-[[5-chloro-2-fluoro-4-[(1-methyl-1H-indol-3-ylcarbonyl)amino]phenyl]acetyl]-(4S)-[cis-2,5-bis(methoxymethyl)-1-pyrrolidinyl]-(2S)-pyrrolidinylmethoxy]cyclohexanecarboxylic acid Trans-4-[1-(tert-butoxycarbonyl)-(4S)-[cis-2,5-bis(methoxymethyl)pyrrolidin-1-yl]-(2S)-pyrrolidinylmethoxy]cyclohexanecarboxylic acid ethyl ester NMR (CDCl$_3$) δ: 1.19-1.30 (5H, m), 1.39-1.59 (11H, m), 1.53-1.72 (2H, m), 1.73-1.89 (3H, m), 1.93-2.10 (4H, m), 2.30-2.12 (2H, m), 2.95 (1H, t, J=10.3 Hz), 3.92-3.02 (18H, m), 4.11 (2H, q, J=7.2 Hz).
MS (ESI) m/z: 513 (M$^+$+1).

Trans-4-[1-[[5-chloro-2-fluoro-4-[(1-methyl-1H-indol-3-ylcarbonyl)amino]phenyl]acetyl]-(4S)-[cis-2,5-bis(methoxymethyl)pyrrolidin-1-yl]-(2S)-pyrrolidinylmethoxy]cyclohexanecarboxylic acid ethyl ester NMR (CDCl$_3$) δ: 1.11-1.32 (5H, m), 1.34-1.52 (2H, m), 1.55-1.71 (2H, m), 1.75-2.09 (7H, m), 2.15-2.28 (2H, m), 3.05-3.30 (8H, m), 3.33 (6H, d, J=5.1 Hz), 3.46-3.84 (6H, m), 3.89 (3H, s), 4.04-4.26 (3H, m), 7.45-7.33 (4H, m), 7.82 (1H, d, J=4.9 Hz), 8.17-8.12 (1H, m), 8.30 (1H, s), 8.52 (1H, d, J=12.0 Hz).
MS (ESI) m/z: 755 (M$^+$+1), 757 (M$^+$+3).

Trans-4-[1-[[5-chloro-2-fluoro-4-[(1-methyl-1H-indol-3-ylcarbonyl)amino]phenyl]acetyl]-(4S)-[cis-2,5-bis(methoxymethyl)pyrrolidin-1-yl]-(2S)-pyrrolidinylmethoxy]cyclohexanecarboxylic acid

[Formula 139]

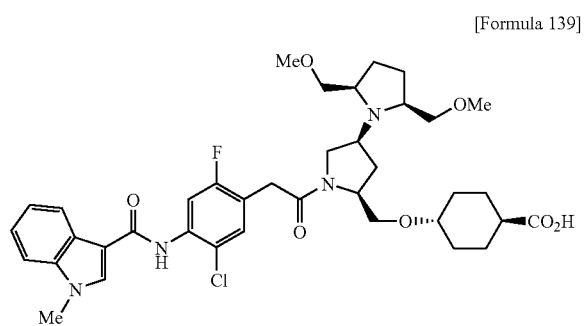

NMR (CDCl$_3$) δ: 1.07-1.35 (3H, m), 1.35-1.55 (2H, m), 1.57-1.74 (2H, m), 1.75-2.10 (6H, m), 2.13-2.43 (2H, m), 3.07-3.37 (14H, m), 3.46-3.85 (6H, m), 3.88 (3H, s), 4.10-4.30 (1H, m), 7.32-7.37 (2H, m), 7.38-7.44 (2H, m), 7.81 (1H, s), 8.10-8.16 (1H, m), 8.30 (1H, s), 8.53-8.46 (1H, m).
MS (ESI) m/z: 727 (M$^+$+1), 729 (M$^+$+3).
Anal. Calcd for C$_{38}$H$_{48}$ClFN$_4$O$_7$·0.25H$_2$O: C, 62.37; H, 6.68; N, 7.66; Cl, 4.84; F, 2.60.
Found: C, 62.07; H, 6.84; N, 7.33; Cl, 4.81; F, 2.64.

Example 49

Trans-4-[1-[[4-[(benzo[b]thiophen-3-ylcarbonyl)amino]-5-chloro-2-fluorophenyl]acetyl]-(4S)-[(2R,5R)-bis(methoxymethyl)pyrrolidin-1-yl]]-(2S)-pyrrolidinylmethoxy]cyclohexanecarboxylic acid Trans-4-[1-(tert-butoxycarbonyl)-(4S)-[(2R,5R)-bis(methoxymethyl)pyrrolidinyl]-(2S)-pyrrolidinylmethoxy]cyclohexanecarboxylic acid ethyl ester NMR (CDCl$_3$) δ: 1.18-1.25 (total 6H, series of m, including 3H, t, J=7.2 Hz, δ 1.21), 1.39-1.44 (total 11H, series of m), 1.68-1.74 (total 3H, series of m), 1.83-2.05 (total 6H, series of m), 2.16-2.43 (2H, m), 2.98-3.20 (total 6H, series of m), 3.27-3.86 (total 12H, series of m), 4.08 (2H, q, J=7.2 Hz).
MS (ESI) m/z: 513 (M$^+$+1).

Trans-4-[(4S)-[(2R,5R)-bis(methoxymethyl)pyrrolidin-1-yl]-(2S)-pyrrolidinylmethoxy]cyclohexanecarboxylic acid ethyl ester dihydrochloride NMR (CDCl$_3$) δ: 1.10-1.41 (total 7H, series of m, including 3H, t, J=7.1 Hz, δ 1.30), 1.72-2.44 (total 9H, series of m), 2.69-2.77 (1H, m), 3.31 (6H, s), 3.49-3.54 (2H, m), 3.59 (2H, s), 3.65-3.90 (total 8H, series of m), 3.96-4.38 (total 4H, series of m, including 2H, q, J=7.1 Hz, δ 3.98), 9.31 (1H, br s), 10.39 (1H, br s), 11.81 (1H, br s).
MS (ESI) m/z: 413 (M$^+$+1-2HCl).

Trans-4-[1-[[4-[(benzo[b]thiophen-3-ylcarbonyl)amino]-5-chloro-2-fluorophenyl]acetyl]-(4S)-[(2R,5R)-bis(methoxymethyl)pyrrolidin-1-yl]]-(2S)-pyrrolidinylmethoxy]cyclohexanecarboxylic acid ethyl ester NMR (CDCl$_3$) δ: 1.02-1.19 (total 5H, series of m, including 3H, t, J=7.1 Hz, δ1.12), 1.25-1.43 (2H, m), 1.57-1.73 (2H, m), 1.80-1.99 (total 7H, series of m), 2.05-2.50 (2H, m), 2.98-3.28 (total 14H, series of m), 3.40-3.76 (total 5H, series of m), 3.95-4.26 (total 3H, m, including 2H, q, J=7.1 Hz, δ 3.98), 7.28-7.36 (2H, m), 7.40 (1H, tt, J=8.0, 1.2 Hz), 7.80 (1H, d, J=8 and 8.04 (total 1H, each s, amide isomers), 8.26-8.33 (2H, m), 8.39 (1H, d, J=8.1 Hz).
MS (ESI) m/z: 758 [(M$^+$+1), $^{35}$Cl], 760 [(M$^+$+3), $^{37}$Cl].
IR (ATR) ν: 2935, 2868, 1724, 1676, 1637 cm$^{-1}$.

Trans-4-[1-[[4-[(benzo[b]thiophen-3-ylcarbonyl)amino]-5-chloro-2-fluorophenyl]acetyl]-(4S)-[(2R,5R)-bis(methoxymethyl)pyrrolidin-1-yl]]-(2S)-pyrrolidinylmethoxy]cyclohexanecarboxylic acid

[Formula 140]

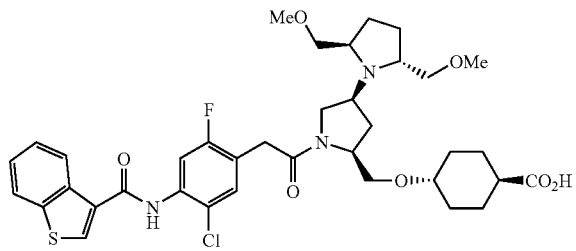

NMR (CDCl$_3$) δ: 1.11-1.24 (2H, m), 1.35-1.47 (2H, m), 1.64-1.79 (3H, m), 1.89-2.05 (total 7H, series of m), 2.17-2.57 (2H, m), 3.11-3.84 (total 19H, series of m), 4.06-4.28 (2H, m), 7.37-7.51 (3H, m), 7.88 (1H, d, J=7.8 Hz), 8.07 and 8.08 (total 1H, each s, amide isomers), 8.31 and 8.33 (total 1H, each s, amide isomers), 8.37-8.46 (2H, m).

MS (ESI) m/z: 730 [(M$^+$+1), $^{35}$Cl], 732 [(M$^+$+3), $^{37}$Cl].

IR (ATR) ν: 2929, 2864, 1720, 1676, 1622 cm$^{-1}$.

Example 50

Trans-4-[1-[[5-chloro-2-fluoro-4-[(1-methyl-1H-indol-3-ylcarbonyl)amino]phenyl]acetyl]-(4S)-[(3S)-methoxy-(2R)-methoxymethylpyrrolidin-1-yl]-(2S)-pyrrolidinylmethoxy]cyclohexanecarboxylic acid

1-(Tert-butoxycarbonyl)-(3S)-methoxyproline methyl ester 1-(Tert-butoxycarbonyl)-(3S)-hydroxyproline methyl ester (1.97 g, 8.03 mmol) was dissolved in N,N-dimethylformamide (25 mL), and iodomethane (1.00 mL, 16.06 mmol) was added thereto. The mixture was cooled to 0° C. Sodium hydride (55% oily, 0.53 g, 12.05 mmol) was added to the reaction solution with stirring, and the mixture was slowly allowed to warm to room temperature, and stirred for 18 hours. Water was added to the reaction liquor, and the mixture was extracted with ethyl acetate. The extract was washed with saturated brine, and dried over anhydrous sodium sulfate, and then the solvent was concentrated under reduced pressure. The obtained residue was purified by flash column chromatography (Flash Chromatography System from Biotage AB, column size: 40S, elution solvent n-hexane:ethyl acetate=9:1 to 3:1), to obtain the title compound (2.00 g, 966) as an oily matter.

NMR (CDCl$_3$) δ: 1.41 and 1.46 (total 9H, each s), 1.96-2.10 (2H, m), 3.38 (3H, s), 3.41-3.68 (2H, m), 3.74 and 3.75 (total 3H, each s), 3.88-3.91 (1H, m), 4.26 and 4.42 (total 1H, each s).

1-(Tert-butoxycarbonyl)-(3S)-methoxy-(2R)-pyrrolidine methanol 1-(Tert-butoxycarbonyl)-(3S)-methoxyproline methyl ester (2.00 g, 7.71 mmol) was dissolved in toluene (30 mL), and sodium borohydride (0.73 g, 19.28 mmol) was added thereto at 0° C. while stirring. Methanol (3.71 mL, 115.70 mmol) was added dropwise to the reaction liquor at 0° C., and the mixture was stirred for 18 hours while heating to room temperature. Water was added to the reaction liquor, and the mixture was extracted with ethyl acetate. The extract was washed with saturated brine, and dried over anhydrous sodium sulfate, and then the solvent was concentrated under reduced pressure. The obtained residue was purified by flash column chromatography (Flash Chromatography System from Biotage AB, column size: 40S, elution solvent n-hexane:ethylacetate=4:1 to 1:1), to obtain the title compound (1.76 g, 99%) as an oily matter.

NMR (CDCl$_3$) δ: 1.47 (9H, s), 1.95 (2H, broad s), 3.31-3.93 (total 9H, series of m, including 3H, s, at δ 3.34).

MS (ESI) m/z: 254 (M$^+$+Na).

1-(Tert-butoxycarbonyl)-(3S)-methoxy-(2R)-methoxymethylpyrrolidine 1-(Tert-butoxycarbonyl)-(3S)-methoxy-(2R)-pyrrolidine methanol (1.76 g, 7.61 mmol) and iodomethane (0.95 mL, 15.22 mmol) were dissolved in N,N-dimethylformamide (20 mL), and sodium hydride (0.50 g, 11.41 mmol, 55% oily) was added thereto at 0° C. while stirring. The mixture was allowed to warm to room temperature, and stirred for 16 hours. Water was added to the reaction liquor, and the mixture was extracted with ethyl acetate. The extract was washed with saturated brine, and dried over anhydrous sodium sulfate, and then the solvent was concentrated under reduced pressure. The obtained residue was purified by flash column chromatography (Flash Chromatography System from Biotage AB, column size: 40M, elution solvent: n-hexane:ethyl acetate=9:1 to 3:1), to obtain the title compound (1.65 g, 88%) as an oily matter.

NMR (CDCl$_3$) δ: 1.46 (9H, s), 1.96 (2H, broad s), 3.15-3.55 (total 10H, series of m, including 3H, s, at δ 3.33, and including 3H, s, at δ 3.36), 3.85 and 3.96 (total 2H, each broad s).

MS (ESI) m/z: 268 (M$^+$+Na), 146 (M$^+$+1-Boc).

Trans-4-[1-(tert-butoxycarbonyl)-(4S)-[(3S)-methoxy-(2R)-methoxymethylpyrrolidin-1-yl]-(2S)-pyrrolidinylmethoxy]cyclohexanecarboxylic acid ethyl ester NMR (CDCl$_3$) δ: 1.20-1.29 (5H, m, including 3H, t, J=7.1 Hz, at δ 1.24), 1.40-1.47 (11H, m, including 9H, s, at δ 1.45), 1.77-2.06 (7H, m), 2.20-2.26 (2H, m), 2.64-2.70 (1H, m), 2.84-2.87 (1H, m), 2.93-3.38 (total 13H, series of m, including 3H, s, at δ 3.29, and including 3H, s, at δ 3.35), 3.46-3.85 (4H, m), 4.11 (2H, q, J=7.1 Hz).

MS (ESI) m/z: 499.6 (M$^+$+1).

Trans-4-[(4S)-[(3S)-methoxy-(2R)-methoxymethylpyrrolidin-1-yl]-(2S)-pyrrolidinylmethoxy]cyclohexanecarboxylic acid ethyl ester hydrochloride NMR (CDCl$_3$) δ: 1.18-1.52 (total 7H, m, including 3H, t, J=7.1 Hz, at δ 1.24), 1.96-2.73 (9H, m), 3.33-4.13 (total 20H, series of m, including 3H, s, at δ 3.35, and including 3H, s, at δ 3.43, and including 2H, q, J=7.1 Hz, at δ 4.11), 4.40-4.44 (1H, m).

MS (ESI) m/z: 399 (M$^+$+1)

Trans-4-[1-[[5-chloro-2-fluoro-4-[(1-methyl-1H-indol-3-ylcarbonyl)amino]phenyl]acetyl]-(4S)-[(3S)-methoxy-(2R)-methoxymethylpyrrolidin-1-yl]-(2S)-pyrrolidinylmethoxy]cyclohexanecarboxylic acid ethyl ester NMR (CDCl$_3$) δ: 1.13-1.30 (5H, m, including 3H, t, J=7.1 Hz, at δ 1.21), 1.37-1.48 (2H, m), 1.76-2.07 (7H, m), 2.18-2.37 (2H, m), 2.66-2.72 (1H, m), 2.88-3.37 (total 13H, series of m, including 3H, s, at δ 3.30, and including 3H, s, at δ3.35), 3.48-4.27 (total 12H, series of m, including 3H, s, at δ 3.89, and including 2H, q, J=7.1 Hz, at δ 4.08), 7.33-7.43 (4H, m), 7.81 and 7.82 (total 1H, each s), 8.13-8.16 (1H, m), 8.30 (1H, s), 8.48-8.53 (1H, m).

MS (ESI) m/z: 741 (M$^+$+1).

Trans-4-[1-[[5-chloro-2-fluoro-4-[(1-methyl-1H-indol-3-ylcarbonyl)amino]phenyl]acetyl]-(4S)-[(3S)-methoxy-(2R)-methoxymethylpyrrolidin-1-yl]-(2S)-pyrrolidinylmethoxy]cyclohexanecarboxylic acid

[Formula 141]

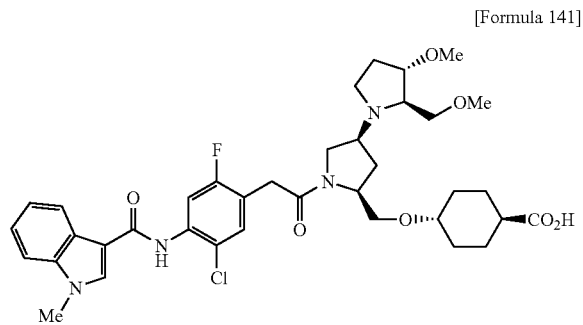

NMR (DMSO-d$_6$) δ: 1.14-1.40 (4H, m), 1.68-2.01 (7H, m), 2.12-2.33 (2H, m), 2.58-3.27 (total 14H, series of m, including 3H, s, at δ 3.20, and including 3H, s, at δ 3.27), 3.55-4.25 (total 10H, series of m, including 3H, s, at δ 3.89), 7.20-7.30 (2H, m), 7.42-7.43 (1H, m), 7.56 (1H, d, J=8.1 Hz), 7.68-7.72 (1H, m), 8.15 (1H, d, J=7.8 Hz), 8.31 (1H, s), 9.30 (1H, s), 12.07 (1H, broad s).
IR (ATR) cm$^{-1}$: 1643, 1518, 1404, 1099, 744.
MS (ESI) m/z: 713 (M$^+$+1).
Anal. Calcd for $C_{37}H_{46}ClFN_4O_7 \cdot \frac{1}{2}H_2O$: C, 61.53; H, 6.56; N, 7.76; Cl, 4.91; F, 2.63.
Found: C, 61.60; H, 6.60; N, 7.35; Cl, 4.91; S, 2.57.

Example 51

Trans-4-[1-[[2,5-dichloro-4-[(1-methyl-1H-indol-3-ylcarbonyl)amino]phenyl]acetyl]-(4S)-[(3S,4S)-dimethoxypyrrolidin-1-yl]-(2S)-pyrrolidinyl-methoxy]cyclohexanecarboxylic acid Trans-4-[1-(tert-butoxycarbonyl)-(4S)-[(3S,4S)-dimethoxypyrrolidin-1-yl]-(2S)-pyrrolidinyl-methoxy]cyclohexanecarboxylic acid ethyl ester NMR (CDCl$_3$) δ: 1.17-1.31 (5H, m), 1.46 (6H, s), 1.50-1.61 (11H, m), 1.94-2.08 (4H, m), 2.14-2.29 (1H, m), 2.45-2.68 (2H, m), 2.82-2.91 (2H, m), 3.02-3.58 (6H, m), 3.59-3.98 (4H, m), 4.06-4.17 (3H, m).
MS (ESI) m/z: 485 (M$^+$+1).

Trans-4-[(4S)-[(3S,4S)-dimethoxypyrrolidin-1-yl]-(2S)-pyrrolidinylmethoxy]cyclohexanecarboxylic acid ethyl ester MS (ESI) m/z: 385 (M$^+$+1).

Trans-4-[1-[[2,5-dichloro-4-[(1-methyl-1H-indol-3-ylcarbonyl)amino]phenyl]acetyl]-(4S)-[(3S,4S)-dimethoxypyrrolidin-1-yl]-(2S)-pyrrolidinyl-methoxy]cyclohexanecarboxylic acid ethyl ester NMR (CDCl$_3$) δ: 1.08-1.60 (7H, m), 1.89-2.36 (7H, m), 2.48-3.03-7.45 (4H, m), 7.79 and 7.80 (total 1H, each s, amide isomers), 8.11-8.17 (1H, m), 8.24 (1H, s), 8.75-8.81 (1H, m).
MS (ESI) m/z: 743 (M$^+$+1), 745 (M$^+$+3).

Trans-4-[1-[[2,5-dichloro-4-[(1-methyl-1H-indol-3-ylcarbonyl)amino]phenyl]acetyl]-(4S)-[(3S,4S)-dimethoxypyrrolidin-1-yl]-(2S)-pyrrolidinyl-methoxy]cyclohexanecarboxylic acid

[Formula 142]

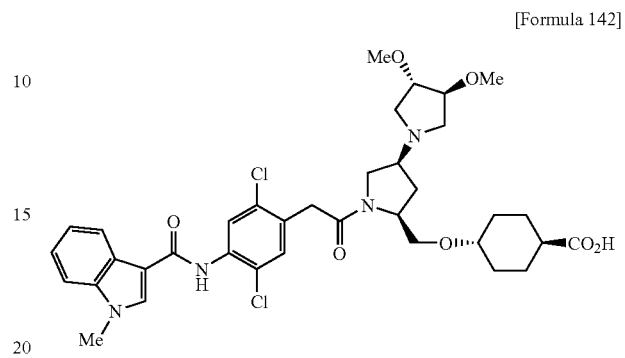

NMR (CDCl$_3$) δ: 1.10-1.54 (4H, m), 1.71-2.41 (7H, m), 2.54-3.00 and 8.24 (total 1H, each s, amide isomers), 8.74 and 8.77 (total 1H, each s, amide isomers).
MS (ESI) m/z: 714 (M$^+$+1), 716 (M$^+$+3).
IR (ATR) cm$^{-1}$: 3417, 2933, 2860, 1825, 1722, 1645, 1568, 1533.
Anal. Calcd for $C_{36}H_{44}Cl_2N_4O_7 \cdot 1.75H_2O$: C, 57.87; H, 6.41; Cl, 9.49; N, 7.50.
Found: C, 57.83; H, 6.25; Cl, 9.53; N, 7.04.

Example 52

Trans-4-[1-[[4-[(benzo[b]thiophen-3-ylcarbonyl)amino]-5-chloro-2-fluorophenyl]acetyl]-(4S)-[(3S,4S)-dimethoxypyrrolidin-1-yl]-(2S)-pyrrolidinyl-methoxy]cyclohexanecarboxylic acid Trans-4-[1-[[4-[(benzo[b]thiophen-3-ylcarbonyl)amino]-5-chloro-2-fluorophenyl]acetyl]-(4S)-[(3S,4S)-dimethoxypyrrolidin-1-yl]-(2S)-pyrrolidinyl-methoxy]cyclohexanecarboxylic acid ethyl ester NMR (CDCl$_3$) δ: 1.06-1.53 (7H, m), 1.71-2.36 (7H, m), 2.48-2.78 (3H, m), 2.86-2.93 (2H, m), 3.11-3.35 (2H, m), 3.36 (3H, s), 3.37 (3H, s), 3.46-3.89 (6H, m), 4.01-4.25 (4H, m), 7.38-7.54 (3H, m), 7.91 (1H, d, J=7.8 Hz), 8.09 and 8.11 (total 1H, each s, amide isomers), 8.35 (1H, d, J=8.8 Hz), 8.39-8.50 (2H, m).
MS (ESI) m/z: 730 (M$^+$+1), 732 (M$^+$+3).

Trans-4-[1-[[4-[(benzo[b]thiophen-3-ylcarbonyl)amino]-5-chloro-2-fluorophenyl]acetyl]-(4S)-[(3S,4S)-dimethoxypyrrolidin-1-yl]-(2S)-pyrrolidinyl-methoxy]cyclohexanecarboxylic acid

[Formula 143]

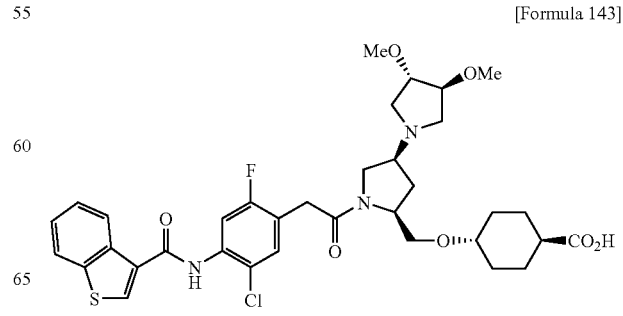

NMR (CDCl$_3$) δ: 1.05-1.57 (4H, m), 1.70-1.80 (1H, m), 1.88-2.39 (7H, m), 2.52-3.00 (5H, m), 3.11-3.87 (15H, m), 4.12-4.26 (1H, m), 7.37-7.49 (2H, m), 7.52 (1H, t, J=7.6 Hz), 7.91 (1H, d, J=8.3 Hz), 8.09 and 8.11 (total 1H, each s, amide isomers), 8.33 and 8.35 (total 1H, each s, amide isomers), 8.43 (1H, t, J=11.5 Hz), 8.47 (1H, d, J=8.5 Hz).

MS (ESI) m/z: 702 (M$^+$+1), 704 (M$^+$+3).

IR (ATR) cm$^{-1}$: 3408, 2931, 2858, 2821, 1722, 1674, 1624.

Anal. Calcd for C$_{35}$H$_{41}$ClFN$_3$O$_7$S.1.5H$_2$O: C, 57.64; H, 6.08; Cl, 4.86; F, 2.61; N, 5.76; S, 4.40.

Found: C, 57.49; H, 5.73; Cl, 4.89; F, 2.48; N, 5.53; S, 4.50.

Example 53

Trans-4-[1-[[4-[(benzo[b]furan-3-ylcarbonyl)amino]-5-chloro-2-fluorophenyl]acetyl]-(4S)-[(3S,4S)-dimethoxypyrrolidin-1-yl]-(2S)-pyrrolidinyl-methoxy]cyclohexanecarboxylic acid Trans-4-[1-[[4-[(benzo[b]furan-3-ylcarbonyl)amino]-5-chloro-2-fluorophenyl]acetyl]-(4S)-[(3S,4S)-dimethoxypyrrolidin-1-yl]-(2S)-pyrrolidinyl-methoxy]cyclohexanecarboxylic acid ethyl ester NMR (CDCl$_3$) δ: 1.04-1.55 (7H, m), 1.89-2.11 (5H, m), 2.14-2.37 (2H, m), 2.46-2.78 (3H, m), 2.86-2.93 (2H, m), 3.10-3.44 (8H, m), 3.47-3.88 (7H, m), 4.01-4.28 (3H, m), 7.39-7.47 (3H, m), 7.57-7.63 (1H, m), 8.02-8.10 (1H, m), 8.27 and 8.29 (total 1H, each s, amide isomers), 8.30 and 8.31 (total 1H, each d, each J=2.0 Hz, amide isomers), 8.43 and 8.45 (total 1H, each dd, J=11.7, 1.5 and 11.7, 1.7 Hz respectively, amide isomers).

MS (ESI) m/z: 714 (M$^+$+1), 716 (M$^+$+3).

Trans-4-[1-[[4-[(benzo[b]furan-3-ylcarbonyl)amino]-5-chloro-2-fluorophenyl]acetyl]-(4S)-[(3S,4S)-dimethoxypyrrolidin-1-yl]-(2S)-pyrrolidinyl-methoxy]cyclohexanecarboxylic acid

[Formula 144]

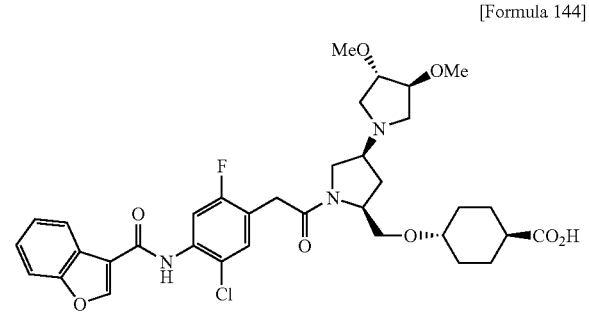

NMR (CDCl$_3$) δ: 1.07-1.54 (4H, m), 1.63-1.81 (1H, m), 1.88-2.43 (7H, m), 2.54-3.04 (5H, m), 3.07-3.89 (15H, m), 4.12-4.26 (1H, m), 7.39-7.46 (3H, m), 7.56-7.65 (1H, m), 8.02-8.08 (1H, m), 8.27 and 8.28 (total 1H, each s, amide isomers), 8.30 and 8.31 (total 1H, each s, amide isomers), 8.41 and 8.44 (total 1H, each d, J=11.0 and 11.5 Hz respectively, amide isomers).

MS (ESI) m/z: 686 (M$^+$+1), 688 (M$^+$+3).

IR (ATR) cm$^{-1}$: 3288, 3132, 3086, 2935, 2856, 1676, 1635, 1585.

Example 54

Trans-4-[1-[[4-[(benzo[b]furan-3-ylcarbonyl)amino]-2,5-dichlorophenyl]acetyl]-(4S)-[(3S,4S)-dimethoxypyrrolidin-1-yl]-(2S)-pyrrolidinyl-methoxy]cyclohexanecarboxylic acid Trans-4-[1-[[4-[(benzo[b]furan-3-ylcarbonyl)amino]-2,5-dichlorophenyl]acetyl]-(4S)-[(3S,4S)-dimethoxypyrrolidin-1-yl]-(2S)-pyrrolidinyl-methoxy]cyclohexanecarboxylic acid ethyl ester NMR (CDCl$_3$) δ: 1.10-1.53 (7H, m), 1.72-1.83 (2H, m), 1.91-2.36 (7H, m), 2.48-3.05 (4H, m), 3.12-3.44 (7H, m), 3.46-3.82 (5H, m), 4.04-4.27 (4H, m), 7.41-7.47 (4H, m), 7.57-7.65 (1H, m), 8.03-8.09 (1H, m), 8.22 and 8.30 (total 1H, each s, amide isomers), 8.31 (1H, s), 8.70 and 8.72 (total 1H, each s, amide isomers).

MS (ESI) m/z: 730 (M$^+$+1), 732 (M$^+$+3).

Trans-4-[1-[[4-[(benzo[b]furan-3-ylcarbonyl)amino]-2,5-dichlorophenyl]acetyl]-(4S)-[(3S,4S)-dimethoxypyrrolidin-1-yl]-(2S)-pyrrolidinyl-methoxy]cyclohexanecarboxylic acid

[Formula 145]

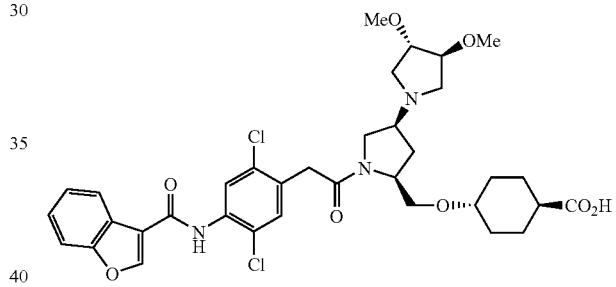

NMR (CDCl$_3$) δ: 1.13-1.53 (4H, m), 1.71-2.41 (8H, m), 2.55-2.98 (5H, m), 3.12-3.97 (15H, m), 4.11-4.30 (1H, m), 7.40-7.46 (3H, m), 7.57-7.64 (1H, m), 8.02-8.08 (1H, m), 8.22 and 8.24 (total 1H, each s, amide isomers), 8.29 and 8.30 (total 1H, each s, amide isomers), 8.68 and 8.70 (total 1H, each s, amide isomers).

MS (ESI) m/z: 702 (M$^+$+1), 703 (M$^+$+3).

IR (ATR) cm$^{-1}$: 3278, 3130, 3080, 2931, 2854, 2823, 1676, 1635.

Example 55

Trans-4-[1-[[5-chloro-2-fluoro-4-[(1-methyl-1H-indol-3-ylcarbonyl)amino]phenyl]acetyl]-(4S)-(cis-3,4-dimethoxypyrrolidin-1-yl)-(2S)-pyrrolidinyl-methoxy]cyclohexanecarboxylic acid Trans-4-[1-(tert-butoxycarbonyl)-(4S)-(cis-3,4-dimethoxypyrrolidin-1-yl)-(2S)-pyrrolidinyl-methoxy]cyclohexanecarboxylic acid ethyl ester NMR (CDCl$_3$) δ: 1.14-1.31 (5H, m), 1.37-1.48 (11H, m), 1.80-2.31 (7H, m), 2.52-2.87 (3H, m), 2.96-3.26 (4H, m), 3.41 (6H, s), 3.44-3.97 (6H, m), 4.16-4.07 (3H, m).

MS (ESI) m/z: 485 (M$^+$+1).

Trans-4-[1-[[5-chloro-2-fluoro-4-[(1-methyl-1H-indol-3-ylcarbonyl)amino]phenyl]acetyl]-(4S)-(cis-3,4-dimethoxypyrrolidin-1-yl)-(2S)-pyrrolidinyl-methoxy]cyclohexanecarboxylic acid ethyl ester NMR (CDCl$_3$) δ: 1.09-1.33 (5H, m), 1.34-1.54 (2H, m), 1.72-2.35 (7H, m), 2.57-2.68 (2H, m), 2.75-3.31 (5H, m), 3.40-3.43 (6H, m), 3.48-3.78 (5H, m), 3.81-3.87 (2H, m), 3.89 (3H, s), 4.24-4.04 (3H, m), 7.45-7.32 (4H, m), 7.82 (1H, d, J=3.9 Hz), 8.17-8.11 (1H, m), 8.30 (1H, s), 8.50 (1H, dd, J=11.8, 9.6 Hz).

MS (ESI) m/z: 727 (M$^+$+1), 729 (M$^+$+3).

Trans-4-[1-[[5-chloro-2-fluoro-4-[(1-methyl-1H-indol-3-ylcarbonyl)amino]phenyl]acetyl]-(4S)-(cis-3,4-dimethoxypyrrolidin-1-yl)-(2S)-pyrrolidinyl-methoxy]cyclohexanecarboxylic acid

[Formula 146]

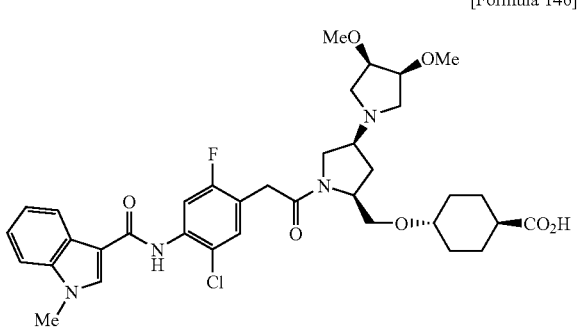

NMR (CDCl$_3$) δ: 1.12-1.35 (2H, m), 1.36-1.55 (2H, m), 1.66-2.45 (7H, m), 2.61-2.71 (2H, m), 2.93-3.35 (7H, m), 3.37-3.95 (16H, m), 4.15-4.34 (2H, m), 7.32-7.44 (4H, m), 7.81 (1H, s), 8.10-8.16 (1H, m), 8.28-8.31 (1H, m), 8.53-8.46 (1H, m). MS (ESI) m/z: 699 (M$^+$+1), 701 (M$^+$+3).

Anal. Calcd for C$_{36}$H$_{44}$ClFN$_4$O$_7$·0.5H$_2$O: C, 61.05; H, 6.43; N, 7.81; Cl, 5.01; F, 2.68.

Found: C, 61.01; H, 6.43; N, 7.81; Cl, 5.18; F, 2.67.

Example 56

Trans-4-[1-[[2,5-dichloro-4-[(1-methyl-1H-indol-3-ylcarbonyl)amino]phenyl]acetyl]-(4S)-(cis-3,4-dimethoxypyrrolidin-1-yl)-(2S)-pyrrolidinyl-methoxy]cyclohexanecarboxylic acid Trans-4-[1-[[2,5-dichloro-4-[(1-methyl-1H-indol-3-ylcarbonyl)amino]phenyl]acetyl]-(4S)-(cis-3,4-dimethoxypyrrolidin-1-yl)-(2S)-pyrrolidinyl-methoxy]cyclohexanecarboxylic acid ethyl ester NMR (CDCl$_3$) δ: 1.18-1.33 (5H, m), 1.36-1.54 (2H, m), 1.72-2.36 (6H, m), 2.59-2.80 (2H, m), 2.76-3.33 (5H, m), 3.36-4.02 (16H, m), 4.06-4.27 (3H, m), 7.30-7.48 (4H, m), 7.80-7.85 (1H, m), 8.11-8.19 (1H, m), 8.23-8.30 (1H, m), 8.84-8.77 (1H, m).

MS (ESI) m/z: 743 (M$^+$+1), 745 (M$^+$+3), 747 (M$^+$+5).

Trans-4-[1-[[2,5-dichloro-4-[(1-methyl-1H-indol-3-ylcarbonyl)amino]phenyl]acetyl]-(4S)-(cis-3,4-dimethoxypyrrolidin-1-yl)-(2S)-pyrrolidinyl-methoxy]cyclohexanecarboxylic acid

[Formula 147]

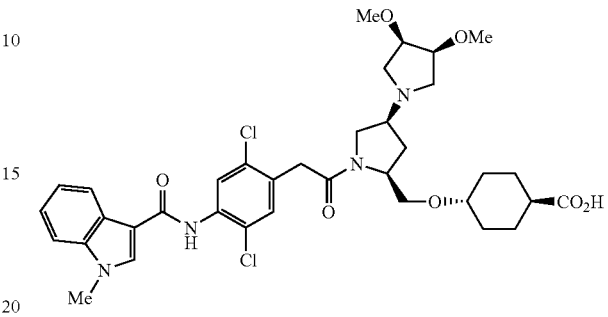

NMR (CDCl$_3$) δ: 1.15-1.35 (2H, m), 1.36-1.54 (2H, m), 1.65-2.44 (7H, m), 2.61-2.71 (2H, m), 2.88-3.97 (23H, m), 4.15-4.37 (2H, m), 7.31-7.43 (4H, m), 7.80 (1H, d, J=1.7 Hz), 8.09-8.15 (1H, m), 8.23 (1H, d, J=3.7 Hz), 8.77 (1H, d, J=10.5 Hz).

MS (ESI) m/z: 715 (M$^+$+1), 717 (M$^+$+3), 719 (M$^+$+5).

Anal. Calcd for C$_{36}$H$_{44}$Cl$_2$N$_4$O$_7$·H$_2$O: C, 58.93; H, 6.32; N, 7.64.

Found: C, 59.18; H, 6.38; N, 7.37.

Example 57

Trans-4-[1-[[4-[(benzo[b]thiophen-3-ylcarbonyl)amino]-5-chloro-2-fluorophenyl]acetyl]-(4S)-(cis-3,4-dimethoxypyrrolidin-1-yl)-(2S)-pyrrolidinyl-methoxy]cyclohexanecarboxylic acid Trans-4-[1-[[4-[(benzo[b]thiophen-3-ylcarbonyl)amino]-5-chloro-2-fluorophenyl]acetyl]-(4S)-(cis-3,4-dimethoxypyrrolidin-1-yl)-(2S)-pyrrolidinyl-methoxy]cyclohexanecarboxylic acid ethyl ester NMR (CDCl$_3$) δ: 1.09-1.53 (5H, m), 1.73-2.36 (7H, m), 2.60-2.68 (2H, m), 2.77-3.31 (5H, m), 3.39-3.44 (6H, m), 3.49-3.89 (7H, m), 4.04-4.24 (3H, m), 7.39-7.55 (3H, m), 7.92 (1H, d, J=8.2 Hz), 8.11 (1H, d, J=9.8 Hz), 8.50-8.32 (3H, m).

MS (ESI) m/z: 730 (M$^+$+1), 732 (M$^+$+3).

Trans-4-[1-[[4-[(benzo[b]thiophen-3-ylcarbonyl)amino]-5-chloro-2-fluorophenyl]acetyl]-(4S)-(cis-3,4-dimethoxypyrrolidin-1-yl)-(2S)-pyrrolidinyl-methoxy]cyclohexanecarboxylic acid

[Formula 148]

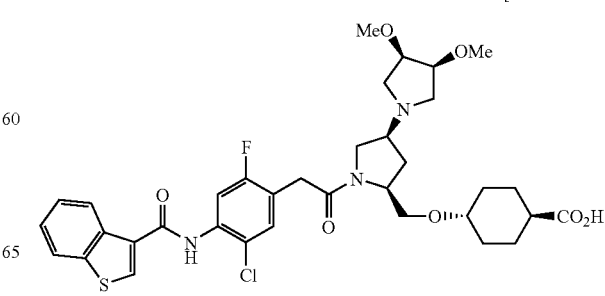

NMR (CDCl$_3$) δ: 1.14-1.54 (4H, m), 1.66-2.47 (7H, m), 2.71-2.62 (2H, m), 4.37-2.96 (19H, m), 7.55-7.38 (3H, m), 7.94-7.89 (1H, m), 8.10 (1H, d, J=5.6 Hz), 8.34 (1H, d, J=8.1 Hz), 8.50-8.40 (2H, m).
MS (ESI) m/z: 702 (M$^+$+1), 704 (M$^+$+3).
Anal. Calcd for C$_{35}$H$_{41}$ClFN$_3$O$_7$S.H$_2$O: C, 59.10; H, 5.95; N, 5.91; S, 4.51.
Found: C, 58.81; H, 5.80; N, 5.66; S, 4.51.

Example 58

Trans-4-[1-[[4-[(benzo[b]thiophen-3-ylcarbonyl)amino]-2,5-dichlorophenyl]acetyl]-(4S)-(cis-3,4-dimethoxypyrrolidin-1-yl)-(2S)-pyrrolidinyl-methoxy]cyclohexanecarboxylic acid Trans-4-[1-[[4-[(benzo[b]thiophen-3-ylcarbonyl)amino]-2,5-dichlorophenyl]acetyl]-(4S)-(cis-3,4-dimethoxypyrrolidin-1-yl)-(2S)-pyrrolidinyl-methoxy]cyclohexanecarboxylic acid ethyl ester NMR (CDCl$_3$) δ: 1.14-1.32 (5H, m), 1.35-1.54 (2H, m), 1.72-2.35 (7H, m), 2.60-2.69 (2H, m), 2.82-3.30 (5H, m), 3.38-3.46 (6H, m), 3.47-4.00 (7H, m), 4.05-4.26 (3H, m), 7.41-7.56 (3H, m), 7.90-7.94 (1H, m), 8.08-8.12 (1H, m), 8.28-8.31 (1H, m), 8.46-8.50 (1H, m), 8.74-8.71 (1H, m).
MS (ESI) m/z: 746 (M$^+$+1), 748 (M$^+$+3), 750 (M$^+$+5).

Trans-4-[1-[[4-[(benzo[b]thiophen-3-ylcarbonyl)amino]-2,5-dichlorophenyl]acetyl]-(4S)-(cis-3,4-dimethoxypyrrolidin-1-yl)-(2S)-pyrrolidinyl-methoxy]cyclohexanecarboxylic acid

[Formula 149]

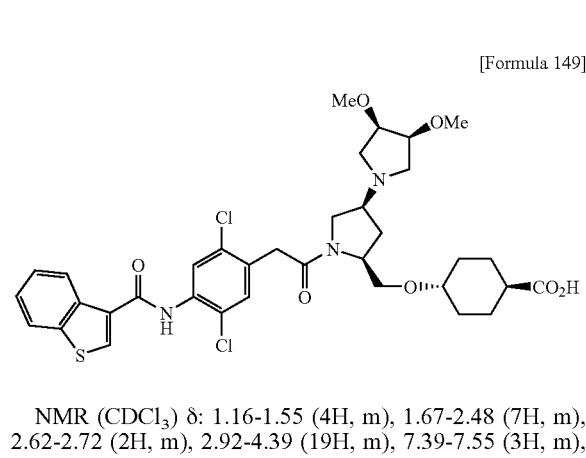

NMR (CDCl$_3$) δ: 1.16-1.55 (4H, m), 1.67-2.48 (7H, m), 2.62-2.72 (2H, m), 2.92-4.39 (19H, m), 7.39-7.55 (3H, m), 7.89-7.94 (1H, m), 8.09 (1H, d, J=2.4 Hz), 8.29 (1H, d, J=7.3 Hz), 8.45-8.50 (1H, m), 8.70 (1H, d, J=7.6 Hz).
MS (ESI) m/z: 718 (M$^+$+1), 720 (M$^+$+3), 722 (M$^+$+5).
Anal. Calcd for C$_{35}$H$_{41}$Cl$_2$N$_3$O$_7$S.H$_2$O: C, 57.06; H, 5.88; N, 5.70; S, 4.35.
Found: C, 56.86; H, 5.65; N, 5.45; S, 4.32.

Example 59

Trans-4-[1-[[4-[(benzo[b]furan-3-ylcarbonyl)amino]-5-chloro-2-fluorophenyl]acetyl]-(4S)-(cis-3,4-dimethoxypyrrolidin-1-yl)-(2S)-pyrrolidinyl-methoxy]cyclohexanecarboxylic acid Trans-4-[1-[[4-[(benzo[b]furan-3-ylcarbonyl)amino]-5-chloro-2-fluorophenyl]acetyl]-(4S)-(cis-3,4-dimethoxypyrrolidin-1-yl)-(2S)-pyrrolidinyl-methoxy]cyclohexanecarboxylic acid ethyl ester NMR (CDCl$_3$) δ: 1.10-1.31 (5H, m), 1.32-1.54 (2H, m), 1.71-2.37-3.78 (5H, m), 3.80-3.88 (2H, m), 4.04-4.24 (3H, m), 7.39-7.46 (3H, m), 7.57-7.63 (1H, m), 8.03-8.09 (1H, m), 8.27-8.33 (2H, m), 8.38-8.46 (1H, m).
MS (ESI) m/z: 714 (M$^+$+1), 716 (M$^+$+3).

Trans-4-[1-[[4-[(benzo[b]furan-3-ylcarbonyl)amino]-5-chloro-2-fluorophenyl]acetyl]-(4S)-(cis-3,4-dimethoxypyrrolidin-1-yl)-(2S)-pyrrolidinyl-methoxy]cyclohexanecarboxylic acid

[Formula 150]

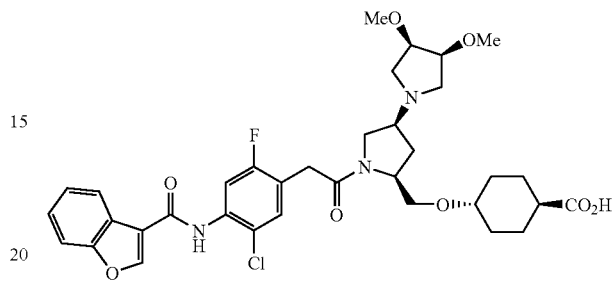

NMR (CDCl$_3$) δ: 1.12-1.55 (4H, m), 1.65-2.48 (6H, m), 2.62-2.72 (2H, m), 2.94-3.36 (5H, m), 3.40-3.43 (6H, m), 3.45-3.93 (6.5H, m), 4.15-4.34 (1.5H, m), 7.40-7.46 (3H, m), 7.57-7.63 (1H, m), 8.02-8.10 (1H, m), 8.30 (1H, d, J=3.2 Hz), 8.44 (1H, dd, J=11.7, 8.5 Hz).
MS (ESI) m/z: 686 (M$^+$+1), 688 (M$^+$+3).
Anal. Calcd for C$_{35}$H$_{41}$ClFN$_3$O$_8$: C, 61.26; H, 6.02; N, 6.12; Cl, 5.17; F, 2.77.
Found: C, 60.90; H, 6.19; N, 5.67; Cl, 5.03; F, 2.63.

Example 60

Trans-4-[1-[[4-[(benzo[b]furan-3-ylcarbonyl)amino]-2,5-dichlorophenyl]acetyl]-(4S)-(cis-3,4-dimethoxy-pyrrolidin-1-yl)-(2S)-pyrrolidinylmethoxy]cyclohexanecarboxylic acid Trans-4-[1-[[4-[(benzo[b]furan-3-ylcarbonyl)amino]-2,5-dichlorophenyl]acetyl]-(4S)-(cis-3,4-dimethoxy-pyrrolidin-1-yl)-(2S)-pyrrolidinylmethoxy]cyclohexanecarboxylic acid ethyl ester NMR (CDCl$_3$) δ: 1.12-1.31 (5H, m), 1.34-1.53 (2H, m), 1.74-2.10-3.43 (6H, m), 3.44-4.01 (7H, m), 4.05-4.26 (3H, m), 7.39-7.45 (3H, m), 7.56-7.62 (1H, m), 8.01-8.08 (1H, m), 8.25 (1H, d, J=4.6 Hz), 8.31 (1H, d, J=4.0 Hz), 8.68 (1H, d, J=7.6 Hz).
MS (ESI) m/z: 730 (M$^+$+1), 732 (M$^+$+3), 734 (M$^+$+5).

Trans-4-[1-[[4-[(benzo[b]furan-3-ylcarbonyl)amino]-2,5-dichlorophenyl]acetyl]-(4S)-(cis-3,4-dimethoxy-pyrrolidin-1-yl)-(2S)-pyrrolidinylmethoxy]cyclohexanecarboxylic acid

[Formula 151]

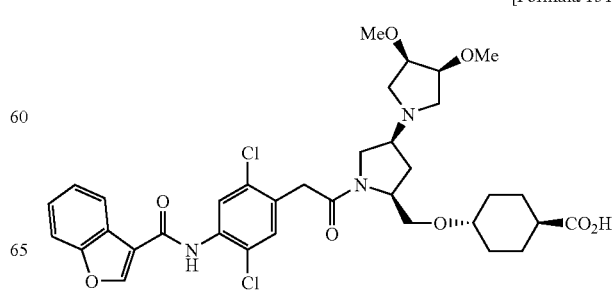

NMR (CDCl₃) δ: 1.15-1.53 (4H, m), 1.65-2.47 (7H, m), 2.63-2.73 (2H, m), 2.96-3.37 (5H, m), 3.40-3.43 (6H, m), 3.44-3.97 (6.5H, m), 4.16-4.37 (1.5H, m), 7.40-7.45 (3H, m), 7.57-7.63 (1H, m), 8.01-8.10 (1H, m), 8.22 (1H, d, J=6.1 Hz), 8.31-8.27 (1H, m), 8.70 (1H, d, J=6.3 Hz).

MS (ESI) m/z: 702 (M⁺+1), 704 (M⁺+3), 706 (M⁺+5).

Anal. Calcd for $C_{35}H_{41}Cl_2N_3O_8$: C, 59.83; H, 5.88; N, 5.98; Cl, 10.09.

Found: C, 59.48; H, 6.03; N, 5.65; Cl, 9.81.

Example 61

Trans-4-[1-[[4-[(benzo[b]furan-3-ylcarbonyl)amino]-3-chlorophenyl]acetyl]-(4S)-(cis-3,4-dimethoxypyr-rolidin-1-yl)-(2S)-pyrrolidinylmethoxy]cyclohexan-ecarboxylic acid Trans-4-[1-[[4-[(benzo[b]furan-3-ylcarbonyl)amino]-3-chlorophenyl]acetyl]-(4S)-(cis-3,4-dimethoxypyr-rolidin-1-yl)-(2S)-pyrrolidinylmethoxy]cyclohexan-ecarboxylic acid ethyl ester NMR (CDCl₃) δ: 1.10-1.48 (7H, m), 1.93-2.23 (7H, m), 2.61-2.63 (2H, m), 2.78-3.24 (5H, m), 3.40-3.41 (6H, m), 3.47-3.83 (6H, m), 3.72-3.72 (7H, m), 4.05-4.19 (4H, m), 7.22 (1H, d, J=8.3 Hz), 7.40-7.44 (3H, m), 7.59-7.61 (1H, m), 8.07-8.09 (1H, m), 8.24-8.31 (2H, m), 8.50 (1H, d, J=8.5 Hz).

MS (ESI) m/z: 696 (M⁺+1).

Trans-4-[1-[[4-[(benzo[b]furan-3-ylcarbonyl)amino]-3-chlorophenyl]acetyl]-(4S)-(cis-3,4-dimethoxypyr-rolidin-1-yl)-(2S)-pyrrolidinylmethoxy]cyclohexan-ecarboxylic acid

[Formula 152]

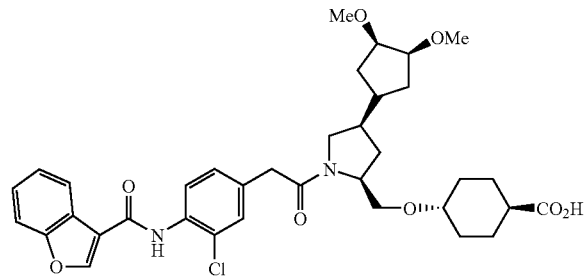

NMR (CDCl₃) δ: 8.50 (1H, dd, J=8.5, 1.3 Hz), 8.30-8.23 (2H, m), 8.07-8.05 (1H, m), 7.61-7.57 (1H, m), 7.43-7.37 (3H, m), 7.21 (1H, d, J=0.66 (0H, m), 1.51-1.12 (4H, m).

IR (ATR) cm⁻¹: 2933, 2859, 1635, 1515, 1448, 1305.

MS (ESI) m/z: 668 (M⁺+1).

Anal. Calcd for $C_{35}H_{42}ClN_3O_8 \cdot 0.5H_2O$: C, 62.08; H, 6.40; Cl, 5.24; N, 6.21.

Found: C, 61.83; H, 6.42; Cl, 5.23; N, 6.05.

Example 62

Trans-4-[1-[[4-[(1-methyl-1H-indazol-3-ylcarbonyl)amino]-3-chlorophenyl]acetyl]-(4S)-(cis-3,4-dimethoxypyrrolidin-1-yl)-(2S)-pyrrolidinyl-methoxy]cyclohexanecarboxylic acid Trans-4-[1-[[4-[(1-methyl-1H-indazol-3-ylcarbonyl)amino]-3-chlorophenyl]acetyl]-(4S)-(cis-3,4-dimethoxypyrrolidin-1-yl)-(2S)-pyrrolidinyl-methoxy]cyclohexanecarboxylic acid ethyl ester NMR (CDCl₃) δ: 1.19-1.28 (5H, m), 1.37-1.52 (2H, m), 1.93-2.29-3.41 (6H, m), 3.56-3.74 (4H, m), 3.80-3.86 (2H, m), 4.05-4.17 (7H, m), 7.19 (1H, dd, J=8.1, 2.0 Hz), 7.31-7.38 (2H, m), 7.46-7.47 (2H, m), 8.41 (1H, d, J=8.1 Hz), 8.56-8.61 (1H, m), 9.45-9.46 (1H, m).

MS (ESI) m/z: 710 (M⁺+1).

Trans-4-[1-[[4-[(1-methyl-1H-indazol-3-ylcarbonyl)amino]-3-chlorophenyl]acetyl]-(4S)-(cis-3,4-dimethoxypyrrolidin-1-yl)-(2S)-pyrrolidinyl-methoxy]cyclohexanecarboxylic acid

[Formula 153]

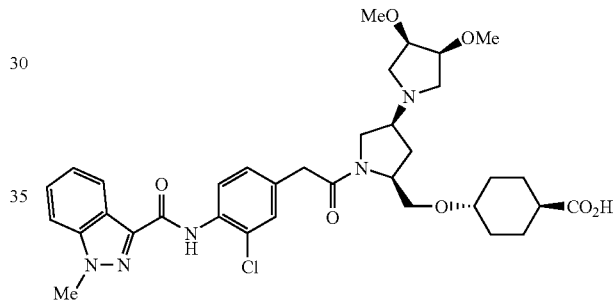

NMR (CDCl₃) δ: 9.45 (1H, d, J=3.7 Hz), 8.58 (1H, dd, J=11.2, 8.5H z), 8.40 (1H, dd, J=8.2, 4.8 Hz), 7.47-7.43 (2H, m), 7.37-7.30 (2H, m), 7.19 (1H, d, J=8.2 Hz), 4.34-4.16 (5H, m), 3.91-3.52 (6H, m), 3.46-3.40 (6H, m), 3.26-2.91 (5H, m), 2.68-2.58 (2H, m), 2.35-1.94 (6H, m), 1.47-1.20 (5H, m).

IR (ATR) cm⁻¹: 2933, 2859, 1639, 1521, 1396, 1108.

MS (ESI) m/z: 682 (M⁺+1).

Anal. Calcd for $C_{35}H_{44}ClN_5O_7 \cdot 0.75H_2O$: C, 60.42; H, 6.59; Cl, 5.10; N, 10.07.

Found: C, 60.85; H, 6.73; Cl, 4.66; N, 9.50.

Example 63

Trans-4-[1-[[2,5-dichloro-4-[(1-methyl-1H-indol-3-ylcarbonyl)amino]phenyl]acetyl]-(4S)-(3,4-cis-di-ethoxypyrrolidin-1-yl)-(2S)-pyrrolidinylmethoxy]cyclohexanecarboxylic acid Cis-1-(benzyloxycarbonyl)-3,4-diethoxypyrrolidine Cis-1-(benzyloxycarbonyl)-3,4-dihydroxypyrrolidine (3.00 g, 12.64 mmol) and ethyl iodide (5.08 mL, 63.2 mmol) were dissolved in DMF (50 mL), and the solution was cooled to 0° C. Subsequently, sodium hydride (1.66 g, 37.9 mmol) was added in small amounts with stirring, and the mixture was stirred for 12 hours at the same temperature. A saturated aqueous solution of ammonium chloride was added to the reaction liquor to make the reaction liquor weakly acidic, and then the reaction liquor was extracted with ethylacetate (200 mL). The extract was washed with saturated brine (2×200 mL), and dried over anhydrous sodium sulfate, and then the solvent was concentrated under reduced pressure. The obtained residue was purified by column chromatography using silica gel [hexane-ethyl acetate (4:1 to 2:1, v/v)], to obtain the title compound (3.13 g, 84%) as an oily matter.

NMR (CDCl$_3$) δ: 1.23 (6H, td, J=7.1, 1.2 Hz), 3.41-3.48 (1H, m), 3.51-3.66 (7H, m), 3.91-3.96 (2H, m), 5.10 and 5.13 (1H, ABq, J=12.5 Hz, each), 7.39-7.27 (5H, m).

MS (ESI) m/z: 294 (M$^+$+1).

Cis-3,4-diethoxypyrrolidine hydrochloride

Cis-1-(benzyloxycarbonyl)-3,4-diethoxypyrrolidine (3.13 g, 10.7 mmol) was dissolved in ethanol (50 mL), and 10% palladium hydroxide/carbon (3.00 g) was added thereto. The mixture was stirred for 24 hours under a hydrogen stream at normal pressure. The catalyst was separated by filtration, and 4N—HCl/1,4-dioxane (10 mL) was added to the filtrate. Then, the mixture was concentrated under reduced pressure and dried, to obtain the title compound (2.12 g, 100%) as an oily matter.

NMR (CDCl$_3$) δ: 1.23 (6H, t, J=6.8 Hz), 3.33-3.53 (4H, m), 3.55-3.67 (4H, m), 4.03-4.10 (2H, m), 4.44-4.77 (2H, m), 9.51 (1H, br s), 9.76 (1H, br s).

MS (ESI) m/z: 160 (M$^+$+1).

Trans-4-[1-(tert-butoxycarbonyl)-(4S)-(3,4-cis-diethoxypyrrolidin-1-yl)-(2S)-pyrrolidinylmethoxy]cyclohexanecarboxylic acid ethyl ester NMR (CDCl$_3$) δ: 1.19-1.27 (11H, m), 1.41-1.49 (11H, m), 1.81-1.90 (1H, m), 1.94-2.08 (4H, m), 2.12-2.28 (2H, m), 2.50-2.59 (2H, m), 2.69-2.81 (1H, m), 2.96-3.11 (3H, m), 3.25-3.15 (1H, m), 3.95-3.37 (10H, m), 4.11 (2H, q, J=7.2 Hz).

MS (ESI) m/z: 513 (M$^+$+1).

Trans-4-[1-[[2,5-dichloro-4-[(1-methyl-1H-indol-3-ylcarbonyl)amino]phenyl]acetyl]-(4S)-(3,4-cis-diethoxypyrrolidin-1-yl)-(2S)-pyrrolidinylmethoxy]cyclohexanecarboxylic acid ethyl ester NMR (CDCl$_3$) δ: 1.15-1.28 (11H, m), 1.36-1.53 (2H, m), 1.64-2.14-3.29 (4H, m), 3.46-3.78 (9H, m), 3.88-3.94 (5H, m), 4.05-4.23 (3H, m), 7.32-7.45 (4H, m), 7.81 (1H, d, J=3.2 Hz), 8.11-8.17 (1H, m), 8.23-8.26 (1H, m), 8.78 (1H, d, J=7.2 Hz).

MS (ESI) m/z: 771 (M$^+$+1), 773 (M$^+$+3), 775 (M$^+$+5).

Trans-4-[1-[[2,5-dichloro-4-[(1-methyl-1H-indol-3-ylcarbonyl)amino]phenyl]acetyl]-(4S)-(3,4-cis-diethoxypyrrolidin-1-yl)-(2S)-pyrrolidinylmethoxy]cyclohexanecarboxylic acid

[Formula 154]

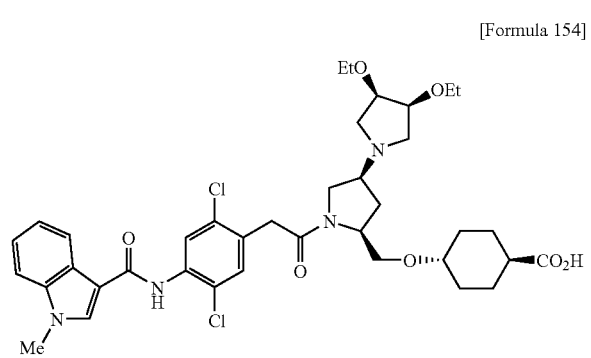

NMR (CDCl$_3$) δ: 1.14-1.34 (8H, m), 1.35-1.53 (2H, m), 1.6-2.47 (7H, m), 2.58-2.68 (2H, m), 2.93-3.35 (5H, m), 3.42-3.80 (9H, m), 3.84-4.39 (6H, m), 7.31-7.43 (4H, m), 7.79 (1H, s), 8.16-8.10 (1H, m), 8.23 (1H, d, J=5.1 Hz), 8.77 (1H, d, J=9.5 Hz).

MS (ESI) m/z: 743 (M$^+$+1), 745 (M$^+$+3), 747 (M$^+$+5).

Anal. Calcd for C$_{38}$H$_{48}$Cl$_2$N$_4$O$_7$·0.5H$_2$O: C, 60.63; H, 6.56; N, 7.44; Cl, 9.42.

Found: C, 60.68; H, 6.58; N, 7.31; Cl, 9.50.

Example 64

Trans-4-[1-[[2,5-dichloro-4-[(1-methyl-1H-indol-3-ylcarbonyl)amino]phenyl]acetyl]-(4S)-[(3R,4R)-dimethoxypyrrolidin-1-yl]-(2S)-pyrrolidinylmethoxy]cyclohexanecarboxylic acid 1,4-Di-O-tosyl-D-threitol To an ethanol (100 mL) suspension of 1,4 di-O-tosyl-2,3-O-isopropylidene-L-threitol (10.0 g, 21.25 mmol), p-toluenesulfonic acid monohydrate (0.40 g) was added, and the mixture was heated to reflux for 4 days with stirring. The reaction liquor was cooled, and then the solvent was concentrated under reduced pressure. A saturated aqueous solution of sodium hydrogen carbonate (50 mL) was added to the obtained residue, and the mixture was extracted with ethyl acetate. The extract was washed with saturated brine, dried over anhydrous sodium sulfate, and then concentrated under reduced pressure, to obtain the title compound as a solid. This compound was used in the subsequent reaction without performing further purification.

(3R,4R)-1-benzylpyrrolidine-3,4-diol

To a 1,4-dioxane (20 mL) solution of 1,4-di-O-tosyl-D-threitol (9.15 g, 21.25 mmol), benzylamine (9.29 mL, 85.0 mmol) was added, and the mixture was heated to reflux under a nitrogen stream for 4 days while stirring. The reaction liquor was returned to room temperature, and then a saturated aqueous solution of sodium hydrogen carbonate (50 mL) was added. The mixture was extracted with ethyl acetate. The extract was washed with saturated brine, dried over anhydrous sodium sulfate, and concentrated under reduced pressure. The obtained residue was purified by column chromatography using silica gel [NH(basic)-silica gel 100 g, ethyl acetate to chloroform/methanol (10/1)], to obtain the title compound (1.88 g, 46%) as an oily matter.

NMR (CDCl$_3$) δ: 2.49 (2H, dd, J=10.4, 3.3 Hz), 3.01 (2H, dd, J=10.0, 5.4 Hz), 3.68 (2H, s), 4.08-4.13 (2H, m), 7.35-7.27 (5H, m).

(3R,4R)-1-(tert-butoxycarbonyl)-3,4-dihydroxypyrrolidine (3R,4R)-1-benzylpyrrolidine-3,4-diol (1.88 g, 9.73 mmol) di-tert-butyl dicarbonate (4.25 g, 19.46 mmol) and 5% palladium hydroxide/carbon (1.0 g) were suspended in ethyl acetate (100 mL), and the suspension was stirred for 15 hours at room temperature under a hydrogen stream at normal pressure. The catalyst was separated by filtration, and the reaction liquor was concentrated under reduced pressure. The residue was solidified using dichloromethane/ethyl acetate/ether, to obtain the title compound (0.95 g, 48%) as a solid. Furthermore, the mother liquor was concentrated, and then the obtained residue was purified by flash chromatography (Flash Chromatography System from Biotage AB, column size: 40S, ethyl acetate to ethyl acetate:methanol=1:9), to obtain the title compound (0.22 g, 11%).

NMR (CDCl$_3$) δ: 1.47 (9H, s), 1.79-1.91 (2H, m), 3.36 (2H, dd, J=27.0, 11.8 Hz), 3.72-3.62 (2H, m), 4.19 (2H, s).

MS (ESI) m/z: 204 (M$^+$+1).

(3R,4R)-1-(tert-butoxycarbonyl)-3,4-dimethoxypyrrolidine (3S,4S)-1-(tert-butoxycarbonyl)-3,4-dihydroxypyrrolidine (1.33 g, 6.52 mmol) was suspended in DMF (3 mL), and methyl iodide (0.86 mL, 14.34 mmol) and 55% sodium hydride (oily: 0.71 g, 16.30 mmol) were added at 0° C. under a nitrogen stream while stirring. The reaction mixture was stirred for 4 hours at 0° C., and then poured onto ice water, and the mixture was extracted with ethyl acetate. The extract was washed with ice water and saturated brine, and dried over anhydrous sodium sulfate, and then the solvent was concentrated under reduced pressure. The obtained residue was purified by flash chromatography (Flash Chromatography System from Biotage AB, column size: 40S, ethyl acetate:n-hexane=1:4 to 2:3), to obtain the title compound (1.19 g, 79%) as an oily matter.

NMR (CDCl$_3$) δ: 1.46 (9H, s), 3.37 (6H, s), 3.52-3.44 (3H, m), 3.78 (2H, s).

MS (ESI) m/z: 254 (M$^+$+Na).

(3R,4R)-3,4-dimethoxypyrrolidine hydrochloride

MS (ESI) m/z: 131 (M$^+$+1-HCl).

Trans-4-[1-(tert-butoxycarbonyl)-(4S)-[(3R,4R)-dimethoxypyrrolidin-1-yl]-(2S)-pyrrolidinyl-methoxy]cyclohexanecarboxylic acid ethyl ester NMR (CDCl$_3$) δ: 1.18-1.30 (7H, m), 1.38-1.62 (11H, m), 1.84-2.31 (7H, m), 2.43-2.67 (3H, m), 2.82-3.11 (3H, m), 3.36 (6H, s), 3.62-3.95 (4H, m), 4.08-4.16 (3H, m).

MS (ESI) m/z: 485 (M$^+$+1).

Trans-4-[(4S)-[(3R,4R)-dimethoxypyrrolidin-1-yl]-(2S)-pyrrolidinylmethoxy]cyclohexanecarboxylic acid ethyl ester MS (ESI) m/z: 385 (M$^+$+1).

Trans-4-[1-[[2,5-dichloro-4-[(1-methyl-1H-indol-3-ylcarbonyl)amino]phenyl]acetyl]-(4S)-[(3R,4R)-dimethoxypyrrolidin-1-yl]-(2S)-pyrrolidinyl-methoxy]cyclohexanecarboxylic acid ethyl ester NMR (CDCl$_3$) δ: 1.11-1.51 (7H, m), 1.71-1.86 (1H, m), 1.93-2.34 (7H, m), 2.47-2.77 (3H, m), 3.04-3.32 (3H, m), 3.36 and 3.37 (total 6H, each s, amide isomers), 3.82-3.48 (6H, m), 3.89 (3H, s), 4.03-4.32 (3H, m), 7.31-7.47 (5H, m), 7.80 and 7.81 (total 1H, each s, amide isomers), 8.16-8.10 (1H, m), 8.27-8.23 (1H, m), 8.80 (1H, t, J=8.2 Hz)

MS (ESI) m/z: 743 (M$^+$+1) 745 (M$^+$+3).

Trans-4-[1-[[2,5-dichloro-4-[(1-methyl-1H-indol-3-ylcarbonyl)amino]phenyl]acetyl]-(4S)-[(3R,4R)-dimethoxypyrrolidin-1-yl]-(2S)-pyrrolidinyl-methoxy]cyclohexanecarboxylic acid

[Formula 155]

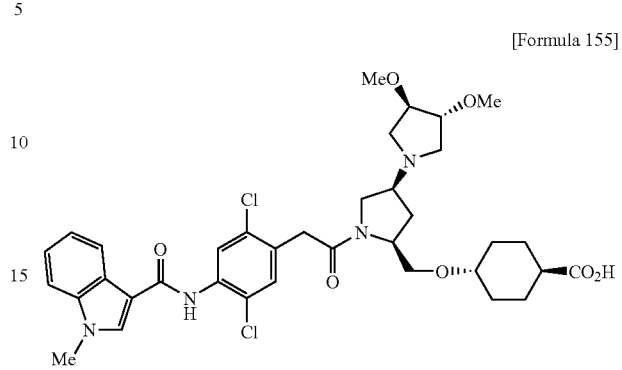

NMR (CDCl$_3$) δ: 1.15-1.53 (4H, m), 1.72-1.83 (1H, m), 1.94-2.41 and 3.36 (total 6H, each s, amide isomers), 3.38-3.50 (1H, m), 3.51-3.81 (6H, m), 3.88 (3H, s), 3.91-3.98 (1H, m), 4.08-4.36 (1H, m), 7.32-7.44 (4H, m), 7.80 (1H, s), 8.10-8.16 (1H, m), 8.23 and 8.24 (total 1H, each s, amide isomers), 8.75 and 8.78 (total 1H, each s, amide isomers).

MS (ESI) m/z: 714 (M$^+$+1), 716 (M$^+$+3).
IR (ATR) cm$^{-1}$: 2933, 2860, 2823, 1718, 1641, 1568, 1533. 1500.
Anal. Calcd for C$_{36}$H$_{44}$Cl$_2$N$_4$O$_7$H$_2$O: C, 58.93; H, 6.32; Cl, 9.66; N, 7.64.
Found: C, 59.14; H, 6.25; Cl, 9.48; N, 7.55.

Example 65

Trans-4-[1-[[4-[(benzo[b]furan-3-ylcarbonyl)amino]-2,5-dichlorophenyl]acetyl]-(4S)-[(3R,4R)-dimethoxypyrrolidin-1-yl]-(2S)-pyrrolidinyl-methoxy]cyclohexanecarboxylic acid Trans-4-[1-[[4-[(benzo[b]furan-3-ylcarbonyl)amino]-2,5-dichlorophenyl]acetyl]-(4S)-[(3R,4R)-dimethoxypyrrolidin-1-yl]-(2S)-pyrrolidinyl-methoxy]cyclohexanecarboxylic acid ethyl ester NMR (CDCl$_3$) δ: 1.10-1.56 (7H, m), 1.90-2.37 (7H, m), 2.48-2.78-4.34 (3H, m), 7.41-7.46 (3H, m), 7.54-7.70 (2H, m), 8.02-8.08 (1H, m), 8.22 and 8.23 (total 1H, each s, amide isomers), 8.29 and 8.30 (total 1H, each s, amide isomers), 8.71 and 8.72 (total 1H, each s, amide isomers).

MS (ESI) m/z: 730 (M$^+$+1), 732 (M$^+$+3).

Trans-4-[1-[[4-[(benzo[b]furan-3-ylcarbonyl)amino]-2,5-dichlorophenyl]acetyl]-(4S)-[(3R,4R)-dimethoxypyrrolidin-1-yl]-(2S)-pyrrolidinyl-methoxy]cyclohexanecarboxylic acid

[Formula 156]

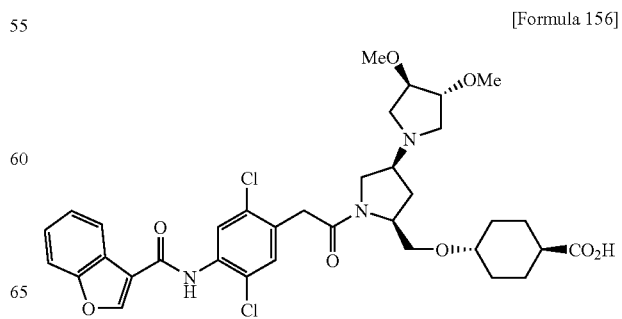

NMR (CDCl$_3$) δ: 1.12-1.53 (4H, m), 1.72-1.82 (1H, m), 1.92-2.43 (7H, m), 2.52-3.02 (5H, m), 3.08-3.34 (2H, m), 3.36 and 3.37 (6H, each s, amide isomers), 3.44-4.01 (6H, m), 4.04-4.40 (1H, m), 7.39-7.45 (3H, m), 7.57-7.63 (1H, m), 7.79-7.86 (1H, m), 8.02-8.07 (1H, m), 8.22 and 8.23 (total 1H, each s, amide isomers), 8.30 (1H, s), 8.67 and 8.70 (total 1H, each s, amide isomers).

MS (ESI) m/z: 702 (M$^+$+1), 703 (M$^+$+3).

IR (ATR) cm$^{-1}$: 2933, 2860, 2823, 1718, 1682, 1637, 1572, 1508.

Anal. Calcd for C$_{35}$H$_{41}$Cl$_2$N$_3$O$_8$·H$_2$O: C, 58.33; H, 6.01; Cl, 9.84; N, 5.83.

Found: C, 58.77; H, 5.91; Cl, 9.36; N, 5.91.

Example 66

Trans-4-[1-[[4-[(benzo[b]thiophen-3-ylcarbonyl)amino]-5-chloro-2-fluorophenyl]acetyl]-(4S)-[(3S)-acetamidopyrrolidin-1-yl]-(2S)-pyrrolidinylmethoxy]cyclohexanecarboxylic acid Trans-4-[1-(tert-butoxycarbonyl)-(4S)-[(3S)-acetamido pyrrolidin-1-yl]-(2S)-pyrrolidinylmethoxy]cyclohexanecarboxylic acid ethyl ester NMR (CDCl$_3$) δ: 1.25-2.26 (41H, m), 4.37-4.53 (1H, m), 5.62-5.98 (1H, m).

MS (ESI) m/z: 482 (M$^+$+H).

Trans-4-[1-[[4-[(benzo[b]thiophen-3-ylcarbonyl)amino]-5-chloro-2-fluorophenyl]acetyl]-(4S)-[(3S)-acetamidopyrrolidin-1-yl]-(2S)-pyrrolidinylmethoxy]cyclohexanecarboxylic acid

[Formula 157]

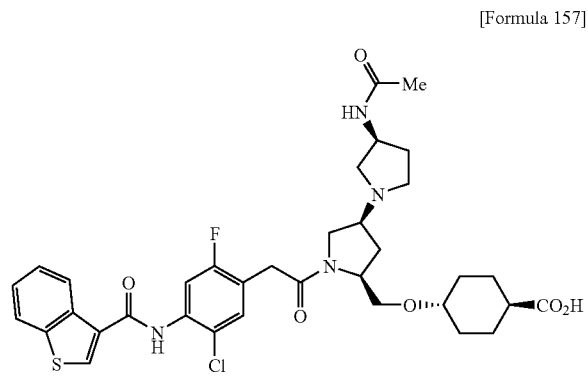

NMR (DMSO-d$_6$) δ: 0.82-4.31 (28H, m), 7.44-7.52 (3H, m), 7.53-7.59 (1H, m), 7.96-8.02 (1H, m), 8.10 (1H, d, J=8.0 Hz), 8.45 (1H, d, J=8.0 Hz), 8.65 (1H, s), 10.12 (1H, s).

IR (ATR) cm$^{-1}$: 3278, 3064, 2935, 2861, 1637, 1517.

MS (ESI) m/z: 699 (M$^+$+H).

Anal. Calcd for C$_{35}$H$_{40}$ClFN$_4$O$_6$S·0.5H$_2$O: C, 59.36; H, 5.83; Cl, 5.01; F, 2.68; N, 7.91; S, 4.53.

Found: C, 59.21; H, 5.96; Cl, 4.86; F, 2.53; N, 7.57; S, 4.56.

Example 67

Trans-4-[1-[[4-[(benzo[b]thiophen-3-ylcarbonyl)amino]-5-chloro-2-fluorophenyl]acetyl]-(4S)-(imidazol-1-yl)-(2S)-pyrrolidinylmethoxy]cyclohexanecarboxylic acid Trans-4-[1-(tert-butoxycarbonyl)-(4S)-(imidazol-1-yl)-(2S)-pyrrolidinylmethoxy]cyclohexanecarboxylic acid ethyl ester MS (ESI) m/z: 422 (M$^+$+1).

Trans-4-[1-[[4-[(benzo[b]thiophen-3-ylcarbonyl)amino]-5-chloro-2-fluorophenyl]acetyl]-(4S)-(imidazol-1-yl)-(2S)-pyrrolidinylmethoxy]cyclohexanecarboxylic acid ethyl ester NMR (CDCl$_3$) δ: 1.12-1.52 (7H, m), 1.90-2.68 (7H, m), 3.12-3.22 (1H, m), 3.50-4.72 (10H, m), 7.06 (1H, s), 7.11 (1H, s), 7.43-7.54 (3H, m), 7.61 (1H, s), 7.92 (1H, J=8.1 Hz), 8.12 (1H, s), 8.36 (1H, s), 8.45-8.48 (2H, m).

Trans-4-[1-[[4-[(benzo[b]thiophen-3-ylcarbonyl)amino]-5-chloro-2-fluorophenyl]acetyl]-(4S)-(imidazol-1-yl)-(2S)-pyrrolidinylmethoxy]cyclohexanecarboxylic acid

[Formula 158]

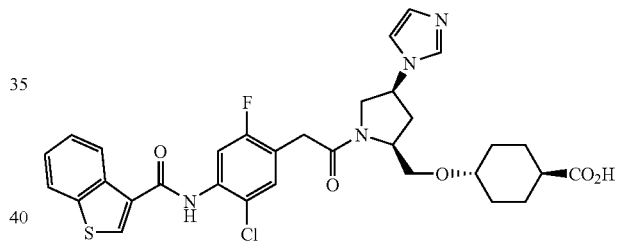

NMR (DMSO-d$_6$) δ: 1.10-1.40 (4H, m), 1.82-2.20 (6H, m), 2.52-2.80 (1H, m), 3.15-4.89 (9H, m), 6.94 and 6.97 (total 1H amide isomer, each s), 7.31 and 7.33 (total 1H amide isomer, each s), 7.44-7.59 (4H, m), 7.78 (1H, s), 8.10 (1H, J=7.6 Hz), 8.45 (1H, d, J=8.1 Hz), 8.65 (1H, s), 10.12 (1H, s).

IR (ATR) cm$^{-1}$: 2935, 1643, 1513, 1402, 1216, 1085, 765.

MS (ESI) m/z: 639 (M$^+$+1), 641 (M$^+$+3).

Anal. Calcd for C$_{32}$H$_{32}$ClFN$_4$O$_5$S·0.5H$_2$O: C, 59.30; H, 5.13; N, 8.64.

Found: C, 59.31; H, 5.38; N, 8.59.

Example 68

Trans-4-[1-[[4-[(benzo[b]thiophen-3-ylcarbonyl)amino]-2,5-dichlorophenyl]acetyl]-(4S)-(imidazol-1-yl)-(2S)-pyrrolidinylmethoxy]cyclohexanecarboxylic acid Trans-4-[1-[[4-[(benzo[b]thiophen-3-ylcarbonyl)amino]-2,5-dichlorophenyl]acetyl]-(4S)-(imidazol-1-yl)-(2S)-pyrrolidinylmethoxy]cyclohexanecarboxylic acid ethyl ester NMR (CDCl$_3$) δ: 1.12-1.52 (7H, m), 1.90-2.68 (7H, m), 3.12-3.22 (1H, m), 3.50-4.72 (10H, m), 7.06 (1H, s), 7.11

(1H, s), 7.43-7.54 (3H, m), 7.61 (1H, s), 7.92 (1H, J=8.1 Hz), 8.12 (1H, s), 8.31 (1H, s), 8.48 (1H, d, J=8.1 Hz), 8.75 (1H, s).

Trans-4-[1-[[4-[(benzo[b]thiophen-3-ylcarbonyl) amino]-2,5-dichlorophenyl]acetyl]-(4S)-(imidazol-1-yl)-(2S)-pyrrolidinylmethoxy]cyclohexanecarboxylic acid

[Formula 159]

NMR (DMSO-$d_6$) δ: 1.10-1.40 (4H, m), 1.82-2.20 (6H, m), 2.52-2.80 (1H, m), 3.15-4.89 (9H, m), 6.94 and 6.97 (total 1H amide isomer, each s), 7.32 (1H, s), 7.44-7.51 (2H, m), 7.56 (1H, s), 7.78 (1H, s), 7.79 (1H, s), 8.08-8.11 (1H, m), 8.44-8.46 (1H, m), 8.64 (1H, s), 10.16 (1H, s).
IR (ATR) cm$^{-1}$: 2859, 1643, 1502, 1211, 1081, 765. MS (ESI) m/z: 655 (M$^+$+1), 657 (M$^+$+3).
Anal. Calcd for $C_{32}H_{32}Cl_2N_4O_5S \cdot 0.5H_2O$: C, 57.83; H, 5.00; N, 8.43.
Found: C, 57.88; H, 5.12; N, 8.28.

Example 69

Trans-4-[1-[[5-chloro-2-fluoro-4-[(1-methyl-1H-indol-3-ylcarbonyl)amino]phenyl]acetyl]-(4S)-(isoxazolidin-2-yl)-(2S)-pyrrolidinylmethoxy]cyclohexanecarboxylic acid Trans-4-[1-(tert-butoxycarbonyl)-(4S)-(isoxazolidin-2-yl)-(2S)-pyrrolidinylmethoxy]cyclohexanecarboxylic acid ethyl ester NMR (CDCl$_3$) δ: 1.18-1.30 (6H, m), 1.45 (11H, s), 1.75-2.40 (10H, m), 2.46-2.82 (2H, m), 3.03-3.29 (2H, m), 3.31-3.62 (1H, m), 3.62-4.02 (4H, m), 4.06-4.16 (2H, m).
MS (ESI) m/z: 427 (M$^+$+1).

Trans-4-[(4S)-(isoxazolidin-2-yl)-(2S)-pyrrolidinylmethoxy]cyclohexanecarboxylic acid ethyl ester NMR (CDCl$_3$) δ: 1.33-1.33 (7H, m), 1.65-2.78 (10H, m), 2.86-3.38 (4H, m), 3.40-3.57 (2H, m), 3.72-3.98 (2H, m), 4.11 (2H, q, J=8.2 Hz).
MS (ESI) m/z: 327 (M$^+$+1).

Trans-4-[1-[[5-chloro-2-fluoro-4-[(1-methyl-1H-indol-3-ylcarbonyl)amino]phenyl]acetyl]-(4S)-(isoxazolidin-2-yl)-(2S)-pyrrolidinylmethoxy]cyclohexanecarboxylic acid ethyl ester NMR (CDCl$_3$) δ: 1.04-1.52 (8H, m), 1.90-2.75 (9H, m), 3.09-3.34 (4H, m), 3.47-4.01 (8H, m), 4.01-4.44 (5H, m), 7.32-7.47 (4H, m), 7.81 and 7.81 (total 1H, each s, amide isomers), 8.11-8.17 (1H, m), 8.29 (1H, s), 8.49 and 8.51 (total 1H, each d, J=12.2 and 12.0 Hz respectively, amide isomers).
MS (ESI) m/z: 669 (M$^+$+1), 671 (M$^+$+3).

Trans-4-[1-[[5-chloro-2-fluoro-4-[(1-methyl-1H-indol-3-ylcarbonyl)amino]phenyl]acetyl]-(4S)-(isoxazolidin-2-yl)-(2S)-pyrrolidinylmethoxy]cyclohexanecarboxylic acid

[Formula 160]

NMR (CDCl$_3$) δ: 1.08-1.56 (4H, m), 1.90-2.37 (9H, m), 2.51-2.81 (1H, m), 3.11-3.35 (3H, m), 3.41-4.04 (11H, m), 4.09-4.29 (1H, m), 7.31-7.44 (4H, m), 7.81 (1H, s), 8.10-8.16 (1H, m), 8.29 (1H, s), 8.47 and 8.49 (total 1H, each d, J=11.7 and 12.0 Hz respectively, amide isomers).
MS (ESI) m/z: 641 (M$^+$+1), 643 (M$^+$+3).
IR (ATR) cm$^{-1}$: 3049, 2937, 2862, 1720, 1641, 1624, 1585.
Anal. Calcd for $C_{33}H_{38}ClFN_4O_6 \cdot H_2O$: C, 60.13; H, 6.12; Cl, 5.38; F, 2.88; N, 8.50.
Found: C, 59.82; H, 6.10; Cl, 5.15; F, 2.78; N, 8.07.

Example 70

Trans-4-[1-[[4-[(benzo[b]furan-3-ylcarbonyl)amino]-5-chloro-2-fluorophenyl]acetyl]-(4S)-(1,1-dioxo-1λ$^6$-isothiazolidin-2-yl)-(2S)-pyrrolidinylmethoxy]cyclohexanecarboxylic acid Trans-4-[1-(tert-butoxycarbonyl)-(4S)-(3-chloropropyl sulfonyl)amino-(2S)-pyrrolidinylmethoxy]cyclohexanecarboxylic acid ethyl ester Trans-4-[(4S)-amino-1-(tert-butoxycarbonyl)-(2S)-pyrrolidinylmethoxy]cyclohexanecarboxylic acid ethyl ester (1.75 g, 4.72 mmol) was dissolved in dichloromethane (20 mL), and triethylamine (0.79 mL, 5.67 mmol) was added. The mixture was cooled to 0° C., and 3-chloropropylsulfonyl chloride (0.57 mL, 4.72 mmol) was added to the solution at 0° C. The mixture was stirred for two days while heating to room temperature. 1 N hydrochloric acid was added to the reaction liquor to make the reaction liquor weakly acidic, and the reaction liquor was extracted with chloroform. The extract was washed with saturated brine, and dried over anhydrous sodium sulfate, and then the solvent was concentrated under reduced pressure. The obtained residue was purified by flash column chromatography (Flash Chromatography System from Biotage AB, column size: 40S, elution solvent: n-hexane:ethyl acetate=3:1 to 1:1), to obtain the title compound (1.71 g, 71%) as an oily matter.
NMR (CDCl$_3$) δ: 1.22-1.53 (total 16H, m, including 3H, t, J=7.2 Hz, at δ 1.24 and including 9H, s, at δ 1.46), 1.85-2.46 (total 9H, series of m), 3.14 (2H, t, J=7.4 Hz), 3.28-3.31 (1H, m), 3.43-3.71 (5H, m), 3.95-4.15 (5H, m, including 2H, q, J=7.2 Hz at δ 4.11), 6.87-6.89 and 7.05-7.08 (total 1H, each m).
MS (ESI) m/z: 411 (M$^+$+1-Boc), 533 (M$^+$+Na).

Trans-4-[1-(tert-butoxycarbonyl)-(4S)-(1,1-dioxo-1λ⁶-isothiazolidin-2-yl)-(2S)-pyrrolidinylmethoxy]cyclohexanecarboxylic acid ethyl ester Trans-4-[1-(tert-butoxycarbonyl)-(4S)-(3-chloropropyl-sulfonyl)amino-(2S)-pyrrolidinylmethoxy]cyclohexanecarboxylic acid ethyl ester (1.71 g, 3.35 mmol) was dissolved in N,N-dimethylformamide (20 mL), and 1,8-diazabicyclo[5.4.0]-7-undecene (2.50 mL, 16.73 mmol) was added thereto. The mixture was stirred for 15 hours at room temperature. The reaction liquor was diluted with water, and then extracted with ethyl acetate. The extract was washed with saturated brine, and dried over anhydrous sodium sulfate, and then the solvent was concentrated under reduced pressure. The obtained residue was purified by flash column chromatography (Flash Chromatography System from Biotage AB, column size: 40S, elution solvent n-hexane:ethyl acetate=1:1 to 1:3), to obtain the title compound (1.44 g, 91%) as an oily matter.

NMR (CDCl₃) δ: 1.21-1.29 (5H, m, including 3H, t, J=7.1 Hz, at δ 1.24), 1.40-1.50 (11H, m, including 9H, s, at δ 1.46), 1.97-2.39 (total 9H, series of m), 3.16-3.28 (7H, m), 3.66-3.90 (4H, m), 4.11 (2H, q, J=7.1 Hz).

MS (ESI) m/z: 375 (M⁺+1-Boc), 497 (M⁺+Na)

Trans-4-[(4S)-(1,1-dioxo-1λ⁶-isothiazolidin-2-yl)-(2S)-pyrrolidinylmethoxy]cyclohexanecarboxylic acid ethyl ester NMR (DMSO-d₆) δ: 1.15-1.26 (5H, m, including 3H, t J=7.1 Hz, at 1.17), 1.32-1.42 (2H, m), 1.75-2.02 (5H, m), 2.20-2.30 (4H, m), 3.14-3.35 (7H, m), 3.69 (3H, broad s), 3.98-4.07 (3H, m, including 2H, q, J=7.1 Hz, at δ 4.04), 9.37 (1H, broad s).

MS (ESI) m/z: 375 (M⁺+1)

Trans-4-[1-[[4-[(benzo[b]furan-3-ylcarbonyl)amino]-5-chloro-2-fluorophenyl]acetyl]-(4S)-(1,1-dioxo-1λ⁶-isothiazolidin-2-yl)-(2S)-pyrrolidinylmethoxy]cyclohexanecarboxylic acid ethyl ester NMR (CDCl₃) δ: 1.08-1.28 (5H, m, including 3H, t, J=7.1 Hz, at δ 1.21), 1.34-1.48 (2H, m), 1.92-2.43 (9H, m), 3.10-3.37 (5H, m), 3.44-4.37 (total 10H, series of m, including 2H, q, J=7.1 Hz, at δ 4.08), 7.39-7.46 (3H, m), 7.58-7.62 (1H, m), 8.05-8.08 (1H, m), 8.29-8.32 (2H, m), 8.45 (1H, d, J=11.5 Hz).

MS (ESI) m/z: 704 (M⁺+1).

Trans-4-[1-[[4-[(benzo[b]furan-3-ylcarbonyl)amino]-5-chloro-2-fluorophenyl]acetyl]-(4S)-(1,1-dioxo-1λ⁶-isothiazolidin-2-yl)-(2S)-pyrrolidinylmethoxy]cyclohexanecarboxylic acid

[Formula 161]

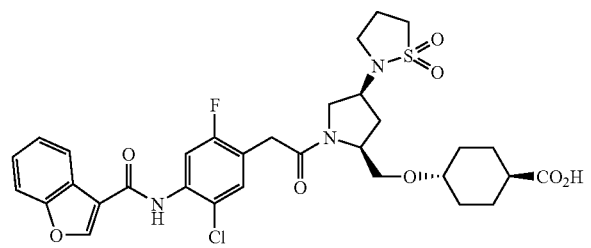

NMR (DMSO-d₆) δ: 1.13-1.37 (4H, m), 1.86-2.33 (9H, m), 3.12-4.31 (total 13H, series of m), 7.38-7.49 (3H, m), 7.55-7.59 (1H, m), 7.71-7.73 (1H, m), 8.08-8.10 (1H, m), 8.83 and 8.84 (total 1H, each s), 10.00-10.01 (1H, m), 12.08 (1H, broad s).

IR (ATR) cm⁻¹: 1522, 1450, 1406, 1304, 1124, 1103.
MS (LC-ESI) m/z: 676 (M⁺+1).
Anal. Calcd for C₃₂H₃₅ClFN₃O₈S·¾H₂O: C, 55.73; H, 5.33; N, 6.09; Cl, 5.14; F, 2.75; S, 4.65.
Found: C, 55.74; H, 5.10; N, 6.11; Cl, 5.12; F, 2.83; S, 4.74.

Example 71

Trans-4-[1-[[4-[(benzo[b]thiophen-3-ylcarbonyl)amino]-5-chloro-2-fluorophenyl]acetyl]-(4S)-[3-azabicyclo[3.1.0]hexan-3-yl]-(2S)-pyrrolidinylmethoxy]cyclohexanecarboxylic acid

Trans-4-[(1-(tert-butoxycarbonyl))-(4S)-[3-azabicyclo[3.1.0]hexan-3-yl]-(2S)-pyrrolidinylmethoxy]cyclohexanecarboxylic acid ethyl ester NMR (CDCl₃) δ: 0.28-0.36 (1H, m), 0.61-0.68 (1H, m), 1.19-1.29 (5H, m), 1.30-1.35 (2H, m), 1.42-1.48 (11H, m), 1.76-1.86 (1H, m), 1.92-2.15 (3H, m), 2.18-2.35 (3H, m), 2.58-2.68 (1H, m), 2.89-3.04 (3H, m), 3.26-3.15 (1H, m), 3.99-3.28 (5H, m), 4.16-4.07 (3H, m).

MS (ESI) m/z: 437 (M⁺+1).

Trans-4-[1-[[4-[(benzo[b]thiophen-3-ylcarbonyl)amino]-5-chloro-2-fluorophenyl]acetyl]-(4S)-[3-azabicyclo[3.1.0]hexan-3-yl]-(2S)-pyrrolidinylmethoxy]cyclohexanecarboxylic acid ethyl ester NMR (CDCl₃) δ: 0.31-0.39 (1H, m), 0.58-0.69 (1H, m), 1.12-1.53 (9H, m), 1.72-2.40 (9H, m), 2.71-2.75 (1H, m), 2.93 (1H, d, J=8.3 Hz), 2.98-3.07 (1H, m), 3.12-3.27 (2H, m), 3.42-4.02 (5H, m), 4.05-4.20 (3H, m), 7.39-7.56 (3H, m), 7.92 (1H, d, J=7.8 Hz), 8.10 (1H, d, J=9.0 Hz), 8.34 (1H, d, J=11.5 Hz), 8.51-8.41 (2H, m).

MS (ESI) m/z: 682 (M⁺+1), 683 (M⁺+3).

Trans-4-[1-[[4-[(benzo[b]thiophen-3-ylcarbonyl)amino]-5-chloro-2-fluorophenyl]acetyl]-(4S)-[3-azabicyclo[3.1.0]hexan-3-yl]-(2S)-pyrrolidinylmethoxy]cyclohexanecarboxylic acid

[Formula 162]

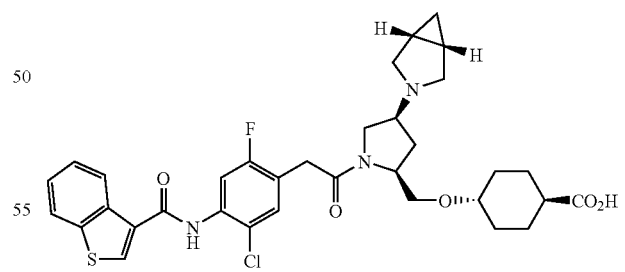

NMR (CDCl₃) δ: 0.36-0.49 (1H, m), 0.62-0.71 (1H, m), 1.12-1.83-3.33 (4H, m), 3.42-4.25 (6H, m), 7.37-7.47 (2H, m), 7.48-7.54 (1H, m), 7.91 (1H, d, J=8.1 Hz), 8.09 (1H, d, J=8.1 Hz), 8.34 (1H, d, J=8.1 Hz), 8.50-8.38 (2H, m).

MS (ESI) m/z: 654 (M⁺+1), 655 (M⁺+3).
Anal. Calcd for C₃₄H₃₇ClFN₄O₅S·0.5H₂O: C, 61.58; H, 5.78; Cl, 5.35; F, 2.86; N, 6.34.
Found: C, 61.74; H, 5.72; Cl, 6.04; F, 2.77; N, 6.06.

Example 72

Trans-4-[1-[[5-chloro-2-fluoro-4-[(1-methyl-1H-indol-3-ylcarbonyl)amino]phenyl]acetyl]-(4S)-[(3a,6a-cis)-hexahydrofuro[3,4-c]pyrrol]-5-yl]-(2S)-pyrrolidinylmethoxy]cyclohexanecarboxylic acid Trans-4-[1-(tert-butoxycarbonyl)-(4S)-[(3a,6a-cis)-hexahydrofuro[3,4-c]pyrrol]-5-yl]-(2S)-pyrrolidinylmethoxy]cyclohexanecarboxylic acid ethyl ester NMR (CDCl$_3$) δ: 1.23-1.30 (5H, m, including 3H, t, J=7.1 Hz, at δ 1.24), 1.40-1.54 (11H, m, including 9H, s, at δ 1.46), 1.82-1.89 (1H, m), 1.98-2.07 (4H, m), 2.23-2.34 (4H, m), 2.53-2.56 (1H, m), 2.69-2.80 (4H, m), 3.01-3.06 (1H, m), 3.18-3.24 (1H, m), 3.42-3.88 (total 8H, series of m), 4.11 (2H, q, J=7.1 Hz).
MS (ESI) m/z: 467 (M$^+$+1).

Trans-4-[(4S)-[(3a,6a-cis)-hexahydrofuro[3,4-c]pyrrol]-5-yl]-(2S)-pyrrolidinylmethoxy]cyclohexanecarboxylic acid ethyl ester NMR (CDCl$_3$) δ: 1.23-1.31 (5H, m, including 3H, t, J=7.2 Hz, at δ 1.24), 1.42-1.51 (2H, m), 1.64-1.72 (1H, m), 1.98-2.37 (8H, m), 2.73-2.90 (5H, m), 3.01-3.06 (1H, m), 3.25-3.34 (2H, m), 3.56-3.64 (5H, m), 3.75-3.79 (2H, m), 4.11 (2H, q, J=7.2 Hz).
MS (ESI) m/z: 367 (M$^+$+1)

Trans-4-[1-[[5-chloro-2-fluoro-4-[(1-methyl-1H-indol-3-ylcarbonyl)amino]phenyl]acetyl]-(4S)-[(3a,6a-cis)-hexahydrofuro[3,4-c]pyrrol]-5-yl]-(2S)-pyrrolidinylmethoxy]cyclohexanecarboxylic acid ethyl ester NMR (CDCl$_3$) δ: 1.14-1.30 (5H, m, including 3H, t, J=7.1 Hz, at δ 1.22), 1.38-1.49 (2H, m), 1.74-2.03 (5H, m), 2.14-2.39 (4H, m), 2.56-2.80 (5H, m), 3.11-3.27 (2H, m), 3.50-3.84 (9H, m), 3.89 (3H, s), 4.06-4.18 (3H, m, including 2H, q, J=7.1 Hz, at δ 4.08), 7.34-7.43 (4H, m), 7.81 and 7.82 (total 1H, each s), 8.13-8.16 (1H, m), 8.29-8.30 (1H, m), 8.48-8.53 (1H, m).
MS (ESI) m/z: 709 (M$^+$+1).

Trans-4-[1-[[5-chloro-2-fluoro-4-[(1-methyl-1H-indol-3-ylcarbonyl)amino]phenyl]acetyl]-(4S)-[(3a,6a-cis)-hexahydrofuro[3,4-c]pyrrol]-5-yl]-(2S)-pyrrolidinylmethoxy]cyclohexanecarboxylic acid

[Formula 163]

NMR (DMSO-d$_6$) δ: 1.13-1.39 (4H, m), 1.81-2.18 (7H, m), 2.29-2.70 (7H, m), 3.00-3.40 (4H, m), 3.52-4.23 (total 11H, series of m, including 3H, s, at δ 3.88), 7.19-7.28 (2H, m), 7.42 (1H, d, J=7.4 Hz), 7.55 (1H, d, J=8.1 Hz), 7.66-7.71 (1H, m), 8.14 (1H, d, J=7.8 Hz), 8.30 (1H, s), 9.30 (1H, s), 12.07 (1H, broad s).
IR (ATR) cm$^{-1}$: 1644, 1516, 1404, 1219, 1099, 744. MS (ESI) m/z: 681 (M$^+$+1).
HRMS (FAB) Theoretical m/z: 681.2855. Observed m/z: 681.2864
Anal. Calcd for C$_{36}$H$_{42}$ClFN$_4$O$_6$·¾H$_2$O: C, 62.24; H, 6.31; N, 8.06; Cl, 5.10; F, 2.73.
Found: C, 62.27; H, 6.19; N, 7.72; Cl, 5.51; S, 2.70.

Example 73

Trans-4-[1-[[4-[(benzo[b]furan-3-ylcarbonyl)amino]-2,5-dichlorophenyl]acetyl]-(4S)-[(3a,6a-cis)-tetrahydro[1,3]dioxolo[4,5-c]pyrrol-5-yl]-(2S)-pyrrolidinylmethoxy]cyclohexanecarboxylic acid Trans-4-[1-(tert-butoxycarbonyl)-(4S)-[(3a,6a-cis)-tetrahydro[1,3]dioxolo[4,5-c]pyrrol-5-yl]-(2S)-pyrrolidinylmethoxy]cyclohexanecarboxylic acid ethyl ester NMR (CDCl$_3$) δ: 1.21-1.28 (5H, m), 1.41-1.47 (total 11H, m, including 9H, s, at δ 1.46), 1.87-2.47 (9H, m), 3.07-4.22 (total 12H, series of m), 4.57-4.58 and 4.88-4.89 (total 2H, each m) 5.05-5.12 (1H, m).
MS (ESI) m/z: 469 (M$^+$+1).

Trans-4-[(4S)-[(3a,6a-cis)-tetrahydro[1,3]dioxolo[4,5-c]pyrrol-5-yl]-(2S)-pyrrolidinylmethoxy]cyclohexanecarboxylic acid ethyl ester NMR (DMSO-d$_6$) δ: 1.14-1.26 (5H, m, including 3H, t, J=7.1 Hz, at δ 1.16), 1.31-1.40 (2H, m), 1.51-1.54 and 1.88-2.02 (total 5H, each m), 2.16-2.29 and 2.41-2.45 (total 4H, each m), 3.02-4.06 (total 12H, series of m, including 2H, q, J=7.1 Hz at δ 4.03), 4.34-5.18 (total 3H, series of m).
MS (ESI) m/z: 369 (M$^+$+1).

Trans-4-[1-[[4-[(benzo[b]furan-3-ylcarbonyl)amino]-2,5-dichlorophenyl]acetyl]-(4S)-[(3a,6a-cis)-tetrahydro[1,3]dioxolo[4,5-c]pyrrol-5-yl]-(2S)-pyrrolidinylmethoxy]cyclohexanecarboxylic acid ethyl ester NMR (CDCl$_3$) δ: 1.16-1.32 (5H, m), 1.38-1.51 (2H, m), 1.83-2.61 (9H, m), 3.01-4.39 (total 14H, series of m), 4.58-4.60 and 4.86-4.90 (total 2H, each m), 5.10-5.27 (1H, m), 7.39-7.48 (3H, m), 7.58-7.61 (1H, m), 8.04-8.07 (1H, m), 8.25-8.31 (2H, m), 8.68-8.71 (1H, m).
MS (ESI) m/z: 714 (M$^+$+1).

Trans-4-[1-[[4-[(benzo[b]furan-3-ylcarbonyl)amino]-2,5-dichlorophenyl]acetyl]-(4S)-[(3a,6a-cis)-tetrahydro[1,3]dioxolo[4,5-c]pyrrol-5-yl]-(2S)-pyrrolidinylmethoxy]cyclohexanecarboxylic acid

[Formula 164]

NMR (DMSO-d$_6$) δ: 1.14-1.39 (4H, m), 1.81-2.21 (9H, m), 2.57-4.23 (total 11H, series of m), 4.55-4.59 (2H, m), 4.82-4.85 (1H, m), 4.94-4.96 (1H, m), 7.37-7.45 (2H, m), 7.53-7.55 (1H, m), 7.69-7.71 (1H, m), 7.76 and 7.77 (total 1H, each s), 8.07-8.09 (1H, m), 8.81 (1H, s), 10.02 (1H, s), 12.02 (1H, broad s).

IR (ATR) cm$^{-1}$: 1637, 1572, 1508, 1448, 1377, 1304, 1078, 750.

MS (ESI) m/z: 686 (M$^+$+1).

Anal. Calcd for C$_{34}$H$_{37}$Cl$_2$N$_3$O$_8$·¼H$_2$O: C, 59.09; H, 5.47; N, 6.08; Cl, 10.26.

Found: C, 58.97; H, 5.47; N, 5.95; Cl, 10.14.

Example 74

Trans-4-[1-[[4-[(benzo[b]furan-3-ylcarbonyl)amino]-5-chloro-2-fluorophenyl]acetyl]-(4S)-[(3a,6a-cis)-tetrahydro[1,3]dioxolo[4,5-c]pyrrol-5-yl]-(2S)-pyr-rolidinylmethoxy]cyclohexanecarboxylic acid Trans-4-[1-[[4-[(benzo[b]furan-3-ylcarbonyl)amino]-5-chloro-2-fluorophenyl]acetyl]-(4S)-[(3a,6a-cis)-tetrahydro[1,3]dioxolo[4,5-c]pyrrol-5-yl]-(2S)-pyr-rolidinylmethoxy]cyclohexanecarboxylic acid ethyl ester NMR (CDCl$_3$) δ: 1.16-1.29 (5H, m, including 3H, t, J=7.1 Hz, at δ 1.22), 1.38-1.49 (2H, m), 1.85-2.60 (9H, m), 3.07-4.37 (total 14H, series of m, including 2H, q, J=7.1 Hz, at δ 4.09), 4.57-4.62 and 4.86-4.90 (total 2H, each m), 5.09-5.24 (1H, m), 7.42-7.44 (3H, m), 7.58-7.61 (1H, m), 8.05-8.07 (1H, m), 8.27-8.32 (2H, m), 8.41-8.47 (1H, m).

MS (ESI) m/z: 698 (M$^+$+1).

Trans-4-[1-[[4-[(benzo[b]furan-3-ylcarbonyl)amino]-5-chloro-2-fluorophenyl]acetyl]-(4S)-[(3a,6a-cis)-tetrahydro[1,3]dioxolo[4,5-c]pyrrol-5-yl]-(2S)-pyr-rolidinylmethoxy]cyclohexanecarboxylic acid

[Formula 165]

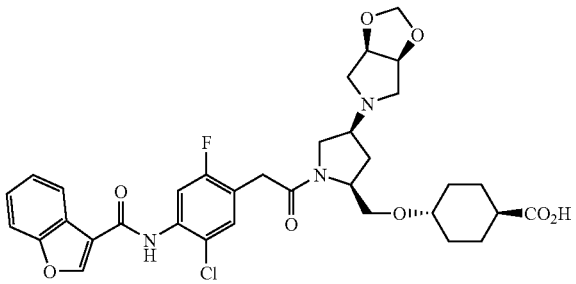

NMR (DMSO-d$_6$) δ: 1.10-1.39 (4H, m), 1.79-2.19 (9H, m), 2.57-3.37 (5H, m), 3.53-4.23 (6H, m), 4.55-4.59 (2H, m), 4.82-4.85 (1H, m), 4.93-4.95 (1H, m), 7.37-7.48 (3H, m), 7.54-7.58 (1H, m), 7.69-7.71 (1H, m), 8.07-8.09 (1H, m), 8.82 and 8.83 (total 1H, each s), 9.98 (1H, s), 12.04 (1H, broad s).

IR (ATR) cm$^{-1}$: 1522, 1448, 1404, 1120, 1103, 748. MS (ESI) m/z: 670 (M$^+$+1).

Anal. Calcd for C$_{34}$H$_{37}$ClFN$_3$O$_8$·¼H$_2$O: C, 60.53; H, 5.60; N, 6.23; Cl, 5.26; F, 2.82.

Found: C, 60.35; H, 5.63; N, 5.95; Cl, 5.36; F, 2.81.

Example 75

Trans-4-[1-[[4-[(benzo[b]thiophen-3-ylcarbonyl) amino]-2,5-dichlorophenyl]acetyl]-(4S)-[(3a,6a-cis)-2,2-dimethyltetrahydro[1,3]dioxo[4,5-c]pyrrol-5-yl]-(2S)-pyrrolidinylmethoxy]cyclohexanecarboxylic acid (3a,6a-Cis)-2,2-dimethyltetrahydro[1,3]dioxolo[4,5-c]pyrrole-5-carboxylic acid benzyl ester To a dichloromethane (40 mL) solution of cis 3,4-dihydroxypyrrolidine-1-carboxylic acid benzyl ester (2.0 g, 8.43 mmol) and 2,2-dimethoxypropane (2.07 mL, 16.86 mmol), p-toluenesulfonic acid monohydrate (150 mg, 0.84 mmol) was added, and the mixture was stirred for 4 days at room temperature. A saturated aqueous solution of sodium hydrogen carbonate (30 mL) was added to the reaction liquor, and then the mixture was extracted with dichloromethane. The extract was washed with saturated brine, and dried over anhydrous sodium sulfate, and then the solvent was concentrated under reduced pressure. The obtained residue was purified by flash chromatography (Flash Chromatography System from Biotage AB, column size: 40M, ethyl acetate:n-hexane=1:9 to 4:6), to obtain the title compound (1.89 g, 81%) as an oily matter.

NMR (CDCl$_3$) δ: 1.32 (3H, s), 1.44 (3H, s), 3.32-3.42 (2H, m), 3.81 (2H, t, J=13.2 Hz), 4.69-4.74 (2H, m), 5.14 (2H, s), 7.28-7.38 (5H, m).

MS (ESI) m/z: 278 (M$^+$+1).

(3a,6a-Cis)-2,2-dimethyltetrahydro[1,3]dioxolo[4,5-c]pyrrole (3a,6a-Cis)-2,2-dimethyltetrahydro[1,3]dioxolo[4,5-c]pyrrole-5-carboxylic acid benzyl ester (1.89 g, 6.82 mmol) and 10% palladium hydroxide/carbon (0.50 g) were suspended in ethanol (100 mL), and the suspension was stirred for 17 hours at room temperature under a hydrogen stream at normal pressure. The catalyst was separated by filtration, and then the solvent was concentrated under reduced pressure to obtain the title compound (0.93 g, 95%) as an oily matter.

MS (ESI) m/z: 144 (M$^+$+1).

Trans-4-[1-benzyloxycarbonyl-(4S)-[(3a,6a-cis)-2,2-dimethyltetrahydro[1,3]dioxo[4,5-c]pyrrol-5-yl]-(2S)-pyrrolidinylmethoxy]cyclohexanecarboxylic acid ethyl ester To a dichloroethane solution (50 mL) of trans-4-[1-benzyloxycarbonyl-4-oxo-(2S)-pyrrolidinylmethoxy]cyclohexanecarboxylic acid ethyl ester (1.31 g, 3.25 mmol) and (3a,6a-cis)-2,2-dimethyltetrahydro[1,3]dioxolo[4,5-c]pyrrole (0.93 g, 6.50 mmol), sodium triacetoxyborohydride (2.75 g, 12.99 mmol) was added, and the mixture was stirred for 18 hours at room temperature. A saturated aqueous solution of sodium hydrogen carbonate (50 mL) was added to the reaction liquor, and the mixture was stirred for 15 minutes, and then extracted with dichloromethane. The extract was washed with saturated brine, and dried over anhydrous sodium sulfate, and then the solvent was concentrated under reduced pressure. The obtained residue was purified by flash chromatography (Flash Chromatography System from Biotage AB, column size: 40M, ethyl acetate/n-hexane=1:9 to ethyl acetate), to obtain the title compound (1.70 g, 99%) as an oily matter.

NMR (CDCl$_3$) δ: 1.22-1.28 (7H, m), 1.30 (3H, s), 1.35-1.46 (2H, m), 1.49 (3H, s), 1.85-2.29 (8H, m), 2.57-2.66 (1H, m), 2.96-3.30 (4H, m), 3.47-3.86 (2H, m), 3.88-4.19 (3H, m), 4.60-4.65 (2H, m), 5.07-5.21 (2H, m), 7.28-7.37 (5H, m).

MS (ESI) m/z: 531 ($M^+$+1).

Trans-4-[(4S)-[(3a,6a-cis)-2,2-dimethyltetrahydro[1,3]dioxo[4,5-c]pyrrol-5-yl]-(2S)-pyrrolidinylmethoxy]cyclohexanecarboxylic acid ethyl ester Trans-4-[1-benzyloxycarbonyl-(4S)-[(3a,6a-cis)-2,2-dimethyltetrahydro[1,3]dioxo[4,5-c]pyrrol-5-yl]-(2S)-pyrrolidinylmethoxy]cyclohexanecarboxylic acid ethyl ester (1.70 g, 3.20 mmol) and 10% palladium hydroxide/carbon (0.50 g) were suspended in ethanol (50 mL), and the suspension was stirred for 20 hours at room temperature under a hydrogen stream at normal pressure. The catalyst was separated by filtration, and the solvent was concentrated under reduced pressure and dried, to obtain the title compound (1.10 g, 87%) as an oily matter.

MS (ESI) m/z: 397 ($M^+$+1).

Trans-4-[1-[[4-[(benzo[b]thiophen-3-ylcarbonyl)amino]-2,5-dichlorophenyl]acetyl]-(4S)-[(3a,6a-cis)-2,2-dimethyltetrahydro[1,3]dioxo[4,5-c]pyrrol-5-yl]-(2S)-pyrrolidinylmethoxy]cyclohexanecarboxylic acid ethyl ester NMR (CDCl$_3$) δ: 1.15-1.54 (13H, m), 1.91-2.29 (7H, m), 2.62-2.75 (2H, m), 2.98-3.82 (8H, m), 3.94-4.23 (4H, m), 4.61-4.68 (2H, m), 7.43 (1H, s), 7.46 (1H, d, J=7.4 Hz), 7.49-7.55 (1H, m), 7.92 (1H, d, J=8.1 Hz), 8.09 and 8.10 (total 1H, each s, amide isomers), 8.28 and 8.30 (total 1H, each s, amide isomers), 8.49 (1H, d, J=8.1 Hz), 8.70 and 8.72 (total 1H, each s, amide isomers).

MS (ESI) m/z: 758 ($M^+$+1), 760 ($M^+$+3).

Trans-4-[1-[[4-[(benzo[b]thiophen-3-ylcarbonyl)amino]-2,5-dichlorophenyl]acetyl]-(4S)-[(3a,6a-cis)-2,2-dimethyltetrahydro[1,3]dioxo[4,5-c]pyrrol-5-yl]-(2S)-pyrrolidinylmethoxy]cyclohexanecarboxylic acid

[Formula 166]

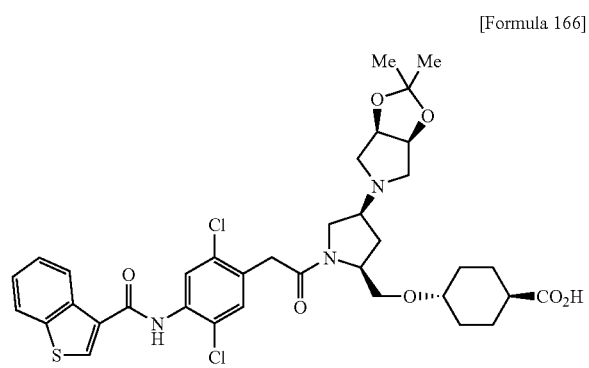

NMR (CDCl$_3$) δ: 1.16-1.56 (10H, m), 1.87-2.35 (7H, m), 2.64-2.78 (2H, m), 3.04 and 3.14 (total 2H, each d, each J=10.8 Hz, amide isomers), 3.18-3.45 (2H, m), 3.59-3.80 (4H, m), 3.91-4.32 (3H, m), 4.62-4.69 (2H, m), 7.42 (1H, s), 7.43-7.55 (2H, m), 7.90-7.93 (1H, m), 8.08 and 8.09 (total 1H, each s, amide isomers), 8.28 and 8.29 (total 1H, each s, amide isomers), 8.46-8.50 (1H, m), 8.69 and 8.72 (total 1H, each s, amide isomers).

MS (ESI) m/z: 730 ($M^+$+1), 732 ($M^+$+3).

IR (ATR) cm$^{-1}$: 2935, 2862, 2797, 1722, 1637, 1572, 1504, 1454.

Anal. Calcd for $C_{36}H_{41}Cl_2N_3O_7S \cdot H_2O$: C, 57.75; H, 5.79; Cl, 9.47; N, 5.61; S, 4.28.

Found: C, 57.90; H, 5.66; Cl, 9.49; N, 5.71; S, 4.55.

Example 76

Trans-4-[1-[[5-chloro-2-fluoro-4-[(1-methyl-1H-indol-3-ylcarbonyl)amino]phenyl]acetyl]-(4S)-[(3a,6a-cis)-hexahydrothieno[3,4-c]pyrrol-5-yl]-(2S)-pyrrolidinylmethoxy]cyclohexanecarboxylic acid

Trans 4-[1-(tert-butoxycarbonyl)-(4S)-[(3a,6a-cis)-hexahydrothieno[3,4-c]pyrrol-5-yl]-(2S)-pyrrolidinylmethoxy]cyclohexanecarboxylic acid ethyl ester Trans 4-(1-(tert-butoxycarbonyl)-4-oxo-(2S)-pyrrolidinylmethoxy)cyclohexanecarboxylic acid ethyl ester (400 mg, 1.08 mmol) and (3a,6a-cis)-hexahydrothieno[3,4-c]pyrrole hydrochloride (215 mg, 1.30 mmol) were dissolved in 1,2-dichloroethane (20 mL), and sodium triacetoxyborohydride (688 mg, 3.25 mmol) was added thereto at 0° C. with stirring. The reaction liquor was allowed to warm to room temperature, and stirred for 16 hours. Water was added to the reaction liquor, and the mixture was extracted with chloroform. The extract was washed with saturated brine, and dried over anhydrous sodium sulfate, and then the solvent was concentrated under reduced pressure. The obtained residue was purified by flash column chromatography (Flash Chromatography System from Biotage AB, column size: 40S, elution solvent: n-hexane:ethyl acetate=1:1 to chloroform:methanol=95:5), to obtain the title compound (514 mg, 98%) as an oily matter.

NMR (CDCl$_3$) δ: 1.20-1.28 (5H, m, including 3H, t, J=7.1 Hz, at δ 1.24), 1.40-1.48 (11H, m, including 9H, s, at δ 1.46), 1.72-2.23 (9H, m), 2.53-2.63 (3H, m, including 2H, d, J=11.5 Hz, at δ 2.54), 2.86-3.04 (7H, m), 3.17-3.24 (1H, m), 3.39-3.57 (1H, m), 3.67-3.89 (3H, m), 4.11 (2H, q, J=7.1 Hz).

MS (LC-ESI) m/z: 483 ($M^+$+1).

Trans-4-[(4S)-[(3a,6a-cis)-hexahydrothieno[3,4-c]pyrrol-5-yl]-(2S)-pyrrolidinylmethoxy]cyclohexanecarboxylic acid ethyl ester NMR (CDCl$_3$) δ: 1.20-1.29 (5H, m, including 3H, t, J=7.1 Hz, at δ 1.24), 1.41-1.56 (3H, m), 1.99-2.28 (9H, m), 2.54 (2H, d, J=12.0 Hz), 2.83-3.29 (10H, m), 3.46-3.54 (3H, m), 4.11 (2H, q, J=7.1 Hz).

MS (ESI) m/z: 383 ($M^+$+1)

Trans-4-[1-[[5-chloro-2-fluoro-4-[(1-methyl-1H-indol-3-ylcarbonyl)amino]phenyl]acetyl]-(4S)-[(3a,6a-cis)-hexahydrothieno[3,4-c]pyrrol-5-yl]-(2S)-pyrrolidinylmethoxy]cyclohexanecarboxylic acid ethyl ester NMR (CDCl$_3$) δ: 1.13-1.30 (5H, m, including 3H, t, J=7.1 Hz, at δ 1.22), 1.36-1.51 (2H, m), 1.91-2.32 (9H, m), 2.53-2.67 (3H, m), 2.87-3.25 (8H, m), 3.49-4.20 (11H, m, including 3H, s, at δ 3.89, and including 2H, q, J=7.1 Hz, at δ 4.08), 7.34-7.43 (4H, m), 7.80 and 7.81 (total 1H, each s), 8.12-8.16 (1H, m), 8.30 (1H, s), 8.48-8.53 (1H, m).

MS (ESI) m/z: 725 ($M^+$+1).

Trans-4-[1-[[5-chloro-2-fluoro-4-[(1-methyl-1H-indol-3-ylcarbonyl)amino]phenyl]acetyl]-(4S)-[(3a,6a-cis)-hexahydrothieno[3,4-c]pyrrol-5-yl]-(2S)-pyrrolidinylmethoxy]cyclohexanecarboxylic acid

[Formula 167]

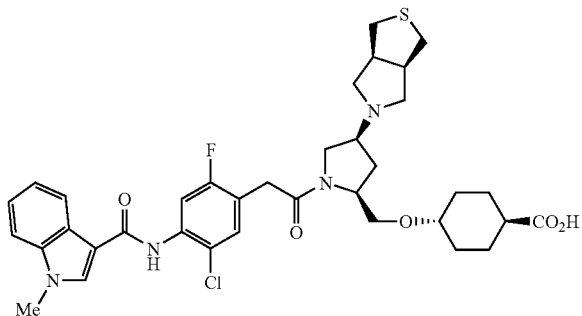

NMR (DMSO-d$_6$) δ: 1.12-1.39 (4H, m), 1.76-2.20 (9H, m), 2.62-3.31 (total 11H, series of m), 3.52-4.23 (9H, m, including 3H, s, at δ 3.88), 7.19-7.29 (2H, m), 7.42 (1H, d, J=7.6 Hz), 7.55 (1H, d, J=8.1 Hz), 7.67-7.71 (1H, m), 8.14 (1H, d, J=7.6 Hz), 8.30 (1H, s), 9.29 (1H, s), 12.03 (1H, broad s).
IR (ATR) cm$^{-1}$: 1647, 1518, 1404, 1099, 744.
MS (ESI) m/z: 697 (M$^+$+1).
Anal. Calcd for C$_{36}$H$_{42}$ClFN$_4$O$_5$S.½H$_2$O: C, 61.22; H, 6.14; N, 7.93; Cl, 5.02; F, 2.69; S, 4.54.
Found: C, 61.17; H, 6.06; N, 7.89; Cl, 5.15; F, 2.69; S, 4.59.

Example 77

Trans-4-[1-[[4-[(benzo[b]furan-3-ylcarbonyl)amino]-5-chloro-2-fluorophenyl]acetyl]-(4S)-[(3a,6a-cis)-hexahydro-2,2-dioxo-2λ$^6$-thieno[3,4-c]pyrrol-5-yl]-(2S)-pyrrolidinylmethoxy]cyclohexanecarboxylic acid (3a,6a-cis)-hexahydrothieno[3,4-c]pyrrol-5-ylcarboxylic acid tert-butyl (3a,6a-Cis)-hexahydrothieno[3,4-c]pyrrole hydrochloride (180 mg, 1.09 mmol) was dissolved in a mixed solvent of acetonitrile (10 mL) and water (10 mL), and sodium hydrogen carbonate (183 mg, 2.17 mmol) and di-tert-butyldicarbonate (285 mg, 1.30 mmol) were added thereto. The mixture was stirred for 20 hours at room temperature. The reaction liquor was diluted with water (20 mL), and then extracted with ethyl acetate. The extract was washed with saturated brine, and dried over anhydrous sodium sulfate, and then the solvent was concentrated under reduced pressure. The obtained residue was purified by flash column chromatography (Flash Chromatography System from Biotage AB, column size: 25S, elution solvent: n-hexane:ethyl acetate=9:1 to 4:1), to obtain the title compound (240 mg, 96%) as an oily matter.
NMR (CDCl$_3$) δ: 1.46 (9H, s), 2.73 (2H, dd, J=10.9, 4.0 Hz), 2.97 (2H, broad s), 3.06 (2H, dd, J=10.9, 7.2 Hz), 3.23-3.27 (2H, m), 3.58 (2H, broad s).
MS (ESI) m/z: 252 (M$^+$+Na)

(3a,6a-Cis)-hexahydro-2,2-dioxo-2λ$^6$-thieno[3,4-c]pyrrol-5-ylcarboxylic acid tert-butyl ester NMR (CDCl$_3$) δ: 1.47 (9H, s), 2.97-3.02 (2H, m), 3.07-3.17 (2H, m), 3.29-3.42 (4H, m), 3.70-3.75 (2H, m).
MS (ESI) m/z: 262 (M$^+$+1).

Trans-4-[1-(tert-butoxycarbonyl)-(4S)-[(3a,6a-cis)-hexahydro-2,2-dioxo-2λ$^6$-thieno[3,4-c]pyrrol-5-yl]-(2S)-pyrrolidinylmethoxy]cyclohexanecarboxylic acid ethyl ester NMR (CDCl$_3$) δ: 1.21-1.28 (5H, m, including 3H, t, J=7.1 Hz, at δ 1.25), 1.43-1.50 (11H, m, including 9H, s, at δ 1.46), 1.81-1.88 (1H, m), 1.99-2.07 (4H, m), 2.18-2.27 (2H, m), 2.55-2.69 (5H, m), 2.88-3.03 (5H, m), 3.21-3.26 (3H, m), 3.45-3.84 (4H, m), 4.12 (2H, q, J=7.1 Hz).
MS (ESI) m/z: 515 (M$^+$+1).

Trans-4-[(4S)-[(3a,6a-cis)-hexahydro-2,2-dioxo-2λ$^6$-thieno[3,4-c]pyrrol-5-yl]-(2S)-pyrrolidinylmethoxy]cyclohexanecarboxylic acid ethyl ester NMR (CDCl$_3$) δ: 1.20-1.52 (7H, m, including 3H, t, J=7.1 Hz, at δ 1.25), 1.99-2.09 (7H, m), 2.21-2.28 (1H, m), 2.55-2.62 (4H, m), 2.72-3.06 (7H, m), 3.20-3.48 (6H, m), 4.11 (2H, q, J=7.1 Hz). MS (ESI) m/z: 415 (M$^+$+1)

Trans-4-[1-[[4-[(benzo[b]furan-3-ylcarbonyl)amino]-5-chloro-2-fluorophenyl]acetyl]-(4S)-[(3a,6a-cis)-hexahydro-2,2-dioxo-2λ$^6$-thieno[3,4-c]pyrrol-5-yl]-(2S)-pyrrolidinylmethoxy]cyclohexanecarboxylic acid ethyl ester NMR (CDCl$_3$) δ: 1.14-1.54 (7H, m, including 3H, t, J=7.2 Hz, at δ 1.22), 1.92-2.08 (5H, m), 2.16-2.37 (2H, m), 2.56-2.75 (5H, m), 2.86-3.28 (total 8H, series of m), 3.50-3.87 and 4.06-4.24 (total 8H, each m), 7.43-7.45 (3H, m), 7.59-7.62 (1H, m), 8.05-8.07 (1H, m), 8.27-8.32 (2H, m), 8.43-8.47 (1H, m).
MS (ESI) m/z: 744 (M$^+$+1).

Trans-4-[1-[[4-[(benzo[b]furan-3-ylcarbonyl)amino]-5-chloro-2-fluorophenyl]acetyl]-(4S)-[(3a,6a-cis)-hexahydro-2,2-dioxo-2λ$^6$-thieno[3,4-c]pyrrol-5-yl]-(2S)-pyrrolidinylmethoxy]cyclohexanecarboxylic acid

[Formula 168]

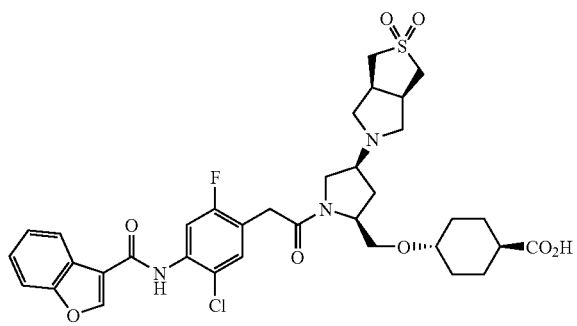

NMR (DMSO-d$_6$) δ: 1.12-1.36 (4H, m), 1.81-2.23 (7H, m), 2.53-2.87 and 3.02-3.28 (total 13H, each m), 3.52-4.26 (6H, m), 7.37-7.47 (3H, m), 7.54-7.58 (1H, m), 7.70 (1H, d, J=7.8 Hz), 8.06-8.09 (1H, m), 8.82 (1H, s), 9.99 (1H, s), 12.05 (1H, broad s).
IR (ATR) cm$^{-1}$: 1522, 1448, 1404, 1304, 1120, 1103, 748.
MS (ESI) m/z: 716 (M$^+$+1).

Anal. Calcd for $C_{35}H_{39}ClFN_3O_8S \cdot 1H_2O$: C, 57.25; H, 5.63; N, 5.72; Cl, 4.83; F, 2.59; S, 4.37.

Found: C, 57.12; H, 5.42; N, 5.69; Cl, 4.98; F, 2.55; S, 4.50.

Example 78

Trans-4-[1-[[5-chloro-2-fluoro-4-[(1-methyl-1H-indol-3-ylcarbonyl)amino]phenyl]acetyl]-(4S)-(morpholin-4-yl)-(2S)-pyrrolidinylmethoxy]cyclohexanecarboxylic acid Trans-4-[1-(tert-butoxycarbonyl)-(4S)-(morpholin-4-yl)-(2S)-pyrrolidinylmethoxy]cyclohexanecarboxylic acid ethyl ester NMR (CDCl$_3$) δ: 1.15-1.50 (7H, m), 1.70-1.80 (1H, m), 1.90-2.30-4.20 (19H, m).

MS (ESI) m/z: 441 (M$^+$+1).

Trans-4-[1-[[5-chloro-2-fluoro-4-[(1-methyl-1H-indol-3-ylcarbonyl)amino]phenyl]acetyl]-(4S)-(morpholin-4-yl)-(2S)-pyrrolidinylmethoxy]cyclohexanecarboxylic acid ethyl ester NMR (CDCl$_3$) δ: 1.10-1.55 (7H, m), 1.85-2.30 (7H, m), 2.35-2.80 (4H, m), 3.00-3.30 (2H, m), 3.50-4.35 (16H, m), 7.33-7.40 (4H, m), 7.81 and 7.82 (total 1H, each s), 8.12-8.14 (1H, m), 8.30 (1H, brs), 8.50 and 8.53 (total 1H, each d, J=9.3 Hz).

Trans-4-[1-[[5-chloro-2-fluoro-4-[(1-methyl-1H-indol-3-ylcarbonyl)amino]phenyl]acetyl]-(4S)-(morpholin-4-yl)-(2S)-pyrrolidinylmethoxy]cyclohexanecarboxylic acid

[Formula 169]

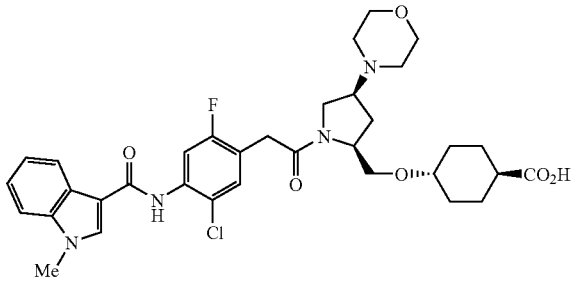

NMR (DMSO-d$_6$) δ: 1.10-1.40 (4H, m), 1.60-2.20 (7H, m), 2.30-2.90 (6H, m), 3.15-4.30 (14H, m), 7.21-7.27 (2H, m), 7.41-7.43 (1H, m), 7.56 (1H, d, J=8.1 Hz), 7.68-7.71 (1H, m), 8.14 (1H, d, J=7.8 Hz), 8.31 (1H, s), 9.31 (1H, s).

IR (ATR) cm$^{-1}$: 2935, 1644, 1517, 1403, 1099, 873, 744.

MS (ESI) m/z: 655 (M$^+$+1).

Anal. Calcd for $C_{34}H_{40}ClFN_4O_6 \cdot 0.8H_2O$: C, 60.99; H, 6.26; N, 8.37.

Found: C, 61.10; H, 6.33; N, 8.15.

Example 79

Trans-4-[1-[[4-[(benzo[b]thiophen-3-ylcarbonyl)amino]-5-chloro-2-fluorophenyl]acetyl]-(4S)-(cis-2,6-dimethylmorpholin-4-yl)-(2S)-pyrrolidinylmethoxy]cyclohexanecarboxylic acid Trans-4-[1-(tert-butoxycarbonyl)-(4S)-(2,5-cis-dimethylmorpholin-4-yl)-(2S)-pyrrolidinylmethoxy]cyclohexanecarboxylic acid ethyl ester MS (ESI) m/z: 469 (M$^+$+1).

Trans-4-[1-[[4-[(benzo[b]thiophen-3-ylcarbonyl)amino]-5-chloro-2-fluorophenyl]acetyl]-(4S)-(cis-2,6-dimethylmorpholin-4-yl)-(2S)-pyrrolidinylmethoxy]cyclohexanecarboxylic acid

[Formula 170]

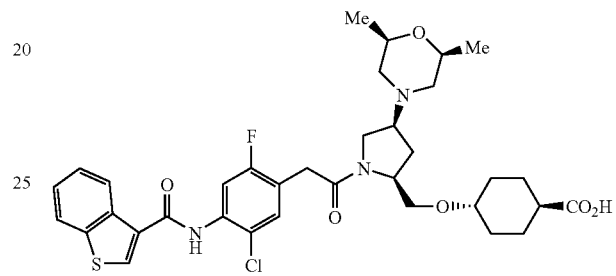

NMR (DMSO-d$_6$) δ: 0.94-2.32 (22H, m), 2.61-2.91 (2H, m), 3.11-4.28 (8H, m), 7.44-7.52 (3H, m), 7.56 (1H, dd, J=10.5, 5.4 Hz), 8.09 (1H, d, J=7.0 Hz), 8.45 (1H, d, J=7.0 Hz), 8.65 (1H, s), 10.12 (1H, s), 12.05 (1H, br s).

IR (ATR) cm$^{-1}$: 2933, 2861, 1517, 1403, 1216.

MS (ESI) m/z: 686 (M$^+$+1).

Anal. Calcd for $C_{35}H_{41}ClFN_3O_6S$: C, 61.26; H, 6.02 Cl, 5.17; F, 2.77; N, 6.12; S, 4.67.

Found: C, 61.10; H, 6.12; Cl, 4.86; F, 2.61; N, 5.87; S, 4.70.

Example 80

Trans-4-[1-[[2,5-dichloro-4-[(1-methyl-1H-indol-3-ylcarbonyl)amino]phenyl]acetyl]-(4S)-(cis-2,6-dimethylmorpholin-4-yl)-(2S)-pyrrolidinylmethoxy]cyclohexanecarboxylic acid

[Formula 171]

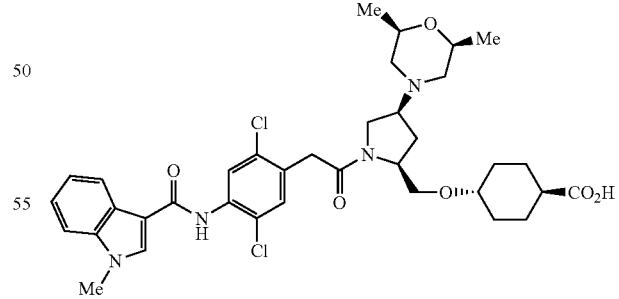

NMR (CDCl$_3$) δ: 1.02-4.44 (35H, m), 7.31-7.43 (4H, m), 7.80 (1H, s), 8.10-8.15 (1H, m), 8.23 (1H, d, J=3.4 Hz), 8.77 (1H, d, J=10.8 Hz).

IR (ATR) cm$^{-1}$: 2935, 2859, 1643, 1500, 1373.

MS (ESI) m/z: 699 (M$^+$+1).

Anal. Calcd for $C_{36}H_{44}Cl_2N_4O_6 \cdot H_2O$: C, 60.25; H, 6.46; Cl, 9.88; N, 7.81.

Found: C, 60.61; H, 6.40; Cl, 9.80; N, 7.60.

Example 81

Trans-4-[1-[[5-chloro-2-fluoro-4-[(1-methyl-1H-indol-3-ylcarbonyl)amino]phenyl]acetyl]-(4S)-(cis-2,6-dimethylmorpholin-4-yl)-(2S)-pyrrolidinylmethoxy]cyclohexanecarboxylic acid

[Formula 172]

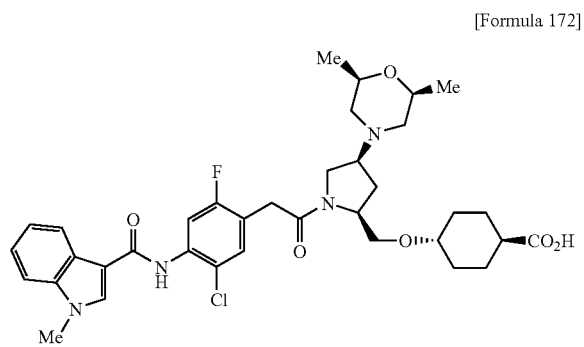

NMR (CDCl$_3$) δ: 1.01-4.41 (36H, m), 7.30-7.43 (4H, m), 7.81 (1H, s), 8.10-8.16 (1H, m), 8.29 (1H, s), 8.49 (1H, t, J=12.1 Hz).
IR (ATR) cm$^{-1}$: 2937, 2861, 1643, 1500, 1373.
MS (ESI) m/z: 683 (M$^+$+1).
Anal. Calcd for C$_{36}$H$_{44}$ClFN$_4$O$_6$·H$_2$O: C, 61.66; H, 6.61; Cl, 5.06; F, 2.71; N, 7.99.
Found: C, 62.12; H, 6.60; Cl, 5.07; F, 2.71; N, 7.82.

Example 82

Trans-4-[1-[[4-[(benzo[b]thiophen-3-ylcarbonyl)amino]-2,5-dichlorophenyl]acetyl]-(4S)-(cis-2,6-dimethylmorpholin-4-yl)-(2S)-pyrrolidinylmethoxy]cyclohexanecarboxylic acid

[Formula 173]

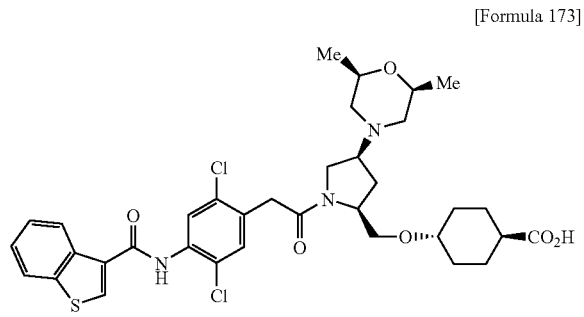

NMR (CDCl$_3$) δ: 1.15-4.44 (32H, m), 7.41 (1H, d, J=2.7 Hz), 7.45 (1H, t, J=8.1 Hz), 7.51 (1H, t, J=6.9 Hz), 7.91 (1H, d, J=7.6 Hz), 8.09 (1H, d, J=2.0 Hz), 8.29 (1H, d, J=7.1 Hz), 8.47 (1H, d, J=8.3 Hz), 8.70 (1H, d, J=8.3 Hz).
IR (ATR) cm$^{-1}$: 2935, 2859, 1637, 1504, 1079.
MS (ESI) m/z: 702 (M$^+$+1).
Anal. Calcd for C$_{35}$H$_{41}$Cl$_2$N$_3$O$_6$S·H$_2$O: C, 58.33; H, 6.01; Cl, 9.84; N, 5.83; S, 4.45.
Found: C, 58.51; H, 5.64; Cl, 9.65; N, 5.62; S, 4.47.

Example 83

Trans-4-[1-[[4-[(benzo[b]furan-3-ylcarbonyl)amino]-2,5-dichlorophenyl]acetyl]-(4S)-(cis-2,6-dimethylmorpholin-4-yl)-(2S)-pyrrolidinylmethoxy]cyclohexanecarboxylic acid

[Formula 174]

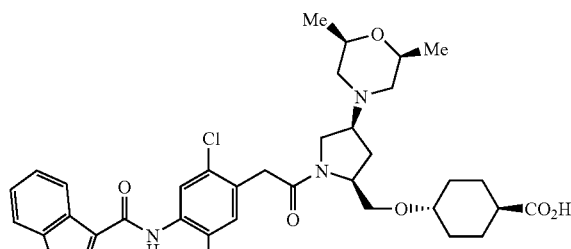

NMR (CDCl$_3$) δ: 1.15-4.44 (32H, m), 7.40-7.45 (3H, m), 7.57-7.62 (1H, m), 8.01-8.07 (1H, m), 8.22 (1H, d, J=4.7 Hz), 8.30 (1H, s), 8.70 (1H, d, J=7.8 Hz).
IR (ATR) cm$^{-1}$: 2935, 2861, 1637, 1448, 1120.
MS (ESI) m/z: 686 (M$^+$+1).
Anal. Calcd for C$_{35}$H$_{41}$Cl$_2$N$_3$O$_7$·H$_2$O: C, 59.66; H, 6.15; Cl, 10.06; N, 5.96.
Found: C, 60.13; H, 5.96; Cl, 9.46; N, 5.49.

Example 84

Trans-4-[1-[[4-[(benzo[b]furan-3-ylcarbonyl)amino]-5-chloro-2-fluorophenyl]acetyl]-(4S)-(cis-2,6-dimethylmorpholin-4-yl)-(2S)-pyrrolidinylmethoxy]cyclohexanecarboxylic acid

[Formula 175]

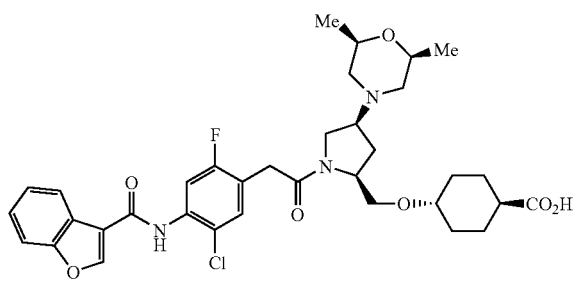

NMR (CDCl$_3$) δ: 1.03-4.50 (31H, m), 7.39-7.45 (3H, m), 7.57-7.62 (1H, m), 8.02-8.07 (1H, m), 8.27 (1H, d, J=6.6 Hz), 8.30 (1H, d, J=3.7 Hz), 8.43 (1H, dd, J=12.0, 9.6 Hz).
IR (ATR) cm$^{-1}$: 2935, 2861, 1521, 1450, 1403.
MS (ESI) m/z: 670 (M$^+$+1).
Anal. Calcd for C$_{35}$H$_{41}$ClFN$_3$O$_7$·H$_2$O: C, 61.09; H, 6.30; Cl, 5.15; F, 2.76; N, 6.11.
Found: C, 60.98; H, 6.27; Cl, 5.22; F, 2.80; N, 5.97.

Example 85

Trans-4-[1-[[3-chloro-4-[(1-methyl-1H-indol-3-yl-carbonyl)amino]phenyl]acetyl]-(4S)-(cis-2,6-dimethylmorpholin-4-yl)-(2S)-pyrrolidinylmethoxy]cyclohexanecarboxylic acid Trans-4-[1-[[3-chloro-4-[(1-methyl-1H-indol-3-yl-carbonyl)amino]phenyl]acetyl]-(4S)-(cis-2,6-dimethylmorpholin-4-yl)-(2S)-pyrrolidinylmethoxy]cyclohexanecarboxylic acid ethyl ester NMR (CDCl$_3$) δ: 1.10-1.51 (13H, m), 1.62-2.41 (9H, m), 2.45-2.83 (2H, m), 2.93-3.04 (1H, m), 3.10-3.28 (2H, m), 3.39-3.86 (6H, m), 3.88 (3H, s), 3.99-4.40 (4H, m), 7.19 (1H, dt, J=8.4, 2.1 Hz), 7.31-7.44 (4H, m), 7.80 and 7.82 (total 1H, each s, amide isomers), 8.13-8.19 (1H, m), 8.27 and 8.28 (total 1H, each s, amide isomers), 8.57 and 8.58 (total 1H, each d, J=8.4 and 8.5 Hz respectively, amide isomers).
MS (ESI) m/z: 693 (M$^+$+1), 695 (M$^+$+3).

Trans-4-[1-[[3-chloro-4-[(1-methyl-1H-indol-3-yl-carbonyl)amino]phenyl]acetyl]-(4S)-(cis-2,6-dimethylmorpholin-4-yl)-(2S)-pyrrolidinylmethoxy]cyclohexanecarboxylic acid

[Formula 176]

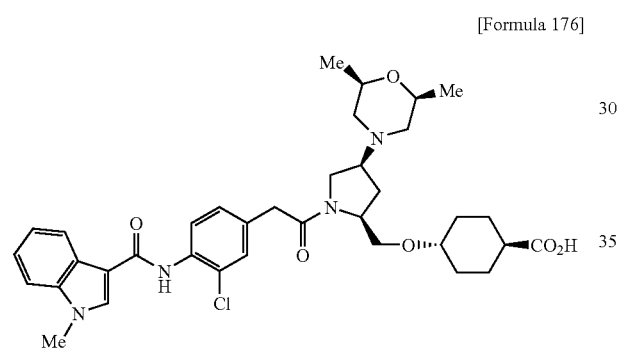

NMR (CDCl$_3$) δ: 1.01-1.54 (10H, m), 1.57-2.42 (8H, m), 2.48-3.33 (5H, m), 3.35-3.86 (7H, m), 3.87 and 3.88 (total 3H, each s, amide isomers), 4.06-4.46 (1H, m), 7.19 (1H, dd, J=8.6, 2.0 Hz), 7.31-7.44 (4H, m), 7.80-7.83 (1H, m), 8.10-8.17 (1H, m), 8.26 and 8.28 (total 1H, each s, amide isomers), 8.55 and 8.56 (total 1H, each d, J=8.1 and 8.3 Hz respectively, amide isomers).
MS (ESI) m/z: 665 (M+1), 667 (M$^+$+3).
IR (ATR) cm$^{-1}$: 2935, 2862, 1724, 1637, 1577, 1510, 1464.
Anal. Calcd for C$_{36}$H$_{45}$ClN$_4$O$_6$·0.25HCl·H$_2$O: C, 62.45; H, 6.88; Cl, 6.40; N, 8.09.
Found: C, 62.83; H, 6.86; Cl, 6.60; N, 7.67.

Example 86

Trans-4-[1-[[3-chloro-4-[(isoquinolin-1-ylcarbonyl)am S)-pyrrolidinylmethoxy]cyclohexanecarboxylic acid Trans-4-[1-[[3-chloro-4-[(isoquinolin-1-ylcarbonyl)amino]phenyl]acetyl]-(4S)-(cis-2,6-dimethylmorpholin-4-yl)-(2S)-pyrrolidinylmethoxy]cyclohexanecarboxylic acid ethyl ester NMR (CDCl$_3$) δ: 1.14-1.26 (11H, m, including 3H, t, J=7.1 Hz, at δ 7.2 Hz), 1.38-1.49 (2H, m), 1.70-2.04 (8H, m), 2.18-2.32 (2H, m), 2.51-3.03 (3H, m), 3.16-3.89 (total 8H, series of m), 4.04-4.37 (3H, m, including 2H, q, J=7.1 Hz, at δ 4.06), 7.22-7.24 (1H, m), 7.38 and 7.40 (total 1H, each d, J=2.0 Hz), 7.71-7.78 (2H, m), 7.87-7.91 (2H, m), 8.58-8.67 (2H, m), 9.70-9.73 (1H, m), 11.00 and 11.02 (total 1H, each s). MS (ESI) m/z: 691 (M$^+$+1).

Trans-4-[1-[[3-chloro-4-[(isoquinolin-1-ylcarbonyl)amino]phenyl]acetyl]-(4S)-(cis-2,6-dimethylmorpholin-4-yl)-(2S)-pyrrolidinylmethoxy]cyclohexanecarboxylic acid

[Formula 177]

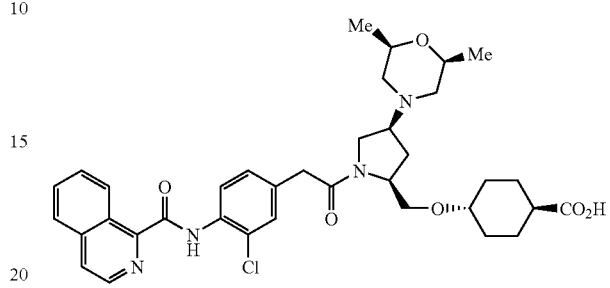

NMR (DMSO-d$_6$) δ: 1.03-1.40 (10H, m), 1.56-1.99 (7H, m), 2.10-2.28 (2H, m), 2.57-2.90 (3H, m), 3.09-3.24 (2H, m), 3.51-3.78 (6H, m), 3.96-4.27 (2H, m), 7.27-7.31 (1H, m), 7.44-7.45 (1H, m), 7.80-7.90 (2H, m), 8.12-8.22 (3H, m), 8.67 (1H, d, J=5.4 Hz), 9.32 (1H, d, J=8.3 Hz), 0.83 and 10.84 (total 1H, each s), 12.06 (1H, broad s).
IR (ATR) cm$^{-1}$: 1687, 1643, 1518, 1128, 1092.
MS (ESI) m/z: 663 (M$^+$+1).
Anal. Calcd for C$_{36}$H$_{43}$ClN$_4$O$_6$·0.25H$_2$O: C, 64.76; H, 6.57; N, 8.39; Cl, 5.31.
Found: C, 64.84; H, 6.67; N, 8.06; Cl, 5.34.

Example 87

Trans-4-[1-[[4-[(benzo[b]furan-3-ylcarbonyl)amino]-3-chlorophenyl]acetyl]-(4S)-(cis-2,6-dimethylmorpholin-4-yl)-(2S)-pyrrolidinylmethoxy]cyclohexanecarboxylic acid Trans-4-[1-[[4-[(benzo[b]furan-3-ylcarbonyl)amino]-3-chlorophenyl]acetyl]-(4S)-(cis-2,6-dimethylmorpholin-4-yl)-(2S)-pyrrolidinylmethoxy]cyclohexanecarboxylic acid ethyl ester NMR (CDCl$_3$) δ: 1.10-1.23 (11H, m), 1.30-1.52 (2H, m), 1.67-2.04 (8H, m), 2.16-2.37 (2H, m), 2.51-2.81 (3H, m), 3.10-3.88 (total 8H, series of m), 4.05-4.36 (3H, m), 7.20-7.23 (1H, m), 7.40-7.45 (3H, m), 7.59-7.61 (1H, m), 8.06-8.10 (1H, m), 8.24-8.32 (2H, m), 8.51 (1H, d, J=8.3 Hz).
MS (ESI) m/z: 680 (M$^+$+1).

Trans-4-[1-[[4-[(benzo[b]furan-3-ylcarbonyl)amino]-3-chlorophenyl]acetyl]-(4S)-(cis-2,6-dimethylmorpholin-4-yl)-(2S)-pyrrolidinylmethoxy]cyclohexanecarboxylic acid

[Formula 178]

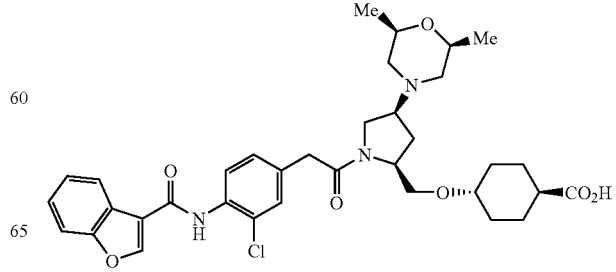

NMR (DMSO-d₆) δ: 1.03-1.40 (10H, m), 1.56-1.99 (7H, m), 2.11-2.26 (2H, m), 2.59-2.90 (3H, m), 3.08-3.27 (2H, m), 3.49-3.78 (6H, m), 3.95-4.26 (2H, m), 7.21-7.25 (1H, m), 7.36-7.45 (3H, m), 7.54-7.57 (1H, m), 7.69-7.72 (1H, m), 8.08-8.09 (1H, m), 8.80 (1H, s), 9.93 (1H, s), 12.05 (1H, broad s).

IR (ATR) cm⁻¹: 1516, 1450, 1308, 1120, 1103, 748. MS (ESI) m/z: 652 (M++1).

Anal. Calcd for $C_{35}H_{42}ClN_3O_7 \cdot \frac{1}{4}H_2O$: C, 64.02; H, 6.52; N, 6.40; Cl, 5.40.

Found: C, 63.92; H, 6.62; N, 6.07; Cl, 5.45.

Example 88

Trans-4-[1-[[3-chloro-4-[(1-methyl-1H-indazol-3-ylcarbonyl)amino]phenyl]acetyl]-(4S)-(cis-2,6-dimethylmorpholin-4-yl)-(2S)-pyrrolidinylmethoxy]cyclohexanecarboxylic acid Trans-4-[1-[[3-chloro-4-[(1-methyl-1H-indazol-3-ylcarbonyl)amino]phenyl]acetyl]-(4S)-(cis-2,6-dimethylmorpholin-4-yl)-(2S)-pyrrolidinylmethoxy]cyclohexanecarboxylic acid ethyl ester NMR (CDCl₃) δ: 1.09-1.33 (11H, m), 1.35-1.54 (2H, m), 1.58-2.10-3.89 (7H, m), 4.01-4.38 (6H, m), 7.16-7.22 (1H, m), 7.30-7.39 (2H, m), 7.43-7.50 (2H, m), 8.41 (1H, d, J=8.3 Hz), 8.59 (1H, t, J=9.2 Hz), 9.47-9.43 (1H, m).

MS (ESI) m/z: 694 (M⁺+1), 696 (M⁺+3).

Trans-4-[1-[[3-chloro-4-[(1-methyl-1H-indazol-3-ylcarbonyl)amino]phenyl]acetyl]-(4S)-(cis-2,6-dimethylmorpholin-4-yl)-(2S)-pyrrolidinylmethoxy]cyclohexanecarboxylic acid

[Formula 179]

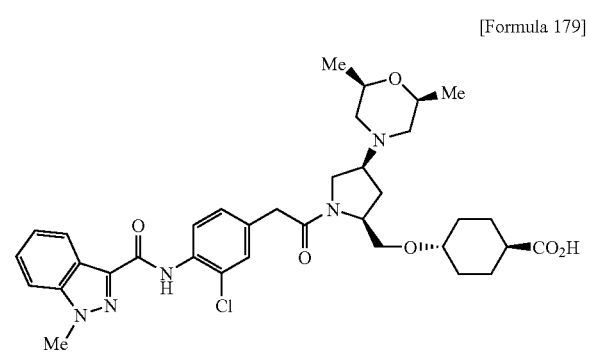

NMR (CDCl₃) δ: 1.11-1.35 (8H, m), 1.36-1.53 (2H, m), 1.57-2.15-3.87 (7H, m), 4.12-4.45 (5H, m), 7.19 (1H, dd, J=8.5, 2.0 Hz), 7.30-7.38 (2H, m), 7.43-7.50 (2H, m), 8.37-8.42 (1H, m), 8.55-8.61 (1H, m), 9.47-9.44 (1H, m).

MS (ESI) m/z: 666 (M⁺+1), 668 (M⁺+3).

Anal. Calcd for $C_{35}H_{44}ClN_5O_6 \cdot 1.25H_2O$: C, 61.04; H, 681; N, 10.17; Cl, 10.09.

Found: C, 60.70; H, 6.46; N, 9.93.

Example 89

Trans-4-[1-[[2,5-dichloro-4-[(1H-indol-3-ylcarbonyl)amino]phenyl]acetyl]-(4S)-(cis-2,6-dimethylmorpholin-4-yl)-(2S)-pyrrolidinylmethoxy]cyclohexanecarboxylic acid Trans-4-[1-[[2,5-dichloro-4-[(1H-indol-3-ylcarbonyl)amino]phenyl]acetyl]-(4S)-(cis-2,6-dimethylmorpholin-4-yl)-(2S)-pyrrolidinylmethoxy]cyclohexanecarboxylic acid ethyl ester NMR (CDCl₃) δ: 1.15-1.52 (total 13H, series of m), 1.76-2.05 (total 7H, series of m), 2.20-2.45 (2H, m), 2.55-2.82 (3H, m), 3.01-3.27 (2H, m), 3.44-3.95 (total 7H, series of m), 4.09-4.46 (3H, m), 7.12-7.48 (4H, m), 7.78-7.80 (1H, s), 8.09-8.11 (1H, m), 8.20-8.23 (1H, m), 8.67 and 8.71 (1H, each s, amide isomers) 9.10 and 9.20 (total 1H, each s).

IR (ATR) ν: 3419, 3159, 2937, 2856, 2771, 2660, 1618, 1568 cm⁻¹.

MS (FAB) m/z: 713 (M⁺+1).

Anal. Calcd for $C_{37}H_{46}Cl_2N_4O_6$: C, 62.27; H, 6.50; N, 7.85.

Found: C, 62.03: H, 6.35; N, 7.81.

Trans-4-[1-[[2,5-dichloro-4-[(1H-indol-3-ylcarbonyl)amino]phenyl]acetyl]-(4S)-(cis-2,6-dimethylmorpholin-4-yl)-(2S)-pyrrolidinylmethoxy]cyclohexanecarboxylic acid

[Formula 180]

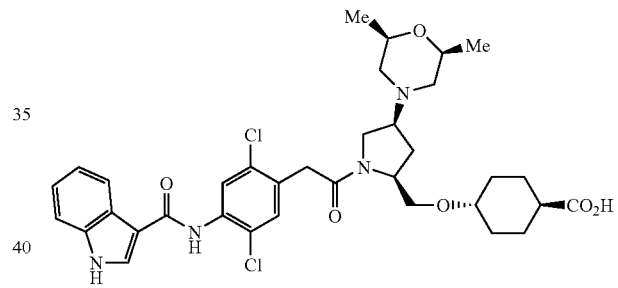

NMR (DMSO-d₆) δ: 1.05-1.34 (total 13H, series of m), 1.62-1.90 (total 7H, series of m), 2.15-2.17 (2H, m), 2.51-2.83 (3H, m), 3.15-3.17 (2H, m), 3.35-4.25 (total 12H, series of m), 7.14-7.22 (2H, m), 7.48-7.50 (2H, m), 7.86-7.88 (1H, m), 8.14 (1H, d, J=7.3 Hz), 8.31-8.32 (1H, m), 9.42 (1H, broad s), 11.82 (1H, broad s).

IR (ATR) ν: 3419, 3159, 2937, 2862, 1732, 1662, 1618, 1568 cm⁻¹.

MS (FAB) m/z: 685 (M⁺+1).

Anal. Calcd for $C_{35}H_{42}Cl_2N_4O_6 \cdot 0.5H_2O$: C, 60.51; H, 6.24; N, 8.07.

Found: C, 60.51; H, 6.09; N, 7.94.

Example 90

Trans-4-[1-[[5-chloro-2-fluoro-4-[(1H-indol-3-ylcarbonyl)amino]phenyl]acetyl]-(4S)-(cis-2,6-dimethylmorpholin-4-yl)-(2S)-pyrrolidinylmethoxy]cyclohexanecarboxylic acid Trans-4-[1-[[5-chloro-2-fluoro-4-[(1H-indol-3-ylcarbonyl)amino]phenyl]acetyl]-(4S)-(cis-2,6-dimethylmorpholin-4-yl)-(2S)-pyrrolidinylmethoxy]cyclohexanecarboxylic acid ethyl ester NMR (CDCl₃) δ: 1.15-1.52 (total 13H, series of m), 1.76-2.05 (total 7H, series of 5 (total 7H, series of m), 4.09-4.46

(3H, m), 7.26-7.44 (4H, m), 7.71-7.77 (total 1H, each m), 8.10-8.12 (1H, m), 8.22-8.42 (2H, series of m), 8.67 and 8.71 (1H, each s, amide isomers) 9.35 and 9.50 (total 1H, each s)

IR (ATR) ν: 3430, 3174, 2937, 2862, 1728, 1658, 1618, 1583, 1510 cm$^{-1}$.

MS (FAB) m/z: 697 (M$^+$+1).

Anal. Calcd for $C_{37}H_{46}ClFN_4O_6 \cdot 1.0HCl$: C, 60.57; H, 6.46; N, 7.64.

Found: C, 60.53: H, 6.34; N, 7.30.

Trans-4-[1-[[5-chloro-2-fluoro-4-[(1H-indol-3-ylcarbonyl)amino]phenyl]acetyl]-(4S)-(cis-2,6-dimethylmorpholin-4-yl)-(2S)-pyrrolidinylmethoxy]cyclohexanecarboxylic acid

[Formula 181]

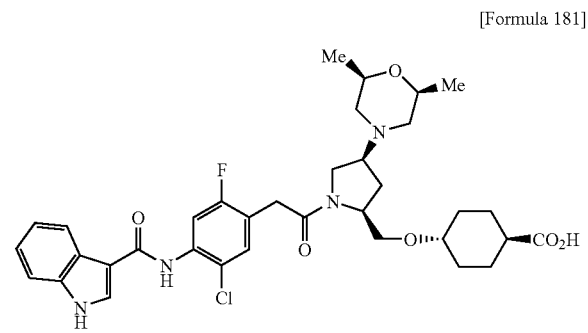

NMR (DMSO-d$_6$) δ: 1.03-1.34 (total 13H, series of m), 1.64-1.91 (total 7H, series of m), 2.15-2.45 (2H, m), 2.55-2.82 (3H, m), 3.06-3.27 (2H, m), 3.44-4.25 (total 10H, series of m), 7.15-7.22 (2H, m), 7.42-7.50 (total 2H, series of m), 7.65-7.69 (1H, m), 8.14 (1H, d, J=7.3 Hz), 8.32 (1H, d, J=3.1 Hz), 9.35 (1H, s), 11.83 (1H, s).

IR (ATR) ν: 3425, 3215, 3172, 2937, 2864, 1730, 1660, 1618, 1585, 1510 cm$^{-1}$.

MS (FAB) m/z: 669 (M$^+$+1).

Anal. Calcd for $C_{35}H_{42}ClFN_4O_6 \cdot 0.5H_2O$: C, 61.99; H, 6.39; N, 8.26.

Found: C, 62.18: H, 6.26; N, 8.11.

Example 91

Trans-4-[1-[[2,5-dichloro-4-[(1-methyl-1H-indol-3-ylcarbonyl)amino]phenyl]acetyl]-(4S)-(2,6-dimethylmorpholin-4-yl)-(2S)-pyrrolidinylmethoxy]cyclohexanecarboxylic acid (mixture of 2,6-cis/trans isomers at the morpholine site)

4-Benzyl-2,6-dimethylmorpholine (mixture of cis/trans isomers)

To a tetrahydrofuran solution (500 mL) of 2,6-dimethylmorpholine (Aldrich Co.) (mixture of cis/trans isomers) (25.02 g, 217.24 mmol), triethylamine (51.48 mL, 369.31 mmol) was added at room temperature, and the mixture was stirred for 15 minutes. Then, benzyl bromide (43.93 mL, 369.31 mmol) was added dropwise over 30 minutes, and the mixture was stirred for 4 days. A saturated aqueous solution of sodium hydrogen carbonate (200 mL) was added to the reaction liquor, and the mixture was stirred for 30 minutes, and then extracted with ethyl acetate. The extract was washed with saturated brine, and dried over anhydrous sodium sulfate, and then the solvent was concentrated under reduced pressure. The obtained residue was purified by flash chromatography (Flash Chromatography System from Biotage AB, column size: 65i, n-hexane to ethyl acetate/n-hexane 1:1), to obtain the title compound (10.7 g, 24%) as an oily matter.

NMR (CDCl$_3$) δ: 1.23 (6H, d, J=6.6 Hz), 2.14 (2H, dd, J=11.0, 5.6 Hz), 2.46 (2H, dd, J=10.5, 2.9 Hz), 3.43 (2H, dd, J=31.9, 13.2 Hz), 3.97-4.06 (2H, m), 7.41-7.21 (5H, m).

2,6-Dimethylmorpholine acetate

4-Benzyl-2,6-dimethylmorpholine (10.72 mg, 45.76 mmol) was dissolved in acetic acid (10 mL) and ethanol (200 mL), and 10% palladium hydroxide/carbon (5 g) was added thereto. The mixture was stirred for two days at room temperature under a hydrogen stream at normal pressure. The catalyst was separated by filtration, and then the reaction liquor was concentrated under reduced pressure and dried, to obtain the title compound (7.36 g, 92%) as an oily matter. This compound was used in the subsequent reaction without performing further purification.

Trans-4-[1-(tert-butoxycarbonyl)-(4S)-(2,6-dimethylmorpholin-4-yl)-(2S)-pyrrolidinylmethoxy]cyclohexanecarboxylic acid ethyl ester Trans-4-[1-(tert-butoxycarbonyl)-4-oxo-(2S)-pyrrolidinylmethoxy]cyclohexanecarboxylic acid ethyl ester (4.43 g, 12.0 mmol) and 2,6-dimethylmorpholine acetate (7.01 g, 40.0 mmol) were dissolved in dichloroethane (200 mL), and sodium triacetoxyborohydride (12.72 g, 60.0 mmol) was added thereto. The mixture was stirred for 14 hours. A saturated aqueous solution of sodium hydrogen carbonate (100 mL) was added to the reaction liquor, and the mixture was stirred for 15 minutes, and then extracted with dichloromethane. The extract was washed with saturated brine, and dried over anhydrous sodium sulfate, and then the solvent was concentrated under reduced pressure. The obtained residue was purified by flash chromatography (Flash Chromatography System from Biotage AB, column size: 40M, ethyl acetate/n-hexane=1:9 to 4:6), to obtain the title compound (5.81 g, quant.) as an oily matter. This compound was used in the subsequent reaction without performing further purification.

Trans-4-[(4S)-(2,6-dimethylmorpholin-4-yl)-(2S)-pyrrolidinylmethoxy]cyclohexanecarboxylic acid ethyl ester hydrochloride (isomer mixture)

To trans-4-[1-(tert-butoxycarbonyl)-(4S)-(2,6-dimethylmorpholin-4-yl)-(2S)-pyrrolidinylmethoxy]cyclohexanecarboxylic acid ethyl ester (5.81 g, 12.40 mmol), a 4N-hydrochloric acid/1,4-dioxane solution (100 mL) was added, and the mixture was stirred for 14 hours. The reaction liquor was concentrated under reduced pressure, and then solidified using ether to obtain the title compound as a solid.

MS (ESI) m/z: 369 (M$^+$+1).

Trans-4-[1-[[2,5-dichloro-4-[(1-methyl-1H-indol-3-ylcarbonyl)amino]phenyl]acetyl]-(4S)-(2,6-dimethylmorpholin-4-yl)-(2S)-pyrrolidinylmethoxy]cyclohexanecarboxylic acid ethyl ester MS (ESI) m/z: 727 (M$^+$+1), 729 (M$^+$+3).

Trans-4-[1-[[2,5-dichloro-4-[(1-methyl-1H-indol-3-ylcarbonyl)amino]phenyl]acetyl]-(4S)-(2,6-dimethylmorpholin-4-yl)-(2S)-pyrrolidinylmethoxy]cyclohexanecarboxylic acid (mixture of 2,6-cis/trans isomers at the morpholine site)

[Formula 182]

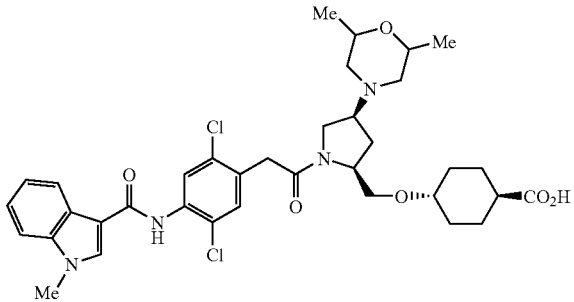

MS (ESI) m/z: 699 (M$^+$+1), 701 (M$^+$+3).

Example 92

Trans-4-[1-[[4-[(benzo[b]thiophen-3-ylcarbonyl)amino]-3-chlorophenyl]acetyl]-(4S)-(cis-2,6-dimethylmorpholin-4-yl)-(2S)-pyrrolidinylmethoxy]cyclohexanecarboxylic acid Trans-4-[1-[[4-[(benzo[b]thiophen-3-ylcarbonyl)amino]-3-chlorophenyl]acetyl]-(4S)-(cis-2,6-dimethylmorpholin-4-yl)-(2S)-pyrrolidinylmethoxy]cyclohexanecarboxylic acid ethyl ester NMR (CDCl$_3$) δ: 1.10-1.51 (total 13H, series of m), 1.59-2.05 (total 7H, series of m), 2.16-2.38 (2H, m), 2.46-2.81 (3H, m), 2.96-3.27 (2H, m), 3.42-3.87 (total 7H, series of m), 4.04-4.38 (3H, m), 7.22 (1H, dt, J=8.4, 1.8 Hz), 7.38-7.40 (1H, m), 7.44 (1H, tt, J=8.1, 1.5 Hz), 7.51 (1H, tt, J=8.1, 1.5 Hz), 7.91 (1H, d, J=8.1 Hz), 8.09 and 8.12 (total 1H, each s), 8.30 and 8.34 (total 1H, each s), 8.47-8.51 (2H, m).

IR (ATR) ν: 2935, 2862, 1724, 1672, 1635 cm$^{-1}$.

MS (ESI) m/z: 696 [(M$^+$+1), $^{35}$Cl], 698 [(M$^+$+3), $^{37}$Cl].

Anal. Calcd for C$_{37}$H$_{46}$ClN$_3$O$_6$S.0.25H$_2$O: C, 63.41; H, 6.69; N, 6.00; S, 4.58; Cl, 5.06.

Found: C, 63.25; H, 6.46; N, 5.93; S, 4.75; Cl, 5.05.

Trans-4-[1-[[4-[(benzo[b]thiophen-3-ylcarbonyl)amino]-3-chlorophenyl]acetyl]-(4S)-(cis-2,6-dimethylmorpholin-4-yl)-(2S)-pyrrolidinylmethoxy]cyclohexanecarboxylic acid

[Formula 183]

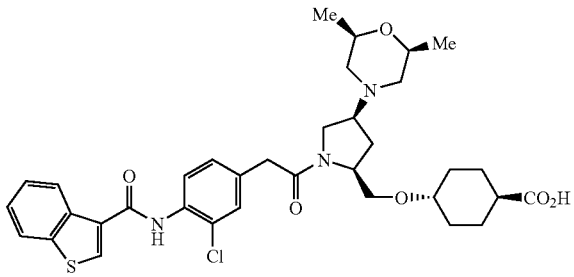

NMR (CDCl$_3$) δ: 1.10-1.47 (total 11H, series of m), 1.58-2.37 (total 9H, series of m), 2.50-2.85 (3H, m), 2.96-3.85 (total 8H, series of m), 4.10-4.40 (1H, m), 7.18 (1H, d, J=8.3 Hz), 7.32-7.36 (1H, m), 7.41 (1H, t, J=7.6 Hz), 7.47 (1H, t, J=7.6 Hz), 7.88 (1H, d, J=7.6 Hz), 8.09 and 8.11 (total 1H, each s, amide isomers), 8.33-8.43 (2H, m), 8.47 (1H, d, J=8.1 Hz), 9.75 (1H, br s).

IR (ATR) ν: 2939, 2860, 1637, 1577 cm$^{-1}$.

MS (ESI) m/z: 668 [(M$^+$+1), 35Cl].

Example 93

Trans-4-[1-[[2,5-dichloro-4-[(1-methyl-1H-indol-3-ylcarbonyl)amino]phenyl]acetyl]-(4S)-(cis-3,5-dimethylmorpholin-4-yl)-(2S)-pyrrolidinylmethoxy]cyclohexanecarboxylic acid 2-[(S)-2-hydroxy-1-methylethylamino]propan-1-ol (2S)-amino-1-propanol (Aldrich Co.) (10.0 g, 133.14 mmol) and hydroxyacetone (10.94 mL, 159.77 mmol) were dissolved in methanol (100 mL), and platinum dioxide (100 mg) was added thereto. The mixture was stirred for 23 hours at room temperature under a hydrogen stream at normal pressure. The catalyst was separated by filtration, and then the reaction liquor was concentrated under reduced pressure to obtain the title compound (410 mg, 83%) as a solid. This compound was used in the subsequent reaction without performing further purification.

MS (ESI) m/z: 133 (M$^+$+1).

4-Tert-butoxycarbonyl-2,6-dimethylmorpholine

To 2-[(S)-2-hydroxy-1-methylethylamino]propan-1-ol g, 133.14 mmol), concentrated sulfuric acid (20 mL) was added dropwise over one hour at 0° C. with stirring. The reaction liquor was returned to room temperature over one hour, and then the temperature was elevated to 180° C., where the reaction liquor was heated for 17 hours. The reaction liquor was returned to room temperature, then a 4N-aqueous solution of potassium hydroxide (200 mL) was added, and the mixture was stirred for 30 minutes. Precipitated insoluble matter was separated by filtration, and 1,4-dioxane (500 mL) was added to the obtained mother liquor. Di-tert-butyl dicarbonate (43.6 g, 200 mmol) was further added, and the mixture was stirred for 7 hours. Potassium hydrogen carbonate (50 g) and di-tert-butyl dicarbonate (21.8 g, 100 mmol) were further added to the reaction liquor, and the mixture was stirred for 14 hours. The insoluble was separated by filtration, and the obtained mother liquor was extracted with ethyl acetate. The extract was washed with saturated brine, and dried over anhydrous sodium sulfate, and then the solvent was concentrated under reduced pressure. The obtained residue was purified by flash chromatography (Flash Chromatography System from Biotage AB, column size: 40S; eluent n-hexane to ethyl acetate/n-hexane 6:4), to obtain trans-(2S,5S)-1-(tert-butoxycarbonyl)-2,5-dimethylmorpholin e [5.33 g, 19% (from two processes)] as a less polar fraction, and cis-1-(tert-butoxycarbonyl)-2,5-dimethylmorpholine [1.76 g, 7% (from two processes)] as a more polar fraction, each as an oily matter.

Trans-(2S,5S)-1-(tert-butoxycarbonyl)-2,5-dimethylmorpholine

NMR (CDCl$_3$) δ: 1.29 (6H, d, J=6.4 Hz), 1.47 (9H, s), 3.50-3.43 (2H, m), 3.87-3.77 (4H, m).

MS (ESI) m/z: 116 (M$^+$+1-Boc)

[α]$_D^{25}$=+75.8° (c=0.99, CHCl$_3$).

Cis-1-(tert-butoxycarbonyl)-2,5-dimethylmorpholine

NMR (CDCl₃) δ: 1.30 (6H, d, J=7.4 Hz), 1.466 and 1.474 (total 9H, each s, amide isomers), 3.55 (2H, dd, J=11.5, 3.7 Hz), 3.70 (2H, d, J=11.5 Hz), 3.89-3.97 (2H, m).
MS (ESI) m/z: 116 (M⁺+1-Boc).

Cis-3,5-dimethylmorpholine hydrochloride

Cis-4-tert-butoxycarbonyl-3,5-dimethylmorpholine g, 8.18 mmol) was dissolved in 4N-hydrochloric acid/1,4-dioxane (50 mL), and the solution was stirred for 3 days at room temperature. The reaction liquor was concentrated under reduced pressure and dried, to obtain the title compound as an oily matter. This compound was used in the subsequent reaction without performing further purification.

Trans-4-[1-(tert-butoxycarbonyl)-(4S)-(cis-3,5-dimethylmorpholin-4-yl)-(2S)-pyrrolidinylmethoxy]cyclohexanecarboxylic acid ethyl ester NMR (CDCl₃) δ: 1.00-1.34 (13H, m), 1.46 (9H, s), 1.65-1.80 (1H, m), 1.93-2.52 (8H, m), 2.81-2.99 (4H, m), 3.14-3.25 (2H, m), 3.28-4.02 (4H, m), 4.07-4.17 (3H, m).
MS (ESI) m/z: 469 (M⁺+1).

Trans-4-[1-[[2,5-dichloro-4-[(1-methyl-1H-indol-3-ylcarbonyl)amino]phenyl]acetyl]-(4S)-(cis-3,5-dimethylmorpholin-4-yl)-(2S)-pyrrolidinylmethoxy]cyclohexanecarboxylic acid ethyl ester NMR (CDCl₃) δ: 1.23-1.23 (13H, m), 1.54-2.57 (8H, m), 2.66-3.03 (2H, m), 3.09-3.27 (1H, m), 3.38-3.83 (9H, m), 3.87 (3H, s), 4.02-4.61 (4H, m), 7.31-7.45 (4H, m), 7.77-7.81 (1H, m), 8.10-8.16 (1H, m), 8.19-8.26 (1H, m), 8.82-8.75 (1H, m).
MS (ESI) m/z: 727 (M⁺+1), 729 (M⁺+3).

Trans-4-[1-[[2,5-dichloro-4-[(1-methyl-1H-indol-3-ylcarbonyl)amino]phenyl]acetyl]-(4S)-(cis-3,5-dimethylmorpholin-4-yl)-(2S)-pyrrolidinylmethoxy]cyclohexanecarboxylic acid

[Formula 184]

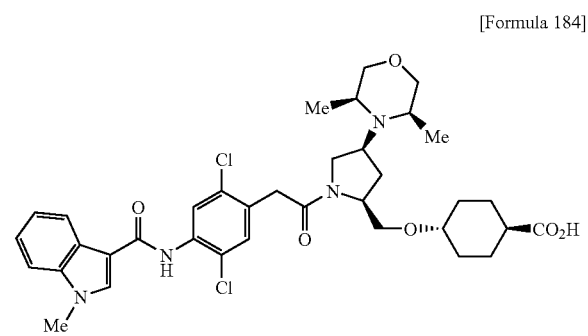

NMR (CDCl₃) δ: 1.04-1.54 (10H, m), 1.60-2.14 (5H, m), 2.15-2.59 (4H, m), 2.71-3.10 (2H, m), 3.09-3.28 (1H, m), 3.28-4.04 (12H, m), 4.07-4.41 (1H, m), 7.32-7.37 (2H, m), 7.38-7.43 (2H, m), 7.80 (1H, s), 8.09-8.15 (1H, m), 8.23 and 8.24 (total 1H, each s, amide isomers), 8.75 and 8.78 (total 1H, each s, amide isomers).
MS (ESI) m/z: 699 (M⁺+1), 701 (M⁺+3).
IR (ATR) cm⁻¹: 2935, 2858, 1720, 1641, 1568, 1533, 1500, 1466.
Anal. Calcd for C₃₆H₄₄Cl₂N₄O₆·H₂O: C, 60.25; H, 6.46; Cl, 9.88; N, 7.81.
Found: C, 60.37; H, 6.40; Cl, 9.65; N, 7.29.

Example 94

Trans-4-[1-[[4-[(benzo[b]thiophen-3-ylcarbonyl)amino]-5-chloro-2-fluorophenyl]acetyl]-(4S)-(piperidin-1-yl)-(2S)-pyrrolidinylmethoxy]cyclohexanecarboxylic acid

Trans-4-[1-(tert-butoxycarbonyl)-(4S)-(piperidin-1-yl)-(2S)-pyrrolidinylmethoxy]cyclohexanecarboxylic acid ethyl ester NMR (CDCl₃) δ: 1.11-1.28 (total 5H, series of m, including 3H of t, J=7.2 Hz, at δ 1.22), 1.46 (total 12H, m), 1.54-1.78 (total 5H, series of m), 1.98-2.09 (total 4H, series of m), 2.20-2.55 (total 7H, series of m), 2.98 (1H, m), 3.20 (1H, m), 3.36-3.95 (total 5H, series of m), 4.11 (2H, q, J=7.2 Hz).
MS (ESI) m/z: 439 (M⁺+1).

Trans-4-[(4S)-(piperidin-1-yl)-(2S)-pyrrolidinylmethoxy]cyclohexanecarboxylic acid ethyl ester dihydrochloride NMR (CDCl₃) δ: 1.24 (3H, t, J=7.2 Hz), 1.28-1.35 (total 2H, series of m), 1.41-1.53 (total 3H, series of m), 1.86-2.13 (total 9H, series of m), 2.25 (1H, tt, J=11.4, 3.6 Hz), 2.45 (2H, m), 2.61 (1H, m), 2.98-3.11 (total 2H, series of m), 3.39 (1H, m), 3.56 (1H, d, J=12.0 Hz), 3.64-3.85 (total 3H, series of m), 4.05-4.33 (total 5H, series of m, including 2H of q, J=7.2 Hz, at δ 4.11), 9.32 (1H, m), 10.59 (1H, m), 11.62 (1H, m).
MS (ESI) m/z: 339 (M⁺+1-2×HCl).

Trans-4-[1-[[4-[(benzo[b]thiophen-3-ylcarbonyl)amino]-5-chloro-2-fluorophenyl]acetyl]-(4S)-(piperidin-1-yl)-(2S)-pyrrolidinylmethoxy]cyclohexanecarboxylic acid ethyl ester NMR (CDCl₃) δ: 1.15-1.28 (total 5H, series of m, including 3H of t, J=7.2 Hz, at δ 1.22), 1.37-1.62 (total 9H, series of m), 1.90-2.03 (total 4H, series of m), 2.17-3.25 (total 9H, series of m), 3.44-3.88 (total 4H, series of m), 4.06-4.41 (total 3H, series of m, including 2H of q, J=7.2 Hz, at δ 4.08), 7.41 (2H, d, J=7.2 Hz), 7.46 (1H, t, J=8.0 Hz), 7.52 (1H, t, J=8.0 Hz), 7.92 (1H, d, J=8.0 Hz), 8.09 and 8.11 (total 1H, each s, amide isomers), 8.33-8.35 (1H, m), 8.42-8.49 (total 2H, series of m).
MS (ESI) m/z: 684 (M⁺+1).
IR (ATR) ν: 2935, 1724, 1676, 1637, 1517 cm⁻¹
Anal. Calcd for C₃₆H₄₃ClFN₃O₅S·0.25H₂O: C, 62.78; H, 6.37; N, 6.10.
Found: C, 62.76; H, 6.42; N, 5.90.

Trans-4-[1-[[4-[(benzo[b]thiophen-3-ylcarbonyl)amino]-5-chloro-2-fluorophenyl]acetyl]-(4S)-(piperidin-1-yl)-(2S)-pyrrolidinylmethoxy]cyclohexanecarboxylic acid

[Formula 185]

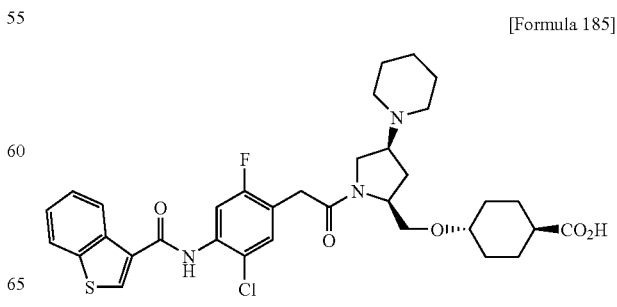

NMR (CDCl$_3$) δ: 1.19-1.30 (total 6H, series of m), 1.68-2.28 (total 10H, series of m), 2.45-3.88 (total 11H, series of m), 4.18-4.47 (total 3H, series of m), 7.40 (1H, d, J=7.6 Hz), 7.45 (1H, dt, J=7.2, 3.6 Hz), 7.51 (1H, dt, J=7.2, 3.6 Hz), 7.91 (1H, dd, J=8.0, 3.2 Hz), 8.10 (1H, d, J=7.6 Hz), 8.34 (1H, d, J=11.6 Hz), 8.43 (1H, m), 8.47 (1H, d, J=8.0 Hz).
MS (LC-MS) m/z: 656 (M$^+$+1).
IR (ATR) ν: 2935, 1639, 1585, 1518 cm$^{-1}$.
Anal. Calcd for C$_{34}$H$_{39}$ClFN$_3$O$_5$S.0.5H$_2$O: C, 61.39; H, 6.06; N, 6.32.
Found: C, 61.36; H, 6.08; N, 6.11.

Example 95

Trans-4-[1-[[4-[(benzo[b]thiophen-3-ylcarbonyl)amino]-2,5-dichlorophenyl]acetyl]-(4S)-(piperidin-1-yl)-(2S)-pyrrolidinylmethoxy]cyclohexanecarboxylic acid Trans-4-[1-[[4-[(benzo[b]thiophen-3-ylcarbonyl)amino]-2,5-dichlorophenyl]acetyl]-(4S)-(piperidin-1-yl)-(2S)-pyrrolidinylmethoxy]cyclohexanecarboxylic acid ethyl ester NMR (CDCl$_3$) δ: 1.17-1.28 (total 5H, series of m, including 3H of t, J=7.2 Hz, at δ 1.23), 1.37-1.62 (total 6H, series of m), 1.88-2.01 (total 7H, series of m), 2.17-2.71 (total 7H, series of m), 3.14-3.99 (total 7H, series of m), 4.07-4.45 (total 3H, series of m, including 2H of q, J=7.2 Hz, at δ 4.09), 7.42 (1H, m), 7.46 (1H, t, J=8.0 Hz), 7.52 (1H, t, J=8.0 Hz), 7.92 and 8.10 (total 1H, each s, amide isomers), 8.28-8.30 (1H, m), 8.48 (1H, t, J=8.0 Hz), 8.70 and 8.72 (total 1H, each s, amide isomers).
MS (ESI) m/z: 700 (M$^+$+1).
IR (ATR) ν: 2931, 1726, 1672, 1637 cm$^{-1}$.
Anal. Calcd for C$_{36}$H$_{43}$Cl$_2$N$_3$O$_5$S.H$_2$O: C, 61.16; H, 6.31; N, 5.85.
Found: C, 60.16; H, 6.12; N, 5.91.

Trans-4-[1-[[4-[(benzo[b]thiophen-3-ylcarbonyl)amino]-2,5-dichlorophenyl]acetyl]-(4S)-(piperidin-1-yl)-(2S)-pyrrolidinylmethoxy]cyclohexanecarboxylic acid

[Formula 186]

NMR (CDCl$_3$) δ: 1.19-1.30 (total 2H, series of m), 1.37-1.47 (total 3H, series of m), 1.69-2.34 (total 10H, series of m), 2.43-2.78 (total 5H, series of m), 3.14-3.98 (total 8H, series of m), 4.20-4.51 (total 2H, series of m), 7.40 (1H, m), 7.42-7.53 (total 2H, series of m), 7.90 (1H, dd, J=8.0, 4.6 Hz), 8.09 (1H, d, J=2.8 Hz), 8.30 (1H, d, J=10.0 Hz), 8.47 (1H, d, J=8.8 Hz), 8.69 (1H, d, J=4.4 Hz).
MS (ESI) m/z: 672 (M$^+$+1).
IR (ATR) ν: 2933, 1641, 1570 cm$^{-1}$.
Anal. Calcd for C$_{34}$H$_{39}$Cl$_2$N$_3$O$_5$S.0.5H$_2$O: C, 59.91; H, 5.91; N, 6.16.
Found: C, 60.08; H, 5.91; N, 5.86.

Example 96

Trans-4-[1-[[2,5-dichloro-4-[(1-methyl-1H-indol-3-ylcarbonyl)amino]phenyl]acetyl]-(4S)-(piperidin-1-yl)-(2S)-pyrrolidinylmethoxy]cyclohexanecarboxylic acid Trans-4-[1-[[2,5-dichloro-4-[(1-methyl-1H-indol-3-ylcarbonyl)amino]phenyl]acetyl]-(4S)-(piperidin-1-yl)-(2S)-pyrrolidinylmethoxy]cyclohexanecarboxylic acid ethyl ester NMR (CDCl$_3$) δ: 1.13-1.71 (total 12H, series of m), 1.81-2.08 (total 6H, series of m), 2.16-2.70 (total 7H, series of m), 2.88-3.99 (total 10H, series of m, including 3.87, 3H, s), 4.04-4.43 (total 3H, series of m, including 4.09, 2H, q, J=7.2 Hz), 7.32-7.37 (2H, m), 7.38-7.42 (2H, m), 7.78-7.80 (1H, m), 8.11-8.16 (1H, m), 8.23 (1H, s), 8.78 (1H, s).
MS (ESI) m/z: 697 (M$^+$+1).
IR (ATR) ν: 2933, 1726, 1639 cm$^{-1}$.
Anal. Calcd for C$_{37}$H$_{46}$Cl$_2$N$_4$O$_5$1.5H$_2$O: C, 61.32; H, 6.81; N, 7.73.
Found: C, 61.00; H, 6.48; N, 7.56.

Trans-4-[1-[[2,5-dichloro-4-[(1-methyl-1H-indol-3-ylcarbonyl)amino]phenyl]acetyl]-(4S)-(piperidin-1-yl)-(2S)-pyrrolidinylmethoxy]cyclohexanecarboxylic acid

[Formula 187]

NMR (CDCl$_3$) δ: 1.16-1.52 (total 6H, series of m), 1.60-1.79 (total 4H, series of m), 1.90-2.79 (total 12H, series of m), 3.08-3.61 (total 4H, series of m), 3.66-3.77 (2H, m), 3.84-3.99 (total 4H, series of m), 4.17-4.51 (2H, m), 7.31-7.44 (total 5H, series of m), 7.78 (1H, d, J=3.4 Hz), 8.10-8.24 (2H, m), 8.77 (1H, d, J=11.5 Hz).
MS (ESI) m/z: 669 (M$^+$+1).
IR (ATR) ν: 2937, 1670, 1641, 1508 cm$^{-1}$.
Anal. Calcd for C$_{35}$H$_{42}$Cl$_2$N$_4$O$_5$.0.25H$_2$O: C, 62.36; H, 6.35; N, 8.31.
Found: C, 62.31; H, 6.27; N, 8.36.

Example 97

Trans-4-[1-[[5-chloro-2-fluoro-4-[(1-methyl-1H-indol-3-ylcarbonyl)amino]phenyl]acetyl]-(3R)-ethoxy-(4R)-(piperidin-1-yl)-(2R)-pyrrolidinylmethoxy]cyclohexanecarboxylic acid 1,2-O-isopropylidene-5-O-(p-toluenesulfonyl)-α-D-xylofuranose

[Formula 188]

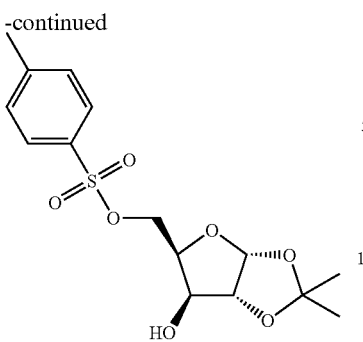

1,2-O-isopropylidene-α-D-xylofuranose (380 mg, 2.0 mmol) was dissolved in methylene chloride (20 mL), and under a nitrogen stream, triethylamine (0.56 mL, 4.0 mmol), p-toluenesulfonyl chloride (305 mg, 1.9 mmol) and 4-(dimethylamino)pyridine (24 mg, 0.20 mmol) were added at 0° C. with stirring. The mixture was allowed to warm to 5° C., and stirred for 13 hours. The reaction liquor was poured onto ice water, and extracted with methylene chloride. The extract was washed with 1N-hydrochloric acid, a saturated aqueous solution of sodium hydrogen carbonate, and saturated brine in this order, and dried over anhydrous sodium sulfate. The solvent was concentrated under reduced pressure, and recrystallization was performed from ethylacetate/n-hexane, to obtain the title compound (317 mg, 46%) as a solid.

NMR (CDCl$_3$) δ: 1.30 (3H, s), 1.47 (3H, s), 2.28 (1H, d, J=3.4 Hz), 2.46 (3H, s), 4.13 (1H, dd, J=13.5, 8.3 Hz), 4.30-4.37 (3H, m), 4.51 (1H, d, J=3.6 Hz), 5.87 (1H, d, J=3.4 Hz), 7.36 (2H, d, J=8.6 Hz), 7.80 (2H, d, J=8.6 Hz).

MS (ESI) m/z: 363 (M$^+$+1+H$_2$O)

5-Azido-1,2-O-isopropylidene-α-D-xylofuranose

[Formula 189]

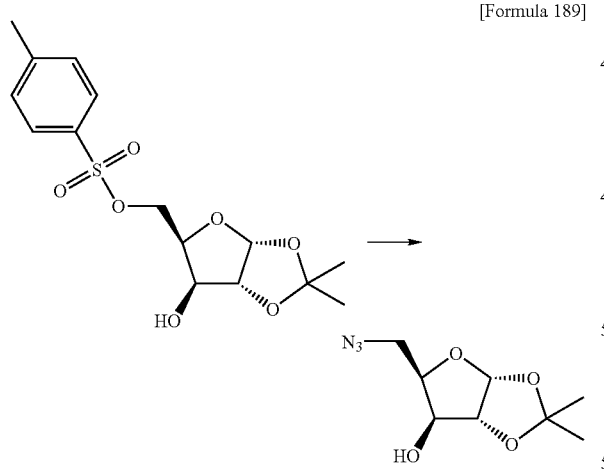

1,2-O-isopropylidene-5-O-(p-toluenesulfonyl)-α-D-xylofuranose (317 mg, 0.92 mmol) was dissolved in DMF (10 mL), and sodium azide (179 mg, 2.76 mmol) was added at room temperature with stirring. The mixture was heated to 80° C., and stirred for 22 hours. The reaction liquor was returned to room temperature, and then poured onto ice water. The mixture was extracted with ethyl acetate. The extract was washed with saturated brine, and dried over anhydrous sodium sulfate. The solvent was concentrated under reduced pressure, to obtain the title compound mg, over yield) as a solid.

NMR (CDCl$_3$) δ: 1.32 (3H, s), 1.50 (3H, s), 2.15 (1H, d, J=5.1 Hz), 3.59 (1H, dd, J=12.7, 5.6 Hz), 3.64 (1H, dd, J=12.7, 5.6 Hz), 4.24-4.28 (1H, m), 4.30 (1H, dd, J=6.9, 2.9 Hz), 4.52 (1H, d, J=3.7 Hz), 5.96 (1H, d, J=3.9 Hz).

MS (FAB) m/z: 216 (M$^+$+1).

5-Azido-3-O-ethyl-1,2-O-isopropylidene-α-D-xylofuranose

[Formula 190]

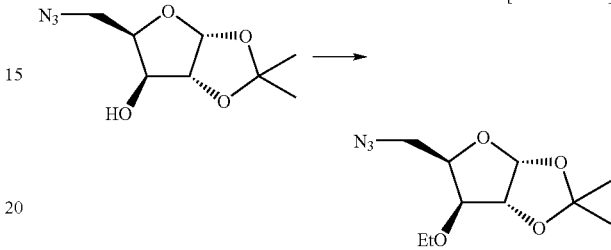

5-Azido-1,2-O-isopropylidene-α-D-xylofuranose (53.0 g, 241.4 mmol) was dissolved in DMF (500 mL), and under a nitrogen stream, ethyl iodide (57.9 mL, 724.2 mmol) and 60% sodium hydride (oily: 19.3 g, 482.8 mmol) were added at 0° C. with stirring. The mixture was stirred for two hours at room temperature. Ice pieces were added to the reaction liquor, and the mixture was stirred for 20 minutes, and then extracted with ethyl acetate. The extract was washed with ice water and saturated brine in this order, and dried over anhydrous sodium sulfate. The solvent was concentrated under reduced pressure, and the obtained residue was purified by silica gel chromatography (200 g, ethyl acetate:n-hexane=1:4, v/v), to obtain the title compound [50.7 g, 86% (from two processes)] as an oily matter.

NMR (CDCl$_3$) δ: 1.21 (3H, t, J=6.8 Hz), 1.33 (3H, s), 1.51 (3H, s), 3.46-3.50 (1H, m), 3.52 (2H, d, J=6.8 Hz), 3.70 (1H, dq, J=6.8, 1.9 Hz), 3.82 (1H, d, J=3.2 Hz), 4.58 (1H, dt, J=6.6, 3.2 Hz), 4.58 (1H, d, J=3.9 Hz), 5.91 (1H, d, J=3.7 Hz).

Methyl 5-azido-5-deoxy-3-O-ethyl-D-xylofuranoside

[Formula 191]

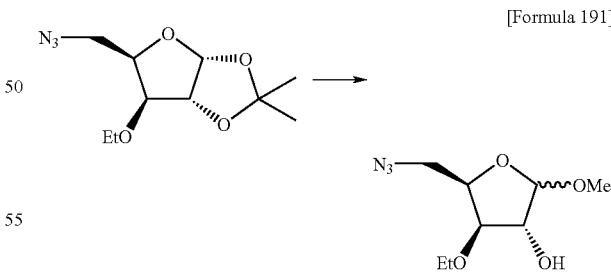

Under a nitrogen stream, acetyl chloride (0.85 mL, 12.0 mmol) was added dropwise to methanol (10 mL) at 0° C. with stirring. To the reaction liquor, a methanol solution (2 mL) of 5-azido-3-O-ethyl-1,2-O-isopropylidene-α-D-xylofuranose (487 mg, 2.0 mmol) was added dropwise at 0° C., and the mixture was stirred for 25 hours while slowly returning the mixture to room temperature. Potassium carbonate was added to the reaction liquor to adjust the reaction liquor to pH 8, the insoluble was separated by filtration, and the mother liquor was concentrated. The obtained residue was purified by silica gel chromatography (20 g, ethyl acetate:n-hexane=1:3, v/v), to obtain an α-anomer (64 mg) as a less polar fraction, a β-anomer (50 mg) as a more polar fraction, and a mixture (233 mg), all as oily matters (total yield=80%).

α-Anomer

NMR (CDCl$_3$) δ: 1.21 (3H, t, J=6.8 Hz), 2.70 (1H, d, J=7.3 Hz), 3.41 (1H, d, J=2.7 Hz), 3.43 (1H, d, J=1.7 Hz), 3.46-3.57 (4H, m), 3.73-3.81 (1H, m), 3.87 (1H, dd, J=5.9, 3.9 Hz), 4.16 (1H, dd, J=5.9, 3.9 Hz), 4.31 (1H, q, J=5.9 Hz), 4.96 (1H, d, J=4.6 Hz).

MS (FAB) m/z: 218 (M$^+$+1)

β-Anomer

NMR (CDCl$_3$) δ: 1.21 (3H, t, J=6.8 Hz), 2.17 (1H, m), 3.37-3.58 (6H, m), 3.65-3.72 (1H, m), 3.91 (1H, dd, J=6.6, 3.4 Hz), 4.21 (1H, s), 4.43 (1H, dq, J=7.6, 1.7 Hz), 4.81 (1H, d, J=1.7 Hz).

MS (FAB) m/z: 218 (M$^+$+1).

Methyl 5-azido-5-deoxy-3-O-ethyl-2-O-trifluoromethane-sulfonyl-D-xylofuranoside

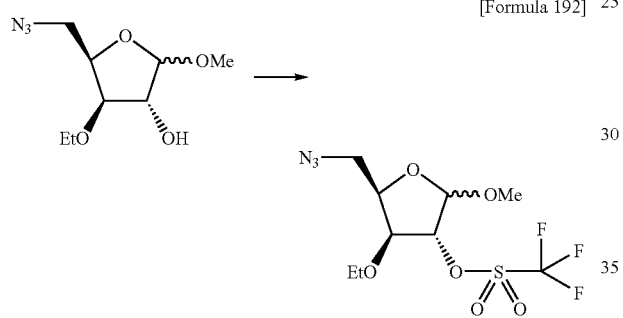

[Formula 192]

Methyl 5-azido-5-deoxy-3-O-ethyl-D-xylofuranoside was dissolved in methylene chloride (1.5 l), and under a nitrogen stream, pyridine (40.4 mL, 249.9 mmol) was added dropwise over 15 minutes at −50° C. with stirring. The reaction liquor was stirred for 10 minutes, and then trifluoromethanesulfonic anhydride (40.1 mL, 249.9 mmol) was added dropwise over one hour at the same temperature. The mixture was stirred for two hours, while the temperature was slowly elevated to −30° C. At −30° C., methanol (20 mL) was added to the reaction liquor, and the mixture was stirred for 30 minutes, subsequently allowed to warm to 0° C., and stirred for 30 minutes. The reaction liquor was poured onto sodium hydrogen carbonate (50 g)-ice water (500 mL), and the mixture was extracted with methylene chloride. The extract was washed with a saturated aqueous solution of sodium hydrogen carbonate and saturated brine in this order, and dried over anhydrous sodium sulfate. The solvent was concentrated under reduced pressure, and the obtained residue was purified by silica gel chromatography (700 g, ethyl acetate:n-hexane=1:4, v/v), to obtain the title compound (72.2 g, 99%) as an oily matter.

α-Anomer

NMR (CDCl$_3$) δ: 1.23 and 1.24 (total 3H, each t, J=7.1 and 6.9 Hz respectively, amide isomers), 3.45 (2H, s), 3.47 (2H, s), 3.48 (1H, q, J=7.4 Hz), 3.51-3.76 and 4.47 (total 1H, dd and q, J=6.4, 2.0 and 6.1 Hz respectively, amide isomers), 4.35 (1H, m), 5.02 and 5.07 (total 1H, t and d, J=4.6 and 4.4 Hz respectively, amide isomers), 5.05 and 5.14 (total 1H, each s, amide isomers).

Methyl 2,5-dideoxy-3-O-ethyl-2,5-imino-D-lyxofuranoside

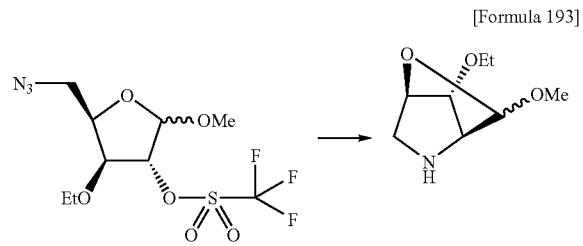

[Formula 193]

Methyl 5-azido-5-deoxy-3-O-ethyl-2-O-trifluoromethanesulfonyl-D-xylofuranoside was dissolved in ethyl acetate (1 l), and 5% palladium/carbon (15 g) was added thereto. The mixture was stirred for 17 hours at room temperature under a hydrogen stream at normal pressure. The catalyst was separated by filtration, and the mother liquor was concentrated under reduced pressure and dried, to obtain the title compound as an oily matter. This compound was used in the subsequent reaction without performing further purification.

Methyl

N-benzyloxycarbonyl-2,5-dideoxy-3-O-ethyl-2,5-imino-D-lyxofuranoside

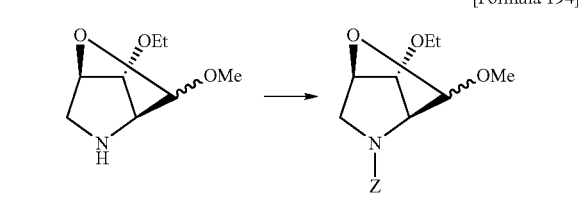

[Formula 194]

Methyl 2,5-dideoxy-3-O-ethyl-2,5-imino-D-lyxofuranoside was dissolved in 1,4-dioxane (500 mL), and a saturated aqueous solution of sodium hydrogencarbonate (500 mL) and di-tert-butyl dicarbonate (183.6 g, 309.9 mmol) were added. The mixture was stirred for 3 hours. The insoluble was separated by filtration, and then the mother liquor was extracted with ethyl acetate. The extract was washed with saturated brine, and dried over anhydrous sodium sulfate. The solvent was concentrated under reduced pressure, and the obtained residue was purified by silica gel chromatography (1 kg, ethyl acetate:n-hexane=1:3, v/v), to obtain a β-anomer [34.98 g, 55% (from two steps)] as a less polar fraction, and an α-anomer [24.89 g, 39.26 (from two steps)] as a more polar fraction, all as oily matters.

α-Anomer

NMR (CDCl$_3$) δ: 1.13-1.18 (3H, m), 1.69 (2H, t, J=5.9 Hz) 3.29 (1H, t, J=9.5 Hz), 3.34 and 3.37 (total 3H, each s, amide isomers), 3.40-3.69 (3H, m), 4.19 and 4.31 (total 1H, each dd, J=8.8, 2.3 and 12.0, 2.3 Hz, amide isomers), 4.23 and 4.53 (total 1H, each s, amide isomers), 5.16 (2H, ABq, J=13.2 Hz), 7.16-7.56 (5H, m).

MS (ESI) m/z: 308 (M$^+$+1)

β-Anomer

NMR (CDCl$_3$) δ: 1.159 and 1.162 (total 3H, each t, J=6.8 and 7.1 Hz respectively, amide isomers) 3.37 and 3.41 (total 3H, each s, amide isomers), 3.44-3.67 (4H, m), 3.92-3.95 and 4.51 (total 1H, m and s, amide isomers), 4.33 and 4.38 (total 1H, d and s, J=12.5 Hz, amide isomers), 5.02 and 5.07 (total 1H, each d, J=1.5 and 1.7 Hz respectively, amide isomers), 5.11-5.22 (3H, m), 7.24-7.36 (5H, m).

MS (ESI) m/z: 308 (M$^+$+1)

N-benzyloxycarbonyl-2,5-dideoxy-3-O-ethyl-2,5-imino-D-lyxose

[Formula 195]

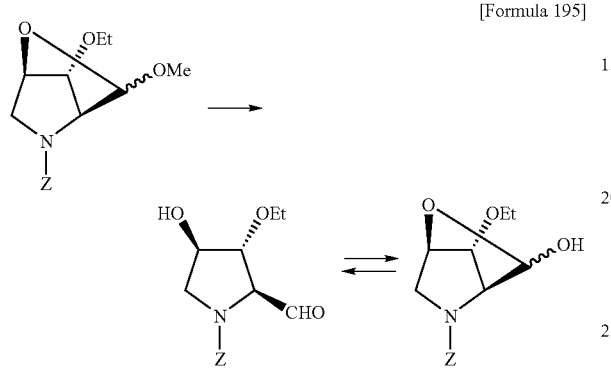

To an aqueous solution (1 mL) of methyl N-benzyloxycarbonyl-2,5-dideoxy-3-O-ethyl-2,5-imino-D-lyxofuranoside, trifluoroacetic acid (1 mL) was added, and the mixture was stirred for three hours. The reaction liquor was concentrated under reduced pressure, and the obtained residue was extracted with methylene chloride. The extract was washed with saturated brine, and dried over anhydrous sodium sulfate. The solvent was concentrated under reduced pressure, and the obtained residue was purified by thin layer chromatography (ethyl acetate:n-hexane=1:1, v/v), to obtain the title compound (92 mg, 77%) as an oily matter.

NMR (CDCl$_3$) δ: 1.198 and 1.203 (total 3H, each t, J=6.9 and 7.1 Hz respectively, amide isomers), 3.39-4.40 (8H, m), 5.11-5.22 (2H, m), 7.26-7.39 (5H, m), 9.50 and 9.60 (total 1H, each s, amide isomers).

MS (ESI) m/z: 294 (M$^+$+1)

N-benzyloxycarbonyl-(3R)-ethoxy-(4R)-hydroxy-(2R)-pyrrolidinemethanol

[Formula 196]

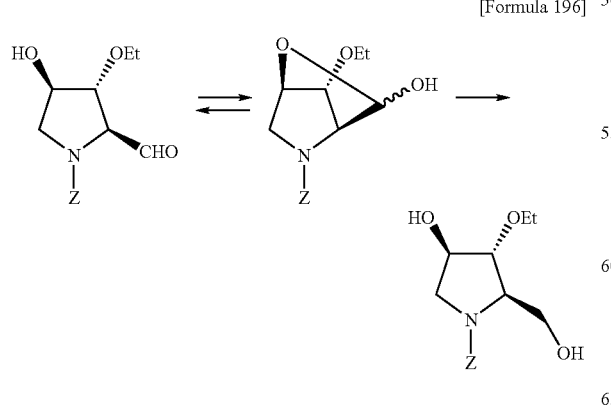

To an ethanol/water mixed solution (2 mL, 1:1) of N-benzyloxycarbonyl-2,5-dideoxy-3-O-ethyl-2,5-imino-D-lyxose (92 mg, 0.314 mmol), sodium borohydride (8.9 mg, 0.236 mmol) was added, and the mixture was stirred for two hours. A saturated aqueous solution of ammonium chloride was added to the reaction liquor, and the mixture was extracted with ethyl acetate. The extract was washed with saturated brine, and dried over anhydrous sodium sulfate. The solvent was concentrated under reduced pressure, and the obtained residue was purified by thin layer chromatography (ethyl acetate:n-hexane=1:1, v/v), to obtain the title compound (56 mg, 60%) as an oily matter.

NMR (CDCl$_3$) δ: 1.19 (3H, t, J=6.9 Hz), 1.65 (1H, br), 3.49-3.62 (3H, m), 3.65-4.26 (6H, m), 5.12 (2H, m), 7.26-7.52 (5H, m).

MS (ESI) m/z: 296 (M$^+$+1)

N-benzyloxycarbonyl-(3R)-ethoxy-(4R)-hydroxy-(2R)-tri phenylmethyloxypyrrolidine

[Formula 197]

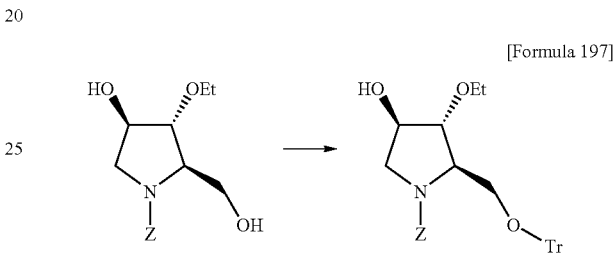

N-benzyloxycarbonyl-(3R)-ethoxy-(4R)-hydroxy-(2R)-pyrrolidinemethanol (16.3 g, 55.1 mmol) was dissolved in methylene chloride (500 mL), and under a nitrogen stream, trityl chloride g, 49.6 mmol), triethylamine (23.0 mL, 165.3 mmol) and dimethylaminopyridine (673 mg, 5.51 mmol) were added at 0° C. with stirring. The mixture was stirred for 15 hours at room temperature. The reaction liquor was poured onto water, and extracted with methylene chloride. The extract was washed with saturated brine, and dried over anhydrous sodium sulfate. The solvent was concentrated under reduced pressure, and the obtained residue was purified by silica gel chromatography (300 g, ethyl acetate:n-hexane=1:1, v/v), to obtain the title compound (21.85 g, 74%) as a glassy solid.

NMR (CDCl$_3$) δ: 1.13 (3H, t, J=6.6 Hz), 3.25 (1H, d, J=9.3 Hz), 3.46 (2H, t, J=6.1 Hz), 3.58 (1H, d, J=11.5 Hz), 3.62-4.00 (5H, m), 4.05-4.15 (1H, m), 4.95 and 5.06 (total 1H, each d, J=12.7 and 11.8 Hz respectively, amide isomers), 5.11 and 5.18 (total 1H, each d, J=12.0 and 12.7 Hz respectively, amide isomers), 7.14-7.46 (20H, m).

MS (ESI) m/z: 561 (M$^+$+1+Na)

(4R)-Benzyloxy-N-benzyloxycarbonyl-(3R)-ethoxy-(2R)-triphenylmethyloxypyrrolidine

[Formula 198]

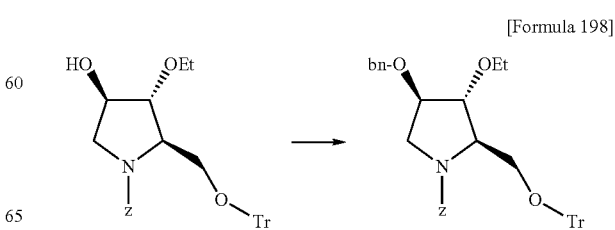

N-benzyloxycarbonyl-(3R)-ethoxy-(4R)-hydroxy-(2R)-tri phenylmethyloxypyrrolidine (21.85 g, 40.6 mmol) was dissolved intetrahydrofuran (500 mL), and under a nitrogen stream, benzyl bromide (9.66 mL, 81.2 mmol), 606 sodium hydride (2.44 g, 60.9 mmol) and n-tetrabutylammonium iodide (296 mg, 0.801 mmol) were added at 0° C. with stirring. The mixture was stirred for 2.5 hours. Benzylbromide (9.66 mL, 81.2 mmol) and 600 sodium hydride (2.44 g, 60.9 mmol) were further added to the reaction liquor, and the mixture was stirred for one hour. DMF (100 mL) was added to the reaction liquor, and the mixture was stirred for 14 hours. Ice pieces were added to the reaction liquor, and the mixture was stirred for 15 minutes, and then extracted with ethylacetate. The extract was washed with ice water and saturated brine in this order, and dried over an hydrous sodium sulfate. The solvent was concentrated under reduced pressure, and the obtained residue was purified by silica gel chromatography (300 g, ethyl acetate:n-hexane=1:3, v/v), to obtain the title compound (40.02 g, over yield) as an oily matter.

NMR (CDCl$_3$) δ: 1.20 (3H, t, J=7.1 Hz), 3.20 (1H, t, J=8.1 Hz), 3.43-4.20 (6H, m), 4.38 (1H, m), 4.40 (1H, s), 4.96-5.08 (2H, m), 7.13-7.47 (25H, m).

MS (ESI) m/z: 628 (M$^+$+1)

(4R)-benzyloxy-N-benzyloxycarbonyl-(3R)-ethoxy-(2R)-pyrrolidinylmethanol

[Formula 199]

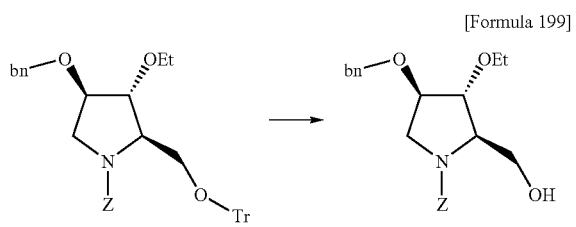

(4R)-benzyloxy-N-benzyloxycarbonyl-(3R)-ethoxy-(2R)-triphenylmethyloxypyrrolidine (40.0 g, 40.6 mmol) was dissolved in 1,4-dioxane (400 mL), and 4N-hydrochloric acid/1,4-dioxane mL) was added thereto at 0° C. The mixture was stirred for 30 minutes. The reaction liquor was concentrated under reduced pressure, and the obtained residue was purified by silica gel chromatography (300 g, ethyl acetate:n-hexane=1:2, v/v), to obtain the title compound (13.6 g, 87%) as an oily matter.

NMR (CDCl$_3$) δ: 1.18 (3H, t, J=6.9 Hz), 3.49-4.04 (9H, m), 4.54 (2H, s), 5.14 (2H, s), 7.25-7.43 (10H, m).

MS (ESI) m/z: 386 (M$^+$+1)

4-[(4R)-benzyloxy-N-benzyloxycarbonyl-(3R)-ethoxy-(2R)-pyrrolidinylmethoxy]benzoic acid ethyl ester

[Formula 200]

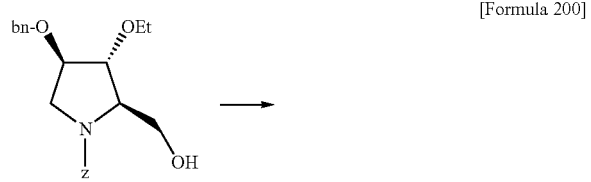

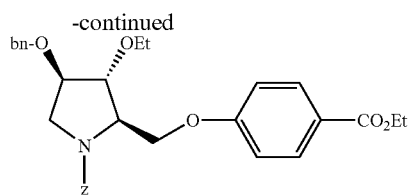

(4R)-benzyloxy-N-benzyloxycarbonyl-(3R)-ethoxy-(2R)-pyrrolidinylmethanol (13.4 g, 34.8 mmol), p-hydroxybenzoic acid ethyl ester (11.6 mg, 69.5 mmol) and triphenylphosphine (18.2 g, 69.5 mmol) were dissolved in tetrahydrofuran (500 mL), and diisopropylazodicarboxylic acid (13.7 mL, 69.5 mmol) was added thereto at room temperature. The reaction liquor was heated to 60° C., and stirred for 30 minutes. The reaction liquor was returned to room temperature, and then the solvent was concentrated under reduced pressure. The obtained residue was dissolved in ether, and the solution was washed with a 1N-aqueous solution of sodium hydroxide, and saturated brine in this order, and dried over anhydrous sodium sulfate. The solvent was concentrated under reduced pressure, and the obtained residue was purified by silica gel chromatography (300 g, ethyl acetate:n-hexane=1:4 v/v, and 500 g, ethyl acetate:n-hexane=1:10 v/v), to obtain the title compound (14.67 g, 79%) as an oily matter.

NMR (CDCl$_3$) δ: 1.15 and 1.17 (total 3H, each t, each J=7.6 Hz, amide isomers), 1.39 (3H, m), 3.44-3.83 (4H, m), 4.02 (1H, d, J=4.4 Hz), 4.08-4.52 (6H, m), 4.54-4.60 (2H, m), 5.09-5.24 (2H, m), 6.80 and 6.99 (total 2H, each d, each J=8.5 Hz, amide isomers), 7.23-7.38 (10 H, m), 7.85 and 7.99 (total 2H, each d, J=8.7 and 8.5 Hz respectively, amide isomers).

MS (ESI) m/z: 534 (M$^+$+1)

4-[(3R)-ethoxy-(4R)-hydroxy-(2R)-pyrrolidinylmethoxy]benzoic acid ethyl ester

4-[(4R)-benzyloxy-N-benzyloxycarbonyl-(3R)-ethoxy-(2R-pyrrolidinylmethoxy]benzoic acid ethyl ester (14.67 g, 27.5 mmol) was dissolved in ethanol/acetic acid (500 mL, 4:1), and 10% palladium hydroxide/carbon (14.7 g) was added thereto. The mixture was stirred for three days at room temperature under a hydrogen stream at normal pressure. The catalyst was separated by filtration, and the mother liquor was concentrated under reduced pressure, to obtain the title compound as an oily matter. This compound was used in the subsequent reaction without performing further purification.

MS (ESI) m/z: 310 (M$^+$+1)

4-[1-Tert-butoxycarbonyl-(3R)-ethoxy-(4R)-hydroxy-(2R)-pyrrolidinylmethoxy]cyclohexanecarboxylic acid ethyl ester (mixture of cis/trans isomers)

To 4-[(3R)-ethoxy-(4R)-hydroxy-(2R)-pyrrolidinylmethoxy]benzoic acid ethyl ester (27.5 mmol), ethanol/acetic acid (600 mL, 5:1), concentrated hydrochloric acid (10 mL) and 56 rhodium/alumina (10 g) were added, and the mixture was stirred for 18 hours at room temperature under a hydrogen stream of 4 kg/cm$^2$. The catalyst was separated by filtration, and them other liquor was concentrated under reduced pressure, to obtain 4-[(3R)-ethoxy-(4R)-hydroxy-(2R)-pyrrolidinylmethoxy]cyclohexanecarboxylic acid ethyl ester (mixture of cis/trans isomers) as an oily matter.

This 4-[(3R)-ethoxy-(4R)-hydroxy-(2R)-pyrrolidinylmethoxy]cyclohexanecarboxylic acid ethyl ester (mixture of cis/trans isomers) (27.5 mmol) was dissolved in 1,4-dioxane (500 mL), and a saturated aqueous solution of sodium hydrogen carbonate (500 mL) and di-tert-butyl dicarbonate (6.00 g, 27.5 mmol) were added. The mixture was stirred for 13 hours at room temperature. The insoluble in the reaction liquor was separated by filtration, and then the reaction liquor was extracted with ethyl acetate. The extract was washed with saturated brine, and dried over anhydrous sodium sulfate. The solvent was concentrated under reduced pressure, and the obtained residue was purified by silica gel chromatography (200 g, ethyl acetate:n-hexane=1:2, v/v), to obtain the title compound [7.09 g, 62% (from three processes)] as an oily matter.

MS (ESI) m/z: 416 (M$^+$+1)

Trans-4-[1-tert-butoxycarbonyl-(3R)-ethoxy-(4R)-hydroxy-(2R)-pyrrolidinylmethoxy]cyclohexanecarboxylic acid ethyl ester 4-[1-Tert-butoxycarbonyl-(3R)-ethoxy-(4R)-hydroxy-(2R)-pyrrolidinylmethoxy]cyclohexanecarboxylic acid ethyl ester (mixture of cis/trans isomers) (7.09 g, 17.1 mmol) was dissolved in ethanol (300 mL), and sodium ethoxide (11.6 g, 171 mmol) was added thereto. The mixture was heated to reflux for 17 hours while stirring. The reaction liquor was returned to room temperature, and then the reaction liquor was concentrated under reduced pressure. The obtained residue was diluted with water and ethyl acetate, 1N-hydrochloric acid was added to adjust the dilution to pH 2, and then the mixture was extracted with ethyl acetate. The extract was washed with saturated brine, and dried over anhydrous sodium sulfate, and then the solvent was concentrated under reduced pressure. The concentrate was dried to obtain 4-[1-tert-butoxycarbonyl-(3R)-ethoxy-(4R)-hydroxy-(2R)-pyrrolidinylmethoxy]cyclohexanecarboxylic acid (mixture of cis/trans isomers)

4-[1-Tert-butoxycarbonyl-(3R)-ethoxy-(4R)-hydroxy-(2R)-pyrrolidinylmethoxy]cyclohexanecarboxylic acid (mixture of cis/trans isomers) was dissolved in DMF (150 mL), and potassium hydrogen carbonate (17.1 g, 171 mmol) and ethyl iodide (6.84 mL, 85.5 mmol) were added thereto at room temperature. The mixture was stirred for 18 hours at 50° C. The reaction liquor was returned to room temperature, water was added, and then the mixture was extracted with ethyl acetate. The extract was washed with ice water and saturated brine in this order, and dried over anhydrous sodium sulfate. The solvent was concentrated under reduced pressure, and the obtained residue was subjected to purification by silica gel chromatography (150 g, ethyl acetate:n-hexane=1:2, v/v), followed by separation of the respective isomers by recycle HPLC (chloroform), to obtain the title compound (less polar fraction) [3.77 g, 53% (from two processes)] as an oily matter, and a cis isomer (more polar fraction) [3.22 g, 45% (from two processes)] as an oily matter.

NMR (CDCl$_3$) δ: 1.14-1.35 (8H, m), 1.39-1.56 (11H, m), 1.94-2.11 (4H, m), 2.19-2.29 (1H, m), 3.32 (1H, m), 3.43 (1H, t, J=12.0 Hz), 3.48-3.71 (5H, m), 3.75-3.77 (total 1H, each s, amide isomers), 3.84-4.20 (4H, m), 4.65 and 4.93 (total 1H, each d, each J=11.8 Hz, amide isomers).

MS (ESI) m/z: 416 (M$^+$+1).

Trans-4-[1-tert-butoxycarbonyl-(3R)-ethoxy-(4S)-hydroxy-(2R)-pyrrolidinylmethoxy]cyclohexanecarboxylic acid ethyl ester Trans-4-[1-tert-butoxycarbonyl-(3R)-ethoxy-(4R)-hydroxy-(2R)-pyrrolidinylmethoxy]cyclohexanecarboxylic acid ethyl ester (480 mg, 1.16 mmol) was dissolved in tetrahydrofuran (5 mL), and while stirring the solution at 0° C., triphenylphosphine (304 mg, 1.16 mmol), formic acid (43.8 μl, 1.16 mmol) and diisopropylazodicarboxylic acid (228 mL, 1.16 mmol) were added thereto. The reaction liquor was stirred for 30 minutes at room temperature, and then stirred for one hour at 60° C. The reaction liquor was cooled again to 0° C., and triphenylphosphine (304 mg, 1.16 mmol), formic acid (43.8 μl, 1.16 mmol) and diisopropylazodicarboxylic acid (228 mL, 1.16 mmol) were added. The mixture was stirred for one hour at room temperature. The reaction liquor was returned to room temperature, and then the solvent was concentrated under reduced pressure. The obtained residue was purified by flash chromatography (ethyl acetate:n-hexane=1:2, v/v), to obtain trans-4-[1-tert-butoxycarbonyl-(3R)-ethoxy-(4S)-formyloxy-(2R)-pyrrolidinylmethoxy]cyclohexanecarboxylic acid methyl ester (210 mg), including impurities, as an oily matter.

NMR (CDCl$_3$) δ: 0.45-0.45 (23H, m), 1.91-2.31 (5H, m), 3.15-3.94 (5H, m), 4.11 (2H, q, J=7.3 Hz), 5.33-5.45 (1H, m), 9.22 (1H, s).

MS (ESI) m/z: 444 (M$^+$+1).

This trans-4-[1-tert-butoxycarbonyl-(3R)-ethoxy-(4S)-formyloxy-(2R)-pyrrolidinylmethoxy]cyclohexanecarboxylic acid ethyl ester (210 mg) was dissolved in ethanol (10 mL), and potassium hydrogen carbonate (237 mg, 2.37 mmol) was added thereto at room temperature. The mixture was stirred for 14 hours, the reaction liquor was concentrated under reduced pressure, and the obtained residue was purified by flash chromatography (ethyl acetate:n-hexane=1:2, v/v), to obtain the title compound [180 mg, 92% (from two processes)] as an oily matter.

NMR (CDCl$_3$) δ: 1.17-1.35 (10H, m), 1.43 (9H, s), 1.94-2.07 (4H, m), 2.24 (1H, m), 2.64 and 2.70 (total 1H, each d, J=7.8 and 8.1 Hz respectively, amide isomers), 3.17-3.28 (2H, m), 3.35-3.65 (6H, m), 3.83 and 3.88 (total 1H, each m, amide isomers), 4.11 (2H, q, J=7.1 Hz), 4.31 (1H, m).

MS (ESI) m/z: 444 (M$^+$+1).

Trans-4-[1-tert-butoxycarbonyl-(3R)-ethoxy-(4S)-methanesulfonyloxy-(2R)-pyrrolidinylmethoxy]cyclohexanecarboxylic acid ethyl ester

[Formula 201]

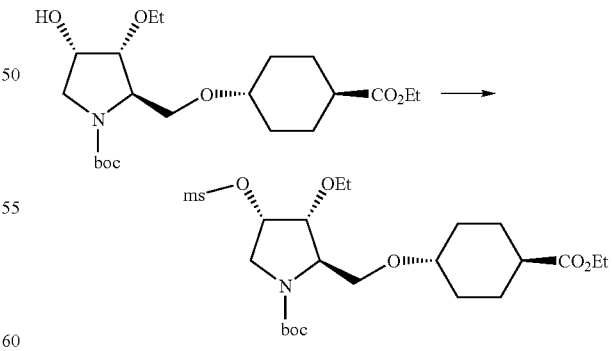

Trans-4-[1-tert-butoxycarbonyl-(3R)-ethoxy-(4S)-hydroxy-(2R)-pyrrolidinylmethoxy]cyclohexanecarboxylic acid ethyl ester (205 mg, 0.493 mmol) was dissolved in methylene chloride mL), and under a nitrogen stream, triethylamine (0.21 mL, 1.48 mmol) and methanesulfonyl chloride (57.3 mL, 0.740 mmol) were added while stirring at 0° C. The mixture was stirred for 21 hours at room temperature. The reaction liquor was poured onto ice water, and the mixture was extracted with methylene chloride. The extract was washed with saturated brine, and dried over anhydrous sodium sulfate. The solvent was concentrated under reduced pressure, to obtain the title compound (197 mg, 81%) as an oily matter.

NMR (CDCl$_3$) δ: 1.39-1.16 (8H, m), 1.46 (9H, s), 1.91-2.10 (4H, m), (3H, m), 5.18-5.26 (1H, m).

MS (ESI) m/z: 494 (M$^+$+1).

Trans-4-[(4R)-azido-1-tert-butoxycarbonyl-(3R)-ethoxy-(2R)-pyrrolidinylmethoxy]cyclohexanecarboxylic acid ethyl ester

[Formula 202]

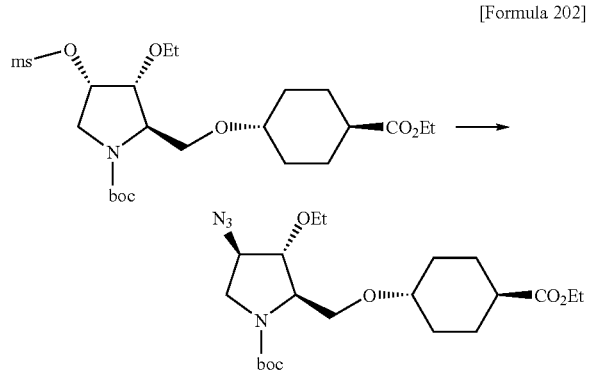

Trans-4-[1-tert-butoxycarbonyl-(3R)-ethoxy-(4S)-methanesulfonyloxy-(2R)-pyrrolidinylmethoxy]cyclohexanecarboxylic acid ethyl ester (197 mg, 0.399 mmol) was dissolved in DMF mL), and under a nitrogen stream, sodium azide (78 mg, 1.20 mmol) was added with stirring. The mixture was stirred for 17 hours at 60° C. The reaction liquor was returned to room temperature, and then poured onto ice water, and the mixture was extracted with ethyl acetate. The extract was washed with ice water, and saturated brine in this order, and dried over anhydrous sodium sulfate. The solvent was concentrated under reduced pressure, and the obtained residue was purified by silica gel chromatography (10 g, ethyl acetate:n-hexane=1:4, v/v), to obtain the title compound (49 mg, 28%) as an oily matter.

NMR (CDCl$_3$) δ: 1.18-1.32 (8H, m), 1.43-1.56 (11H, m), 1.96-2.16-3.98 (2H, m), 4.11 (2H, q, J=7.1 Hz).

MS (ESI) m/z: 441 (M$^+$+1).

Trans-4-[(4R)-amino-1-tert-butoxycarbonyl-(3R)-ethoxy-(2R)-pyrrolidinylmethoxy]cyclohexanecarboxylic acid ethyl ester

[Formula 203]

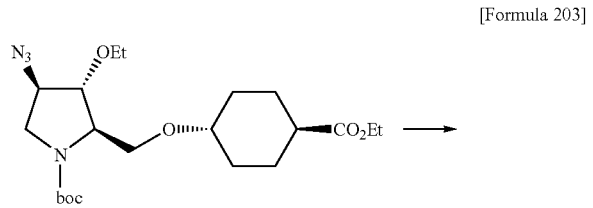

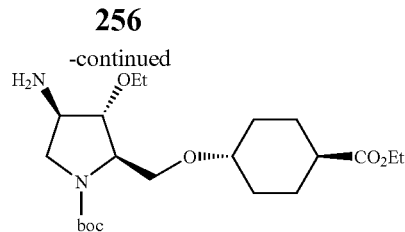

Trans-4-[(4R)-azido-1-tert-butoxycarbonyl-(3R)-ethoxy-(2R)-pyrrolidinylmethoxy]cyclohexanecarboxylic acid ethyl ester (49 mg, 0.111 mmol) and 5% palladium/carbon (20 mg) were stirred in ethanol (3 mL) for two days at room temperature at normal pressure and under a hydrogen stream. The catalyst was separated by filtration, and the filtrate was concentrated under reduced pressure, to obtain the title compound (51 mg, quantitative) as an oily matter.

NMR (CDCl$_3$) δ: 1.14-1.31 (8H, m), 1.42-1.69 (11H, m), 1.91-2.30 (5H, m), 3.07 (1H, m), 3.38 (1H, m), 3.53-4.05 (6H, m), 4.07-4.31 (3H, m) 4.54 (1H, m).

MS (ESI) m/z: 415 (M$^+$+1).

Trans-4-[1-tert-butoxycarbonyl-(3R)-ethoxy-(4R)-(piperidin-1-yl)-(2R)-pyrrolidinylmethoxy]cyclohexanecarboxylic acid ethyl ester

[Formula 204]

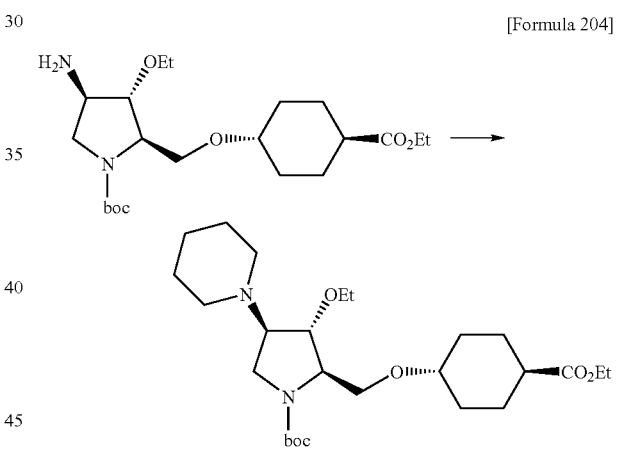

Trans-4-[(4R)-amino-1-tert-butoxycarbonyl-(3R)-ethoxy-(2R)-pyrrolidinylmethoxy]cyclohexanecarboxylic acid ethyl ester (703 mg, 0.704 mmol) was dissolved in ethanol (20 mL), and a 50% aqueous solution of glutaraldehyde (0.91 mL, 5.13 mmol), acetic acid (0.29 mL, 5.13 mmol) and sodium cyanotrihydroboride (322 mg, 5.13 mmol) were added at room temperature. The mixture was stirred for 13 hours. The reaction liquor was poured onto water, and extracted with ethyl acetate. The extract was washed with saturated brine, and dried over anhydrous sodium sulfate. The solvent was concentrated under reduced pressure, and the obtained residue was purified by silica gel chromatography [SiO$_2$ (NH silica) 30 g, ethyl acetate:n-hexane=1:1, v/v], to obtain the title compound (654 mg, 79%) as an oily matter.

NMR (CDCl$_3$) δ: 1.01-1.38 (10H, m), 1.39-1.73 (12H, m), 1.92-2.13 (6H, m), 2.25 (1H, m), 2.35-2.57 (2H, m), 2.70-2.80 (1H, m), 3.08 (1H, m), 3.24 (1H, m), 3.40-3.98 (8H, m), 4.08-4.14 (3H, m).

MS (ESI) m/z: 483 (M$^+$+1)

Trans-4-[(3R)-ethoxy-(4R)-(piperidin-1-yl)-(2R)-pyrrolidinylmethoxy]cyclohexanecarboxylic acid ethyl ester Trans-4-[1-tert-butoxycarbonyl-(3R)-ethoxy-(4R)-(piperidin-1-yl)-(2R)-pyrrolidinylmethoxy]cyclohexanecarboxylic acid ethyl ester (654 mg, 1.36 mmol) was dissolved in methylene chloride (20 mL), and trifluoroacetic acid (2 mL) was added at room temperature. The mixture was stirred for 14 hours. The reaction liquor was concentrated under reduced pressure, and the obtained residue was diluted with methylene chloride. A 1N-aqueous solution of sodium hydroxide was added thereto, and the mixture was adjusted to pH 10, and extracted with methylene chloride. The extract was washed with saturated brine, and dried over anhydrous sodium sulfate. The solvent was concentrated under reduced pressure, to obtain the title compound (488 mg, 94%) as an oily matter.

NMR (CDCl$_3$) δ: 1.10-1.76 (20H, m), 1.97-2.12 (4H, m), 2.25 (1H, m), 2.32-2.57 (1H, m), 2.72-2.97 (2H, m), 3.10-3.30 (3H, m), 3.36-3.78 (5H, m), 4.11 (2H, q, J=7.1 Hz).
MS (ESI) m/z: 383 (M$^+$+1).

Trans-4-[1-[[5-chloro-2-fluoro-4-[(1-methyl-1H-indol-3-ylcarbonyl)amino]phenyl]acetyl]-(3R)-ethoxy-(4R)-(piperidin-1-yl)-(2R)-pyrrolidinylmethoxy]cyclohexanecarboxylic acid ethyl ester NMR (CDCl$_3$) δ: 0.99-1.72 (17H, m), 1.86-2.73 (9H, m), 2.91 and 3.07 (total 1H, q and t, J=6.1 and 10.5 Hz respectively, amide isomers), 3.15-3.90 (11H, m), 4.02-4.42 (4H, m), 7.38-7.42 (4H, m), 7.80 and 7.81 (total 1H, each s, amide isomers), 8.13-8.15 (1H, m), 8.29 (1H, s), 8.49 and 8.51 (total 1H, each d, J=12.0 and 12.2 Hz respectively, amide isomers).
MS (FAB) m/z: 725 (M$^+$+1), 727 (M$^+$+3).

Trans-4-[1-[[5-chloro-2-fluoro-4-[(1-methyl-1H-indol-3-ylcarbonyl)amino]phenyl]acetyl]-(3R)-ethoxy-(4R)-(piperidin-1-yl)-(2R)-pyrrolidinylmethoxy]cyclohexanecarboxylic acid

[Formula 205]

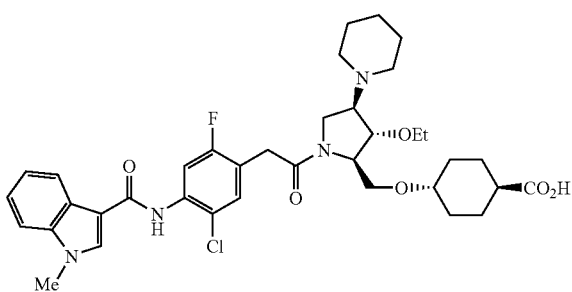

NMR (CDCl$_3$) δ: 1.13-1.58 (10H, m), 1.60-1.79 (3H, m), 1.96-2.28 (5H, m), 2.43-2.98 (6H, m), 3.14 and 3.22 (total 2H, each t, J=11.5 and 9.3 Hz respectively, amide isomers), 3.35-4.56 (11H, m), 7.33-7.41 (4H, m), 7.81 (1H, s), 8.11-8.17 (1H, m), 8.29 (1H, s), 8.50 and 8.51 (total 1H, each d, each J=12.0 Hz, amide isomers).
MS (FAB) m/z: 697 (M$^+$+1), 699 (M$^+$+3).
IR (ATR) cm$^{-1}$: 3419, 3107, 3051, 2933, 2860, 1722, 1647, 1585.

Example 98

Trans-4-[1-[[4-[(benzo[b]thiophen-3-ylcarbonyl)amino]-5-chloro-2-fluorophenyl]acetyl]-(4S)-(4-methylpiperidin-1-yl)-(2S)-pyrrolidinylmethoxy]cyclohexanecarboxylic acid

Trans-4-[1-tert-butoxycarbonyl-(4S)-(4-methylpiperidin-1-yl)-(2S)-pyrrolidinylmethoxy]cyclohexanecarboxylic acid ethyl ester NMR (CDCl$_3$) δ: 0.91 (1H, d, J=6.4 Hz), 1.15-1.23 (7H, m), 1.30-1.50 (11H, m), 1.70-1.80 (1H, m), 1.90-2.60 (7H, m), 2.80-3.95 (7H, m), 4.11 (2H, q, J=7.1 Hz).

Trans-4-[1-[[4-[(benzo[b]thiophen-3-ylcarbonyl)amino]-5-chloro-2-fluorophenyl]acetyl]-(4S)-(4-methylpiperidin-1-yl)-(2S)-pyrrolidinylmethoxy]cyclohexanecarboxylic acid ethyl ester NMR (CDCl$_3$) δ: 0.92-0.93 (3H, m), 1.13-1.66 (8H, m), 1.85-2.31 (7H, m), 2.53-3.25 (4H, m), 3.44-4.42 (15H, m), 7.39-7.55 (3H, m), 7.92 (1H, d, J=8.1 Hz), 8.09-8.11 (1H, m), 8.33-8.49 (3H, m).

Trans-4-[1-[[4-[(benzo[b]thiophen-3-ylcarbonyl)amino]-5-chloro-2-fluorophenyl]acetyl]-(4S)-(4-methylpiperidin-1-yl)-(2S)-pyrrolidinylmethoxy]cyclohexanecarboxylic acid

[Formula 206]

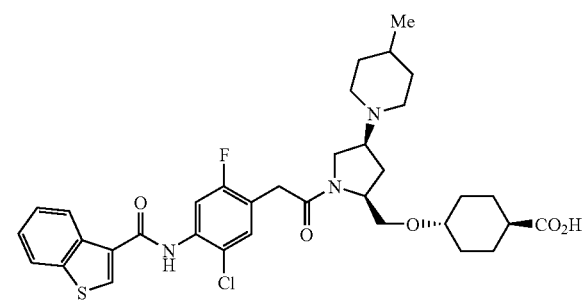

NMR (DMSO-d$_6$) δ: 089 (3H, d, J=6.3 Hz), 1.10-1.40 (5H, m), 1.50-1.75 (3H, m), 1.80-2.20 (7H, m), 2.25-2.90 (3H, m), 3.10-4.30 (11H, m), 7.45-7.57 (4H, m), 8.08-8.11 (1H, m), 8.45 (1H, d, J=8.1 Hz), 8.65 and 8.66 (total 1H, each s), 10.12 (1H, s).
IR (ATR) cm$^{-1}$: 2927, 1720, 1641, 1517, 1403, 1214.
MS (ESI) m/z: 670 (M$^+$+1).
Anal. Calcd for C$_{35}$H$_{41}$ClFN$_3$O$_5$S.0.6H$_2$O: C, 61.73; H, 6.25; N, 6.17.
Found: C, 61.53; H, 5.96; N, 6.22.

Example 99

Trans-4-[1-[[4-[(benzo[b]thiophen-3-ylcarbonyl)amino]-5-chloro-2-fluorophenyl]acetyl]-(4S)-[(4-methoxymethyl)piperidin-1-yl]-(2S)-pyrrolidinylmethoxy]cyclohexanecarboxylic acid

Trans-4-[1-tert-butoxycarbonyl-(4S)-[(4-methoxymethyl)piperidin-1-yl]-(2S)-pyrrolidinylmethoxy]cyclohexanecarboxylic acid ethyl ester NMR (CDCl$_3$) δ: 1.16-1.33 (3H, m), 1.24 (3H, t, J=7.4 Hz), 1.46 (9H, s), 1.65-2.58 (13H, m), 2.85-3.96 (13H, m), 3.33 (3H, s), 4.11 (2H, q, J=7.4 Hz).
MS (ESI) m/z: 483 (M$^+$+1).

Trans-4-[1-[[4-[(benzo[b]thiophen-3-ylcarbonyl)amino]-5-chloro-2-fluorophenyl]acetyl]-(4S)-[(4-methoxymethyl)piperidin-1-yl]-(2S)-pyrrolidinylmethoxy]cyclohexanecarboxylic acid

[Formula 207]

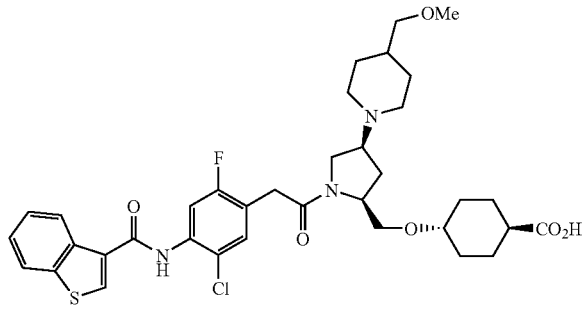

NMR (DMSO-$d_6$) δ: 1.12-2.33 (22H, m), 2.64-4.27 (12H, m) 7.44-7.57 (4H, m), 8.10 (1H, d, J=8.0 Hz), 8.65-8.67 (1H, m), 10.13 (1H, br s).
IR (ATR) cm$^{-1}$: 2929, 2859, 1641, 1517, 1402.
MS (ESI) m/z: 700 (M$^+$+1).
Anal. Calcd for $C_{36}H_{43}ClFN_3O_6S1.5H_2O.0.3HCl$: C, 58.57; H, 6.32; Cl, 6.24; F, 2.57; N, 5.69; S, 4.34.
Found: C, 58.42; H, 6.11; Cl, 6.22; F, 2.42; N, 5.51; S, 4.16.

Example 100

Trans-4-[1-[[4-[(benzo[b]thiophen-3-ylcarbonyl)amino]-5-chloro-2-fluorophenyl]acetyl]-(4S)-(4-fluoropiperidin-1-yl)-(2S)-pyrrolidinylmethoxy]cyclohexanecarboxylic acid Trans-4-[1-(tert-butoxycarbonyl)-(4S)-(4-fluoropiperidin-1-yl)-(2S)-pyrrolidinylmethoxy]cyclohexanecarboxylic acid ethyl ester MS (ESI) m/z: 457 (M$^+$+1).

Trans-4-[1-[[4-[(benzo[b]thiophen-3-ylcarbonyl)amino]-5-chloro-2-fluorophenyl]acetyl]-(4S)-(4-fluoropiperidin-1-yl)-(2S)-pyrrolidinylmethoxy]cyclohexanecarboxylic acid ethyl ester NMR (CDCl$_3$) δ: 1.11-1.29 (5H, m), 1.32-1.53 (2H, m), 1.80-2.81 (14H, m), 3.08-3.31 (1H, m), 3.45-3.89 (5H, m), 4.06-4.40 (3H, m), 4.58-4.79 (1H, m), 7.40-7.55 (3H, m), 7.92 (1H, d, J=7.6 Hz), 8.11 (1H, d, J=10.3 Hz), 8.34 (1H, d, J=10.3 Hz), 8.42-8.50 (2H, m).
MS (ESI) m/z: 702 (M$^+$+1), 704 (M$^+$+3).

Trans-4-[1-[[4-[(benzo[b]thiophen-3-ylcarbonyl)amino]-5-chloro-2-fluorophenyl]acetyl]-(4S)-(4-fluoropiperidin-1-yl)-(2S)-pyrrolidinylmethoxy]cyclohexanecarboxylic acid

[Formula 208]

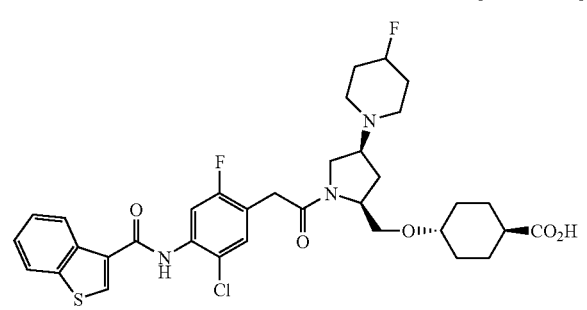

NMR (DMSO-$d_6$) δ: 0.96-1.40 (4H, m), 1.50-4.34 (20H, m), 4.56-4.78 (1H, m), 7.43-7.57 (4H, m), 8.07-8.11 (1H, m), 8.44-8.50 (1H, m), 8.67-8.76 (1H, m), 10.07-10.43 (1H, m).
MS (ESI) m/z: 674 (M$^+$+1), 676 (M$^+$+3).
Anal. Calcd for $C_{34}H_{38}ClF_2N_3O_5.H_2O$: C, 58.99; H, 5.82; N, 6.07.
Found: C, 58.78; H, 5.68; N, 6.23.

Example 101

Trans-4-[1-[[5-chloro-2-fluoro-4-[(1-methyl-1H-indol-3-ylcarbonyl)amino]phenyl]acetyl]-(4S)-(4,4-difluoropiperidin-1-yl)-(2S)-pyrrolidinylmethoxy]cyclohexanecarboxylic acid Trans-4-[1-tert-butoxycarbonyl-(4S)-(4,4-difluoropiperidin-1-yl)-(2S)-pyrrolidinylmethoxy]cyclohexanecarboxylic acid ethyl ester NMR (CDCl$_3$) δ: 1.17-1.30 (6H, m), 1.46 (9H, br s), 1.72-1.83 (2H, m), 1.89-2.10 (8H, m), 2.16-2.38 (3H, m), 2.44-2.77 (4H, m), 2.92-3.03 (1H, m), 3.15-3.26 (1H, m), 3.36-3.64 (1H, m), 3.68-4.01 (3H, m), 4.12 (2H, dq, J=14.3, 3.6 Hz).
MS (ESI) m/z: 475 (M$^+$+1).

Trans-4-[(4S)-(4,4-difluoropiperidin-1-yl)-(2S)-pyrrolidinylmethoxy]cyclohexanecarboxylic acid ethyl ester NMR (CDCl$_3$) δ: 1.19-1.32 (5H, m), 1.34-1.56 (3H, m), 1.74-2.33 (11H, m), 2.48-2.66 (4H, m), 2.81-2.97 (2H, m), 3.12-3.31 (2H, m), 3.33-3.60 (2H, m), 4.11 (2H, q, J=7.1 Hz).

Trans-4-[1-[[5-chloro-2-fluoro-4-[(1-methyl-1H-indol-3-ylcarbonyl)amino]phenyl]acetyl]-(4S)-(4,4-difluoropiperidin-1-yl)-(2S)-pyrrolidinylmethoxy]cyclohexanecarboxylic acid ethyl ester NMR (CDCl$_3$) δ: 1.11-1.33 (6H, m), 1.33-1.73 (2H, m), 1.83-2.09 (10H, m), 2.13-2.48 (2H, m), 2.48-3.04 (5H, m), 3.12-3.27 (1H, m), 3.43-3.95 (7H, m), 3.97-4.45 (3H, m), 7.34-7.43 (4H, m), 7.81 and 7.82 (total 1H, each s, amide isomers), 8.11-8.18 (1H, m), 8.29 and 8.30 (total 1H, each s, amide isomers), 8.50 and 8.52 (total 1H, each d, J=11.8 and 12.0 Hz respectively, amide isomers).
MS (ESI) m/z: 718 (M$^+$+1), 720 (M$^+$+3)

Trans-4-[1-[[5-chloro-2-fluoro-4-[(1-methyl-1H-indol-3-ylcarbonyl)amino]phenyl]acetyl]-(4S)-(4,4-difluoropiperidin-1-yl)-(2S)-pyrrolidinylmethoxy]cyclohexanecarboxylic acid

[Formula 209]

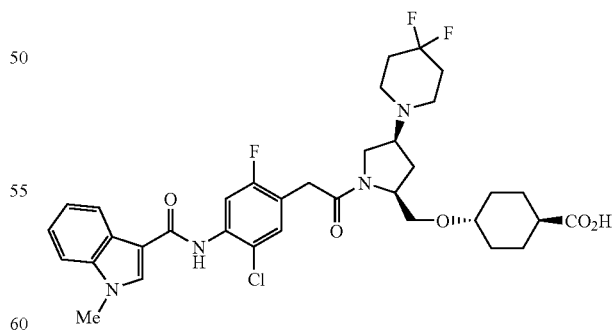

NMR (CDCl$_3$) δ: 1.08-1.71 (6H, m), 1.85-2.15 (8H, m), 2.19-2.33 (2H, m), 2.35-3.32 (7H, m), 3.38-3.79 (4H, m), 3.79-3.92 (4H, m), 4.13-4.45 (1H, m), 7.31-7.44 (4H, m), 7.81 (1H, s), 8.09-8.17 (1H, m), 8.30 (1H, s), 8.50 (1H, t, J=11.9 Hz).
MS (ESI) m/z: 689 (M$^+$+1), 691 (M$^+$+3).
IR (ATR) cm$^{-1}$: 937, 2858, 1720, 1643, 1624, 1585.

Example 102

Trans-4-[1-[[4-[(benzo[b]thiophen-3-ylcarbonyl)amino]-yl)-(2S)-pyrrolidinylmethoxy]cyclohexanecarboxylic acid Trans-4-[1-tert-butoxycarbonyl-(4S)-(4-phenoxypiperidin-1-yl)-(2S)-pyrrolidinylmethoxy]cyclohexanecarboxylic acid ethyl ester NMR (CDCl$_3$) δ: 1.18-1.30 (3H, m), 1.24 (3H, t, J=7.2 Hz), 1.46 (9H, s), 1.74-2.29 (12H, m), 2.64-3.96 (9H, m), 4.11 (2H, q, J=7.2 Hz), 4.26-4.63 (1H, m), 6.89-7.00 (3H, m), 7.23-7.31 (4H, m).
ESI-MS m/z: 531 (M$^+$+1).

Trans-4-[1-[[4-(benzo[b]thiophen-3-ylcarbonyl)amino]-5-chloro-2-fluorophenyl]acetyl]-(4S)-(4-phenoxypiperidin-1-yl)-(2S)-pyrrolidinylmethoxy]cyclohexanecarboxylic acid

[Formula 210]

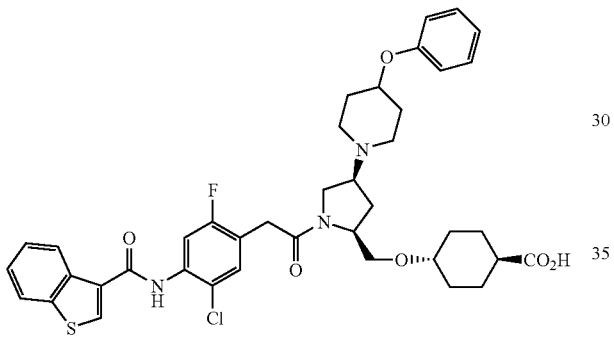

NMR (DMSO-d$_6$) δ: 0.84-4.39 (29H, m), 6.89-6.96 (3H, m), 7.25-7.29 (2H, m), 7.44-7.52 (3H, m), 7.54-7.58 (1H, m), 8.10 (1H, d, J=8.0 Hz), 8.45 (1H, d, J=8.0 Hz), 8.65 (1H, s), 10.12 (1H, s), 12.07 (1H, br s).
IR (ATR) cm$^{-1}$: 2931, 2859, 1517, 1403, 1220.
MS (ESI) m/z: 748 (M$^+$+1).
Anal. Calcd for C$_{40}$H$_{43}$ClFN$_3$O$_6$S.0.25H$_2$O: C, 63.82; H, 5.82; Cl, 4.71; F, 2.52; N, 5.58; S, 4.26.
Found: C, 63.65; H, 5.88; Cl, 4.60; F, 2.43; N, 5.39; S, 4.35.

Example 103

Trans-4-[1-[[4-[(benzo[b]thiophen-3-ylcarbonyl)amino]-5-chloro-2-fluorophenyl]acetyl]-(4S)-(4-methoxypiperidin-1-yl)-(2S)-pyrrolidinylmethoxy]cyclohexanecarboxylic acid Trans-4-[(1-tert-butoxycarbonyl)-(4S)-(4-methoxypiperidin-1-yl)-(2S)-pyrrolidinylmethoxy]cyclohexanecarboxylic acid ethyl ester NMR (CDCl$_3$) δ: 1.12-1.29 (5H, m), 1.37-1.50 (11H, m), 1.52-2.36 (13H, m), 2.47-2.88 (3H, m), 2.92-3.03 (1H, m), 3.11-3.26 (2H, m), 3.33 (3H, s), 3.46-3.99 (4H, m), 4.07-4.15 (2H, m).
MS (ESI) m/z: 469 (M$^+$+1).

Trans-4-[(4S)-(4-methoxypiperidin-1-yl)-(2S)-pyrrolidinylmethoxy]cyclohexanecarboxylic acid ethyl ester dihydrochloride NMR (DMSO-d$_6$) δ: 0.99-1.27 (5H, m), 1.29-1.44 (2H, m), 1.62-2.55 (12H, m), 2.94-3.17 (2H, m), 3.22-3.77 (12H, m), 3.90-4.10 (3H, m), 9.43 (1H, br s), 10.42 (1H, br s), 11.84 (1H, br s).
MS (ESI) m/z: 369 (M$^+$+1).

Trans-4-[1-[[4-[(benzo[b]thiophen-3-ylcarbonyl)amino]-5-chloro-2-fluorophenyl]acetyl]-(4S)-4-methoxypiperidin-1-yl)-(2S)-pyrrolidinylmethoxy]cyclohexanecarboxylic acid ethyl ester NMR (CDCl$_3$) δ: 1.06-1.29 (5H, m), 1.32-1.50 (2H, m), 1.53-1.69 (2H, m), 1.81-2.33 (9H, m), 2.38-3.90 (16H, m), 4.00-4.42 (3H, m), 7.36-7.55 (3H, m), 7.92 (1H, d, J=7.6 Hz), 8.11 (1H, d, J=9.5 Hz), 8.30-8.51 (3H, m).
MS (ESI) m/z: 714 (M$^+$+1), 716 (M$^+$+3).

Trans-4-[1-[[4-[(benzo[b]thiophen-3-ylcarbonyl)amino]-5-chloro-2-fluorophenyl]acetyl]-(4S)-(4-methoxypiperidin-1-yl)-(2S)-pyrrolidinylmethoxy]cyclohexanecarboxylic acid

[Formula 211]

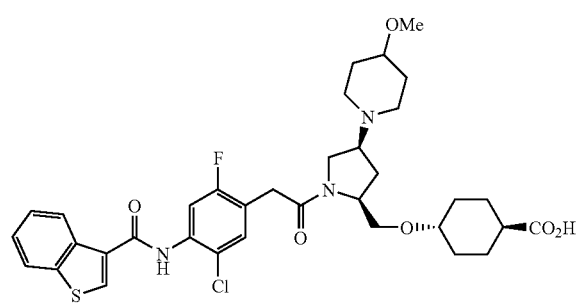

NMR (DMSO-d$_6$) δ: 1.05-2.88 (15H, series of m), 3.03-4.35 (17H, series of m), 7.43-7.59 (4H, m), 8.10 (1H, dd, J=8.2, 1.1 Hz), 8.45 (1H, d, J=7.8Hz), 8.65 (1H, d, J=1.7 Hz), 10.12 (1H, s).
MS (ESI) m/z: 686 (M$^+$+1), 688 (M$^+$+3), 691 (M$^+$+5).
Anal. Calcd for C$_{35}$H$_{41}$ClFN$_3$O$_6$.0.75H$_2$O: C, 60.08; H, 6.12; N, 6.00.
Found: C, 60.05; H, 5.91; N, 5.93.

Example 104

Trans-4-[2-[1-[[2,5-dichloro-4-[(1-methyl-1H-indol-3-ylcarbonyl)amino]phenyl]acetyl]-(4S)-(4-methoxypiperidin-1-yl)-(2S)-pyrrolidinyl]ethyl]cyclohexanecarboxylic acid (4R)-benzyloxy-1-(tert-butoxycarbonyl)-(2S)-pyrrolidine-2-carbaldehyde (4R)-benzyloxy-1-(tert-butoxycarbonyl)-(2S)-pyrrolidine-2-methanol (6.70 g, 21.8 mmol) was dissolved in methylene chloride (50 mL), and while stirring the solution at 0° C., trichloroisocyanuric acid (5.57 g, 24.0 mmol), and then 2,2,6,6,-tetramethylpiperidine-1-oxyl, free radical (TEMPO, 341 mg, 2.18 mmol) were added thereto. The mixture was stirred for two hours at the same temperature, and then the reaction liquor was filtered under reduced pressure using Celite to remove the insoluble. The filtrate was diluted with ethylacetate (300 mL), washed with a saturated aqueous solution of sodium hydrogen carbonate (100 mL) and saturated brine (100 mL), and then dried over anhydrous sodium sulfate, and the solvent was concentrated under reduced pressure. The obtained residue was purified by column chromatography using silica gel [hexane-ethyl acetate (4:1)], to obtain the title compound (2.72 g, 41%) as an oily matter.

NMR (CDCl$_3$) δ: 1.43 and 1.47 (total 9H, s, due to double bond character of the C(O)—N bond in amide), 2.02-1.90 (1H, m), 2.34-2.19 (1H, m), 3.42-3.86 (2H, m), 4.59-4.08 (4H, m), 7.28-7.39 (5H, m), 9.43 and 9.55 (total 1H, d, J=3.7, 2.7 Hz, respectively, due to double bond character of the C(O)—N bond in amide).

MS (ESI) m/z: 306 (M$^+$+1).

Trans-4-[2-[(4R)-benzyloxy-1-(tert-butoxycarbonyl)-(2S)-pyrrolidinyl]-1-ethenyl]benzoic acid methyl ester

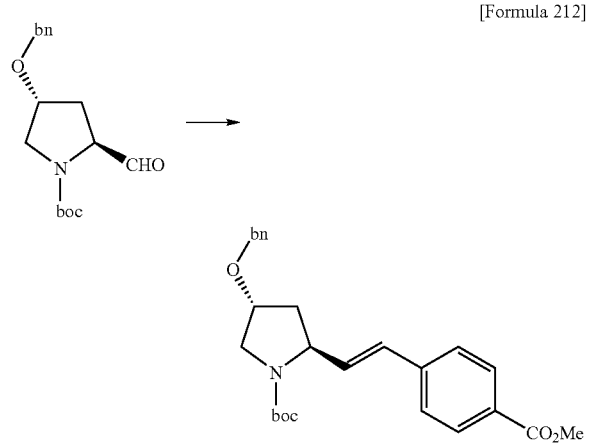

[Formula 212]

Diethyl 4-(methoxycarbonyl)phenylmethylphosphonate (3.06 g, 10.7 mmol) was dissolved in THF (20 mL), and while stirring the solution at −78° C., lithium hexamethyldisilazide (1.0 M tetrahydrofuran solution, 10.7 mL, 10.7 mmol) was added dropwise. After stirring the mixture for one hour, a THF (10 mL) solution of (4R)-benzyloxy-1-(tert-butoxycarbonyl)-(2S)-pyrrolidine-2-carbaldehyde (2.72 g, 8.91 mmol) was added there to using a dropping funnel. Stirring was continued for two hours while the reaction temperature was slowly returned to 0° C. A saturated aqueous solution of ammonium chloride was added to the reaction mixture, and the mixture was extracted with ethyl acetate (300 mL). The extract was washed with saturated brine (100 mL), and then dried over anhydrous sodium sulfate, and the solvent was concentrated. The obtained residue was purified by column chromatography using silica gel [hexane-ethyl acetate (4:1)], to obtain the title compound (3.57 g, 92%) as an oily matter.

NMR (CDCl$_3$) δ: 1.28-1.50 (9H, m), 1.89-2.00 (1H, m), 2.22-2.37 (1H, m), 3.48-3.57 (1H, m), 3.74-3.84 (1H, m), 3.91 (3H, s), 4.11-4.19 (1H, m), 4.43-4.61 (3H, m), 6.07-6.32 (1H, m), 6.39-6.55 (1H, m), 7.27-7.42 (7H, m), 7.97 (2H, d, J=7.8 Hz).

MS (ESI) m/z: 338 (M$^+$−99(tert-butoxycarbonyl)).

4-[2-[1-(Tert-butoxycarbonyl)-(4R)-hydroxy-(2S)-pyrrolidinyl]ethyl]benzoic acid methyl ester

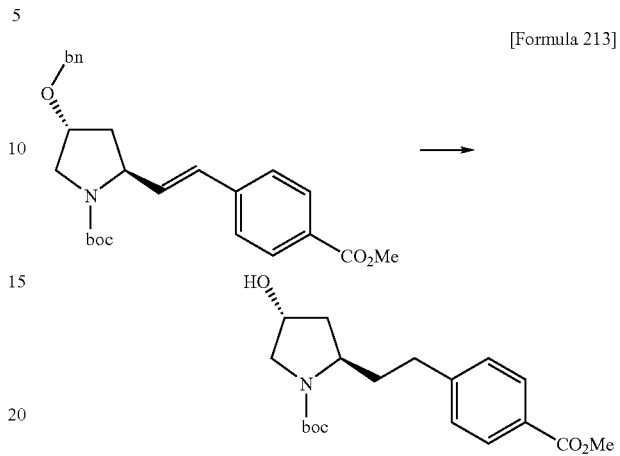

[Formula 213]

Trans-4-[2-[(4R)-benzyloxymethoxy-1-(tert-butoxycarbonyl)-(2S)-pyrrolidinyl]-1-ethenyl]benzoic acid methyl ester (3.57 g, 8.16 mmol) was dissolved in methanol (50 mL), and palladium hydroxide (3 g) was added thereto. The mixture was stirred for 12 hours at room temperature under a hydrogen stream at normal pressure. The catalyst was separated by filtration, and the filtrate was concentrated under reduced pressure. The obtained residue was purified by column chromatography using silica gel [chloroform-methanol (20:1)], to obtain the title compound (1.79 g, 63%) as an oily matter.

NMR (CDCl$_3$) δ: 1.46 (9H, s), 1.59-1.89 (2H, m), 2.02-2.43 (2H, m (1H, m), 7.23-7.30 (2H, m), 7.95 (2H, d, J=7.8 Hz).

MS (ESI) m/z: 250 (M$^+$−99 (Boc)).

Trans-4-[2-[-1-(tert-butoxycarbonyl)-(4R)-hydroxy-(2S)-pyrrolidinyl]ethyl]cyclohexanecarboxylic acid methyl ester

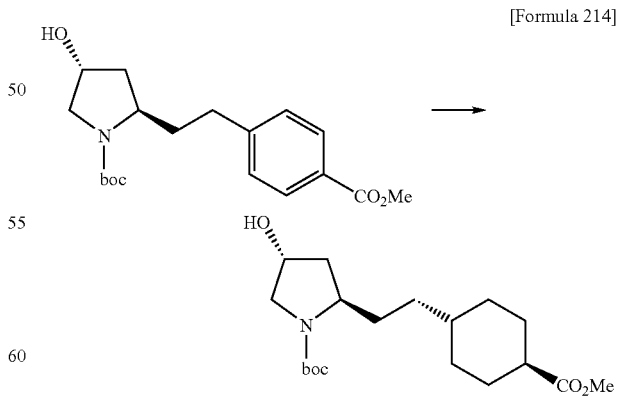

[Formula 214]

4-[(4R)-hydroxy-1-(tert-butoxycarbonyl)-(2S)-pyrrolidinylethynyl]benzoic acid methyl ester (1.79 g, 5.12 mmol) was dissolved in methanol (50 mL)-acetic acid (5 mL), and rhodium/alumina (1.8 g) was added thereto. The mixture was stirred for three hours at room temperature under a hydrogen stream at 15 atmospheres. The catalyst was separated by filtration, and the filtrate was concentrated under reduced pressure. The obtained residue was purified by column chromatography using silica gel [hexane-ethyl acetate (1:1)], to obtain a cis-trans (3.5:1) mixture (1.50 g, 90%) of 4-[2-[1-(tert-butoxycarbonyl)-(4R)-hydroxy-(2S)-pyrrolidinyl]ethyl]cyclohexanecarboxylic acid methyl ester as an oily matter. Subsequently, this compound (1.50 g, 4.20 mmol) was dissolved in methylene chloride (20 mL), and while stirring the solution at room temperature, diisopropylethylamine (1.46 mL, 8.40 mmol) and benzyloxymethoxymethyl chloride (BOMCl) (1.2 mL, 8.40 mmol) were added thereto. The mixture was heated to reflux for two hours. The reaction liquor was left to cool naturally, and then diluted with ethyl acetate (200 mL). The dilution was washed with saturated brine (100 mL), and dried over anhydrous sodium sulfate, and then the solvent was concentrated under reduced pressure. The obtained residue was purified by silica gel chromatography [hexane-ethyl acetate (4:1)], to obtain a benzyloxymethoxymethyl ether product (1.00 g, 50%) as an oily matter. Subsequently, the benzyloxymethoxymethyl ether product (1.00 g, 2.10 mmol) was dissolved in methanol (20 mL), and sodium methoxide (341 mg, 6.30 mmol) was added thereto. The mixture was heated to reflux for 12 hours with stirring. The reaction liquor was left to cool naturally, and then poured onto 1N—HCl (50 mL), and the mixture was extracted with chloroform (2×150 mL). The extract was dried over anhydrous sodium sulfate, and the solvent was concentrated. The obtained residue was purified by recycle column chromatography [Japan Analytical Industry Co., Ltd., JAIJEL-40, eluent: chloroform], to obtain a trans isomer (480 mg, 48%) of the benzyloxymethoxymethyl ether product.

This trans isomer (430 mg, 0.904 mmol) was dissolved in methanol (20 mL), and palladium hydroxide (400 mg) was added thereto. The mixture was stirred for 12 hours at room temperature under a hydrogen stream at normal pressure. The catalyst was separated by filtration, and the filtrate was concentrated under reduced pressure. The obtained residue was purified by column chromatography using silica gel [chloroform-ethyl acetate (4:1)], to obtain the title compound (256 mg, 79%).

NMR (CDCl$_3$) δ: 0.83-0.99 (2H, m), 1.07-2.11 (23H, m), 2.17-2.22 (1H, m).

MS (ESI) m/z: 258 (M$^+$+1-Boc).

Trans-4-[2-[1-(tert-butoxycarbonyl)-4-oxo-(2S)-pyrrolidinyl]ethyl]cyclohexanecarboxylic acid methyl ester Trans-4-[2-[-1-(tert-butoxycarbonyl)-(4R)-hydroxy-(2S)-pyrrolidinyl]ethyl]cyclohexanecarboxylic acid methyl ester (256 mg, 0.716 mmol) was dissolved in methylene chloride (50 mL), and while stirring the solution at 0° C., trichloroisocyanuric acid (183 mg, 0.788 mmol), and then 2,2,6,6-tetramethylpiperidine-1-oxyl, free radical (TEMPO, 11 mg, 0.0716 mmol) were added thereto. The mixture was stirred for one hour at the same temperature, and then the reaction liquor was filtered under reduced pressure using Celite to remove the insoluble. The filtrate was diluted with ethyl acetate (200 mL), washed with a saturated aqueous solution of sodium hydrogen carbonate (100 mL) and saturated brine (100 mL), and then dried over anhydrous sodium sulfate, and the solvent was concentrated. The obtained residue was purified by column chromatography using silica gel [hexane-ethyl acetate (4:1)], to obtain the title compound (280 mg, quant.) as an oily matter.

NMR (CDCl$_3$) δ: 0.84-0.99 (2H, m), 1.11-1.86 (19H, m), 1.92-2.01 (2H, m), 2.17-2.30 (2H, m), 2.67-2.80 (1H, m), 3.56-3.62 (1H, m), 3.67 (3H, s), 3.81-4.03 (1H, m), 4.24-4.37 (1H, m).

MS (ESI) m/z: 254 (M$^+$-Boc).

Trans-4-[2-[1-(tert-butoxycarbonyl)-(4S)-(4-methoxypiperidin-1-yl)-(2S)-pyrrolidinyl]ethyl]cyclohexanecarboxylic acid methyl ester Trans-4-[2-[-1-(tert-butoxycarbonyl)-4-oxo-(2S)-pyrrolidinyl]ethyl]cyclohexanecarboxylic acid methyl ester (270 mg, 0.763 mmol) was dissolved in tetrahydrofuran (20 mL), and while stirring the solution at room temperature, 4-methoxypiperidine hydrochloride (347 mg, 2.29 mmol), and then sodium triacetoxyborohydride (485 mg, 2.29 mmol) were added thereto. The mixture was stirred for 12 hours, and then a saturated aqueous solution of sodium hydrogen carbonate (100 mL) was added to make the mixture basic. The mixture was extracted with ethyl acetate (200 mL). The extract was washed with saturated brine (100 mL), and dried over anhydrous sodium sulfate, and then the solvent was concentrated under reduced pressure. The obtained residue was purified by column chromatography using silica gel [hexane-ethyl acetate (1:3)], to obtain the title compound (215 mg, 62%) as an oily matter.

NMR (CDCl$_3$) δ: 0.80-0.98 (2H, m), 1.01-2.36 (27H, m), 2.44-3.02 (4H, m), 3.17-3.26 (1H, m), 3.32-3.34 (4H, m), 3.60-3.85 (5H, m), 3.92-4.01 (1H, m).

MS (ESI) m/z: 453 (M$^+$+1).

Trans-4-[2-[1-[[2,5-dichloro-4-[(1-methyl-1H-indol-3-ylcarbonyl)amino]phenyl]acetyl]-(4S)-(4-methoxypiperidin-1-yl)-(2S)-pyrrolidinyl]ethyl]cyclohexanecarboxylic acid methyl ester 4N—HCl (10 mL) was added to trans-4-[2-[1-(tert-butoxycarbonyl)-(4S)-(4-methoxypiperidin-1-yl)-(2S)-pyrrolidinyl]ethyl]cyclohexanecarboxylic acid methyl ester (200 mg, 0.442 mmol), and the mixture was stirred for 12 hours. Then, the mixture was concentrated under reduced pressure to obtain the hydrochloride salt of de-Boc product as a solid. Subsequently, this was dissolved in DMF (10 mL), and [2,5-dichloro-4-[(1-methyl-1H-indol-3-ylcarbonyl)amino]phenyl]acetic acid (167 mg, 0.442 mmol), EDC.HCl (127 mg, 0.663 mmol), HOBt (90 mg, 0.663 mmol) and triethylamine (0.61 mL, 4.42 mmol) were added thereto. The mixture was stirred for 12 hours. The reaction liquor was diluted with ethyl acetate (200 mL), washed with saturated brine (2×100 mL), and dried over anhydrous sodium sulfate, and then the solvent was concentrated under reduced pressure. Then, DMF was removed by boiling azeotropically with toluene. The obtained residue was purified by column chromatography using silica gel [chloroform-ethylacetate (4:1) to chloroform-ethyl acetate-methanol (5:5:1)], to obtain the title compound (260 mg, 83%) as an oily matter.

NMR (CDCl$_3$) δ: 0.81-0.97 (2H, m), 1.07-2.36 (20H, m), 2.39-3.08 (1H, m).

Trans-4-[2-[1-[[2,5-dichloro-4-[(1-methyl-1H-indol-3-ylcarbonyl)amino]phenyl]acetyl]-(4S)-(4-methoxypiperidin-1-yl)-(2S)-pyrrolidinyl]ethyl]cyclohexanecarboxylic acid

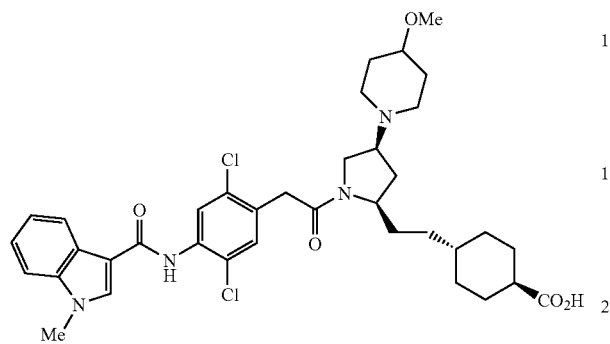

[Formula 215]

To THF solution (5 mL) of trans-4-[2-[1-[[2,5-dichloro-4-[(1-methyl-1H-indol-3-ylcarbonyl)amino]phenyl]acetyl]-(4S)-(4-methoxypiperidin-1-yl)-(2S)-pyrrolidinyl]ethyl]cyclohexanecarboxylic acid methyl ester (260 mg, 0.365 mmol), 0.25N-sodium hydroxide (3 mL, 0.75 mmol) was added, and the mixture was stirred for 12 hours at room temperature. The mixture was neutralized with 1N—HCl, subsequently diluted with saturated brine (50 mL), and extracted with chloroform-methanol (5:1, 2×150 mL). The extract was dried over anhydrous sodium sulfate, and then the solvent was concentrated under reduced pressure. THE obtained oily residue was purified by column chromatography using silica gel [chloroform-methanol (10:1)], and the obtained oily matter was solidified using ethylacetate-hexane, and pulverized, to obtain the title compound (125 mg, 49%) as an amorphous matter.

NMR (DMSO-$d_6$) δ: 0.84-2.76 (26H, m), 3.08-3.25 (5H, m), 3.63-4.11 (6H, m), 7.19-7.31 (2H, m), 7.49-7.58 (2H, m), 7.89 (1H, s), 8.15 (1H, d, J=7.8 Hz), 8.29-8.32 (1H, m), 9.37-9.41 (1H, m).

MS (ESI) m/z: 697 (M$^+$+1), 699 (M$^+$+3), 701 (M$^+$+5).

Anal. Calcd for $C_{37}H_{46}Cl_2N_4O_5 \cdot H_2O$: C, 62.09; H, 6.76; N, 7.83.

Found: C, 61.97; H, 6.85; N, 7.59.

Example 105

Trans-4-[1-[[4-[(benzo[b]furan-3-ylcarbonyl)amino]-2,5-dichlorophenyl]acetyl]-(4S)-(4-ethoxypiperidin-1-yl)-(2S)-pyrrolidinylmethoxy]cyclohexanecarboxylic acid

Trans-4-[1-(tert-butoxycarbonyl)-(4S)-(4-ethoxypiperidin-1-yl)-(2S)-pyrrolidinylmethoxy]cyclohexanecarboxylic acid ethyl ester NMR (CDCl$_3$) δ: 1.14-1.28 (total 10H, series of m), 1.41-1.60 (total 13H, series of m), 1.71-2.33 (total 10H, series of m), 2.52-3.02 (total 4H, series of m), 3.16-3.41 (2H, m), 3.49 (2H, q, J=7.2 Hz), 3.71-3.96 (3H, m), 4.11 (2H, q, J=7.3 Hz).

MS (ESI) m/z: 483 (M$^+$+1).

Trans-4-[(4S)-(4-ethoxypiperidin-1-yl)-(2S)-pyrrolidinylmethoxy]cyclohexanecarboxylic acid ethyl ester dihydrochloride NMR (CDCl$_3$) δ: 1.15-1.38 (total 8H, series of m), 1.40-1.54 (2H, m), 1.97-2.15 (total 6H, series of m), 2.25 (2H, tt, J=11.2, 3.4 Hz), 2.41-2.61 (total 3H, m), 3.12-3.29 (2H, m), 3.35-3.71 (total 6H, series of m), 3.86 (2H, d, J=4.9 Hz), 4.01-4.22 (total 6H, series of m, including 2H, q, δ 4.11), 9.20 (1H, br s), 10.49-10.81 (1H, m), 11.73-12.01 (1H, m).

MS (ESI) m/z: 383 (M$^+$+1-2HCl).

Trans-4-[1-[[4-[(benzo[b]furan-3-ylcarbonyl)amino]-2,5-dichlorophenyl]acetyl]-(4S)-(4-ethoxypiperidin-1-yl)-(2S)-pyrrolidinylmethoxy]cyclohexanecarboxylic acid ethyl ester NMR (CDCl$_3$) δ: 1.18-1.27 (total 8H, series of m), 1.35-1.66 (total 4H, series of m), 1.85-2.30 (total 10H, series of m), 2.36-2.88 (total 4H, series of m), 2.93-3.35 (total 3H, series of m), 3.44-3.97 (total 7H, series of m), 4.06-4.39 (total 3H, series of m, including 2H, q, J=7.1 Hz, δ 4.09), 7.37-7.42 (total 3H, series of m), 7.55-7.60 (1H, m), 8.02-8.07 (1H, m), 8.28-8.32 (2H, m), 8.58-8.63 (1H, m).

IR (ATR) ν: 2973, 2862, 1726, 1680, 1635 cm$^{-1}$.

MS (ESI) m/z: 728 [(M$^+$+1), $^{35}$Cl], 730 [(M$^+$+3), $^{37}$Cl].

Anal. Calcd for $C_{38}H_{47}Cl_2N_3O_7 \cdot 0.75H_2O$: C, 60.20; H, 6.45; N, 5.54; Cl, 9.35.

Found: C, 60.33: H, 6.33; N, 5.40; Cl, 9.72.

Trans-4-[1-[[4-[(benzo[b]furan-3-ylcarbonyl)amino]-2,5-dichlorophenyl]acetyl]-(4S)-(4-ethoxypiperidin-1-yl)-(2S)-pyrrolidinylmethoxy]cyclohexanecarboxylic acid

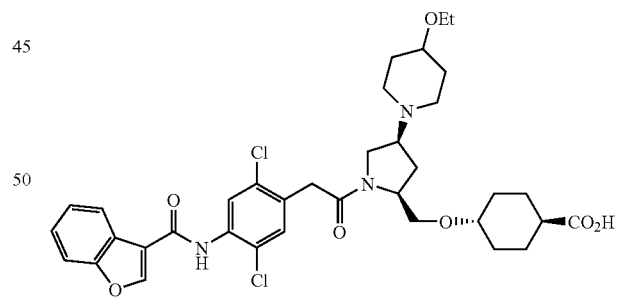

[Formula 216]

NMR (CDCl$_3$) δ: 1.11-2.50 (total 22H, series of m), 2.71-2.89 (2H, m), 3.08-3.30 (2H, m), 3.33-4.00 (total 8H, series of m), 4.17-4.50 (1H, m), 7.40-7.45 (2H, m), 7.51-7.62 (1H, m), 8.02-8.07 (1H, m), 8.23 (1H, d, J=8.3 Hz), 8.30 (1H, s), 8.69 (1H, d, J=5.1 Hz).

IR (ATR) ν: 2935, 2862, 1718, 1682, 1629, 1571 cm$^{-1}$.

MS (ESI) m/z: 700 [(M$^+$+1), $^{35}$Cl], 702 [(M$^+$+3), $^{37}$Cl].

Anal. Calcd for $C_{36}H_{43}Cl_2N_3O_7 \cdot 0.5H_2O$: C, 60.93; H, 6.25; N, 5.92.

Found: C, 60.94; H, 6.26; N, 5.89.

Example 106

Trans-4-[1-[[4-[(benzo[b]thiophen-3-ylcarbonyl)amino]-5-chloro-2-fluorophenyl]acetyl]-(4S)-[(3R)-methoxypiperidin-1-yl]-(2S)-pyrrolidinylmethoxy]cyclohexanecarboxylic acid Trans-4-[1-tert-butoxycarbonyl-(4S)-[(3R)-methoxypiperidin-1-yl]-(2S)-pyrrolidinylmethoxy]cyclohexanecarboxylic acid ethyl ester NMR (CDCl$_3$) δ: 1.18-1.27 (total 5H, m, including t, J=7.1 Hz, 3H, at δ 1.24), 1.42-1.55 (total 12H, m, including s, 9H, at δ 1.45), 1.72-2.26 (total 12H, series of m), 2.63-2.80 (3H, m), 3.01 (1H, t, J=10.2 Hz), 3.20-3.51 (6H, m), 3.66-3.96 (3H, m), 4.11 (2H, q, J=7.1 Hz).

MS (ESI) m/z: 469 (M$^+$+1).

Trans-4-[1-[[4-[(benzo[b]thiophen-3-ylcarbonyl)amino]-5-chloro-2-fluorophenyl]acetyl]-(4S)-[(3R)-methoxypiperidin-1-yl]-(2S)-pyrrolidinylmethoxy]cyclohexanecarboxylic acid ethyl ester NMR (CDCl$_3$) δ: 1.15-1.54 (total 9H, m, including 3H, t, J=7.1 Hz, at δ 1.22), 1.77-2.03 (7H, m), 2.17-2.29 (4H, m), 2.60-2.77 (3H, m), 3.12-3.38 (6H, m), 3.46-3.74 (4H, m), 3.83-3.87 (1H, m), 4.06-4.38 (3H, m, including 2H, q, J=7.1 Hz, at δ 4.08), 7.40-7.54 (3H, m), 7.92 (1H, d, J=8.1 Hz), 8.09 and 8.12 (total 1H, each s), 8.33-8.35 (1H, m), 8.42-8.50 (2H, m).

MS (ESI) m/z: 714 (M$^+$+1).

Trans-4-[1-[[4-[(benzo[b]thiophen-3-ylcarbonyl)amino]-5-chloro-2-fluorophenyl]acetyl]-(4S)-[(3R)-methoxypiperidin-1-yl]-(2S)-pyrrolidinylmethoxy]cyclohexanecarboxylic acid

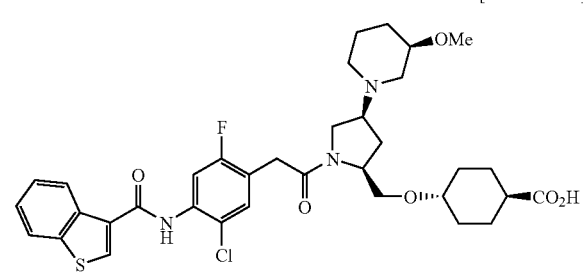

[Formula 217]

NMR (DMSO-d$_6$) δ: 1.14-1.38 (6H, m), 1.58-1.77 (2H, m), 1.86-2.01 (7H, m), 2.09-2.33 (2H, m), 2.55-2.93 (3H, m), 3.11-3.29 (6H, m), 3.51-4.28 (6H, m), 7.44-7.58 (4H, m), 8.09-8.11 (1H, m), 8.44-8.46 (1H, m), 8.65-8.66 (1H, m), 10.12 (1H, s), 12.07 (1H, broad s).

IR (ATR) cm$^{-1}$: 1518, 1404, 1215, 1095, 766.

MS (ESI) m/z: 686 (M$^+$+1).

Anal. Calcd for C$_{35}$H$_{41}$ClFN$_3$O$_6$S·¾H$_2$O: C, 60.08; H, 6.12; N, 6.00; S, 4.58; Cl, 5.07; F, 2.72.

Found: C, 59.73; H, 5.75; N, 5.99; S, 4.85; Cl, 5.15; F, 2.67.

Example 107

Trans-4-[1-[[4-[(benzo[b]furan-3-ylcarbonyl)amino]-2,5-dichlorophenyl]acetyl]-(4S)-[4-(dimethylcarbamoyl)piperidin-1-yl]-(2S)-pyrrolidinylmethoxy]cyclohexanecarboxylic acid Trans-4-[1-tert-butoxycarbonyl-(4S)-[4-(dimethylcarbamoyl)piperidin-1-yl]-(2S)-pyrrolidinylmethoxy]cyclohexanecarboxylic acid ethyl ester NMR (CDCl$_3$) δ: 1.19-1.29 (5H, m), 1.35-1.93 (14H, m), 1.93-2.11 (8H, m), 2.17 (2H, s), 2.19-2.26 (1H, m), 2.42-2.69 (2H, m), 2.94 and 3.01 (total 6H, each s, amide isomers), 3.04 (2H, s), 3.15-4.00 (5H, m), 4.07-4.16 (2H, m).

MS (ESI) m/z: 510 (M$^+$+1).

Trans-4-[1-[[4-[(benzo[b]furan-3-ylcarbonyl)amino]-2,5-dichlorophenyl]acetyl]-(4S)-[4-(dimethylcarbamoyl)piperidin-1-yl]-(2S)-pyrrolidinylmethoxy]cyclohexanecarboxylic acid

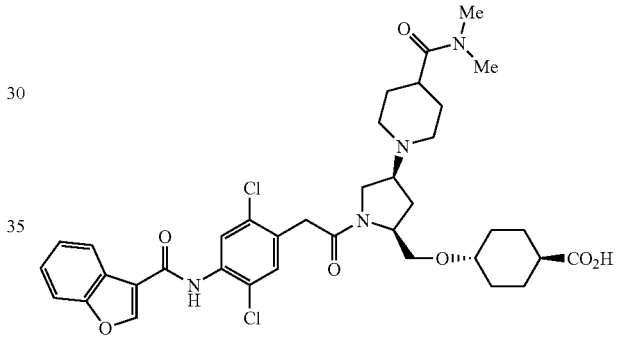

[Formula 218]

NMR (CDCl$_3$) δ: 1.13-1.52 (4H, m), 1.63-2.83 (15H, m), 2.86-3.99 (14H, m), 4.13-4.48 (2H, m), 7.39-7.45 (3H, m), 7.55-7.62 (1H, m), 8.02-8.08 (1H, m), 8.24 and 8.28 (total 1H, each s, amide isomers), 8.30 and 8.31 (total 1H, each s, amide isomers), 8.67 (1H, s).

MS (ESI) m/z: 727 (M$^+$+1), 729 (M$^+$+3).

Example 108

Trans-4-[1-[[2,5-dichloro-4-[(1-methyl-1H-indol-3-ylcarbonyl)amino]phenyl]acetyl]-(4S)-(4-methanesulfonylpiperidin-1-yl)-(2S)-pyrrolidinylmethoxy]cyclohexanecarboxylic acid Trans-4-[1-(tert-butoxycarbonyl)-(4S)-[4-methanesulfonylpiperidin-1-yl]-(2S)-pyrrolidinylmethoxy]cyclohexanecarboxylic acid ethyl ester MS (EI) m/z: 517 (M+1)$^+$.

Trans-4-[1-[[2,5-dichloro-4-[(1-methyl-1H-indol-3-ylcarbonyl)amino]phenyl]acetyl]-(4S)-(4-methanesulfonylpiperidin-1-yl)-(2S)-pyrrolidinylmethoxy]cyclohexanecarboxylic acid ethyl ester NMR (CDCl$_3$) δ: 8.80 (1H, s), 8.25 (1H, br s), 8.16-8.11 (1H, m), 7.81 (1H, s), 7.44-7.34 (4H, m), 4.28-4.16 (1H, m), 4.09 (2H, q, J=7.0 Hz), 3.89 (3H, s), 3.83 (1H, dd, J=9.8, 6.8 Hz), 3.77-3.63 (4H, m), 3.57-3.45 (1H, m), 3.25-3.14 (2H, m), 3.10-2.94 (1H, m), 2.83 (5H, br s), 2.30-1.79 (14H, m), 1.45 (2H, dd, J=14.2, 10.5 Hz), 1.23 (3H, t, J=7.1 Hz).

MS (EI) m/z: 775 ($M^+$).

Trans-4-[1-[[2,5-dichloro-4-[(1-methyl-1H-indol-3-ylcarbonyl)amino]phenyl]acetyl]-(4S)-(4-methanesulfonylpiperidin-1-yl)-(2S)-pyrrolidinylmethoxy]cyclohexanecarboxylic acid

[Formula 219]

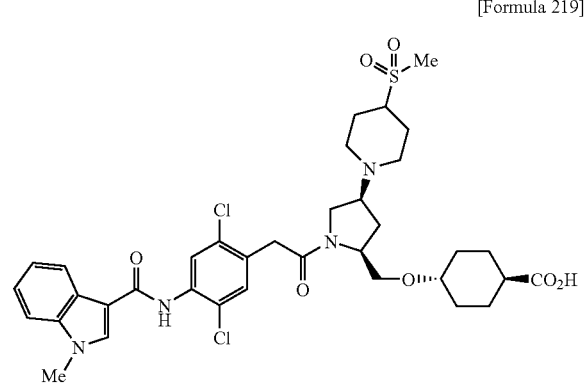

NMR (CDCl$_3$) δ: 9.37 (1H, s), 8.29 (1H, s), 8.14 (1H, d, J=7.8 Hz), 7.89 (1H, t, J=5.5 Hz), 7.55 (1H, d, J=8.1 Hz), 7.48 (1H, s), 7.23 (2H, dt, J=24.5, 7.4 Hz), 4.40-4.24 (1H, m), 4.16-3.95 (2H, m), 3.76 (2H, dt, J=15.9, 15.9 Hz), 3.62-3.51 (2H, m), 3.32 (3H, br s), 3.14 (1H, t, J=9.6 Hz), 2.91 (2H, s), 2.91 (3H, d, J=3.9 Hz), 2.76-2.76 (1H, m), 2.24-2.10 (2H, m), 2.07-1.83 (10H, m), 1.74 (1H, dd, J=20.0, 9.8 Hz), 1.66-1.55 (3H, m), 1.31 (2H, dd, J=24.2, 11.2 Hz), 1.22-1.11 (2H, m).

MS (EI) m/z: 747 ($M^+$).

Anal. Calcd for $C_{36}H_{44}N_4O_7Cl_2S \cdot 0.25EtOH$, $1.5H_2O$, 0.25 HCl: C, 55.12; H, 6.18; N, 7.04; Cl, 10.03; S, 4.03. Found: C, 54.90; H, 5.90; N, 6.91; Cl, 9.76; S, 4.13.

Example 109

Trans-4-[1-[[5-chloro-2-fluoro-4-[(1-methyl-1H-indol-3-ylcarbonyl)amino]phenyl]acetyl]-(4S)-[4-(N,N-dimethylamino)piperidin-1-yl]-(2S)-pyrrolidinylmethoxy]cyclohexanecarboxylic acid Trans-4-[1-tert-butoxycarbonyl-(4S)-[4-(N,N-dimethylamino)piperidin-1-yl]-(2S)-pyrrolidinylmethoxy]cyclohexanecarboxylic acid ethyl ester NMR (CDCl$_3$) δ: 1.22-1.27 (5H, m, including 3H, t, J=7.1 Hz, at δ 1.24), 1.43-1.62 (13H, m, including 9H, s, at δ 1.46), 1.72-2.06 (10H, m), 2.20-2.39 (8H, m, including 6H, s, at δ 2.37), 2.58-2.60 (1H, m), 2.92-3.21 (4H, m), 3.39-3.54 (1H, m), 3.71-3.82 (3H, m), 4.11 (2H, q, J=7.1 Hz).

MS (ESI) m/z: 482 ($M^++1$)

Trans-4-[(4S)-[4-(N,N-dimethylamino)piperidin-1-yl]-(2S)-pyrrolidinylmethoxy]cyclohexanecarboxylic acid ethyl ester MS (ESI) m/z: 382.6 ($M^++1$)

Trans-4-[1-[[5-chloro-2-fluoro-4-[(1-methyl-1H-indol-3-ylcarbonyl)amino]phenyl]acetyl]-(4S)-[4-(N,N-dimethylamino)piperidin-1-yl]-(2S)-pyrrolidinylmethoxy]cyclohexanecarboxylic acid ethyl ester NMR (CDCl$_3$) δ: 1.13-1.26 (5H, m, including 3H, t, J=7.1 Hz, at δ 1.22), 1.37-1.62 (4H, m), 1.81-2.29 (total 18H, m, including 6H, s, at δ 2.29), 2.40-2.69 (1H, m), 2.87-3.23 (4H, m), 3.45-3.89 (8H, m, including 3H, s, at δ 3.89), 4.06-4.39 (3H, m, including 2H, q, J=7.1 Hz, at 4.08), 7.34-7.43 (4H, m), 7.80 and 7.82 (total 1H, each s), 8.13-8.15 (1H, m), 8.30 (1H, s), 8.47-8.53 (1H, m).

MS (ESI) m/z: 724 ($M^++1$).

Trans-4-[1-[[5-chloro-2-fluoro-4-[(1-methyl-1H-indol-3-ylcarbonyl)amino]phenyl]acetyl]-(4S)-[4-(N,N-dimethylamino)piperidin-1-yl]-(2S)-pyrrolidinylmethoxy]cyclohexanecarboxylic acid

[Formula 220]

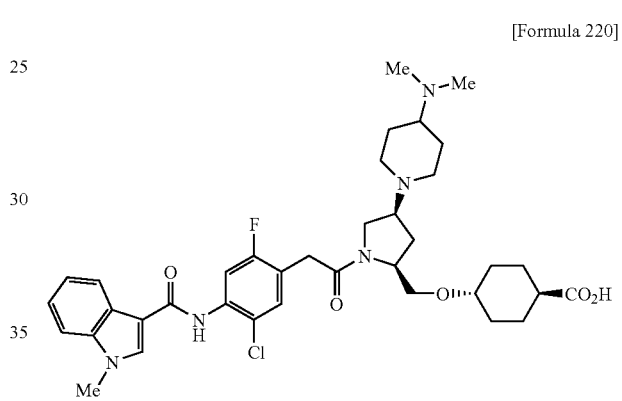

NMR (DMSO-d$_6$) δ: 1.16-1.37 (4H, m), 1.57-1.77 (3H, m), 1.89-2.33 (total 9H, m), 2.52 (6H, s), 2.70-4.28 (total 16H, series of m, including 3H, s, at δ 3.89), 7.20-7.30 (2H, m), 7.43 (1H, d, J=7.4 Hz), 7.56 (1H, d, J=8.1 Hz), 7.67-7.72 (1H, m), 8.15 (1H, d, J=7.8 Hz), 8.32 (1H, s), 9.34 (1H, s).

IR (ATR) cm$^{-1}$: 1639, 1518, 1232, 1099, 746.

MS (ESI) m/z: 696 ($M^++1$).

HRMS (FAB) m/z: Theoretical 696.3328; Observed 696.3347.

Example 110

Trans-4-[1-[[4-[(benzo[b]thiophen-3-ylcarbonyl)amino]-5-chloro-2-fluorophenyl]acetyl]-(4S)-[4-(morpholin-4-yl)piperidin-1-yl]-(2S)-pyrrolidinylmethoxy]cyclohexanecarboxylic acid Trans-4-[(4S)-[4-(morpholin-4-yl)piperidin-1-yl]-(2S)-pyrrolidinylmethoxy]cyclohexanecarboxylic acid ethyl ester NMR (CDCl$_3$) δ: 1.17-1.31 (4H, m), 1.46 (9H, s), 1.61-2.23 (19H, m), 2.50-2.58 (4H, m), 2.78-3.97 (11H, m), 4.08-4.16 (2H, m).

MS (ESI) m/z: 524 ($M^++1$).

Trans-4-[1-[[4-[(benzo[b]thiophen-3-ylcarbonyl)amino]-5-chloro-2-fluorophenyl]acetyl]-(4S)-[4-(morpholin-4-yl)piperidin-1-yl]-(2S)-pyrrolidinylmethoxy]cyclohexanecarboxylic acid

[Formula 221]

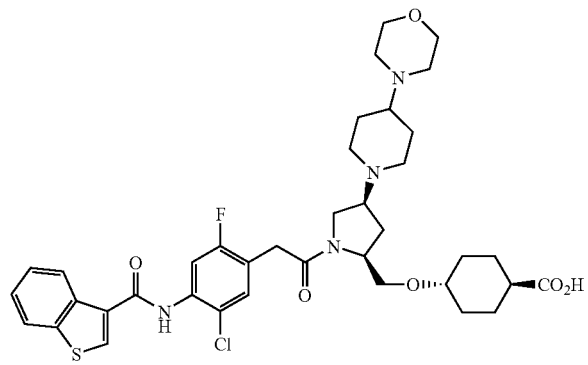

NMR (DMSO-$d_6$) δ: 1.08-1.47 (9H, m), 1.51-2.38 (12H, m), 2.44 (4H, br s), 2.59-4.28 (31H, m), 7.44-7.58 (4H, m), 8.10 (1H, d, J=8.0 Hz), 8.45 (1H, d, J=8.0 Hz), 8.65-8.68 (1H, m), 10.14 (1H, s).
IR (ATR) $cm^{-1}$: 2933, 2857, 2811, 1517, 1402.
MS (ESI) m/z: 741 ($M^+$+H).
MS (FAB) m/z: 741 ($M^+$+H).
MS (High Resolution FAB) m/z: 741.2922 (Calcd. For $C_{38}H_{47}O_6N_4ClFS$: 741.2889).
Anal. Calcd for $C_{38}H_{46}ClFN_4O_6S \cdot 0.25HCl \cdot 2.5H_2O$: C, 57.38; H, 6.49; Cl, 5.57; F, 2.39; N, 7.04; S, 4.03.
Found: C, 57.11; H, 6.07; Cl, 5.89; F, 2.22; N, 6.66; S, 3.99.

Example 111

Trans-4-[1-[[4-[(benzo[b]thiophen-3-ylcarbonyl)amino]-5-chloro-2-fluorophenyl]acetyl]-(4S)-(4-methylpiperazin-1-yl)-(2S)-pyrrolidinylmethoxy]cyclohexanecarboxylic acid Trans-4-[1-(tert-butoxycarbonyl)-(4S)-(4-methylpiperazin-1-yl)-(2S)-pyrrolidinylmethoxy]cyclohexanecarboxylic acid ethyl ester NMR ($CDCl_3$) δ: 1.24 (3H, t, J=7.1 Hz), 1.45 (9H, s), 1.71-2.72 (19H, m), 3.12-4.01 (10H, m), 4.11 (2H, q, J=7.1 Hz).
MS (ESI) m/z: 454 ($M^+$+1).

Trans-4-[1-[[4-[(benzo[b]thiophen-3-ylcarbonyl)amino]-5-chloro-2-fluorophenyl]acetyl]-(4S)-(4-methylpiperazin-1-yl)-(2S)-pyrrolidinylmethoxy]cyclohexanecarboxylic acid

[Formula 222]

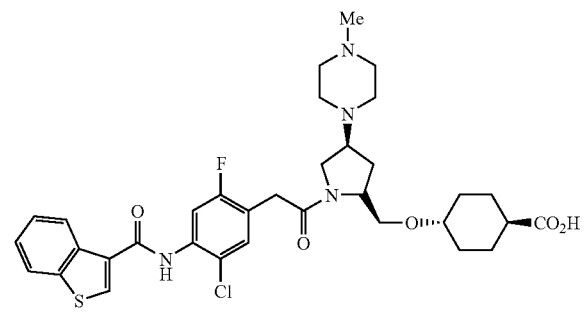

NMR (DMSO-$d_6$) δ: 1.07-1.43 (4H, m), 1.54-2.73 (16H, m), 2.83-4.28 (11H, m), 7.44-7.59 (4H, m), 8.10 (1H, d, J=7.8 Hz), 8.45 (1H, d, J=7.6 Hz), 8.66 (1H, s), 10.13 (1H, s).
IR (ATR) $cm^{-1}$: 3423, 2927, 2856, 1635, 1521.
MS (ESI) m/z: 671 ($M^+$+1); MS (FAB) m/z: 671 ($M^+$+1); MS (FAB) m/z: 671.2455 (Calcd. for $C_{34}H_{41}ClFN_4O_5S$: 671.2470).
Anal. Calcd for $C_{34}H_{40}ClFN_4O_5S \cdot 0.5HCl \cdot 2.5H_2O$: C, 55.60; H, 6.24; Cl, 7.24; F, 2.59; N, 7.63; S, 4.37.
Found: C, 55.39; H, 5.62; Cl, 7.13; F, 2.54; N, 7.55; S, 4.47.

Example 112

Trans-4-[1-[[2,5-dichloro-4-[(1-methyl-1H-indol-3-ylcarbonyl)amino]phenyl]acetyl]-(4S)-(4-methylpiperazin-1-yl)-(2S)-pyrrolidinylmethoxy]cyclohexanecarboxylic acid 4-[1-(Tert-butoxycarbonyl)-(4S)-(4-methylpiperazin-1-yl)-(2S)-pyrrolidinylmethoxy]cyclohexanecarboxylic acid ethyl ester NMR ($CDCl_3$) δ: 1.24 (3H, t, J=7.1 Hz), 1.45 (9H, s), 1.71-2.72 (19H, m), 3.12-4.01 (10H, m), 4.11 (2H, q, J=7.1 Hz).
MS (ESI) m/z: 454 ($M^+$+1).

Trans-4-[1-[[2,5-dichloro-4-[(1-methyl-1H-indol-3-ylcarbonyl)amino]phenyl]acetyl]-(4S)-(4-methylpiperazin-1-yl)-(2S)-pyrrolidinylmethoxy]cyclohexanecarboxylic acid

[Formula 223]

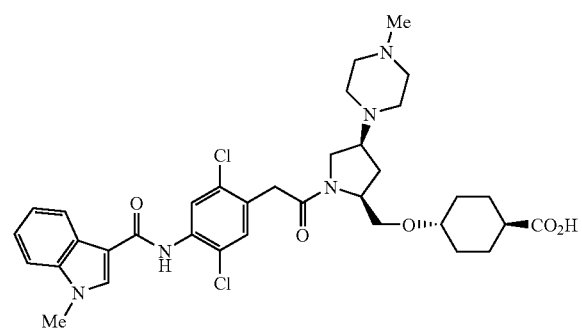

NMR ($CDCl_3$) δ: 1.14-1.50 (4H, m), 1.90-2.42 (7H, m), 2.60-3.24 Hz), 8.09-8.13 (1H, m), 8.23 (1H, d, J=6.9 Hz), 8.36 (1H, s), 8.74 (1H, d, J=6.4 Hz).
IR (ATR) $cm^{-1}$: 2935, 2857, 1639, 1502, 1371.
MS (ESI) m/z: 684 ($M^+$+1).
Anal. Calcd for $C_{35}H_{43}Cl_2N_5O_5 \cdot 0.5HCl \cdot 3.0H_2O$: C, 55.54; H, 6.59; Cl, 11.71; N, 9.25.
Found: C, 55.96; H, 6.42; Cl, 11.30; N, 8.45.

Example 113

Trans-4-[1-[[2,5-dichloro-4-[(1-methyl-1H-indol-3-ylcarbonyl)amino]phenyl]acetyl]-(4S)-(4-isopropylpiperazin-1-yl)-(2S)-pyrrolidinylmethoxy]cyclohexanecarboxylic acid 4-[1-(Tert-butoxycarbonyl)-(4S)-(4-isopropylpiperazin-1-yl)-(2S)-pyrrolidinylmethoxy]cyclohexanecarboxylic acid ethyl ester NMR (CDCl$_3$) δ: 1.05 (6H, d, J=10.0 Hz) 1.23-1.26 (2H, m), 1.24 (3H, t, J=7.1 Hz), 1.41-1.46 (1H, m), 1.46 (9H, s), 1.61-3.95 (24H, m), 4.11 (2H, q, J=8.2 Hz).

Trans-4-[1-[[2,5-dichloro-4-[(1-methyl-1H-indol-3-ylcarbonyl)amino]phenyl]acetyl]-(4S)-(4-isopropylpiperazin-1-yl)-(2S)-pyrrolidinylmethoxy]cyclohexanecarboxylic acid

[Formula 224]

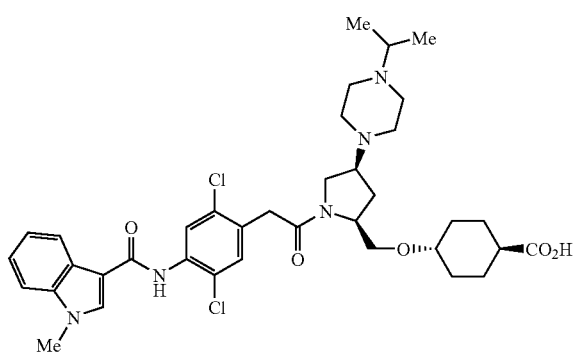

NMR (CDCl$_3$) δ: 1.13-1.71 (6H, m), 1.34 (6H, d, J=6.6 Hz), 1.89-2.42 (7H, m), 2.81-4.38 (19H, m), 7.30-7.41 (4H, m), 7.80 (1H, d, J=4.4 Hz), 8.10-8.14 (1H, m), 8.23 (1H, d, J=9.8 Hz), 8.41 (1H, s), 8.73 (1H, d, J=6.4 Hz).
IR (ATR) cm$^{-1}$: 2935, 2857, 1643, 1500, 1371.
MS (ESI) m/z: 712 (M$^+$+1).
Anal. Calcd for C$_{37}$H$_{47}$Cl$_2$N$_5$O$_5$·HCl·3.0H$_2$O: C, 55.33; H, 6.78; Cl, 13.24; N, 8.72.
Found: C, 55.49; H, 6.55; Cl, 13.05; N, 8.02.

Example 114

Trans-4-[1-[[4-[(benzo[b]furan-3-ylcarbonyl)amino]-2,5-dichlorophenyl]acetyl]-(4S)-[4-(tert-butyl)piperazin-1-yl]-(2S)-pyrrolidinylmethoxy]cyclohexanecarboxylic acid Trans-4-[1-tert-butoxycarbonyl-(4S)-[4-(tert-butyl)piperazin-1-yl]-(2S)-pyrrolidinylmethoxy]cyclohexanecarboxylic acid ethyl ester NMR (CDCl$_3$) δ: 1.07 (8H, s), 1.15-1.33 (5H, m), 1.41-1.55 (11H, m), 1.68-2.10 (7H, m), 2.12-3.06 (11H, m), 3.11-4.03 (4H, m), 4.07-4.17 (3H, m).
MS (ESI) m/z: 496 (M$^+$+1).

Ethyl trans-4-[(4S)-[4-(tert-butyl)piperazin-1-yl]-(2S)-pyrrolidinylmethoxy]cyclohexanecarboxylic acid ethyl hydrochloride MS (ESI) m/z: 396 (M$^+$+1-3HCl).

Trans-4-[1-[[4-[(benzo[b]furan-3-ylcarbonyl)amino]-2,5-dichlorophenyl]acetyl]-(4S)-[4-(tert-butyl)piperazin-1-yl]-(2S)-pyrrolidinylmethoxy]cyclohexanecarboxylic acid ethyl ester NMR (CDCl$_3$) δ: 1.11-1.49 (16H, m), 1.82-2.47 (7H, m), 2.49-3.01 (7H, m), 3.09-3.27 (3H, m), 3.56-3.98 (4H, m), 4.04-4.43 (3H, m), 7.37-7.46 (3H, m), 7.54-7.63 (1H, m), 8.01-8.08 (1H, m), 8.20-8.32 (2H, m), and 8.70 (total 1H, each s, amide isomers).
MS (ESI) m/z: 741 (M$^+$+1), 743 (M$^+$+3).

Trans-4-[1-[[4-[(benzo[b]furan-3-ylcarbonyl)amino]-2,5-dichlorophenyl]acetyl]-(4S)-[4-(tert-butyl)piperazin-1-yl]-(2S)-pyrrolidinylmethoxy]cyclohexanecarboxylic acid

[Formula 225]

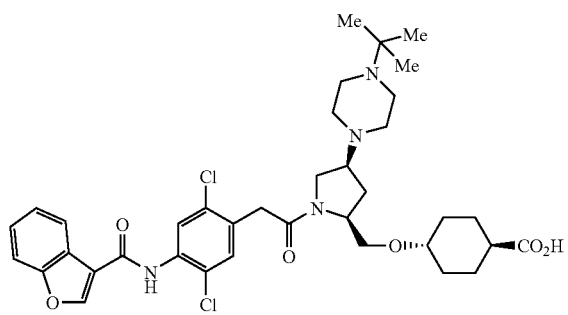

NMR (CDCl$_3$) δ: 1.09-1.74 (14H, m), 1.85-2.49 (7H, m), 2.67-3.34 (9H, m), 3.33-3.99 (7H, m), 4.05-4.57 (1H, m), 7.37-7.45 (3H, m), 7.55-7.63 (1H, m), 8.02-8.08 (1H, m), 8.23-8.39 (2H, m), 8.62 (1H, s).
MS (ESI) m/z: 713 (M$^+$+1), 714 (M$^+$+3).
IR (ATR) cm$^{-1}$: 2937, 2856, 1670, 1641, 1570, 1508, 1448.

Example 115

Trans-4-[1-[[2,5-dichloro-4-[(1-methyl-1H-indol-3-ylcarbonyl)amino]phenyl]acetyl]-(4S)-[(4-cyclopropylmethyl)piperazin-1-yl]-(2S)-pyrrolidinylmethoxy]cyclohexanecarboxylic acid Trans-4-[1-(tert-butoxycarbonyl)-(4S)-[(4-cyclopropyl methyl)piperazin-1-yl]-(2S)-pyrrolidinylmethoxy]cyclohexane carboxylic acid ethyl ester NMR (CDCl$_3$) δ: 0.06-0.12 (2H, m), 0.47-0.54 (2H, m), 0.80-0.90 (1H, m), 1.20-1.27 (5H, m), 1.41-1.47 (11H, m), 1.70-2.73 (17H, m), 2.93-3.03 (1H, m), 3.14-3.25 (1H, m), 3.32-3.58 (1H, m), 3.67-4.15 (6H, m).
MS (ESI) m/z: 494 (M$^+$+1).

Trans-4-[1-[[2,5-dichloro-4-[(1-methyl-1H-indol-3-ylcarbonyl)amino]phenyl]acetyl]-(4S)-[(4-cyclopropylmethyl)piperazin-1-yl]-(2S)-pyrrolidinylmethoxy]cyclohexanecarboxylic acid ethyl ester NMR (CDCl$_3$) δ: 0.07-0.13 (2H, m), 0.48-0.54 (2H, m), 0.80-0.90 (1H, m), 1.18-1.27 (5H, m), 1.36-1.51 (2H, m), 1.80-2.05 (18H, m), 3.15-3.25 (2H, m), 3.42-4.44 (11H, m), 7.32-7.45 (4H, m), 7.81 (1H, d, J=2.9 Hz), 8.11-8.16 (1H, m), 8.26-8.23 (1H, m), 8.79 (1H, d, J=8.5 Hz).

MS (ESI) m/z: 752 (M$^+$+1), 754 (M$^+$+3), 756 (M$^+$+5).

Trans-4-[1-[[2,5-dichloro-4-[(1-methyl-1H-indol-3-ylcarbonyl)amino]phenyl]acetyl]-(4S)-[(4-cyclopropylmethyl)piperazin-1-yl]-(2S)-pyrrolidinylmethoxy]cyclohexanecarboxylic acid

[Formula 226]

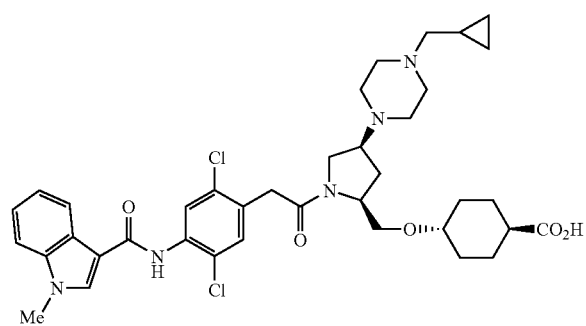

NMR (CDCl$_3$) δ: 0.14-0.22 (2H, m), 0.52-0.63 (2H, m), 0.91-1.01 (1H, m), 1.13-1.34 (2H, m), 1.35-1.52 (2H, m), 1.58-2.11 (5H, m), 2.12-2.28 (2H, m), 2.32-3.10 (11H, m), 3.13-3.29 (2H, m), 3.39-4.44 (9H, m), 7.29-7.41 (4H, m), 7.78 (1H, d, J=5.9 Hz), 8.09-8.15 (1H, m), 8.21 (1H, d, J=11.0 Hz), 8.73 (1H, d, J=8.5 Hz).

MS (ESI) m/z: 724 (M$^+$+1), 726 (M$^+$+3), 728 (M$^+$+5).

Anal. Calcd for C$_{38}$H$_{47}$Cl$_2$N$_5$O$_5$·0.75H$_2$O: C, 61.83; H, 6.62; N, 9.49; Cl, 9.60.

Found: C, 62.01; H, 6.77; N, 9.02; Cl, 9.60.

Example 116

Trans-4-[(4S)-(4-benzylpiperazin-1-yl)-1-[[4-[(benzo[b]thiophen-3-ylcarbonyl)amino]-5-chloro-2-fluorophenyl]acetyl]-(2S)-pyrrolidinylmethoxy]cyclohexanecarboxylic acid Trans-4-[(4S)-(4-benzylpiperazin-1-yl)-1-(tert-butoxycarbonyl)-(2S)-pyrrolidinylmethoxy]cyclohexanecarboxylic acid ethyl ester NMR (CDCl$_3$) δ: 1.24 (3H, t, J=7.1 Hz), 1.45 (9H, s), 1.70-2.65 (16H, m), 2.91-3.98 (10H, m), 3.49 (2H, s), 4.11 (2H, q, J=7.1 Hz), 7.23-7.31 (5H, m).

MS (ESI) m/z: 530 (M$^+$+H).

Trans-4-[(4S)-(4-benzylpiperazin-1-yl)-1-[[4-[(benzo[b]thiophen-3-ylcarbonyl)amino]-5-chloro-2-fluorophenyl]acetyl]-(2S)-pyrrolidinylmethoxy]cyclohexanecarboxylic acid

[Formula 227]

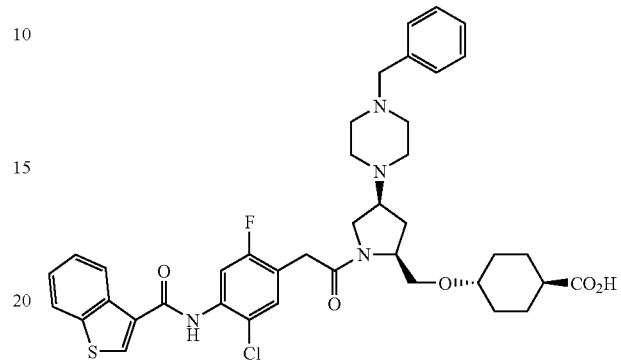

NMR (DMSO-d$_6$) δ: 1.04-1.43 (4H, m), 1.58-2.87 (16H, m), 3.12-4.27 (10H, m), 7.23-7.37 (5H, m), 7.44-7.60 (4H, m), 8.10 (1H, d, J=7.2 Hz), 8.45 (1H, d, J=7.2 Hz), 8.66 (1H, s), 10.13 (1H, s).

IR (ATR) cm$^{-1}$: 3423, 2935, 2854, 1637, 1523.

MS (ESI) m/z: 747 (M$^+$+H).

Anal. Calcd for C$_{40}$H$_{44}$ClFN$_4$O$_5$S·0.4HCl·1.25H$_2$O: C, 61.25; H, 6.03; Cl, 6.33; F, 2.42; N, 7.14; S, 4.09.

Found: C, 61.02; H, 5.62; Cl, 6.09; F, 2.39; N, 7.17; S, 4.16.

Example 117

Trans-4-[1-[[2,5-dichloro-4-[(1-methyl-1H-indol-3-ylcarbonyl)amino]phenyl]acetyl]-(4S)-[4-(2-fluoroethyl)piperazin-1-yl]-(2S)-pyrrolidinylmethoxy]cyclohexanecarboxylic acid Trans-4-[1-(tert-butoxycarbonyl)-(4S)-[4-(2-fluoroethyl)piperazin-1-yl]-(2S)-pyrrolidinylmethoxy]cyclohexanecarboxylic acid ethyl ester NMR (CDCl$_3$) δ: 1.16-1.31 (5H, m), 1.38-1.50 (11H, m), 1.70-1.82 (1H, m), 1.93-2.08 (4H, m), 2.17-2.37 (2H, m), 2.40-2.76 (11H, m), 2.94-3.04 (1H, m), 3.15-3.26 (1H, m), 3.34-3.61 (1H, m), 4.01-3.68 (3H, m), 4.11 (2H, q, J=7.1 Hz), 4.57 (2H, dt, J=47.6, 4.9 Hz).

MS (ESI) m/z: 486 (M$^+$+1).

Trans-4-[1-[[2,5-dichloro-4-[(1-methyl-1H-indol-3-ylcarbonyl)amino]phenyl]acetyl]-(4S)-[4-(2-fluoroethyl)piperazin-1-yl]-(2S)-pyrrolidinylmethoxy]cyclohexanecarboxylic acid ethyl ester NMR (CDCl$_3$) δ: 1.14-1.31 (5H, m), 1.36-1.53 (2H, m), 1.85-2.09 (7H, m), 2.16-2.32 (2H, m), 2.35-2.78 (11H, m), 3.15-3.26 (2H, m), 3.42-4.26 (9H, m), 4.57 (2H, dt, J=47.6, 4.9 Hz), 7.32-7.45 (4H, m), 7.80-7.83 (1H, m), 8.11-8.17 (1H, m), 8.27-8.23 (1H, m), 8.79 (1H, d, J=8.3 Hz)

MS (ESI) m/z: 744 (M$^+$+1), 746 (M$^+$+3), 748 (M$^+$+5).

Trans-4-[1-[[2,5-dichloro-4-[(1-methyl-1H-indol-3-ylcarbonyl)amino]phenyl]acetyl]-(4S)-[4-(2-fluoroethyl)piperazin-1-yl]-(2S)-pyrrolidinylmethoxy]cyclohexanecarboxylic acid

[Formula 228]

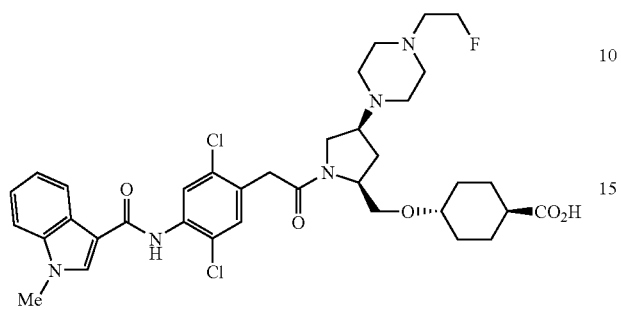

NMR (CDCl$_3$) δ: 1.14-1.53 (4H, m), 1.62-2.17 (7H, m), 2.17-2.89 (15H, m), 2.97-4.47 (7H, m), 4.58 (2H, dt, J=47.6, 4.9 Hz), 7.32-7.43 (4H, m), 7.80 (1H, s), 8.10-8.15 (1H, m), 8.24 (1H, d, J=5.4 Hz), 8.78-8.74 (1H, m).
MS (ESI) m/z: 716 (M$^+$+1), 718 (M$^+$+3), 720 (M$^+$+5).
Anal. Calcd for C$_{36}$H$_{44}$Cl$_2$FN$_5$O$_5$·0.75H$_2$O: C, 59.22; H, 6.28; N, 9.59.
Found: C, 58.94; H, 6.41; N, 8.94.

Example 118

Trans-4-[1-[[5-chloro-2-fluoro-4-[(1-methyl-1H-indol-3-ylcarbonyl)amino]phenyl]acetyl]-(4S)-[4-(2-fluoroethyl)piperazin-1-yl]-(2S)-pyrrolidinylmethoxy]cyclohexanecarboxylic acid Trans-4-[1-[[5-chloro-2-fluoro-4-[(1-methyl-1H-indol-3-ylcarbonyl)amino]phenyl]acetyl]-(4S)-[4-(2-fluoroethyl)piperazin-1-yl]-(2S)-pyrrolidinylmethoxy]cyclohexanecarboxylic acid ethyl ester NMR (CDCl$_3$) δ: 1.10-1.32 (4H, m), 1.34-1.54 (2H, m), 1.83-2.09 (7H, m), 2.15-2.31 (2H, m), 2.35-2.81 (11H, m), 3.12-3.27 (2H, m), 3.45-3.87 (4H, m), 3.89 (3H, s), 4.04-4.13 (2H, m), 4.57 (2H, dt, J=47.7, 4.8 Hz), 7.32-7.45 (4H, m), 7.82 (1H, d, J=4.6 Hz), 8.11-8.17 (1H, m), 8.28-8.32 (1H, m), 8.50 (1H, dd, J=12.0, 9.8 Hz).
MS (ESI) m/z: 728 (M$^+$+1), 730 (M$^+$+3).

Trans-4-[1-[[5-chloro-2-fluoro-4-[(1-methyl-1H-indol-3-ylcarbonyl)amino]phenyl]acetyl]-(4S)-[4-(2-fluoroethyl)piperazin-1-yl]-(2S)-pyrrolidinylmethoxy]cyclohexanecarboxylic acid

[Formula 229]

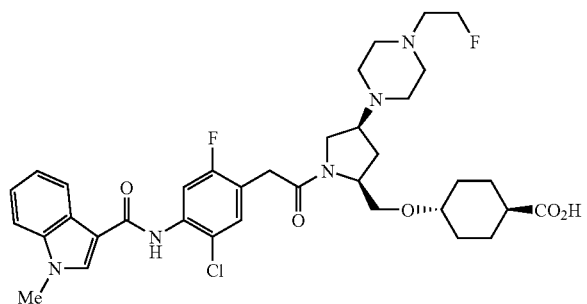

NMR (CDCl$_3$) δ: 1.10-2.33 (11H, m), 2.35-3.08 (11H, m), 3.12-3.31 (2H, m), 3.42-3.91 (7H, m), 4.13-4.44 (2H, m), 4.48-4.67 (2H, m), 7.31-7.44 (4H, m), 7.80-7.82 (1H, m), 8.10-8.16 (1H, m), 8.31-8.27 (1H, m), 8.49 (1H, t, J=11.6 Hz).
MS (ESI) m/z: 700 (M+1), 703 (M$^+$+3).
Anal. Calcd for C$_{36}$H$_{44}$ClF$_2$N$_5$O$_5$·1.75H$_2$O: C, 59.09; H, 6.54; N, 9.57.
Found: C, 59.23; H, 6.35; N, 9.21.

Example 119

Trans-4-[1-[[2,5-dichloro-4-[(1-methyl-1H-indol-3-ylcarbonyl)amino]phenyl]acetyl]-(4S)-[4-(1,1-dimethyl-2-fluoro ethyl)piperazin-1-yl]-(2S)-pyrrolidinylmethoxy]cyclohexanecarboxylic acid 4-(1,1-Dimethyl-2-fluoroethyl)piperazine-1-carboxylic acid benzyl ester Bis-(2-oxoethyl)carbamic acid benzyl ester (0.81 g, 3.45 mmol) and 1,1-dimethyl-2-fluoroethylamine hydrochloride (0.40 g, 3.14 mmol) were dissolved dichloroethane (50 mL), and sodium triacetoxyborohydride (1.99 g, 9.41 mmol) was added thereto. The mixture was stirred for three days at room temperature. A saturated aqueous solution of sodium hydrogen carbonate (20 mL) was added to the reaction liquor, and the mixture was stirred for 30 minutes, and then extracted with methylenechloride. The extract was washed with saturated brine, and dried over anhydrous sodium sulfate, and then the solvent was concentrated under reduced pressure. The obtained residue was purified by flash chromatography (Flash Chromatography System from Biotage AB, column size: 40S, n-hexane/ethyl acetate=1/1 to ethyl acetate), to obtain the title compound (370 mg, 29%), partially including impurities, as an oily matter.
NMR (CDCl$_3$) δ: 1.08 (6H, d, J=2.0 Hz), 2.55-2.65 (4H, m), 3.49 (4H, t, J=5.0 Hz), 5.13 (2H, s), 5.74-5.84 (2H, m), 7.41-7.27 (5H, m).
MS (ESI) m/z: 295 (M$^+$+1).

4-(1,1-Dimethyl-2-fluoroethyl)piperazine 4-(1,1-Dimethyl-2-fluoroethyl)piperazine-1-carboxylic acid benzyl ester (270 mg, 0.92 mmol) was dissolved in ethanol (20 mL), and 10% palladium hydroxide/carbon (100 mg) was added thereto. The mixture was stirred for two days at room temperature under a hydrogen stream at normal pressure. The catalyst was separated by filtration, and then the reaction liquor was concentrated under reduced pressure, and dried to obtain the title compound (97 mg, 66%) as an oily matter. This compound was used in the subsequent reaction without performing further purification.
NMR (CDCl$_3$) δ: 1.09 (6H, d, J=1.7 Hz), 2.89-2.95 (4H, m), 3.14-3.22 (4H, m), 4.26 (2H, d, J=47.8 Hz), 7.36-8.01 (1H, m).

Trans-4-[1-[[2,5-dichloro-4-[(1-methyl-1H-indol-3-ylcarbonyl)amino]phenyl]acetyl]-(4S)-[4-(1,1-dimethyl-2-fluoro ethyl)piperazin-1-yl]-(2S)-pyrrolidinylmethoxy]cyclohexanecarboxylic acid ethyl ester NMR (CDCl$_3$) δ: 1.08 (6H, d, J=1.5 Hz), 1.13-1.51 (7H, m), 1.57-2.09 (7H, m), 2.12-2.32 (2H, m), 2.36-2.76 (7H, m), 3.87-2.92 (9H, m), 3.89 (3H, s), 4.25-4.25 (3H, m), 7.30-7.46 (4H, m), 7.80 and 7.81 (total 1H, each s, amide isomers), 8.11-8.17 (1H, m), 8.24 (1H, s), 8.78 and 8.80 (total 1H, each s, amide isomers).
MS (ESI) m/z: 772 (M$^+$+1), 774 (M$^+$+3).

281

Trans-4-[1-[[2,5-dichloro-4-[(1-methyl-1H-indol-3-ylcarbonyl)amino]phenyl]acetyl]-(4S)-[4-(1,1-dimethyl-2-fluoro ethyl)piperazin-1-yl]-(2S)-pyrrolidinylmethoxy]cyclohexanecarboxylic acid

[Formula 230]

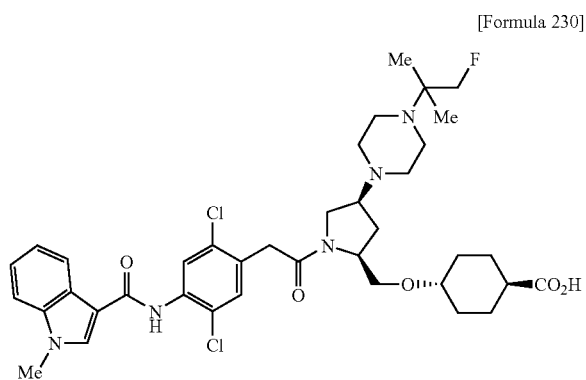

NMR (CDCl$_3$) δ: 1.10 (6H, d, J=4.2 Hz), 1.14-1.73 (6H, m), 1.81-2.48 (6H, m), 2.49-2.88 (8H, m), 2.99-3.55 (3H, m), 3.60-3.97 (7H, m), 4.30-4.30 (3H, m), 7.31-7.43 (4H, m), 7.79 (1H, s), 8.10-8.15 (1H, m), 8.22 and 8.23 (total 1H, each s, amide isomers), 8.75 and 8.78 (total 1H, each s, amide isomers).

MS (ESI) m/z: 744 (M$^+$+1), 746 (M$^+$+3).

Example 120

Trans-4-[1-[[2,5-dichloro-4-[(1-methyl-1H-indol-3-ylcarbonyl)amino]phenyl]acetyl]-(4S)-[4-(2,2-difluoroethyl)piperazin-1-yl]-(2S)-pyrrolidinylmethoxy]cyclohexanecarboxylic acid Trans-4-[1-(tert-butoxycarbonyl)-(4S)-[4-(2,2-difluoroethyl)piperazin-1-yl]-(2S)-pyrrolidinylmethoxy]cyclohexane carboxylic acid ethyl ester NMR (CDCl$_3$) δ: 1.17-1.29 (5H, m), 1.39-1.50 (11H, m), 1.69-1.89 (1H, m), 1.94-2.08 (4H, m), 2.17-2.35 (2H, m), 2.41-2.67 (9H, m), 2.73 (2H, td, J=15.0, 4.4 Hz), 2.93-3.02 (1H, m), 3.15-3.25 (1H, m), 3.32-3.60 (1H, m), 3.68-3.98 (3H, m), 4.12 (2H, q, J=7.1 Hz), 5.87 (1H, tt, J=56.4, 4.6 Hz).

MS (ESI) m/z: 504 (M$^+$+1).

Trans-4-[1-[[2,5-dichloro-4-[(1-methyl-1H-indol-3-ylcarbonyl)amino]phenyl]acetyl]-(4S)-[4-(2,2-difluoroethyl)piperazin-1-yl]-(2S)-pyrrolidinylmethoxy]cyclohexanecarboxylic acid ethyl ester NMR (CDCl$_3$) δ: 1.14-1.32 (5H, m), 1.36-1.52 (2H, m), 1.83-2.34 (7H, m), 2.33-2.81 (11H, m), 2.95-3.27 (2H, m), 3.43-3.84 (4H, m), 3.89 (3H, s), 3.92-4.41 (4H, m), 5.87 (1H, tt, J=55.9, 4.4 Hz), 7.32-7.45 (4H, m), 7.81 (1H, d, J=2.9 Hz), 8.11-8.17 (1H, m), 8.26-8.23 (1H, m), 8.79 (1H, d, J=8.1 Hz).

MS (ESI) m/z: 762 (M$^+$+1), 764 (M$^+$+3), 766 (M$^+$+5).

282

Trans-4-[1-[[2,5-dichloro-4-[(1-methyl-1H-indol-3-ylcarbonyl)amino]phenyl]acetyl]-(4S)-[4-(2,2-difluoroethyl)piperazin-1-yl]-(2S)-pyrrolidinylmethoxy]cyclohexanecarboxylic acid

[Formula 231]

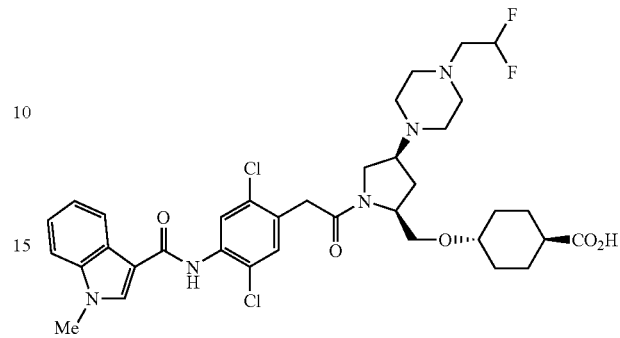

NMR (CDCl$_3$) δ: 1.14-1.36 (4H, m), 1.36-1.56 (2H, m), 1.95-2.14 (4H, m), 2.18-3.79 (18H, m), 3.81-4.51 (5H, m), 5.70-6.04 (1H, m), 7.31-7.37 (2H, m), 7.38-7.44 (2H, m), 7.80 (1H, s), 8.10-8.16 (1H, m), 8.23 (1H, d, J=3.4 Hz), 8.77 (1H, d, J=10.5 Hz).

MS (ESI) m/z: 734 (M$^+$+1), 736 (M$^+$+3), 738 (M$^+$+5).

Anal. Calcd for C$_{36}$H$_{43}$Cl$_2$F$_2$N$_5$O$_5$.H$_2$O: C, 57.45; H, 6.03; N, 9.30.
Found: C, 57.72; H, 6.11; N, 9.01.

Example 121

Trans-4-[1-[[5-chloro-2-fluoro-4-[(1-methyl-1H-indol-3-ylcarbonyl)amino]phenyl]acetyl]-(4S)-[4-(2,2-difluoroethyl)piperazin-1-yl]-(2S)-pyrrolidinylmethoxy]cyclohexanecarboxylic acid Trans-4-[1-[[5-chloro-2-fluoro-4-[(1-methyl-1H-indol-3-ylcarbonyl)amino]phenyl]acetyl]-(4S)-[4-(2,2-difluoroethyl)piperazin-1-yl]-(2S)-pyrrolidinylmethoxy]cyclohexanecarboxylic acid ethyl ester NMR (CDCl$_3$) δ: 1.12-1.34 (5H, m), 1.35-1.51 (2H, m), 1.82-2.10 (5H, m), 2.16-2.30 (2H, m), 2.37-2.81 (11H, m), 2.93-3.27 (2H, m), 3.44-3.85 (4.5H, m), 3.89-3.90 (3H, m), 4.04-4.39 (3.5H, m), 5.71-6.04 (1H, m), 7.33-7.45 (4H, m), 7.82 (1H, d, J=4.6 Hz), 8.12-8.17 (1H, m), 8.30 (1H, br s), 8.51 (1H, dd, J=12.1, 9.6 Hz).

MS (ESI) m/z: 746 (M$^+$+1), 748 (M$^+$+3).

Trans-4-[1-[[5-chloro-2-fluoro-4-[(1-methyl-1H-indol-3-ylcarbonyl)amino]phenyl]acetyl]-(4S)-[4-(2,2-difluoroethyl)piperazin-1-yl]-(2S)-pyrrolidinylmethoxy]cyclohexanecarboxylic acid

[Formula 232]

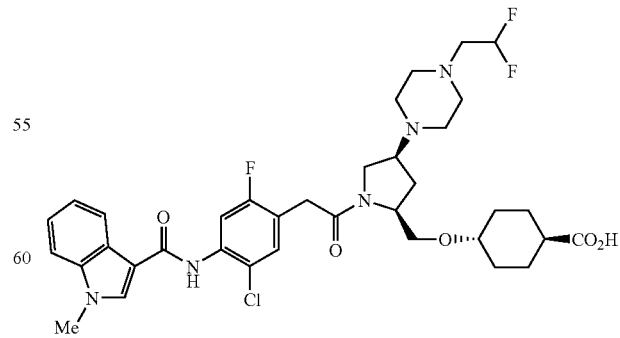

NMR (CDCl$_3$) δ: 1.10-1.36 (4H, m), 1.36-1.55 (2H, m), 1.91-2.15 (4H, m), 2.16-3.76 (18H, m), 3.79-4.70 (5H, m), 5.68-6.06 (1H, m), 7.32-7.44 (4H, m), 7.81 (1H, s), 8.09-8.16 (1H, m), 8.32-8.27 (1H, m), 8.49 (1H, t, J=11.5 Hz).

MS (ESI) m/z: 718 (M⁺+1), 720 (M⁺+3).
Anal. Calcd for $C_{36}H_{43}ClF_3N_5O_5 \cdot 2H_2O$: C, 57.33; H, 6.28; N, 9.29.
Found: C, 57.40; H, 6.28; N, 9.01.

Example 122

Trans-4-[1-[[2,5-dichloro-4-[(1-methyl-1H-indol-3-ylcarbonyl)amino]phenyl]acetyl]-(4S)-[4-(2,2,2-trifluoroethyl)piperazin-1-yl]-(2S)-pyrrolidinylmethoxy]cyclohexanecarboxylic acid Trans-4-[1-(tert-butoxycarbonyl)-(4S)-[4-(2,2,2-trifluoroethyl)piperazin-1-yl]-(2S)-pyrrolidinylmethoxy]cyclohexanecarboxylic acid ethyl ester NMR (CDCl₃) δ: 1.2-1.3 (2H, m), 1.2 (3H, t, J=7.1 Hz), 1.4 (9H, s), 1.8 (1H, q, J=10.5 Hz), 1.9-2.1 (6H, m), 2.2-2.7 (12H, m), 3.0 (2H, q, J=9.6 Hz), 3.2-4.0 (5H, m), 4.1-4.2 (2H, m).
MS (ESI) m/z: 522 (M⁺+1).

Trans-4-[1-[[2,5-dichloro-4-[(1-methyl-1H-indol-3-ylcarbonyl)amino]phenyl]acetyl]-(4S)-[4-(2,2,2-trifluoroethyl)piperazin-1-yl]-(2S)-pyrrolidinylmethoxy]cyclohexanecarboxylic acid

[Formula 233]

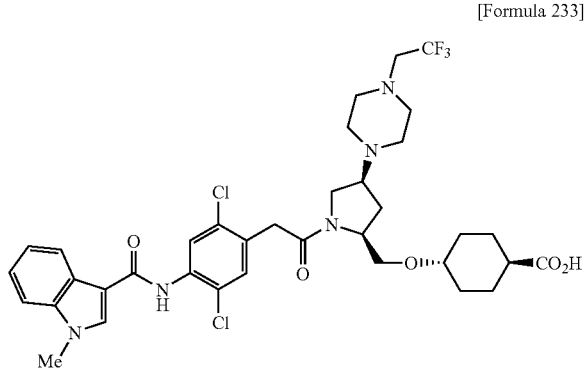

NMR (CDCl₃) δ: 1.2-1.5 (4H, m), 1.9-4.4 (29H, m), 7.3-7.4 (2H, m), 7.4-7.4 (3H, m), 7.8 (1H, s), 8.1-8.1 (1H, m), 8.2 (1H, d, J=4.9 Hz), 8.8 (1H, d, J=9.1 Hz).
IR (ATR) cm⁻¹: 2937, 2857, 1643, 1500, 1099.
MS (FAB) m/z: 752.2593 (calcd for $C_{36}H_{43}Cl_2F_3N_5O_5$: 752.2593).
Anal. Calcd for $C_{36}H_{42}Cl_2F_3N_5O_5 \cdot H_2O$: C, 56.11; H, 5.75; N, 9.09.
Found: C, 56.11; H, 5.73; N, 8.65.

Example 123

Trans-4-[1-[[4-[(benzo[b]thiophen-3-ylcarbonyl)amino]-5-chloro-2-fluorophenyl]acetyl]-(4S)-[4-(2,2,2-trifluoroethyl)piperazin-1-yl]-(2S)-pyrrolidinylmethoxy]cyclohexanecarboxylic acid

[Formula 234]

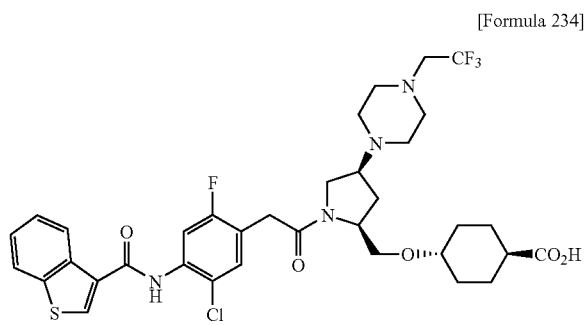

NMR (DMSO-d₆) δ: 1.08-1.42 (8H, m), 1.54-4.32 (22H, m), 7.41-7.53 (3H, m), 7.56 (1H, dd, J=10.8, 6.1 Hz), 8.10 (1H, d, J=7.4 Hz), 8.45 (1H, d, J=7.4 Hz), 8.65 (1H, s), 10.11 (1H, s).
IR (ATR) cm⁻¹: 2935, 2861, 1517, 1403, 1095.
MS (FAB) m/z: 739.2317 (calcd for $C_{35}H_{40}ClF_4N_4O_5S$: 739.2344).
Anal. Calcd for $C_{35}H_{39}ClF_4N_4O_5S \cdot 0.5$hexane$\cdot 0.7H_2O$: C, 57.49; H, 5.89; Cl, 4.47; F, 9.57; N, 7.06; S, 4.04.
Found: C, 57.11; H, 5.61; Cl, 4.61; F, 9.04; N, 6.89; S, 4.56.

Example 124

Trans-4-[1-[[5-chloro-2-fluoro-4-[(1-methyl-1H-indol-3-ylcarbonyl)amino]phenyl]acetyl]-(4S)-[4-(2,2,2-trifluoroethyl)piperazin-1-yl]-(2S)-pyrrolidinylmethoxy]cyclohexanecarboxylic acid

[Formula 235]

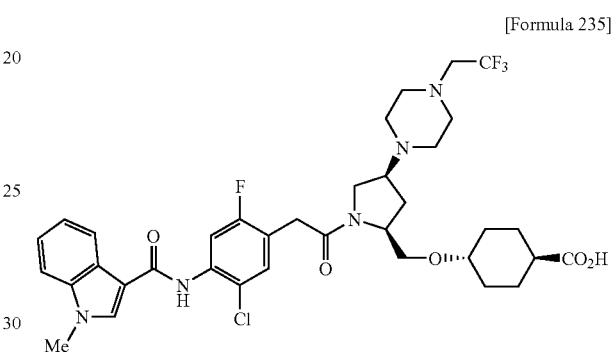

NMR (DMSO-d₆) δ: 1.08-1.42 (8H, m), 1.60-4.29 (25H, m), 7.22 (1H, t, J=7.6 Hz), 7.28 (1H, dt, J=1.1, 7.6 Hz), 7.43 (1H, d, J=7.6 Hz), 7.56 (1H, d, J=8.1 Hz), 7.70 (1H, dd, J=11.2, 7.6 Hz), 8.15 (1H, d, J=8.1 Hz), 8.31 (1H, s), 9.31 (1H, s), 12.05 (1H, br s).
IR (ATR) cm⁻¹: 2937, 2859, 1646, 1517, 1099.
MS (FAB) m/z: 736.2927 (calcd for $C_{36}H_{43}ClF_4N_5O_5$: 736.2889).
Anal. Calcd for $C_{36}H_{42}ClF_4N_5O_5 \cdot 0.5$hexane$\cdot 0.2HCl \cdot 0.2H_2O$: C, 58.49; H, 5.94; Cl, 5.57; F, 9.95; N, 9.17.
Found: C, 58.11; H, 6.09; Cl, 5.68; F, 9.68; N, 8.82.

Example 125

Trans-4-[1-[[4-[(benzo[b]furan-3-ylcarbonyl)amino]-2,5-dichlorophenyl]acetyl]-(4S)-[4-(2,2,2-trifluoroethyl)piperazin-1-yl]-(2S)-pyrrolidinylmethoxy]cyclohexanecarboxylic acid

[Formula 236]

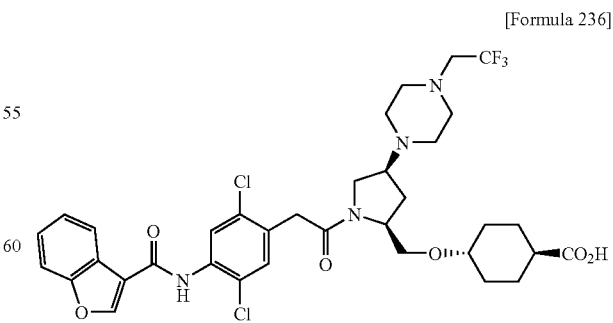

NMR (DMSO-d₆) δ: 1.11-1.40 (4H, m), 1.56-4.33 (26H, m), 7.37-7.46 (2H, m), 7.54 (1H, s), 7.72 (1H, d, J=7.4 Hz), 7.77 (1H, d, J=4.4 Hz), 8.09 (1H, t, J=4.4 Hz), 8.83 (1H, d, J=3.7 Hz), 10.07 (1H, br s).

IR (ATR) cm$^{-1}$: 2937, 2859, 1508, 1450, 1103.

MS (FAB) m/z: 739.2267 (calcd for $C_{35}H_{40}Cl_2F_3N_4O_6$: 736.2889).

Anal. Calcd for $C_{35}H_{39}Cl_2F_3N_4O_6 \cdot 0.45H_2O$: C, 56.22; H, 5.38; Cl, 9.48; F, 7.62; N, 7.49.

Found: C, 56.69; H, 5.64; Cl, 9.24; F, 7.13; N, 7.27.

Example 126

Trans-4-[1-[[4-[(benzo[b]furan-3-ylcarbonyl)amino]-5-chloro-2-fluorophenyl]acetyl]-(4S)-[4-(2,2,2-trifluoroethyl)piperazin-1-yl]-(2S)-pyrrolidinylmethoxy]cyclohexanecarboxylic acid

[Formula 237]

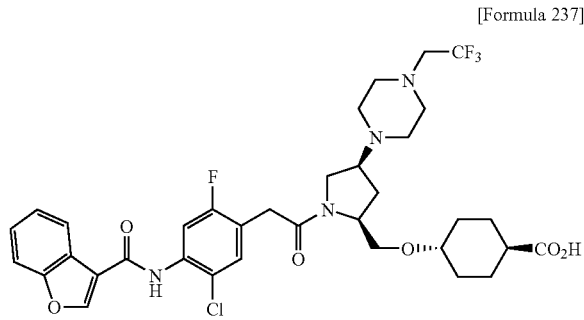

NMR (DMSO-d$_6$) δ: 1.08-1.41 (4H, m), 1.59-4.27 (26H, m), 7.37-7.46 (2H, m), 7.47 (1H, d, J=7.4 Hz), 7.56 (1H, dd, J=11.0, 5.9 Hz), 7.71 (1H, dd, J=7.4, 1.2 Hz), 8.09 (1H, d, J=7.4 Hz), 8.84 (1H, d, J=4.9 Hz), 9.98-10.05 (1H, m).

IR (ATR) cm$^{-1}$: 2937, 2859, 1521, 1450, 1405.

MS (FAB) m/z: 723.2599 (calcd for $C_{35}H_{40}ClF_4N_4O_6$: 723.2573).

Anal. Calcd for $C_{35}H_{39}ClF_4N_4O_6 \cdot 0.45H_2O$: C, 57.74; H, 5.61; Cl, 4.79; F, 10.26; N, 7.57.

Found: C, 57.96; H, 5.67; Cl, 4.82; F, 9.78; N, 7.47.

Example 127

Trans-4-[1-[[3-chloro-4-[(isoquinolin-1-ylcarbonyl)amino]phenyl]acetyl]-(4S)-[4-(2,2,2-trifluoroethyl)piperazin-1-yl]-(2S)-pyrrolidinylmethoxy]cyclohexanecarboxylic acid Trans-4-[1-[[3-chloro-4-[(isoquinolin-1-ylcarbonyl)amino]phenyl]acetyl]-(4S)-[4-(2,2,2-trifluoroethyl)piperazin-1-yl]-(2S)-pyrrolidinylmethoxy]cyclohexanecarboxylic acid ethyl ester NMR (CDCl$_3$) δ: 1.12-1.31 (5H, m, including 3H, t, J=7.1 Hz, at δ 1.20), 1.38-1.62 (2H, m), 1.84-2.04 (5H, m), 2.18-2.70 (total 11H, series of m), 2.92-3.21 (4H, m), 3.43-3.88 and 4.04-4.38 (total 8H, each m, including 2H, q, J=7.1 Hz, at δ 4.06), 7.21-7.25 (1H, m), 7.37-7.39 (1H, m), 7.71-7.78 (2H, m), 7.88-7.91 (2H, m), 8.58-8.66 (2H, m), 9.70-9.72 (1H, m), 10.99 and 11.01 (total 1H, each s).

MS (ESI) m/z: 744 (M$^+$+1).

Trans-4-[1-[[3-chloro-4-[(isoquinolin-1-ylcarbonyl)amino]phenyl]acetyl]-(4S)-[4-(2,2,2-trifluoroethyl)piperazin-1-yl]-(2S)-pyrrolidinylmethoxy]cyclohexanecarboxylic acid

[Formula 238]

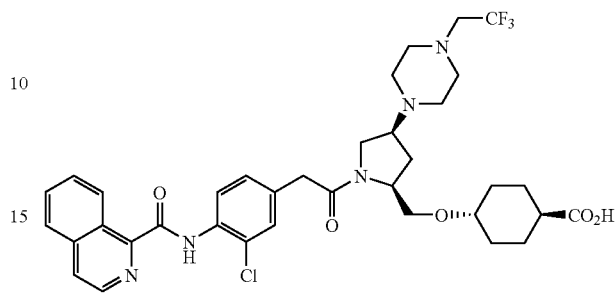

NMR (DMSO-d$_6$) δ: 1.05-1.32 (4H, m), 1.61-1.99 (5H, m), 2.10-2.66 (total 11H, series of m), 2.82-3.24 (4H, m), 3.49-3.79 (4H, m), 3.94-4.27 (2H, m), 7.26-7.37 (1H, d, J=5.6 Hz), 9.31-9.33 (1H, m), 10.83 and 10.84 (total 1H, each s), 12.04 (1H, broad s).

IR (ATR) cm$^{-1}$: 1637, 1522, 1421, 1271, 1149, 1128, 1107, 1092.

MS (LC-ESI) m/z: 716 (M$^+$+1).

Anal. Calcd for $C_{36}H_{41}ClF_3N_5O_5 \cdot \frac{1}{2}H_2O$: C, 59.62; H, 5.84; N, 9.66; Cl, 4.89; F, 7.86.

Found: C, 59.87; H, 5.77; N, 9.34; Cl, 4.91; F, 7.80.

Example 128

Trans-4-[1-[[3-chloro-4-[(1-methyl-1H-indazol-3-ylcarbonyl)amino]phenyl]acetyl]-(4S)-[4-(2,2,2-trifluoroethyl)piperazin-1-yl]-(2S)-pyrrolidinylmethoxy]cyclohexanecarboxylic acid Trans-4-[1-[[3-chloro-4-[(1-methyl-1H-indazol-3-ylcarbonyl)amino]phenyl]acetyl]-(4S)-[4-(2,2,2-trifluoroethyl)piperazin-1-yl]-(2S)-pyrrolidinylmethoxy]cyclohexanecarboxylic acid ethyl ester NMR (CDCl$_3$) δ: 1.10-1.31 (5H, m), 1.36-1.52 (2H, m), 1.81-2.09 (5H, m), 2.16-2.63 (6H, m), 2.65-2.75 (4H, m), 2.87-3.27 (4H, m), 3.40-3.88 (5H, m), 4.04-4.40 (7H, m), 7.16-7.22 (1H, m), 7.31-7.39 (2H, m), 7.44-7.53 (2H, m), 8.41 (1H, d, J=8.3 Hz), 8.59 (1H, t, J=8.8 Hz), 9.47-9.44 (1H, m).

MS (ESI) m/z: 747 (M$^+$+1), 749 (M$^+$+3).

Trans-4-[1-[[3-chloro-4-[(1-methyl-1H-indazol-3-ylcarbonyl)amino]phenyl]acetyl]-(4S)-[4-(2,2,2-trifluoroethyl)piperazin-1-yl]-(2S)-pyrrolidinylmethoxy]cyclohexanecarboxylic acid

[Formula 239]

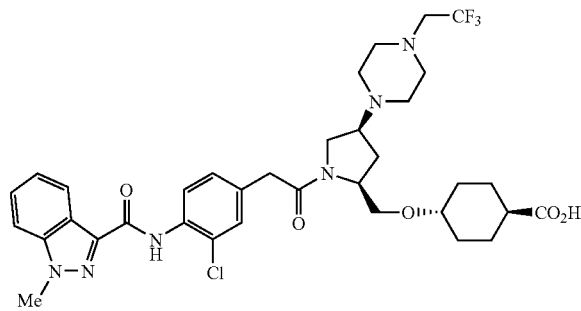

NMR (CDCl$_3$) δ: 1.10-1.67 (4H, m), 2.14-1.83 (5H, m), 2.80-2.17 (11H, m), 3.26-2.90 (4H, m), 3.86-3.39 (5H, m), 4.45-4.14 (5H, m), 7.21-7.16 (1H, m), 7.29-7.40 (2H, m), 7.50-7.43 (2H, m), 8.42-8.38 (1H, m), 8.61-8.55 (1H, m), 9.45 (1H, d, J=4.6 Hz).

MS (ESI) m/z: 719 (M$^+$+1), 721 (M$^+$+3).

Anal. Calcd for C$_{36}$H$_{44}$ClF$_3$N$_4$O$_7$·1.5H$_2$O: C, 59.54; H, 6.52; N, 7.71.

Found: C, 59.22; H, 6.08; N, 7.27.

Example 129

Trans-4-[1-[[2,5-dichloro-4-[(1H-indol-3-ylcarbonyl)amino]phenyl]acetyl]-(4S)-[4-(2,2,2-trifluoroethyl)piperazin-1-yl]-(2S)-pyrrolidinylmethoxy]cyclohexanecarboxylic acid Trans-4-[1-[[2,5-dichloro-4-[(1H-indol-3-ylcarbonyl)amino]phenyl]acetyl]-(4S)-[4-(2,2,2-trifluoroethyl)piperazin-1-yl]-(2S)-pyrrolidinylmethoxy]cyclohexanecarboxylic acid ethyl ester NMR (CDCl$_3$) δ: 1.16-1.72 (7H, m), 1.82-2.08 (6H, m), 2.20-2.90 (9H, m), 2.93-3.08 (2H, m), 3.25-3.34 (2H, m), 3.50-3.94 (5H, m), 4.10 and 7.67 (1H, each d, each J=2.9 Hz), 8.02-8.07 (1H, m), 8.12 and 8.17 (1H, each s), 8.57 and 8.62 (1H, each s), 9.71 and 9.80 (1H, each broad s).

MS (EI) m/z: 765 (M$^+$).

Trans-4-[1-[[2,5-dichloro-4-[(1H-indol-3-ylcarbonyl)amino]phenyl]acetyl]-(4S)-[4-(2,2,2-trifluoroethyl)piperazin-1-yl]-(2S)-pyrrolidinylmethoxy]cyclohexanecarboxylic acid

[Formula 240]

NMR (DMSO-d$_6$) δ: 1.10-1.39 (4H, m), 1.55-2.20 (7H, m), 2.30-2.95 (9H, m), 3.10-3.18 (4H, m), 3.52-3.62 (2H, m), 3.84-4.35 (4H, m), 7.48 (1H, m), 7.49 (1H, s), 7.87 (1H, m), 8.14 (1H, d, J=7.6 Hz), 8.32 (1H, d, J=2.9 Hz), 9.41 (1H, s), 11.82 and 12.03 (each 1H, each s).

IR (ATR) cm$^{-1}$: 3170, 2943, 1732, 1664, 1616, 1568, 1500.

MS (FAB) m/z: 738 (M$^+$+1).

Anal. Calcd for C$_{35}$H$_{40}$Cl$_2$F$_3$N$_5$O$_5$: C, 56.91; H, 5.46; N, 9.48.

Found: C, 56.68; H, 5.41; N, 9.32.

Example 130

Trans-4-[1-[[3-chloro-4-[(1-methyl-1H-indol-3-ylcarbonyl)amino]phenyl]acetyl]-(4S)-[4-(2,2,2-trifluoroethyl)piperazin-1-yl]-(2S)-pyrrolidinylmethoxy]cyclohexanecarboxylic acid Trans-4-[1-[[3-chloro-4-[(1-methyl-1H-indol-3-ylcarbonyl)amino]phenyl]acetyl]-(4S)-[4-(2,2,2-trifluoroethyl)piperazin-1-yl]-(2S)-pyrrolidinylmethoxy]cyclohexanecarboxylic acid ethyl ester NMR (CDCl$_3$) δ: 1.07-1.72 (7H, m), 1.82-2.10 (6H, m), 2.13-2.82 and 7.82 (total 1H, each s, amide isomers), 8.02 (1H, s), 8.13-8.19 (1H, m), 8.27 (1H, s), 8.56 and 8.58 (total 1H, each d, J=8.4 and 8.3 Hz respectively, amide isomers).

MS (ESI) m/z: 746 (M$^+$+1), 748 (M$^+$+3).

Trans-4-[1-[[3-chloro-4-[(1-methyl-1H-indol-3-ylcarbonyl)amino]phenyl]acetyl]-(4S)-[4-(2,2,2-trifluoroethyl)piperazin-1-yl]-(2S)-pyrrolidinylmethoxy]cyclohexanecarboxylic acid

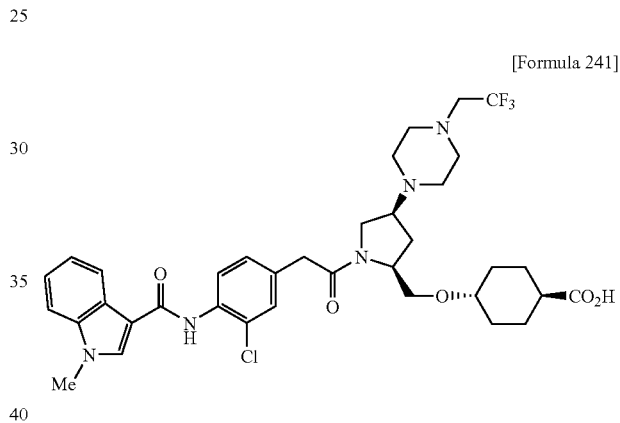

[Formula 241]

NMR (CDCl$_3$) δ: 1.06-1.67 (7H, m), 1.86-2.43 (6H, m), 2.45-2.81-7.20 (1H, m), 7.32-7.44 (4H, m), 7.805 and 7.813 (total 1H, each s, amide isomers), 8.11-8.17 (1H, m), 8.26 and 8.28 (total 1H, each s, amide isomers), 8.54 and 8.56 (total 1H, each d, each J=8.6 Hz, amide isomers).

MS (ESI) m/z: 718 (M$^+$+1), 720 (M$^+$+3).

IR (ATR) cm$^{-1}$: 2937, 2860, 1724, 1639, 1577, 1512, 1466.

Example 131

Trans-4-[1-[[5-chloro-2-fluoro-4-[(1H-indol-3-ylcarbonyl)amino]phenyl]acetyl]-(4S)-[4-(2,2,2-trifluoroethyl)piperazin-1-yl]-(2S)-pyrrolidinylmethoxy]cyclohexanecarboxylic acid Trans-4-[1-[[5-chloro-2-fluoro-4-[(1H-indol-3-ylcarbonyl)amino]phenyl]acetyl]-(4S)-[4-(2,2,2-trifluoroethyl)piperazin-1-yl]-(2S)-pyrrolidinylmethoxy]cyclohexanecarboxylic acid ethyl ester NMR (CDCl$_3$) δ: 1.14-1.65 (7H, m), 1.84-2.08 (6H, m), 2.18-2.80-4.45 (3H, m), 7.25-7.35 (2H, m), 7.47 (1H, n), 7.86 and 7.89 (1H, each d, each J=2.7 Hz), 8.02 (1H, broad s), 8.13 (1H, m), 8.29 and 8.31 (1H, each broad s), 8.43 and 8.48 (1H, each m), 8.92 and 9.00 (1H, each broad s).

MS (EI) m/z: 749 (M$^+$).

Trans-4-[1-[[5-chloro-2-fluoro-4-[(1H-indol-3-ylcarbonyl)amino]phenyl]acetyl]-(4S)-[4-(2,2,2-trifluoroethyl)piperazin-1-yl]-(2S)-pyrrolidinylmethoxy]cyclohexanecarboxylic acid

[Formula 242]

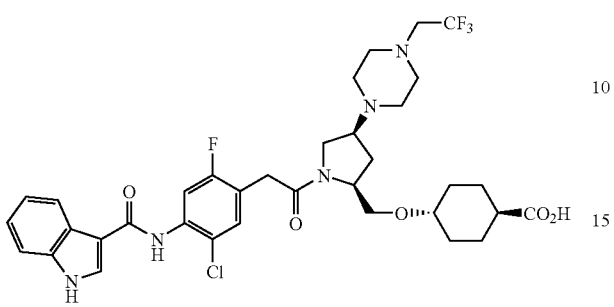

NMR (DMSO-$d_6$) δ: 1.00-1.32 (4H, series of m), 1.58-2.90 (16H, series of m), 3.05-4.35 (10H, series of m), 7.15-7.22 (2H, m), 7.43-7.50 (2H, m), 7.63-7.67 (1H, m), 8.13 and 8.15 (1H, each s), 8.33 and 8.42 (each 1H, each s), 9.65 (1H, broads).
IR (ATR) cm$^{-1}$: 3427, 3172, 2935, 2860, 1716, 1658, 1583, 1512.
MS (FAB) m/z: 722 (M$^+$+1).
Anal. Calcd for $C_{35}H_{40}ClF_4N_5O_5 \cdot 2HCl$: C, 52.87; H, 5.32; N, 8.81.
Found: C, 52.70; H, 5.14; N, 8.55.

Example 132

Trans-4-[1-[[4-[(benzo[b]furan-3-ylcarbonyl)amino]-3-chlorophenyl]acetyl]-(4S)-[4-(2,2,2-trifluoroethyl)piperazin-1-yl]-(2S)-pyrrolidinylmethoxy]cyclohexanecarboxylic acid Trans-4-[1-[[4-[(benzo[b]furan-3-ylcarbonyl)amino]-3-chlorophenyl]acetyl]-(4S)-[4-(2,2,2-trifluoroethyl)piperazin-1-yl]-(2S)-pyrrolidinylmethoxy]cyclohexanecarboxylic acid ethyl ester NMR (CDCl$_3$) δ: 1.10-1.59 (7H, m, including 3H, t, J=7.1 Hz, at δ 1.21), 1.85-2.03 (5H, m), 2.17-2.71 (total 11H, series of m), 2.93-3.00 (2H, m), 3.09-3.20 and 3.43-3.47 (total 2H, each m), 3.52-3.86 and 4.05-4.38 (total 8H, each m, including 2H, q, J=7.1 Hz, at δ 4.08), 7.20-7.22 (1H, m), 7.39-7.45 (3H, m), 7.58-7.61 (1H, m), 8.06-8.09 (1H, m), 8.24-8.32 (2H, m), 8.50 (1H, d, J=8.5 Hz).
MS (ESI) m/z: 733 (M$^+$+1).

Trans-4-[1-[[4-[(benzo[b]furan-3-ylcarbonyl)amino]-3-chlorophenyl]acetyl]-(4S)-[4-(2,2,2-trifluoroethyl)piperazin-1-yl]-(2S)-pyrrolidinylmethoxy]cyclohexanecarboxylic acid

[Formula 243]

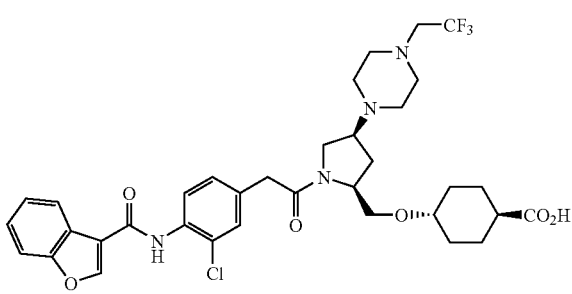

NMR (DMSO-$d_6$) δ: 1.06-1.40 (4H, m), 1.61-1.99 (5H, m), 2.12-2.87 (total 11H, series of m), 3.06-3.24 (4H, m), 3.49-3.78 (4H, m), 3.93-4.27 (2H, m), 7.21-7.25 (1H, m), 7.37-7.45 (3H, m), 7.54-7.57 (1H, m), 7.70 (1H, d, J=7.6 Hz), 8.07-8.09 (1H, m), 8.80 and 8.81 (total 1H, each s), 9.93 and 9.94 (total 1H, each s), 12.06 (1H, broad s).
IR (ATR) cm$^{-1}$: 1518, 1450, 1308, 1271, 1120, 1105, 748.
MS (ESI) m/z: 705 (M$^+$+1).
Anal. Calcd for $C_{35}H_{40}ClF_3N_4O_6 \cdot \frac{1}{4}H_2O$: C, 59.24; H, 5.75; N, 7.89; Cl, 5.00; F, 8.03.
Found: C, 59.18; H, 5.78; N, 7.61; Cl, 5.03; F, 8.20.

Example 133

Trans-4-[1-[[4-[(benzo[b]thiophen-3-ylcarbonyl)amino]-3-methoxyphenyl]acetyl]-(4S)-[4-(2,2,2-trifluoroethyl)piperazin-1-yl]-(2S)-pyrrolidinylmethoxy]cyclohexanecarboxylic acid Trans-4-[1-[[4-[(benzo[b]thiophen-3-ylcarbonyl)amino]-3-methoxyphenyl]acetyl]-(4S)-[4-(2,2,2-trifluoroethyl)piperazin-1-yl]-(2S)-pyrrolidinylmethoxy]cyclohexanecarboxylic acid ethyl ester NMR (CDCl$_3$) δ: 1.06-1.32 (5H, m), 1.32-1.52 (2H, m), 1.80-2.09 (5H, m), 2.14-2.38 (2H, m), 2.39-2.63 (4H, m), 2.66-2.74 (4H, m), 2.91-3.25 (4H, m), 3.40-3.85 (5H, m), 3.91-3.92 (3H, m), 4.03-4.39 (4H, m), 6.84-7.00 (2H, m), 7.53-7.41 (2H, m), 7.90 (1H, d, J=8.1 Hz), 8.04 (1H, d, J=7.3 Hz), 8.49-8.38 (3H, m).
MS (ESI) m/z: 745 (M$^+$+1).

Trans-4-[1-[[4-[(benzo[b]thiophen-3-ylcarbonyl)amino]-3-methoxyphenyl]acetyl]-(4S)-[4-(2,2,2-trifluoroethyl)piperazin-1-yl]-(2S)-pyrrolidinylmethoxy]cyclohexanecarboxylic acid

[Formula 244]

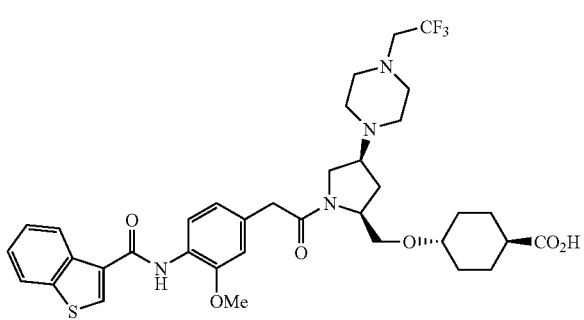

NMR (CDCl$_3$) δ: 1.05-1.68 (6.5H, m), 1.82-2.13 (4.5H, m), 2.17-2.41 (2H, m), 2.45-2.79 (9H, m), 2.90-3.27 (4H, m), 3.38-3.88 (3.5H, m), 3.90-3.92 (3H, m), 4.15-4.24 (1H, m), 4.43-4.35 (0.5H, m), 6.96-6.83 (2H, m), 7.52-7.40 (2H, m), 7.90 (1H, d, J=7.8 Hz), 8.03 (1H, d, J=4.9 Hz), 8.47-8.38 (3H, m).
MS (ESI) m/z: 717 (M$^+$+1).
Anal. Calcd for $C_{36}H_{43}F_3N_4O_6S$: C, 60.32; H, 6.05; N, 7.82; S, 4.47.
Found: C, 60.10; H, 6.09; N, 7.56; S, 4.48.

Example 134

Trans-4-[1-[[4-[(benzo[b]thiophen-3-ylcarbonyl)amino]-3-chlorophenyl]acetyl]-(4S)-[4-(2,2,2-trifluoroethyl)piperazin-1-yl]-(2S)-pyrrolidinylmethoxy]cyclohexanecarboxylic acid Trans-4-[1-[[4-[(benzo[b]thiophen-3-ylcarbonyl)amino]-3-chlorophenyl]acetyl]-(4S)-[4-(2,2,2-trifluoroethyl)piperazin-1-yl]-(2S)-pyrrolidinylmethoxy]cyclohexanecarboxylic acid ethyl ester NMR (CDCl$_3$) δ: 1.10-1.59 (total 7H, m, including 3H, t, J=7.1 Hz, δ 1.21), 1.71-2.07 (total 6H, m), 2.17-2.71 (total 10H, m), 2.88-3.21 (total 4H, m), 3.43-3.86 (total 5H, m), 4.05-4.37 (3H, m, including 2H, q, J=7.1 Hz, δ 4.07), 7.19-7.23 (1H, m), 7.38 and 7.39 (total 1H, each d, each J=2.0 Hz), 7.42-7.47 (1H, m), 7.51 (1H, ddd, J=7.8, 7.6, 1.2 Hz), 7.91 (1H, d, J=8.1 Hz), 8.08 and 8.12 (total 1H, each s), 8.29 and 8.33 (total 1H, each br s), 8.49 (2H, d, J=8.5 Hz).

IR (ATR) ν: 2939, 2862, 1724, 1672, 1635 cm$^{-1}$.

MS (ESI) m/z: 749 [(M$^+$+1), $^{35}$Cl], 750 (M$^+$+2).

Anal. Calcd for C$_{37}$H$_{44}$ClF$_3$N$_4$O$_5$S.0.25H$_2$O: C, 58.96; H, 5.95; N, 7.43; S, 4.25; Cl, 4.70; F, 7.56.

Found: C, 58.84: H, 5.78; N, 7.41; S, 4.36; Cl, 4.81; F, 7.54.

Trans-4-[1-[[4-[(benzo[b]thiophen-3-ylcarbonyl)amino]-3-chlorophenyl]acetyl]-(4S)-[4-(2,2,2-trifluoroethyl)piperazin-1-yl]-(2S)-pyrrolidinylmethoxy]cyclohexanecarboxylic acid

[Formula 245]

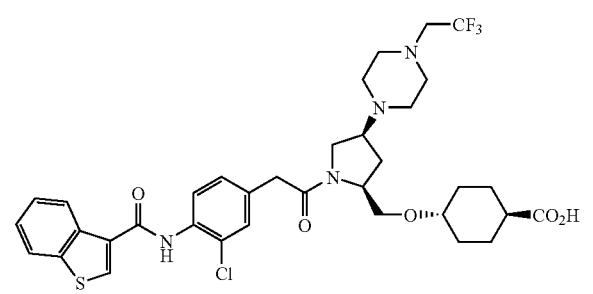

NMR (CDCl$_3$) δ: 1.04-1.60 (total 5H, series of m), 1.82-2.72 (total 14H, series of m), 2.89-4.26 (total 11H, series of m), 7.16 (1H, t, J=7.1 Hz), 7.30-7.33 (1H, m), 7.39 (1H, t, J=7.4 Hz), 7.46 (1H, t, J=7.4 Hz), 7.86 (1H, d, J=8.1 Hz), 8.08 and 8.12 (total 1H, each s, amide isomers), 8.33-8.48 (3H, m), 10.50 (1H, br s).

IR (ATR) ν: 2939, 2862, 2819, 1724, 1672, 1635 cm$^{-1}$.

MS (ESI) m/z: 721 [(M$^+$+1), $^{35}$Cl], 723 [(M$^+$+3), $^{37}$Cl].

Anal. Calcd for C$_{35}$H$_{40}$ClF$_3$N$_4$O$_5$S.H$_2$O: C, 56.87; H, 5.73; N, 7.58; S, 4.34.

Found: C, 57.13; H, 5.61; N, 7.27; S, 4.34.

Example 135

Trans-4-[1-[[3-methoxy-4-[(1-methyl-1H-indol-3-ylcarbonyl)amino]phenyl]acetyl]-(4S)-[4-(2,2,2-trifluoroethyl)piperazin-1-yl]-(2S)-pyrrolidinylmethoxy]cyclohexanecarboxylic acid Trans-4-[1-[[3-methoxy-4-[(1-methyl-1H-indol-3-ylcarbonyl)amino]phenyl]acetyl]-(4S)-[4-(2,2,2-trifluoroethyl)piperazin-1-yl]-(2S)-pyrrolidinylmethoxy]cyclohexanecarboxylic acid ethyl ester NMR (CDCl$_3$) δ: 0.99-1.67 (9H, m), 1.70-2.08 (7H, m), 2.15-2.35 (2H, m), 2.38-2.61 (4H, m), 2.63-2.74 (4H, m), 2.95 (2H, q, J=9.6 Hz), 3.10-3.24 (2H, m), 3.39-3.84 (2H, m), 3.87 (3H, s), 3.88-4.01 (2H, m), 4.00-4.40 (4H, m), 6.84 (1H, d, J=8.5 Hz), 6.90 and 6.95 (total 1H, each s, amide isomers), 7.30-7.42 (3H, m), 7.78 and 7.79 (total 1H, each s, amide isomers), 8.06-8.12 (1H, m), 8.42 (1H, s), 8.51-8.46 (1H, m).

MS (ESI) m/z: 742 (M$^+$+1).

Trans-4-[1-[[3-methoxy-4-[(1-methyl-1H-indol-3-ylcarbonyl)amino]phenyl]acetyl]-(4S)-[4-(2,2,2-trifluoroethyl)piperazin-1-yl]-(2S)-pyrrolidinylmethoxy]cyclohexanecarboxylic acid

[Formula 246]

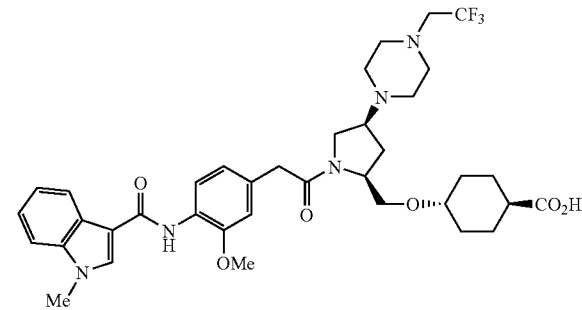

NMR (CDCl$_3$) δ: 0.99-1.74 (6H, m), 1.83-2.40 (8H, m) 2.42-2.80 and 3.86 (total 3H, each s, amide isomers) 3.96 and 3.96 (total 3H, each s, amide isomers), 4.15-4.25 (1H, m), 6.81-6.97 (2H, m), 7.31-7.36 (2H, m), 7.37-7.43 (1H, m), 7.78-7.82 (1H, m), 8.05-8.11 (1H, m), 8.41-8.50 (2H, m).

MS (ESI) m/z: 714 (M$^+$+1).

IR (ATR) cm$^{-1}$: 3427, 2937, 2858, 1718, 1639, 1610, 1597, 1522, 1454.

Anal. Calcd for C$_{37}$H$_{46}$F$_3$N$_6$O$_6$.0.5Na.0.5EtOH: C, 60.99; H, 6.60; F, 7.62; N, 9.36.

Found: C, 60.78; H, 6.66; F, 7.36; N, 9.03

Example 136

Trans-4-[1-[[3-methyl-4-[(1-methyl-1H-indol-3-ylcarbonyl)amino]phenyl]acetyl]-(4S)-[4-(2,2,2-trifluoroethyl)piperazin-1-yl]-(2S)-pyrrolidinylmethoxy]cyclohexanecarboxylic acid Trans-4-[1-[[3-methyl-4-[(1-methyl-1H-indol-3-ylcarbonyl)amino]phenyl]acetyl]-(4S)-[4-(2,2,2-trifluoroethyl)piperazin-1-yl]-(2S)-pyrrolidinylmethoxy]cyclohexanecarboxylic acid ethyl ester NMR (CDCl$_3$) δ: 1.04-1.52 (9H, m), 1.82-2.27 (7H, m), 2.36 (3H, s), 2.39-2.62 (2H, m), 2.64-2.74 (4H, m), 2.87-3.30

(4H, m), 3.39-3.90 (8H, m), 4.01-4.54 (4H, m), 7.06-7.44 (5H, m), 7.52 and 7.61 (total 1H, each s, amide isomers), 7.77 and 7.80 (total 1H, each s, amide isomers), 7.90-8.00 (1H, m), 8.03 and 8.07 (total 1H, each d, J=7.6 and 7.3 Hz respectively, amide isomers).

MS (ESI) m/z: 726 (M⁺+1).

Trans-4-[1-[[3-methyl-4-[(1-methyl-1H-indol-3-ylcarbonyl)amino]phenyl]acetyl]-(4S)-[4-(2,2,2-trifluoroethyl)piperazin-1-yl]-(2S)-pyrrolidinyl-methoxy]cyclohexanecarboxylic acid

[Formula 247]

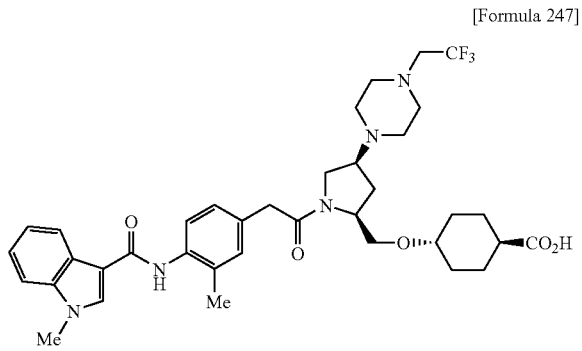

NMR (CDCl₃) δ: 0.96-1.70 (6H, m), 1.86-2.13 (5H, m), 2.13-2.29 (2H, m), 2.336 and 2.343 (total 3H, each s, amide isomers), 2.44-2.77 (8H, m), 2.88-3.29 (4H, m), 3.31-3.79 (4H, m), 3.79-3.86 (4H, m), 4.06-4.58 (1H, m), 7.10 (1H, d, J=8.8 Hz), 7.14 (1H, s), 7.28-7.42 (3H, m), 7.60 and 7.67 (total 1H, each s, amide isomers), 7.75 and 7.77 (total 1H, each s, amide isomers), 7.93-7.86 (1H, m), 8.05-8.00 (1H, m).

MS (ESI) m/z: 698 (M⁺+1).

IR (ATR) cm⁻¹: 2937, 2858, 1718, 1641, 1535, 1512, 1466.
Anal. Calcd for C₃₇H₄₆F₃N₆O₅·H₂O: C, 62.08; H, 6.76; F, 7.96; N, 9.78.

Found: C, 62.21; H, 6.68; F, 7.76; N, 9.51.

Example 137

Trans-4-[1-[[2,5-dichloro-4-[(1-methyl-1H-indol-3-ylcarbonyl)amino]phenyl]acetyl]-(4S)-(4-(2-methoxyethyl)piperazin-1-yl)-(2S)-pyrrolidinylmethoxy]cyclohexanecarboxylic acid Trans-4-[1-(tert-butoxycarbonyl)-(4S)-[4-(2-methoxyethyl)piperazin-1-yl]-(2S)-pyrrolidinylmethoxy]cyclohexanecarboxylic acid ethyl ester NMR (CDCl₃) δ: 1.17-1.30 (2H, m), 1.24 (3H, t, J=7.1 Hz), 1.41-1.47 (1H, m), 1.45 (9H, s), 1.61-1.80 (4H, m), 1.94-2.06 (4H, m), 2.17-2.66 (12H, m), 2.94-3.02 (1H, m), 3.15-3.25 (1H, m), 3.35 (3H, s), 3.48-3.53 (2H, m), 3.61-3.99 (3H, m), 4.11 (2H, q, J=7.1 Hz).

MS (ESI) m/z: 498 (M⁺+H).

Trans-4-[1-[[2,5-dichloro-4-[(1-methyl-1H-indol-3-ylcarbonyl)amino]phenyl]acetyl]-(4S)-(4-(2-methoxyethyl)piperazin-1-yl)-(2S)-pyrrolidinylmethoxy] cyclohexanecarboxylic acid

[Formula 248]

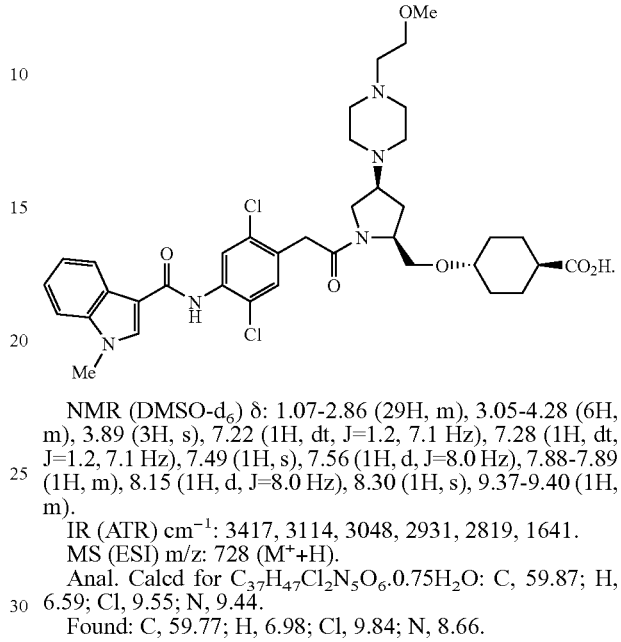

NMR (DMSO-d₆) δ: 1.07-2.86 (29H, m), 3.05-4.28 (6H, m), 3.89 (3H, s), 7.22 (1H, dt, J=1.2, 7.1 Hz), 7.28 (1H, dt, J=1.2, 7.1 Hz), 7.49 (1H, s), 7.56 (1H, d, J=8.0 Hz), 7.88-7.89 (1H, m), 8.15 (1H, d, J=8.0 Hz), 8.30 (1H, s), 9.37-9.40 (1H, m).

IR (ATR) cm⁻¹: 3417, 3114, 3048, 2931, 2819, 1641.
MS (ESI) m/z: 728 (M⁺+H).
Anal. Calcd for C₃₇H₄₇Cl₂N₅O₆·0.75H₂O: C, 59.87; H, 6.59; Cl, 9.55; N, 9.44.

Found: C, 59.77; H, 6.98; Cl, 9.84; N, 8.66.

Example 138

Trans-4-[1-[[4-[(benzo[b]thiophen-3-ylcarbonyl)amino]-2,5-dichlorophenyl]acetyl]-(4S)-(4-cyclopropylpiperazin-1-yl)-(2S)-pyrrolidinylmethoxy]cyclohexanecarboxylic acid Trans-4-[1-(tert-butoxycarbonyl)-(4S)-(4-cyclopropylppiperazin-1-yl)-(2S)-pyrrolidinylmethoxy]cyclohexanecarboxylic acid ethyl ester MS (ESI) m/z: 480 (M⁺+1).

Trans-4-[1-[[4-[(benzo[b]thiophen-3-ylcarbonyl)amino]-2,5-dichlorophenyl]acetyl]-(4S)-(4-cyclopropylpiperazin-1-yl)-(2S)-pyrrolidinylmethoxy]cyclohexanecarboxylic acid

[Formula 249]

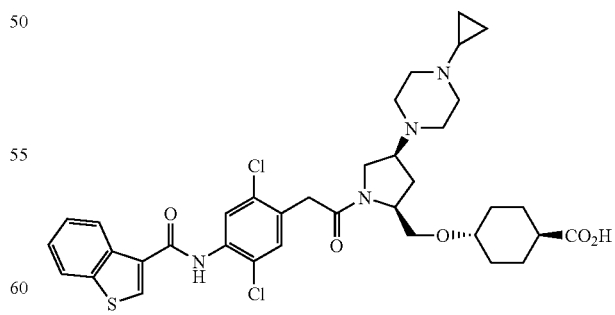

NMR (DMSO-d₆) δ: 0.24-0.31 (2H, m), 0.36-0.43 (2H, m), 0.84-4.28 (29H, m), 7.44-7.52 (2H, m), 7.53 (1H, s), 7.76 (1H, d, J=5.1 Hz), 8.10 (1H, dd, J=7.1, 1.7 Hz), 8.45 (1H, dd, J=7.4, 1.7 Hz), 8.65 (1H, s), 10.17 (1H, d, J=4.9 Hz), 12.05 (1H, br s).

IR (ATR) cm$^{-1}$: 2933, 2859, 2817, 1637, 1504.
MS (ESI) m/z: 713 (M$^+$+1).
Anal. Calcd for C$_{36}$H$_{42}$Cl$_2$N$_4$O$_5$S.0.23HCl.0.63H$_2$O: C, 58.95; H, 5.98; Cl, 10.78; N, 7.64; S, 4.37. Found: C, 59.48; H, 6.11; Cl, 10.34; N, 7.11; S, 4.15.

Example 139

Trans-4-[1-[[2,5-dichloro-4-[(1-methyl-1H-indol-3-ylcarbonyl)amino]phenyl]acetyl]-(4S)-(4-cyclopropylpiperazin-1-yl)-(2S)-pyrrolidinylmethoxy]cyclohexanecarboxylic acid

[Formula 250]

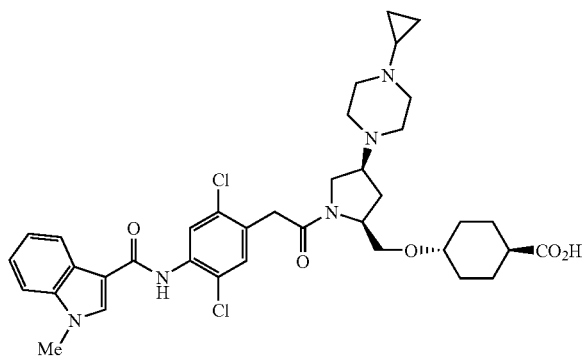

NMR (DMSO-d$_6$) δ: 0.24-0.30 (2H, m), 0.36-0.42 (2H, m), 0.86-4.27 (32H, m), 7.21 (1H, t, J=7.1 Hz), 7.28 (1H, dt, J=1.0, 7.4 Hz), 7.49 (1H, s), 7.56 (1H, d, J=8.3 Hz), 7.88 (1H, d, J=4.9 Hz), 8.15 (1H, d, J=7.8 Hz), 8.30 (1H, d, J=2.0 Hz), 9.38 (1H, d, J=4.4 Hz).
IR (ATR) cm$^{-1}$: 2929, 2859, 2813, 1646, 1500.
MS (ESI) m/z: 710 (M$^+$+1).
Anal. Calcd for C$_{37}$H$_{45}$Cl$_2$N$_5$O$_5$.0.6hexane.1.2H$_2$O: C, 62.29; H, 7.03; Cl, 9.06; N, 8.95.
Found: C, 61.90; H, 6.96; Cl, 9.03; N, 8.57.

Example 140

Trans-4-[1-[[4-[(benzo[b]furan-3-ylcarbonyl)amino]-2,5-dichloro-4-[(1-methyl-1H-indol-3-ylcarbonyl)amino]phenyl]acetyl]-(4S)-(4-cyclopropylpiperazin-1-yl)-(2S)-pyrrolidinylmethoxy]cyclohexanecarboxylic acid

[Formula 251]

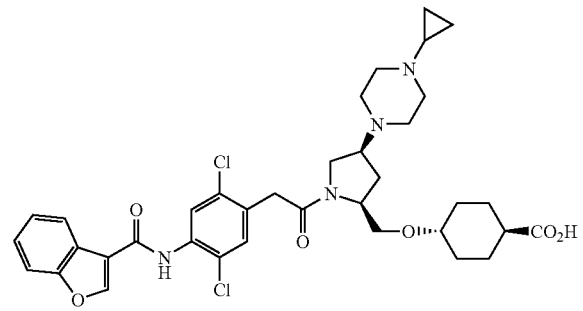

NMR (DMSO-d$_6$) δ: 0.24-0.31 (2H, m), 0.36-0.42 (2H, m), 1.12-4.28 (29H, m), 7.37-7.46 (2H, m), 7.53 (1H, s), 7.71 (1H, d, J=7.6 Hz), 7.77 (1H, d, J=4.9 Hz), 8.09 (1H, d, J=7.1 Hz), 8.83 (1H, d, J=2.5 Hz), 10.05 (1H, s), 12.05 (1H, br s).
IR (ATR) cm$^{-1}$: 2935, 2859, 2817, 1506, 1448.
MS (ESI) m/z: 697 (M$^+$+1).
Anal. Calcd for C$_{36}$H$_{42}$Cl$_2$N$_4$O$_6$.0.5H$_2$O: C, 61.19; H, 6.13; Cl, 10.03; N, 7.93.
Found: C, 61.19; H, 6.33; Cl, 9.75; N, 7.60.

Example 141

Trans-4-[1-[[5-chloro-2-fluoro-4-[(1-methyl-1H-indol-3-ylcarbonyl)amino]phenyl]acetyl]-(4S)-[4-(1-methylcyclopropan-1-yl)piperazin-1-yl]-(2S)-pyrrolidinylmethoxy]cyclohexa necarboxylic acid 4-(1-Methylcyclopropan-1-yl)piperazine-1-carboxylic acid benzyl ester Bis-(2-oxoethyl)carbamicacidbenzylester (0.90 g, 3.81 mmol) and 1-methyl-cyclopropylamine (0.41 g, 3.81 mmol) were dissolved in dichloroethane (20 mL), and sodium triacetoxyborohydride (3.23 g, 15.24 mmol) was added thereto. The mixture was stirred for 4 days at room temperature. A saturated aqueous solution of sodium hydrogen carbonate (20 mL) was added to the reaction liquor, and the mixture was stirred for 20 minutes, and then extracted with methylene chloride. The extract was washed with saturated brine, and dried over anhydrous sodium sulfate, and then the solvent was concentrated under reduced pressure. The obtained residue was purified by flash chromatography (Flash Chromatography System from Biotage AB, column size: 25S, n-hexane/ethyl acetate=5/1 to ethyl acetate), to obtain the title compound (509 mg, 49%) as an oily matter.
NMR (CDCl$_3$) δ: 0.34 (2H, dd, J=5.6, 3.7 Hz), 0.52-0.57 (2H, m), 1.02 (3H, s), 2.53-2.63 (4H, m), 3.39-3.48 (4H, m), 5.13 (2H, s), 7.34-7.38 (5H, m).
MS (ESI) m/z: 275 (M$^+$+1).

4-(1-Methylcyclopropan-1-yl)piperazine 4-(1-Methylcyclopropan-1-yl)piperazine-1-carboxylic acid benzyl ester (509 mg, 1.86 mmol) was dissolved in ethanol (20 mL), and 10% palladium hydroxide/carbon (100 mg) was added thereto. The mixture was stirred for 20 hours at room temperature under a hydrogen stream at normal pressure. The catalyst was separated by filtration, and then the reaction liquor was concentrated under reduced pressure, and dried to obtain the title compound (193 mg, 74%) as an oily matter. This compound was used in the subsequent reaction without performing further purification.
NMR (CDCl$_3$) δ: 0.30-0.35 (2H, m), 0.52-0.57 (2H, m), 1.05 (3H, s), 2.58-2.63 (4H, m), 2.86-2.79 (4H, m).
MS (ESI) m/z: 141 (M$^+$+1).

Trans-4-[1-(tert-butoxycarbonyl)-(4S)-[4-(1-methylcyclopropan-1-yl)piperazin-1-yl]-(2S)-pyrrolidinylmethoxy]cyclohexanecarboxylic acid ethyl ester NMR (CDCl$_3$) δ: 0.30-0.35 (2H, m), 0.50-0.56 (2H, m), 1.05 (3H, s), 1.14-1.30 (5H, m), 1.32-1.53 (11H, m), 1.66-2.11 (7H, m), 2.12-2.79 (7H, m), 2.93-3.04 (1H, m), 3.10-4.02 (7H, m), 4.07-4.16 (2H, m).
MS (ESI) m/z: 494 (M$^+$+1).

Trans-4-[1-[[5-chloro-2-fluoro-4-[(1-methyl-1H-indol-3-ylcarbonyl)amino]phenyl]acetyl]-(4S)-[4-(1-methylcyclopropan-1-yl)piperazin-1-yl]-(2S)-pyrrolidinylmethoxy]cyclohexa necarboxylic acid ethyl ester NMR (CDCl$_3$) δ: 0.30-0.36 (2H, m), 0.53 (2H, s), 1.05 (3H, s), 1.11-1.52 (7H, m), 1.69-2.32 (9H, m), 2.32-2.62 (4H, m), 2.64-2.73 (4H, m), 2.93-3.28 (2H, m), 3.41-3.86 (3H, m), 3.89 (3H, s), 4.04-4.40 (4H, m and 7.82 (total 1H, each s, amide isomers), 8.11-8.18 (1H, m), 8.30 (1H, s), 8.49 and 8.51 (total 1H, each d, J=11.5 and 12.0 Hz respectively, amide isomers).

MS (ESI) m/z: 736 (M$^+$+1), 738 (M$^+$+3).

Trans-4-[1-[[5-chloro-2-fluoro-4-[(1-methyl-1H-indol-3-ylcarbonyl)amino]phenyl]acetyl]-(4S)-[4-(1-methylcyclopropan-1-yl)piperazin-1-yl]-(2S)-pyrrolidinylmethoxy]cyclohexa necarboxylic acid

[Formula 252]

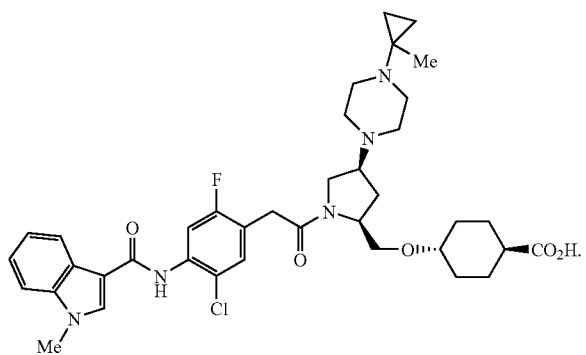

NMR (CDCl$_3$) δ: 0.30-0.38 (2H, m), 0.57 (2H, d, J=12.5 Hz), 1.05 and 1.06 (total 3H, each s, amide isomers), 1.12-1.53 (4H, m), 1.87-2.31 (6H, m), 2.36-2.84 (8H, m), 2.97-3.79 (9H, m), 3.79-3.87 (1H, m), 3.87 and 3.88 (total 3H, each s, amide isomers), 4.10-4.47 (1H, m), 7.31-7.44 (4H, m), 7.80 and 7.81 (total 1H, each s, amide isomers), 8.10-8.16 (1H, m), 8.28 and 8.29 (total 1H, each s, amide isomers), 8.48 (1H, t, J=12.0 Hz).

MS (ESI) m/z: 708 (M$^+$+1), 710 (M$^+$+3).

IR (ATR) cm$^{-1}$: 2941, 2856, 1711, 1668, 1637, 1583, 1512, 1466.

Example 142

Trans-4-[1-[[5-chloro-2-fluoro-4-[(1-methyl-1H-indol-3-ylcarbonyl)amino]phenyl]acetyl]-(4S)-[4-cyclopentylpiperazin-1-yl]-(2S)-pyrrolidinylmethoxy]cyclohexanecarboxylic acid Trans-4-[1-(tert-butoxycarbonyl)-(4S)-[4-cyclopentylppiperazin-1-yl]-(2S)-pyrrolidinylmethoxy]cyclohexanecarboxylic acid ethyl ester NMR (CDCl$_3$) δ: 1.08-1.30 (2H, m), 1.24 (3H, t, J=7.4 Hz), 1.45 (9H, s), 1.55-3.93 (33H, m), 4.11 (2H, q, J=7.4 Hz).

Trans-4-[1-[[5-chloro-2-fluoro-4-[(1-methyl-1H-indol-3-ylcarbonyl)amino]phenyl]acetyl]-(4S)-[4-cyclopentylpiperazin-1-yl]-(2S)-pyrrolidinylmethoxy]cyclohexanecarboxylic acid

[Formula 253]

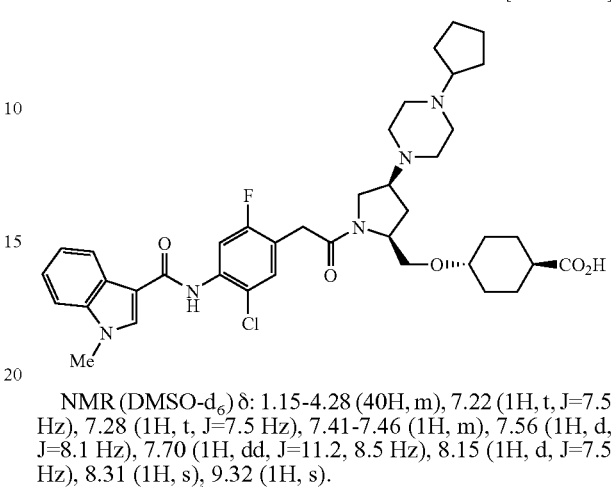

NMR (DMSO-d$_6$) δ: 1.15-4.28 (40H, m), 7.22 (1H, t, J=7.5 Hz), 7.28 (1H, t, J=7.5 Hz), 7.41-7.46 (1H, m), 7.56 (1H, d, J=8.1 Hz), 7.70 (1H, dd, J=11.2, 8.5 Hz), 8.15 (1H, d, J=7.5 Hz), 8.31 (1H, s), 9.32 (1H, s).

IR (ATR) cm$^{-1}$: 2938, 2861, 1644, 1517, 1099.
MS (FAB) m/z: 722.3518 (calcd for C$_{39}$H$_{50}$ClFN$_5$O$_5$: 722.3485)
Anal. Calcd for C$_{39}$H$_{49}$ClFN$_5$O$_5$ 0.5HCl.0.75H$_2$O: C, 62.12; H, 6.82; Cl, 7.05; F, 2.52; N, 9.29.
Found: C, 62.19; H, 7.16; Cl, 6.66; F, 2.42; N, 9.36.

Example 143

Trans-4-[1-[[4-[(benzo[b]furan-3-ylcarbonyl)amino]-2,5-dichlorophenyl]acetyl]-(4S)-[4-cyclohexylpiperazin-1-yl]-(2S)-pyrrolidinylmethoxy]cyclohexanecarboxylic acid Trans-4-[1-(tert-butoxycarbonyl)-(4S)-[4-cyclohexylpiperazin-1-yl]-(2S)-pyrrolidinylmethoxy]cyclohexanecarboxylic acid ethyl ester NMR (CDCl$_3$) δ: 1.0-1.3 (6H, m), 1.2 (3H, t, J=6.9 Hz), 1.4 (9H, s), 1.7-2.7 (24H, m), 2.9-4.0 (7H, m), 4.1 (2H, q, J=7.1 Hz).

MS (ESI) m/z: 522 (M$^+$+1).

Trans-4-[1-[[4-[(benzo[b]furan-3-ylcarbonyl)amino]-2,5-dichlorophenyl]acetyl]-(4S)-[4-cyclohexylpiperazin-1-yl]-(2S)-pyrrolidinylmethoxy]cyclohexanecarboxylic acid

[Formula 254]

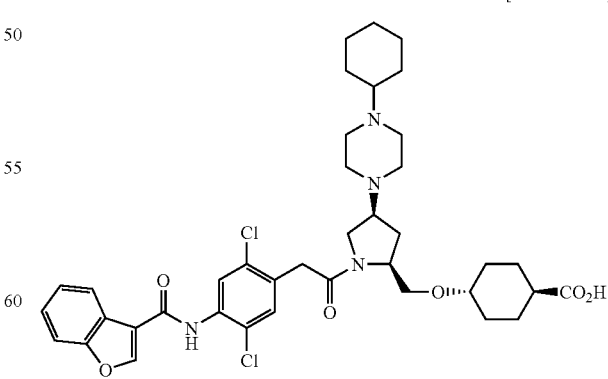

NMR (DMSO-d$_6$) δ: 0.95-1.40 (11H, m), 1.55-4.28 (28H, m), 7.38-7.46 (2H, m), 7.53 (1H, s), 7.71 (1H, d, J=7.6 Hz), 7.77 (1H, d, J=5.4 Hz), 8.09 (1H, d, J=7.8 Hz), 8.84 (1H, s), 10.07 (1H, s).

IR (ATR) cm$^{-1}$: 2931, 2856, 1637, 1569, 1448.
MS (FAE) m/z: 739.396 (calcd for $C_{39}H_{49}Cl_2N_4O_6$: 739.3029)
Anal. Calcd for $C_{39}H_{48}Cl_2N_4O_6 \cdot 0.5HCl \cdot 2.5H_2O$: C, 58.33; H, 6.72; Cl, 11.04; N, 6.98.
Found: C, 58.72; H, 6.43; Cl, 10.99; N, 6.97.

Example 144

Trans-4-[1-[[5-chloro-2-fluoro-4-[(1-methyl-1H-indol-3-ylcarbonyl)amino]phenyl]acetyl]-(4S)-[4-(2-pyridyl)piperazin-1-yl]-(2S)-pyrrolidinylmethoxy]cyclohexanecarboxylic acid Trans-4-[1-(tert-butoxycarbonyl)-(4S)-[4-(2-pyridyl)piperazin-1-yl]-(2S)-pyrrolidinylmethoxy]cyclohexanecarboxylic acid ethyl ester NMR (CDCl$_3$) δ: 1.17-1.32 (5H, m), 1.41-1.46 (2H, m), 1.47 (9H, s (4H, m), 3.67-4.05 (2H, m), 4.12 (2H, dq, J=14.3, 3.6 Hz), 4.16-4.23 (1H, m), 6.61-6.67 (2H, m), 7.45-7.51 (1H, m), 8.19 (1H, dd, J=4.9, 1.7 Hz).
MS (ESI) m/z: 517 (M$^+$+1).

Trans-4-[(4S)-[4-(2-pyridyl)piperazin-1-yl]-(2S)-pyrrolidinylmethoxy]cyclohexanecarboxylic acid ethyl ester NMR (CDCl$_3$) δ: 1.21-1.32 (5H, m), 1.39-1.70 (2H, m), 1.94-2.31-3.66 (8H, m), 4.11 (2H, q, J=7.2 Hz), 6.63 (1H, d, J=7.2 Hz), 6.64 (1H, d, J=7.6 Hz), 7.47 (1H, dd, J=7.6, 2.2 Hz), 7.49 (1H, dd, J=8.8, 2.0 Hz), 8.17-8.21 (1H, m).
MS (ESI) m/z: 417 (M$^+$+1).

Trans-4-[1-[[5-chloro-2-fluoro-4-[(1-methyl-1H-indol-3-ylcarbonyl)amino]phenyl]acetyl]-(4S)-[4-(2-pyridyl)piperazin-1-yl]-(2S)-pyrrolidinylmethoxy]cyclohexanecarboxylic acid ethyl ester NMR (CDCl$_3$) δ: 1.10-1.55 (7H, m), 1.90-2.10 (7H, m), 2.13-2.36-3.90 (4H, m), 4.04-4.43 (4H, m), 6.60-6.70 (2H, m), 7.31-7.51 (5H, m), 7.79 and 7.80 (total 1H, each s, amide isomers), 8.11-8.17 (1H, m), 8.19 (1H, dd, J=4.9, 2.5 Hz), 8.28 and 8.29 (total 1H, each s, amide isomers) 8.49 and 8.52 (total 1H, each d, each J=11.8 Hz, amide isomers).
MS (ESI) m/z: 759 (M$^+$+1), 761 (M$^+$+3).

Trans-4-[1-[[5-chloro-2-fluoro-4-[(1-methyl-1H-indol-3-ylcarbonyl)amino]phenyl]acetyl]-(4S)-[4-(2-pyridyl)piperazin-1-yl]-(2S)-pyrrolidinylmethoxy]cyclohexanecarboxylic acid NMR (CDCl$_3$) δ: 1.11-1.51 (4H, m), 1.67-2.33 (6H, m), 2.38-2.86-4.48 (2H, m), 6.63 (1H, d, J=5.1 Hz), 6.65 (1H, d, J=5.6 Hz), 7.31-7.43 and 8.30 (total 1H, each s, amide isomers), 8.47 (1H, d, J=12.0 Hz), 8.51 (1H, d, J=12.3 Hz).
MS (ESI) m/z: 731 (M$^+$+1), 733 (M$^+$+3).
IR (ATR) cm$^{-1}$: 3435, 2922, 2856, 1703, 1666, 1647, 1587, 1523, 1462.

Example 145

Trans-4-[1-[[5-chloro-2-fluoro-4-[(1-methyl-1H-indol-3-ylcarbonyl)amino]phenyl]acetyl]-(4S)-[4-(4-pyridyl)piperazin-1-yl]-(2S)-pyrrolidinylmethoxy]cyclohexanecarboxylic acid Trans-4-[1(-tert-butoxycarbonyl)-(4S)-[4-(4-pyridyl)piperazin-1-yl]-(2S)-pyrrolidinylmethoxy]cyclohexanecarboxylic acid ethyl ester NMR (CDCl$_3$) δ: 0.94-1.53 (16H, m), 1.62-2.39 (7H, m), 2.48-2.77 (6H, m), 2.97-3.28 (2H, m), 3.31-4.03 (7H, m), 4.08-4.16 (2H, m), 6.68-6.73 (2H, m), 8.21-8.37 (2H, m).
MS (ESI) m/z: 517 (M$^+$+1).

Trans-4-[(4S)-[4-(4-pyridyl)piperazin-1-yl]-(2S)-pyrrolidinylmethoxy]cyclohexanecarboxylic acid ethyl ester NMR (CDCl$_3$) δ: 1.22-1.31 (5H, m), 1.39-1.53 (2H, m), 1.78-2.30 (6H, m), 2.52-2.72 (4H, m), 2.83-2.97 (2H, m), 3.12-3.61 (10H, m), 4.12 (2H, q, J=7.1 Hz), 6.66 (2H, dd, J=5.1, 1.5 Hz), 8.27 (2H, dd, J=5.6, 1.2 Hz).
MS (ESI) m/z: 417 (M$^+$+1).

Trans-4-[1-[[5-chloro-2-fluoro-4-[(1-methyl-1H-indol-3-ylcarbonyl)amino]phenyl]acetyl]-(4S)-[4-(4-pyridyl)piperazin-1-yl]-(2S)-pyrrolidinylmethoxy]cyclohexanecarboxylic acid ethyl ester NMR (CDCl$_3$) δ: 1.07-1.52 (7H, m), 1.62-2.50 (7H, m), 2.51-2.88 (4H, m), 2.99-3.39 (6H, m), 3.44-3.80 (5H, m), 3.83-3.87 (1H, m), 3.88 (3H, s), 4.03-4.42 (3H, m), 6.64-6.69 (2H, m), 7.32-7.44 (4H, m), 7.81 and 7.82 (total 1H, each s, amide isomers), 8.17-8.11 (1H, m), 8.33-8.24 (3H, m), 8.51 (1H, t, J=11.9 Hz).
MS (ESI) m/z: 759 (M$^+$+1), 761 (M$^+$+3).

Trans-4-[1-[[5-chloro-2-fluoro-4-[(1-methyl-1H-indol-3-ylcarbonyl)amino]phenyl]acetyl]-(4S)-[4-(4-pyridyl)piperazin-1-yl]-(2S)-pyrrolidinylmethoxy]cyclohexanecarboxylic acid

[Formula 255]

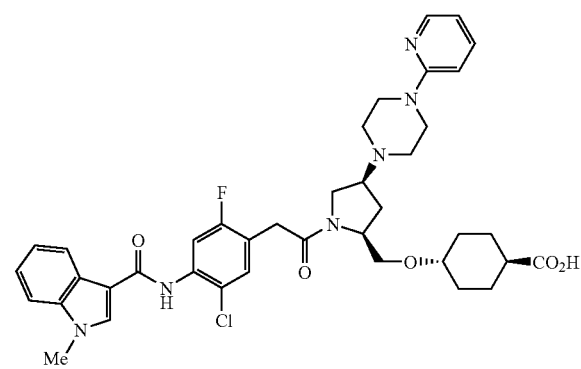

[Formula 256]

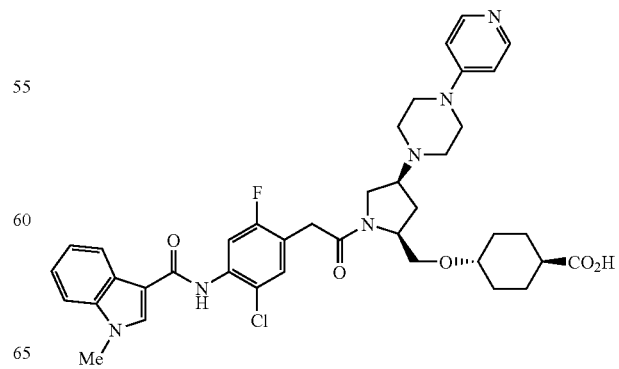

NMR (CDCl₃) δ: 1.09-1.78 (5H, m), 1.88-2.88 (11H, m), 3.00-3.30 (2H, m), 3.35-3.43 (4H, m), 3.46-3.86 (3H, m), 3.87 and 3.88 (total 3H, each s, amide isomers), 3.90-4.43 (4H, m), 6.67 (2H, d, J=5.4 Hz), 7.31-7.44 (4H, m) and 7.82 (total 1H, each s, amide isomers), 8.10-8.16 (1H, m), 8.26 (2H, d, J=6.4 Hz), 8.29 and 8.31 (total 1H, each s, amide isomers), 8.49 and 8.50 (total 1H, each d, J=12.0 and 12.3 Hz respectively, amide isomers).

MS (ESI) m/z: 731 (M⁺+1), 733 (M⁺+3).

IR (ATR) cm⁻¹: 2933, 2854, 1712, 1641, 1595, 1514, 1464.

Anal. Calcd for $C_{39}H_{44}ClFN_6O_5 \cdot 1.5H_2O$: C, 61.77; H, 6.25; Cl, 4.68; F, 2.51; N, 11.08.

Found: C, 61.96; H, 6.21; Cl, 4.54; F, 2.57; N, 10.63.

Example 146

Trans-4-[1-[[4-[(benzo[b]furan-3-ylcarbonyl)amino]-5-chloro-2-fluorophenyl]acetyl]-(4S)-(cis-1,2,6-trimethylpiperazin-4-yl)-(2S)-pyrrolidinylmethoxy]cyclohexanecarboxylic acid Trans-4-[1-(tert-butoxycarbonyl)-(4S)-(cis-1,2,6-trimethylpiperazin-4-yl)-(2S)-pyrrolidinylmethoxy]cyclohexanecarboxylic acid ethyl ester NMR (CDCl₃) δ: 1.01-1.54 (26H, m), 1.60-2.15 (7H, m), 2.15-2.34 (4H, m), 2.42-2.77 (2H, m), 2.83 (1H, d, J=10.0 Hz), 2.98 (1H, t, J=10.0 Hz), 3.15-3.26 (1H, m), 3.31-3.61 (1H, m), 3.64-3.99 (2H, m), 4.06-4.28 (2H, m).

MS (ESI) m/z: 482 (M⁺+1).

Trans-4-[1-[[4-[(benzo[b]furan-3-ylcarbonyl)amino]-5-chloro-2-fluorophenyl]acetyl]-(4S)-(cis-1,2,6-trimethylpiperazin-4-yl)-(2S)-pyrrolidinylmethoxy]cyclohexanecarboxylic acid ethyl ester NMR (CDCl₃) δ: 1.04-1.55 (14H, m), 1.57-2.57 (13H, m), 2.60-3.30 (4H, m), 3.44-3.93 (6H, m), 4.03-4.38 (3H, m), 7.38-7.51 (3H, m), 7.58-7.64 (1H, m), 8.03-8.09 (1H, m), 8.25-8.33 (2H, m), 8.43 and 8.45 (total 1H, each d, J=11.6 and 11.8 Hz respectively, amide isomers).

MS (ESI) m/z: 711 (M⁺+1), 713 (M⁺+3).

Trans-4-[1-[[4-[(benzo[b]furan-3-ylcarbonyl)amino]-5-chloro-2-fluorophenyl]acetyl]-(4S)-(cis-1,2,6-trimethylpiperazin-4-yl)-(2S)-pyrrolidinylmethoxy]cyclohexanecarboxylic acid

[Formula 257]

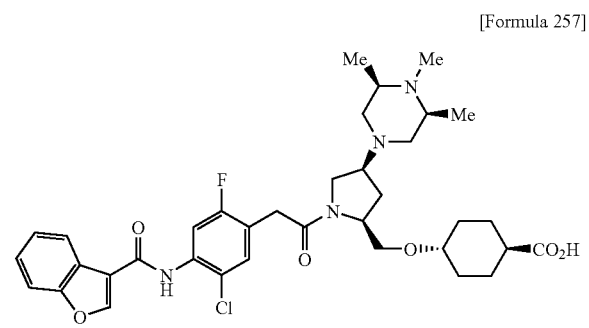

NMR (CDCl₃) δ: 0.98-1.72 (10H, m), 1.83-2.54 (12H, m), 2.57-3.02-8.08 (1H, m), 8.26-8.34 (2H, m), 8.390 and 8.401 (total 1H, each d, each J=11.8 Hz, amide isomers).

MS (ESI) m/z: 683 (M⁺+1), 685 (M⁺+3)

IR (ATR) cm⁻¹: 2935, 2856, 2790, 1678, 1637, 1587, 1558, 1521, 1448.

Example 147

Trans-4-[1-[[5-chloro-2-fluoro-4-[(1-methyl-1H-indol-3-ylcarbonyl)amino]phenyl]acetyl]-(4S)-[cis-2,6-dimethyl-1-(2-fluoroethyl)piperazin-4-yl]-(2S)-pyrrolidinylmethoxy]cyclohexanecarboxylic acid Trans-4-[1-(tert-butoxycarbonyl)-(4S)-[cis-2,6-dimethyl-1-(2-fluoroethyl)piperazin-4-yl]-(2S)-pyrrolidinylmethoxy]cyclohexanecarboxylic acid ethyl ester Trans-4-[1-tert-butoxycarbonyl-(4S)-(cis-2,6-dimethylpiperazin-4-yl)-(2S)-pyrrolidinylmethoxy]cyclohexanecarboxylic acid ethyl ester (0.68 g, 1.46 mmol) and toluenesulfonic acid 2-fluoroethyl ester (1.59 g, 7.30 mmol) were dissolved in DMF (10 mL), and potassium carbonate (1.01 g, 7.30 mmol) was added thereto. The mixture was stirred for 30 minutes at room temperature, and successively for two days at 50° C. The reaction liquor was poured onto ice water, and extracted with ethylacetate. The extract was washed with saturated brine, and dried over anhydrous sodium sulfate, and then the solvent was concentrated under reduced pressure. The obtained residue was purified by flash chromatography (Flash Chromatography System from Biotage AB, column size: 40S, chloroform to methanol/chloroform=8/92), to obtain the title compound (0.72 g, 96%) as an oily matter.

NMR (CDCl₃) δ: 1.00-1.30 (4H, m), 1.39-1.50 (9H, m), 1.68-2.35 (11H, m), 2.45-2.86 (6H, m), 2.92-3.04 (4H, m), 3.05-3.98 (10H, m), 4.21 (2H, d, J=7.1 Hz), 4.29-4.56 (2H, m).

MS (ESI) m/z: 514 (M⁺+1)

Trans-4-[1-[[5-chloro-2-fluoro-4-[(1-methyl-1H-indol-3-ylcarbonyl)amino]phenyl]acetyl]-(4S)-[cis-2,6-dimethyl-1-(2-fluoroethyl)piperazin-4-yl]-(2S)-pyrrolidinylmethoxy]cyclohexanecarboxylic acid ethyl ester NMR (CDCl₃) δ: 1.24-1.24 (13H, m), 1.57-2.31 (8H, m), 2.32-3.27 (9H, m), 3.40-3.87 (6H, m), 3.89 (3H, s), 4.01-4.74 (5H, m), 7.32-7.44 (4H, m), 7.80 and 7.81 (total 1H, each s, amide isomers), 7.98-8.18 (1H, m), 8.29 (1H, s), 8.49 and 8.52 (total 1H, each d, J=10.7 and 10.5 Hz respectively, amide isomers).

MS (ESI) m/z: 756 (M⁺+1), 758 (M⁺+3).

Trans-4-[1-[[5-chloro-2-fluoro-4-[(1-methyl-1H-indol-3-ylcarbonyl)amino]phenyl]acetyl]-(4S)-[cis-2,6-dimethyl-1-(2-fluoroethyl)piperazin-4-yl]-(2S)-pyrrolidinylmethoxy]cyclohexanecarboxylic acid

[Formula 258]

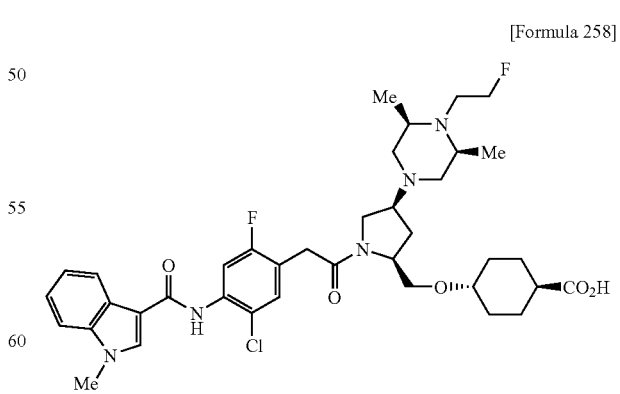

NMR (CDCl₃) δ: 0.97-1.69 (10H, m), 2.52-2.53 (17H, m), 3.41-3.85 (6H, m), 3.87 and 3.88 (total 3H, each d, J=1.2 and 1.5 Hz respectively, amide isomers), 4.10-4.65 (3H, m), 7.31-7.44 (4H, m), 7.80 (1H, d, J=1.2 Hz), 8.10-8.16 (1H, m), 8.29 (1H, s), 8.49 (1H, t, J=11.0 Hz).

303

MS (ESI) m/z: 728 (M⁺+1), 730 (M⁺+3).
IR (ATR) cm⁻¹: 2937, 2858, 1718, 1645, 1585, 1516, 1464.
Anal. Calcd for $C_{38}H_{48}F_2ClN_5O_5 \cdot 1.5H_2O$: C, 60.43; H, 6.81; F, 5.03; N, 9.27.
Found: C, 60.80; H, 6.75; F, 4.86; N, 8.83.

Example 148

Trans-4-[1-[[4-[(benzo[b]thiophen-3-ylcarbonyl)amino]-chloro-2-fluorophenyl]acetyl]-(4S)-(4-acetylpiperazin-1-yl)-(2S)-pyrrolidinylmethoxy]cyclohexanecarboxylic acid Trans-4-[1-(tert-butoxycarbonyl)-(4S)-(4-acetylpiperazin-1-yl)-(2S)-pyrrolidinylmethoxy]cyclohexanecarboxylic acid ethyl ester NMR (CDCl₃) δ: 1.25 (3H, dt, J=1.2, 7.1 Hz), 1.46 (9H, s), 1.76-2 Hz).
MS (ESI) m/z: 482 (M⁺+H).

Trans-4-[1-[[4-[(benzo[b]thiophen-3-ylcarbonyl)amino]-5-chloro-2-fluorophenyl]acetyl]-(4S)-(4-acetylpiperazin-1-yl)-(2S)-pyrrolidinylmethoxy]cyclohexanecarboxylic acid

[Formula 259]

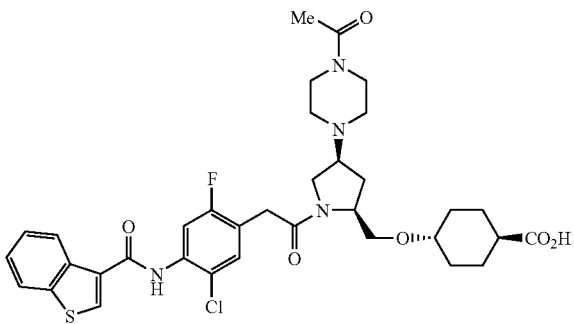

NMR (DMSO-d₆) δ: 1.07-1.39 (5H, m), 1.62-2.91 (16H, m), 3.11-4.31 Hz), 8.67-8.69 (1H, m), 10.15 (1H, br s).
IR (ATR) cm⁻¹: 2933, 2859, 1623, 1517, 1421, 1402.
MS (ESI) m/z: 699 (M⁺+H).
MS (FAB) m/z: 699 (M⁺+H).
MS (FAB) m/z: 699.2460 (Calcd. for $C_{35}H_{41}ClFN_4O_6S$: 699.2419)
Anal. Calcd for $C_{35}H_4OClFN_4O_6S \cdot HCl \cdot 2.5H_2O$: C, 53.84; H, 5.94; Cl, 9.08; F, 2.43; N, 7.18; S, 4.11.
Found: C, 53.90; H, 5.29; Cl, 8.41; F, 2.37; N, 7.11; S, 4.18.

Example 149

Trans-4-[1-[[2,5-dichloro-4-[(1-methyl-1H-indol-3-ylcarbonyl)amino]phenyl]acetyl]-(4S)-(4-pivaloylpiperazin-1-yl)-(2S)-pyrrolidinylmethoxy]cyclohexanecarboxylic acid Trans-4-(4S)-(4-benzyloxycarbonylpiperazin-1-yl)-1-tert-butoxycarbonyl-(2S)-pyrrolidinylmethoxy]cyclohexanecarboxylic acid ethyl ester Trans-4-[1-(tert-butoxycarbonyl)-4-oxo-(2S)-pyrrolidinylmethoxy]cyclohexanecarboxylic acid ethyl ester (1.14 g, 3.09 mmol) and 1-benzyloxycarbonylpiperazine (1.36 g, 6.17 mmol) were dissolved in methanol (20 mL) and acetic acid (1

304 mL), and sodium cyanoborohydride (0.58 g, 9.26 mmol) was added at 0° C. with stirring. The mixture was stirred for two days at room temperature. A saturated aqueous solution of sodium hydrogen carbonate (50 mL) was added to the reaction liquor, and the mixture was extracted with ethyl acetate. The extract was washed with saturated brine, and dried over anhydrous sodium sulfate, and then the solvent was concentrated under reduced pressure. The obtained residue was purified by flash column chromatography (Flash Chromatography System from Biotage AB, column size: 40 M, elution solvent: n-hexane:ethyl acetate=3:1 to 1:3), to obtain the title compound (1.47 g, 83%) as an oily matter.
NMR (CDCl₃) δ: 1.23-1.28 (5H, m), 1.42-1.49 (11H, m, including 9H, s, at δ 1.46), 1.73-2.05 (5H, m), 2.23-2.62 (7H, m), 2.95-3.01 (1H, m), 3.18-3.23 (1H, m), 3.41-3.87 (8H, m), 4.09-4.15 (2H, m), 5.13 (2H, s), 7.30-7.36 (5H, m).
MS (ESI) m/z: 574 (M⁺+1).

Trans-4-[1-(tert-butoxycarbonyl)-(4S)-(1-piperazinyl)-(2S)-pyrrolidinylmethoxy]cyclohexanecarboxylic acid ethyl ester Trans-4-[(4S)-(4-benzyloxycarbonylpiperazin-1-yl)-1-(tert-butoxycarbonyl)-(2S)-pyrrolidinylmethoxy]cyclohexanecarboxylic acid ethyl ester (609 mg, 1.06 mmol) was dissolved in methanol (20 mL), and 10% palladium hydroxide/carbon (100 mg) was added thereto. While stirring the mixture at room temperature, hydrogen at normal pressure was added for 18 hours. The catalyst was separated by filtration, and the filtrate was concentrated under reduced pressure, to obtain the title compound (469 mg, 100%) as an oily matter.
NMR (CDCl₃) δ: 1.19-1.28 (5H, m, including 3H, t, J=7.1 Hz, at δ 1.24), 1.40-1.49 (11H, m, including 9H, s, at δ 1.46), 1.73-1.81 (1H, m), 1.98-2.05 (4H, m), 2.20-2.32 (2H, m), 2.54-2.63 (5H, m), 2.95-3.04 (5H, m), 3.18-3.23 (1H, m), 3.41-3.85 (4H, m), 4.11 (2H, q, J=7.1 Hz), 4.77 (1H, broad s).
MS (ESI) m/z: 440 (M⁺+1).

Trans-4-[1-(tert-butoxycarbonyl)-(4S)-(4-pivaloylpiperazin-1-yl)-(2S)-pyrrolidinylmethoxy]cyclohexanecarboxylic acid ethyl ester Trans-4-[1-(tert-butoxycarbonyl)-(4S)-(1-piperazinyl)-(2S)-pyrrolidinylmethoxy]cyclohexanecarboxylic acid ethyl ester (469 mg, 1.07 mmol) and triethylamine (446 μl, 3.20 mmol) were dissolved in methylene chloride (10 mL), and pivaloyl chloride (263 μl, 2.13 mmol) was added thereto at 0° C. with stirring. The mixture was stirred for 3 days at room temperature. A saturated aqueous solution of sodium hydrogen carbonate (10 mL) was added to the reaction liquor, and the mixture was extracted with chloroform. The extract was washed with saturated brine, and dried over anhydrous sodium sulfate, and then the solvent was concentrated under reduced pressure. The obtained residue was purified by flash column chromatography (Flash Chromatography System from Biotage AB, column size: 25S, elution solvent: n-hexane:ethyl acetate=1:1 to 1:9), to obtain the title compound (550 mg, 98%) as an oily matter.
NMR (CDCl₃) δ: 1.23-1.30 (14H, m, including 3H, t, J=7.2 Hz, at 51.24, and including 9H, s, at (1.27), 1.42-1.49 (11H, m, including 9H, s, at δ 1.46), 1.75-2.06 (5H, m), 2.21-2.60 (7H, m), 2.97-3.02 (1H, m), 3.18-3.24 (1H, m), 3.40-3.94 (8H, m), 4.11 (2H, q, J=7.2 Hz).
MS (ESI) m/z: 524 (M⁺+1).

Trans-4-[(4S)-(4-pivaloylpiperazin-1-yl)-(2S)-pyrrolidinylmethoxy]cyclohexanecarboxylic acid ethyl ester Trans-4-[1-(tert-butoxycarbonyl)-(4S)-(4-pivaloylpiperazin-1-yl)-(2S)-pyrrolidinylmethoxy]cyclohexanecarboxylic acid ethyl ester (550 mg, 1.05 mmol) was dissolved in methylene chloride (5 mL), and trifluoroacetic acid (5 mL) was added thereto. The mixture was stirred for 3 hours at room temperature. A saturated aqueous solution of sodium hydrogen carbonate was added to the reaction liquor to make the reaction liquor weakly alkaline, and the mixture was extracted with chloroform. The extract was washed with saturated brine, and dried over anhydrous sodium sulfate, and then the solvent was concentrated uner reduced pressure, to obtain the title compound (310 mg, 70%) as a solid.

NMR (CDCl$_3$) δ: 1.23-1.31 (total 14H, m, including 3H, t, J=7.1 Hz, at δ 1.24, and including 9H, s, at δ 1.27), 1.42-1.63 (3H, m), 1.99-2.50 (total 10H, series of m), 2.90-3.02 (2H, m), 3.27-3.34 (2H, m), 3.52-3.65 (7H, m), 4.11 (2H, q, J=7.1 Hz), 5.28 (1H, broad s).

MS (ESI) m/z: 424 (M$^+$+1).

Trans-4-[1-[[2,5-dichloro-4-[(1-methyl-1H-indol-3-ylcarbonyl)amino]phenyl]acetyl]-(4S)-(4-pivaloylpiperazin-1-yl)-(2S)-pyrrolidinylmethoxy]cyclohexanecarboxylic acid ethyl ester NMR (CDCl$_3$) δ: 1.18-1.28 (14H, m, including 3H, t, J=7.1 Hz, at δ 1.23, and including 9H, s, at δ 1.28), 1.39-1.48 (2H, m), 1.88-2.06 (5H, m), 2.18-2.74 (7H, m), 2.96-3.04 and 3.16-3.24 (total 2H, each m), 3.46-4.40 (total 15H, series of m, including 3H, s, at δ 3.89, and including 2H, q, J=7.1 Hz, at δ 4.09), 7.34-7.43 (4H, m), 7.80 and 7.81 (total 1H, each s), 8.12-8.15 (1H, m) 8.25 (1H, s), 8.78 and 8.80 (total 1H, each s).

MS (LC-ESI) m/z: 782 (M$^+$+1).

Trans-4-[1-[[2,5-dichloro-4-[(1-methyl-1H-indol-3-ylcarbonyl)amino]phenyl]acetyl]-(4S)-(4-pivaloylpiperazin-1-yl)-(2S)-pyrrolidinylmethoxy]cyclohexanecarboxylic acid

[Formula 260]

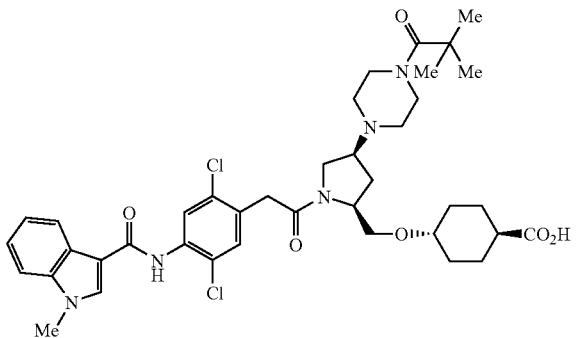

NMR (DMSO-d$_6$) δ: 1.18-1.36 (13H, m), 1.76-2.87 (total 12H, series of m), 3.15-4.29 (total 15H, series of m, including 3H, s, at δ 3.89), 7.20-7.29 (2H, m), 7.49 (1H, s), 7.55-7.57 (1H, m), 7.88 and 8.89 (total 1H, each s), 8.14-8.16 (1H, m), 8.30 and 8.31 (total 1H, each s), 9.37 and 9.39 (total 1H, each s), 12.09 (1H, broad s)

IR (ATR) cm$^{-1}$: 1628, 1500, 1371, 1188, 1101, 1078, 744.

MS (LC-ESI) m/z: 754 (M$^+$+1).

Anal. Calcd for C$_{39}$H$_{49}$Cl$_2$N$_5$O$_6$·½H$_2$O: C, 61.33; H, 6.60; N, 9.17; Cl, 9.28.

Found: C, 61.23; H, 6.63; N, 9.02; Cl, 9.37.

Example 150

Trans-4-[1-[[4-[(benzo[b]furan-3-ylcarbonyl)amino]-5-chloro-2-fluorophenyl]acetyl]-(4S)-(4-methanesulfonylpiperazin-1-yl)-(2S)-pyrrolidinylmethoxy]cyclohexanecarboxylic acid Trans-4-[1-(tert-butoxycarbonyl)-4-(4-methanesulfonyl piperazin-1-yl)-(2S)-pyrrolidinylmethoxy]cyclohexanecarboxylic acid ethyl ester NMR (CDCl$_3$) δ: 1.20-1.30 (5H, m, including 3H, t, J=7.2 Hz, at δ 1.24), 1.40-1.50 (11H, m, including 9H, s, at δ 1.46), 1.74-1.82 (1H, m), 1.98-2.06 (4H, m), 2.20-2.32 (2H, m), 2.51-2.82 (8H, m, including 3H, s, at δ 2.78), 2.95-3.00 (1H, m), 3.21-3.26 (5H, m), 3.44-3.95 (4H, m), 4.11 (2H, q, J=7.1 Hz).

MS (ESI) m/z: 518 (M$^+$+1).

Trans-4-[4-(4-methanesulfonylpiperazin-1-yl)-(2S)-pyrrolidinylmethoxy]cyclohexanecarboxylic acid ethyl ester NMR (CDCl$_3$) δ: 1.20-1.51 (7H, m, including 3H, t, J=7.1 Hz, at δ 1.24), 1.99-2.11 (7H, m), 2.20-2.28 (1H, m), 2.53-2.64 (4H, m), 2.77 (3H, s), 2.82-2.94 (2H, m), 3.09-3.49 (total 9H, series of m), 4.11 (2H, q, J=7.1 Hz).

MS (ESI) m/z: 418 (M$^+$+1).

Trans-4-[1-[[4-[(benzo[b]furan-3-ylcarbonyl)amino]-5-chloro-2-fluorophenyl]acetyl]-(4S)-(4-methanesulfonylpiperazin-1-yl)-(2S)-pyrrolidinylmethoxy]cyclohexanecarboxylic acid ethyl ester NMR (CDCl$_3$) δ: 1.11-1.48 (7H, m, including 3H, t, J=7.1 Hz, at δ 1.21), 1.88-2.04 (5H, m), 2.17-2.29 (2H, m), 2.42-3.00 (8H, m, including 3H, s, at δ 2.79), 3.11-3.27 (6H, m), 3.48-4.39 (8H, m, including 2H, q, J=7.1 Hz, at δ 4.08), 7.42-7.46 (3H, m), 7.59-7.63 (1H, m), 8.04-8.08 (1H, m), 8.28-8.33 (2H, m), 8.42-8.46 (1H, m).

MS (ESI) m/z: 747 (M#+1).

Trans-4-[1-[[4-[(benzo[b]furan-3-ylcarbonyl)amino]-5-chloro-2-fluorophenyl]acetyl]-(4S)-(4-methanesulfonylpiperazin-1-yl)-(2S)-pyrrolidinylmethoxy]cyclohexanecarboxylic acid

[Formula 261]

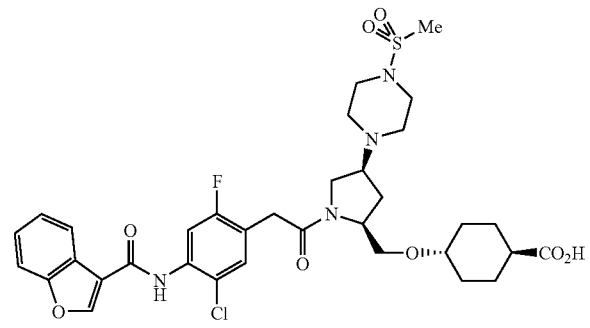

NMR (DMSO-d$_6$) δ: 1.15-1.36 (4H, m), 1.72-2.90 (total 15H, series of m, including 3H, s, at δ 2.88), 3.11-3.17 (6H, m), 3.53-4.30 (6H, m), 7.38-7.48 (3H, m), 7.55-7.59 (1H, m), 7.71-7.72 (1H, m), 8.07-8.10 (1H, m), 8.83 and 8.84 (total 1H, each s), 10.00 and 10.01 (total 1H, each s), 12.06 (1H, broad s).

IR (ATR) cm$^{-1}$: 1523, 1450, 1325, 1163, 1124, 960. MS (ESI) m/z: 719 (M$^+$+1).

Anal. Calcd for $C_{34}H_{40}ClFN_4O_8S \cdot \frac{3}{4}H_2O$: C, 55.73; H, 5.71; N, 7.65; S, 4.38.

Found: C, 55.67; H, 5.47; N, 7.53; S, 4.44.

Example 151

Trans-4-[1-[[2,5-dichloro-4-[(1-methyl-1H-indol-3-ylcarbonyl)amino]phenyl]acetyl]-(4S)-(4-N,N-dimethylsulfamoylpiperazin-1-yl)-(2S)-pyrrolidinylmethoxy]cyclohexanecarboxylic acid Trans-4-[(4S)-(4-benzyloxycarbonylpiperazin-1-yl)-1-(tert-butoxycarbonyl)-(2S)-pyrrolidinylmethoxy]cyclohexanecarboxylic acid ethyl ester NMR (CDCl$_3$) δ: 1.12-1.33 (7H, m), 1.41-1.49 (11H, m), 1.69-2.11 (5H, m), 2.14-2.73 (6H, m), 2.98 (1H, t, J=9.2 Hz), 3.15-3.25 (1H, m), 3.33-4.01 (5H, m), 4.08-4.15 (3H, m), 5.13 (2H, s), 7.29-7.38 (5H, m).
MS (ESI) m/z: 574 (M$^+$+1).

Trans-4-[1-(tert-butoxycarbonyl)-(4S)-(piperazin-1-yl)-(2S)-pyrrolidinylmethoxy]cyclohexanecarboxylic acid ethyl ester Ethanol/acetic acid (55 mL, 10:1) was added to trans-4-[(4S)-(4-benzyloxycarbonylpiperazin-1-yl)-1-(tert-butoxycarbonyl)-(2S)-pyrrolidinylmethoxy]cyclohexanecarboxylic acid ethyl ester (3.10 g, 5.41 mmol) and 10% palladium hydroxide/carbon (1.0 g), and the mixture was stirred for 4 days at room temperature under a hydrogen stream at normal pressure. The catalyst was separated by filtration, and then the solvent was concentrated under reduced pressure, to obtain the title compound (2.91 g, quantitative) as an oily matter. This compound was used in the subsequent reaction without performing further purification.

NMR (CDCl$_3$) δ: 1.17-1.30 (5H, m), 1.43-1.49 (11H, m), 1.74-2.09 (7H, m), 2.13-2.37 (2H, m), 2.47-2.75 (4H, m), 2.89-3.10 (4H, m), 3.13-3.31 (4H, m), 3.36-3.99 (2H, m), 4.11 (2H, q, J=7.1 Hz). MS (ESI) m/z: 440 (M$^+$+1).

Trans-4-[1-(tert-butoxycarbonyl)-(4S)-(4-N,N-dimethyl sulfamoylpiperazin-1-yl)-(2S)-pyrrolidinylmethoxy]cyclohexa necarboxylic acid ethyl ester Trans-4-[1-(tert-butoxycarbonyl)-(4S)-(piperazin-1-yl)-(2S)-pyrrolidinylmethoxy]cyclohexanecarboxylic acid ethyl ester (2.38 g, 5.41 mmol) was dissolved in tetrahydrofuran (50 mL), and while stirring the solution under a nitrogen stream, triethylamine (3.02 mL, 21.64 mmol) and N,N-dimethylsulfamoyl chloride (0.87 mL, 8.12 mmol) were added thereto. The mixture was stirred for 14 hours at room temperature. A saturated aqueous solution of sodium hydrogen carbonate (50 mL) was added to the reaction liquor, and the mixture was stirred for 30 minutes, and then extracted with ethyl acetate. The extract was washed with saturated brine, and dried over anhydrous sodium sulfate, and then the solvent was concentrated under reduced pressure. The obtained residue was purified by flash chromatography (Flash Chromatography System from Biotage AB, column size: 40M, ethyl acetate/n-hexane=3/7 to ethyl acetate), to obtain the title compound (2.12 g, 72%) as an oily matter.

NMR (CDCl$_3$) δ: 1.19-1.32 (5H, m), 1.43-1.48 (11H, m), 1.72-1.83 (1H, m), 1.91-2.36 (6H, m), 2.40-2.74 (6H, m), 2.83 (6H, s), 3.14-3.62 (6H, m), 3.65-3.99 (2H, m), 4.08-4.17 (3H, m).
MS (ESI) m/z: 547 (M$^+$+1).

Trans-4-[(4S)-1-(4-N,N-dimethylsulfamoylpiperazin-1-yl)-(2S)-pyrrolidinylmethoxy]cyclohexanecarboxylic acid ethyl ester MS (ESI) m/z: 447 (M$^+$+1-2HCl).

Trans-4-[1-[[2,5-dichloro-4-[(1-methyl-1H-indol-3-ylcarbonyl)amino]phenyl]acetyl]-(4S)-(4-N,N-dimethylsulfamoylpiperazin-1-yl)-(2S)-pyrrolidinylmethoxy]cyclohexanecarboxylic acid ethyl ester NMR (CDCl$_3$) δ: 1.09-1.55 (7H, m), 1.72-2.33 (7H, m), 2.42-2.81 and 3.89 (total 3H, each s, amide isomers), 3.91-4.42 (3H, m), 7.32-7.45 (4H, m), 7.79-7.83 (1H, m), 8.11-8.16 (1H, m), 8.24 (1H, s), 8.76-8.80 (1H, m).
MS (ESI) m/z: 805 (M$^+$+1), 807 (M$^+$+3).

Trans-4-[1-[[2,5-dichloro-4-[(1-methyl-1H-indol-3-ylcarbonyl)amino]phenyl]acetyl]-(4S)-(4-N,N-dimethylsulfamoylpiperazin-1-yl)-(2S)-pyrrolidinylmethoxy]cyclohexanecarboxylic acid

[Formula 262]

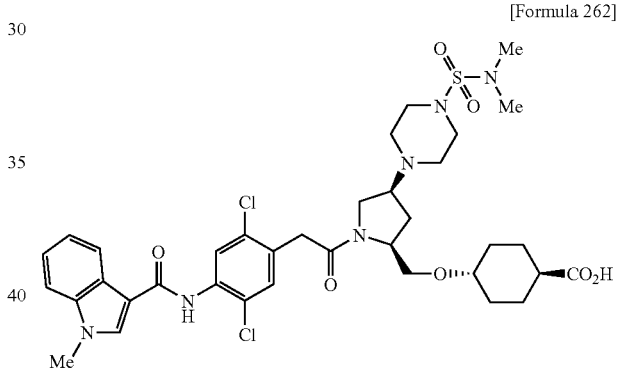

NMR (DMSO-d$_6$) δ: 1.11-1.39 (4H, m), 1.61-2.23 (9H, m), 2.32-2.58 (8H, m), 3.29 and 3.31 (total 6H, each s, amide isomers), 3.50-3.87 (4H, m), 3.88 (3H, s), 3.89-4.33 (3H, m), 7.20 (1H, t, J=7.8 Hz), 7.24-7.30 (1H, m), 7.48 (1H, s), 7.55 (1H, d, J=8.3 Hz), 7.88 (1H, t, J=5.6 Hz), 8.14 (1H, d, J=7.8 Hz), 8.28-8.31 (1H, m), 9.36 and 9.37 (total 1H, each s, amide isomers), 12.03 (1H, s).
MS (ESI) m/z: 777 (M$^+$+1), 779 (M$^+$+3).
IR (ATR) cm$^{-1}$: 2933, 2862, 1720, 1641, 1567, 1533, 1500, 1454.

Example 152

Trans-4-[1-[[2,5-dichloro-4-[(1-methyl-1H-indol-3-ylcarbonyl)amino]phenyl]acetyl]-(4S)-(4-methyl-3-oxopiperazin-1-yl)-(2S)-pyrrolidinylmethoxy]cyclohexanecarboxylic acid Trans-4-[1-(tert-butoxycarbonyl)-(4S)-(4-methyl-3-oxo piperazin-1-yl)-(2S)-pyrrolidinylmethoxy]cyclohexanecarboxylic acid ethyl ester NMR (CDCl$_3$) δ: 1.23-1.28 (5H, m, including 3H, t, J=7.1 Hz, at δ 1.24), 1.41-1.48 (11H, m, including 9H, s, at δ 1.46), 1.79-1.86 (1H, m), 1.98-2.04 (4H, m), 2.19-2.28 (2H, m), 2.65-3.92 (total 16H, series of m, including 3H, s, at δ 2.95), 4.11 (2H, q, J=7.1 Hz).
MS (ESI) m/z: 468 (M⁺+1).

Trans-4-[1-[[2,5-dichloro-4-[(1-methyl-1H-indol-3-ylcarbonyl)amino]phenyl]acetyl]-(4S)-(4-methyl-3-oxopiperazin-1-yl)-(2S)-pyrrolidinylmethoxy]cyclohexanecarboxylic acid ethyl ester NMR (CDCl₃) δ: 1.16-1.30 (5H, m, including 3H, t, J=7.1 Hz, at δ 1.23), 1.38-1.51 (2H, m), 1.91-2.05 (5H, m), 2.18-2.43 (2H, m), 2.64-2.80 (3H, m), 2.96-3.41 (total 9H, series of m, including 3H, s, at δ 2.96), 3.47-3.97 (total 8H, series of m, including 3H, s, at δ 3.89), 4.09 (2H, q, J=7.1 Hz), 4.21-4.40 (1H, m), 7.33-7.44 (4H, m), 7.80 and 7.81 (total 1H, each s), 8.13-8.15 (1H, m), 8.25 (1H, s), 8.78 and 8.80 (total 1H, each s).
MS (ESI) m/z: 726 (M⁺+1).

Trans-4-[1-[[2,5-dichloro-4-[(1-methyl-1H-indol-3-ylcarbonyl)amino]phenyl]acetyl]-(4S)-(4-methyl-3-oxopiperazin-1-yl)-(2S)-pyrrolidinylmethoxy]cyclohexanecarboxylic acid

[Formula 263]

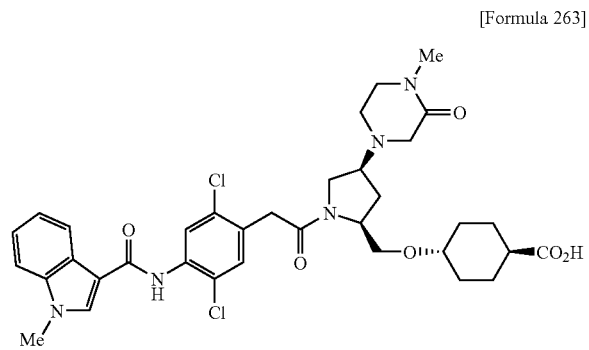

NMR (DMSO-d₆) δ: 1.11-1.40 (4H, m), 1.67-2.36 (7H, m), 2.66-3.30 (total 12H, series of m, including 3H, s, at δ 2.83), 3.54-3.63 (2H, m), 3.73-4.30 (7H, m, including 3H, s, at δ 3.89), 7.20-7.30 (2H, m), 7.50 (1H, s), 7.55 (1H, t, J=9.7 Hz), 7.88 and 7.89 (total 1H, each s), 8.15 (1H, d, J=7.8 Hz), 8.31 (1H, s), 9.38 and 9.39 (total 1H, each s), 12.05 (1H, broad s).
IR (ATR) cm⁻¹: 1639, 1504, 1373, 1101, 1078, 744. MS (ESI) m/z: 698 (M⁺+1).
Anal. Calcd for C₃₅H₄₁Cl₂N₅O₆.1H₂O: C, 58.66; H, 6.05; N, 9.77; Cl, 9.89.
Found: C, 58.69; H, 6.00; N, 9.54; Cl, 10.01.

Example 153

Trans-4-[1-[[4-[(benzo[b]thiophen-3-ylcarbonyl)amino]-2,5-dichlorophenyl]acetyl]-(4S)-(4-methyl-3-oxopiperazin-1-yl)-(2S)-pyrrolidinylmethoxy]cyclohexanecarboxylic acid Trans-4-[1-[[4-[(benzo[b]thiophen-3-ylcarbonyl)amino]-2,5-dichlorophenyl]acetyl]-(4S)-(4-methyl-3-oxopiperazin-1-yl)-(2S)-pyrrolidinylmethoxy]cyclohexanecarboxylic acid ethyl ester NMR (CDCl₃) δ: 1.16-1.30 (5H, m), 1.37-1.48 (2H, m), 1.93-2.03 (5H, m), 2.18-2.41 (2H, m), 2.64-3.07 (7H, m, including 3H, s, at δ 2.96), 3.13-3.97 (total 10H, series of m), 4.06-4.14 (2H, m), 4.20-4.39 (1H, m), 7.42-7.54 (3H, m), 7.91-7.93 (1H, m), 8.10 and 8.11 (total 1H, each s), 8.30 and 8.32 (total 1H, each s), 8.49 (1H, d, J=7.6 Hz), 8.70 and 8.72 (total 1H, each s).
MS (ESI) m/z: 729 (M⁺+1).

Trans-4-[1-[[4-[(benzo[b]thiophen-3-ylcarbonyl)amino]-2,5-dichlorophenyl]acetyl]-(4S)-(4-methyl-3-oxopiperazin-1-yl)-(2S)-pyrrolidinylmethoxy]cyclohexanecarboxylic acid

[Formula 264]

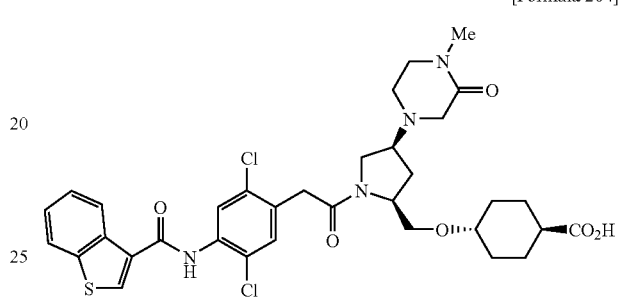

NMR (DMSO-d₆) δ: 1.06-1.39 (4H, m), 1.78-1.98 (5H, m), 2.11-2.35 (2H, m) 2.65-3.38 (total 13H, series of m, including 3H, s, at δ 2.82), 3.54-3.63 (2H, m), 3.74-3.89 (2H, m), 4.07-4.30 (1H, m), 7.43-7.55 (3H, m), 7.75 and 7.76 (total 1H, each s), 8.08-8.10 (1H, m), 8.43-8.45 (1H, m), 8.64 (1H, s), 10.15 (1H, s), 12.05 (1H, broad s).
IR (ATR) cm⁻¹: 1635, 1504, 1425, 1373, 1080, 768. MS (ESI) m/z: 701 (M⁺+1).
Anal. Calcd for C₃₄H₃₈Cl₂N₄O₆S.¾H₂O: C, 57.10; H, 5.57; N, 7.83; Cl, 9.91; S, 4.48.
Found: C, 57.14; H, 5.34; N, 7.54; Cl, 9.52; S, 4.52.

Example 154

Trans-4-[1-[[4-[(benzo[b]thiophen-3-ylcarbonyl)amino]-5-chloro-2-fluorophenyl]acetyl]-(4S)-(4-ethyl-3-oxopiperazin-1-yl)-(2S)-pyrrolidinylmethoxy]cyclohexanecarboxylic acid Trans-4-[1-benzyloxycarbonyl-(4R)-hydroxy-(2S)-pyrrolidinylmethoxy]cyclohexanecarboxylic acid ethyl ester Trans-4-[(4R)-hydroxy-(2S)-pyrrolidinylmethoxy]cyclohexanecarboxylic acid ethyl ester hydrochloride (5.00 g, 16.24 mmol) was dissolved in acetonitrile (50 mL) and a saturated aqueous solution of sodium hydrogen carbonate (50 mL), and benzyloxycarbonyl chloride (2.78 mL, 19.49 mmol) was added dropwise while stirring at room temperature. The mixture was stirred for three days at room temperature. A saturated aqueous solution of sodium hydrogen carbonate (50 mL) was added to the reaction liquor, and the mixture was extracted with ethyl acetate. The extract was washed with saturated brine, and dried over anhydrous sodium sulfate, and then the solvent was concentrated under reduced pressure. The obtained residue was purified by flash column chromatography (Flash Chromatography System from Biotage AB, column size: 40M, elution solvent: n-hexane:ethyl acetate=2:1 to 1:9), to obtain the title compound (7.10 g, 108%) as an oily matter.

NMR (CDCl$_3$) δ: 1.16-1.28 (5H, m, including 3H, t, J=7.1 Hz, at δ 1.25), 1.40-1.53 (2H, m), 1.95-2.21 (7H, m), 3.07-3.19 (1H, m), 3.51-3.69 (4H, m), 4.08-4.16 (3H, m, including 2H, q, J=7.1 Hz, at δ 4.11), 4.49-4.51 (1H, m), 5.06-5.25 (2H, m), 7.30-7.36 (5H, m).

MS (LC-ESI) m/z: 406 (M$^+$+1).

Trans-4-[1-benzyloxycarbonyl-4-oxo-(2S)-pyrrolidinylmethoxy]cyclohexanecarboxylic acid ethyl ester Trans-4-[1-benzyloxycarbonyl-(4R)-hydroxy-(2S)-pyrrolidinylmethoxy]cyclohexanecarboxylic acid ethyl ester (7.10 g, 17.51 mmol) was dissolved in DMSO (70 mL), and triethylamine (12.20 mL, 87.55 mmol) was added to the solution. A pyridine-sulfur trioxide complex (8.36 g, 52.53 mmol) was added to this reaction solution, and the mixture was stirred for 20 hours at room temperature. A saturated aqueous solution of sodium hydrogen carbonate (100 mL) was added to the reaction solution, and the mixture was extracted with ethyl acetate. The extract was washed with saturated brine, and dried over anhydrous sodium sulfate, and then the solvent was concentrated under reduced pressure. The obtained residue was purified by flash column chromatography (Flash Chromatography System from Biotage AB, column size: 40M, elution solvent: n-hexane:ethyl acetate=9:1 to 1:1), to obtain the title compound (6.59 g, 93%) as a solid.

NMR (CDCl$_3$) δ: 1.11-1.28 (5H, m, including 3H, t, J=7.1 Hz, at δ 1.24), 1.37-1.47 (2H, m), 1.88-1.98 (4H, m), 2.18-2.24 (1H, m), 2.42-2.47 (1H, m), 2.64-2.71 (1H, m), 3.13-3.18 (1H, m), 3.42-3.47 (1H, m), 3.68-3.95 (3H, m), 4.11 (2H, q, J=7.1 Hz), 4.46-4.51 (1H, m), 5.14-5.22 (2H, m), 7.32-7.36 (5H, m).

MS (LC-ESI) m/z: 404 (M$^+$+1).

Trans-4-[1-benzyloxycarbonyl-(4S)-(4-ethyl-3-oxopiperazin-1-yl)-(2S)-pyrrolidinylmethoxy]cyclohexanecarboxylic acid ethyl ester Trans-4-[1-benzyloxycarbonyl-4-oxo-(2S)-pyrrolidinylmethoxy]cyclohexanecarboxylic acid ethyl ester (3.00 g, 7.44 mmol) and 1-ethyl-2-oxopiperazine bis(trifluoroacetate) (3.97 g, 11.15 mmol) were dissolved in 1,2-dichloroethane (50 mL), and while stirring the solution at 0° C., sodium triacetoxyborohydride (4.73 g, 22.31 mmol) was added thereto. The mixture was stirred for 16 hours at room temperature. A saturated aqueous solution of sodium hydrogen carbonate (100 mL) was added to the reaction liquor, and the mixture was extracted with chloroform. The extract was washed with saturated brine, and dried over anhydrous sodium sulfate, and then the solvent was concentrated under reduced pressure. The obtained residue was purified by flash column chromatography (Flash Chromatography System from Biotage AB, column size: 40S, elution solvent: n-hexane:ethyl acetate=2:1 to 1:1, then chloroform:methanol=9:1), to obtain the title compound (2.95 g, 77%) as an oily matter.

NMR (CDCl$_3$) δ: 1.12-1.27 (8H, m, including 3H, t, J=7.2 Hz, at δ 1.14, and including 3H, t, J=7.2 Hz, at δ 1.25), 1.36-1.44 (2H, m), 1.82-2.04 (5H, m), 2.18-2.31 (2H, m), 2.62-2.78 (3H, m), 3.06-3.45 (total 9H, series of m, including 2H, q, J=7.2 Hz, at δ 3.43), 3.61-3.64 (1H, m), 3.75-3.97 (2H, m), 4.11 (2H, q, J=7.2 Hz), 5.06-5.21 (2H, m), 7.30-7.36 (5H, m).

MS (ESI) m/z: 516 (M$^+$+1).

Trans-4-[(4S)-(4-ethyl-3-oxopiperazin-1-yl)-(2S)-pyrrolidinylmethoxy]cyclohexanecarboxylic acid ethyl ester Trans-4-[1-benzyloxycarbonyl-(4S)-(4-ethyl-3-oxopiperazin-1-yl)-(2S)-pyrrolidinylmethoxy]cyclohexanecarboxylic acid ethyl ester (2.95 g, 5.72 mmol) was dissolved in methanol (30 mL), and 10% palladium hydroxide/carbon (0.60 g) was added thereto. The mixture was stirred at room temperature under a current of hydrogen at normal pressure 16 hours. The catalyst was separated by filtration, and then the filtrate was concentrated, to obtain the title compound (1.85 g, 85%) as a solid.

NMR (CDCl$_3$) δ: 1.12-1.37 (8H, m, including 3H, t, J=7.2 Hz, at δ 1.14, and including 3H, t, J=7.2 Hz, at δ 1.24), 1.43-1.52 (2H, m), 1.90-2.28 (7H, m), 2.71-2.78 (2H, m), 3.07-3.54 (total 10H, series of m), 3.67-3.71 (1H, m), 3.82-3.91 (2H, m), 4.11 (2H, q, J=7.2 Hz), 9.06 (1H, broad s).

MS (ESI) m/z: 382 (M$^+$+1)

Trans-4-[1-[[4-[(benzo[b]thiophen-3-ylcarbonyl)amino]-5-chloro-2-fluorophenyl]acetyl]-(4S)-(4-ethyl-3-oxopiperazin-1-yl)-(2S)-pyrrolidinylmethoxy]cyclohexanecarboxylic acid ethyl ester NMR (CDCl$_3$) δ: 1.13-1.30 (8H, m, including 3H, t, J=7.1 Hz, at δ 1.15, and including 3H, t, J=7.2 Hz, at δ 1.21), 1.35-1.51 (2H, m), 1.67-2.04 (5H, m), 2.17-2.43 (2H, m), 2.62-2.85 (3H, m), 3.02-3.87 (total 13H, series of m), 4.05-4.37 (3H, m, including 2H, q, J=7.2 Hz, at δ 4.08), 7.41-7.54 (3H, m), 7.91-7.93 (1H, m), 8.09 and 8.12 (total 1H, each s), 8.33-8.49 (3H, m).

MS (ESI) m/z: 727 (M$^+$+1).

Trans-4-[1-[[4-[(benzo[b]thiophen-3-ylcarbonyl)amino]-5-chloro-2-fluorophenyl]acetyl]-(4S)-(4-ethyl-3-oxopiperazin-1-yl)-(2S)-pyrrolidinylmethoxy]cyclohexanecarboxylic acid

[Formula 265]

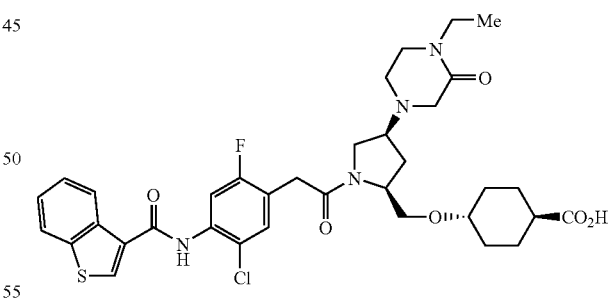

NMR (DMSO-d$_6$) δ: 1.01-1.37 (7H, m, including 3H, t, J=7.2 Hz, at 1.04), 1.77-2.33 (7H, m), 2.64-3.29 (total 11H, series of m), 3.54-3.86 (4H, m), 4.00-4.30 (2H, m), 7.44-7.58 (4H, m), 8.09-8.11 (1H, m), 8.44-8.46 (1H, m), 8.65 and 8.66 (total 1H, each s), 10.10 and 10.11 (total 1H, each s), 12.04 (1H, broad s).

IR (ATR) cm$^{-1}$: 1635, 1516, 1404, 1217, 768.

MS (ESI) m/z: 699 (M$^+$+1).

Anal. Calcd for C$_{35}$H$_{40}$ClFN$_4$O$_6$S·¾H$_2$O: C, 58.98; H, 5.87; N, 7.86; Cl, 4.97; F, 2.67; S, 4.50.

Found: C, 58.97; H, 5.52; N, 7.70; Cl, 5.19; F, 2.64; S, 4.64.

Example 155

Trans-4-[1-[[4-[(benzo[b]furan-3-ylcarbonyl)amino]-2,5-dichlorophenyl]acetyl]-(4S)-(4-methyl-3-oxopiperazin-1-yl)-(2S)-pyrrolidinylmethoxy]cyclohexanecarboxylic acid Trans-4-[1-[[4-[(benzo[b]furan-3-ylcarbonyl)amino]-2,5-dichlorophenyl]acetyl]-(4S)-(4-methyl-3-oxopiperazin-1-yl)-(2S)-pyrrolidinylmethoxy]cyclohexanecarboxylic acid ethyl ester NMR (CDCl$_3$) δ: 1.16-1.30 (5H, m, including 3H, t, J=7.1 Hz, at δ 1.23), 1.36-1.51 (2H, m), 1.95-2.03 (5H, m), 2.19-2.42 (2H, m), 2.64-3.07 (7H, m, including 3H, s, at δ 2.96), 3.14-3.97 (10H, m), 4.09 (2H, q, J=7.1 Hz), 4.20-4.39 (1H, m), 7 and 8.24 (total 1H, each s), 8.30 and 8.31 (total 1H, each s), 8.71 and 8.73 (total 1H, each s).
MS (ESI) m/z: 713 (M$^+$+1).

Trans-4-[1-[[4-[(benzo[b]furan-3-ylcarbonyl)amino]-2,5-dichlorophenyl]acetyl]-(4S)-(4-methyl-3-oxopiperazin-1-yl)-(2S)-pyrrolidinylmethoxy]cyclohexanecarboxylic acid

[Formula 266]

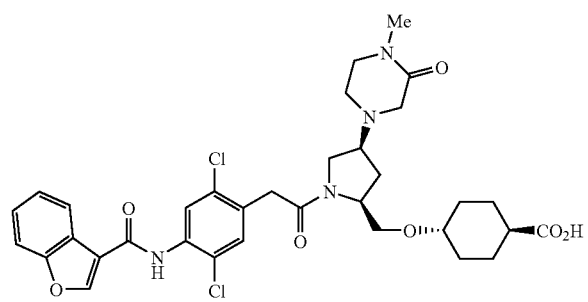

NMR (DMSO-d$_6$) δ: 1.12-1.40 (4H, m), 1.75-2.25 (7H, m), 2.66-3.36 (total 12H, series of m, including 3H, s, at δ 2.83), 3.56-3.63 (2H, m), 3.75-4.30 (4H, m), 7.38-7.46 (2H, m), 7.54 (1H, s), 7.71-7.73 (1H, m), 7.77 and 7.78 (total 1H, each s), 8.08-8.10 (1H, m), 8.83 (1H, s), 10.05 (1H, s), 12.05 (1H, broad s).
IR (ATR) cm$^{-1}$: 1635, 1508, 1448, 1122, 1105, 1080, 750.
MS (ESI) m/z: 685 (M$^+$+1)
Anal. Calcd for C$_{34}$H$_{38}$Cl$_2$N$_4$O$_7$·½H$_2$O: C, 58.79; H, 5.66; N, 8.07; Cl, 10.21.
Found: C, 58.64; H, 5.70; N, 7.87; Cl, 10.23.

Example 156

Trans-4-[(4S)-(4-benzyl-3-oxopiperazin-1-yl)-1-[[2,5-dichloro-4-[(1-methyl-1H-indol-3-ylcarbonyl)amino]phenyl]acetyl]-(2S)-pyrrolidinylmethoxy]cyclohexanecarboxylic acid Trans-4-[(4S)-(4-benzyl-3-oxopiperazin-1-yl)-1-(tert-butoxycarbonyl)-(2S)-pyrrolidinylmethoxy]cyclohexanecarboxylic acid ethyl ester NMR (CDCl$_3$) δ: 1.14-1.27 (5H, m, including 3H, t, J=7.1 Hz, at δ 1.24), 1.41-1.53 (11H, m, including 9H, s, at δ 1.46), 1.72-2.26 (7H, m), 2.59-2.75 (2H, m), 2.98-4.15 (14H, m), 4.57-4.60 (1H, m), 7.28-7.35 (5H, m).
MS (ESI) m/z: 544 (M$^+$+1), 444 (M$^+$+1-Boc).

Trans-4-[(4S)-(4-benzyl-3-oxopiperazin-1-yl)-1-[[2,5-dichloro-4-[(1-methyl-1H-indol-3-ylcarbonyl)amino]phenyl]acetyl]-(2S)-pyrrolidinylmethoxy]cyclohexanecarboxylic acid ethyl ester MS (ESI) m/z: 802 (M$^+$+1).

Trans-4-[(4S)-(4-benzyl-3-oxopiperazin-1-yl)-1-[[2,5-dichloro-4-[(1-methyl-1H-indol-3-ylcarbonyl)amino]phenyl]acetyl]-(2S)-pyrrolidinylmethoxy]cyclohexanecarboxylic acid

[Formula 267]

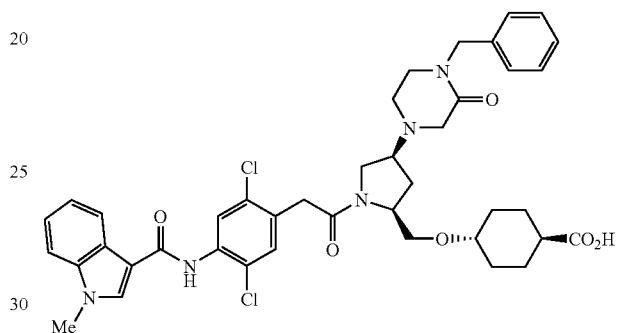

NMR (DMSO-d$_6$) δ: 1.11-1.40 (4H, m), 1.69-1.99 (5H, m), 2.11-2.33 (2H, m), 2.65-2.95 (3H, m), 3.06-3.26 (6H, m), 3.54-4.29 (total 9H, series of m, including 3H, s, at δ 3.89), 4.47-4.57 (2H, m), 7.19-7.37 (7H, m), 7.49 (1H, s), 7.56 (1H, d, J=8.1 Hz), 7.88 and 7.89 (total 1H, each s), 8.15 (1H, d, J=7.6 Hz), 8.30 (1H, s), 9.38 (1H, s), 12.07 (1H, broad s).
IR (ATR) cm$^{-1}$: 1645, 1500, 1373, 1101, 1078, 744. MS (ESI) m/z: 774 (M++1).
Anal. Calcd for C$_{41}$H$_{45}$Cl$_2$N$_5$O$_6$·½H$_2$O: C, 62.83; H, 5.92; N, 8.94; Cl, 9.05.
Found: C, 62.52; H, 5.84; N, 8.83; Cl, 9.30.

Example 157

Trans-4-[1-[[5-chloro-2-fluoro-4-[(1-methyl-1H-indol-3-ylcarbonyl)amino]phenyl]acetyl]-(4S)-([1,2]oxazinan-2-yl)-(2S)-pyrrolidinylmethoxy]cyclohexanecarboxylic acid Trans-4-[1-(tert-butoxycarbonyl)-(4S)-([1,2]oxazinan-2-yl)-(2S)-pyrrolidinylmethoxy]cyclohexanecarboxylic acid ethyl ester NMR (CDCl$_3$) δ: 1.16-1.32 (4H, m), 1.41-1.59 (15H, m), 1.88-2.28 (6H, m), 3.13-3.26 (3H, m), 3.34-4.00 (10H, m), 4.07-4.15 (2H, m).
MS (ESI) m/z: 441 (M$^+$+1).

Trans-4-[(4S)-([1,2]oxazinan-2-yl)-(2S)-pyrrolidinylmethoxy]cyclohexanecarboxylic acid ethyl ester NMR (CDCl$_3$) δ: 1.21-1.31 (4H, m), 1.38-1.82 (13H, m), 1.90-2.33 (5H, m), 2.47-2.89 (2H, m), 3.24-3.68 (3H, m), 3.77-3.93 (2H, m), 4.16-4.08 (2H, m).
MS (ESI) m/z: 341 (M$^+$+1).

Trans-4-[1-[[5-chloro-2-fluoro-4-[(1-methyl-1H-indol-3-ylcarbonyl)amino]phenyl]acetyl]-(4S)-([1,2]oxazinan-2-yl)-(2S)-pyrrolidinylmethoxy]cyclohexanecarboxylic acid ethyl ester NMR (CDCl₃) δ: 1.14-1.35 (6H, m), 1.35-1.85 (8H, m), 1.90-2.67 (8H, m), 2.91-3.38 (2H, m), 3.40-4.01 (9H, m), 4.02-4.28 (3H, m), 7.33-7.46 (4H, m), 7.81 and 7.82 (total 1H, each s, amide isomers), 8.11-8.18 (1H, m), 8.30 (1H, s), 8.49 and 8.51 (total 1H, each d, J=12.0 and 11.7 Hz respectively, amide isomers).
MS (ESI) m/z: 683 (M⁺+1), 685 (M⁺+3).

Trans-4-[1-[[5-chloro-2-fluoro-4-[(1-methyl-1H-indol-3-ylcarbonyl)amino]phenyl]acetyl]-(4S)-([1,2]oxazinan-2-yl)-(2S)-pyrrolidinylmethoxy]cyclohexanecarboxylic acid

[Formula 268]

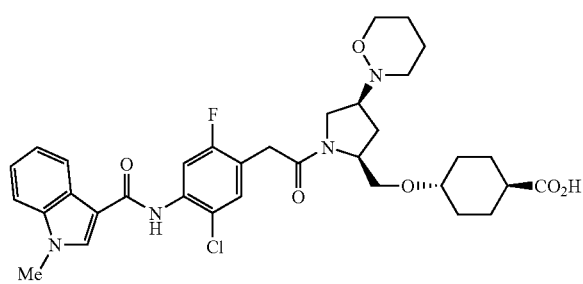

NMR (CDCl₃) δ: 1.07-1.64 (7H, m), 1.72-1.85 (2H, m), 1.90-2.38-4.29 (2H, m), 7.31-7.45 (4H, m), 7.81 (1H, s), 8.10-8.17 (1H, m), 8.30 and 8.50 (total 1H, each d, J=11.8 and 11.7 Hz respectively, amide isomers).
MS (ESI) m/z: 655 (M⁺+1), 657 (M⁺+3).
IR (ATR) cm⁻¹: 3419, 2939, 2858, 1724, 1643, 1622, 1585.

Example 158

Trans-4-[1-[[5-chloro-2-fluoro-4-[(1-methyl-1H-indol-3-ylcarbonyl)amino]phenyl]acetyl]-(4S)-(thiomorpholin-4-yl)-(2S)-pyrrolidinylmethoxy]cyclohexanecarboxylic acid Trans-4-[1-(tert-butoxycarbonyl)-(4S)-(thiomorpholin-4-yl)-(2S)-pyrrolidinylmethoxy]cyclohexanecarboxylic acid ethyl ester NMR (CDCl₃) δ: 1.19-1.28 (5H, m, including 3H, t, J=7.1 Hz, at δ 1.24), 1.40-1.49 (11H, m, including 9H, s, at δ 1.46), 1.71-1.78 (1H, m), 1.98-2.06 (4H, m), 2.21-2.26 (2H, m), 2.65-2.83 (9H, m), 2.92-2.98 (1H, m), 3.18-3.24 (1H, m), 3.38-3.96 (4H, m), 4.11 (2H, q, J=7.1 Hz).
MS (ESI) m/z: 457 (M⁺+1).

Trans-4-[(4S)-(thiomorpholin-4-yl)-(2S)-pyrrolidinylmethoxy]cyclohexanecarboxylic acid ethyl ester NMR (CDCl₃) δ: 1.20-1.30 (5H, m, including 3H, t, J=7.1 Hz, at δ 1.24), 1.40-1.49 (2H, m), 1.98-2.08 (5H, m), 2.20-2.35 (2H, m), 2.80-2.81 (4H, m), 3.00-3.09 (4H, m), 3.28-3.41 (2H, m), 3.62-3.78 (4H, m), 3.84-3.90 (1H, m), 4.11 (2H, q, J=7.1 Hz).
MS (ESI) m/z: 357 (M⁺+1)

Trans-4-[1-[[5-chloro-2-fluoro-4-[(1-methyl-1H-indol-3-ylcarbonyl)amino]phenyl]acetyl]-(4S)-(thiomorpholin-4-yl)-(2S)-pyrrolidinylmethoxy]cyclohexanecarboxylic acid ethyl ester NMR (CDCl₃) δ: 1.13-1.58 (7H, m, including 3H, t, J=7.1 Hz, at δ 1.22), 1.84-2.44 (7H, m), 2.70-3.23 (total 11H, series of m), 3.45-3.92 (8H, m, including 3H, s, at δ 3.89), 4.05-4.40 (3H, m, including 2H, q, J=7.1 Hz, at δ 4.08), 7.33-7.43 (4H, m), 7.81 and 7.82 (total 1H, each s), 8.13-8.15 (1H, m), 8.30 (1H, s), 8.48-8.54 (1H, m).
MS (ESI) m/z: 699 (M⁺+1).

Trans-4-[1-[[5-chloro-2-fluoro-4-[(1-methyl-1H-indol-3-ylcarbonyl)amino]phenyl]acetyl]-(4S)-(thiomorpholin-4-yl)-(2S)-pyrrolidinylmethoxy]cyclohexanecarboxylic acid

[Formula 269]

NMR (DMSO-d₆) δ: 1.14-1.37 (4H, m), 1.67-2.33 (7H, m), 2.62-3.16 (total 11H, series of m), 3.51-4.27 (9H, m, including 3H, s, at δ 3.89), 7.20-7.30 (2H, m), 7.42 (1H, d, J=7.6 Hz), 7.56 (1H, d, J=8.1 Hz), 7.67-7.72 (1H, m), 8.15 (1H, d, J=7.6 Hz), 8.31 (1H, s), 9.31 (1H, s), 12.06 (1H, broad s).
IR (ATR) cm⁻¹: 1643, 1518, 1404, 1219, 1099, 744. MS (ESI) m/z: 671 (M++1).
Anal. Calcd for $C_{34}H_{40}ClFN_4O_5S \cdot \frac{3}{4}H_2O$: C, 59.64; H, 6.11; N, 8.18; Cl, 5.18; F, 2.77; S, 4.68.
Found: C, 59.60; H, 5.78; N, 8.17; Cl, 5.18; F, 2.90; S, 4.84.

Example 159

Trans-4-[1-[[4-[(benzo[b]furan-3-ylcarbonyl)amino]-5-chloro-2-fluorophenyl]acetyl]-(4S)-(thiomorpholin-4-yl)-(2S)-pyrrolidinylmethoxy]cyclohexanecarboxylic acid Trans-4-[1-[[4-[(benzo[b]furan-3-ylcarbonyl)amino]-5-chloro-2-fluorophenyl]acetyl]-(4S)-(thiomorpholin-4-yl)-(2S)-pyrrolidinylmethoxy]cyclohexanecarboxylic acid ethyl ester NMR (CDCl₃) δ: 1.12-1.51 (7H, m, including 3H, t, J=7.1 Hz, at δ 1.22), 1.86-2.42 (7H, m), 2.69-3.00 (9H, m), 3.11-3.23 (2H, m), 3.46-3.86 (5H, m), 4.06-4.37 (3H, m, including 2H, q, J=7.1 Hz, at δ 4.08), 7.42-7.46 (3H, m), 7.59-7.63 (1H, m), 8.04-8.08 (1H, m), 8.27-8.32 (2H, m), 8.42-8.47 (1H, m).
MS (ESI) m/z: 686 (M⁺+1).

Trans-4-[1-[[4-[(benzo[b]furan-3-ylcarbonyl)amino]-5-chloro-2-fluorophenyl]acetyl]-(4S)-(thiomorpholin-4-yl)-(2S)-pyrrolidinylmethoxy]cyclohexanecarboxylic acid

[Formula 270]

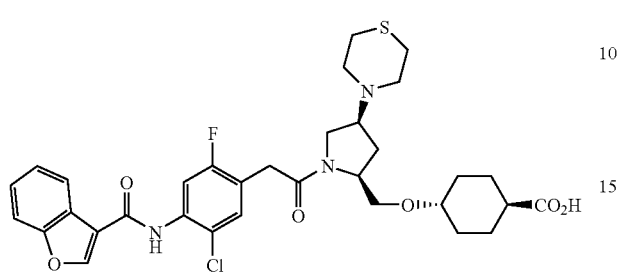

NMR (DMSO-$d_6$) δ: 1.09-1.40 (4H, m), 1.55-2.33 (7H, m), 2.61-3.16 (total 11H, series of m), 3.51-4.28 (6H, m), 7.38-7.47 (3H, m), 7.55-7.59 (1H, m), 7.71-7.73 (1H, m), 8.08-8.10 (1H, m), 8.83 and 8.84 (total 1H, each s), 10.00 (1H, s), 12.06 (1H, broad s).
IR (ATR) cm$^{-1}$: 1522, 1450, 1406, 1122, 1103, 748. MS (ESI) m/z: 658 (M$^+$+1).
Anal. Calcd for $C_{33}H_{37}ClFN_3O_6S \cdot \frac{1}{2}H_2O$: C, 59.41; H, 5.74; N, 6.30; Cl, 5.31; F, 2.85; S, 4.81.
Found: C, 59.28; H, 5.42; N, 6.25; Cl, 5.22; F, 2.95; S, 4.98.

Example 160

Trans-4-[1-[[5-chloro-2-fluoro-4-[(1-methyl-1H-indol-3-ylcarbonyl)amino]phenyl]acetyl]-(4S)-(1,1-dioxo-1λ$^6$-thiomorpholin-4-yl)-(2S)-pyrrolidinylmethoxy]cyclohexanecarboxylic acid Trans-4-[1-(tert-butoxycarbonyl)-(4S)-(1,1-dioxo-1λ$^6$-thiomorpholin-4-yl)-(2S)-pyrrolidinylmethoxy]cyclohexanecarboxylic acid ethyl ester NMR (CDCl$_3$) δ: 1.22-1.30 (5H, m, including 3H, t, J=7.1 Hz, at δ 1.25), 1.41-1.50 (11H, m, including 9H, s, at δ 1.46), 1.78-1.86 (1H, m), 1.98-2.06 (4H, m), 2.21-2.27 (2H, m), 2.97-3.24 (11H, m), 3.48-3.89 (4H, m), 4.09-4.15 (2H, m). MS (ESI) m/z: 489 (M$^+$+1).

Trans-4-[(4S)-(1,1-dioxo-1λ$^6$-thiomorpholin-4-yl)-(2S)-pyrrolidinylmethoxy]cyclohexanecarboxylic acid ethyl ester NMR (CDCl$_3$) δ: 1.20-1.51 (8H, m, including 3H, t, J=7.1 Hz, at δ 1.24), 1.99-2.08 (5H, m), 2.20-2.28 (1H, m), 2.85-2.88 (1H, m), 2.96-3.34 (12H, m), 3.38-3.51 (2H, m), 4.12 (2H, q, J=7.1 Hz).
MS (ESI) m/z: 389 (M$^+$+1).

Trans-4-[1-[[5-chloro-2-fluoro-4-[(1-methyl-1H-indol-3-ylcarbonyl)amino]phenyl]acetyl]-(4S)-(1,1-dioxo-1λ$^6$-thiomorpholin-4-yl)-(2S)-pyrrolidinylmethoxy]cyclohexanecarboxylic acid ethyl ester NMR (CDCl$_3$) δ: 1.09-1.31 (5H, m, including 3H, t, J=7.2 Hz, at δ 1.21), 1.36-1.48 (2H, m), 1.90-2.06 (5H, m), 2.17-2.45 (2H, m), 2.91-3.22 (12H, m), 3.51-3.84 (4H, m), 3.89 (3H, s), 4.05-4.14 (2H, m), 4.20-4.38 (1H, m), 7.33-7.43 (4H, m), 7.81 and 7.83 (total 1H, each s), 8.12-8.15 (1H, m), 8.30 (1H, s), 8.49-8.54 (1H, m).
MS (ESI) m/z: 731 (M$^+$+1), 729 (M$^+$−1).

Trans-4-[1-[[5-chloro-2-fluoro-4-[(1-methyl-1H-indol-3-ylcarbonyl)amino]phenyl]acetyl]-(4S)-(1,1-dioxo-1)-6-thiomorpholin-4-yl)-(2S)-pyrrolidinylmethoxy]cyclohexanecarboxylic acid

[Formula 271]

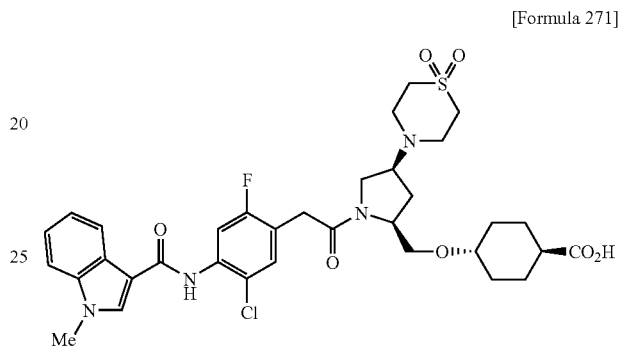

NMR (DMSO-$d_6$) δ: 1.12-1.38 (4H, m), 1.69-2.01 (5H, m), 2.12-2.24 (2H, m), 2.86-3.13 (11H, m), 3.53-3.82 (4H, m), 3.89 (3H, s), 3.99-4.29 (2H, m), 7.20-7.30 (2H, m), 7.41-7.44 (1H, m), 7.56 (1H, d, J=8.1 Hz), 7.68-7.73 (1H, m), 8.15 (1H, d, J=7.8 Hz), 8.31 (1H, s), 9.31 (1H, s), 12.07 (1H, broad s).
IR (ATR) cm$^{-1}$: 1645, 1518, 1404, 1300, 1227, 1186, 1122, 1101, 746.
MS (ESI) m/z: 703 (M$^+$+1)
Anal. Calcd for $C_{34}H_{40}ClFN_4O_7S \cdot \frac{1}{4}H_2O$: C, 57.70; H, 5.77; N, 7.92; Cl, 5.01; F, 2.68; S, 4.53.
Found: C, 57.47; H, 5.70; N, 7.77; Cl, 5.19; F, 2.69; S, 4.56.

Example 161

Trans-4-[1-[[4-[(benzo[b]furan-3-ylcarbonyl)amino]-5-chloro-2-fluorophenyl]acetyl]-(4S)-(1,1-dioxo-1λ$^6$-thiomorpholin-4-yl)-(2S)-pyrrolidinylmethoxy]cyclohexanecarboxylic acid Trans-4-[1-[[4-[(benzo[b]furan-3-ylcarbonyl)amino]-5-chloro-2-fluorophenyl]acetyl]-(4S)-(1,1-dioxo-1λ$^6$-thiomorpholin-4-yl)-(2S)-pyrrolidinylmethoxy]cyclohexanecarboxylic acid ethyl ester NMR (CDCl$_3$) δ: 1.13-1.49 (7H, m, including 3H, t, J=7.1 Hz, at 6-3.25 (1H, m), 3.52-3.85 (4H, m), 4.05-4.14 (2H, m), 4.20-4.39 (1H, m), 7.42-7.46 (3H, m), 7.59-7.62 (1H, m), 8.05-8.07 (1H, m), 8.28-8.33 (2H, m), 8.43-8.47 (1H, m).
MS (ESI) m/z: 718 (M$^+$+1).

Trans-4-[1-[[4-[(benzo[b]furan-3-ylcarbonyl)amino]-5-chloro-2-fluorophenyl]acetyl]-(4S)-(1,1-dioxo-1λ⁶-thiomorpholin-4-yl)-(2S)-pyrrolidinylmethoxy]cyclohexanecarboxylic acid

[Formula 272]

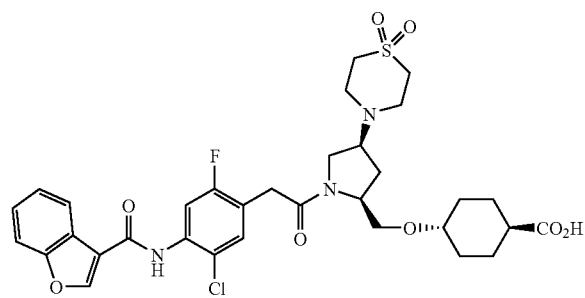

NMR (DMSO-d$_6$) δ: 1.12-1.37 (4H, m), 1.72-2.01 (5H, m), 2.12-2.24 (2H, m), 2.86-3.14 (11H, m), 3.53-3.89 (4H, m), 4.01-4.29 (2H, m), 7.38-7.48 (3H, m), 7.55-7.59 (1H, m), 7.70-7.73 (1H, m), 8.08-8.10 (1H, m), 8.83 and 8.84 (total 1H, each s), 10.00 (1H, s), 12.05 (1H, broad s).
IR (ATR) cm$^{-1}$: 1523, 1450, 1404, 1300, 1120, 858, 748.
MS (ESI) m/z: 690 (M$^+$+1).
Anal. Calcd for $C_{33}H_{37}ClFN_3O_8S \cdot \frac{1}{4}H_2O$: C, 57.06; H, 5.44; N, 6.05; Cl, 5.10; F, 2.73.
Found: C, 56.91; H, 5.49; N, 5.92; Cl, 4.93; F, 2.59.

Example 162

Trans-4-[1-[[2,5-dichloro-4-[1-methyl-1H-indol-3-ylcarbonylamino]phenyl]acetyl]-(4S)-[(1S,4S)-2-oxa-5-azabicyclo[2.2.1]heptan-5-yl]-(2S)-pyrrolidinylmethoxy]cyclohexanecarboxylic acid Trans-4-[2-[1-(tert-butoxycarbonyl)-(4S)-[(1S,4S)-2-oxa-5-azabicyclo[2.2.1]heptan-5-yl]-(2S)-pyrrolidinylmethoxy]cyclohexanecarboxylic acid ethyl ester NMR (CDCl$_3$) δ: 0.80-0.98 (2H, m), 1.01-2.36 (27H, m), 2.44-3.02 (4H, m), 3.17-3.26 (1H, m), 3.32-3.34 (4H, m), 3.60-3.85 (5H, m), 3.92-4.01 (1H, m).
MS (ESI) m/z: 453 (M$^+$+1).

Trans-4-[2-[(4S)-[(1S,4S)-2-oxa-5-azabicyclo[2.2.1]heptan-5-yl]-(2S)-pyrrolidinylmethoxy]cyclohexanecarboxylic acid ethyl ester dihydrochloride NMR (CDCl$_3$) δ: 1.17-1.54 (7H, m), 1.89-3.16 (11H, m), 3.31-5.03 (14H, m), 9.03 and 9.30 (total 1H, br s, each), 10.47 and 10.63 (total 1H, br s), 12.05 and 12.57 (total 1H, s).
MS (ESI) m/z: 353 (M$^+$+1).

Trans-4-[1-[[2,5-dichloro-4-[1-methyl-1H-indol-3-ylcarbonylamino]phenyl]acetyl]-(4S)-[(1S,4S)-2-oxa-5-azabicyclo[2.2.1]heptan-5-yl]-(2S)-pyrrolidinylmethoxy]cyclohexanecarboxylic acid ethyl ester NMR (CDCl$_3$) δ: 1.15-1.31 (5H, m), 1.37-1.53 (2H, m), 1.72-1.87 (3H, m), 1.92-2.09 (4H, m), 2.16-2.35 (2H, m), 2.51-2.63 (1H, m), 2.88-2.97 (1H, m), 3.07-3.29 (3H, m), 3.44-3.80 (6H, m), 3.89 (3H, s), 3.94-4.27 (5H, m), 4.38-4.42 (1H, m), 7.32-7.33 (2H, m), 7.39-7.45 (2H, m), 7.81 (1H, d, J=2.2 Hz), 8.11-8.16 (1H, m), 8.25 (1H, d, J=2.7 Hz), 8.79 (1H, d, J=7.1 Hz).
MS (ESI) m/z: 711 (M$^+$+1), 713 (M$^+$+3), 715 (M$^+$+5).

Trans-4-[1-[[2,5-dichloro-4-[1-methyl-1H-indol-3-ylcarbonylamino]phenyl]acetyl]-(4S)-[(1S,4S)-2-oxa-5-azabicyclo[2.2.1]heptan-5-yl]-(2S)-pyrrolidinylmethoxy]cyclohexanecarboxylic acid

[Formula 273]

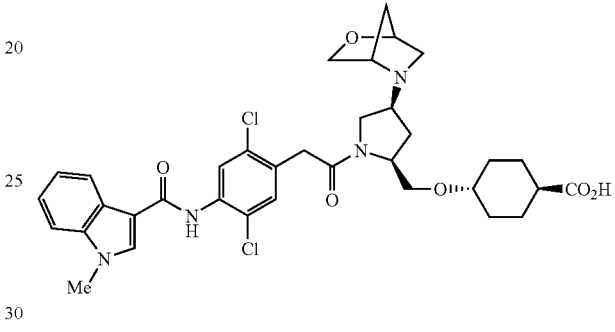

NMR (CDCl$_3$) δ: 1.15-1.35 (2H, m), 1.35-1.54 (2H, m), 1.62-2.65 (10H, m), 3.04-4.45 (17H, m), 7.30-7.44 (4H, m), 7.80 (1H, d, J=2.4 Hz), 8.08-8.16 (1H, m), 8.24 (1H, d, J=3.2 Hz), 8.77 (1H, d, J=9.8 Hz).
MS (ESI) m/z: 683 (M$^+$+1), 685 (M$^+$+3), 687 (M$^+$+5).
Anal. Calcd for $C_{35}H_{40}Cl_2N_4O_6 \cdot \frac{3}{4}H_2O$: C, 60.30; H, 6.00; Cl, 10.17; N, 8.04.
Found: C, 60.49; H, 6.13; Cl, 10.66; N, 7.62.

Example 163

Trans-4-[1-[[5-chloro-2-fluoro-4-[(1-methyl-1H-indol-3-ylcarbonyl)amino]phenyl]acetyl]-(4S)-[(1S,4S)-2-oxa-5-azabicyclo[2.2.1]heptan-5-yl]-(2S)-pyrrolidinylmethoxy]cyclohexanecarboxylic acid Trans-4-[1-[[5-chloro-2-fluoro-4-[(1-methyl-1H-indol-3-ylcarbonyl)amino]phenyl]acetyl]-(4S)-[(1S,4S)-2-oxa-5-azabicyclo[2.2.1]heptan-5-yl]-(2S)-pyrrolidinylmethoxy]cyclohexanecarboxylic acid ethyl ester NMR (CDCl$_3$) δ: 1.10-1.54 (7H, m), 1.61-2.37 (9H, m), 2.50-2.63 (1H, m), 2.87-2.97 (1H, m), 3.06-3.30 (3H, m), 3.43-4.27 (14H, m), 4.37-4.44 (1H, m), 7.31-7.47 (4H, m), 7.82 (1H, d, J=3.2 Hz), 8.10-8.18 (1H, m), 8.11-8.18 (1H, m), 8.46-8.55 (1H, m).
MS (ESI) m/z: 695 (M$^+$+1), 697 (M$^+$+3).

Trans-4-[1-[[5-chloro-2-fluoro-4-[(1-methyl-1H-indol-3-ylcarbonyl)amino]phenyl]acetyl]-(4S)-[(1S,4S)-2-oxa-5-azabicyclo[2.2.1]heptan-5-yl]-(2S)-pyrrolidinylmethoxy]cyclohexanecarboxylic acid

[Formula 274]

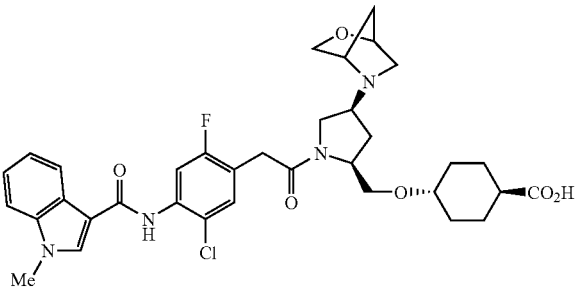

NMR (CDCl$_3$) δ: 1.11-1.54 (4H, m), 1.64-1.85 (1.5H, m), 1.94-2.14 (5.5H, m), 2.16-2.29 (1.5H, m), 2.36-2.47 (0.5H, m), 2.57 (1H, dd, J=18.8, 10.3 Hz), 3.00-3.36 (4H, m), 3.44-3.74 (6H, m), 3.82-3.89 (3.5H, m), 4.09 (1H, dd, J=24.9, 8.5 Hz), 4.16-4.32 (1.5H, m), 4.42 (1H, s), 7.31-7.44 (4H, m), 7.81 (1H, s), 8.10-8.16 (1H, m), 8.29 (1H, d, J=3.9 Hz), 8.49 (1H, t, J=11.6 Hz).

MS (ESI) m/z: 667 (M$^+$+1), 669 (M$^+$+3).

Anal. Calcd for C$_{35}$H$_{40}$ClFN$_4$O$_6$·½H$_2$O: C, 62.17; H, 6.11; Cl, 5.24; F, 2.81; N, 8.29.

Found: C, 61.91; H, 6.24; Cl, 5.39; F, 2.84; N, 7.96.

Example 164

Trans-4-[1-[[2,5-dichloro-4-[(1-methyl-1H-indol-3-ylcarbonyl)amino]phenyl]acetyl]-(4S)-[(1S,4S)-2-cyclopropyl-2,5-diazabicyclo[2.2.1]heptan-5-yl]-(2S)-pyrrolidinylmethoxy]cyclohexanecarboxylic acid

(1S,4S)-2-cyclopropyl-2,5-diazabicyclo[2.2.1]heptan-5-ylcarboxylic acid tert-butyl ester (1S,4S)-(−)-2,5-diazabicyclo[2.2.1]heptan-5-ylcarboxylic acid tert-butyl ester (3.00 g, 15.13 mmol) and [(1-ethoxycyclopropyl)oxy]trimethylsilane (3.96 g, 22.70 mmol) were dissolved in methanol (30 mL), and while stirring the solution at room temperature, acetic acid (0.87 mL, 5.13 mmol) and then sodium cyanoborohydride (1.06 g, 15.13 mmol) were added thereto. Then, the mixture was heated to reflux for 21 hours. The reaction liquor was left to cool naturally, then a saturated aqueous solution of sodium hydrogen carbonate (100 mL) was added thereto, and the mixture was extracted with ethyl acetate (200 mL). The extract was washed with saturated brine (100 mL), and then dried over anhydrous sodium sulfate, and then the solvent was concentrated under reduced pressure. The obtained residue was purified by column chromatography using silica gel [chloroform-methanol (10:1)], to obtain the title compound (3.61 g, 100%) as an oily matter.

NMR (CDCl$_3$) δ: 0.38-0.47 (4H, m), 1.19-1.26 (1H, m), 1.44-1.48 (9H, m), 1.80 (1H, d, J=9.5 Hz), 1.89-2.00 (1H, m), 2.68 (0.5H, d, J=9.8 Hz), 2.81 (0.5H, d, J=9.8 Hz), 2.98 (1H, dd, J=23.1, 9.9 Hz), 3.18 (1H, t, J=9.0 Hz), 3.52 (1.5H, br s), 3.65 (0.5H, d, J=10.5 Hz), 4.23 (0.5H, s), 4.36 (0.5H, s).

MS (ESI) m/z: 239 (M$^+$+1).

(1S,4S)-2-cyclopropyl-2,5-diazabicyclo[2.2.1]heptane dihydrochloride

4N—HCl/1,4-dioxane (10 mL) was added to (1S,4S)-(−)-2-cyclopropyl-2,5-diazabicyclo[2.2.1]heptan-5-ylcarboxylic acid tert-butyl ester (4.46 g, 18.71 mmol), and the mixture was stirred for 7 hours at room temperature. The reaction liquor was concentrated under reduced pressure, to obtain the title compound (3.34 g, 85%) as an oily matter.

MS (ESI) m/z: 139 (M$^+$+1).

Trans-4-[1-(tert-butoxycarbonyl)-(4S)-[(1S,4S)-2-cyclopropyl-2,5-diazabicyclo[2.2.1]heptan-5-yl]-(2S)-pyrrolidin ylmethoxy]cyclohexanecarboxylic acid ethyl ester MS (ESI) m/z: 492 (M$^+$+1).

Trans-4-[1-[[2,5-dichloro-4-[(1-methyl-1H-indol-3-ylcarbonyl)amino]phenyl]acetyl]-(4S)-[(1S,4S)-2-cyclopropyl-2, cyclohexanecarboxylic acid ethyl ester NMR (CDCl$_3$) δ: 0.35-0.48 (4H, m), 1.13-1.31 (5H, m), 1.36-1.53 (2H, m), 1.59-1.78 (2H, m), 1.90-2.10 (6H, m), 2.15-2.33 (2H, m), 2.66-2.80 (2H, m), 2.86-3.27 (4H, m), 3.29-3.40 (2H, m), 3.51-3.81 (5H, m), 3.88-3.90 (3H, m), 3.94-4.25 (4H, m), 7.32-7.45 (4H, m), 7.81 (1H, d, J=2.2 Hz), 8.11-8.17 (1H, m), 8.23-8.27 (1H, m), 8.81-8.77 (1H, m).

MS (ESI) m/z: 750 (M$^+$+1), 752 (M$^+$+3), 754 (M$^+$+5).

Trans-4-[1-[[2,5-dichloro-4-[(1-methyl-1H-indol-3-ylcarbonyl)amino]phenyl]acetyl]-(4S)-[(1S,4S)-2-cyclopropyl-2,5-diazabicyclo[2.2.1]heptan-5-yl]-(2S)-pyrrolidinylmethoxy]cyclohexanecarboxylic acid

[Formula 275]

NMR (CDCl$_3$) δ: 0.39-0.68 (4H, m), 1.15-1.51 (4H, m), 1.63-2.47 (10H, m), 2.64-3.03 (2H, m), 3.06-3.36 (4H, m), 3.41-3.99 (10H, m), 4.06-4.96 (3H, m), 7.28-7.43 (4H, m), 7.79 (1H, s), 8.16-8.09 (1H, m), 8.23 (1H, d, J=8.1 Hz), 8.76 (1H, d, J=12.2 Hz).

MS (ESI) m/z: 722 (M$^+$+1), 724 (M$^+$+3), 726 (M$^+$+5).

Example 165

Trans-4-[1-[[2,5-dichloro-4-[(1-methyl-1H-indol-3-ylcarbonyl)amino]phenyl]acetyl]-(4S)-([1,4]-oxazepan-4-yl)-(2S)-pyrrolidinylmethoxy]cyclohexanecarboxylic acid Trans-4-[1-(tert-butoxycarbonyl)-(4S)-([1,4]-oxazepan-4-yl)-(2S)-pyrrolidinylmethoxy]cyclohexanecarboxylic acid ethyl ester NMR (CDCl$_3$) δ: 1.13-1.31 (2H, m), 1.25 (3H, t, J=7.0 Hz), 1.45 (9H, s), 1.61 (3H, s), 1.73-2.34 (9H, m), 2.60-3.97 (14H, m), 4.11 (2H, q, J=7.0 Hz).
MS (ESI) m/z: 455 (M$^+$+H).

Trans-4-[1-[[2,5-dichloro-4-[(1-methyl-1H-indol-3-ylcarbonyl)amino]phenyl]acetyl]-(4S)-([1,4]-oxazepan-4-yl)-(2S)-pyrrolidinylmethoxy]cyclohexanecarboxylic acid

[Formula 276]

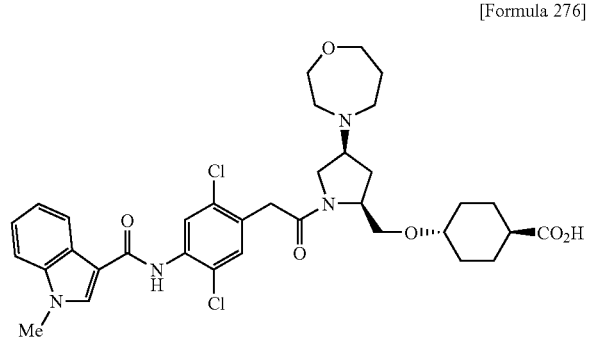

NMR (DMSO-d$_6$) δ: 1.12-1.40 (6H, m), 1.74-2.83 (16H, m), 3.10-4.28 (11H, m), 7.22 (1H, t, J=7.5 Hz), 7.28 (1H, t, J=7.5 Hz), 7.49 (1H, s), 7.56 (1H, d, J=8.1 Hz), 7.88 (1H, d, J=4.4 Hz), 8.15 (1H, d, J=7.8 Hz), 8.31 (1H, d, J=3.9 Hz), 9.39 (1H, d, J=3.9 Hz).
MS (ESI) m/z: 685 (M$^+$+H).
IR (ATR) cm$^{-1}$: 3423, 3110, 2933, 2859, 1639, 1502.
Anal. Calcd for C$_{35}$H$_{42}$Cl$_2$N$_4$O$_6$·0.5HCl·2.5H$_2$O: C, 56.13; H, 6.39; Cl, 11.83; N, 7.48.
Found: C, 56.18; H, 6.02; Cl, 11.57; N, 7.37.

Example 166

Trans-4-[1-[[4-[(benzo[b]thiophen-3-ylcarbonyl)amino]-2,5-dichlorophenyl]acetyl]-(4S)-([1,4]-oxazepan-4-yl)-(2S)-pyrrolidinylmethoxy]cyclohexanecarboxylic acid

[Formula 277]

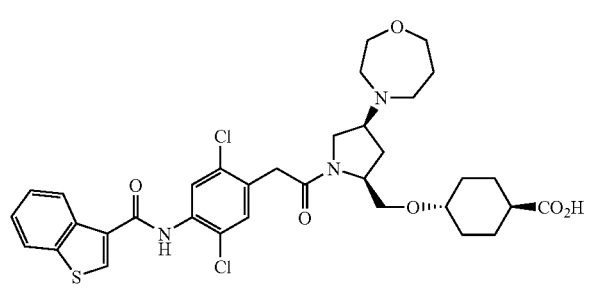

NMR (CDCl$_3$) δ: 1.18-1.52 (4H, m), 1.74-2.63 (10H, m), 2.79-2.90 (4H, m), 3.08-5.05 (12H, m), 7.42 (1H, s), 7.48 (2H, dt, J=26.0, 8.1 Hz), 7.91 (1H, d, J=7.8 Hz), 8.09 (1H, d, J=2.7 Hz), 8.30 (1H, d, J=7.4 Hz), 8.47 (1H, d, J=8.3 Hz), 8.72 (1H, d, J=15.0 Hz).
IR (ATR) cm$^{-1}$: 2933, 2857, 1639, 1504, 1079.
MS (ESI) m/z: 688 (M$^+$+1).
Anal. Calcd for C$_{34}$H$_{39}$Cl$_2$N$_3$O$_6$S·0.75H$_2$O: C, 58.16; H, 5.81; Cl, 10.10; N, 5.98; S, 4.57.
Found: C, 57.96; H, 5.51; Cl, 9.91; N, 5.73; S, 4.49.

Example 167

Trans-4-[1-[[4-[(benzo[b]furan-3-ylcarbonyl)amino]-2,5-dichlorophenyl]acetyl]-(4S)-([1,4]-oxazepan-4-yl)-(2S)-pyrrolidinylmethoxy]cyclohexanecarboxylic acid

[Formula 278]

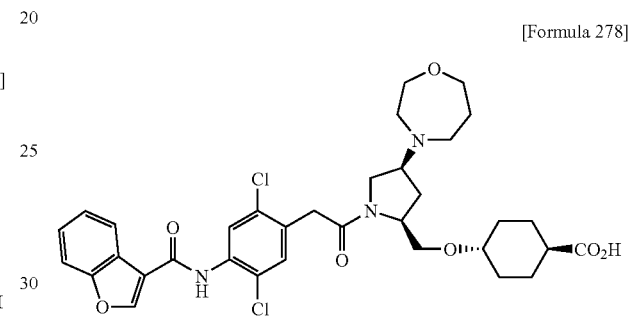

NMR (CDCl$_3$) δ: 1.18-4.43 (30H, m), 7.39-7.45 (3H, m), 7.57-7.62 (1H, m), 8.02-8.07 (1H, m), 8.21-8.33 (2H, m), 8.65-8.72 (1H, m).
IR (ATR) cm$^{-1}$: 2935, 2859, 1635, 1508, 1448.
MS (FAB) m/z: 672.2259 (calcd. for C$_{34}$H$_{40}$O$_7$N$_3$Cl$_2$: 672.2243).

Example 168

Trans-4-[1-[[4-[(benzo[b]furan-3-ylcarbonyl)amino]-5-chloro-2-fluorophenyl]acetyl]-(4S)-([1,4]-oxazepan-4-yl)-(2-S)-pyrrolidinylmethoxy]cyclohexanecarboxylic acid

[Formula 279]

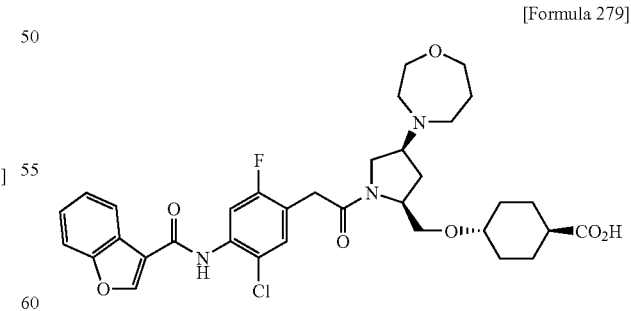

NMR (CDCl$_3$) δ: 1.12-4.55 (30H, m), 7.38-7.48 (3H, m), 7.56-7.64 (1H, m), 8.01-8.10 (1H, m), 8.23-8.35 (2H, m), 8.43 (1H, dd, J=11.6, 8.0 Hz).
IR (ATR) cm$^{-1}$: 2935, 2859, 1521, 1448, 1403.
MS (FAB) m/z: 656.2540 (calcd. for C$_{34}$H$_{40}$ClFN$_3$O$_7$: 656.2539).

Example 169

Trans-4-[1-[[4-[(benzo[b]thiophen-3-ylcarbonyl)amino]2,5-dichlorophenyl]acetyl]-(4S)-(4-cyclopropyl-[1,4]-diazepan-1-yl)-(2S)-pyrrolidinylmethoxy]cyclohexanecarboxylic acid Trans-4-[1-(tert-butoxycarbonyl)-(4S)-(4-cyclopropyl-[1,4]-diazepan-1-yl)-(2S)-pyrrolidinylmethoxy]cyclohexanecarboxylic acid ethyl ester NMR (CDCl$_3$) δ: 0.7-1.0 (4H, m), 1.2 (3H, t, J=7.1 Hz), 1.5 (9H, s), 1.9-2.4 (10H, m), 2.8-3.9 (19H, m), 4.1 (2H, q, J=7.1 Hz).
MS (ESI) m/z: 494 (M$^+$+1).

Trans-4-[1-[[4-[(benzo[b]thiophen-3-ylcarbonyl)amino]-2,5-dichlorophenyl]acetyl]-(4S)-(4-cyclopropyl-[1,4]-diazepan-1-yl)-(2S)-pyrrolidinylmethoxy]cyclohexanecarboxylic acid

[Formula 280]

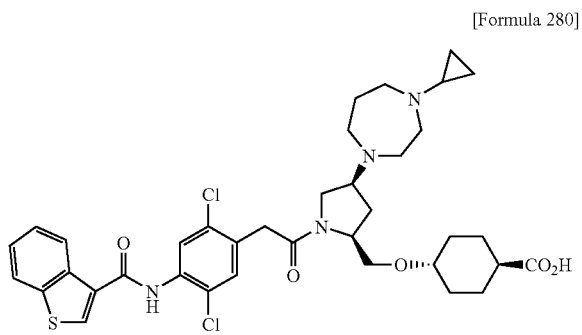

NMR (CDCl$_3$) δ: 0.4-0.6 (4H, m), 1.2-1.5 (4H, m), 1.7-4.4 (28H, m), 7.4-7.5 (3H, m), 7.9 (1H, dd, J=7.8, 2.7 Hz), 8.1 (1H, d, J=7.8 Hz), 8.3 (1H, d, J=16.2 Hz), 8.5 (1H, d, J=8.3 Hz), 8.7 (1H, d, J=2.0 Hz).
IR (ATR) cm$^{-1}$: 2931, 2857, 1639, 1504, 1079.
MS (FAB) m/z: 727.2504 (calcd for C$_{37}$H$_{45}$Cl$_2$N$_4$O$_5$S: 727.2488)
Anal. Calcd for C$_{37}$H$_{44}$Cl$_2$N$_4$O$_5$S.0.1hexane.2.0H$_2$O: C, 58.48; H, 6.42; Cl, 9.18; N, 7.26; S, 4.15.
Found: C, 58.18; H, 5.66; N, 7.30; S, 4.23.

Example 170

Trans-4-[1-[[4-[(benzo[b]furan-3-ylcarbonyl)amino]-5-chloro-2-fluorophenyl]acetyl]-(4S)-(4-methanesulfonyl[1,4]-diazepan-1-yl)-(2S)-pyrrolidinylmethoxy]cyclohexanecarboxylic acid Trans-4-[1-(tert-butoxycarbonyl)-(4S)-(4-benzyloxycarbonyl-[1,4]-diazepan-1-yl)-(2S)-pyrrolidinylmethoxy]cyclohexanecarboxylic acid ethyl ester Trans-4-[1-tert-butoxycarbonyl-4-oxo-(2S)-pyrrolidinylmethoxy]cyclohexanecarboxylic acid ethyl ester (1.20 g, 3.25 mmol) and 1-benzyloxycarbonylhomopiperazine (1.52 g, 6.50 mmol) were dissolved in methanol (20 mL), and while stirring the solution at 0° C., acetic acid (1 mL) and sodium-cyanoborohydride (0.61 g, 9.74 mmol) were added thereto. The mixture was stirred for three hours at room temperature. A saturated aqueous solution of sodium hydrogen carbonate (10 mL) was added to the reaction liquor, and the mixture was extracted with ethyl acetate. The extract was washed with saturated brine, and dried over anhydrous sodium sulfate, and then the solvent was concentrated under reduced pressure. The obtained residue was purified by flash column chromatography (Flash Chromatography System from Biotage AB, column size: 40S, elution solvent: n-hexane:ethyl acetate=1:1 to 1:9), to obtain the title compound (1.48 g, 78%) as an oily matter.
NMR (CDCl$_3$) δ: 1.23-1.30 (5H, m), 1.41-1.49 (11H, m, including 9H, s, at δ 1.46), 1.75-1.86 (3H, m), 1.97-2.26 (6H, m), 2.60-2.75 (4H, m), 2.92-2.99 (2H, m), 3.18-3.23 (1H, m), 3.44-4.15 (total 10H, series of m), 5.14 (2H, s), 7.30-7.38 (5H, m).
MS (ESI) m/z: 588 (M$^+$+1)

Trans-4-[1-(tert-butoxycarbonyl)-(4S)-([1,4]-diazepan-1-yl)-(2S)-pyrrolidinylmethoxy]cyclohexanecarboxylic acid ethyl ester Trans 4-[1-(tert-butoxycarbonyl)-(4S)-(4-benzyloxycarbonyl-[1,4]-diazepan-1-yl)-(2S)-pyrrolidinylmethoxy]cyclohexanecarboxylic acid ethyl ester (1.48 g, 2.52 mmol) was dissolved in methanol (30 mL), and 10% palladium hydroxide-carbon catalyst (0.30 g, 20 wt %) was added thereto. The mixture was stirred for 21 hours at room temperature. The reaction liquor was filtered by aspiration to separate the catalyst by filtration, and the filtrate was concentrated to obtain the title compound (1.13 g, 99%) was an oily matter.
MS (ESI) m/z: 454 (M$^+$+1)

Trans-4-[1-(tert-butoxycarbonyl)-(4S)-(4-methanesulfonyl-[1,4]-diazepan-1-yl)-(2S)-pyrrolidinylmethoxy]cyclohexa necarboxylic acid ethyl ester Trans-4-[1-(tert-butoxycarbonyl)-(4S)-([1,4]-diazepan-1-yl)-(2S)-pyrrolidinylmethoxy]cyclohexanecarboxylic acid ethyl ester (1.13 g, 2.49 mmol) and triethylamine (0.69 mL, 4.98 mmol) were dissolved in methylene chloride (20 mL), and while stirring the solution at 0° C., methanesulfonyl chloride (0.29 mL, 3.74 mmol) was added thereto. The mixture was stirred for 18 hours at room temperature. The reaction liquor was diluted with water, and extracted with chloroform. The extract was washed with saturated brine, and dried over anhydrous sodium sulfate, and then the solvent was concentrated under reduced pressure. The obtained residue was purified by flash column chromatography (Flash Chromatography System from Biotage AB, column size: 40M, elution solvent: chloroform to chloroform:methanol=20:1), to obtain the title compound (1.20 g, 91%) as an oily matter.
NMR (CDCl$_3$) δ: 1.23-1.29 (5H, m, including 3H, t, J=7.1 Hz, at δ 1.25), 1.41-1.47 (11H, m, including 9H, s, at δ 1.46), 1.76-2.06 (8H, m), 2.21-2.27 (2H, m), 2.71-2.88 (7H, m, including 3H, s, at δ 2.84), 2.93-3.21 (3H, m), 3.40-3.51 (4H, m), 3.70-3.88 (3H, m), 4.11 (2H, q, J=7.1 Hz).
MS (ESI) m/z: 532 (M$^+$+1).

Trans-4-[(4S)-(4-methanesulfonyl-[1,4]-diazepan-1-yl)-(2S)-pyrrolidinylmethoxy]cyclohexanecarboxylic acid ethyl ester NMR (CDCl$_3$) δ: 1.21-1.30 (5H, m, including 3H, t, J=7.1 Hz, at δ 1.24), 1.42-1.59 (3H, m), 1.85-1.91 (2H, m), 1.99-2.13 (5H, m), 2.21-2.28 (1H, m), 2.66-3.00 (9H, m, including 3H, s, at δ 2.84), 3.23-3.52 (9H, m), 3.61-3.64 (1H, m), 4.11 (2H, q, J=7.1 Hz).
MS (ESI) m/z: 432 (M$^+$+1)

Trans-4-[1-[[4-[(benzo[b]furan-3-ylcarbonyl)amino]-5-diazepan-1-yl)-(2S)-pyrrolidinylmethoxy]cyclohexanecarboxylic acid ethyl ester NMR (CDCl$_3$) δ: 1.10-1.28 (5H, m, including 3H, t, J=7.1 Hz, at δ 1.22), 1.35-1.48 (2H, m), 1.87-2.03 (7H, m), 2.17-2.39 (2H, m), 2.75-3.22 (10H, m, including 3H, s, at δ 2.84), 3.41-4.35 (total 12H, series of m, including 2H, q, J=7.1 Hz, at δ 4.08), 7.42-7.46 (3H, m), 7.58-7.62 (1H, m), 8.04-8.08 (1H, m), 8.27-8.32 (2H, m), 8.42-8.46 (1H, m).

MS (ESI) m/z: 761 (M$^+$+1).

Trans-4-[1-[[4-[(benzo[b]furan-3-ylcarbonyl)amino]-5-diazepan-1-yl)-(2S)-pyrrolidinylmethoxy]cyclohexanecarboxylic acid

[Formula 281]

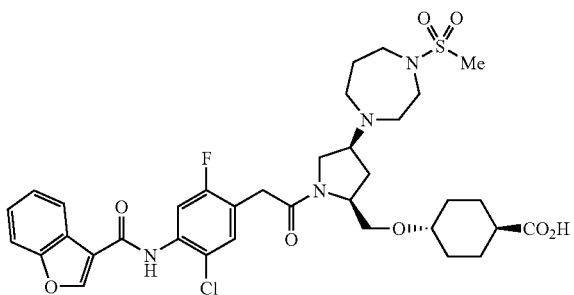

NMR (DMSO-d$_6$) δ: 1.15-1.37 (4H, m), 1.73-1.98 (7H, m), 2.12-2.33 (2H, m), 2.67-2.98 (8H, m, including 3H, s, at δ 2.90), 3.12-3.17 (2H, m), 3.30-3.35 (4H, m), 3.54-4.27 (total 6H, series of m), 7.38-7.47 (3H, m), 7.44-7.59 (1H, m), 7.71-7.72 (1H, m), 8.08-8.10 (1H, m), 8.84 (1H, s), 10.00 (1H, s), 12.05 (1H, broad s).

IR (ATR) cm$^{-1}$: 1523, 1450, 1323, 1146, 1122, 1103, 750.

MS (ESI) m/z: 733 (M$^+$+1).

Anal. Calcd for C$_{35}$H$_{42}$ClFN$_4$O$_8$S.½H$_2$O: C, 56.64; H, 5.84; N, 7.55; Cl, 4.78; F, 2.56; S, 4.32.

Found: C, 56.42; H, 5.57; N, 7.52; Cl, 4.76; F, 2.59; S, 4.43.

Example 171

[4-[(Benzo[b]furan-3-ylcarbonyl)amino]-3-chlorophenyl]acetic acid

[Formula 282]

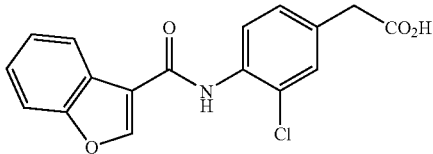

1-Benzofuran-3-yl trifluoromethanesulfonic acid

To a methylene chloride (80 mL) solution of 1-benzofuran-3 (2H)-one (5.45 g, 39.4 mmol), diisopropylethylamine (7.90 mL, 45.4 mmol) and trifluoromethanesulfonic anhydride (7.90 mL, 47.0 mmol) were added thereto at −10° C. The mixture was stirred for 14 hours at room temperature. Water (100 mL) was added, and the mixture was partitioned. Subsequently, the aqueous layer was extracted with methylene chloride (50 mL). The organic layer was combined and dried over anhydrous sodium sulfate, and then the solvent was concentrated under reduced pressure. The obtained residue was purified using silica gel flash column chromatography (Biotage AB: column No. 40M, hexane:diethyl ether=95:5), to obtain the title compound (10.4 g, 39.1 mmol, 99%) as a transparent oily matter.

NMR (CDCl$_3$) δ: 7.33-7.38 (1H, m), 7.38-7.44 (1H, m), 7.50-7.60 (1H, m), 7.62 (1H, d, J=7.3 Hz) 7.82 (1H, s).

1-Benzofuran-3-carboxylic acid methyl ester

To a DMF (8.0 mL) solution of 1-benzofuran-3-yl trifluoromethanesulfonic acid (1.00 g, 3.76 mmol), 1,1'-diphenylphosphinoferrocene (128 mg, 231 µmol) and palladium acetate (26.0 mg, 116 µmol), methanol (3.5 mL) and triethylamine (1.05 mL, 7.53 mmol) were added thereto at room temperature. Carbon monoxide gas was bubbled for 20 minutes, and then under a carbon monoxide atmosphere, the mixture was heated and stirred at 60° C. for 3 hours. Water (50 mL) was added, and then the mixture was extracted with ethyl acetate (2×30 mL). The organic layer was combined, washed with 1N-hydrochloric acid (30 mL), and then dried over anhydrous magnesium sulfate. The solvent was concentrated under reduced pressure. The obtained residue was purified using silica gel flash column chromatography (Biotage AB: column No. 40M, hexane:diethyl ether=95:5), to obtain the title compound (570 mg, 3.24 mmol, 86%) as a transparent oily matter.

NMR (CDCl$_3$) δ: 3.95 (3H, s), 7.33-7.40 (2H, m), 7.50-7.57 (1H, m), 8.04-8.11 (1H, m), 8.26 (1H, s).

MS (EI) m/z: 177 (M+H)$^+$.

1-Benzofuran-3-carboxylic acid

To a methanol (30 mL) solution of 1-benzofuran-3-carboxylic acid methyl ester (5.25 g, 29.8 mmol) tetrahydrofuran (60 mL), water (30 mL) and lithium hydroxide (2.50 g, 59.9 mmol) were added at room temperature. The mixture was stirred for 15 hours at room temperature. 1N-hydrochloric acid (60 mL, 60 mmol) was added to the reaction liquor, and then methanol was distilled off under reduced pressure. 1N-hydrochloric acid (15 mL, 15 mmol) was added to the obtained aqueous layer, and solids generated therefrom were collected by filtration. The solids were washed with water, and then dried for two days at 50° C. with a vacuum pump, to obtain the title compound (4.41 g, 27.2 mmol, 91%) as a solid.

$^1$H-NMR (DMSO-d$_6$) δ: 7.67-7.75 (2H, m), 7.98-8.04 (1H, m), 8.27-8.33 (1H, m), 8.98 (1H, s), 13.31 (1H, br s).

MS (EI) m/z: 163 (M+H)$^+$.

[4-[(Benzo[b]furan-3-ylcarbonyl)amino]-3-chlorophenyl]acetic acid ethyl ester Benzofuran-3-carboxylic acid (1.00 g, 6.17 mmol) was suspended in methylene chloride (20 mL), and oxalyl chloride (1.08 mL, 12.34 mmol) was added dropwise. To this reaction liquor, a catalytic amount of DMF (one drop) was added, and the reaction liquor was stirred for one hour at room temperature. The solvent was distilled off under reduced pressure, to obtain benzofuran-3-carboxylic acid chloride as a solid. The obtained acid chloride was suspended in 1,2-dichloroethane (20 mL), and (4-amino-3-chlorophenyl)acetic acid ethyl ester hydrochloride (1.54 g, 6.17 mmol) was added. The mixture was heated and stirred for 20 hours. The mixture was left to cool naturally to room temperature, and then the solvent was distilled off under reduced pressure. The obtained residue was purified by flash column chromatography (Flash Chromatography System from Biotage AB, column size: 40S, elution solvent: n-hexane:ethyl acetate=95:5 to 75:25), to obtain the title compound (2.08 g, 94%) as a solid.

NMR (CDCl$_3$) δ: 1.27 (3H, t, J=7.1 Hz), 3.59 (2H, s), 4.17 (2H, q, J=7.1 Hz), 7.25-7.28 (1H, m), 7.40-7.45 (3H, m), 7.58-7.61 (1H, m), 8.05-8.09 (1H, m), 8.24 (1H, broad s), 8.29 (1H, s), 8.55 (1H, d, J=8.3 Hz).

MS (ESI) m/z: 358 (M$^+$+1).

[4-[(Benzo[b]furan-3-ylcarbonyl)amino]-3-chlorophenyl]acetic acid

[4-[(Benzo[b]furan-3-ylcarbonyl)amino]-3-chlorophenyl]acetic acid ethyl ester (2.08 g, 5.81 mmol) was dissolved in tetrahydrofuran (15 mL) and methanol (5 mL), and a 1N-aqueous solution of sodium hydroxide (11.60 mL, 11.60 mmol) was added thereto. The mixture was stirred for three hours at room temperature. The reaction liquor was poured onto ice-1N-hydrochloric acid, and precipitated solids were collected by filtration, and dried under reduced pressure, to obtain the title compound (1.70 g, 89%) as a solid.

NMR (DMSO-d$_6$) δ: 3.65 (2H, s), 7.28 (1H, dd, J=8.3, 2.0 Hz), 7.37-7.49 (3H, m), 7.58 (1H, d, J=8.3 Hz), 7.70-7.72 (1H, m), 8.08-8.10 (1H, m), 8.81 (1H, s), 9.95 (1H, s), 12.47 (1H, broad s).

MS (ESI) m/z: 330 (M$^+$+1).

The compounds of Examples 172 and 173 shown below were produced by the same method as in Example 171.

Example 172

[4-[(Benzo[b]furan-3-ylcarbonyl)amino]-5-chloro-2-fluorophenyl]acetic acid

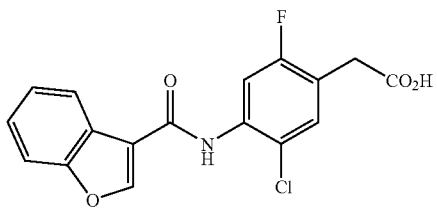

[Formula 283]

[4-[(Benzo[b]furan-3-ylcarbonyl)amino]-5-chloro-2-fluorophenyl]acetic acid ethyl ester NMR (CDCl$_3$) δ: 1.21 (3H, t, J=7.1 Hz), 3.62 (2H, s), 4.19 (2H, d, J=7.1 Hz), 7.37 (1H, d, J=7.4 Hz), 7.41-7.46 (2H, m), 7.58-7.64 (1H, m), 8.03-8.08 (1H, m), 8.31-8.26 (2H, m), 8.48 (1H, d, J=11.8 Hz).

MS (LC) m/z: 376 (M$^+$+1), 398 (M$^+$+Na).

[4-[(Benzo[b]furan-3-ylcarbonyl)amino]-5-chloro-2-fluorophenyl]acetic acid

NMR (DMSO-d$_6$) δ: 3.67 (2H, s), 7.36-7.45 (2H, m), 7.57-7.62 (2H, m), 7.69-7.72 (1H, m), 8.06-8.10 (1H, m), 8.83 (1H, s), 10.00 (1H, s), 12.60 (1H, br s).

MS (ESI) m/z: 348 (M$^+$+1).

Example 173

[4-[(Benzo[b]furan-3-ylcarbonyl)amino]-2,5-dichlorophenyl]acetic acid

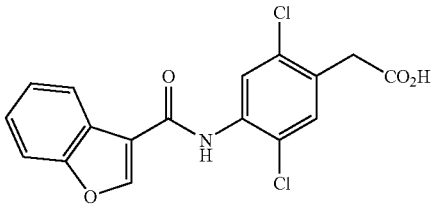

[Formula 284]

[4-[(Benzo[b]furan-3-ylcarbonyl)amino]-2,5-dichlorophenyl]acetic acid ethyl ester NMR (CDCl$_3$) δ: 1.28 (3H, t, J=7.4 Hz), 3.73 (2H, s), 4.20 (2H, q, J=(1H, m), 8.22 (1H, br s), 8.29 (1H, br s), 8.75 (1H, s).

MS (ESI) m/z: 392 (M$^+$+1), 394 (M$^+$+3), 396 (M$^+$+5).

[4-[(Benzo[b]furan-3-ylcarbonyl)amino]-3,5-dichlorophenyl]acetic acid

NMR (DMSO-d$_6$) δ: 3.76 (2H, s), 7.44 (2H, m), 7.68 (1H, s), 7.72 (1H, s), 7.81 (1H, s), 8.09 (1H, m), 8.83 (1H, m), 10.65 (1H, s), 12.61 (1H, br).

Example 174

[4-[(Benzo[b]thiophen-3-ylcarbonyl)amino]-5-chloro-2-fluorophenyl]acetic acid

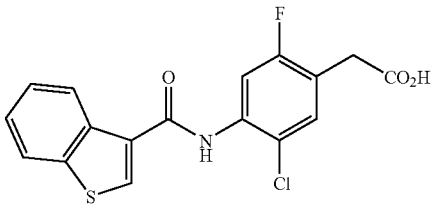

[Formula 285]

1-Benzothiophene-3-carboxylic acid methyl ester

To a methanol (500 mL) solution of 1-benzothiophene-3-carbaldehyde (51.3 g, 300 mmol), sodium cyanide (22.0 g, 449 mmol) was added thereto at room temperature. Then, manganese dioxide (89.0 g, 901 mmol) was added at 0° C. The reaction mixture was stirred for 20 hours at room temperature, and then the reaction liquor was filtered. The filtrate was concentrated under reduced pressure. To the obtained residue, diethyl ether (200 mL), a saturated aqueous solution of sodium hydrogen carbonate (150 mL) and water (150 mL) were added, and the mixture was partitioned. The aqueous layer was extracted with diethyl ether (200 mL), and the organic layer was combined, dried over anhydrous sodium sulfate, and concentrated under reduced pressure. The obtained residue was purified by column chromatography using silica gel (silica gel 300 g, hexane:diethyl ether=100:0 to 85:15), to obtain the title compound (52.1 g, 90%) as a transparent oily matter.

NMR (CDCl$_3$) δ: 3.96 (3H, s), 7.39-7.45 (1H, m), 7.47-7.53 (1H, m), 7.88 (1H, d, J=8.5 Hz), 8.38 (1H, s), 8.60 (1H, d, J=8.3 Hz).
MS (EI) m/z: 193 (M+H)$^+$.

1-Benzothiophene-3-carboxylic acid

To a methanol (100 mL) solution of 1-benzothiophene-3-carboxylic acid methyl ester (20.6 g, 107 mmol), tetrahydrofuran (200 mL), water (100 mL) and lithium hydroxide (9.00 g, 214 mmol) were added at room temperature, and the mixture was stirred for 15 hours at room temperature. 1N-hydrochloric acid (214 mL, 214 mmol) was added to the reaction liquor, and then methanol was distilled off under reduced pressure. To the obtained aqueous layer, 1N-hydrochloric acid (50 mL, 50 mmol) was added, and the solids generated therefrom were collected by filtration, washed with water, and then dried for two days at 50° C. using a vacuum pump, to obtain the title compound (19.1 g, 100%) as a solid.
$^1$H-NMR (DMSO-d$_6$) δ: 7.73-7.83 (2H, m), 8.38-8.42 (1H, m), 8.79-8.83 (1H, m), 8.95 (1H, s), 13.25 (1H, br s).
MS (EI) m/z: 179 (M+H)$^+$.

[4-[(Benzo[b]thiophen-3-ylcarbonyl)amino]-5-chloro-2-fluorophenyl]acetic acid ethyl ester NMR (CDCl$_3$) δ: 1.28 (3H, t, J=7.1 Hz), 3.64 (2H, s), 4.20 (2H, q, J=7.2 Hz), 7.36 (1H, d, J=7.3 Hz), 7.44-7.55 (2H, m), 7.92 (1H, d, J=8.3 Hz), 8.09 (1H, s), 8.34 (1H, br s), 8.47-8.50 (2H, m).
MS (ESI) m/z: 392 [(M+H)$^+$, $^{35}$Cl], 394 [(M+H)$^+$, $^{37}$Cl].

[4-[(Benzo[b]thiophen-3-ylcarbonyl)amino]-5-chloro-2-fluorophenyl]acetic acid

NMR (CDCl$_3$) δ: 1.28 (3H, t, J=7.1 Hz), 3.64 (2H, s), 4.20 (2H, q, J=7.2 Hz), 7.36 (1H, d, J=7.3 Hz), 7.44-7.55 (2H, m), 7.92 (1H, d, J=8.3 Hz), 8.09 (1H, s), 8.34 (1H, br s), 8.47-8.50 (2H, m).
MS (ESI) m/z: 392 [(M+H)$^+$, $^{35}$Cl], 394 [(M+H)$^+$, $^{37}$Cl].
The compounds of Examples 175 to 177 shown below were produced by the same method as in Example 174.

Example 175

[4-[(Benzo[b]thiophen-3-ylcarbonyl)amino]-2,5-dichlorophenyl]acetic acid

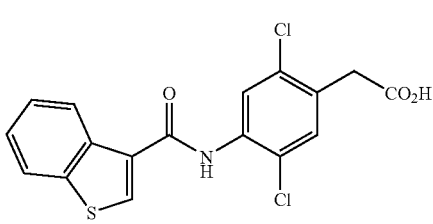

[Formula 286]

[4-[(Benzo[b]thiophen-3-ylcarbonyl)amino]-3,5-dichlorophenyl]acetic acid ethyl ester NMR (CDCl$_3$) δ: 1.28 (3H, t, J=7.2 Hz), 3.73 (2H, s), 4.20 (2H, q, J=7.1 Hz), 7.39 (1H, s), 7.44-7.55 (2H, m), 7.91-7.94 (1H, m), 8.09 (1H, s), 8.29 (1H, br s), 8.47-8.50 (1H, m), 8.75 (1H, s).

MS (ESI) m/z: 408 [(M+H)$^+$, $^{35}$Cl+$^{35}$Cl], 410 [(M+H)$^+$, $^{37}$Cl+$^{35}$Cl, $^{35}$Cl+$^{37}$Cl], 412 [(M+H)$^+$, $^{37}$Cl+$^{37}$Cl].

[4-[(Benzo[b]thiophen-3-ylcarbonyl)amino]-3,5-dichlorophenyl]acetic acid

NMR (DMSO-d$_6$) δ: 3.78 (2H, s), 7.48 (2H, m), 7.68 (1H, s), 7.80 (1H, s), 8.10 (1H, s), 8.45 (1H, m), 8.65 (1H, s), 10.17 (1H, s), 12.61 (1H, br).

Example 176

[4-[(Benzo[b]thiophen-3-ylcarbonyl)amino]-3-chlorophenyl]acetic acid

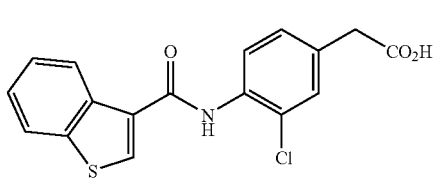

[Formula 287]

[4-[(Benzo[b]thiophen-3-ylcarbonyl)amino]-3-chlorophenyl]acetic acid ethyl ester NMR (CDCl$_3$) δ: 1.27 (3H, t, J=7.1 Hz), 3.59 (2H, s), 4.17 (2H, q, J=7.1 Hz), 7.25-7.28 (1H, m), 7.39 (1H, d, J=2.0 Hz), 7.45 (1H, ddd, J=8.4, 7.2, 1.2 Hz), 7.51 (1H, ddd, J=8.4, 7.2, 1.2 Hz), 7.91 (1H, d, J=8.1 Hz), 8.08 (1H, s), 8.29 (1H, s), 8.48 (1H, d, J=7.8 Hz), 8.53 (1H, d, J=7.8 Hz).
MS (ESI) m/z: 374 [(M$^+$+1), $^{35}$Cl], 376 [(M$^+$+3), $^{37}$Cl].

[4-[(Benzo[b]thiophen-3-ylcarbonyl)amino]-3-chlorophenyl]acetic acid

NMR (DMSO-d$_6$) δ: 2.81 (2H, s), 6.45 (1H, d, J=8.1 Hz), 6.58-6.67 (3H, m), 6.73 (1H, d, J=8.1 Hz), 7.24 (1H, d, J=7.6 Hz), 7.61 (1H, d, J=7.6 Hz), 7.79 (1H, s), 9.22 (1H, s), 11.63 (1H, br s).
MS (ESI) m/z: 345 [(M$^+$+1), $^{35}$Cl], 347 [(M$^+$+3), $^{37}$Cl].

Example 177

4-[(Benzo[b]thiophen-3-ylcarbonyl)amino]-3-methoxyphenylacetic acid

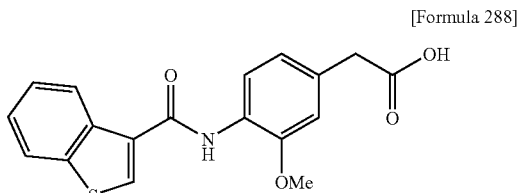

[Formula 288]

4-[(Benzo[b]thiophen-3-ylcarbonyl)amino]-3-methoxyphenylacetic acid tert-butyl ester NMR (CDCl$_3$) δ: 1.45 (9H, s), 3.52 (2H, s), 3.92 (3H, s), 6.89 (1H, d, J=1.7 Hz), 6.93 (1H, dd, J=8.3, 1.7 Hz), 7.40-7.52 (2H, m), 7.88-7.92 (1H, m), 8.02 (1H, s), 8.39 (1H, br s), 8.46 (2H, d, J=8.1 Hz).
MS (ESI) m/z, 398 (M$^+$+1), 420 (M$^+$+23).

4-[(Benzo[b]thiophen-3-ylcarbonyl)amino]-3-methoxyphenylacetic acid

4-[(Benzo[b]thiophen-3-ylcarbonyl)amino]phenylacetic acid tert-butyl ester (2.12 g, 5.33 mmol) and a 4N—HCl-dioxane solution (20 mL) were mixed, and the mixture was stirred for hours at room temperature, and for 8 hours at 70° C. After cooling the mixture naturally, the mixture was diluted with chloroform (200 mL), washed with water (100 mL) and saturate brine (100 mL), and dried over anhydrous sodium sulfate, and then the solvent was distilled off under reduced pressure. The obtained residue was purified with a column (40S) of Biotage AB (5% methanol-chloroform), to obtain the title compound (3.47 g, 94%) as a crystalline powder.

NMR (CDCl$_3$) δ: 3.65 (2H, s), 3.92 (3H, s), 6.88 (1H, d, J=2.0 Hz), 6.95 (1H, dd, J=8.3, 1.7 Hz), 7.40-7.52 (2H, m), 7.88-7.92 (1H, m), 8.02 (1H, s), 8.50-8.39 (3H, m).

MS (ESI) m/z, 342 (M$^+$+1).

Example 178

[3-Methyl-4-[(1-methyl-1H-indol-3-ylcarbonyl)amino]phenyl]acetic acid

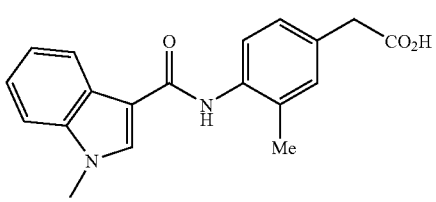

[Formula 289]

[3-Methyl-4-[(1-methyl-1H-indol-3-ylcarbonyl)amino]phenyl]acetic acid ethyl ester NMR (CDCl$_3$) δ: 1.45 (9H, s), 2.34 and 2.37 (total 3H, each s, amide isomers), 3.68 (3H, s), 3.87 (2H, s), 7.03-7.54 (6H, m), 8.06-7.97 (1H, m), 7.77 (1H, s), 8.24 (1H, d, J=7.3 Hz).

[3-Methyl-4-[(1-methyl-1H-indol-3-ylcarbonyl)amino]phenyl]acetic acid

NMR (DMSO-d$_6$) δ: 2.25 (3H, s), 3.53 (2H, s), 3.85 (3H, s), 3.88 (0 H, s), 7.05-7.36 (4H, m), 7.53 (1H, dd, J=7.6, 4.6 Hz), 7.99-8.22 (3H, m), 8.31 (1H, s), 9.24 (1H, s).

MS (ESI) m/z: 323 (M$^+$+1).

The compounds of Examples 179 to 181 shown below were produced by the same method as in Example 178.

Example 179

[3-Methoxy-4-[(1-methyl-1H-indol-3-ylcarbonyl)amino]phenyl]acetic acid

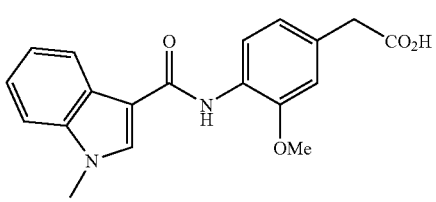

[Formula 290]

[3-Methoxy-4-[(1-methyl-1H-indol-3-ylcarbonyl)amino]phenyl]acetic acid ethyl ester NMR (CDCl$_3$) δ: 1.45 (9H, s), 3.51 (3H, s), 3.87 (3H, s), 3.95 (2H, d, J=13.2 Hz), 6.87-6.95 (2H, m), 7.30-7.44 (3H, m), 7.79 (1H, s), 8.07-8.15 (1H, m), 8.42 (1H, s), 8.50 (1H, d, J=8.5 Hz).

[3-Methoxy-4-[(1-methyl-1H-indol-3-ylcarbonyl)amino]phenyl]acetic acid

NMR (DMSO-d$_6$) δ: 3.05 (3H, s), 3.55 (2H, s), 3.86 (3H, s), 6.78-7.03 (1H, m), 7.17-7.30 (2H, m), 7.53 (1H, d, J=6.8 Hz), 7.92 (1H, d, J=8.3 Hz), 8.06-8.37 (3H, m), 8.74 (1H, s), 9.70 (1H, s).

MS (ESI) m/z: 339 (M$^+$+1)

Example 180

[5-Chloro-2-fluoro-4-[(1H-indol-3-ylcarbonyl)amino]phenyl]acetic acid

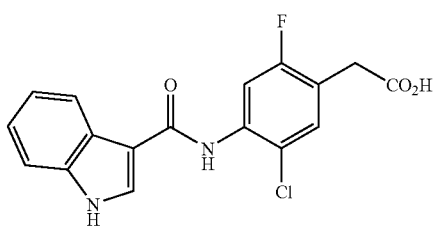

[Formula 291]

[5-Chloro-2-fluoro-4-[(1H-indol-3-ylcarbonyl)amino]phenyl]acetic acid ethyl ester NMR (CDCl$_3$) δ: 1.29 (3H, t, J=7.1 Hz), 3.63 (2H, s), 4.21 (2H, q, J=7.1 Hz), 7.32-7.34 (3H, m), 7.46-7.49 (1H, m), 7.91 (1H, d, J=2.9 Hz), 8.13-8.15 (1H, m), 8.33 (1H, broad s), 8.51 (1H, d)=11.9 Hz), 8.82 (1H, s), 8.55 (1H, broad s).

[5-Chloro-2-fluoro-4-[(1H-indol-3-ylcarbonyl)amino]phenyl]acetic acid

NMR (DMSO-d$_6$) δ: 3.66 (2H, s), 7.17-7.21 (2H, m), 7.41-7.57 (2H, series of m), 7.72 (1H, d, J=11.3 Hz), 8.15 (1H, d, J=7.3 Hz), 8.32 (1H, d, J=2 Hz), 9.35 (1H, s), 11.83 (1H, s), 12.52 (1H, broad s).

MS (EI) m/z: 346 (M$^+$).

IR (ATR) cm$^{-1}$: 3414, 3259, 1695, 1639, 1583, 1516.

Anal. Calcd for C$_{17}$H$_{12}$ClFN$_2$O$_3$·0.25H$_2$O: C, 58.13; H, 3.59; N, 7.98.

Found: C, 58.23; H, 3.59; N, 7.90.

Example 181

[2,5-Dichloro-4-[(1H-indol-3-ylcarbonyl)amino]phenyl]acetic acid

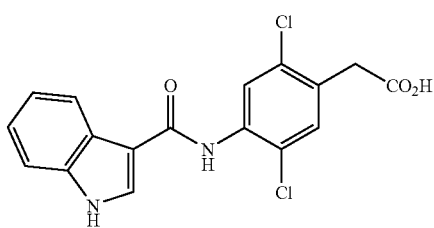

[Formula 292]

1H-indole-3-carboxylic acid (3.00 g, 18.6 mmol) was suspended in 1,2-dichloroethane (15 mL), and oxalyl chloride (2.42 mL, 25.38 mmol) was added dropwise. To this reaction liquor, a catalytic amount of DMF (one drop) was added, and the reaction liquor was stirred for one hour at room temperature. The solvent of the reaction mixture was distilled off under reduced pressure, to obtain 1H-indole-3-carboxylic acid chloride as a solid. The obtained acid chloride was suspended in 1,2-dichloroethane (20 mL), and (4-amino-2,5-dichlorophenyl)acetic acid ethyl ester hydrochloride (4.82 g, 16.92 mmol) was added thereto. The mixture was heated to ref lux for 18 hours with stirring. The reaction mixture was left to cool naturally to room temperature, and then the solvent was distilled off under reduced pressure. The obtained solids were dissolved in chloroform (100 mL), washed with a saturated aqueous solution of sodium hydrogen carbonate and water, and dried over anhydrous sodium sulfate, and then the solvent was distilled off under reduced pressure. The obtained solids were collected by filtration using hexane, to obtain [2,5-d]chloro-4-[(1H-indol-3-ylcarbonyl)amino]phenyl]acetic acid ethyl ester (5.95 g, 90%) as a solid. This compound was used in the subsequent reaction without performing further purification.

This [2,5-dichloro-4-[(1H-indol-3-ylcarbonyl)amino]phenyl]acetic acid ethyl ester (5.7 g, 14.57 mmol) was added to THF (50 mL) and ethanol (30 mL), and a 0.25N-aqueous solution of sodium hydroxide (120 mL) was added thereto. The mixture was stirred for 15 hours at room temperature, and then for one hour at 60° C. The reaction mixture was left to cool naturally to room temperature, and then 1N—HCl (32 mL) was added thereto while stirring the reaction mixture under ice cooling. Precipitated crystals were collected by filtration under reduced pressure, washed with water, and then dried, to obtain the title compound (4.25 g, 80%) as a solid.

NMR (DMSO-$d_6$) δ: 3.72 (2H, s), 7.16-7.21 (2H, m), 7.49 (1H, m), 7.62 (1H, s), 7.89 (1H, s), 8.14 (1H, d, J=7.1 Hz), 8.32 (1H, d, J=2.9 Hz), 9.40 (1H, s), 11.84 (1H, s).

MS (EI) m/z: 362 (M$^+$).

IR (ATR) cm$^{-1}$: 3408, 3267, 1701, 1655, 1612, 1568, 1510.

Anal. Calcd for $C_{17}H_{12}Cl_2N_2O_3$: C, 56.22; H, 3.33; N, 7.71.

Found: C, 55.81; H, 3.19; N, 7.44.

Evaluation Example 1

In Vitro Evaluation of Substance Under Test

CHO cells which forcibly expressed h$α_4$ and $β_1$ integrins through transfection thereof, were inoculated into a Costar 3599 plate (3×10$^4$ cells/100 μl/well), and cultured for two days. The cells in the wells were washed two times with buffer A*, and then Eu$^{3+}$-hVCAM-1 D1D7-IgG diluted with assay buffer** to 2 nM was added in an amount of 50 μl/well. The substance under test diluted with 26 DMSO-assay buffer (in the co-presence or absence of 6% human serum albumin) was added in an amount of 50 μl/well (adding separately diluted solution to the wells for performing Scatchard analysis), the contents were stirred for 5 minutes with a plate mixer, and then the plate was left to stand still for one hour at room temperature. The binding inhibitory activity in the presence of human serum albumin (HSA) was examined by diluting the specimen with 26 DMSO-assay buffer containing 6% HSA (SIGMA Corp., c/n A-1653), and adding the resultant (HSA final concentration 3%). After 30 to 60 minutes of the addition of specimen, the plate contents were washed 4 times with buffer A at 4° C., an enhancing reagent (DELFIA SA) was added in an amount of 100 μl/well, and the plate was shaken for 5 minutes using a plate mixer. Subsequently, the fluorescence intensity was measured with a time-resolved fluorometer (DELFIA Wallac). The IC$_{50}$ of the substance under test (the concentration for 50% inhibition of the binding between CHO cells and Eu$^{3+}$-hVCAM-1 D1D7-IgG) was determined from the binding rate obtained from the calculating expression of [(F$_T$–FNS)–(F$_I$–F$_{NS}$)]/[(F$_T$–F$_{NS}$)]×100. Here, F$_T$ represents the fluorescence intensity of a well not containing the substance under test; F$_{NS}$ represents the fluorescence intensity of a well not containing the substance under test and hVCAM-1 D1D7-IgG; and F$_I$ represents the fluorescence intensity of a well containing the substance under test. The Kd value which represents the strength of binding, and B$_{max}$ (maximum binding amount) were estimated to be in the range of 0.06 to 20 nM according to the Scatchard analysis method. The evaluation results of the Ki value of the substance under test, and of the IC$_{50}$ value in the presence of 3% HSA are presented in Tables 2 to 7.

$$Ki = \frac{IC_{50}}{1 + \frac{[L]}{Kd}} \quad \text{[Expression 1]}$$

The Ki value was calculated according to the above-described expression. ([L] is the ligand concentration)

[* buffer A: 25 mM HEPES (pH 7.5), 150 mM NaCl, 1 mM Ca$^{2+}$, 1 mM Mg$^{2+}$, 4 mM Mn2+;

** assay buffer: 25 mM HEPES (pH=7.5), 150 mM NaCl, 1 mM Ca$^{2+}$, 1 mM Mg$^{2+}$, 4 mM Mn$^{2+}$, 0.1% BSA, 20 μM DTPA, with/without 6% ALBUMIN, HUMAN SERUM (C/N A-1653, SIGMA)]

TABLE 2

Results of in vitro evaluation of substance under test

| Example No. | MW | Ki (nM) | IC$_{50}$ (+3% HSA, nM) |
|---|---|---|---|
| 1 | 655.2 | 1.9 | 15 |
| 2 | 671.6 | 2.2 | 17 |
| 3 | 658.2 | 0.97 | 11 |
| 4 | 674.6 | 0.8 | 19 |
| 5 | 642.1 | 1.4 | 12 |
| 6 | 658.6 | 5.9 | 76 |
| 9 | 628.2 | 1.4 | 8.2 |
| 10 | 655.6 | 9.5 | 37 |
| 11 | 626.1 | 3.5 | 21 |
| 12 | 686.2 | 1.0 | 8.6 |
| 13 | 644.1 | 7.7 | 64 |
| 16 | 669.2 | 5.3 | 41 |
| 17 | 686.2 | 1.8 | 48 |
| 20 | 685.6 | 3.9 | 40 |
| 23 | 687.7 | 2.5 | 14 |
| 27 | 713.3 | 3.8 | 43 |
| 28 | 711.3 | 2.6 | 12 |
| 29 | 682.2 | 4.2 | 12 |
| 30 | 711.2 | 4.6 | 12 |
| 31 | 658.6 | 1.2 | 5.8 |

TABLE 3

| Example No. | MW | Ki (nM) | IC$_{50}$ (+3% HSA, nM) |
|---|---|---|---|
| 32 | 672.2 | 0.74 | 3.5 |
| 33 | 685.6 | 5.6 | 20 |
| 34 | 686.2 | 2.0 | 9.9 |
| 35 | 685.6 | 5.9 | 20 |
| 36 | 699.7 | 5.9 | 24 |
| 37 | 657.1 | 2.1 | 9.2 |
| 38 | 678.2 | 1.7 | 24 |
| 39 | 668.2 | 0.64 | 4.9 |
| 40 | 656.2 | 2.0 | 9.1 |
| 42 | 713.3 | 0.32 | 1.1 |
| 43 | 716.7 | 2.0 | 38 |

TABLE 3-continued

| Example No. | MW | Ki (nM) | IC$_{50}$ (+3% HSA, nM) |
|---|---|---|---|
| 44 | 686.2 | 6.8 | 24 |
| 45 | 717.7 | 14.0 | 15 |
| 46 | 729.7 | 7.3 | 15 |
| 47 | 654.2 | 18.0 | 52 |
| 49 | 730.3 | 4.0 | 62 |
| 51 | 715.7 | 5.8 | 18 |
| 52 | 702.2 | 1.2 | 8.4 |
| 53 | 686.2 | 2.0 | 11 |
| 54 | 702.6 | 3.4 | 25 |
| 55 | 699.2 | 2.6 | 9.2 |
| 56 | 715.7 | 2.4 | 9.2 |
| 57 | 702.2 | 1.4 | 6.2 |
| 58 | 718.7 | 1.5 | 9.3 |
| 59 | 686.2 | 3.0 | 8.1 |
| 60 | 702.6 | 7.9 | 18 |
| 61 | 668.2 | 1.6 | 5.5 |
| 62 | 682.2 | 3.2 | 10 |

TABLE 4

| Example No. | MW | Ki (nM) | IC$_{50}$ (+3% HSA, nM) |
|---|---|---|---|
| 63 | 743.7 | 4.7 | 23 |
| 64 | 715.7 | 5.0 | 33 |
| 65 | 702.6 | 2.9 | 35 |
| 66 | 699.2 | 0.42 | 14 |
| 67 | 639.1 | 1.2 | 12 |
| 68 | 655.6 | 2.1 | 30 |
| 69 | 641.1 | 6.1 | 66 |
| 70 | 676.2 | 18.0 | 62 |
| 71 | 654.2 | 7.5 | 28 |
| 72 | 681.2 | 2.8 | 15 |
| 73 | 686.6 | 1.9 | 22 |
| 74 | 670.1 | 1.5 | 8.8 |
| 75 | 730.7 | 0.52 | 12 |
| 77 | 716.2 | 2.0 | 4.1 |
| 78 | 655.2 | 1.5 | 5.2 |
| 79 | 686.2 | 0.74 | 4.1 |
| 80 | 699.7 | 6.5 | 20 |
| 81 | 683.2 | 3.0 | 12 |
| 82 | 702.7 | 2.4 | 18 |
| 83 | 686.6 | 5.2 | 42 |
| 84 | 670.2 | 2.4 | 23 |
| 85 | 665.2 | 2.0 | 9.2 |
| 86 | 663.2 | 4.5 | 27 |
| 87 | 652.2 | 0.95 | 8.1 |
| 88 | 666.2 | 1.5 | 9 |
| 89 | 685.6 | 0.96 | 2.3 |
| 90 | 669.2 | 1.2 | 2.4 |
| 91 | 699.7 | 2.4 | 81 |

TABLE 5

| Example No. | MW | Ki (nM) | IC$_{50}$ (+3% HSA, nM) |
|---|---|---|---|
| 92 | 668.2 | 1.2 | 10 |
| 93 | 699.7 | 3.6 | 22 |
| 94 | 656.2 | 0.93 | 2.9 |
| 95 | 672.7 | 1.3 | 5.3 |
| 96 | 669.6 | 3.9 | 7.4 |
| 97 | 697.2 | 1.6 | 4.9 |
| 98 | 670.2 | 0.89 | 3 |
| 99 | 700.3 | 0.34 | 3.8 |
| 100 | 674.2 | 0.91 | 3.9 |
| 101 | 689.2 | 4.0 | 17 |
| 102 | 748.3 | 1.2 | 33 |
| 103 | 686.2 | 0.32 | 2.2 |
| 104 | 697.7 | 4.9 | 13 |
| 105 | 700.6 | 2.0 | 15 |
| 106 | 686.2 | 1.2 | 9.2 |
| 107 | 727.7 | 1.8 | 7.6 |
| 108 | 747.7 | 3.1 | 8.2 |
| 109 | 696.3 | 3.6 | 5.2 |

TABLE 5-continued

| Example No. | MW | Ki (nM) | IC$_{50}$ (+3% HSA, nM) |
|---|---|---|---|
| 110 | 741.3 | 0.25 | 30 |
| 111 | 671.2 | 0.29 | 1.2 |
| 112 | 684.7 | 4.2 | 9.5 |
| 113 | 712.7 | 2.8 | 9.5 |
| 114 | 713.7 | 3.0 | 8.9 |
| 115 | 724.7 | 4.2 | 13 |
| 116 | 747.3 | 0.6 | 21 |
| 117 | 716.7 | 4.5 | 12 |
| 118 | 700.2 | 3.9 | 13 |
| 119 | 744.7 | 4.5 | 20 |
| 120 | 734.7 | 3.8 | 16 |
| 121 | 718.2 | 3.2 | 11 |

TABLE 6

| Example No. | MW | Ki (nM) | IC$_{50}$ (+3% HSA, nM) |
|---|---|---|---|
| 122 | 752.7 | 8.8 | 36 |
| 123 | 739.2 | 1.8 | 10 |
| 124 | 736.2 | 4.9 | 17 |
| 125 | 739.6 | 3.4 | 26 |
| 126 | 723.2 | 2.4 | 13 |
| 127 | 716.2 | 9.6 | 34 |
| 128 | 719.2 | 3.9 | 13 |
| 129 | 738.6 | 0.93 | 1.9 |
| 130 | 718.2 | 2.7 | 7.5 |
| 131 | 722.2 | 1.1 | 1.8 |
| 132 | 705.2 | 1.7 | 4 |
| 133 | 716.8 | 1.3 | 3.3 |
| 134 | 721.2 | 1.2 | 6.8 |
| 135 | 713.8 | 1.7 | 4.4 |
| 137 | 728.7 | 2.9 | 8.7 |
| 138 | 713.7 | 0.91 | 7.7 |
| 139 | 710.7 | 2.5 | 13 |
| 140 | 697.6 | 1.8 | 7.6 |
| 141 | 708.3 | 6.3 | 23 |
| 142 | 722.3 | 4.7 | 11 |
| 143 | 739.7 | 3.5 | 14 |
| 145 | 731.3 | 3.9 | 11 |
| 146 | 683.2 | 2.6 | 7.6 |
| 147 | 728.3 | 3.2 | 12 |
| 148 | 699.2 | 0.53 | 2.8 |
| 149 | 754.7 | 1.7 | 24 |
| 150 | 719.2 | 1.6 | 6.8 |

TABLE 7

| Example No. | MW | Ki (nM) | IC$_{50}$ (+3% HSA, nM) |
|---|---|---|---|
| 151 | 777.8 | 4.2 | 26 |
| 152 | 698.6 | 3.9 | 11 |
| 153 | 701.7 | 1.5 | 9.3 |
| 154 | 699.2 | 0.92 | 9.1 |
| 155 | 685.6 | 2.1 | 10 |
| 158 | 671.2 | 4.0 | 16 |
| 159 | 658.2 | 4.4 | 13 |
| 160 | 703.2 | 2.4 | 9.9 |
| 161 | 690.2 | 1.8 | 8.3 |
| 162 | 683.6 | 6.5 | 49 |
| 163 | 667.2 | 6.4 | 36 |
| 164 | 722.7 | 13.0 | 71 |
| 165 | 685.6 | 8.2 | 12 |
| 166 | 688.7 | 1.7 | 8.2 |
| 167 | 672.6 | 4.4 | 19 |
| 168 | 656.1 | 2.0 | 9.4 |
| 169 | 727.7 | 1.1 | 5.9 |
| 170 | 733.2 | 2.6 | 11 |
| Compound A* | 616.5 | 4.3 | 93 |

*Representative compound of International Patent Application Publication Pamphlet No. WO 02/053534

The in vitro evaluation presented in Table 2 to Table 7 will be discussed.

As a comparative control, compound A (representative compound of WO 02/053534) was evaluated simultaneously with the Example compounds of the present invention. As a result, the Example compounds of the present invention indicated high inhibitory activities, with their Ki values being equal to the Ki value of the compound A. Furthermore, the Example compounds of the present invention exhibited an inhibitory activity surpassing the inhibitory activity of compound 8 in the evaluation ($IC_{50}$) in the presence of 3% human serum albumin (+3% HSA, nM). From this, it could be seen that the Example compounds of the present invention were less affected by the adsorption to proteins, and maintained their activities high, compared to the compound A (representative compound of WO 02/053534).

Evaluation Example 2

In Vivo Evaluation of Substance Under Test

Test for eosinophile infiltration in mice actively sensitized with ascaris (antigen to pig roundworm):

It has been reported that infiltration of eosinophilic cells is induced by active sensitization with ascaris {Int. Arch. Immuno., 108, 11-18 (1995)}. An evaluation of the compounds under test was performed according to the evaluation method described herein. The substance under test was orally administered in an amount of 5 mg/kg, two times a day. The total cell count and the eosinophile count in BALF of 48 hours after sensitization were calculated, and the effects were determined by comparing with the group not administered with the substance under test. The results are presented in Table 8.

TABLE 8

Results of test for mouse eosinophile infiltration
(compound under test = administered two times a day)

| Substance under test | Average total eosinophile count of saline-sensitized group ($\times 10^5$) | Average total eosinophile count of ascaris-sensitized group ($\times 10^5$) | Average total eosinophile count ($\times 10^5$) of (ascaris-sensitized + substance under test) group, and suppression rate (%) |
|---|---|---|---|
| R1-2[1) ] | 0.02 | 2.55 | 1.13 (56**) |
| Compound A* | 0.01 | 3.02 | 1.31 (57**) |
| Example 10 | 0.01 | 3.07 | 1.73 (44**) |
| Example 58 | 0.05 | 4.31 | 1.63 (63**) |
| Example 72 | 0.01 | 4.66 | 1.41 (70**) |
| Example 80 | 0.01 | 3.76 | 1.86 (51**) |
| Example 94 | 0.01 | 3.02 | 1.24 (59**) |
| Example 118 | 0.03 | 4.33 | 1.41 (67**) |
| Example 124 | 0.01 | 4.66 | 1.72 (63**) |
| Example 127 | 0.01 | 3.76 | 1.40 (63**) |

*Representative compound of International Patent Application Publication Pamphlet No. WO 02/053534
[1)] Anti-VLA-4 antibody, s.c. administered two times a day;
**p < 0.01: vs [1), ] cont by student's t-test The results of Table 8 will be discussed. In the pathological control group in which mice were sensitized with ascaris, the infiltrated eosinophile count in BALF after 48 hours increased by $2.55 \times 10^5$ cells on the average, compared to the normal control group in which mice were sensitized with saline (physiological saline). On the other hand, in the ascaris-sensitized group administered with mouse anti-VLA-4 antibody (s.c. administration of two times a day), the infiltrated eosinophile count in BALF was $1.13 \times 10^5$ cells on the average, and a significant effect of decreasing the infiltrated eosinophile count by 56% was shown, compared to the pathological control group.

Likewise, in the group of oral administration (5 mg/kg, two times a day) of compound A (representative compound of WO 02/053534), a significant effect of decreasing the infiltrated eosinophile count by 57% was shown, compared to the pathological control group, and the suppressive effects were about the same as those of the mouse anti-VLA-4 antibody.

In the group orally administered with the Example compounds of the present invention, significant effects of decreasing the infiltrated eosinophile count by 44% to 70% were shown, compared to the pathological control group. Thus, the suppressive effects of the Example compounds of the present invention were equal to the suppressive effects of the group administered with the mouse anti-VLA-4 antibody and the compound A.

Evaluation Example 3

In Vivo Evaluation of Substance Under Test Through Once-A-day Administration of Compound Under Test Test for eosinophile infiltration in mice actively sensitized with ascaris (antigen to pig roundworm):

In the same manner as in Evaluation Example 2, the substances under test were orally administered once a day, in an amount of 5 mg/kg for compound A (representative compound of WO 02/053534) and the compound of Example 58, and in an amount of 0.8 mg/kg of the compound of Example 161, and an evaluation was performed in the same manner as in Evaluation Example 2. The results are presented in Table 9.

TABLE 9

Results of test for mouse eosinophile infiltration
(compound under test = administered once a day)

| Substance under test | Average total eosinophile count of saline-sensitized group ($\times 10^5$) | Average total eosinophile count of ascaris-sensitized group ($\times 10^5$) | Average total eosinophile count ($\times 10^5$) of (ascaris-sensitized + substance under test) group, and suppression rate (%) |
|---|---|---|---|
| Compound 8* | 0.01 | 3.02 | 2.93 (30) |
| Example 58 | 0.01 | 3.07 | 1.73 (59**) |
| Example 161 | 0.01 | 3.07 | 2.06 (51**) |

*Representative compound of WO 02/053534

The results of Table 9 will be discussed. The suppression rate of compound A (representative compound of WO 02/053534) was 30% when 5 mg/kg of the compound was orally administered once a day, and no suppressive effect with significant differences was shown compared to the pathological control group. On the other hand, the compound of Example 58 of the present invention exhibited a suppressive effect with a significant difference of 59% when orally administered in an amount of 5 mg/kg once a day, and the compound of Example 161 exhibited a suppressive effect with a significant difference of 51% when orally administered in an amount of 0.8 mg/kg once a day. These suppressive effects surpassed the suppressive effect of the compound A.

Evaluation Example 4

Solubility Test

The solubilities of the substance under test in the first liquid (JP1, pH=1.2) of the Japanese Pharmacopoeia and the second liquid (JP2, pH=6.8) of the Japanese Pharmacopoeia, were evaluated. The results are presented in Tables 10 and 11.

TABLE 10

Results of solubility test

|  | First liquid of Japanese Pharmacopoeia (μg/mL) | Second liquid of Japanese Pharmacopoeia (μg/mL) |
| --- | --- | --- |
| Example 1 | >2000 | >2000 |
| Example 2 | >2000 | >2000 |
| Example 3 | 1848 | 1989 |
| Example 4 | >2000 | >2000 |
| Example 5 | 1970 | >2000 |
| Example 10 | >2000 | >2000 |
| Example 12 | 1908 | 1687 |
| Example 14 | 1100 | 1000 |
| Example 15 | 1100 | 1100 |
| Example 20 | >2000 | 1921 |
| Example 27 | 1000 | 1000 |
| Example 28 | 1100 | 1100 |
| Example 29 | 1000 | 1000 |
| Example 30 | 1100 | 1100 |
| Example 31 | 1844 | 1685 |
| Example 32 | 1702 | 1690 |
| Example 33 | >2000 | >2000 |
| Example 34 | >2000 | 1642 |
| Example 35 | >2000 | >2000 |
| Example 36 | 1936 | 1840 |
| Example 42 | >2000 | >2000 |
| Compound A* | 0.1 | 20 |

*Representative compound of International Patent Application Publication Pamphlet No. WO 02/053534

TABLE 11

Results of solubility test

|  | First liquid of Japanese Pharmacopoeia (μg/mL) | Second liquid of Japanese Pharmacopoeia (μg/mL) |
| --- | --- | --- |
| Example 42 | >2000 | 1931 |
| Example 46 | 1200 | 1200 |
| Example 51 | 1000 | 1000 |
| Example 52 | 1000 | 1000 |
| Example 53 | 1000 | 1000 |
| Example 54 | 1000 | 1000 |
| Example 60 | 1000 | 1000 |
| Example 61 | 1100 | 1300 |
| Example 63 | 1000 | 1000 |
| Example 66 | >2000 | >2000 |
| Example 73 | 1000 | 1000 |
| Example 74 | 1200 | 1300 |
| Example 78 | >2000 | >2000 |
| Example 86 | 1300 | 1200 |
| Example 87 | 1200 | 1200 |
| Example 88 | 1100 | 1300 |
| Example 99 | >2000 | 1016 |
| Example 103 | >2000 | 1363 |
| Example 106 | >2000 | 1584 |
| Example 107 | 1200 | 1200 |
| Example 110 | >2000 | >2000 |

TABLE 11-continued

Results of solubility test

|  | First liquid of Japanese Pharmacopoeia (μg/mL) | Second liquid of Japanese Pharmacopoeia (μg/mL) |
| --- | --- | --- |
| Example 113 | 1000 | 1000 |
| Example 118 | 1000 | 1000 |
| Example 147 | 1400 | 1400 |
| Example 164 | 1000 | 1000 |
| Example 165 | >2000 | >2000 |
| Compound A* | 0.1 | 20 |

*Representative compound of International Patent Application Publication Pamphlet No. WO 02/053534

The results of the solubility evaluation shown in Table 10 and Table 11 will be discussed. The solubilities of compound A (representative compound of WO 02/053534) in the first liquid (JP1, pH=1.2) of the Japanese Pharmacopoeia and in the second liquid (JP2, pH=6.8) of the Japanese Pharmacopoeia were 0.1 μg/ml and 20 μg/ml, respectively, and in particular, the solubility in the acidic first liquid of the Japanese Pharmacopoeia was very low. On the other hand, the solubilities of the Example compounds of the present invention in the first liquid (JP1, pH=1.2) of the Japanese Pharmacopoeia and in the second liquid (JP2, pH=6.8) of the Japanese Pharmacopoeia were all 1000 μg/ml or higher, and the Example compounds exhibited good water solubility.

Evaluation Example 5

Test for Pharmacokinetics and Oral Absorbability

The pharmacokinetic parameters in the case of orally administering (0.5 mg/kg, single agent) the substance under test to monkeys, were as follows. The results are presented in Table 12.

TABLE 12

Results of test for pharmacokinetics and oral absorbability in monkeys

|  | AUC[1] (ng · h/ml) | Cltot[2] (mL/min/kg) |
| --- | --- | --- |
| Example 2 | 22185 | 0.40 |
| Example 3 | 32510 | 0.26 |
| Example 10 | 10799 | 0.80 |
| Example 58 | 7555 | 2.0 |
| Example 83 | 15064 | 0.56 |
| Example 139 | 7329 | 1.2 |
| Compound A[3] | 6738 | 1.3 |

[1]AUC (ng · h/ml): total area under the plasma concentration (measured by LC/MS/MS method) versus time curve;
[2]Cltot (mL/min/kg): apparent plasma clearance;
[3]Representative compound of International Patent Application Publication Pamphlet No. 02/053534

As shown in Table 12, the AUC (ng·h/mL) obtained when the compound of Examples 2, 3, 10, 58, 83 or 139 of the present invention was orally administered (0.5 mg/kg, single agent), was greater than or equal to the AUC (ng·h/mL) obtained when compound A (representative compound of WO 02/053534) was orally administered (0.5 mg/kg, single agent). Furthermore, the blood clearance rates [CLtot (mL/min/kg)] of the compounds of Examples 2, 3, 10, 83 and 139 of the present invention were smaller than that of the compound A (representative compound of WO 02/053534), while the retention in blood of the compounds was superior.

INDUSTRIAL APPLICABILITY

The VLA-4 inhibitory drug of the present invention has good oral absorbability, and exhibits excellent effects in the predominant pharmacological and pathological in vivo model when administered orally. Thus, the inhibitory drug of the invention is to provide an orally administrable medicament which can be used as a prophylactic and/or therapeutic drug for various inflammatory diseases caused by the migration and adhesion of leukocytes mediated by VLA-4, and therefore has high clinical efficacy.

The invention claimed is:

1. A compound represented by the following formula (I):

[Formula 1]

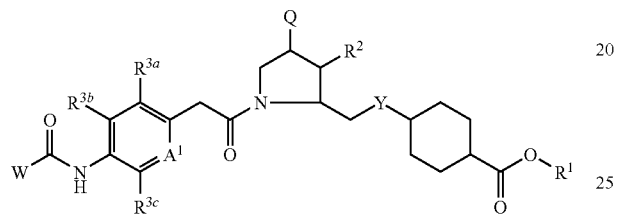

(I)

wherein $R^1$ represents a hydrogen atom or a lower alkyl group; $R^2$ represents a hydrogen atom, a halogen atom, a lower alkoxy group, or a benzyloxy group which may be substituted with one or a plurality of substituents; Q represents a monocyclic or bicyclic nitrogen-containing heterocyclic group which may be substituted with one or a plurality of substituents, and has a nitrogen atom as the bonding site; Y represents an oxygen atom or $CH_2$; W represents a bicyclic aromatic hydrocarbon ring group which may be substituted with one or a plurality of substituents, or a bicyclic aromatic heterocyclic group which may be substituted with one or a plurality of substituents; $R^{3a}$, $R^{3b}$ and $R^{3c}$ each independently represent a hydrogen atom, a halogen atom, a lower alkoxy group or a lower alkyl group; and $A^1$ represents a nitrogen atom or C—$R^{3d}$ (wherein $R^{3d}$ represents a hydrogen atom, a halogen atom, a lower alkoxy group or a lower alkyl group), or a salt thereof.

2. The compound according to claim 1, wherein W in the formula (I) is a group represented by the following formula (i) or (ii):

[Formula 2]

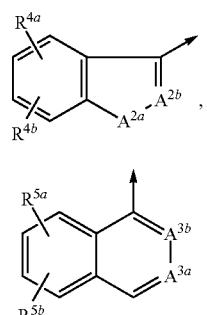

wherein symbol "→" represents the position of attachment; $R^{4a}$ and $R^{4b}$ each independently represent a hydrogen atom, a halogen atom, a lower alkoxy group or a lower alkyl group; $A^{2a}$ represents an oxygen atom, a sulfur atom or N—$R^{4c}$ (wherein $R^{4c}$ represents a hydrogen atom or a lower alkyl group); $A^{2b}$ represents a nitrogen atom or C—$R^{4d}$ (wherein $R^{4d}$ represents a hydrogen atom or a lower alkyl group);

$R^{5a}$ and $R^{5b}$ each independently represent a hydrogen atom, a halogen atom, a lower alkoxy group or a lower alkyl group; $A^{3a}$ represents a nitrogen atom or C—$R^{5c}$ (wherein $R^{5c}$ represents a hydrogen atom or a lower alkyl group); and $A^{3b}$ represents a nitrogen atom or C—$R^{5d}$ (wherein $R^{5d}$ represents a hydrogen atom or a lower alkyl group), or a salt thereof.

3. The compound according to claim 1, wherein W in the formula (I) is any one group among the groups represented by the following formulas (iii-a) to (iii-h):

[Formula 3]

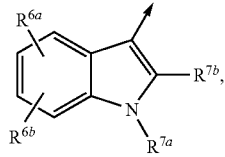

(iii-a)

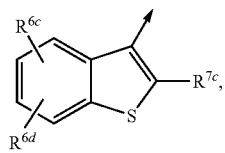

(iii-b)

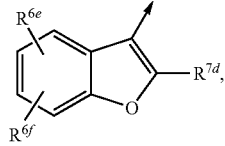

(iii-c)

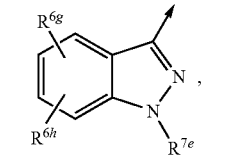

(iii-d)

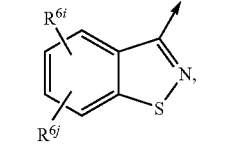

(iii-e)

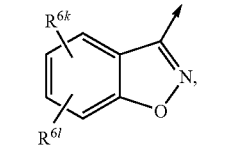

(iii-f)

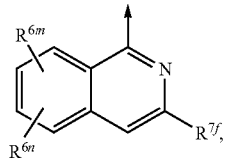

(iii-g)

-continued (iii-h)
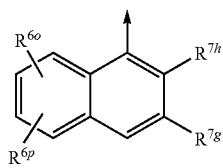

wherein symbol "→" represents the position of attachment; $R^{6a}$, $R^{6b}$, $R^{6c}$, $R^{6d}$, $R^{6e}$, $R^{6f}$, $R^{6g}$, $R^{6h}$, $R^{6i}$, $R^{6j}$, $R^{6k}$, $R^{6l}$, $R^{6m}$, $R^{6n}$, $R^{6o}$ and $R^{6p}$ each independently represent a hydrogen atom, a halogen atom, a lower alkoxy group or a lower alkyl group; and $R^{7a}$, $R^{7b}$, $R^{7c}$, $R^{7d}$, $R^{7e}$, $R^{7f}$, $R^{7g}$ and $R^{7h}$ each independently represent a hydrogen atom or a lower alkyl group, or a salt thereof.

4. The compound according to claim 3, wherein W in the formula (I) is a group represented by the formula (iii-a), (iii-b), (iii-c), (iii-d) or (iii-g), or a salt thereof.

5. The compound according to claim 3, wherein W in the formula (I) is a group represented by the following formula (iii-a), (iii-b) or (iii-c), or a salt thereof.

6. The compound of claim 1, wherein Q in the formula (I) is any one of groups represented by the following formulas (iv-a) to (iv-x):

[Formula 4]

(iv-a)
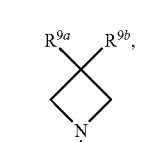

(iv-b)
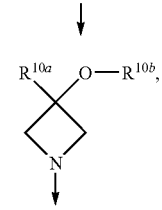

(iv-c)
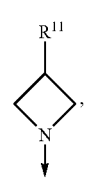

(iv-d)
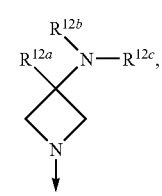

(iv-e)
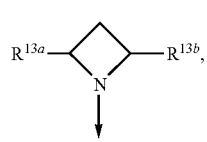

-continued (iv-f)
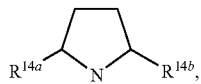

(iv-g)
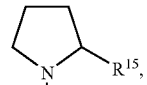

(iv-h)
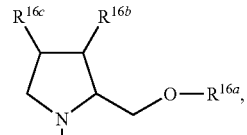

(iv-i)
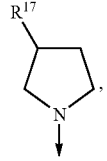

(iv-j)
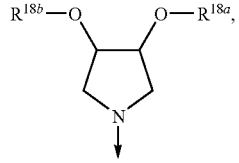

(iv-k)
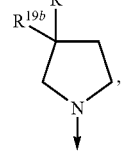

(iv-l)
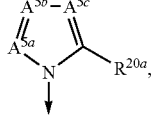

(iv-m)
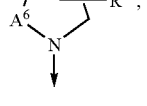

(iv-n)
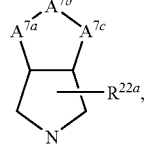

(iv-o)
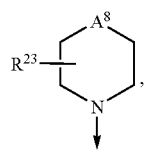

347
-continued (iv-p)
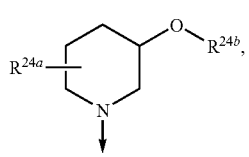

(iv-q)
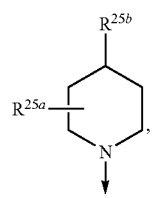

(iv-r)
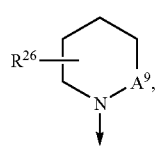

(iv-s)
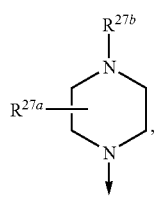

(iv-t)
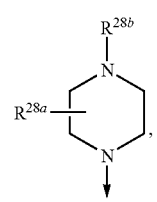

(iv-u)
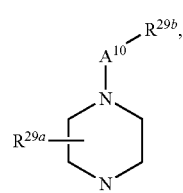

(iv-v)
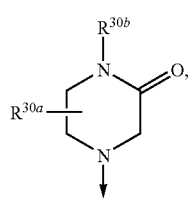

(iv-w)
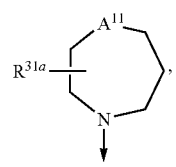

348
-continued (iv-x)
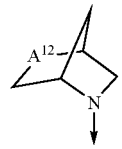

wherein symbol "→" represents the position of attachment;
$R^{9a}$ and $R^{9b}$ each independently represent a hydrogen atom, a halogen atom or a lower alkyl group;
$R^{10a}$ represents a hydrogen atom or a lower alkyl group; $R^{10b}$ represents a lower alkyl group;
$R^{11}$ represents a substituted lower alkyl group;
$R^{12a}$ represents a hydrogen atom or a lower alkyl group; $R^{12b}$ and $R^{12c}$ each independently represent a lower alkyl group or a lower cycloalkyl group which may be substituted with one or a plurality of substituents; or $R^{12b}$ and $R^{12c}$, together with the nitrogen atom to which they are bound, form an azetidin-1-yl group which may be substituted with one or a plurality of substituents, a pyrrolidin-1-yl group which may be substituted with one or a plurality of substituents, a piperidin-1-yl group which may be substituted with one or a plurality of substituents, or a morpholin-1-yl group which may be substituted with one or a plurality of substituents;
$R^{13a}$ and $R^{13b}$ each independently represent a hydrogen atom, a lower alkyl group or a lower alkoxymethyl group;
$R^{14a}$ and $R^{14b}$ each independently represent a lower alkyl group or a lower alkoxymethyl group;
$R^{15}$ represents a hydrogen atom, a lower alkyl group which may be substituted with one or a plurality of substituents, or a carbamoyl group which may be substituted with one or two substituents;
$R^{16a}$ represents a lower alkyl group; $R^{16b}$ and $R^{16c}$ each independently represent a hydrogen atom, a halogen atom or a lower alkoxy group;
$R^{17}$ represents a halogen atom, a lower alkoxy group or an amino group which may be substituted with one or two substituents;
$R^{18a}$ and $R^{18b}$ each independently represent a lower alkyl group;
$R^{19a}$ and $R^{19b}$ each independently represent a halogen atom, or $R^{19a}$ and $R^{19b}$, together with the carbon atoms on the pyrrolidine ring to which they are bound, form a C3 to C6 cycloalkyl ring; $R^{20a}$ represents a hydrogen atom, a halogen atom, a lower alkyl group or a lower alkoxy group; $A^{5a}$ represents a nitrogen atom or C—$R^{20b}$ (wherein $R^{20b}$ represents a hydrogen atom, a halogen atom, a lower alkyl group or a lower alkoxy group); $A^{5b}$ represents a nitrogen atom or C—$R^{20c}$ (wherein $R^{20c}$ represents a hydrogen atom, a halogen atom, a lower alkyl group or a lower alkoxy group); $A^{5c}$ represents a nitrogen atom or C—$R^{20d}$ (wherein $R^{20d}$ represents a hydrogen atom, a halogen atom, a lower alkyl group or a lower alkoxy group);
$R^{21}$ represents a hydrogen atom, or one or a plurality of lower alkyl groups; $A^6$ represents an oxygen atom, a sulfur atom or $S(O)_2$;
$R^{22a}$ represents a hydrogen atom, or one or a plurality of lower alkyl groups; $A^{7a}$ and $A^{7c}$ are directly bound to represent an oxygen atom or $CH_2$; $A^{7b}$ represents 1) an oxygen atom, a sulfur atom or $S(O)_2$ when $A^{7a}$ and $A^{7c}$ together form $CH_2$, 2) represents $CH_2$ when $A^{7a}$ and $A^{7c}$ together form a direct bond, or 3) represents C(—$R^{22b}$)—$R^{22c}$ (wherein $R^{22b}$ and $R^{22c}$ each independently represent a hydrogen atom or a lower alkyl group) when $A^{7a}$ and $A^{7c}$ together form an oxygen atom;

$R^{23}$ represents a hydrogen atom, or one or a plurality of lower alkyl groups; $A^8$ represents an oxygen atom, a sulfur atom, $S(O)_2$ or $CF_2$;

$R^{24a}$ represents a hydrogen atom, or one or a plurality of lower alkyl groups; $R^{24b}$ represents a lower alkyl group;

$R^{25a}$ represents a hydrogen atom, or one or a plurality of lower alkyl groups; $R^{25b}$ represents a hydrogen atom, a halogen atom, a lower alkyl group, a lower alkoxymethyl group which may be substituted with one or a plurality of substituents, a lower alkoxyethyl group which may be substituted with one or a plurality of substituents, a lower alkoxy group which may be substituted with one or a plurality of substituents, a phenoxy group which may be substituted with one or a plurality of substituents, a carbamoyl group which may be substituted with one or two substituents, a lower alkylsulfonyl group which may be substituted with one or a plurality of substituents, an amino group which may be substituted with one or two substituents, or a morpholin-4-yl group which may be substituted with one or a plurality of substituents;

$R^{26}$ represents a hydrogen atom, or one or a plurality of lower alkyl groups; $A^9$ represents an oxygen atom or $S(O)_2$;

$R^{27a}$ represents a hydrogen atom, or one or a plurality of lower alkyl groups; $R^{27b}$ represents a hydrogen atom, a lower alkyl group, a fluoro-lower alkyl group, a lower cycloalkylmethyl group, a lower alkoxyethyl group which may be substituted with one or a plurality of substituents, or a benzyl group which may be substituted with one or a plurality of substituents;

$R^{28a}$ represents a hydrogen atom, or one or a plurality of lower alkyl groups; $R^{28b}$ represents a lower cycloalkyl group which may be substituted with one or a plurality of substituents, or a pyridyl group which may be substituted with one or a plurality of substituents;

$R^{29a}$ represents a hydrogen atom, or one or a plurality of lower alkyl groups; $A^{10}$ represents $C(O)$ or $S(O)_2$; $R^{29b}$ represents a lower alkyl group, a benzyl group which may be substituted with one or a plurality of substituents, or an amino group which may be substituted with one or two substituents;

$R^{30a}$ represents a hydrogen atom, or one or a plurality of lower alkyl groups; $R^{30b}$ represents a hydrogen atom, a lower alkyl group, or a benzyl group which may be substituted with one or a plurality of substituents; $R^{31a}$ represents a hydrogen atom, or one or a plurality of lower alkyl groups; $A^{11}$ represents an oxygen atom, CH—$R^{31b}$ (wherein $R^{31b}$ represents a hydrogen atom or a lower alkyl group), or N—$R^{31c}$ (wherein $R^{31c}$ represents a hydrogen atom, a lower alkyl group which may be substituted with one or a plurality of substituents, a lower cycloalkyl group which may be substituted with one or a plurality of substituents, or a lower alkylsulfonyl group which may be substituted with one or a plurality of substituents); and $A_{12}$ represents an oxygen atom or N—$R^{32}$ (wherein $R^{32}$ represents a hydrogen atom, a lower alkyl group or a lower cycloalkyl group), or a salt thereof.

7. The compound according to claim 6, wherein Q in the formula (I) is a group represented by the formula (iv-a), (iv-b), (iv-c), (iv-d), (iv-h), (iv-i), (iv-j), (iv-n), (iv-o), (iv-p), (iv-q), (iv-s), (iv-t) or (iv-u), or a salt thereof.

8. The compound according to claim 6, wherein Q in the formula (I) is a group represented by the formula (iv-b), (iv-h), (iv-j), (iv-o), (iv-q), (iv-s) or (iv-t), or a salt thereof.

9. The compound according to claim 6, wherein Q in the formula (I) is a group represented by the formula (iv-j), or a salt thereof.

10. The compound according to claim 9, wherein both $R^{18a}$ and $R^{18b}$ in the formula (iv-j) are methyl groups or ethyl groups, or a salt thereof.

11. The compound according to claim 6, wherein Q in the formula (I) is a group represented by the formula (iv-o), or a salt thereof.

12. The compound according to claim 11, wherein $R^{23}$ in the formula (iv-o) is a hydrogen atom, a methyl group or a dimethyl group; and $A^8$ is an oxygen atom or $S(O)2$, or a salt thereof.

13. The compound according to claim 6, wherein Q in the formula (I) is a group represented by the formula (iv-s), or a salt thereof.

14. The compound according to claim 13, whrein $R^{27a}$ in the formula (iv-s) is a hydrogen atom; and $R^{27b}$ is a fluoro-lower alkyl group, or a salt thereof.

15. The compound of claim 1, wherein the formula (I) is a configuration represented by the following formula (I-a):

[Formula 5]

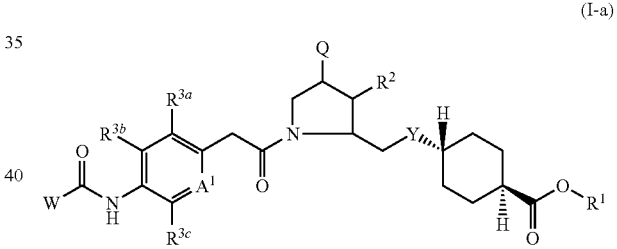

(I-a)

wherein $R^1$, $R^2$, Q, Y, $R^{3a}$, $R^{3b}$, $R^{3c}$, $A^1$ and W represent the same as those in the formula (I), or a salt thereof.

16. The compound of claim 1, wherein the formula (I) is a configuration represented by the following formula (I-b):

[Formula 6]

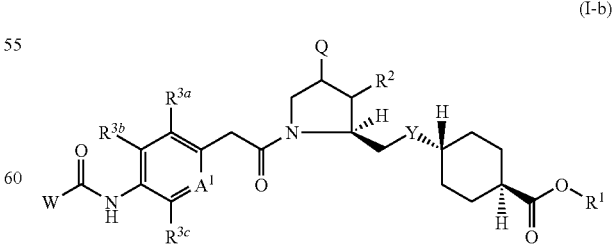

(I-b)

wherein $R^1$, $R^2$, Q, Y, $R^{3a}$, $R^{3b}$, $R^{3c}$, $A^1$ and W represent the same as those in the formula (I), or a salt thereof.

17. The compound of claim 1, wherein the formula (I) is a configuration represented by the following formula (I-c):

[Formula 7]

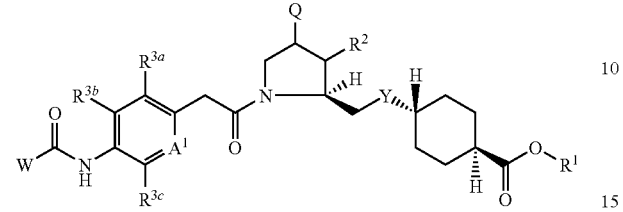

(I-c)

wherein $R^1$, $R^2$, Q, Y, $R^{3a}$, $R^{3b}$, $R^{3c}$, $A^1$ and W represent the same as those in the formula (I), or a salt thereof.

18. The compound of claim 1, wherein $A^1$ in the formula (I) is C—$R^{3d}$ (wherein $R^{3d}$ represents a hydrogen atom, a halogen atom, a lower alkoxy group or a lower alkyl group), or a salt thereof.

19. The compound according to claim 18, wherein $R^{3d}$ is a hydrogen atom, or a salt thereof.

20. The compound of claim 1, wherein $R^{3a}$ in the formula (I) is a hydrogen atom, a fluorine atom or a chlorine atom; $R^{3b}$ is a hydrogen ato; and $R^{3c}$ is a fluorine atom, a chlorine atom, a methoxy group or a methyl group, or a salt thereof.

21. The compound of claim 1, wherein the group represented by the following formula (v) in the formula (I) is any one of the groups represented by the following formulas (v-1) to (v-110):

[Formula 8]

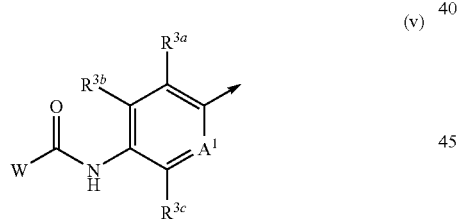

(v)

[Formula 9]

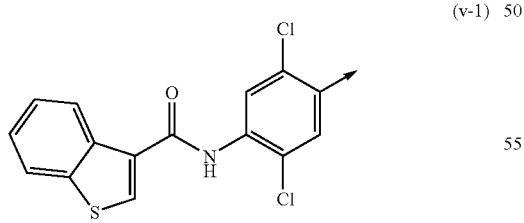

(v-1)

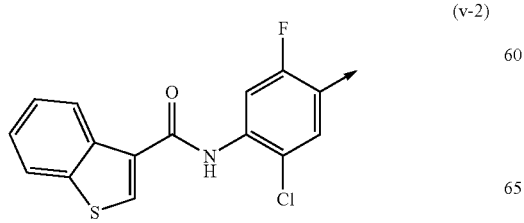

(v-2)

-continued

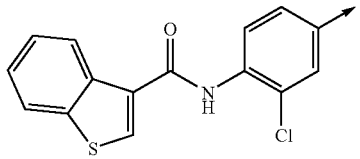

(v-3)

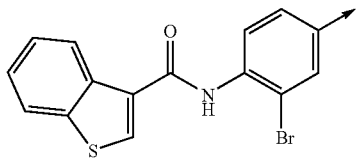

(v-4)

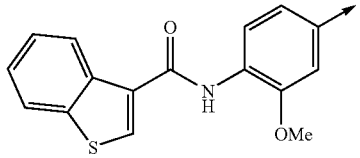

(v-5)

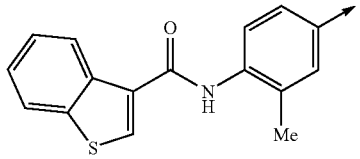

(v-6)

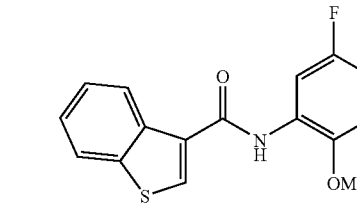

(v-7)

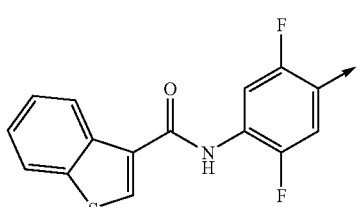

(v-8)

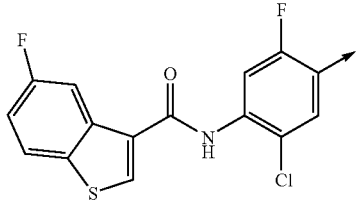

(v-9)

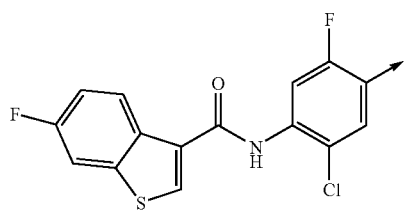

(v-10)

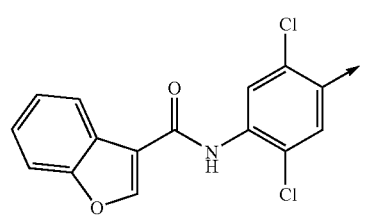 (v-11)
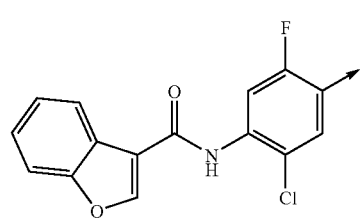 (v-12)
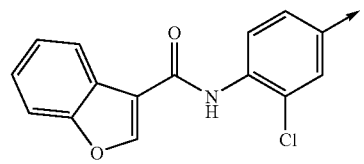 (v-13)
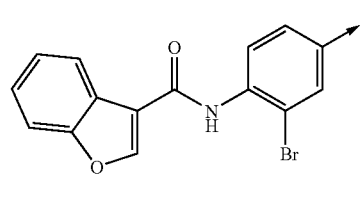 (v-14)
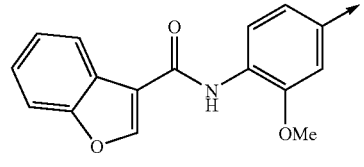 (v-15)
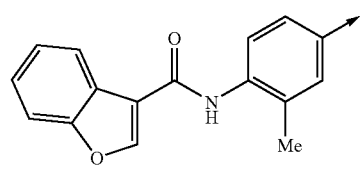 (v-16)
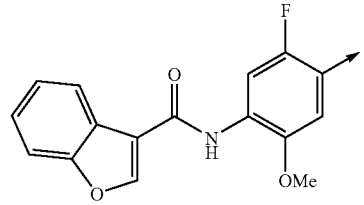 (v-17)
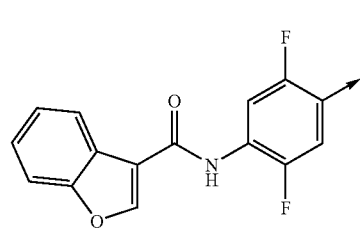 (v-18)
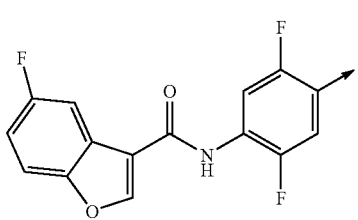 (v-19)
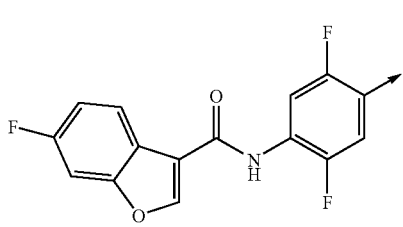 (v-20)
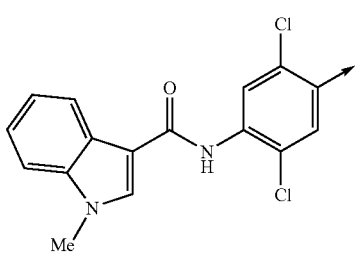 (v-21)
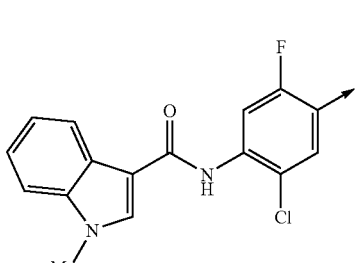 (v-22)
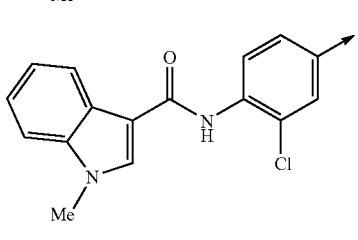 (v-23)
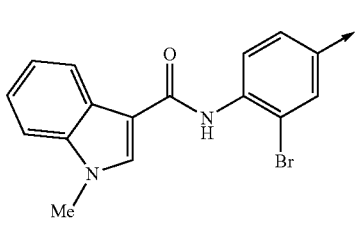 (v-24)
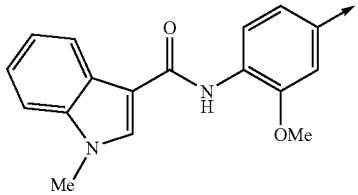 (v-25)

(v-26) 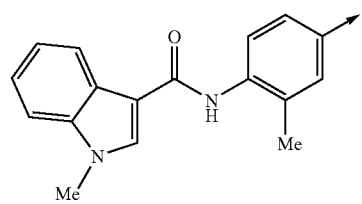
(v-27) 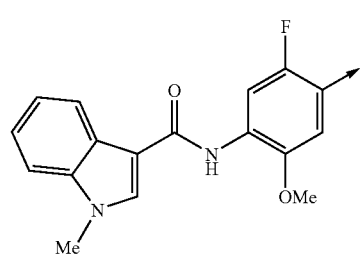
(v-28) 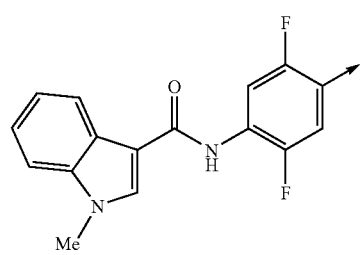
(v-29) 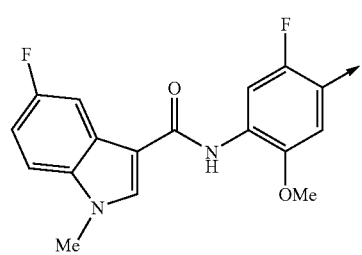
(v-30) 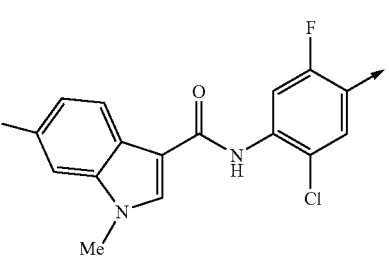
(v-31) 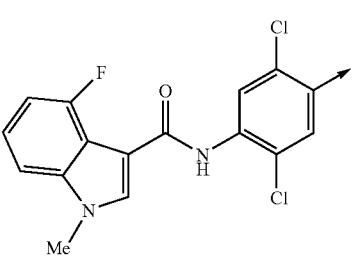
(v-32) 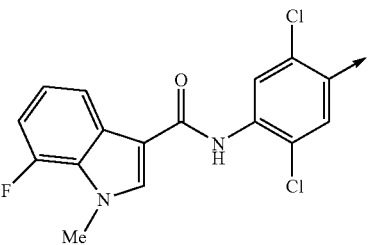
(v-33) 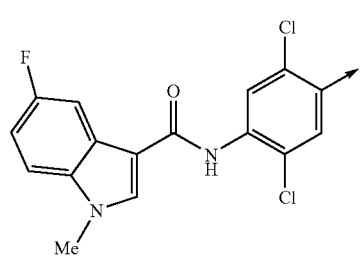
(v-34) 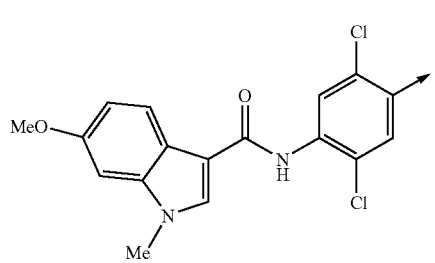
(v-35) 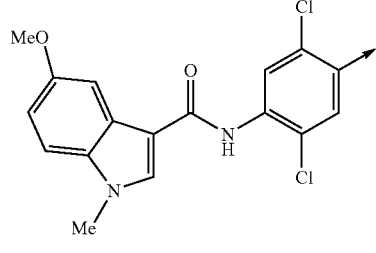
(v-36) 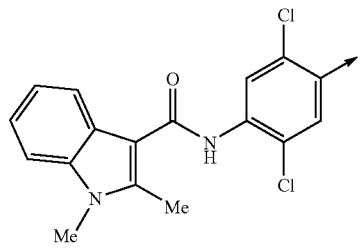
(v-37) 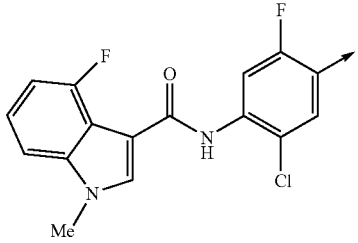

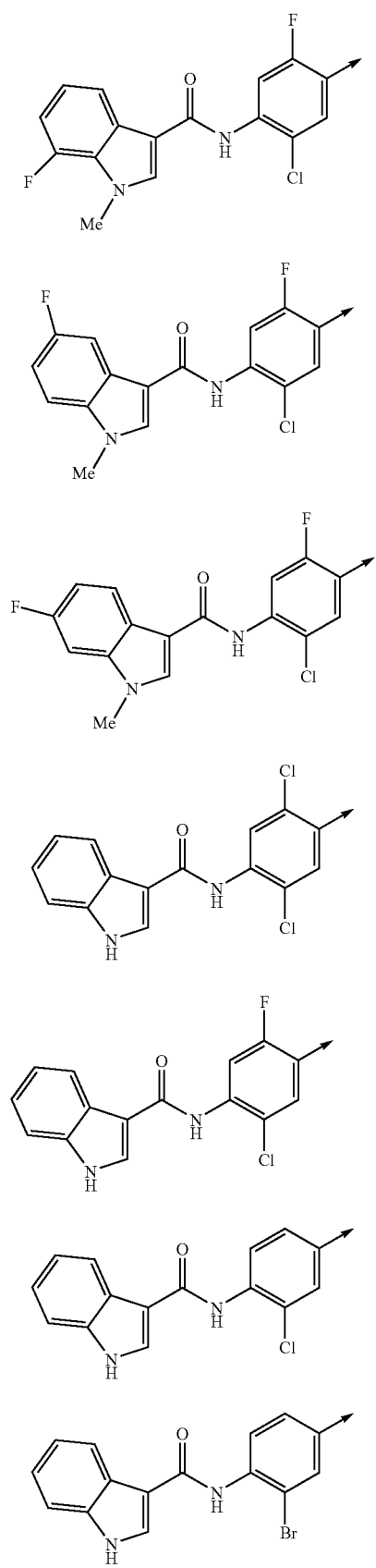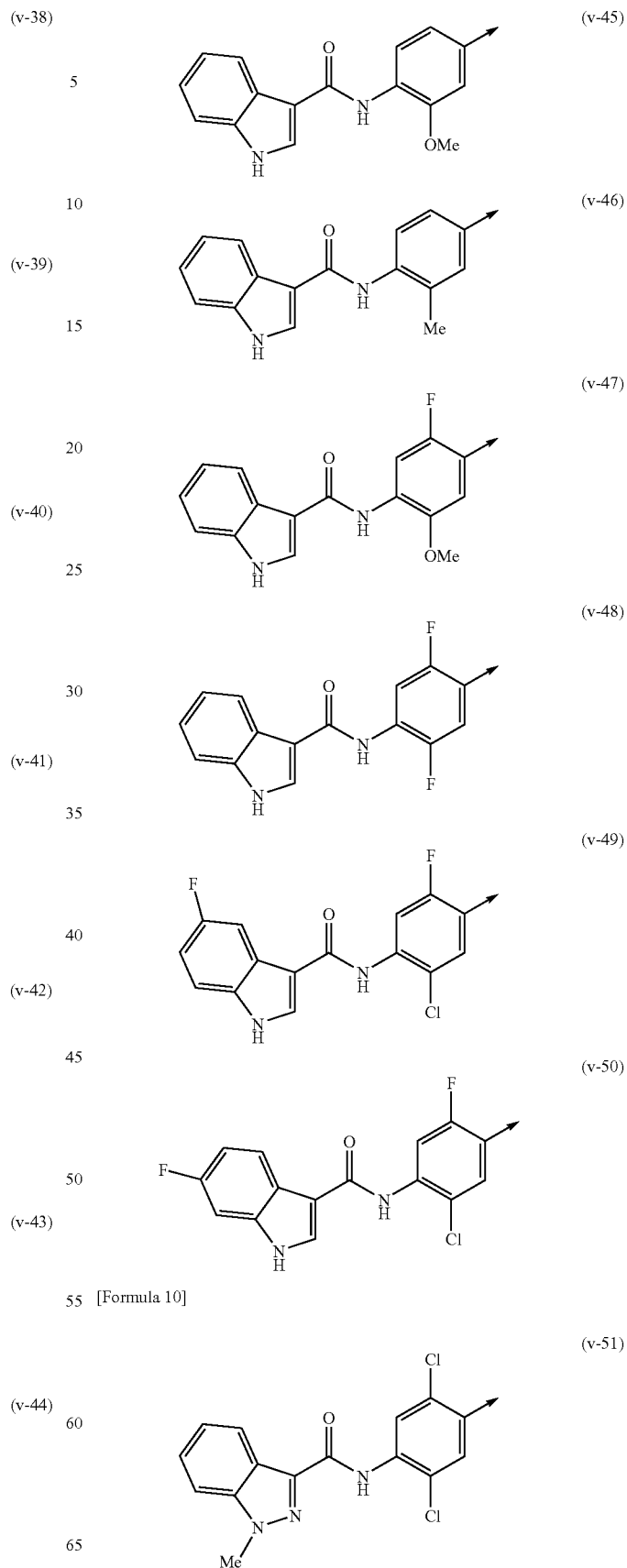

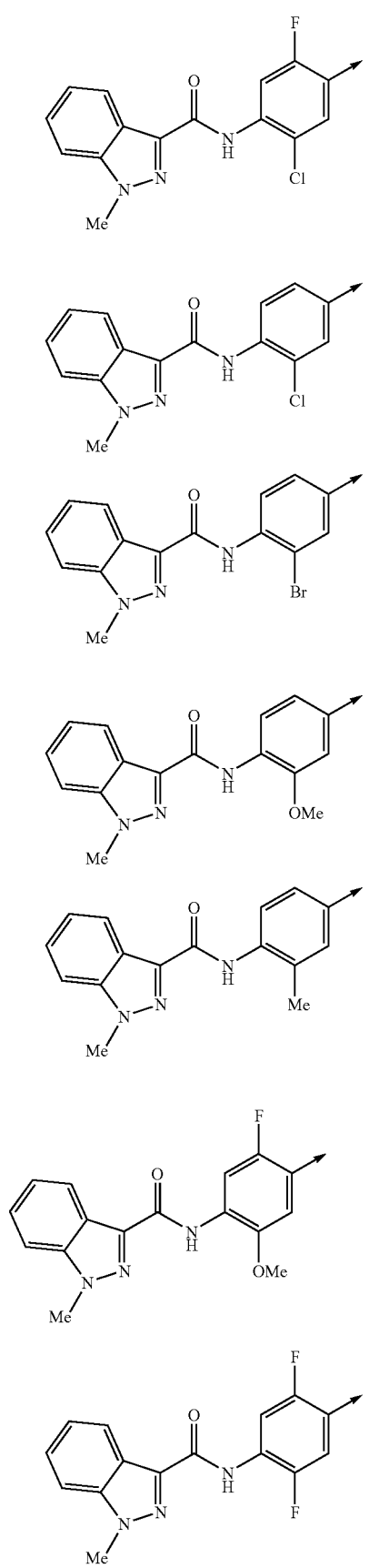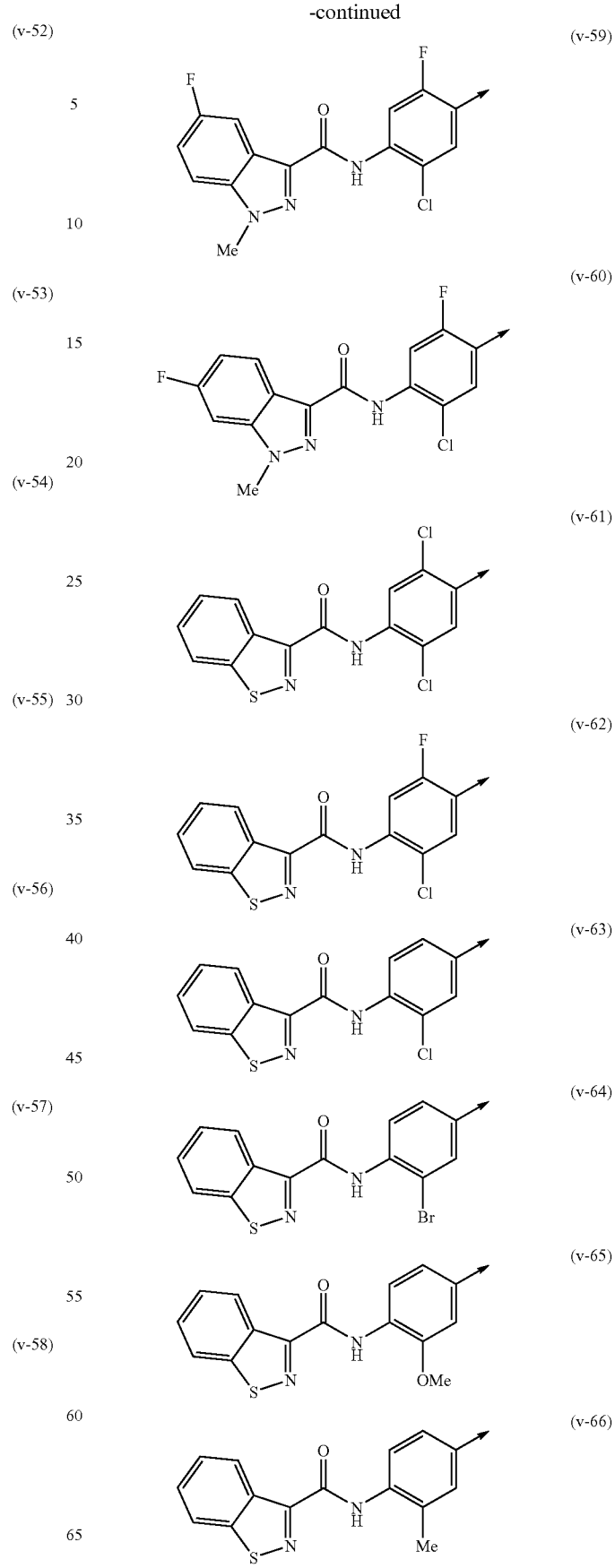

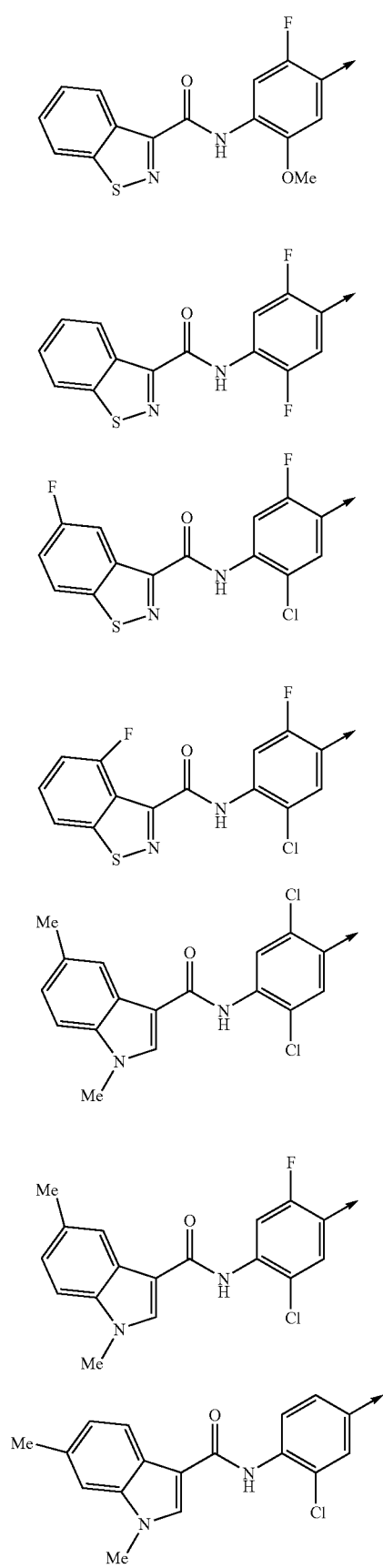
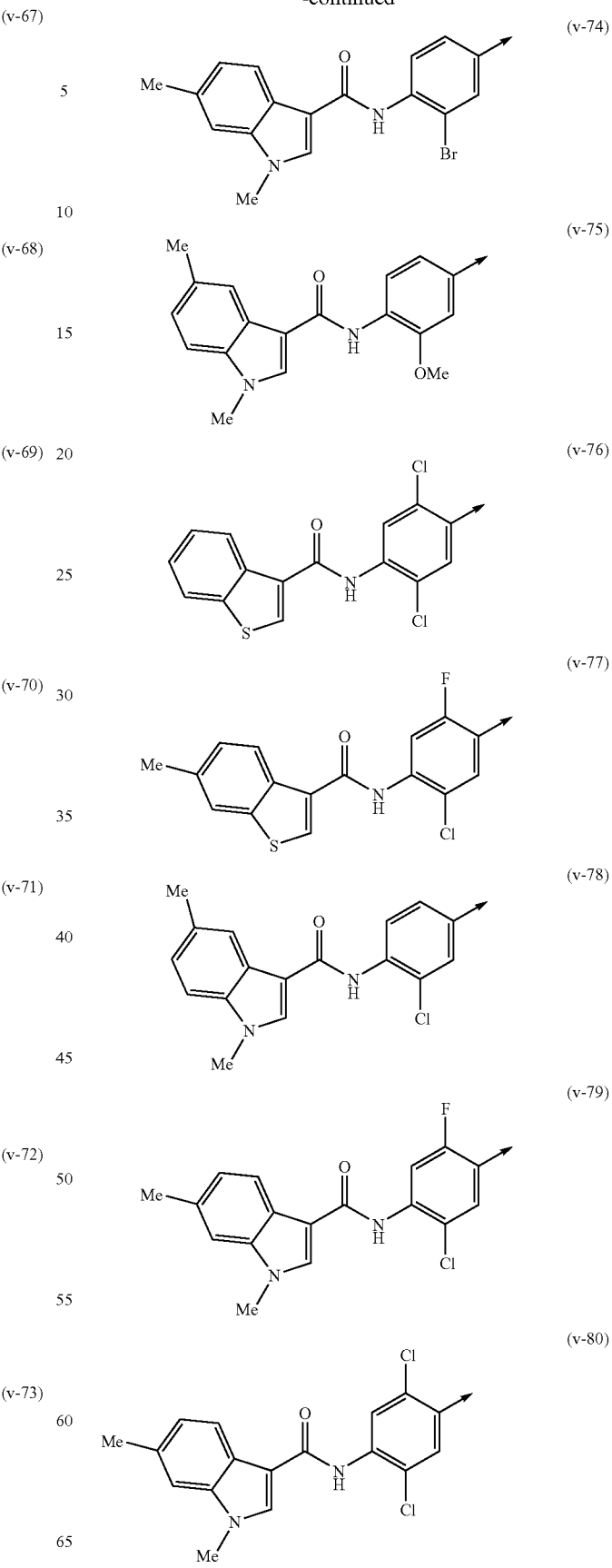

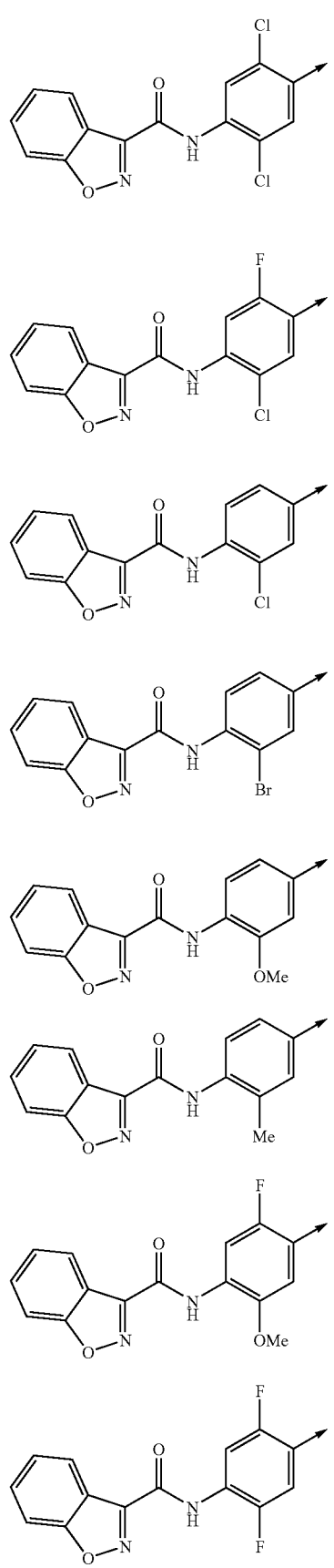
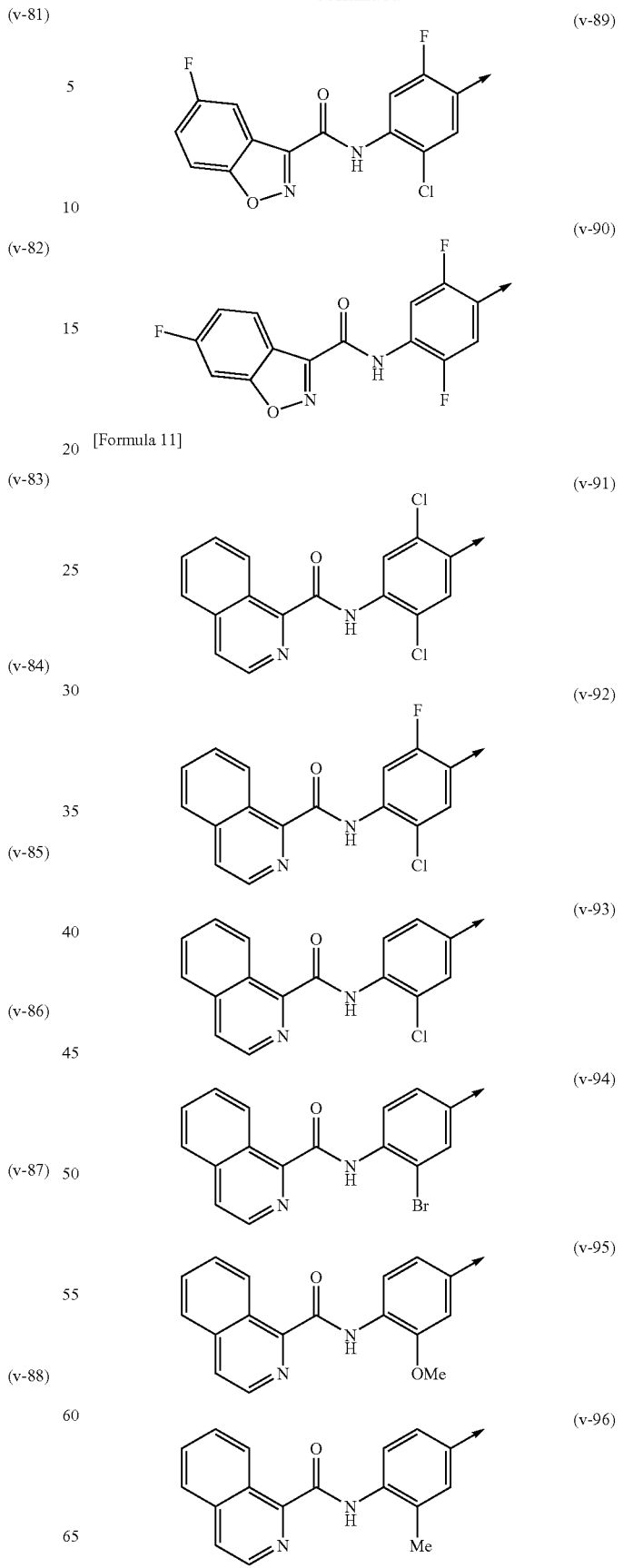

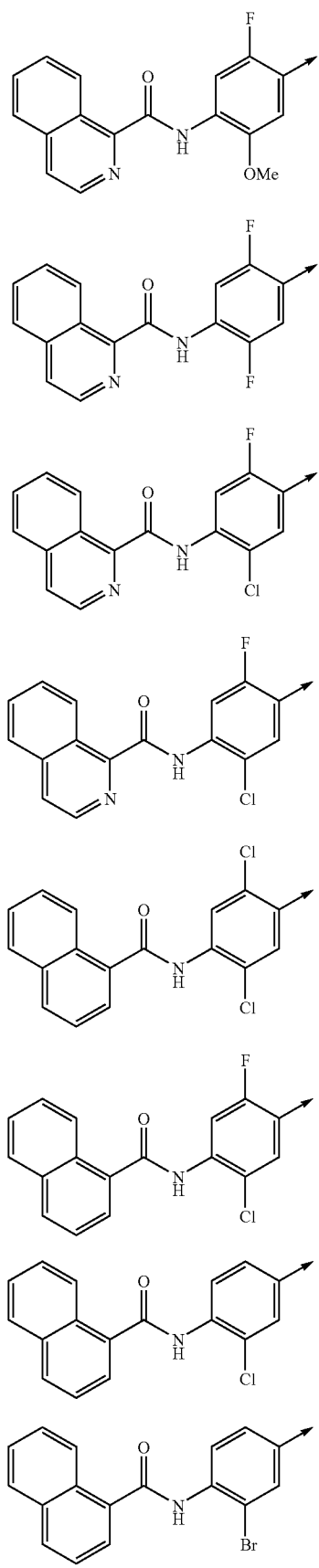
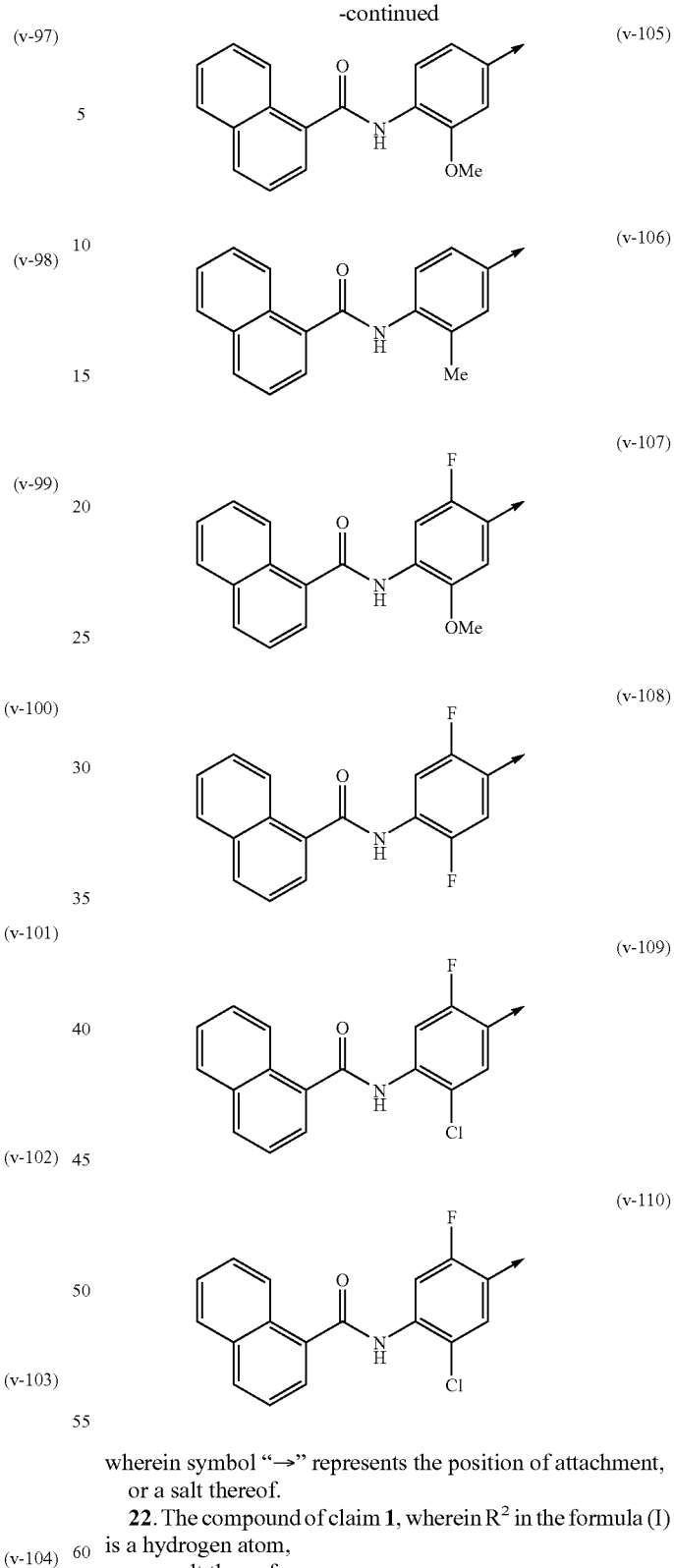
wherein symbol "→" represents the position of attachment, or a salt thereof.
22. The compound of claim 1, wherein $R^2$ in the formula (I) is a hydrogen atom, or a salt thereof.
23. The compound of claim 1, wherein Y in the formula (I) is an oxygen atom, or a salt thereof.
24. The compound of claim 1, wherein $R^1$ in the formula (I) is a hydrogen atom, or a salt thereof.

25. A compound selected from the formulas represented by the following formulas (vi-1) to (vi-127):
[Formula 12]
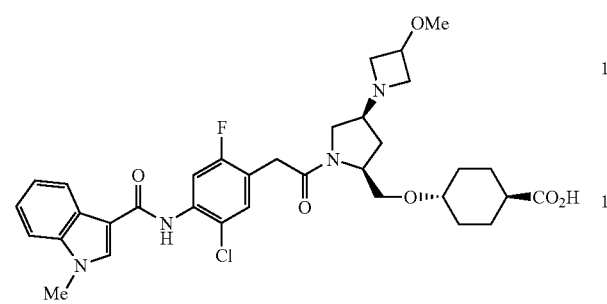
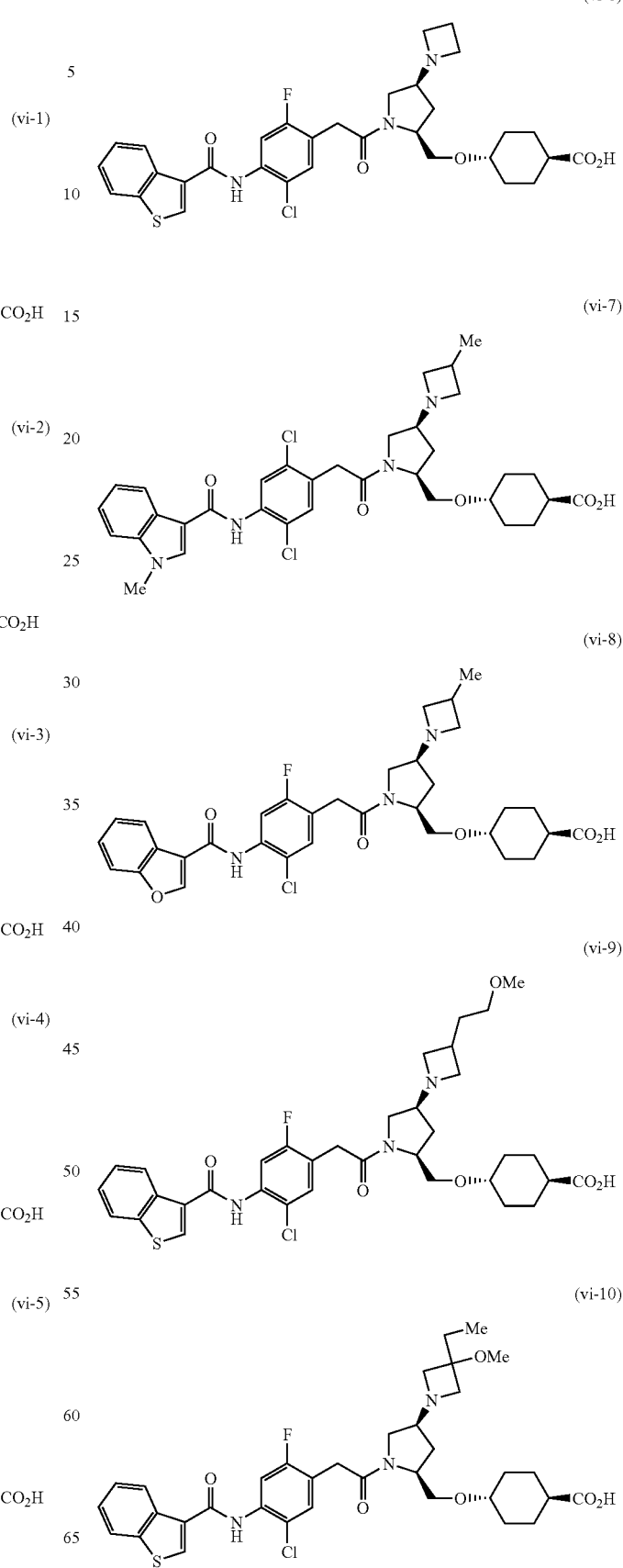

-continued
(vi-11)
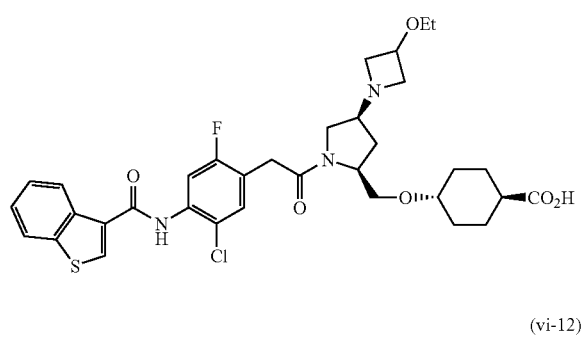
(vi-16)
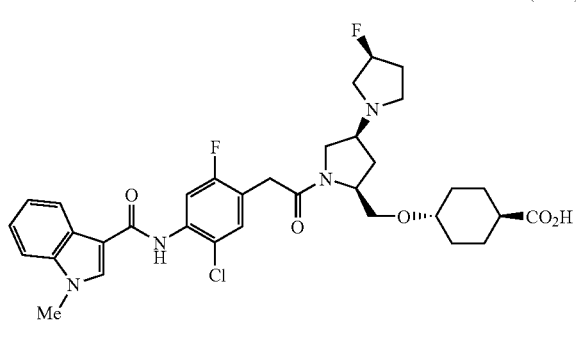
(vi-12)
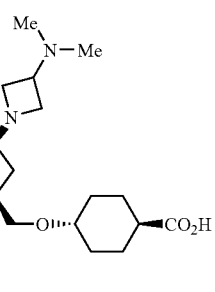
[Formula 13]
(vi-17)
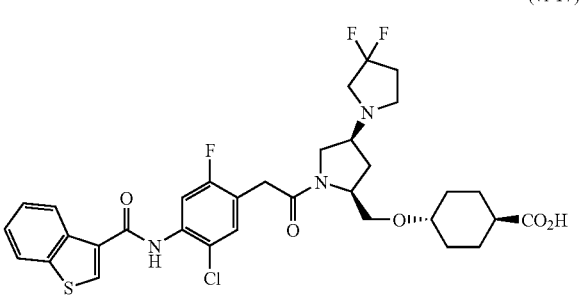
(vi-13)
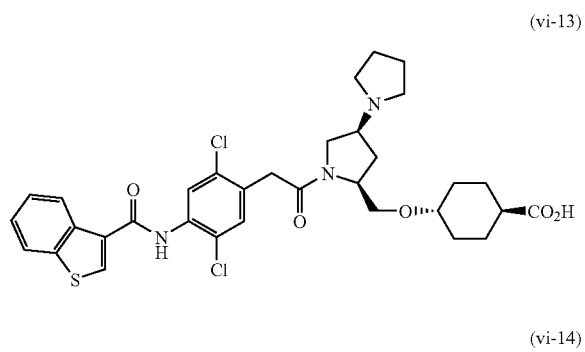
(vi-18)
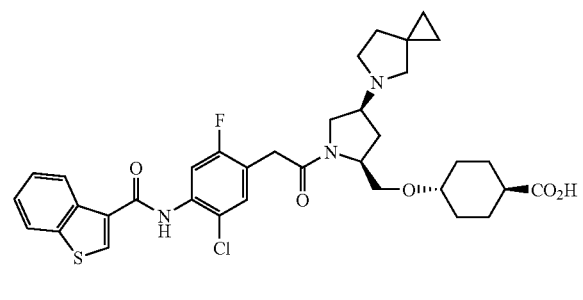
(vi-14)
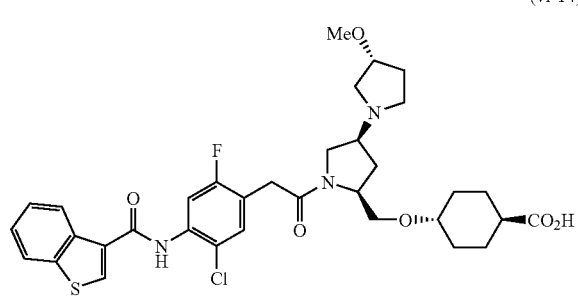
(vi-19)
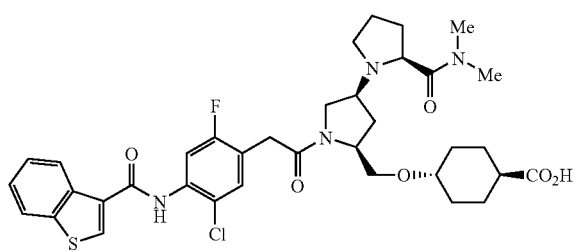
(vi-15)
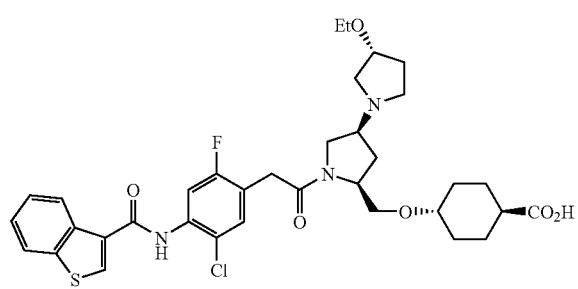
(vi-20)
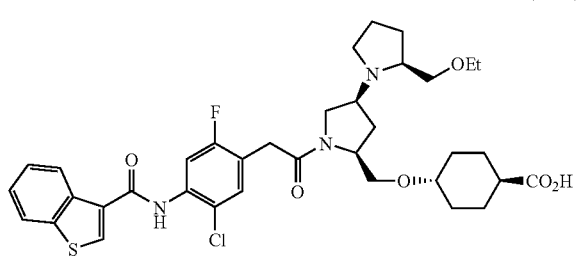

(vi-21)
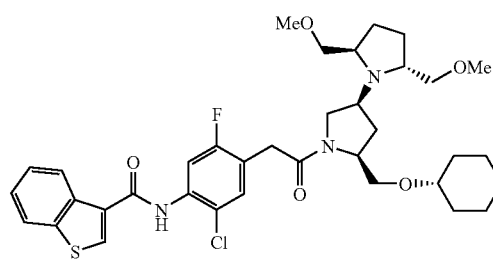
(vi-26)
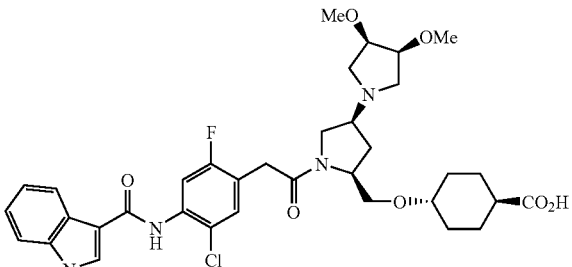
(vi-22)
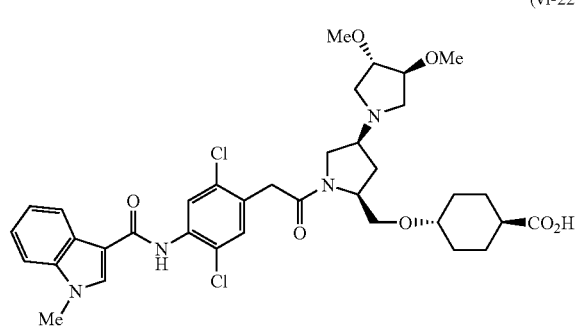
(vi-27)
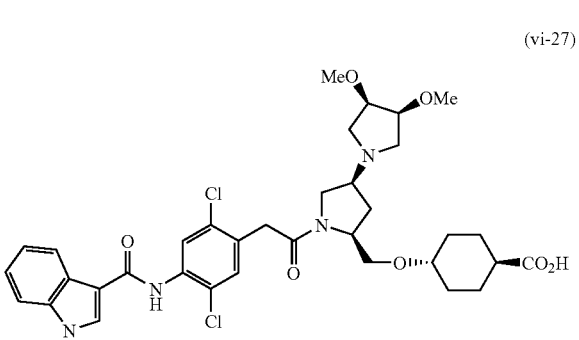
(vi-23)
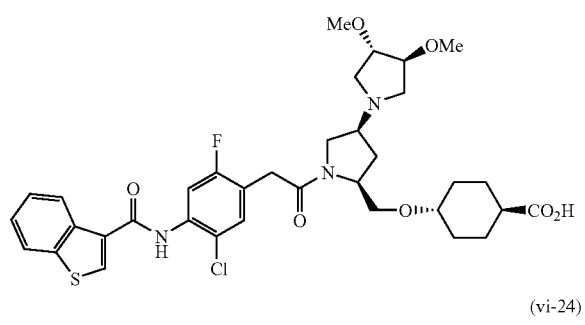
(vi-28)
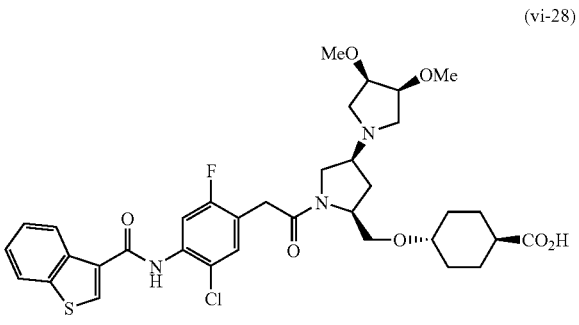
(vi-24)
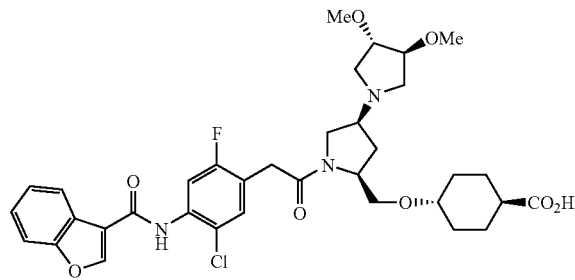
[Formula 14]
(vi-25)
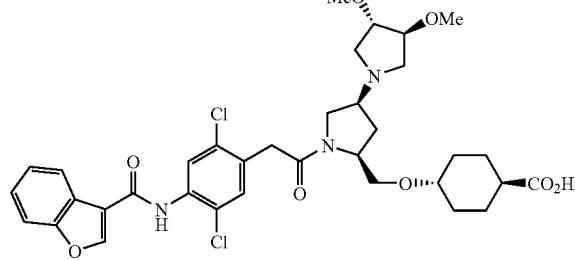
(vi-29)
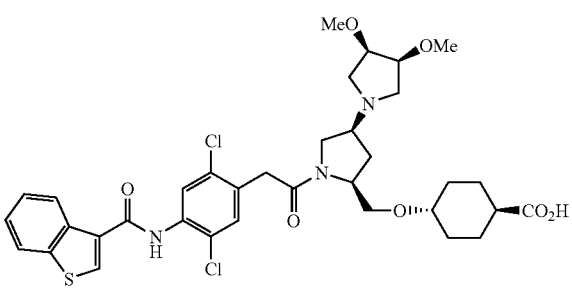
(vi-30)

-continued
(vi-31)
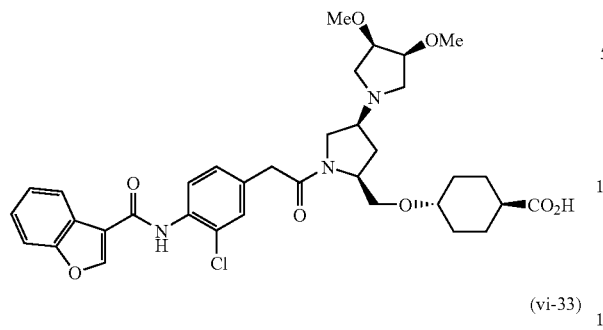
(vi-33)
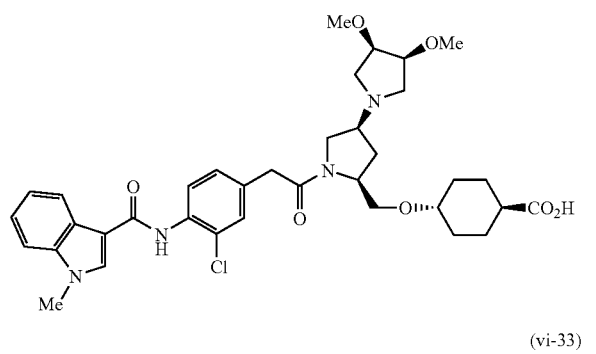
(vi-33)
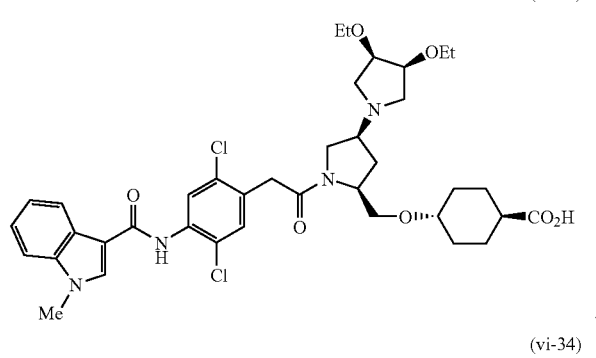
(vi-34)
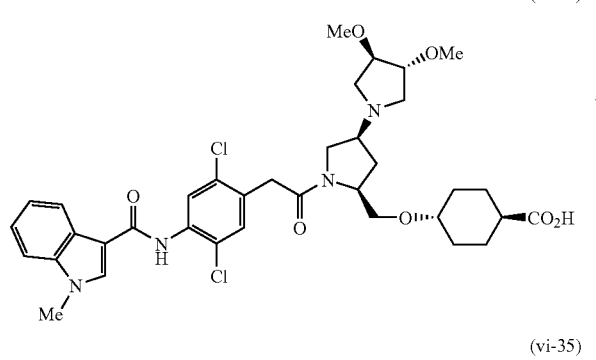
(vi-35)
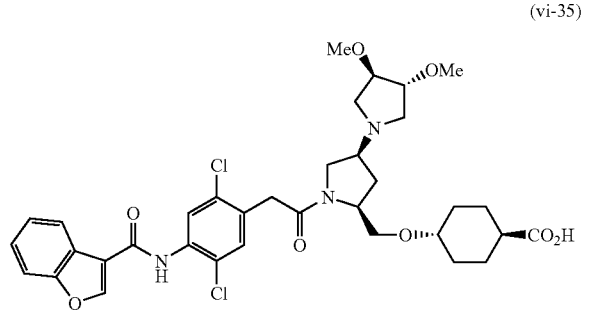
-continued
(vi-36)
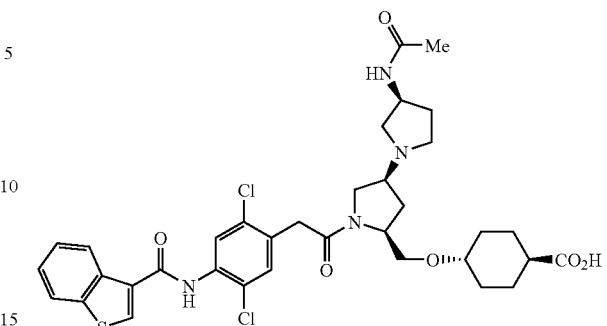
[Formula 15]
(vi-37)
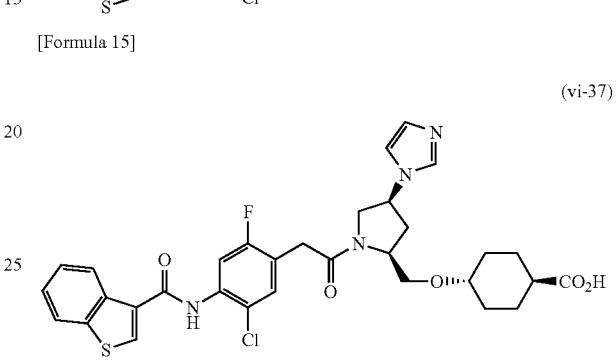
(vi-38)
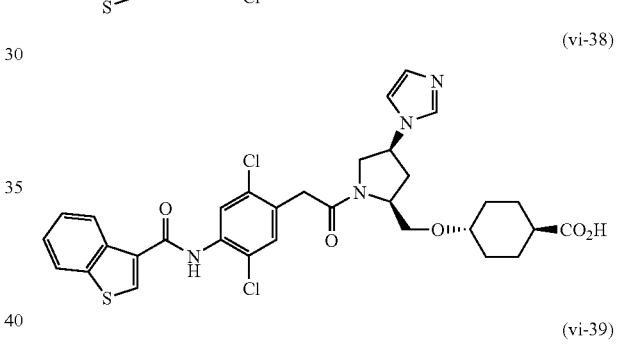
(vi-39)
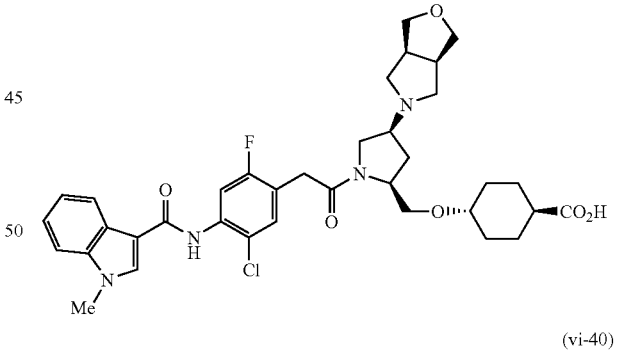
(vi-40)
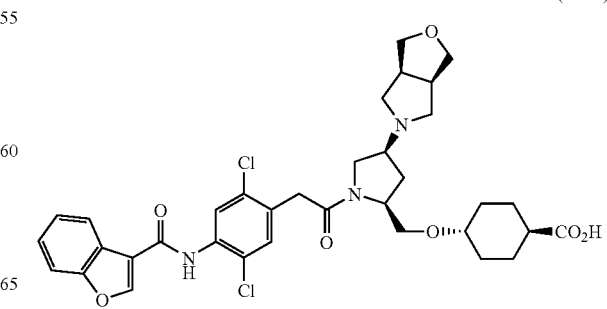

(vi-41)
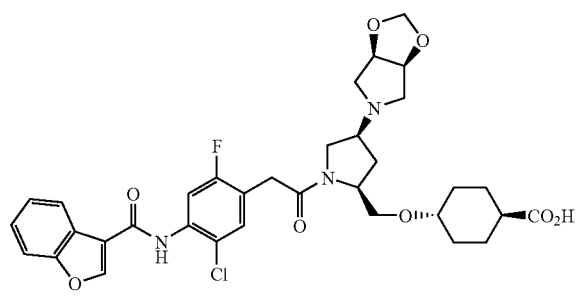
(vi-42)
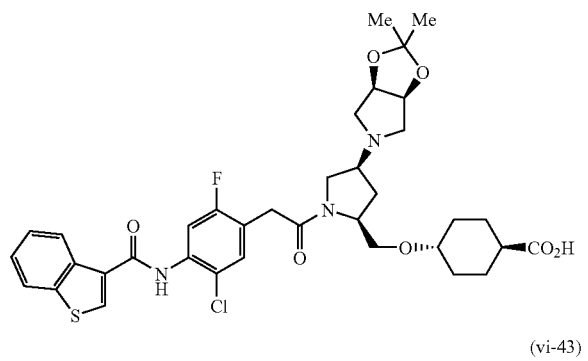
(vi-43)
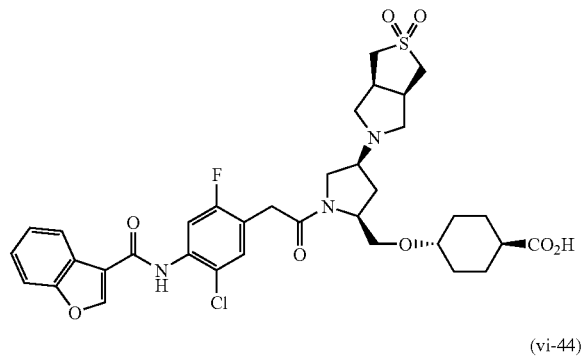
(vi-44)
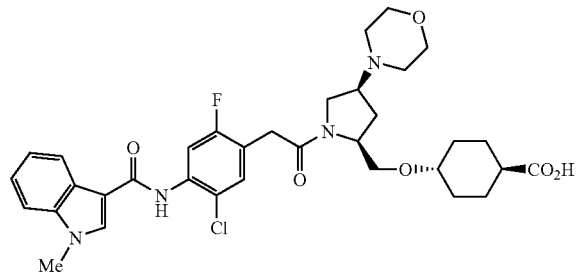
(vi-45)
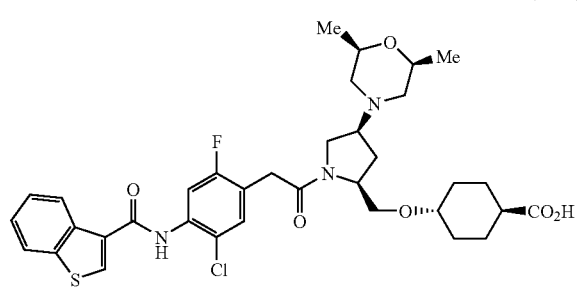
(vi-46)
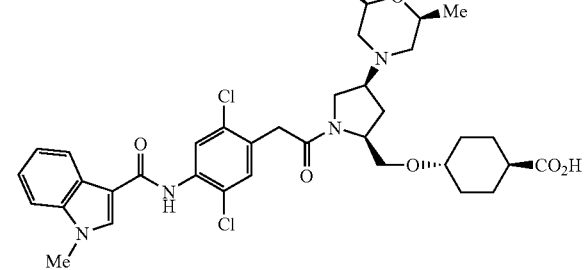
(vi-47)
(vi-48)
[Formula 16]
(vi-49)
(vi-50)
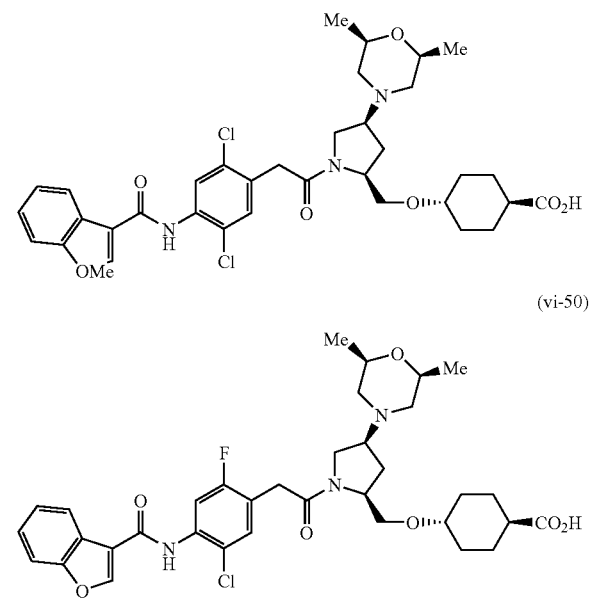

377
-continued
(vi-51)
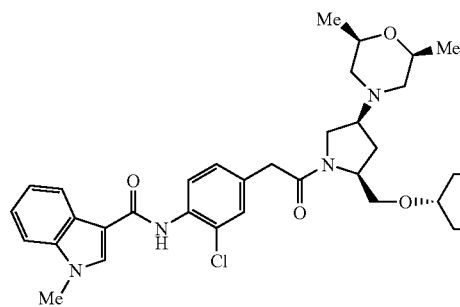
(vi-52)
(vi-53)
(vi-54)
(vi-55)
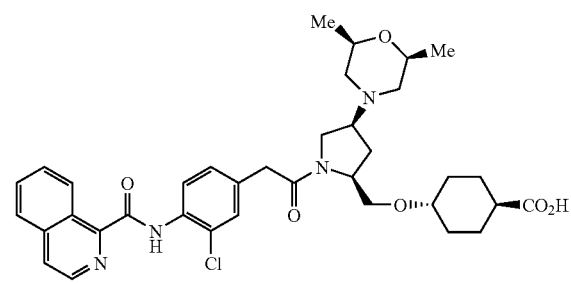
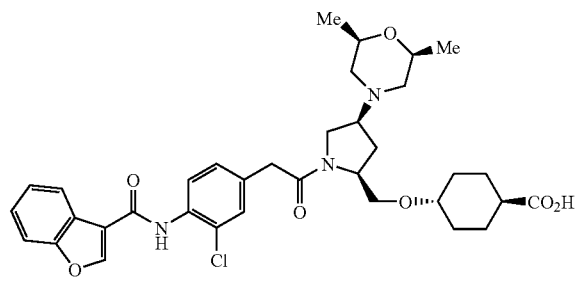
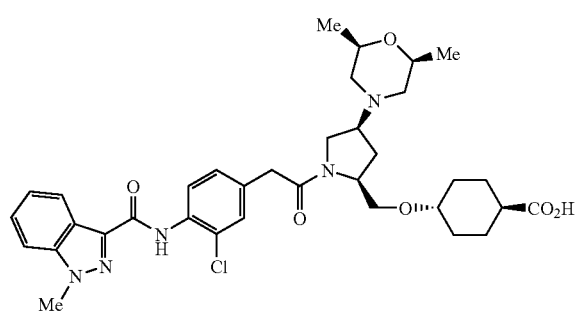
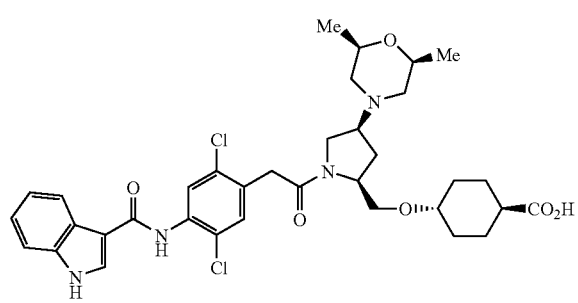
378
-continued
(vi-56)
(vi-57)
(vi-58)
(vi-59)
(vi-60)

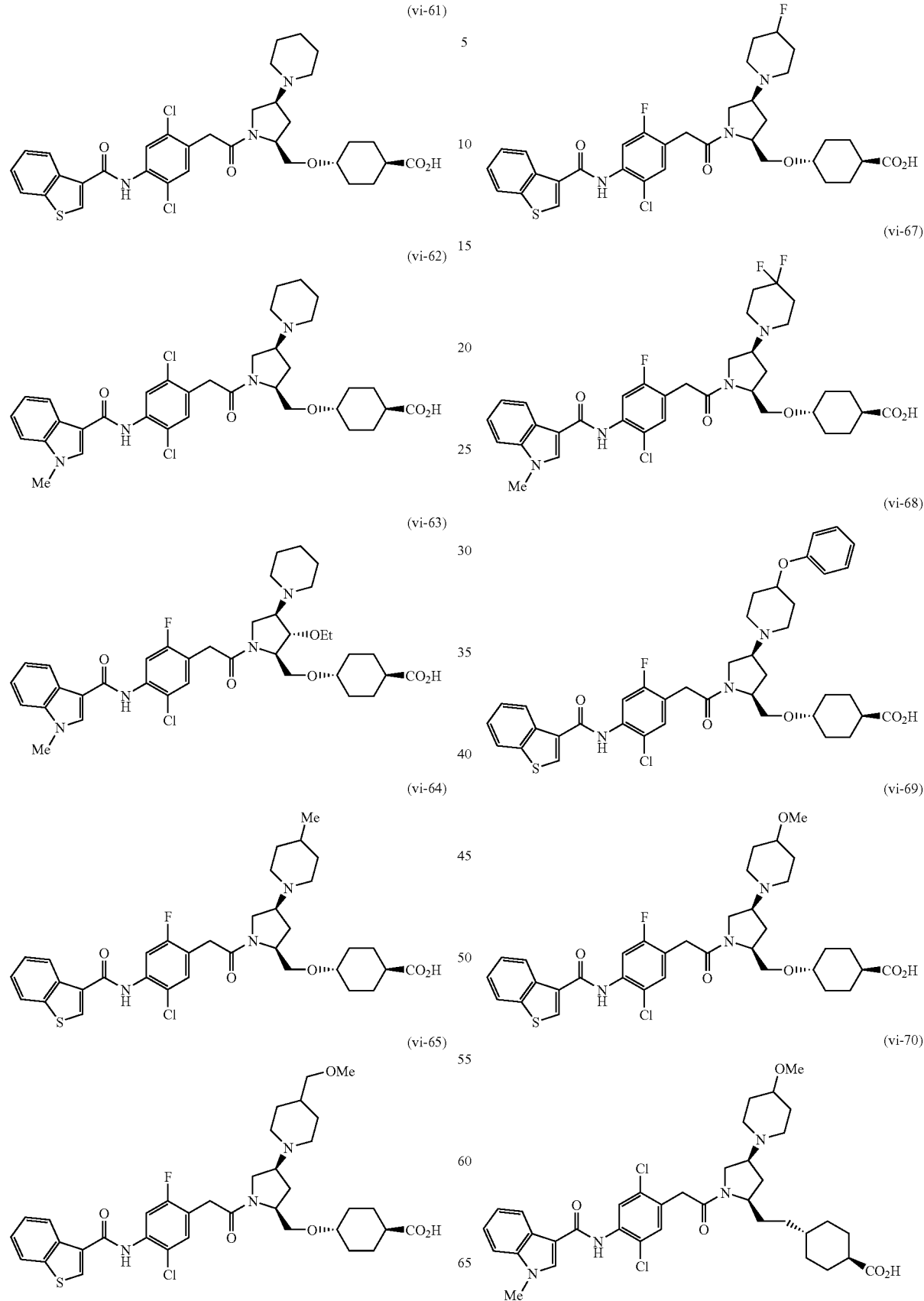

381
-continued
(vi-71)
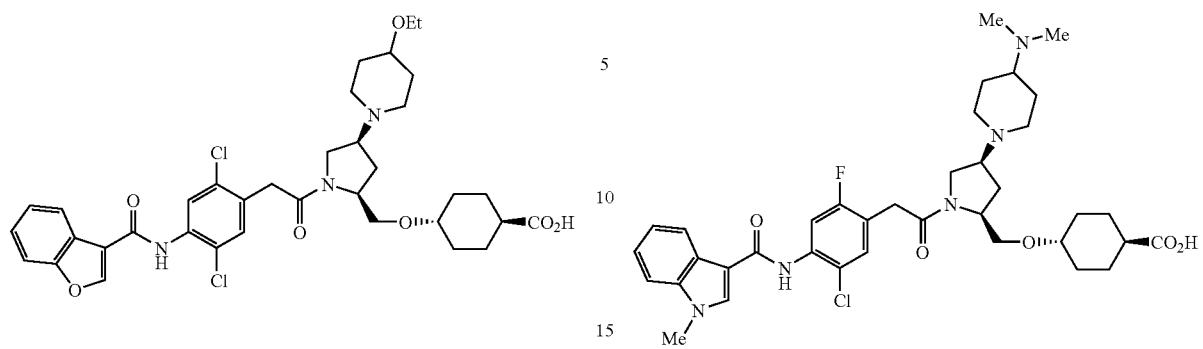
(vi-72)
(vi-73)
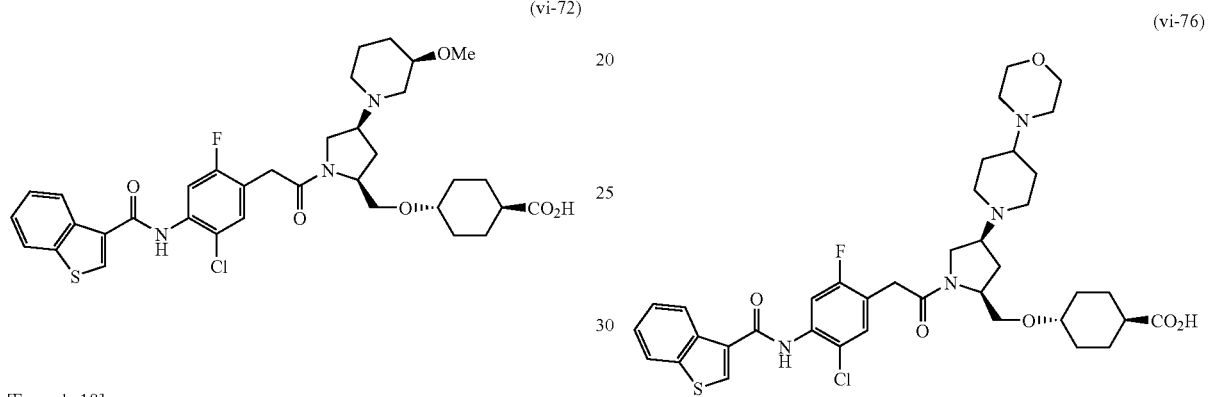
[Formula 18]
(vi-74)
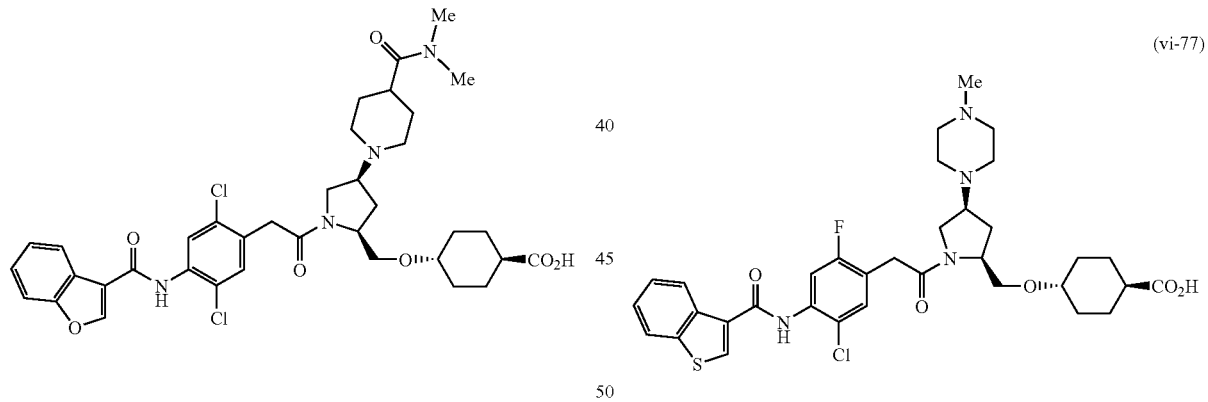
382
-continued
(vi-75)
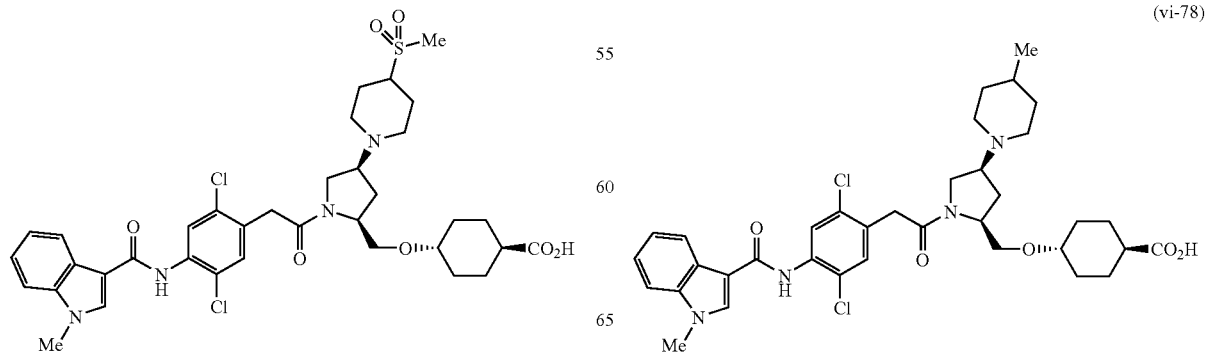
(vi-76)
(vi-77)
(vi-78)

(vi-79)
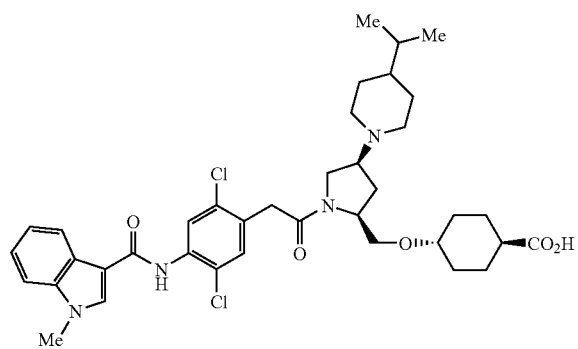
(vi-80)
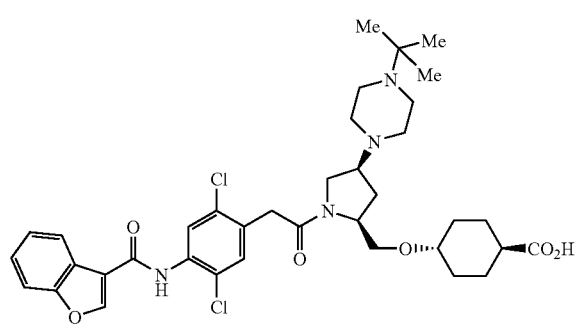
(vi-81)
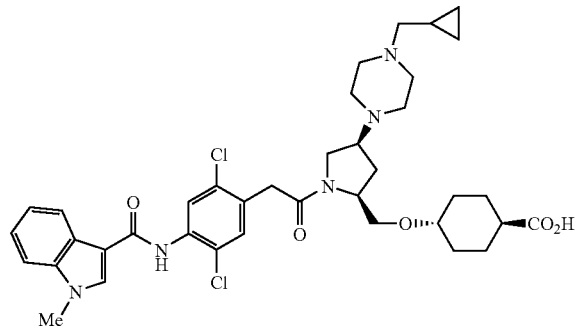
(vi-82)
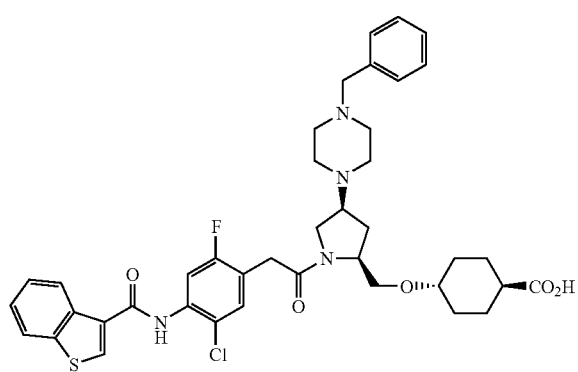
(vi-83)
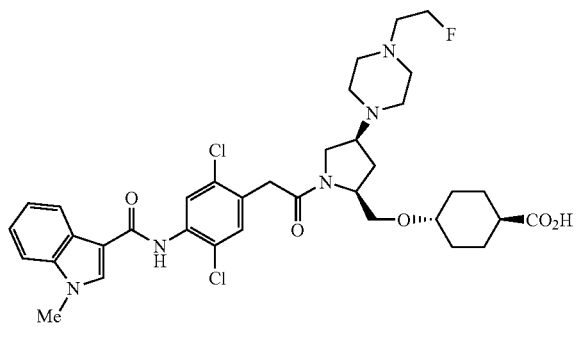
(vi-84)
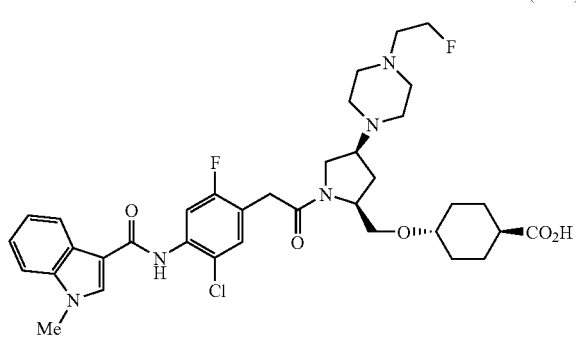
[Formula 19]
(vi-85)
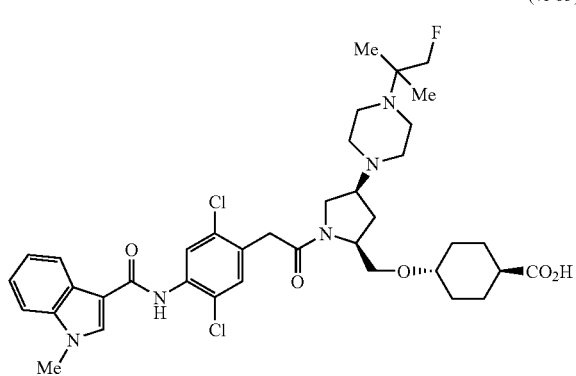
(vi-86)
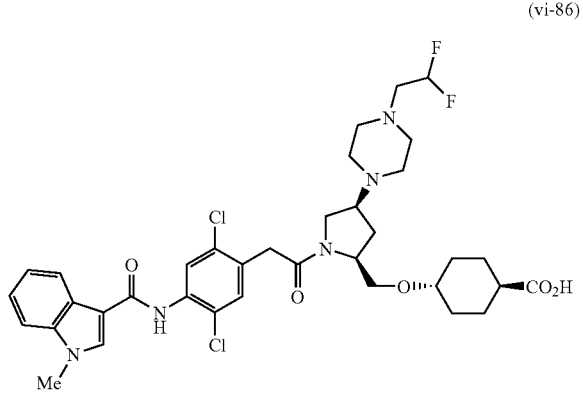

385
-continued
(vi-87)
(vi-88)
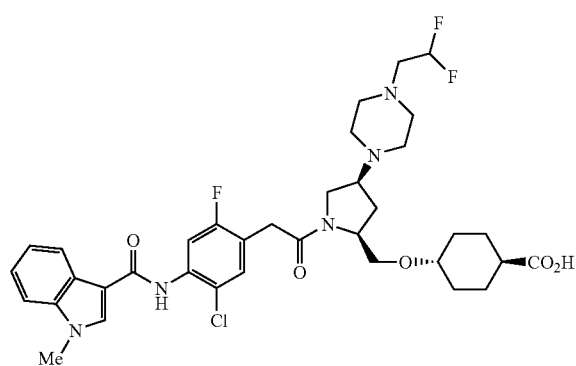
(vi-89)
(vi-90)
386
-continued
(vi-91)
(vi-92)
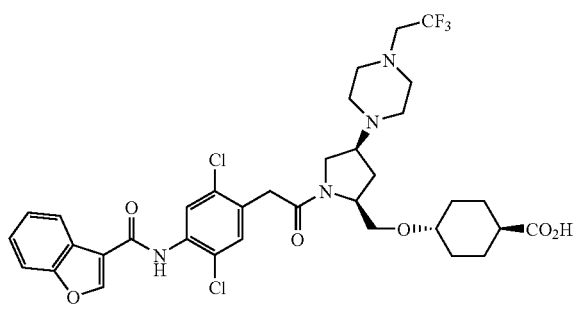
(vi-93)
(vi-94)
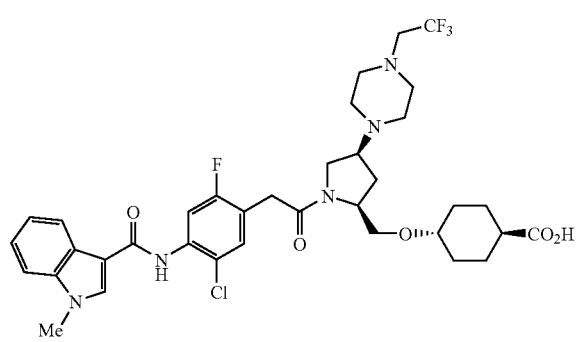
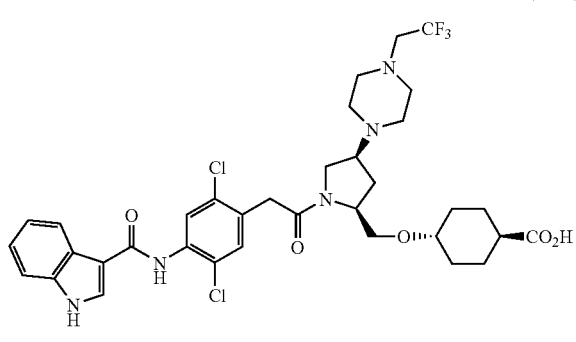

(vi-95)
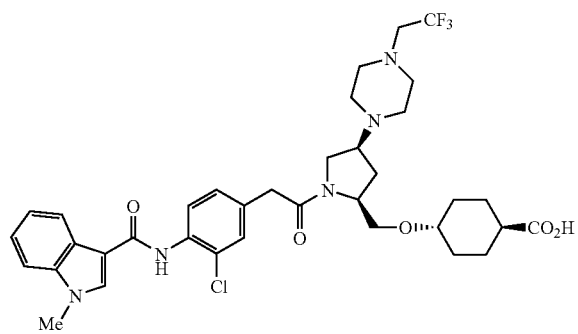
(vi-99)
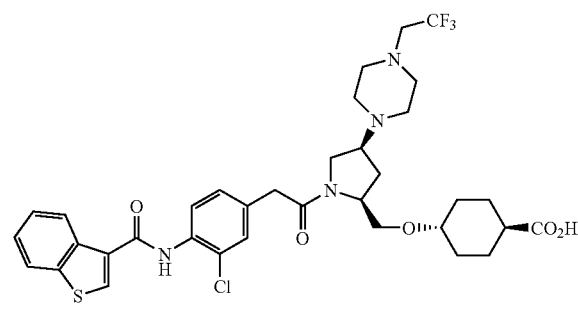
(vi-96)
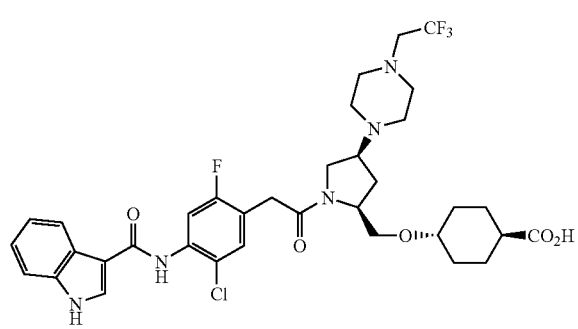
(vi-100)
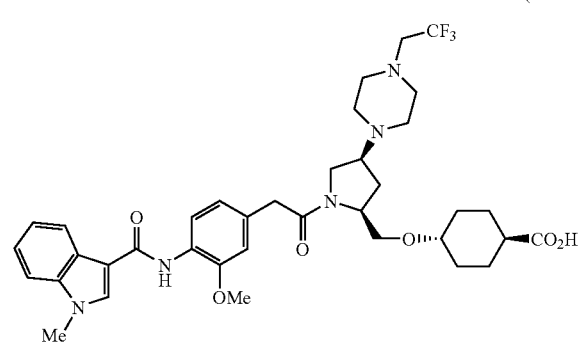
[Formula 20]
(vi-97)
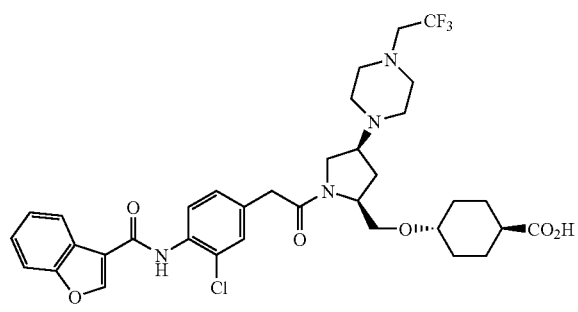
(vi-101)
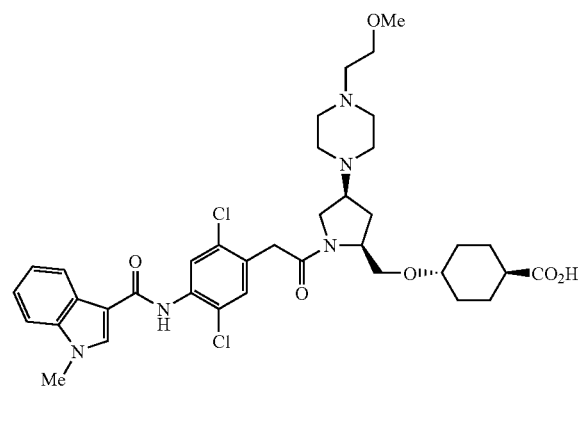
(vi-98)
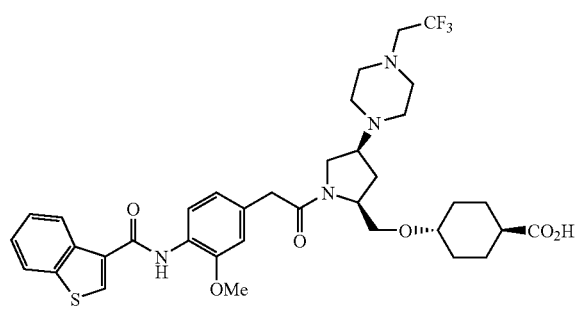
(vi-102)
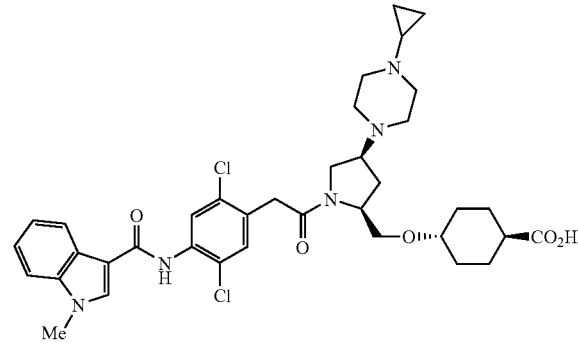

(vi-103)
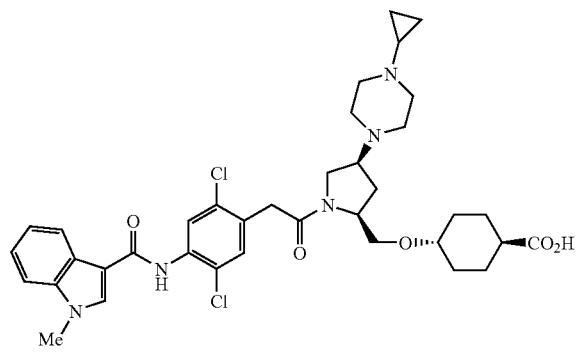
(vi-107)
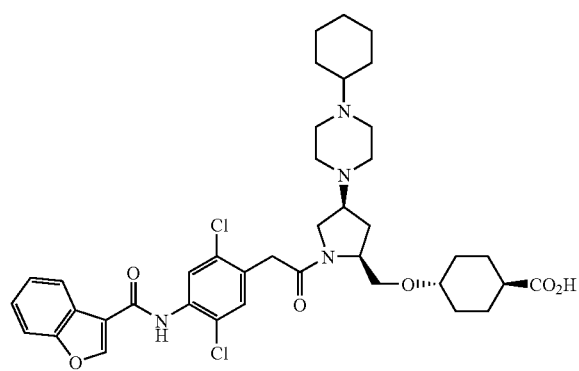
(vi-104)
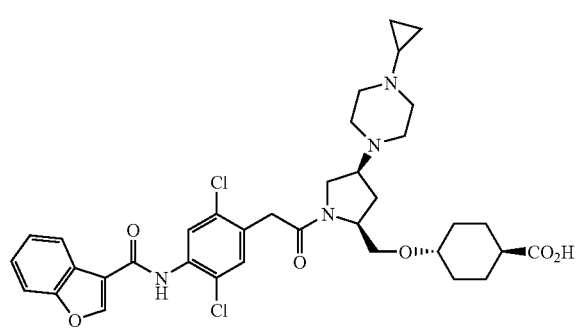
(vi-108)
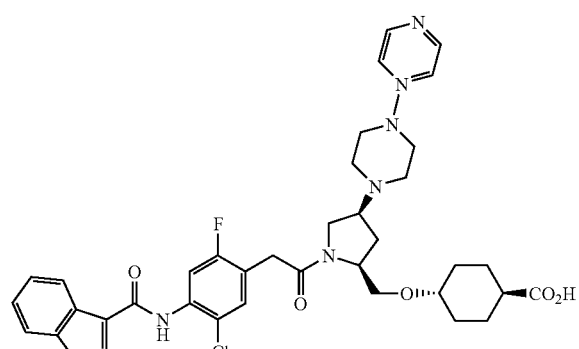
(vi-105)
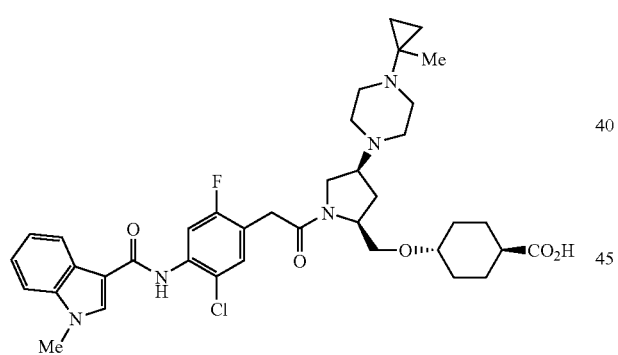
[Formula 21]
(vi-109)
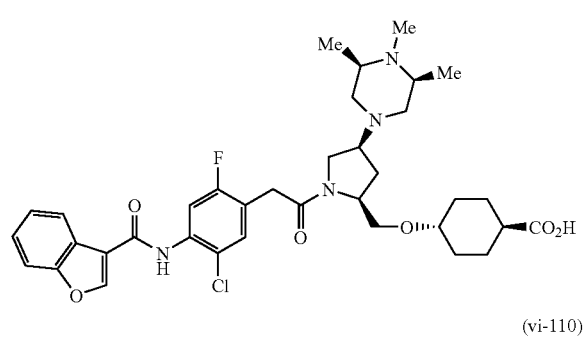
(vi-106)
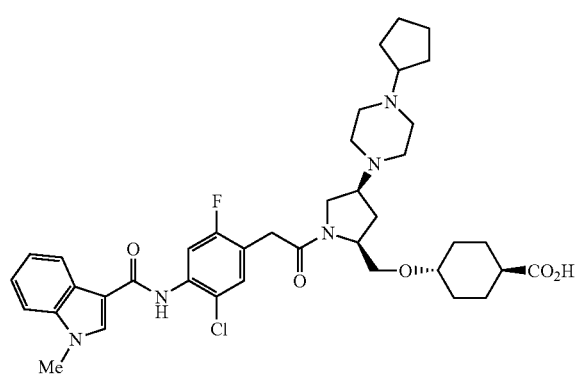
(vi-110)
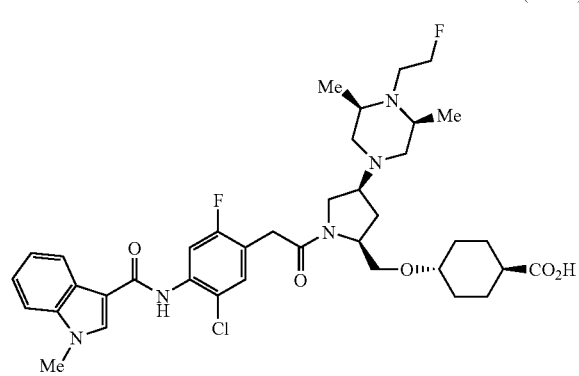

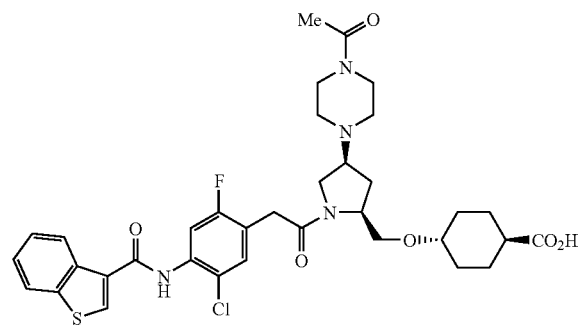
(vi-111)
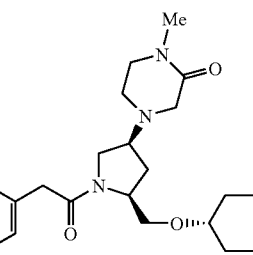
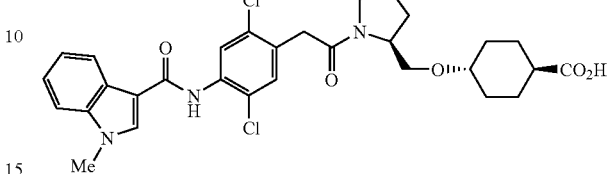
(vi-115)
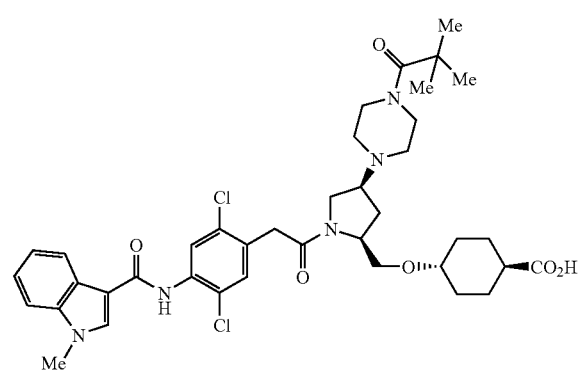
(vi-112)
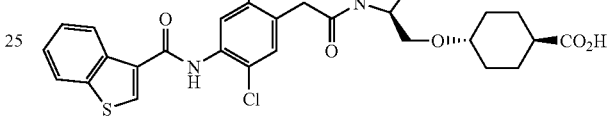
(vi-116)
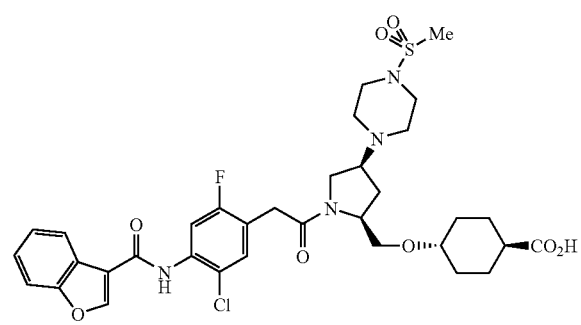
(vi-113)
(vi-117)
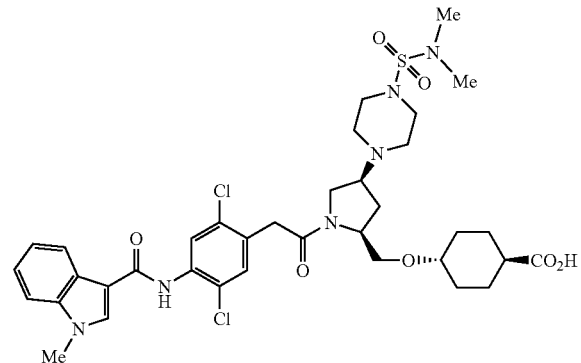
(vi-114)
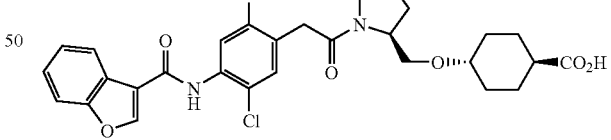
(vi-118)
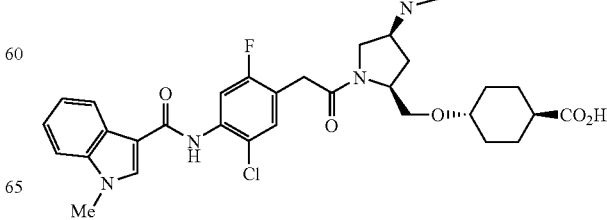
(vi-119)

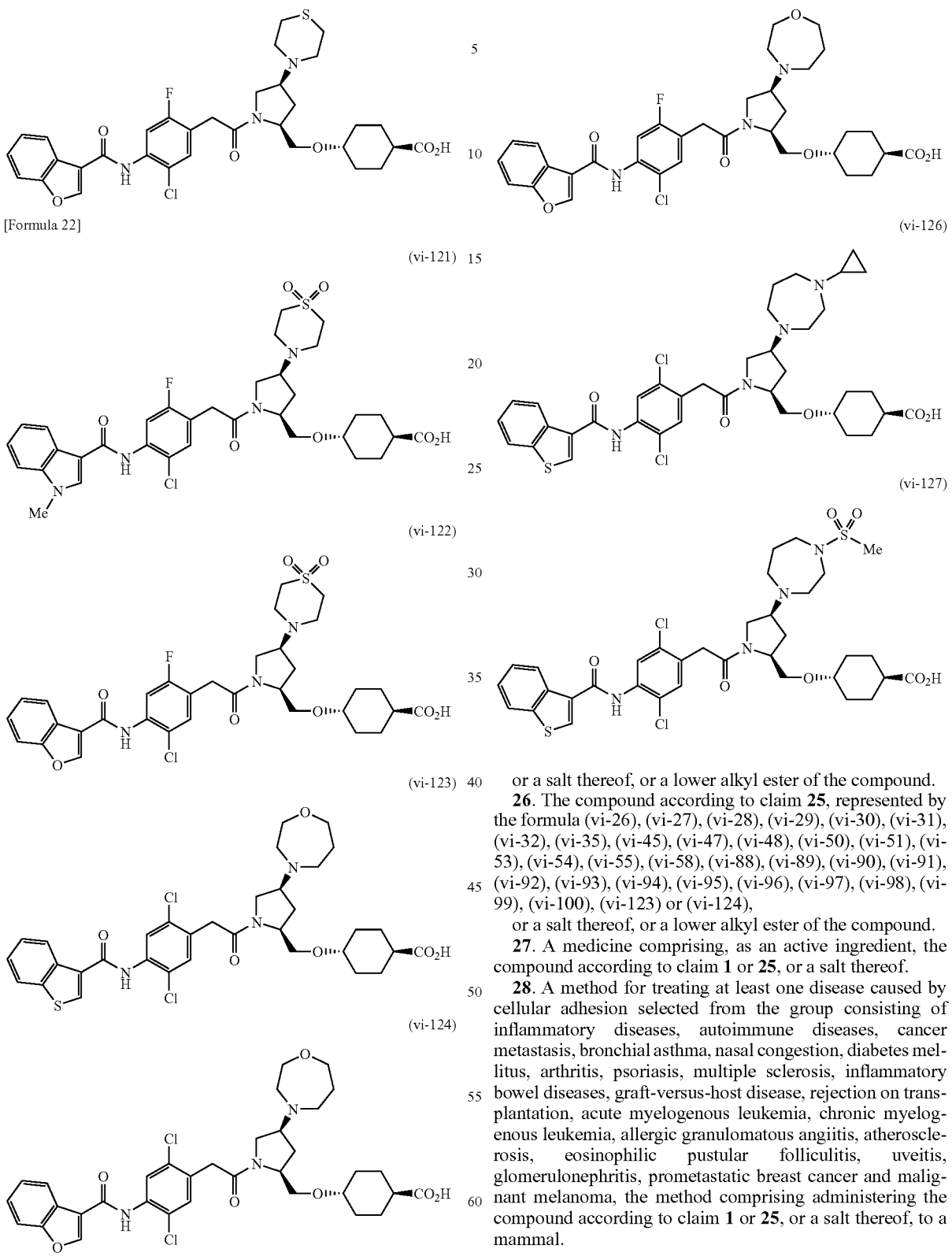

or a salt thereof, or a lower alkyl ester of the compound.

26. The compound according to claim 25, represented by the formula (vi-26), (vi-27), (vi-28), (vi-29), (vi-30), (vi-31), (vi-32), (vi-35), (vi-45), (vi-47), (vi-48), (vi-50), (vi-51), (vi-53), (vi-54), (vi-55), (vi-58), (vi-88), (vi-89), (vi-90), (vi-91), (vi-92), (vi-93), (vi-94), (vi-95), (vi-96), (vi-97), (vi-98), (vi-99), (vi-100), (vi-123) or (vi-124), or a salt thereof, or a lower alkyl ester of the compound.

27. A medicine comprising, as an active ingredient, the compound according to claim 1 or 25, or a salt thereof.

28. A method for treating at least one disease caused by cellular adhesion selected from the group consisting of inflammatory diseases, autoimmune diseases, cancer metastasis, bronchial asthma, nasal congestion, diabetes mellitus, arthritis, psoriasis, multiple sclerosis, inflammatory bowel diseases, graft-versus-host disease, rejection on transplantation, acute myelogenous leukemia, chronic myelogenous leukemia, allergic granulomatous angiitis, atherosclerosis, eosinophilic pustular folliculitis, uveitis, glomerulonephritis, prometastatic breast cancer and malignant melanoma, the method comprising administering the compound according to claim 1 or 25, or a salt thereof, to a mammal.

* * * * *

UNITED STATES PATENT AND TRADEMARK OFFICE
CERTIFICATE OF CORRECTION

| | |
|---|---|
| PATENT NO. | : 8,129,366 B2 |
| APPLICATION NO. | : 12/097269 |
| DATED | : March 6, 2012 |
| INVENTOR(S) | : Machinaga et al. |

It is certified that error appears in the above-identified patent and that said Letters Patent is hereby corrected as shown below:

Claim 20 column 351, lines 28-32 should read as

--The compound according to any one of claims 1 and 19, wherein $R^{3a}$ in the formula (I) is a hydrogen atom, a fluorine atom or a chlorine atom; $R^{3b}$ is a hydrogen atom; and $R^{3c}$ is a fluorine atom, a chlorine atom, a methoxy group or a methyl group, or a salt thereof.--

Signed and Sealed this
Fifth Day of June, 2012

David J. Kappos
*Director of the United States Patent and Trademark Office*